United States Patent
Wilt et al.

(10) Patent No.: US 11,725,645 B2
(45) Date of Patent: Aug. 15, 2023

(54) AUTOMATED CONTROL MECHANISMS AND METHODS FOR CONTROLLING FLUID FLOW IN A HEMODIALYSIS APPARATUS

(71) Applicant: DEKA Products Limited Partnership, Manchester, NH (US)

(72) Inventors: Michael J. Wilt, Windham, NH (US); Dirk A. van der Merwe, Canterbury, NH (US); James D. Dale, Milton, FL (US); Brian D. Tracey, Litchfield, NH (US); Kevin L. Grant, Litchfield, NH (US); Jason A. Demers, Manchester, NH (US); Catharine N. Flynn, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 742 days.

(21) Appl. No.: 16/723,408

(22) Filed: Dec. 20, 2019

(65) Prior Publication Data
US 2020/0171226 A1    Jun. 4, 2020

Related U.S. Application Data

(60) Division of application No. 15/445,683, filed on Feb. 28, 2017, now Pat. No. 10,537,671, which is a
(Continued)

(51) Int. Cl.
*F04B 43/073* (2006.01)
*A61M 1/26* (2006.01)
(Continued)

(52) U.S. Cl.
CPC .......... *F04B 43/0733* (2013.01); *A61M 1/16* (2013.01); *A61M 1/1605* (2014.02);
(Continued)

(58) Field of Classification Search
CPC ...... F04B 43/0733; F04B 7/02; F04B 7/0216; F04B 9/109; F04B 13/02; F04B 43/00;
(Continued)

(56) References Cited

U.S. PATENT DOCUMENTS

| | | | |
|---|---|---|---|
| 2,339,876 A | 1/1944 | Phillips | |
| 3,083,943 A | 4/1963 | Stewart et al. | |

(Continued)

FOREIGN PATENT DOCUMENTS

| | | | |
|---|---|---|---|
| CA | 1119971 A | 3/1982 | |
| CA | 1323312 C | 10/1993 | |

(Continued)

OTHER PUBLICATIONS

Mineshima et al., Efficacy of internal filtration enhanced hemodialysis. Artifical Organs. 1999;28(1):127-33.

(Continued)

*Primary Examiner* — Hayden Brewster
(74) *Attorney, Agent, or Firm* — Wolf, Greenfield & Sacks, P.C.

(57) ABSTRACT

Automated control mechanisms and methods for controlling fluid flow in a hemodialysis apparatus are described. The methods can involve a controller receiving information from a pressure sensor in a control chamber of a reciprocating diaphragm-based blood pump and causing the application of a time-varying pressure waveform on a diaphragm of the blood pump during a fill-stroke of the blood pump. The controller can be configured and programmed to monitor a pressure variation in the control chamber measured by the pressure sensor and to compare the measured pressure variation to a pre-determined value. Based on such comparison, the controller can initiate a procedure to pause or
(Continued)

stop a dialysate pump of the hemodialysis apparatus if the magnitude of the measured pressure variation deviates from the pre-determined value.

24 Claims, 236 Drawing Sheets

Related U.S. Application Data continuation-in-part of application No. 14/666,059, filed on Mar. 23, 2015, now Pat. No. 9,951,768, and a continuation-in-part of application No. 14/525,071, filed on Oct. 27, 2014, now Pat. No. 10,302,075, and a continuation-in-part of application No. 14/213,702, filed on Mar. 14, 2014, now abandoned.

(60) Provisional application No. 61/793,275, filed on Mar. 15, 2013.

(51) Int. Cl.

| | | |
|---|---|---|
| *F04B 7/02* | (2006.01) | |
| *F04B 43/00* | (2006.01) | |
| *F17D 3/00* | (2006.01) | |
| *F04B 13/02* | (2006.01) | |
| *F04B 9/109* | (2006.01) | |
| *F04B 49/22* | (2006.01) | |
| *F04B 45/02* | (2006.01) | |
| *F04B 53/10* | (2006.01) | |
| *A61M 60/268* | (2021.01) | |
| *A61M 60/113* | (2021.01) | |
| *A61M 60/531* | (2021.01) | |
| *A61M 60/37* | (2021.01) | |
| *A61M 1/36* | (2006.01) | |
| *A61M 1/16* | (2006.01) | |
| *A61M 1/28* | (2006.01) | |
| *F04B 49/06* | (2006.01) | |
| *F04B 53/16* | (2006.01) | |
| *F04B 53/06* | (2006.01) | |
| *A61M 60/523* | (2021.01) | |
| *A61M 60/43* | (2021.01) | |
| *A61M 60/892* | (2021.01) | |
| *A61M 60/894* | (2021.01) | |

(52) U.S. Cl.
CPC .......... *A61M 1/166* (2014.02); *A61M 1/1639* (2014.02); *A61M 1/1656* (2013.01); *A61M 1/1664* (2014.02); *A61M 1/1666* (2014.02); *A61M 1/267* (2014.02); *A61M 1/287* (2013.01); *A61M 1/3638* (2014.02); *A61M 1/3672* (2013.01); *A61M 60/113* (2021.01); *A61M 60/268* (2021.01); *A61M 60/37* (2021.01); *A61M 60/523* (2021.01); *A61M 60/531* (2021.01); *F04B 7/02* (2013.01); *F04B 7/0216* (2013.01); *F04B 9/109* (2013.01); *F04B 13/02* (2013.01); *F04B 43/00* (2013.01); *F04B 45/02* (2013.01); *F04B 49/06* (2013.01); *F04B 49/22* (2013.01); *F04B 53/06* (2013.01); *F04B 53/10* (2013.01); *F04B 53/16* (2013.01); *F17D 3/00* (2013.01); *A61M 60/43* (2021.01); *A61M 60/892* (2021.01); *A61M 60/894* (2021.01); *A61M 2205/12* (2013.01); *A61M 2205/128* (2013.01); *A61M 2205/15* (2013.01); *A61M 2205/18* (2013.01); *A61M 2205/3317* (2013.01); *A61M 2205/3324* (2013.01); *A61M 2205/3331* (2013.01); *A61M 2205/3337* (2013.01); *A61M 2205/3368* (2013.01); *A61M 2205/502* (2013.01); *A61M 2205/52* (2013.01); *Y10T 137/0324* (2015.04); *Y10T 137/0379* (2015.04); *Y10T 137/2521* (2015.04); *Y10T 137/85978* (2015.04); *Y10T 137/86139* (2015.04)

(58) Field of Classification Search
CPC .......... F04B 45/02; F04B 49/06; F04B 49/22; F04B 53/06; F04B 53/10; F04B 53/16; A61M 1/16; A61M 1/1605; A61M 1/1639; A61M 1/1656; A61M 1/166; A61M 1/1664; A61M 1/1666; A61M 1/267; A61M 1/287; A61M 1/3638; A61M 1/3672; A61M 60/113; A61M 60/268; A61M 60/37; A61M 60/523; A61M 60/531; A61M 60/43; A61M 60/892; A61M 60/894; A61M 2205/12; A61M 2205/128; A61M 2205/15; A61M 2205/18; A61M 2205/3317; A61M 2205/3324; A61M 2205/3331; A61M 2205/3337; A61M 2205/3368; A61M 2205/502; A61M 2205/52; F17D 3/00; Y10T 137/0324; Y10T 137/0379; Y10T 137/2521; Y10T 137/85978; Y10T 137/86139
USPC .......... 210/85, 96.2, 141, 645, 646
See application file for complete search history.

(56) References Cited

U.S. PATENT DOCUMENTS

| | | |
|---|---|---|
| 3,111,125 A | 11/1963 | Schulte et al. |
| 3,568,214 A | 3/1971 | Goldschmied et al. |
| 3,656,873 A | 4/1972 | Schiff |
| 3,711,770 A | 1/1973 | Wilson |
| RE27,849 E | 12/1973 | Wortman |
| 3,882,861 A | 5/1975 | Kettering et al. |
| 3,946,731 A | 3/1976 | Lichtenstein |
| 4,083,777 A | 4/1978 | Hutchisson |
| 4,137,168 A | 1/1979 | Perrot |
| 4,155,852 A | 5/1979 | Fischel et al. |
| 4,222,127 A | 9/1980 | Donachy et al. |
| 4,267,040 A | 5/1981 | Schal |
| 4,269,708 A | 5/1981 | Bonomini et al. |
| 4,381,545 A | 4/1983 | Biddle, III et al. |
| 4,441,357 A | 4/1984 | Kahn et al. |
| 4,594,058 A | 6/1986 | Fischell |
| 4,661,246 A | 4/1987 | Ash |
| 4,668,400 A | 5/1987 | Veech |
| 4,695,385 A | 9/1987 | Boag |
| 4,778,451 A | 10/1988 | Kamen |
| 4,797,655 A | 1/1989 | Orndal et al. |
| 4,808,161 A | 2/1989 | Kamen |
| 4,826,482 A | 5/1989 | Kamen |
| 4,828,543 A | 5/1989 | Weiss et al. |
| 4,828,693 A | 5/1989 | Lindsay et al. |
| 4,844,072 A | 7/1989 | French et al. |
| 4,927,411 A | 5/1990 | Pastrone et al. |
| 4,950,235 A | 8/1990 | Slate et al. |
| 4,969,363 A | 11/1990 | Mochizuki |
| 4,971,700 A | 11/1990 | Tsuji et al. |
| 4,976,162 A | 12/1990 | Kamen |
| 4,997,570 A | 3/1991 | Polaschegg |
| 5,002,471 A | 3/1991 | Perlov |
| 5,024,756 A | 6/1991 | Sternby |
| 5,088,515 A | 2/1992 | Kamen |
| 5,098,262 A | 3/1992 | Wecker et al. |
| 5,100,554 A | 3/1992 | Polaschegg |
| 5,178,182 A | 1/1993 | Kamen |
| 5,242,384 A | 9/1993 | Robinson et al. |
| 5,247,434 A | 9/1993 | Peterson et al. |
| 5,275,724 A | 1/1994 | Bucchianeri et al. |
| 5,318,414 A | 6/1994 | Lundback |

(56) References Cited

U.S. PATENT DOCUMENTS

| | | |
|---|---|---|
| 5,324,422 A | 6/1994 | Colleran et al. |
| 5,350,357 A | 9/1994 | Kamen et al. |
| 5,351,686 A | 10/1994 | Steuer et al. |
| 5,378,231 A | 1/1995 | Johnson et al. |
| 5,411,472 A | 5/1995 | Steg, Jr. et al. |
| 5,415,528 A | 5/1995 | Ogden et al. |
| 5,421,823 A | 6/1995 | Kamen et al. |
| 5,423,738 A | 6/1995 | Robinson et al. |
| 5,427,509 A | 6/1995 | Chapman et al. |
| 5,431,627 A | 7/1995 | Pastrone et al. |
| 5,431,811 A | 7/1995 | Tusini et al. |
| 5,438,510 A | 8/1995 | Bryant et al. |
| 5,458,468 A | 10/1995 | Ye et al. |
| 5,472,325 A | 12/1995 | Svendsen |
| 5,472,614 A | 12/1995 | Rossi |
| 5,486,286 A | 1/1996 | Peterson et al. |
| 5,487,827 A | 1/1996 | Peterson et al. |
| 5,496,273 A | 3/1996 | Pastrone et al. |
| 5,499,909 A | 3/1996 | Yamada et al. |
| 5,516,429 A | 5/1996 | Snodgrass et al. |
| 5,527,507 A | 6/1996 | Childers et al. |
| 5,575,310 A | 11/1996 | Kamen et al. |
| 5,580,460 A | 12/1996 | Polaschegg |
| 5,586,438 A | 12/1996 | Fahy |
| 5,609,572 A | 3/1997 | Lang |
| 5,609,770 A | 3/1997 | Zimmerman et al. |
| 5,628,908 A | 5/1997 | Kamen et al. |
| 5,645,531 A | 7/1997 | Thompson et al. |
| 5,676,644 A | 10/1997 | Toavs et al. |
| 5,714,060 A | 2/1998 | Kenley et al. |
| 5,744,027 A | 4/1998 | Connell et al. |
| 5,769,811 A | 6/1998 | Stacey et al. |
| 5,788,851 A | 8/1998 | Kenley et al. |
| 5,795,317 A | 8/1998 | Brierton et al. |
| 5,808,181 A | 9/1998 | Wamsiedler et al. |
| 5,827,223 A | 10/1998 | Butterfield |
| 5,846,419 A | 12/1998 | Nederlof |
| 5,863,421 A | 1/1999 | Peter, Jr. et al. |
| 5,906,978 A | 5/1999 | Ash |
| 5,925,011 A | 7/1999 | Faict et al. |
| 6,041,801 A | 3/2000 | Gray et al. |
| 6,044,691 A | 4/2000 | Kenley et al. |
| 6,070,761 A | 6/2000 | Bloom et al. |
| 6,077,055 A | 6/2000 | Wilks |
| 6,146,523 A | 11/2000 | Kenley et al. |
| 6,223,130 B1 | 4/2001 | Gray et al. |
| 6,228,047 B1 | 5/2001 | Dadson |
| 6,234,989 B1 | 5/2001 | Brierton et al. |
| 6,261,065 B1 | 7/2001 | Nayak et al. |
| 6,277,272 B1 | 8/2001 | Nikaido et al. |
| 6,284,131 B1 | 9/2001 | Hogard et al. |
| 6,295,918 B1 | 10/2001 | Simmons et al. |
| 6,302,653 B1 | 10/2001 | Bryant et al. |
| 6,321,597 B1 | 11/2001 | Demers et al. |
| 6,327,895 B1 | 12/2001 | Jeppsson et al. |
| 6,382,923 B1 | 5/2002 | Gray |
| 6,406,426 B1 | 6/2002 | Reuss et al. |
| 6,416,293 B1 | 7/2002 | Bouchard et al. |
| 6,468,241 B1 | 10/2002 | Gelfand et al. |
| 6,485,263 B1 | 11/2002 | Bryant et al. |
| 6,497,676 B1 | 12/2002 | Childers et al. |
| 6,503,062 B1 | 1/2003 | Gray et al. |
| 6,505,691 B2 | 1/2003 | Judge et al. |
| 6,520,747 B2 | 2/2003 | Gray et al. |
| 6,579,253 B1 | 6/2003 | Burbank et al. |
| 6,602,424 B1 | 8/2003 | Kramer et al. |
| 6,604,908 B1 | 8/2003 | Bryant et al. |
| 6,614,008 B2 | 9/2003 | Tidrick |
| 6,638,478 B1 | 10/2003 | Treu et al. |
| 6,649,063 B2 | 11/2003 | Brugger et al. |
| 6,663,353 B2 | 12/2003 | Lipscomb et al. |
| 6,673,314 B1 | 1/2004 | Burbank et al. |
| 6,692,457 B2 | 2/2004 | Flaherty |
| 6,723,062 B1 | 4/2004 | Westberg et al. |
| 6,749,403 B2 | 6/2004 | Bryant et al. |
| 6,752,599 B2 | 6/2004 | Park |
| 6,811,707 B2 | 11/2004 | Rovatti et al. |
| 6,814,547 B2 | 11/2004 | Childers et al. |
| 6,821,441 B2 | 11/2004 | Pedrini et al. |
| 6,852,090 B2 | 2/2005 | Burbank et al. |
| 6,868,309 B1 | 3/2005 | Begelman |
| 6,877,419 B2 | 4/2005 | Ohrle et al. |
| 6,905,314 B2 | 6/2005 | Danby |
| 6,905,479 B1 | 6/2005 | Bouchard et al. |
| 6,929,751 B2 | 8/2005 | Bowmna, Jr. et al. |
| 6,939,471 B2 | 9/2005 | Gross et al. |
| 6,949,079 B1 | 9/2005 | Westberg et al. |
| 6,953,323 B2 | 10/2005 | Childers et al. |
| 7,029,245 B2 | 4/2006 | Maianti et al. |
| 7,041,076 B1 | 5/2006 | Westberg et al. |
| 7,083,719 B2 | 8/2006 | Bowman, Jr. et al. |
| 7,147,616 B2 | 12/2006 | Pedrazzi et al. |
| 7,153,286 B2 | 12/2006 | Busby et al. |
| 7,175,606 B2 | 2/2007 | Bowman, Jr. et al. |
| 7,238,164 B2 | 7/2007 | Childers et al. |
| 7,273,465 B2 | 9/2007 | Ash |
| 7,300,413 B2 | 11/2007 | Burbank et al. |
| 7,303,540 B2 | 12/2007 | O'Mahony et al. |
| 7,318,292 B2 | 1/2008 | Helbling et al. |
| 7,327,273 B2 | 2/2008 | Hung et al. |
| 7,364,563 B2 | 4/2008 | Lucke et al. |
| 7,461,968 B2 | 12/2008 | Demers et al. |
| 7,465,285 B2 | 12/2008 | Hutchinson et al. |
| 7,473,238 B2 | 1/2009 | Brugger et al. |
| 7,500,962 B2 | 3/2009 | Childers et al. |
| 7,524,417 B2 | 4/2009 | Sunohara et al. |
| 7,544,179 B2 | 6/2009 | Distler et al. |
| 7,544,301 B2 | 6/2009 | Shah et al. |
| 7,559,524 B2 | 7/2009 | Gray et al. |
| 7,560,686 B2 | 7/2009 | Bisch et al. |
| 7,563,240 B2 | 7/2009 | Gross et al. |
| 7,575,564 B2 | 8/2009 | Childers |
| 7,615,028 B2 | 11/2009 | O'Mahony |
| 7,632,078 B2 | 12/2009 | Demers et al. |
| 7,648,627 B2 | 1/2010 | Beden et al. |
| 7,699,806 B2 | 4/2010 | Ware et al. |
| 7,744,553 B2 | 6/2010 | Kelly et al. |
| 7,758,532 B2 | 7/2010 | Mori et al. |
| 7,776,006 B2 | 8/2010 | Childers et al. |
| 7,780,619 B2 | 8/2010 | Brugger et al. |
| 7,794,141 B2 | 9/2010 | Perry et al. |
| 7,909,795 B2 | 3/2011 | Childers et al. |
| 7,922,899 B2 | 4/2011 | Vasta et al. |
| 7,935,250 B2 | 5/2011 | Castellano et al. |
| 7,967,022 B2 | 6/2011 | Grant et al. |
| 8,029,454 B2 | 10/2011 | Kelly et al. |
| 8,042,563 B2 | 10/2011 | Wilt et al. |
| 8,105,265 B2 | 1/2012 | Demers et al. |
| 8,113,244 B2 | 2/2012 | Kamen et al. |
| 8,197,439 B2 | 6/2012 | Wang et al. |
| 8,246,826 B2 | 8/2012 | Wilt et al. |
| 8,273,049 B2 | 9/2012 | Demers et al. |
| 8,287,480 B2 | 10/2012 | Sasaki et al. |
| 8,292,594 B2 | 10/2012 | Tracey et al. |
| 8,317,492 B2 | 11/2012 | Demers et al. |
| 8,357,298 B2 | 1/2013 | Demers et al. |
| 8,393,690 B2 | 3/2013 | Grant et al. |
| 8,409,441 B2 | 4/2013 | Wilt |
| 8,425,471 B2 | 4/2013 | Grant et al. |
| 8,459,292 B2 | 6/2013 | Wilt et al. |
| 8,469,331 B2 | 6/2013 | Burbank et al. |
| 8,491,184 B2 | 7/2013 | Kamen et al. |
| 8,499,780 B2 | 8/2013 | Wilt et al. |
| 8,512,553 B2 | 8/2013 | Cicchello et al. |
| 8,545,698 B2 | 10/2013 | Wilt et al. |
| 8,556,225 B2 | 10/2013 | Gray |
| 8,562,834 B2 | 10/2013 | Kamen et al. |
| 8,597,229 B2 | 12/2013 | Pan |
| 8,597,505 B2 | 12/2013 | Fulkerson et al. |
| 8,612,055 B2 | 12/2013 | Ali et al. |
| 8,721,879 B2 | 5/2014 | van der Merwe et al. |
| 8,721,884 B2 | 5/2014 | Wilt et al. |
| 8,728,020 B2 | 5/2014 | Caleffi et al. |
| 8,764,702 B2 | 7/2014 | Childers et al. |

(56) References Cited

U.S. PATENT DOCUMENTS

| | | |
|---|---|---|
| 8,771,508 B2 | 7/2014 | Grant et al. |
| 8,821,475 B2 | 9/2014 | Distler et al. |
| 8,821,476 B2 | 9/2014 | Agah et al. |
| 8,858,787 B2 | 10/2014 | Muller et al. |
| 8,863,772 B2 | 10/2014 | Dale et al. |
| 8,870,549 B2 | 10/2014 | Tracey et al. |
| 8,882,700 B2 | 11/2014 | Chapman et al. |
| 8,888,470 B2 | 11/2014 | Demers et al. |
| 8,906,240 B2 | 12/2014 | Crnkovich et al. |
| 8,926,294 B2 | 1/2015 | Demers et al. |
| 8,968,232 B2 | 3/2015 | Kamen et al. |
| 8,985,133 B2 | 3/2015 | Grant et al. |
| 8,986,252 B2 | 3/2015 | Cummings et al. |
| 8,992,075 B2 | 3/2015 | Kamen et al. |
| 8,992,189 B2 | 3/2015 | Wilt et al. |
| 9,028,691 B2 | 5/2015 | Grant et al. |
| 9,039,395 B2 | 5/2015 | Gray et al. |
| 9,072,831 B2 | 7/2015 | Kelly et al. |
| 9,089,653 B2 | 7/2015 | O'Mahony |
| 9,115,708 B2 | 8/2015 | van der Merwe et al. |
| 9,272,082 B2 | 3/2016 | Demers et al. |
| 9,302,037 B2 | 4/2016 | Wilt et al. |
| 9,302,039 B2 | 4/2016 | Kelly et al. |
| 9,364,655 B2 | 6/2016 | Grant et al. |
| 9,488,167 B2 | 11/2016 | Gray et al. |
| 9,494,151 B2 | 11/2016 | Gray et al. |
| 9,514,283 B2 | 12/2016 | Childers et al. |
| 9,517,295 B2 | 12/2016 | Wilt et al. |
| 9,535,021 B2 | 1/2017 | Kamen et al. |
| 9,539,379 B2 | 1/2017 | Grant et al. |
| 9,550,018 B2 | 1/2017 | Demers et al. |
| 9,555,179 B2 | 1/2017 | Wilt et al. |
| 9,561,317 B2 | 2/2017 | Distler et al. |
| 9,561,318 B2 | 2/2017 | Distler et al. |
| 9,593,678 B2 | 3/2017 | Gray et al. |
| 9,597,442 B2 | 3/2017 | Wilt |
| 9,603,985 B2 | 3/2017 | Wilt et al. |
| 9,649,418 B2 | 5/2017 | Demers et al. |
| 9,677,554 B2 | 6/2017 | Wilt et al. |
| 9,700,660 B2 | 7/2017 | Demers et al. |
| 9,700,711 B2 | 7/2017 | Grant et al. |
| 9,713,667 B2 | 7/2017 | Distler et al. |
| 9,717,834 B2 | 8/2017 | Wilt et al. |
| 9,719,964 B2 | 8/2017 | Blumberg, Jr. |
| 9,724,012 B2 | 8/2017 | Chetham |
| 9,724,458 B2 | 8/2017 | Grant et al. |
| 9,750,865 B2 | 9/2017 | Vasta et al. |
| 9,770,546 B2 | 9/2017 | Vasta |
| 9,795,728 B2 | 10/2017 | Grant et al. |
| 9,907,897 B2 | 3/2018 | Burbank et al. |
| 9,907,972 B2 | 3/2018 | Kameli |
| 9,951,768 B2 | 4/2018 | Grant et al. |
| 9,987,407 B2 | 6/2018 | Grant et al. |
| 9,999,717 B2 | 6/2018 | van der Merwe et al. |
| 10,058,694 B2 | 8/2018 | Norris et al. |
| 10,060,867 B2 | 8/2018 | Kamen et al. |
| 10,077,766 B2 | 9/2018 | Demers et al. |
| 10,098,998 B2 | 10/2018 | Wilt |
| 10,201,647 B2 | 2/2019 | Norris et al. |
| 10,201,650 B2 | 2/2019 | Wilt et al. |
| 10,302,075 B2 | 5/2019 | Tracey et al. |
| 10,415,559 B2 | 9/2019 | Demers et al. |
| 10,441,697 B2 | 10/2019 | Kamen et al. |
| 10,443,591 B2 | 10/2019 | Wilt et al. |
| 10,449,280 B2 | 10/2019 | Wilt et al. |
| 10,463,774 B2 | 11/2019 | Ballantyne et al. |
| 10,500,327 B2 | 12/2019 | Grant et al. |
| 10,537,671 B2 | 1/2020 | Wilt et al. |
| 10,576,194 B2 | 3/2020 | Distler et al. |
| 10,682,450 B2 | 6/2020 | Wilt et al. |
| 10,697,913 B2 | 6/2020 | Kamen et al. |
| 10,780,210 B2 | 9/2020 | Grant et al. |
| 10,780,213 B2 | 9/2020 | Grant et al. |
| 10,799,628 B2 | 10/2020 | Wilt et al. |
| 10,850,089 B2 | 12/2020 | Grant et al. |
| 10,851,769 B2 | 12/2020 | Demers et al. |
| 10,871,157 B2 | 12/2020 | Tracey et al. |
| 11,033,671 B2 | 6/2021 | van der Merwe et al. |
| 11,052,181 B2 | 7/2021 | Wilt et al. |
| 11,103,625 B2 | 8/2021 | Wilt |
| 11,110,212 B2 | 9/2021 | Grant et al. |
| 11,154,646 B2 | 10/2021 | Wilt et al. |
| 11,197,951 B2 | 12/2021 | Wilt et al. |
| 11,253,636 B2 | 2/2022 | McGill et al. |
| 11,311,656 B2 | 4/2022 | Kamen et al. |
| 11,364,329 B2 | 6/2022 | Demers et al. |
| 11,371,498 B2 | 6/2022 | Grant et al. |
| 11,400,272 B2 | 8/2022 | Norris et al. |
| 11,419,965 B2 | 8/2022 | Demers et al. |
| 11,529,444 B2 | 12/2022 | Wilt et al. |
| 2002/0056672 A1 | 5/2002 | Lyle et al. |
| 2002/0103453 A1 | 8/2002 | Burbank et al. |
| 2002/0182090 A1 | 12/2002 | Gray |
| 2003/0004492 A1 | 1/2003 | Munis et al. |
| 2003/0138334 A1 | 7/2003 | Vandlik et al. |
| 2003/0220607 A1 | 11/2003 | Busby et al. |
| 2003/0220627 A1 | 11/2003 | Distler et al. |
| 2004/0001766 A1 | 1/2004 | Maianti et al. |
| 2004/0087895 A1 | 5/2004 | Cho et al. |
| 2004/0194210 A1 | 10/2004 | Foster et al. |
| 2004/0243049 A1 | 12/2004 | Brugger et al. |
| 2004/0254513 A1 | 12/2004 | Shang et al. |
| 2005/0045540 A1 | 3/2005 | Connell et al. |
| 2005/0095141 A1 | 5/2005 | Lanigan et al. |
| 2005/0100450 A1 | 5/2005 | Bryant et al. |
| 2005/0145010 A1 | 7/2005 | Vanderveen et al. |
| 2005/0209563 A1 | 9/2005 | Hopping et al. |
| 2005/0234385 A1 | 10/2005 | Vandlik et al. |
| 2005/0242034 A1 | 11/2005 | Connell et al. |
| 2006/0002823 A1 | 1/2006 | Feldstein |
| 2006/0084906 A1 | 4/2006 | Burbank et al. |
| 2006/0144396 A1 | 7/2006 | DeVries et al. |
| 2007/0023334 A1 | 2/2007 | Hallstadius et al. |
| 2007/0135758 A1 | 6/2007 | Childers et al. |
| 2008/0033346 A1 | 2/2008 | Childers et al. |
| 2008/0058697 A1 | 3/2008 | Kamen et al. |
| 2008/0097283 A1 | 4/2008 | Plahey |
| 2008/0114330 A1 | 5/2008 | Distler et al. |
| 2008/0125693 A1 | 5/2008 | Gavin et al. |
| 2008/0132828 A1 | 6/2008 | Howard |
| 2008/0161751 A1 | 7/2008 | Plahey et al. |
| 2008/0175719 A1 | 7/2008 | Tracey et al. |
| 2008/0203023 A1 | 8/2008 | Burbank et al. |
| 2008/0253911 A1 | 10/2008 | Demers et al. |
| 2008/0286076 A1 | 11/2008 | Elliott et al. |
| 2009/0009290 A1 | 1/2009 | Kneip et al. |
| 2009/0024070 A1 | 1/2009 | Gelfand et al. |
| 2009/0043239 A1 | 2/2009 | Gagel et al. |
| 2009/0043253 A1 | 2/2009 | Podaima |
| 2009/0076434 A1 | 3/2009 | Mischelevich et al. |
| 2009/0107335 A1 | 4/2009 | Wilt et al. |
| 2009/0124963 A1 | 5/2009 | Hogard et al. |
| 2009/0222119 A1 | 9/2009 | Plahey et al. |
| 2009/0294359 A1 | 12/2009 | Hopping et al. |
| 2009/0306573 A1 | 12/2009 | Gagner et al. |
| 2010/0056975 A1 | 3/2010 | Dale et al. |
| 2010/0114027 A1 | 5/2010 | Jacobson et al. |
| 2010/0133153 A1 | 6/2010 | Beden et al. |
| 2010/0191180 A1 | 7/2010 | Childers et al. |
| 2010/0191181 A1 | 7/2010 | Childers et al. |
| 2010/0296953 A1 | 11/2010 | Gray |
| 2010/0312162 A1 | 12/2010 | Masaoka et al. |
| 2011/0005992 A1 | 1/2011 | Kelly et al. |
| 2011/0009797 A1 | 1/2011 | Kelly et al. |
| 2011/0060204 A1 | 3/2011 | Weston |
| 2011/0071465 A1 | 3/2011 | Wang et al. |
| 2011/0105877 A1 | 5/2011 | Wilt et al. |
| 2011/0218600 A1 | 9/2011 | Kamen et al. |
| 2011/0303588 A1 | 12/2011 | Kelly et al. |
| 2011/0303598 A1 | 12/2011 | Lo et al. |
| 2013/0020237 A1* | 1/2013 | Wilt .......... A61M 1/3627 210/85 |
| 2013/0104120 A1 | 4/2013 | Arrizza et al. |
| 2013/0193041 A1 | 8/2013 | Rohde |

(56) References Cited

U.S. PATENT DOCUMENTS

| | | |
|---|---|---|
| 2013/0204174 A1 | 8/2013 | Oide et al. |
| 2013/0304020 A1 | 11/2013 | Wilt et al. |
| 2014/0112828 A1 | 4/2014 | Grant et al. |
| 2014/0199193 A1 | 7/2014 | Wilt et al. |
| 2014/0231319 A1 | 8/2014 | Oide et al. |
| 2014/0260551 A1 | 9/2014 | Gray et al. |
| 2014/0260556 A1 | 9/2014 | Gray et al. |
| 2014/0276428 A1 | 9/2014 | Gray et al. |
| 2014/0286794 A1 | 9/2014 | Gray et al. |
| 2014/0288488 A1 | 9/2014 | Distler et al. |
| 2014/0288489 A1 | 9/2014 | Distler et al. |
| 2014/0288490 A1 | 9/2014 | Distler et al. |
| 2014/0309611 A1 | 10/2014 | Wilt et al. |
| 2014/0322053 A1 | 10/2014 | van der Merwe et al. |
| 2015/0151047 A1 | 6/2015 | Anderson et al. |
| 2015/0196699 A9 | 7/2015 | Wilt et al. |
| 2016/0030657 A1 | 2/2016 | Kelly et al. |
| 2016/0030658 A1 | 2/2016 | van der Merwe et al. |
| 2016/0058933 A1 | 3/2016 | Ballantyne et al. |
| 2016/0082173 A1 | 3/2016 | Coll et al. |
| 2016/0101227 A1 | 4/2016 | Norris et al. |
| 2016/0101278 A1 | 4/2016 | Norris et al. |
| 2016/0144093 A1 | 5/2016 | Demers et al. |
| 2016/0175505 A1 | 6/2016 | Demers et al. |
| 2016/0175506 A1 | 6/2016 | Wilt et al. |
| 2017/0143886 A1 | 5/2017 | Wilt et al. |
| 2018/0296746 A1 | 10/2018 | van der Merwe et al. |
| 2018/0372084 A1 | 12/2018 | Grant et al. |
| 2019/0060629 A1 | 2/2019 | Norris et al. |
| 2019/0099534 A1 | 4/2019 | McGill et al. |
| 2019/0160220 A1 | 5/2019 | Wilt et al. |
| 2019/0321535 A1 | 10/2019 | Beavers et al. |
| 2020/0054809 A1 | 2/2020 | Kamen et al. |
| 2020/0086035 A1 | 3/2020 | Wilt et al. |
| 2020/0139031 A1 | 5/2020 | Wilt et al. |
| 2020/0171226 A1 | 6/2020 | Wilt et al. |
| 2020/0191132 A1 | 6/2020 | Demers et al. |
| 2020/0215252 A1 | 7/2020 | Distler et al. |
| 2020/0222609 A1 | 7/2020 | Ballantyne et al. |
| 2020/0282124 A1 | 9/2020 | Grant et al. |
| 2020/0376185 A1 | 12/2020 | Wilt et al. |
| 2020/0376186 A1 | 12/2020 | Wilt et al. |
| 2020/0400595 A1 | 12/2020 | Kamen et al. |
| 2021/0093770 A1 | 4/2021 | Wilt et al. |
| 2021/0228793 A1 | 7/2021 | Scarpaci et al. |
| 2021/0285435 A1 | 9/2021 | Tracey et al. |
| 2021/0290928 A1 | 9/2021 | Grant et al. |
| 2021/0316058 A1 | 10/2021 | van der Merwe et al. |
| 2021/0332813 A1 | 10/2021 | Wilt et al. |
| 2021/0361841 A1 | 11/2021 | van der Merwe et al. |
| 2022/0096718 A1 | 3/2022 | Grant et al. |
| 2022/0133968 A1 | 5/2022 | Wilt et al. |
| 2022/0152286 A1 | 5/2022 | Wilt et al. |
| 2022/0241479 A1 | 8/2022 | Kamen et al. |
| 2022/0282721 A1 | 9/2022 | Grant et al. |

FOREIGN PATENT DOCUMENTS

| | | |
|---|---|---|
| CA | 2336478 A1 | 2/2000 |
| CA | 2341993 A1 | 3/2000 |
| CA | 2704411 A1 | 5/2009 |
| DE | 19704564 A1 | 8/1998 |
| EP | 0 406 562 A2 | 1/1991 |
| EP | 1195171 A2 | 4/2002 |
| EP | 1356836 A2 | 10/2003 |
| EP | 1 362 604 A1 | 11/2003 |
| EP | 1666078 A2 | 6/2006 |
| EP | 3148607 A2 | 4/2017 |
| GB | 1508116 A | 4/1978 |
| GB | 2110564 A | 6/1983 |
| GB | 2181311 A | 4/1987 |
| JP | S58-169462 A | 10/1983 |
| JP | S59-115049 A | 7/1984 |
| JP | H06-154314 A | 6/1994 |
| JP | H06-207845 A | 7/1994 |
| JP | H06-75504 U | 10/1994 |
| JP | H11-128343 A | 5/1999 |
| JP | 2000-084070 A | 3/2000 |
| JP | 2001-112863 A | 4/2001 |
| JP | 2001-263531 A | 9/2001 |
| JP | 2003-180825 A | 7/2003 |
| JP | 2003-246246 A | 9/2003 |
| JP | 2004-147721 A | 5/2004 |
| JP | 2005-013502 A | 1/2005 |
| JP | 2005-034671 A | 2/2005 |
| JP | 2005-261558 A | 9/2005 |
| JP | 2006-198141 A | 8/2006 |
| JP | 2006-343254 A | 12/2006 |
| JP | 2007-035582 A | 2/2007 |
| JP | 2007-510473 A | 4/2007 |
| WO | WO 84/02473 A1 | 7/1984 |
| WO | WO 96/25214 A1 | 8/1996 |
| WO | WO 97/05913 A1 | 2/1997 |
| WO | WO 97/10013 A1 | 3/1997 |
| WO | WO 97/11771 A1 | 4/1997 |
| WO | WO 01/18396 A1 | 3/2001 |
| WO | WO 2001/037895 A2 | 5/2001 |
| WO | WO 02/30267 A2 | 4/2002 |
| WO | WO 03/099353 A2 | 12/2003 |
| WO | WO 2004/041081 A1 | 5/2004 |
| WO | WO 2005/044435 A2 | 5/2005 |
| WO | WO 2007/062197 A1 | 5/2007 |
| WO | WO 2007/113936 A1 | 10/2007 |
| WO | WO 2007/120812 A2 | 10/2007 |
| WO | WO 2009/006498 A2 | 1/2009 |
| WO | WO 2009/051669 A1 | 4/2009 |
| WO | WO 2010/043905 A1 | 4/2010 |
| WO | WO 2015/183976 A2 | 12/2015 |
| WO | WO 2015/183981 A2 | 12/2015 |

OTHER PUBLICATIONS

Bengtsson etal., Haemo dialysis software architecture design experiences. Proceeedings of the 1999 International Conferene on Software Engineering. IEEE Cat. No. 99CB37002. New York, NY. 1999:516-25.

2008K2 Hemodialysis Machine Operator's Manual. Fresenius Medical Care. https://laz2qm2bxvodlae4oellp3es-wpengine.netdna-ssl.com/wp-content/uploads/2018/09/490136_Rev_K.pdf.

Choppy et al., Architectural patterns for problem frames—relating software requirements and architectures. IEEE Proceedings: Software, IEE. Stevenage, GB. Aug. 5, 2005;52(4):198-208.

Krasner et al., A cookbook for using the model-view-controller user interface paradigm in smalltalk-80. JOOP. Aug. 1, 1988;1(3):26-49.

Harel et al., Statecharts: A visual formalism for complex systems. Retrieved from the Internet: http://www.wisdom.weizmann.ac.il/~harel/Statecharts87.pdf> Retrieved on Jul. 2, 2002.

Genulini et al., Automatic controllers capable of regulating mutliple patient outputs for higher-quality anesthesia treatment. IEEE Engineering in Medicine and Biology Magazine. IEEE Service Centers. Piscataway, NJ. Jan. 1, 2001;20(1):39-53.

[No Author Listed] Homechoice Patient At-Home Guide, Jun. 1998. 84 pages.

No Author Listed, Patient At-Home Guide, HomeChoice Automated PD System. Version 2.0 (published May 1997); Baxter Healthcare Corporation. Copyright 1994. 61 pages.

Office Action for JP Application No. 2016-503118 filed Sep. 14, 2015, which Office Action is dated Dec. 22, 2017, and claims as pending for JP Application No. 2016-503118 as of Dec. 22, 2017.

Office Action for U.S. Appl. No. 14/213,702, published as US 2015-0196699 on Jul. 16, 2015, which Office Action is dated Jan. 5, 2016, and claims as pending for U.S. Appl. No. 14/213,702 as of Jan. 5, 2016.

Office Action for U.S. Appl. No. 14/213,702, filed Mar. 14, 2014, published as US 2015-0196699 on Jul. 16, 2015, which Office Action is dated Aug. 31, 2016, and claims as pending for U.S. Appl. No. 14/213,702 as of Aug. 31, 2016.

Office Action for U.S. Appl. No. 14/213,578, filed Mar. 14, 2014, published as US 2014-0199193 on Jul. 17, 2014, which Office

(56) References Cited

OTHER PUBLICATIONS

Action is dated Dec. 31, 2015, and claims as pending for U.S. Appl. No. 14/213,578 as of Dec. 31, 2015.
Office Action for U.S. Appl. No. 15/199,204, filed Jun. 20, 2016, which Office Action is dated Jul. 26, 2018, and claims as pending for U.S. Appl. No. 15/199,204 as of Jan. 10, 2017.
Invitation to Pay Additional Fees dated Sep. 8, 2014 for Application PCT/US2014/029509.
International Search Report and Written Opinion for Application No. PCT/US2014/029509 dated Nov. 17, 2014.
International Preliminary Report on Patentability for Application No. PCT/US2014/029509 dated Sep. 24, 2015.
Office Action for CA Application No. 3,111,230 dated Jul. 14, 2022 and claims pending as of Jul. 14, 2022.
Notice of Allowance for U.S. Appl. No. 16/723,053 dated Mar. 30, 2023 and allowed claims as of Mar. 30, 2023.
Supplemental Notice of Allowability for U.S. Appl. No. 16/723,053 dated Apr. 19, 2023.

\* cited by examiner

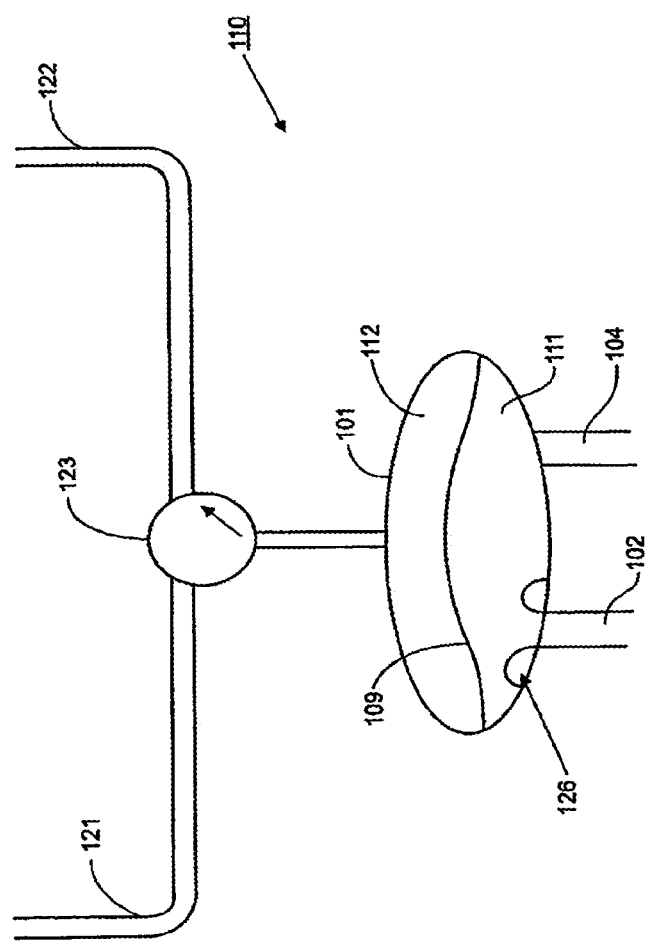

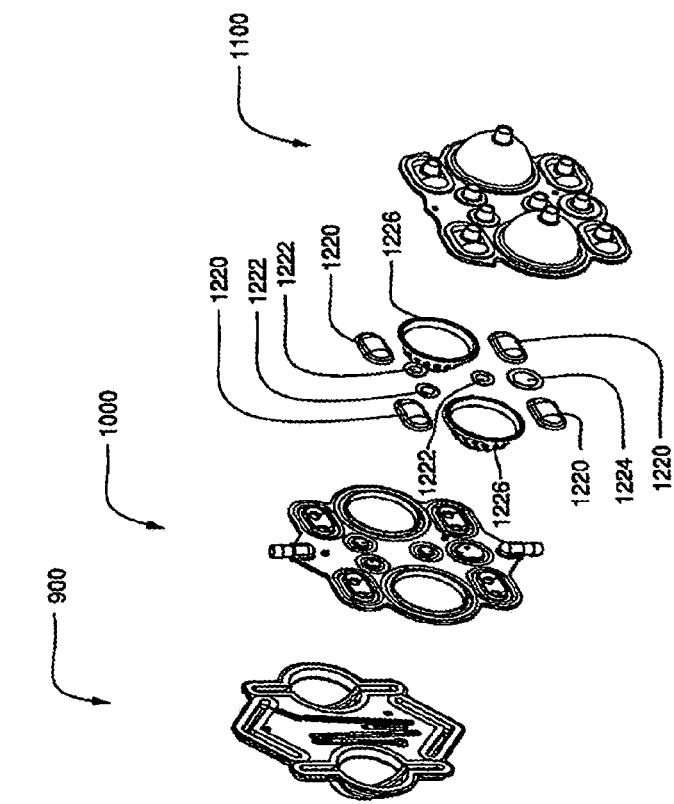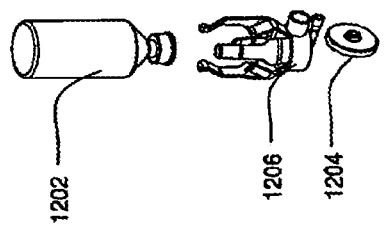
FIG. 33D

1100

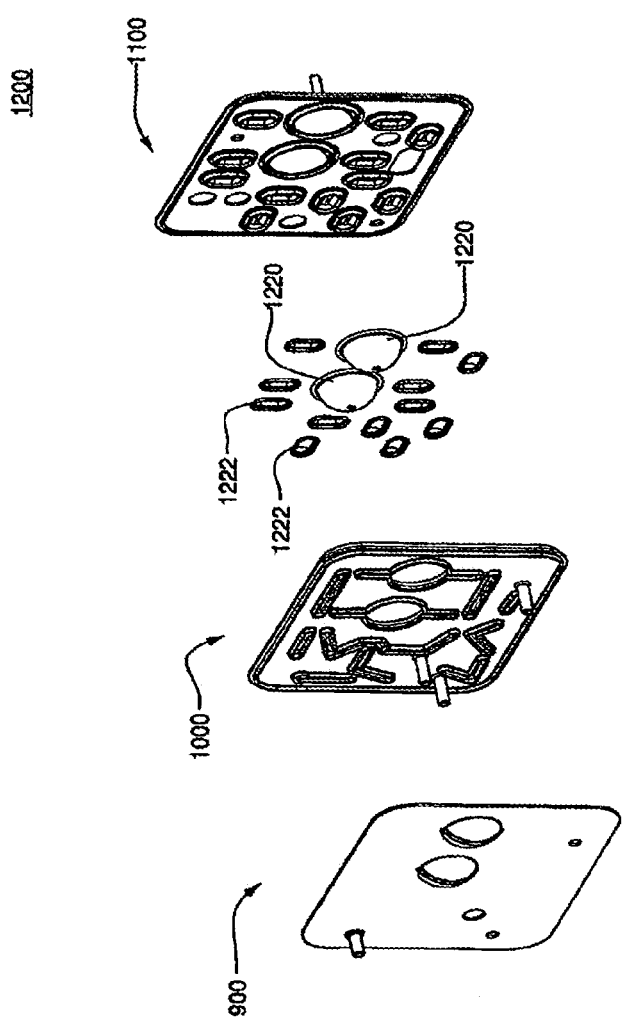

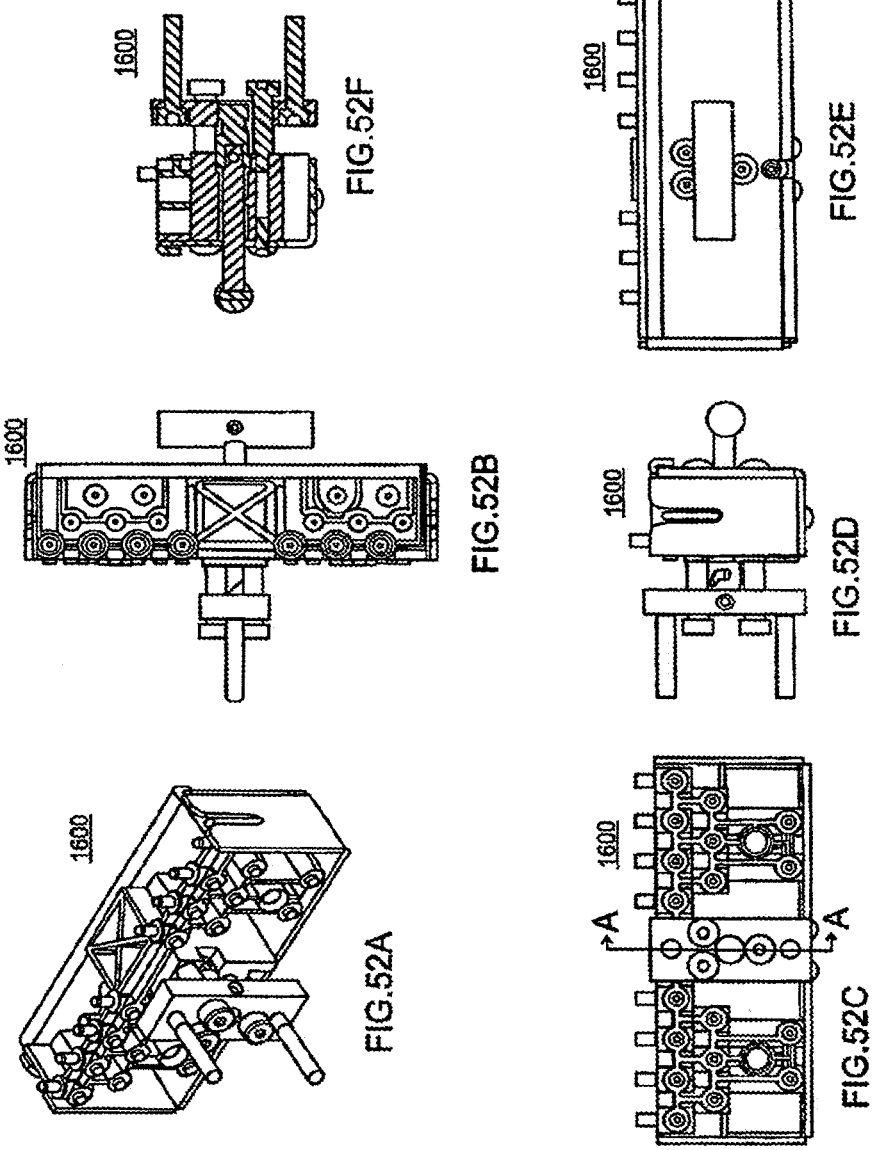

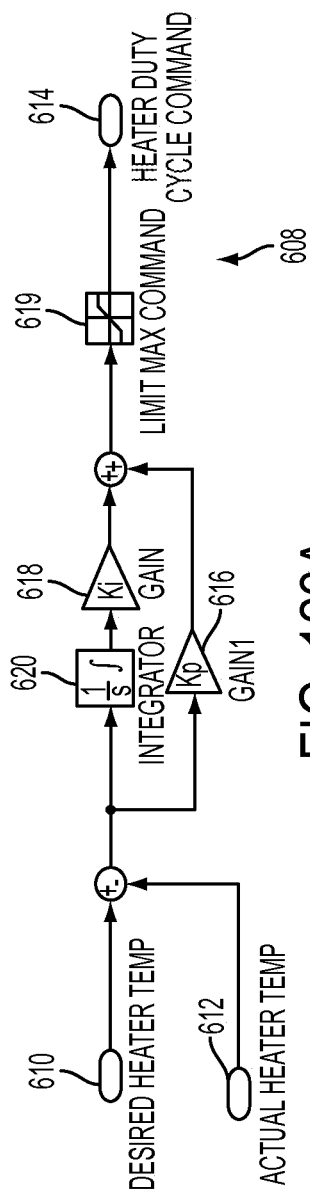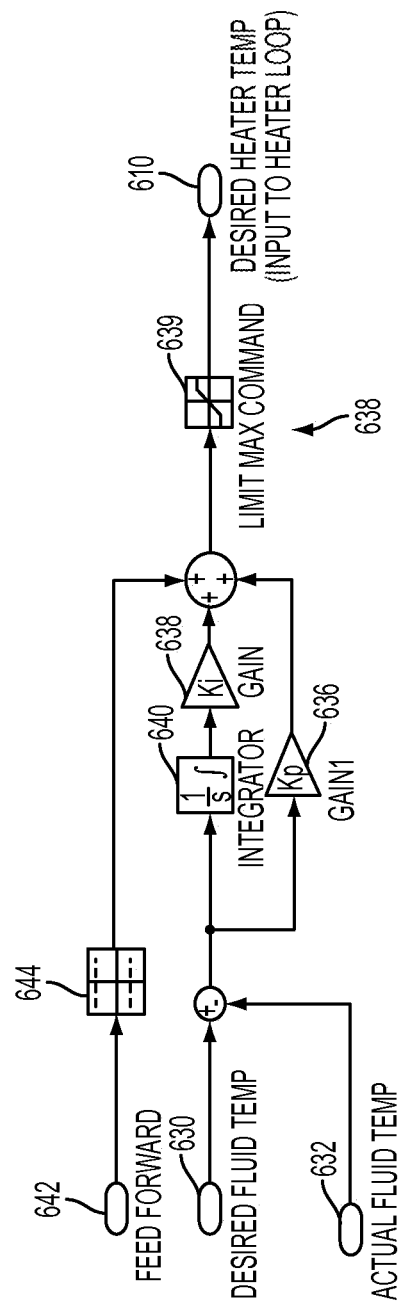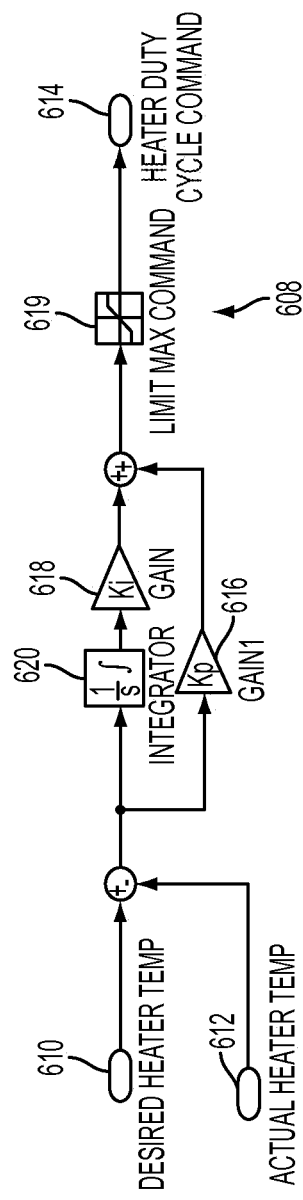
FIG. 123A
FIG. 123B

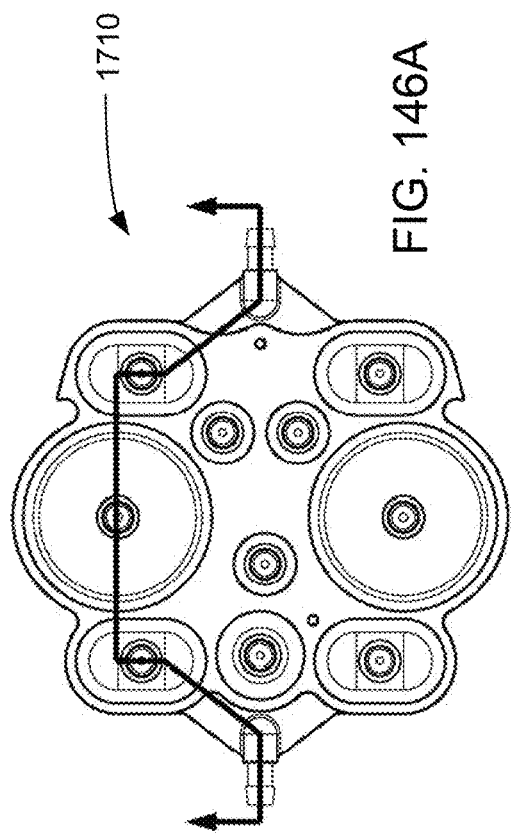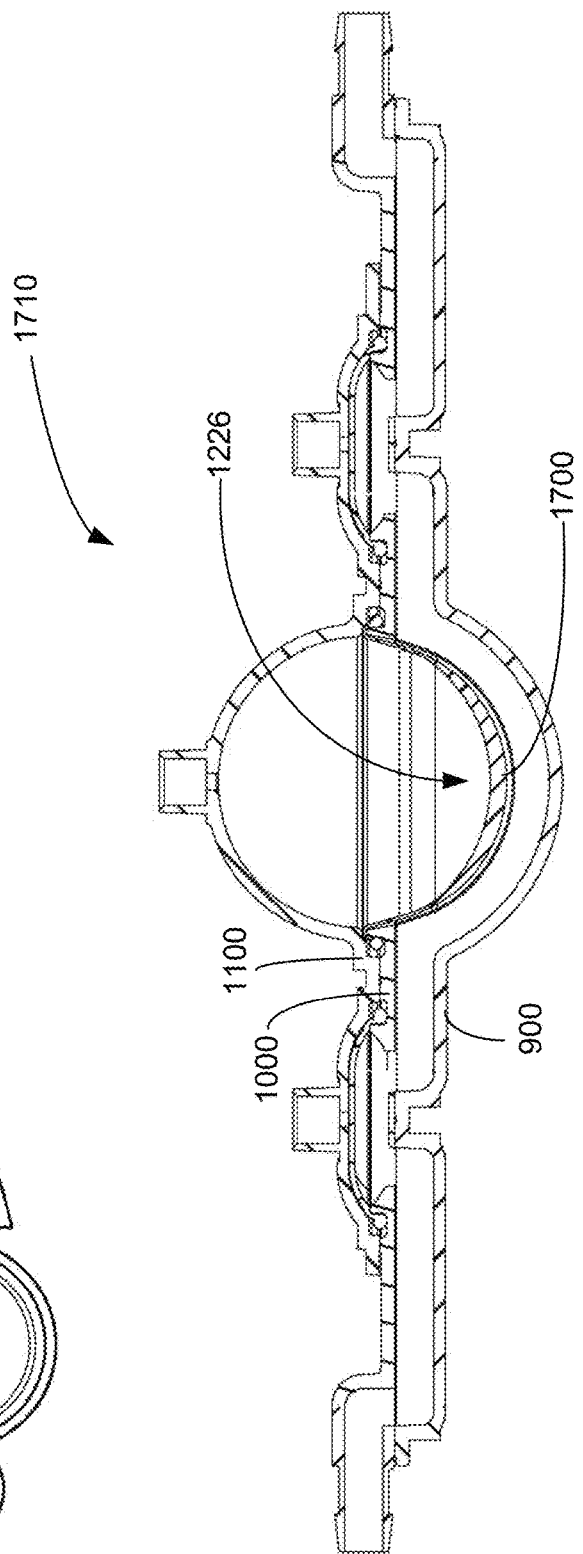
FIG. 146A
FIG. 146B

SECTION A-A

AUTOMATED CONTROL MECHANISMS AND METHODS FOR CONTROLLING FLUID FLOW IN A HEMODIALYSIS APPARATUS

RELATED APPLICATIONS

This application is a division of U.S. patent application Ser. No. 15/445,683, entitled "Automated Control Mechanisms in a Hemodialysis Apparatus," filed on Feb. 28, 2017, which is a continuation-in-part of U.S. patent application Ser. No. 14/213,702, entitled "Blood Treatment Systems and Methods," filed on Mar. 14, 2014, now abandoned, which claims the benefit under 35 U.S.C. § 119(e), of U.S. Provisional Patent Application Ser. No. 61/793,275, entitled "Flexible Membranes for a Membrane-Based Pumping Cassette," filed on Mar. 15, 2013.

U.S. patent application Ser. No. 15/445,683 is also a continuation-in-part of U.S. patent application Ser. No. 14/666,059, entitled "Cassette System Integrated Apparatus," filed on Mar. 23, 2015.

U.S. patent application Ser. No. 15/445,683 is also a continuation-in-part of U.S. patent application Ser. No. 14/525,071, entitled "Fluid Pumping Systems, Devices and Methods," filed on Oct. 27, 2014.

The contents of all of the above-referenced applications are incorporated herein by reference in their entireties.

FIELD OF INVENTION

The present invention generally relates to hemodialysis and similar dialysis systems, e.g., systems able to treat blood or other bodily fluids extracorporeally. In certain aspects, the systems include a variety of systems and methods that would make hemodialysis more efficient, easier, and/or more affordable.

BACKGROUND

Many factors make hemodialysis inefficient, difficult, and expensive. These factors include the complexity of hemodialysis, the safety concerns related to hemodialysis, and the very large amount of dialysate needed for hemodialysis. Moreover, hemodialysis is typically performed in a dialysis center requiring skilled technicians. Therefore any increase in the ease and efficiency of the dialysis process could have an impact on treatment cost or patient outcome.

FIG. 1 is a schematic representation of a hemodialysis system. The system 5 includes two flow paths, a blood flow path 10 and a dialysate flow path 20. Blood is drawn from a patient. A blood flow pump 13 causes the blood to flow around blood flow path 10, drawing the blood from the patient, causing the blood to pass through the dialyzer 14, and returning the blood to the patient. Optionally, the blood may pass through other components, such as a filter and/or an air trap 19, before returning to the patient. In addition, in some cases, anticoagulant may be supplied from an anticoagulant supply 11 via an anticoagulant valve 12.

A dialysate pump 15 draws dialysate from a dialysate supply 16 and causes the dialysate to pass through the dialyzer 14, after which the dialysate can pass through a waste valve 18 and/or return to the dialysate feed via dialysate pump 15. A dialysate valve 17 controls the flow of dialysate from the dialysate supply 16. The dialyzer is a type of filter having a semi-permeable membrane, and is constructed such that the blood from the blood flow circuit flows through tiny tubes and the dialysate solution circulates around the outside of the tubes. Therapy is achieved by the passing of waste molecules (e.g., urea, creatinine, etc.) and water from the blood through the walls of the tubes and into the dialysate solution. At the end of treatment, the dialysate solution is discarded.

SUMMARY OF THE INVENTION

The subject matter of the present invention involves, in some cases, interrelated products, alternative solutions to a particular problem, and/or a plurality of different uses of one or more systems and/or articles. Although the various systems and methods described herein are described in relation to hemodialysis, it should be understood that the various systems and method described herein are applicable to other dialysis systems and/or in any extracorporeal system able to treat blood or other bodily fluids, such as hemofiltration, hemodiafiltration, etc.

In certain embodiments, the invention relates to a flexible diaphragm for use in a reciprocating diaphragm pump. The diaphragm pump may comprise a first rigid body having a curved pumping chamber wall, and a second rigid body having an opposing curved control chamber wall. The diaphragm may be configured to be interposed between the pumping chamber wall and the control chamber wall. In certain such embodiments, the diaphragm comprises: a peripheral bead arranged to locate the diaphragm between the first rigid body and the second rigid body; a diaphragm body having a curved, semi-spheroid or domed shape, the diaphragm body configured to generally conform to a curved inner surface of the pumping chamber wall or a curved inner surface of the control chamber wall, and the diaphragm body may have a pumping side arranged to face the inner surface of the pumping chamber wall and an opposing control side arranged to face the inner surface of the control chamber wall. The diaphragm may further comprise: a transition region between the bead and the diaphragm body, the transition region arranged to be pinched or clamped between a clamping region of the first rigid body and an opposing clamping region of the second rigid body. Such diaphragm may be pre-formed or molded with its control side having a convex shape, such that any elastic tension in the diaphragm is reduced when the control side of the diaphragm body assumes a convex shape when positioned in the diaphragm pump.

In certain embodiments, the invention relates to a reciprocating diaphragm pump comprising a first rigid body having a pumping chamber wall, a second rigid body having an opposing control chamber wall, and a diaphragm configured to be interposed between the pumping chamber wall and the control chamber wall to define a pumping chamber and a control chamber. In certain such embodiments, the diaphragm comprises: a peripheral bead arranged to locate the diaphragm between the first rigid body and the second rigid body; a diaphragm body having a curved, semi-spheroid or domed shape, the diaphragm body configured to generally conform to a curved inner surface of the pumping chamber wall or a curved inner surface of the control chamber wall, and the diaphragm body may have a pumping side arranged to face the inner surface of the pumping chamber wall and a control side arranged to face the inner surface of the control chamber wall. The diaphragm may further comprise a transition region between the bead and the diaphragm body, the transition region arranged to be pinched or clamped between a clamping region of the first rigid body and an opposing clamping region of the second rigid body. Such diaphragm may be pre-formed or molded with its control side having a convex shape, such that any elastic tension in the diaphragm is reduced when the control side of the diaphragm body assumes a convex shape when positioned in the diaphragm pump.

In certain embodiments, the invention relates to a pump cassette for pumping fluid. The pump cassette may comprise a first rigid body having a pumping chamber wall, a second rigid body having an opposing control chamber wall, and a diaphragm configured to be interposed between the pumping chamber wall and the control chamber wall to define a pumping chamber and a control chamber. The pumping chamber may be in fluid communication with a fluid inlet and fluid outlet of the cassette. The control chamber may be in fluid communication with a pneumatic control port for transmission of pneumatic pressure to the control chamber. In certain embodiments, the diaphragm of such pump cassette comprises: a peripheral bead arranged to locate the diaphragm between the first rigid body and the second rigid body; a diaphragm body having a curved, semi-spheroid or domed shape, the diaphragm body configured to generally conform to a curved inner surface of the pumping chamber wall or a curved inner surface of the control chamber wall. The diaphragm body may also have a pumping side arranged to face the inner surface of the pumping chamber wall and an opposing control side arranged to face the inner surface of the control chamber wall. The diaphragm may also include a transition region between the bead and the diaphragm body, the transition region arranged to be pinched or clamped between a clamping region of the first rigid body and an opposing clamping region of the second rigid body. Such diaphragm may be pre-formed or molded with its control side having a convex shape, such that any elastic tension in the diaphragm is reduced when the control side of the diaphragm body assumes a convex shape when positioned in the diaphragm pump.

In one aspect and set of embodiments, a system for controlling fluid flow in a hemodialysis apparatus is disclosed. The system comprises: a dialysate pump configured to receive a fluid from a dialysate outlet of the dialyzer; a reciprocating diaphragm-based blood pump configured to deliver blood from an extracorporeal blood circuit to a blood inlet of the dialyzer, a pumping chamber of the blood pump separated from a control chamber of the blood pump by a flexible diaphragm, the control chamber configured to transmit positive or negative pressure to operate the diaphragm; a pressure sensor configured to measure pressure in the control chamber of the blood pump; and a controller configured to receive information from the pressure sensor, and configured to control the delivery of pressure to the control chamber of the blood pump; wherein the controller is configured to cause the application of a time-varying pressure waveform on the blood pump diaphragm during a fill-stroke of the blood pump, and to monitor a pressure variation in the control chamber measured by the pressure sensor, and wherein a magnitude of the measured pressure variation that deviates from a pre-determined value causes the controller to initiate a procedure to pause or stop the dialysate pump.

Certain embodiments involve a system for monitoring fluid flow in an extracorporeal blood circuit comprising: a pumping chamber of the blood pump separated from a control chamber of the blood pump by a flexible diaphragm, the control chamber configured to transmit positive or negative pressure to operate the diaphragm; a pressure sensor configured to measure pressure in the control chamber of the blood pump; and a controller configured to receive information from the pressure sensor and configured to control the delivery of pressure to the control chamber of the blood pump; wherein the controller is configured to cause the application of a time-varying pressure waveform on the blood pump diaphragm during a fill-stroke of the blood pump, and to monitor a pressure variation in the control chamber measured by the pressure sensor, and wherein the controller transmits a value representing a magnitude of the measured pressure variation to a display associated with the extracorporeal blood circuit.

Certain embodiments involve a method for controlling fluid flow in a hemodialysis apparatus. Such method may comprise: a controller receiving information from a pressure sensor in a control chamber of a reciprocating diaphragm-based blood pump; the controller causing the application of a time-varying pressure waveform on a diaphragm of the blood pump during a fill-stroke of the blood pump; the controller monitoring a pressure variation in the control chamber measured by the pressure sensor; the controller comparing the measured pressure variation to a pre-determined value; and the controller initiating a procedure to pause or stop a dialysate pump of the hemodialysis apparatus if the magnitude of the measured pressure variation deviates from the pre-determined value.

Certain embodiments involve a method for monitoring fluid flow in an extracorporeal blood circuit comprising: a controller receiving information from a pressure sensor in a control chamber of a reciprocating diaphragm-based blood pump; the controller causing the application of a time-varying pressure waveform on a diaphragm of the blood pump during a fill-stroke of the blood pump; the controller monitoring a pressure variation in the control chamber measured by the pressure sensor; and the controller transmitting a value representing a magnitude of the measured pressure variation to a display associated with the extracorporeal blood circuit.

a pre-determined range of values of the measured pressure variation.

In one aspect, hemodialysis and similar extracorporeal blood treatment systems are provided. In certain embodiments, such systems include four fluid paths: blood; inner dialysate; outer dialysate and dialysate mixing. In some embodiments, these four paths are combined in a single cassette. In other embodiments, these four paths are each in a respective cassette. In still other embodiments, two or more fluid paths are included on one cassette.

In one embodiment, there is provided a hemodialysis system having at least two fluid paths integrated into: 1) a blood flow pump cassette, 2) an inner dialysate cassette; 3) an outer dialysate cassette; and 4) a mixing cassette. The cassettes may be fluidly connected one to another. In some embodiments, one or more aspects of these cassettes can be combined into a single cassette.

Also provided, in another embodiment, is a hemodialysis system including a blood flow path through which untreated blood is drawn from a patient and is passed through a dialyzer and through which treated blood is returned to the patient. The blood flow path may include at least one blood flow pump located in a removable cassette. The hemodialysis system also can include a first receiving structure for receiving the blood flow path's cassette, a dialysate flow path through which dialysate flows from a dialysate supply through the dialyzer, a second receiving structure for receiving the dialysate flow path's cassette, and a control fluid path for providing a control fluid from an actuator mechanism to the cassettes for actuating each of the blood flow pump and the dialysate pump. In some instances, the dialysate flow path can include at least one dialysate pump located in a removable cassette.

In yet another embodiment, a hemodialysis system is disclosed. The hemodialysis system, in this embodiment, includes a blood flow path through which untreated blood is drawn from a patient and is passed through a dialyzer and through which treated blood is returned to the patient. The blood flow path may include at least one blood valve. The hemodialysis system may also include a control fluid path for providing a control fluid from an actuator mechanism to the blood valve for actuating the blood valve, a dialysate mixing system fluidly connected to the dialyzer (which may include at least one dialyzer valve), and a heating means or a heater for heating the dialysate.

A hemodialysis system is disclosed in yet another embodiment that includes a blood flow path through which untreated blood is drawn from a patient and passed through a dialyzer and through which treated blood is returned to the patient. The blood flow path can include at least one blood flow pump. The hemodialysis system also can include a dialysate flow path through which dialysate flows from a dialysate supply through the dialyzer. The dialysate flow path may include at least one pneumatic pump.

In one aspect, the invention is directed to a hemodialysis system. In one set of embodiments, the hemodialysis system includes a blood flow path, a first cassette defining an inner dialysate fluid path, a dialyzer in fluid communication with the blood flow path and the inner dialysate fluid path, a second cassette defining an outer dialysate fluid path, and a filter fluidly connecting the first cassette to the second cassette.

In another set of embodiments, the hemodialysis system, includes a blood flow path, an inner dialysate fluid path, a dialyzer in fluid communication with the blood flow path and the inner dialysate fluid path, an outer dialysate fluid path, a filter fluidly connecting the inner dialysate fluid path and the outer dialysate fluid path, a first dialysate pump for pumping dialysate through the inner dialysate fluid path, and a second dialysate pump for pumping dialysate through the outer dialysate fluid path, where the second dialysate pump and the first dialysate pump are operably connected such that flow through the inner dialysate fluid path is substantially equal to flow through the outer dialysate fluid path.

The hemodialysis system, in yet another set of embodiments, includes a blood flow path through which blood is drawn from a patient and passed through a dialyzer, and a dialysate flow path through which dialysate flows from a dialysate supply through the dialyzer. In some cases, the dialysate flow path comprises a balancing cassette which controls the amount of dialysate passing through the dialyzer, a mixing cassette which forms dialysate from water, and a directing cassette which passes water from a water supply to the mixing cassette and passes dialysate from the mixing cassette to the balancing cassette.

In still another set of embodiments, the hemodialysis system includes a cassette system, comprising a directing cassette, a mixing cassette and a balancing cassette. In some cases, the directing cassette is able to direct water from a water supply to the mixing cassette and direct dialysate from the mixing cassette to a balancing cassette, the mixing cassette is able to mix water from the directing cassette with dialysate from a dialysate supply precursor to produce a precursor, and the balancing cassette is able to control the amount of dialysate passing through a dialyzer.

In one set of embodiments, the hemodialysis system includes a blood flow path through which blood is drawn from a patient and passed through a dialyzer, the blood flow path including a blood flow pump, a dialysate flow path through which dialysate flows from a dialysate supply through the dialyzer, where the dialysate flow path includes a dialysate pump, and a control fluid path through which a control fluid actuates the blood flow pump and the dialysate pump.

The hemodialysis system, in another set of embodiments, comprises a blood flow path through which blood is drawn from a patient and passed through a dialyzer; and a dialysate flow path through which dialysate flows from a dialysate supply through the dialyzer. In some cases, the dialysate flow path includes at least one pneumatic pump.

The hemodialysis system, in still another set of embodiments, includes a first pump comprising a pumping chamber and an actuation chamber, a second pump comprising a pumping chamber and an actuation chamber, a control fluid in fluidic communication with each of the actuation chambers of the first and second pumps, and a controller able to pressurize the control fluid to control operation of the first and second pumps.

In yet another set of embodiments, the hemodialysis system includes a first valve comprising a valving chamber and an actuation chamber, a second valve comprising a valving chamber and an actuation chamber, a control fluid in fluidic communication with each of the actuation chambers of the first and second valves, and a controller able to pressurize the control fluid to control operation of the first and second valves.

In one set of embodiments, the hemodialysis system includes a blood flow path through which blood is drawn from a patient and passed through a dialyzer, a cassette containing at least a portion of the blood flow path, and a spike integrally formed with the cassette, the spike able to receive a vial of fluid, the integrally formed spike in fluidic communication with the blood flow path within the cassette.

The hemodialysis system, in another set of embodiments, includes a blood flow path through which untreated blood is drawn from a patient and passed through a dialyzer, a dialysate flow path through which dialysate flows from a dialysate supply through the dialyzer, the dialyzer permitting dialysate to pass from the dialysate flow path to the blood flow path, and a gas supply in fluidic communication with the dialysate flow path so that, when activated, gas from the gas supply causes the dialysate to pass through the dialyzer and urge blood in the blood flow path back to the patient.

In yet another set of embodiments, the hemodialysis system includes a blood flow path through which untreated blood is drawn from a patient and passed through a dialyzer, a dialysate flow path through which dialysate flows from a dialysate supply through the dialyzer, the dialyzer permitting dialysate to pass from the dialysate flow path to the blood flow path, a fluid supply, a chamber in fluid communication with the fluid supply and the dialysate fluid path, the chamber having a diaphragm separating fluid of the fluid supply from dialysate of the dialysate flow path, and a pressurizing device for pressurizing the fluid supply to urge the diaphragm against the dialysate in the chamber, so as to cause the dialysate to pass through the dialyzer and urge blood in the blood flow path back to the patient.

The hemodialysis system, in still another set of embodiments, includes a blood flow path through which untreated blood is drawn from a patient and passed through a dialyzer, a dialysate flow path through which dialysate flows from a dialysate supply through the dialyzer, the dialysate flow path and the blood flow path being in fluidic communication, and a pressure device able to urge dialysate in the dialysate flow path to flow into the blood flow path.

In one set of embodiments, the hemodialysis system includes a first housing containing a positive-displacement pump actuated by a control fluid, a fluid conduit fluidly connecting the positive-displacement pump with a control fluid pump, and a second housing containing the control fluid pump, where the second housing is detachable from the first housing.

In another set of embodiments, the hemodialysis system includes a housing comprising a first compartment and a second compartment separated by an insulating wall, the first compartment being sterilizable at a temperature of at least about 80° C., the second compartment containing electronic components that, when the first compartment is heated to a temperature of at least about 80° C., are not heated to a temperature of more than 60° C.

The hemodialysis system, in yet another set of embodiments, includes a blood flow path through which untreated blood is drawn from a patient and passed through a dialyzer, the blood flow path including at least one blood valve; a control fluid path for providing a control fluid from an actuator mechanism to the blood valve for actuating the blood valve; a dialysate mixing system fluidly connected to the dialyzer, including at least one dialyzer valve; and a heater for heating the dialysate.

Another aspect of the present invention is directed to a valving system. In one set of embodiments, the valving system includes a valve housing containing a plurality of valves, at least two of which valves each comprises a valving chamber and an actuation chamber, each of the at least two valves being actuatable by a control fluid in the actuation chamber; a control housing having a plurality of fluid-interface ports for providing fluid communication with a control fluid from a base unit; and a plurality of tubes extending between the valve housing and the control housing, each tube providing fluid communication between one of the fluid-interface ports and at least one of the actuation chambers, such that the base unit can actuate a valve by pressurizing control fluid in the fluid interface port.

In one set of embodiments, the invention is directed to a valve including a first plate; a second plate, the second plate having an indentation on a side facing the first plate, the indentation having a groove defined therein, the groove being open in a direction facing the first plate; a third plate, wherein the second plate is located between the first and third plate; and a diaphragm located in the indentation between the first plate and the second plate, the diaphragm having a rim, the rim being held in the groove. The second plate may include a valve seat arranged so that the diaphragm may be urged by pneumatic pressure to seal the valve seat closed, the groove surrounding the valve seat. In some cases, a valve inlet and a valve outlet are defined between the second and third plates. In one embodiment, a passage for providing pneumatic pressure is defined between the first and second plates.

Yet another aspect of the present invention is directed to a pumping system. The pumping system, in one set of embodiments, includes a pump housing containing a plurality of pumps, at least two of which pumps each includes a pumping chamber and an actuation chamber, each of the at least two pumps being actuatable by a control fluid in the actuation chamber; a control housing having a plurality of fluid-interface ports for providing fluid communication with a control fluid from a base unit; and a plurality of tubes extending between the pump housing and the control housing, each tube providing fluid communication between one of the fluid-interface ports and at least one of the actuation chambers, such that the base unit can actuate a pump by pressurizing control fluid in the fluid interface port.

The invention is generally directed to a pumping cassette in another aspect. In one set of embodiments, the pumping cassette includes at least one fluid inlet, at least one fluid outlet, a flow path connecting the at least one fluid inlet and the at least one fluid outlet, and a spike for attaching a vial to said cassette. The spike may be in fluidic communication with the flow path in some cases.

In one aspect, the invention is generally directed to a pumping cassette for balancing flow to and from a target. In one set of embodiments, the pumping cassette includes a cassette inlet, a supply line to the target, a return line from the target, a cassette outlet, a pumping mechanism for causing fluid to flow from the cassette inlet to the supply line and from the return line to the cassette outlet, and a balancing chamber. In some cases, the pumping mechanism includes a pod pump comprising a rigid curved wall defining a pumping volume and having an inlet and an outlet, a pump diaphragm mounted within the pumping volume; and an actuation port for connecting the pod pump to a pneumatic actuation system so that the diaphragm can be actuated to urge fluid into and out of the pumping volume, wherein the pump diaphragm separates the fluid from a gas in fluid communication with the pneumatic actuation system. In certain instances, the balancing chamber includes a rigid curved wall defining a balance volume; and a balance diaphragm mounted within the balance volume, where the balance diaphragm separates the balance volume into a supply side and a return side, each of the supply side and the return side having an inlet and an outlet. In some cases, fluid from the cassette inlet flows to the supply side inlet, fluid from the supply side outlet flows to the supply line, fluid from the return line flows to the return side inlet, and fluid from the return side outlet flows to the cassette outlet.

In another set of embodiments, the pumping system includes a system inlet, a supply line to the target, a return line from the target, a system outlet, a pumping mechanism for causing fluid to flow from the system inlet to the supply line and from the return line to the system outlet, and a balancing chamber.

In one embodiment, the pumping mechanism includes a pod pump comprising a rigid spheroid wall defining a pumping volume and having an inlet and an outlet, a pump diaphragm mounted within and to the spheroid wall, and a port for connecting the pod pump to a pneumatic actuation system so that the diaphragm can be actuated to urge fluid into and out of the pumping volume. In some cases, the pump diaphragm separates the fluid from a gas in fluid communication with the pneumatic actuation system;

In certain instances, the balancing chamber includes a rigid spheroid wall defining a balance volume, and a balance diaphragm mounted within and to the spheroid wall. In one embodiment, the balance diaphragm separates the balance volume into a supply side and a return side, each of the supply side and the return side having an inlet and an outlet. In some cases, fluid from the system inlet flows to the supply side inlet, fluid from the supply side outlet flows to the supply line, fluid from the return line flows to the return side inlet, and fluid from the return side outlet flows to the system outlet. The pumping mechanism may also include valving mechanisms located at each of the inlets and outlets of the supply side and the return side. The valving mechanisms may be pneumatically actuated.

Yet another aspect of the invention is directed to a cassette. In one set of embodiments, the cassette includes a first flow path connecting a first inlet to a first outlet, a second flow path connecting a second inlet to a second outlet, a pump able to pump fluid through at least a portion of the second flow path, and at least two balancing chambers, each balancing chamber comprising a rigid vessel containing a diaphragm dividing the rigid vessel into a first compartment and a second compartment, the first compartment of each balancing chamber being in fluidic communication with the first flow path and the second compartment being in fluidic communication with the second flow path.

In another set of embodiments, the cassette includes a first flow path connecting a first inlet to a first outlet; a second flow path connecting a second inlet to a second outlet; a control fluid path; at least two pumps, each pump comprising a rigid vessel containing a diaphragm dividing the rigid vessel into a first compartment and a second compartment, the first compartment of each pump being in fluidic communication with the control fluid path and the second compartment being in fluidic communication with the second flow path; and a balancing chamber able to balance flow between the first flow path and the second flow path.

The cassette, in still another set of embodiments, includes a first flow path connecting a first inlet to a first outlet, a second flow path connecting a second inlet to a second outlet, and a rigid vessel containing a diaphragm dividing the rigid vessel into a first compartment and a second compartment. In some cases, the first compartment are in fluidic communication with the first fluid path and the second compartment being in fluidic communication with the second flow path.

Still another aspect of the invention is generally directed at a pump. The pump includes, in one set of embodiments, a first rigid component; a second rigid component, the second rigid component having on a side facing the first plate a groove defined therein, the groove being open in a direction facing the first rigid component; and a diaphragm having a rim, the rim being held in the groove by a friction fit in the groove but without contact by the first rigid component against the rim. In some cases, the first and second rigid components define, at least partially, a pod-pump chamber divided by the diaphragm into separate chambers, and further define, at least partially, flow paths into the pod-pump chamber, wherein the groove surrounds the pod-pump chamber.

In another set of embodiments, the pump includes a substantially spherical vessel containing a flexible diaphragm dividing the rigid vessel into a first compartment and a second compartment, the first compartment and the second compartment not in fluidic communication with each other, whereby movement of the diaphragm due to fluid entering the first compartment causes pumping of fluid within the second compartment to occur.

In another set of embodiments, the pump is a reciprocating positive-displacement pump. In one embodiment, the pump includes a rigid chamber wall; a flexible diaphragm attached to the rigid chamber wall, so that the flexible diaphragm and rigid chamber wall define a pumping chamber; an inlet for directing flow through the rigid chamber wall into the pumping chamber; an outlet for directing flow through the rigid chamber wall out of the pumping chamber; a rigid limit wall for limiting movement of the diaphragm and limiting the maximum volume of the pumping chamber, the flexible diaphragm and the rigid limit wall forming an actuation chamber; a pneumatic actuation system that intermittently provides a control pressure to the actuation chamber. In some cases, the pneumatic actuation system includes an actuation-chamber pressure transducer for measuring the pressure of the actuation chamber, a gas reservoir having a first pressure, a variable valve mechanism for variably restricting gas flowing between the actuation chamber and the gas reservoir, and a controller that receives pressure information from the actuation-chamber pressure transducer and controls the variable valve so as to create the control pressure in the actuation chamber, the control pressure being less than the first pressure.

Still another aspect of the invention is directed to a method. The method, in one set of embodiments, includes acts of providing a first pump comprising a pumping chamber and an actuation chamber, and a second pump comprising a pumping chamber and an actuation chamber, urging a common fluid into the actuation chambers of each of the first and second pumps, and pressurizing the common fluid to pump fluids through each of the first and second pumps.

In another set of embodiments, the method includes acts of providing a first valve comprising a valving chamber and an actuation chamber, and a second valve comprising a valving chamber and an actuation chamber, urging a common fluid into the actuation chambers of each of the first and second valves, and pressurizing the common fluid to at least partially inhibit fluid flow through each of the first and second valves.

In yet another set of embodiments, the method is a method for measuring the clearance of a dialyzer, the dialyzer being located in a blood flow path, through which untreated blood can be drawn from a patient and passed through the dialyzer, and in a dialysate flow path, through which dialysate can flow from a dialysate supply through the dialyzer, the blood flow path being separated from the dialysate flow path by membranes in the dialyzer. In one embodiment, the method includes acts of urging a liquid through the dialysate flow path to the dialyzer, so as to keep the membranes wet and prevent the flow of a gas through the membranes, urging a gas through the blood flow path to the dialyzer so as to fill the blood flow path in the dialyzer with the gas, measuring the volume of gas in the dialyzer, and calculating the clearance of the dialyzer based on the volume of gas measured in the dialyzer.

The method, in still another set of embodiments, is a method for measuring the clearance of a dialyzer. In one embodiment, the method includes acts of applying a pressure differential across the dialyzer, measuring the flow rate of the dialyzer, and determining the clearance of the dialyzer based on the pressure differential and the flow rate.

In yet another set of embodiments, the method is a method for measuring the clearance of a dialyzer. In one embodiment, the method includes acts of passing water through the dialyzer, measuring the amount of ions collected by the water after passing through the dialyzer, and determining the clearance of the dialyzer based on the amount of ions collected by the water after passing through the dialyzer. In another set of embodiments, the method includes acts of passing water through the dialyzer, measuring the conductivity of the water, and determining the clearance of the dialyzer based on changes in the conductivity of the water.

In one set of embodiments, the method is a method for introducing a fluid into blood. The method includes, in one embodiment, acts of providing a cassette including an integrally formed spike for receiving a vial of fluid, and a valving mechanism for controlling flow of the fluid from the vial into the cassette, attaching a vial containing the fluid to the spike, pumping blood through the cassette, and introducing the fluid from the vial into the blood.

In one set of embodiments, the method includes acts of providing a hemodialysis system comprising a blood flow path through which untreated blood is drawn from a patient and passed through a dialyzer, and a dialysate flow path through which dialysate flows from a dialysate supply through the dialyzer, putting the blood flow path and the dialysate flow path into fluidic communication, and urging dialysate through the dialysate flow path to cause blood in the blood flow path to pass into the patient.

The method, in another set of embodiments, includes acts of providing a hemodialysis system comprising a blood flow path through which untreated blood is drawn from a patient and passed through a dialyzer, and a dialysate flow path through which dialysate flows from a dialysate supply through the dialyzer, putting the blood flow path and the dialysate flow path into fluidic communication, and urging a gas into the dialysate flow path to cause flow of blood in the blood flow path.

The method is a method of performing hemodialysis, in still another set of embodiments. In one embodiment, the method includes acts of providing a blood flow path, through which untreated blood can be drawn from a patient and passed through a dialyzer; providing a dialysate flow path, through which dialysate can flow from a dialysate supply through the dialyzer; providing ingredients for preparing a total volume of dialysate; providing water for mixing with the dialysate ingredients; mixing a volume of water with a portion of the ingredients so as to prepare a first partial volume of dialysate, the first partial volume being less than the total volume; pumping the partial volume of dialysate through the dialysate flow path and through the dialyzer; pumping blood through the blood flow path and through the dialyzer, while the first partial volume of dialysate is being pumped to the dialyzer; and mixing a volume of water with a portion of the ingredients so as to prepare a second partial volume of dialysate and storing the second partial volume of dialysate within a vessel while the blood and the first partial volume of dialysate are pumped through the dialyzer.

In another embodiment, the method includes acts of passing blood from a patient and dialysate through a dialyzer contained within a hemodialysis system at a first rate, and forming dialysate within the hemodialysis system at a second rate that is substantially different from the first rate, wherein excess dialysate is stored within a vessel contained within the hemodialysis system.

Another aspect of the invention is directed to a hemodialysis system comprising a dialysis unit and a user interface unit. The dialysis unit comprises an automation computer and dialysis equipment. The user interface unit comprises a user interface computer and a user interface, the user interface being adapted to display information and receive inputs. The automation computer is configured to receive requests for safety-critical information from the user interface computer and to access the safety-critical information on behalf of the user interface computer. The user interface computer is configured to display information related to a dialysis process via the user interface using the safety-critical information.

A further aspect of the invention is directed to a method of managing a user interface in a hemodialysis system. The method comprises receiving an input related to a dialysis process at a user interface associated with a user interface computer and, in response to the input, transmitting a request for safety-critical information from the user interface computer to an automation computer associated with dialysis equipment. The method further comprises accessing the safety-critical information on behalf of the user interface computer and, using the safety-critical information, displaying information related to the dialysis process via the user interface.

Still another aspect of the invention is directed to a computer storage media encoded with instructions that, when executed, perform a method. The method comprising acts of receiving, from a user interface associated with a user interface computer, an input related to a dialysis process and, in response to the input, transmitting a request for safety-critical information from the user interface computer to an automation computer associated with dialysis equipment. The method further comprises accessing the safety-critical information on behalf of the user interface computer, transmitting the safety-critical information to the user interface computer, accessing screen design information stored within the user interface computer and, using the safety-critical information and the screen design information, causing the user interface to display information related to the dialysis process.

In another aspect, the present invention is directed to a method of making one or more of the embodiments described herein, for example, a hemodialysis system. In another aspect, the present invention is directed to a method of using one or more of the embodiments described herein, for example, a hemodialysis system.

In yet another aspect, the invention relates to a control architecture for such a hemodialysis system comprising a user interface model layer, a therapy layer, below the user interface model layer, and a machine layer below the therapy layer. The user interface model layer is configured to manage the state of a graphical user interface and receive inputs from a graphical user interface. The therapy layer is configured to run state machines that generate therapy commands based at least in part on the inputs from the graphical user interface. The machine layer is configured to provide commands for the actuators based on the therapy commands.

A further aspect of the invention is directed to a method for disinfecting fluid pathways in a dialysis system. The method comprises storing, on at least one storage medium, disinfection parameters including a disinfection temperature and a disinfection time. The method further comprises circulating a fluid in the fluid pathways, monitoring a temperature of the fluid at each of a plurality of temperature sensors, and determining that disinfection of the fluid pathways is complete when the temperature of the fluid at each of the plurality of temperature sensors remains at or above the disinfection temperature for at least the disinfection time.

Another aspect of the invention is directed to at least one computer-readable medium encoded with instructions that, when executed on at least one processing unit, perform a method for disinfecting fluid pathways in a dialysis system. The method comprises electronically receiving disinfection parameters including a disinfection temperature and a disinfection time. The method further comprises controlling a plurality of actuators to circulate a fluid in the fluid pathways, monitoring a temperature of the fluid at each of a plurality of temperature sensors, and determining whether the temperature of the fluid at each of the plurality of temperature sensors remains at or above the disinfection temperature for at least the disinfection time.

A further aspect of the invention is directed to a method for controlling the administration of an anticoagulant in a dialysis system. The method comprises storing, on at least one storage medium, an anticoagulant protocol comprising a maximum amount of anticoagulant, automatically administering the anticoagulant according to the anticoagulant protocol, and prohibiting the administration of additional anticoagulant after determining that the maximum amount of anticoagulant has been administered. Another aspect of the invention is directed to at least one computer-readable medium encoded with instructions that, when executed on at least one processing unit, perform a method for controlling the administration of an anticoagulant in a dialysis system. The method comprises electronically receiving an anticoagulant protocol comprising a maximum amount of anticoagulant, controlling a plurality of actuators to administer the anticoagulant according to the anticoagulant protocol, and prohibiting the administration of additional anticoagulant after determining that the maximum amount of anticoagulant has been administered.

A further aspect of the invention is directed to a method for determining a fluid level in a dialysate tank of a dialysis system. The method comprises tracking a first number of strokes delivering fluid to the dialysate tank, tracking a second number of strokes withdrawing fluid from the dialysate tank, and determining a fluid level in the dialysate tank based, at least in part, on the first number of strokes, the second number of strokes, and a per-stroke volume.

A further aspect of the invention is directed to a method for determining a fluid level in a dialysate tank of a dialysis system. The method comprises charging a reference chamber of a known volume to a predetermined pressure and venting the reference chamber to the dialysate tank. The method further comprises, after venting the reference chamber to the dialysate tank, determining a pressure in the dialysate tank. In addition, the method comprises determining a fluid level in the dialysate tank based, at least in part, on the determined pressure in the dialysate tank.

Another aspect of the invention is directed to a method for returning blood to a patient in the event of a power failure condition in a dialysis system that uses compressed air to actuate pumps and/or valves during a dialysis process, wherein the dialysis system comprises a dialyzer having a membrane that separates a blood flow path from a dialysate flow path. The method comprises identifying a power failure condition in a dialysis system. The method further comprises, in response to the identification of a power failure condition, releasing compressed air from a reservoir associated with the dialysis system. In addition, the method comprises using the released compressed air, increasing a pressure in the dialysate flow path to cause blood in the blood flow path to return to the patient.

A further aspect of the invention is directed to a method for returning extracorporeal blood to a patient, in an extracorporeal treatment system, using a source of compressed gas in the event of a power failure. The extracorporeal treatment system comprises a filter having a semi-permeable membrane that separates a blood flow path from an electrolyte solution flow path. The compressed gas is in valved communication with an electrolyte solution container, and the electrolyte solution container is in valved communication with the electrolyte solution flow path. The method comprises, in response to a termination of electrical power to one or more electrically actuated valves that control a distribution of compressed gas or a distribution of electrolyte solution flow in the extracorporeal treatment system, causing one or more first electrically actuated valves to open a first fluid pathway between the compressed gas and the electrolyte solution container, causing one or more second electrically actuated valves to open a second fluid pathway between said electrolyte solution container and said filter, causing one or more third electrically actuated valves to close an alternate fluid pathway in said electrolyte solution flow path if said alternate fluid pathway diverts electrolyte solution away from said filter; and using the compressed gas to increase pressure in the electrolyte solution flow path to cause blood in the blood flow path to return to the patient.

Another aspect of the invention is directed to a method for returning extracorporeal blood to a patient, in an extracorporeal treatment system, using a source of compressed gas in the event of a power failure. The extracorporeal treatment system comprises a filter having a semi-permeable membrane that separates a blood flow path from an electrolyte solution flow path. The compressed gas is in valved communication with an electrolyte solution container, and the electrolyte solution container is in valved communication with the electrolyte solution flow path. The method comprises, in response to a termination of electrical power to one or more electrically actuated valves that control a distribution of compressed gas or a distribution of electrolyte solution flow in the extracorporeal treatment system: causing one or more electrically actuated valves to open a fluid pathway between the compressed gas and the electrolyte solution container, and, using the compressed gas, causing flow of an electrolyte solution from the electrolyte solution container through the filter to cause blood in the blood flow path to return to the patient.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 11A-11B are schematic views of various pneumatic control system for a pod pump;

FIG. 33D is an exploded view of an assembled exemplary embodiment of a cassette with a vial;

FIG. 44C is an exploded view of an assembled exemplary embodiment of a cassette;

FIGS. 52A-52F are various views of one embodiment of the block for connecting the pneumatic tubes to the manifold according to one embodiment of the present system;

FIG. 68 is a schematic view showing shows an exemplary implementation of the Recycle Preparation application;

FIGS. 69A-69B are schematic views showing shows an exemplary implementation of the Clean Blood Path application;

FIGS. 70A-70B are schematic views showing shows an exemplary implementation of the Disinfect application;

FIG. 71 is a schematic view showing shows an exemplary implementation of the Rinse Endotoxins application;

FIG. 72 is a schematic view showing shows an exemplary implementation of the Treatment Preparation application;

FIGS. 73A-73D are schematic views showing shows an exemplary implementation of the Patient Connect application;

FIGS. 74A-74B are schematic views showing shows an exemplary implementation of the Dialyze application;

FIGS. 75A-75E are schematic views showing shows an exemplary implementation of the Solution Infusion application;

FIGS. 76A-76B are schematic views showing shows an exemplary implementation of the Rinseback application;

Figure 76A:
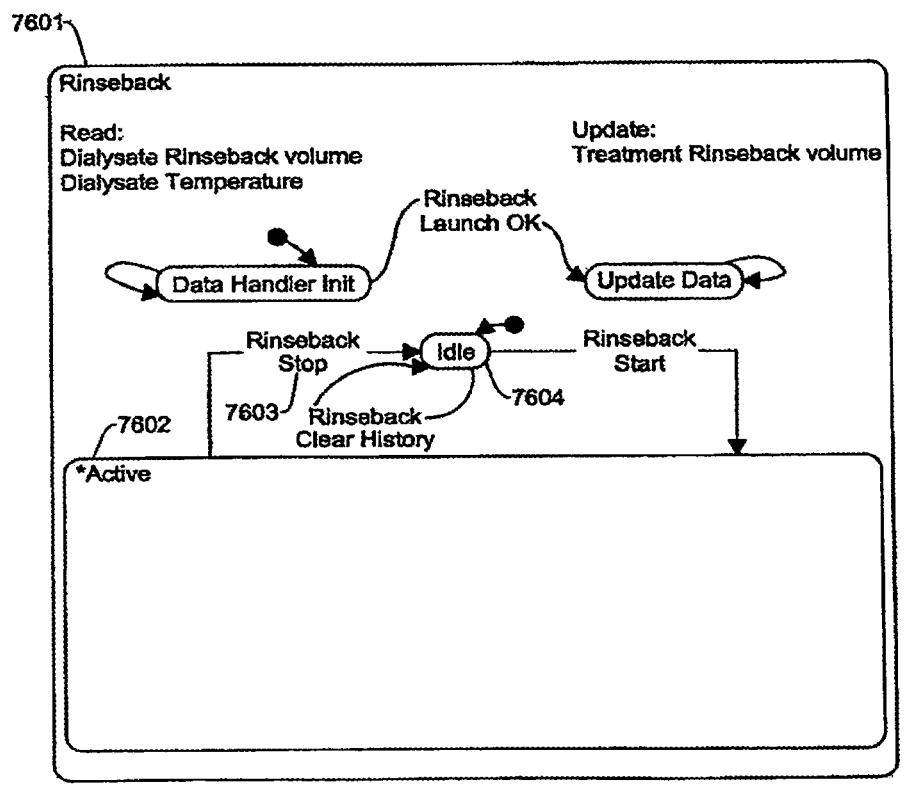
Figure 76B:
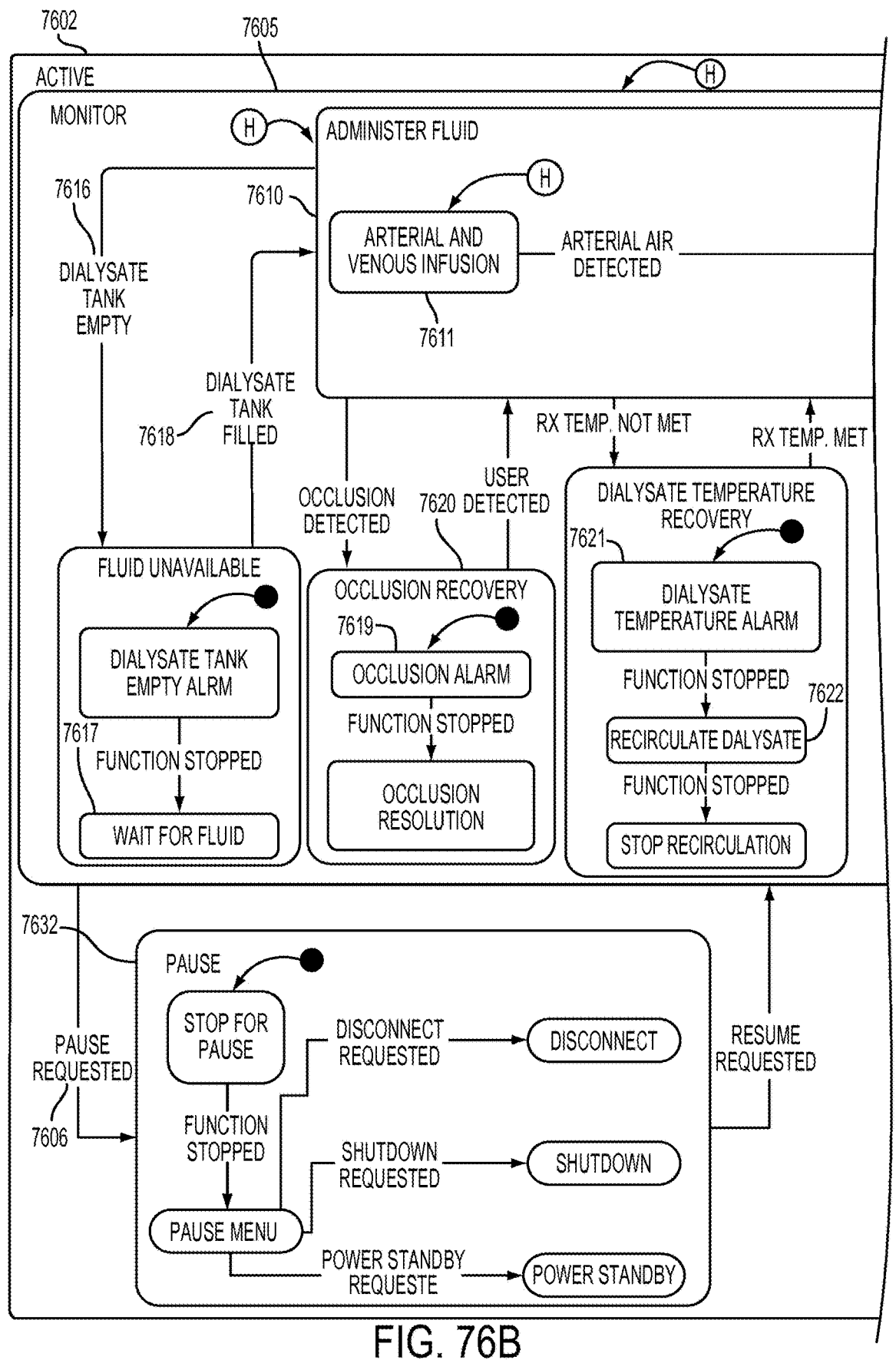
Figure 76B:
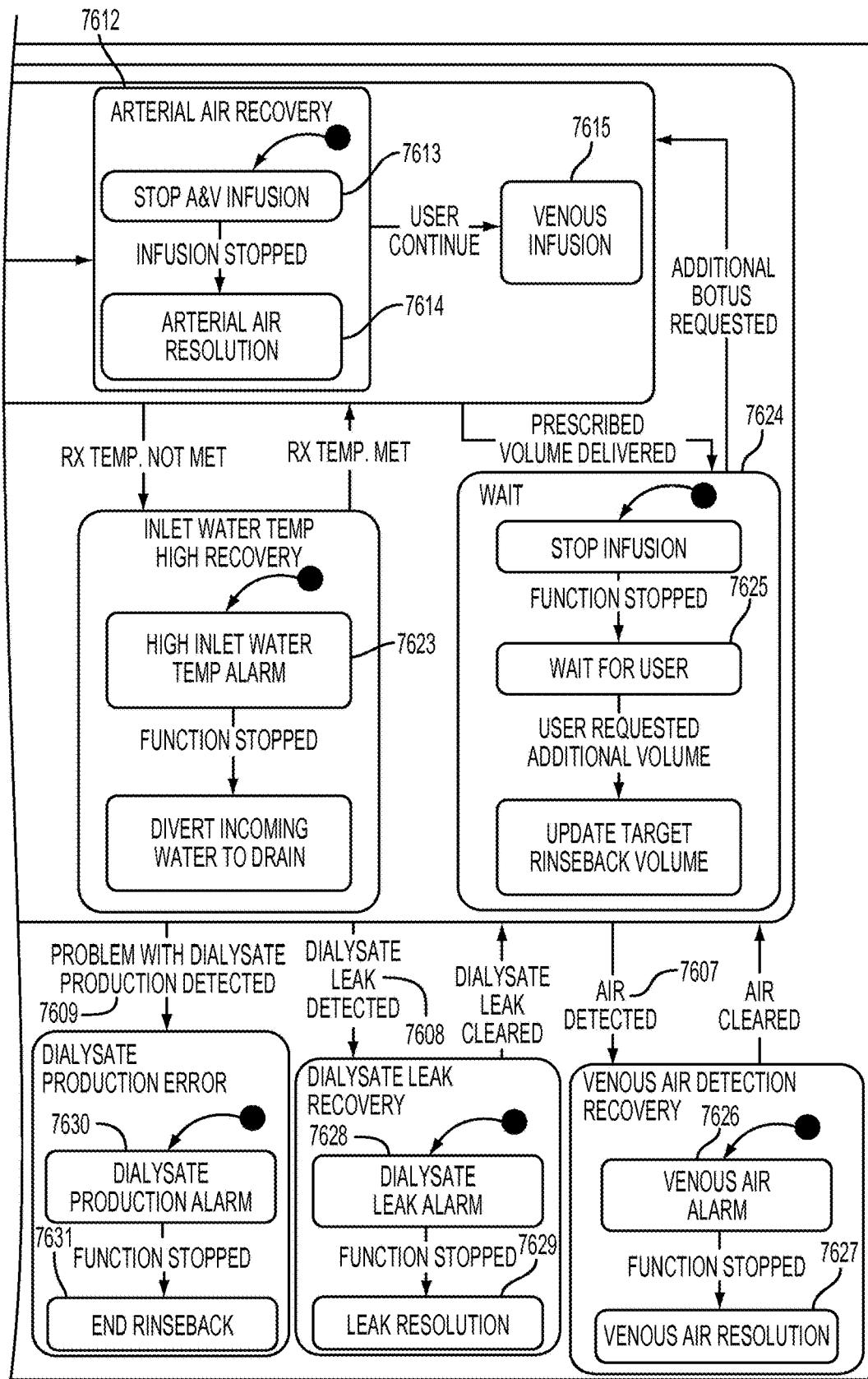
Figure 76C:
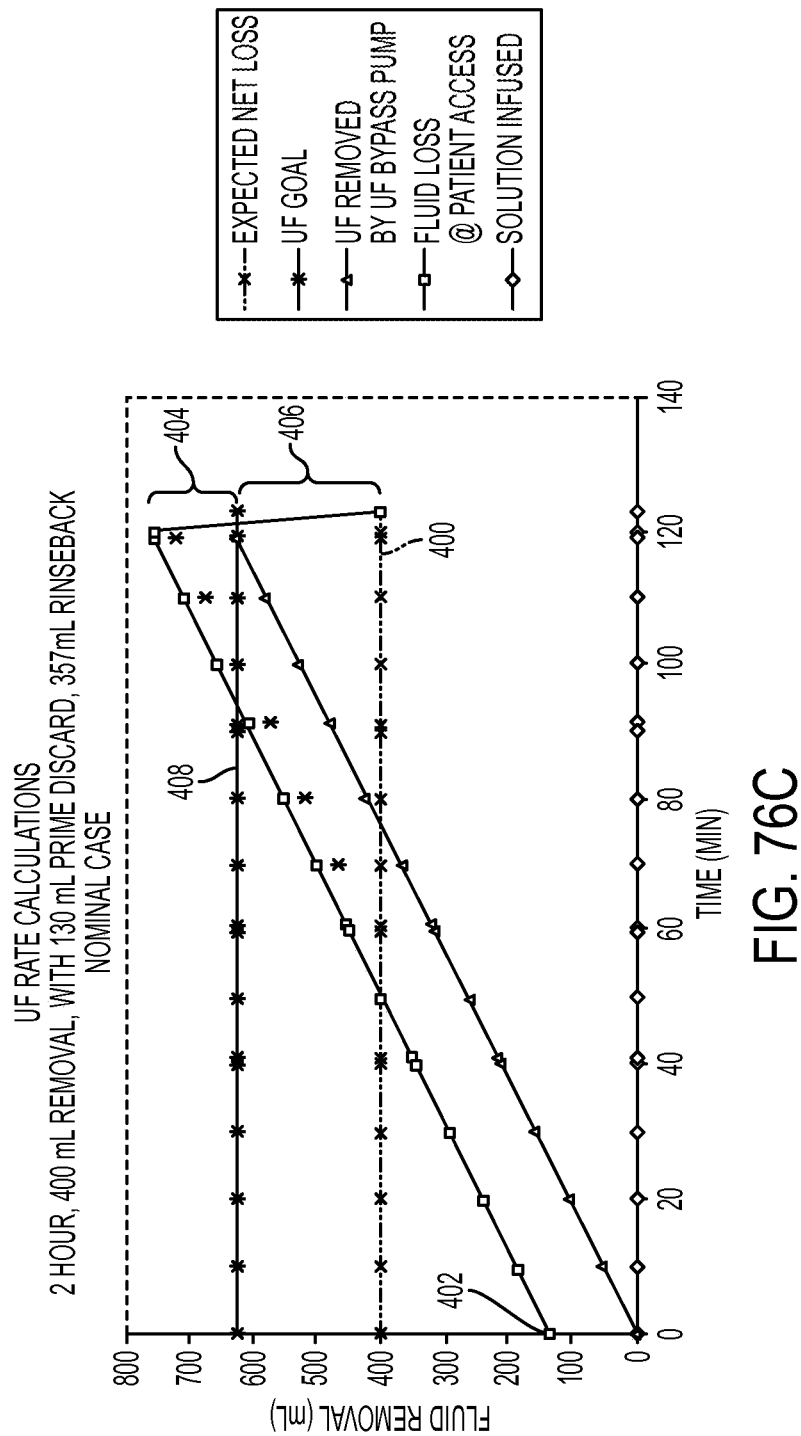
Figure 76D:
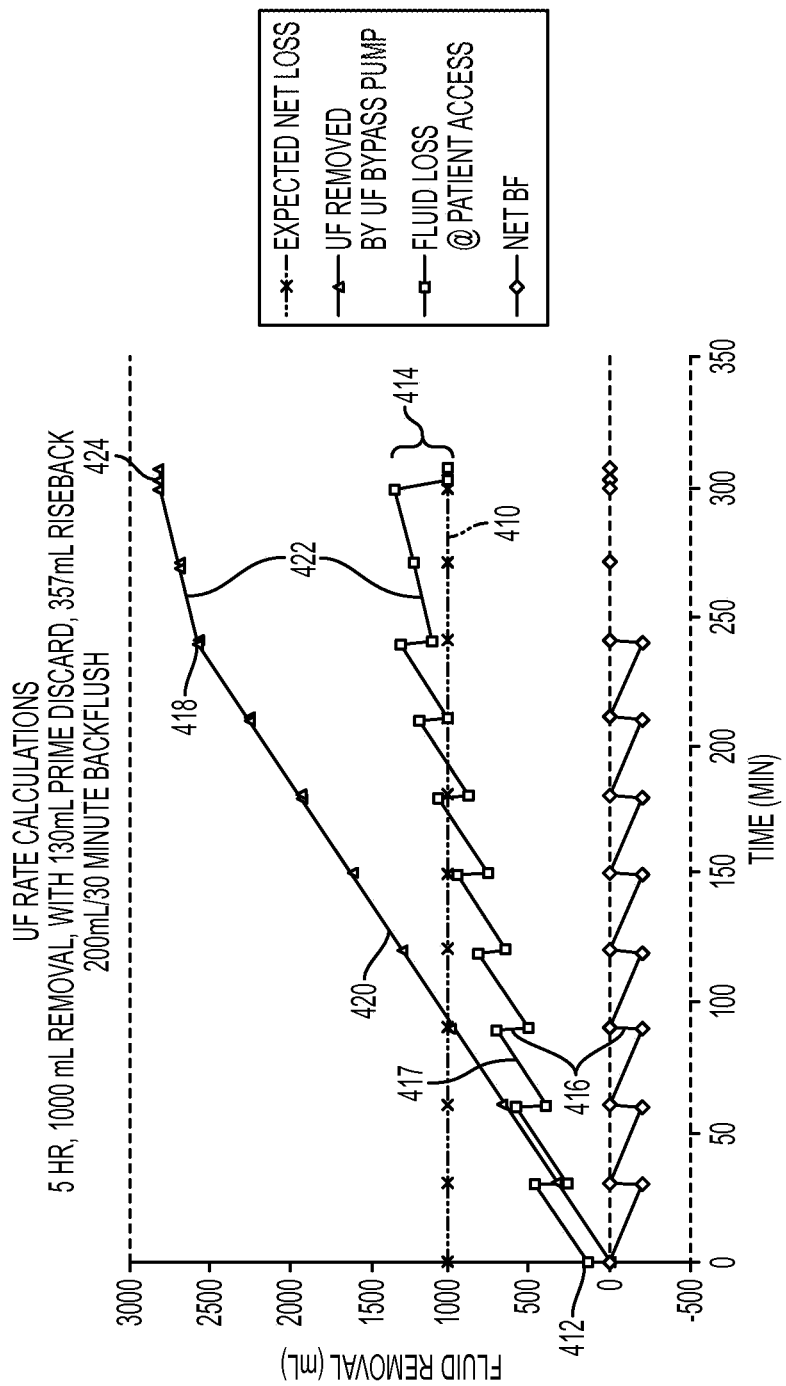
Figure 76E:
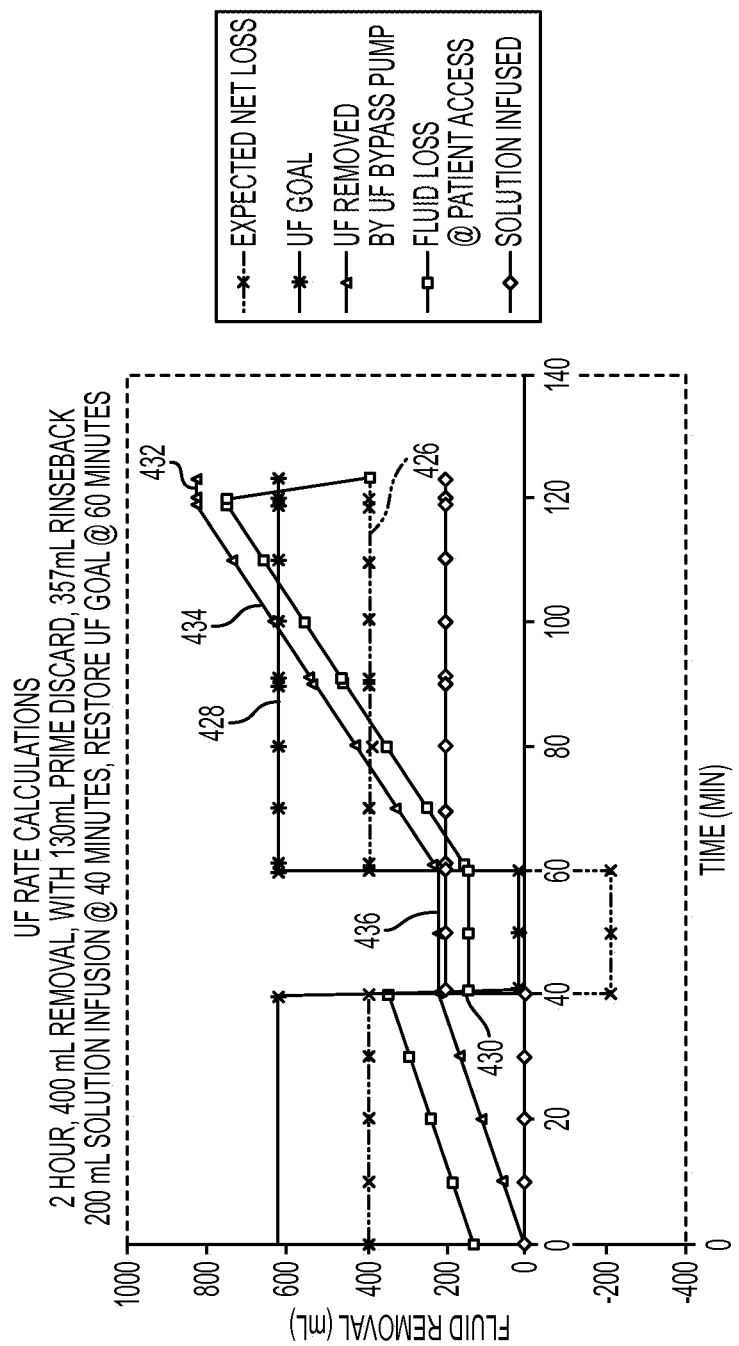
Figure 76F:
Figure 77:
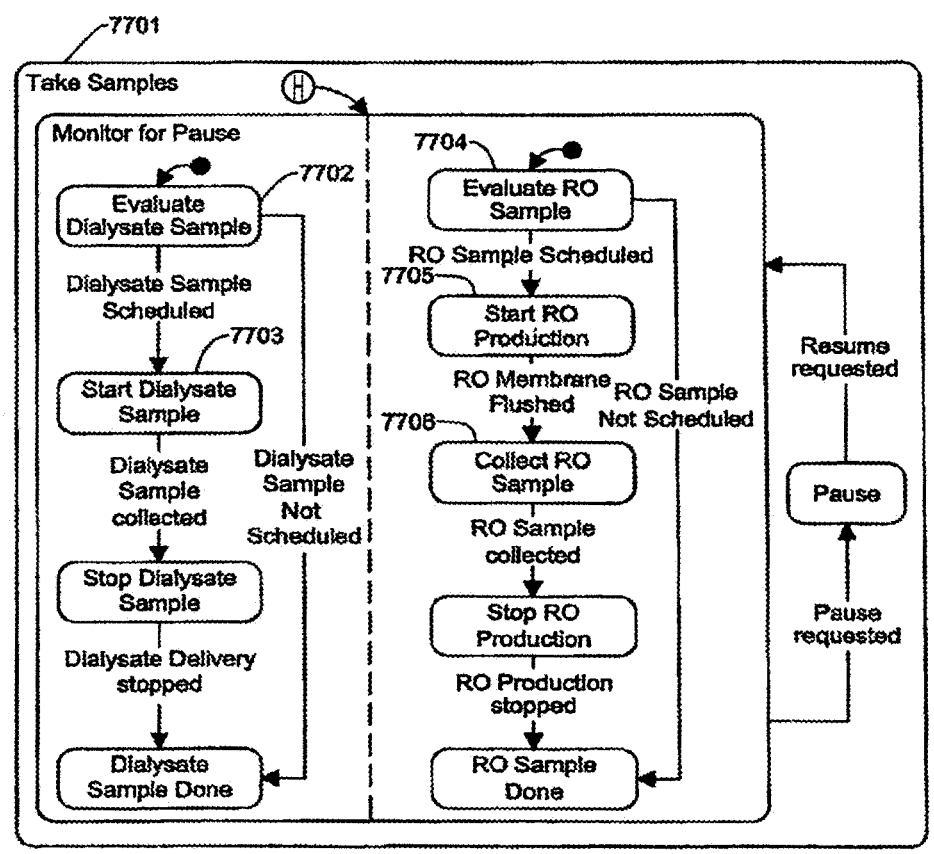
Figure 78A:
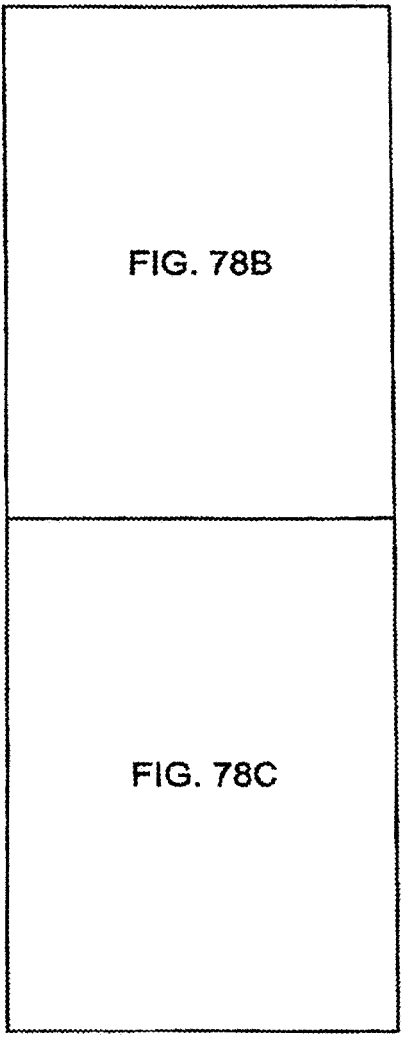
Figure 78B:
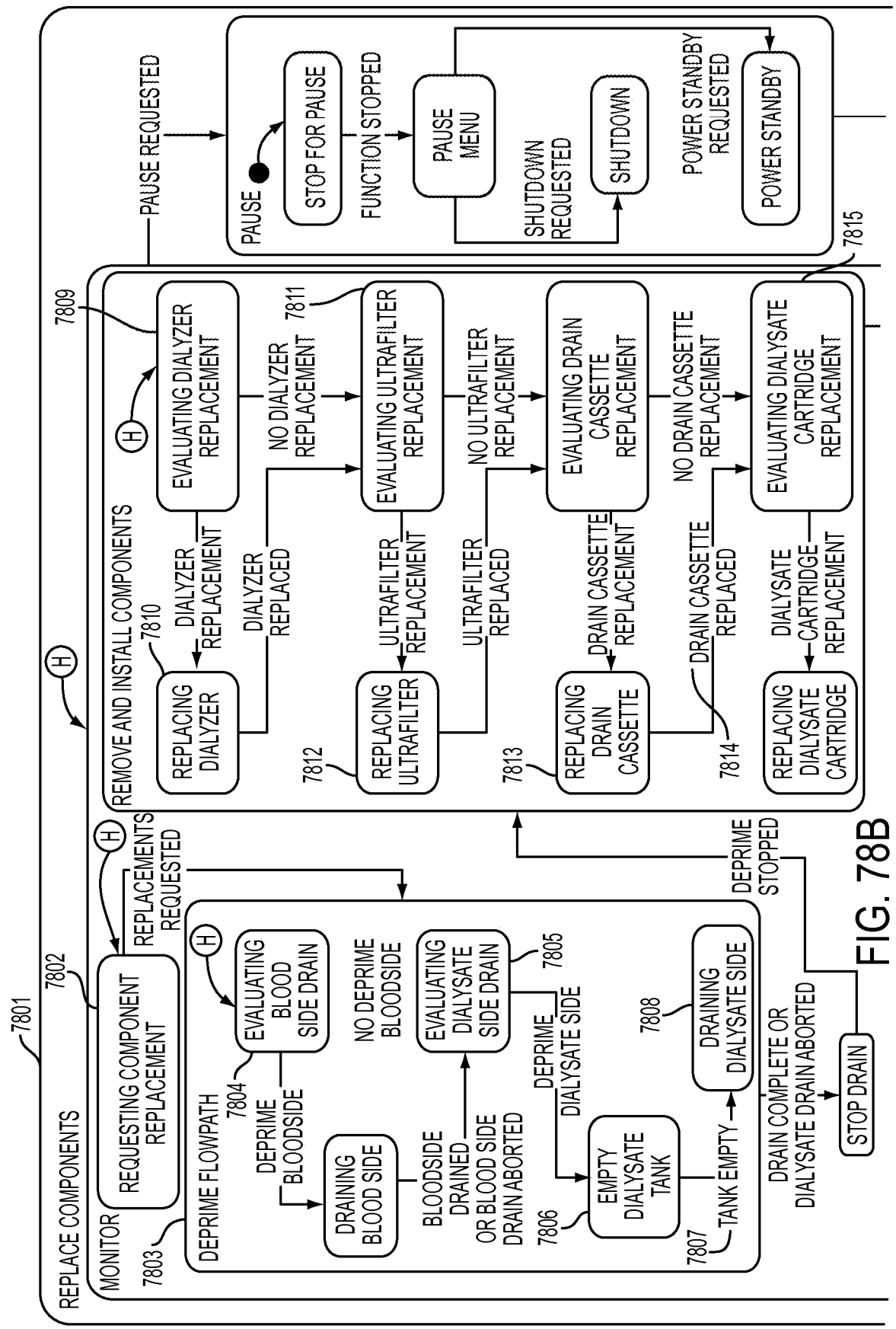
Figure 78C:
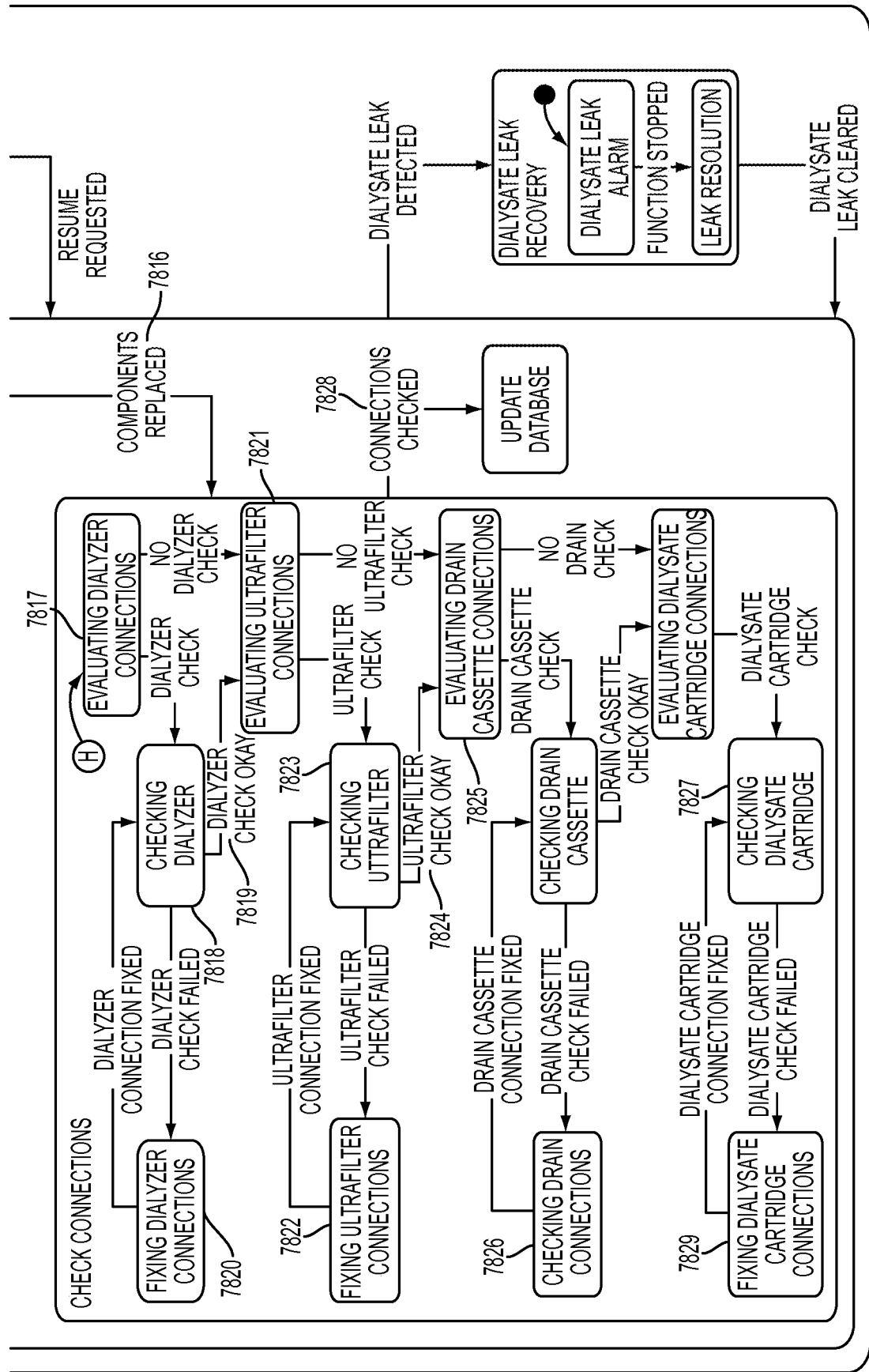
Figure 79A:
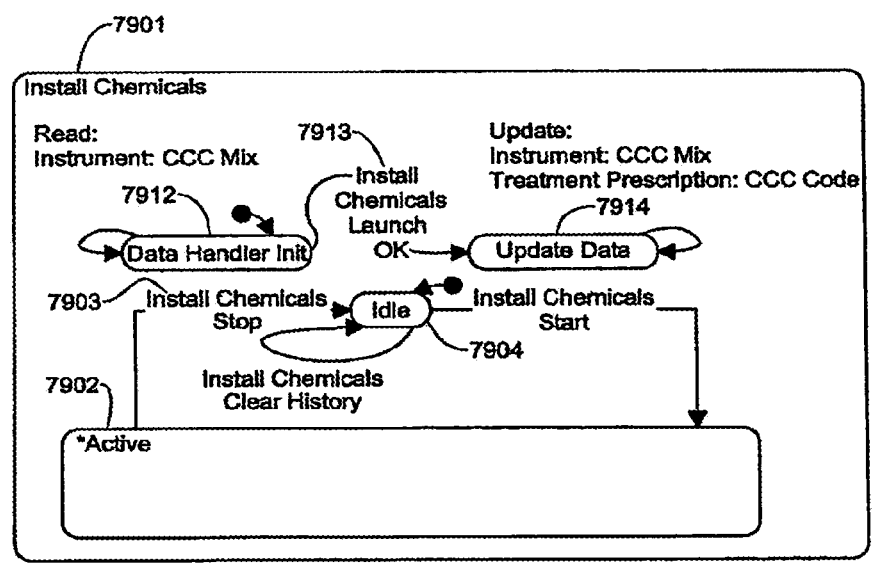
Figure 79B:
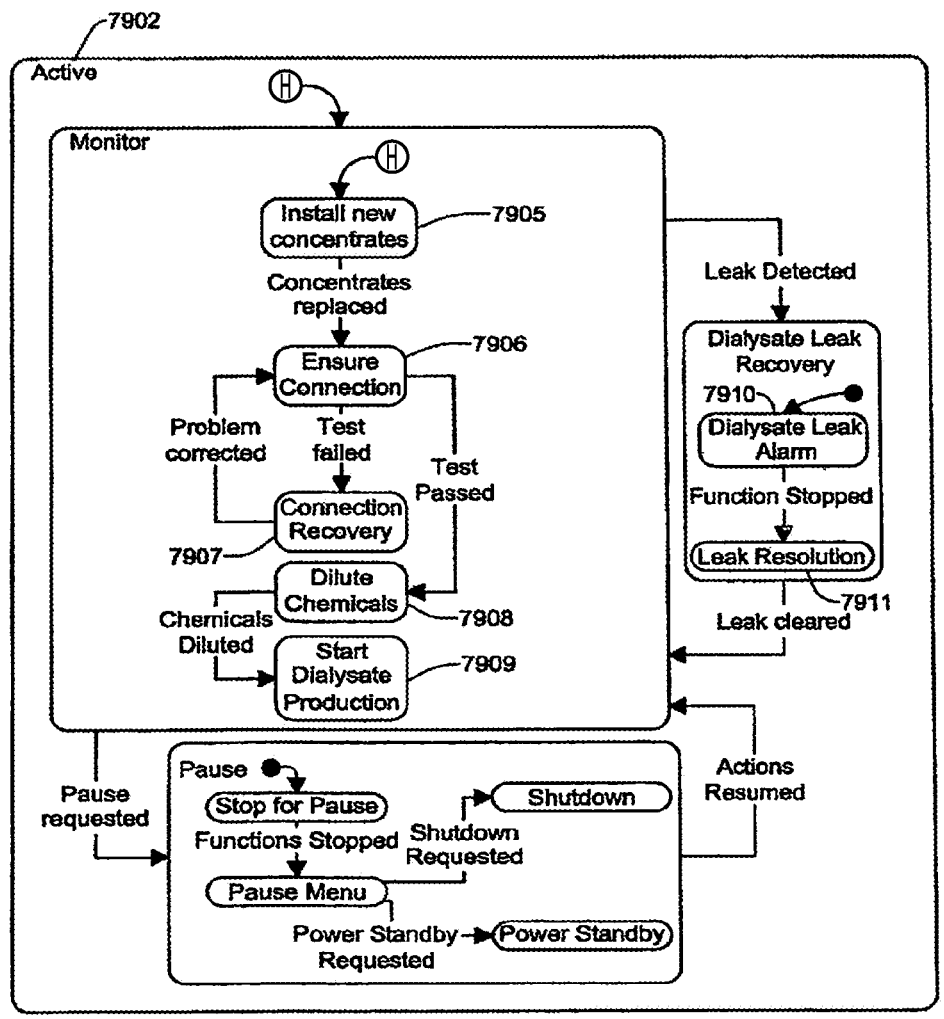
Figure 80:
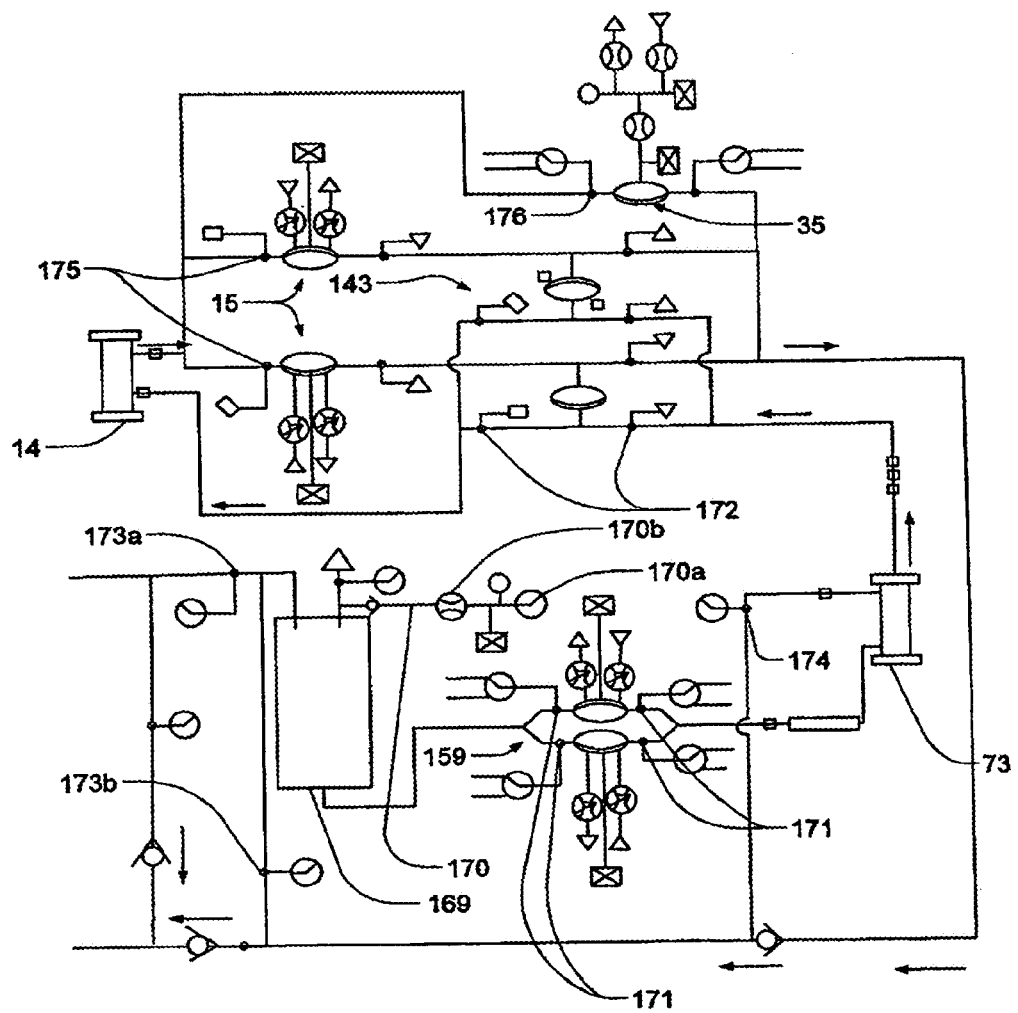
Figure 81:
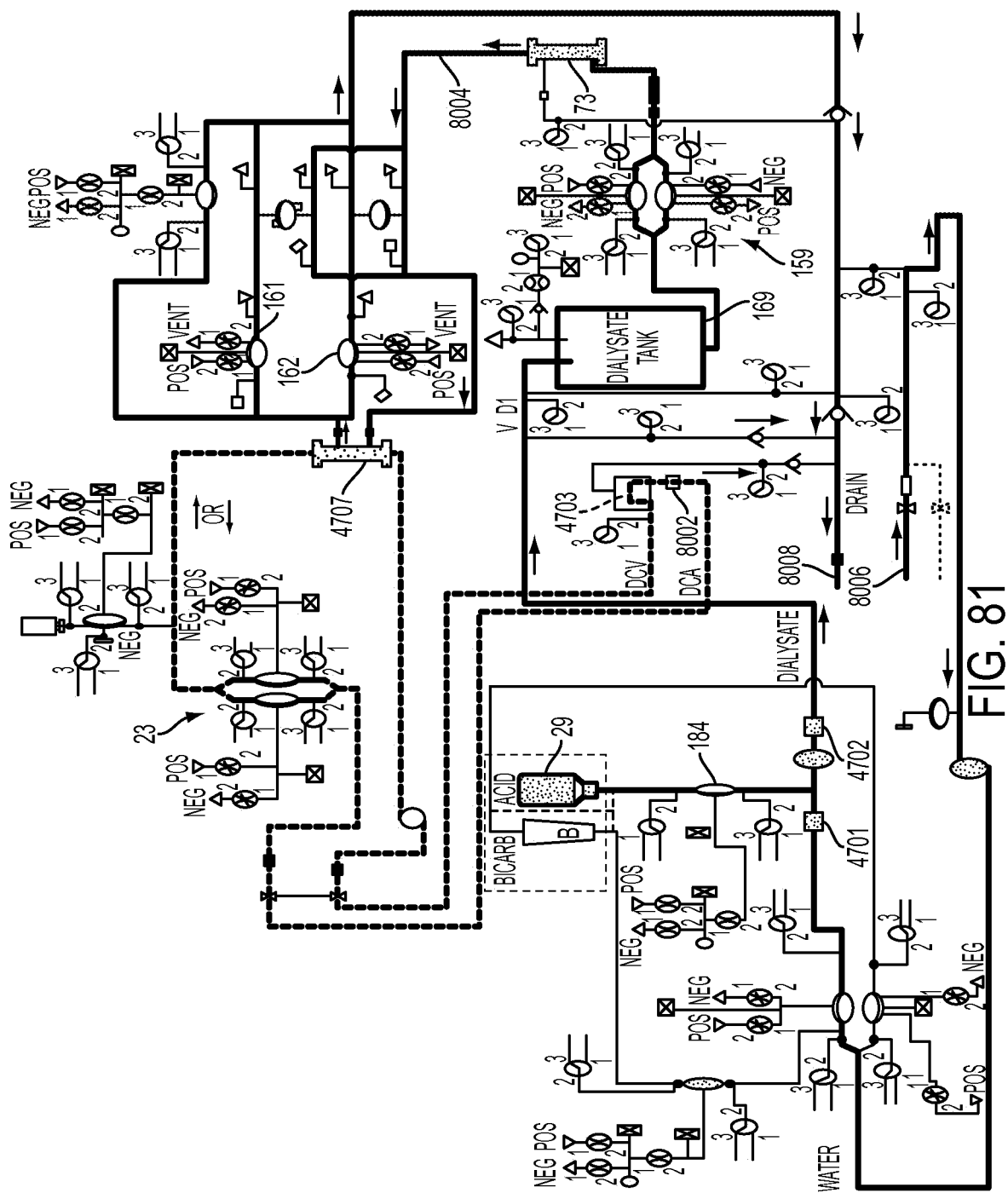
Figure 82:
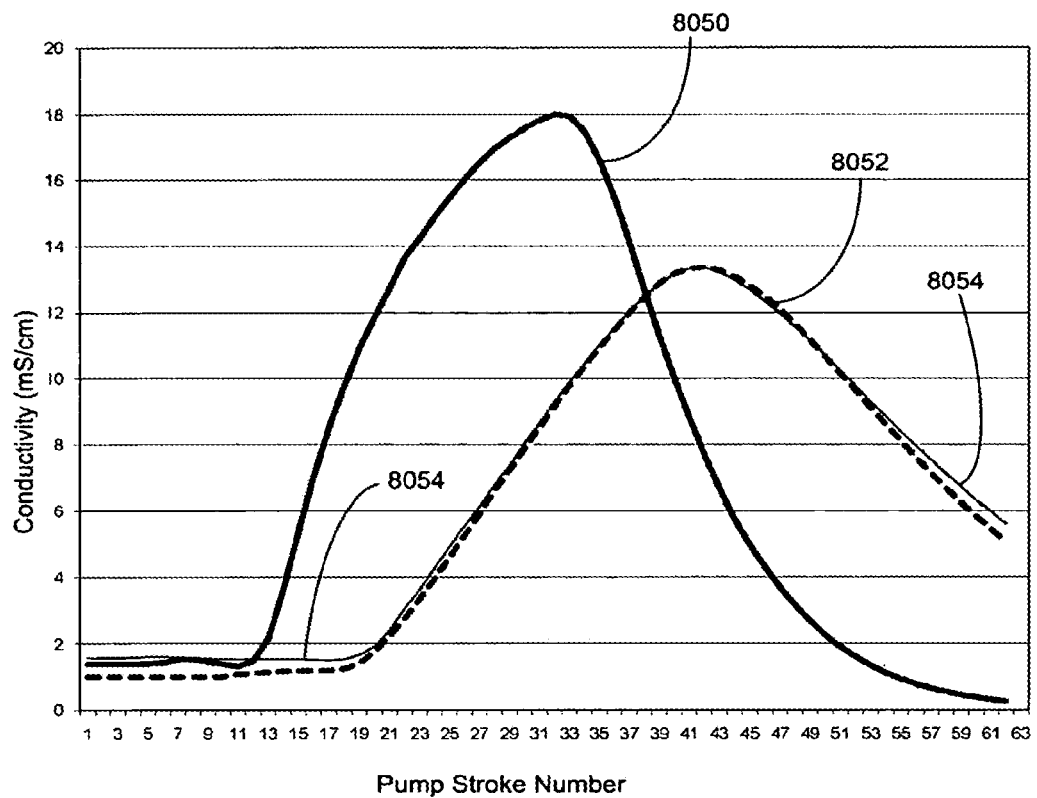
Figure 83:
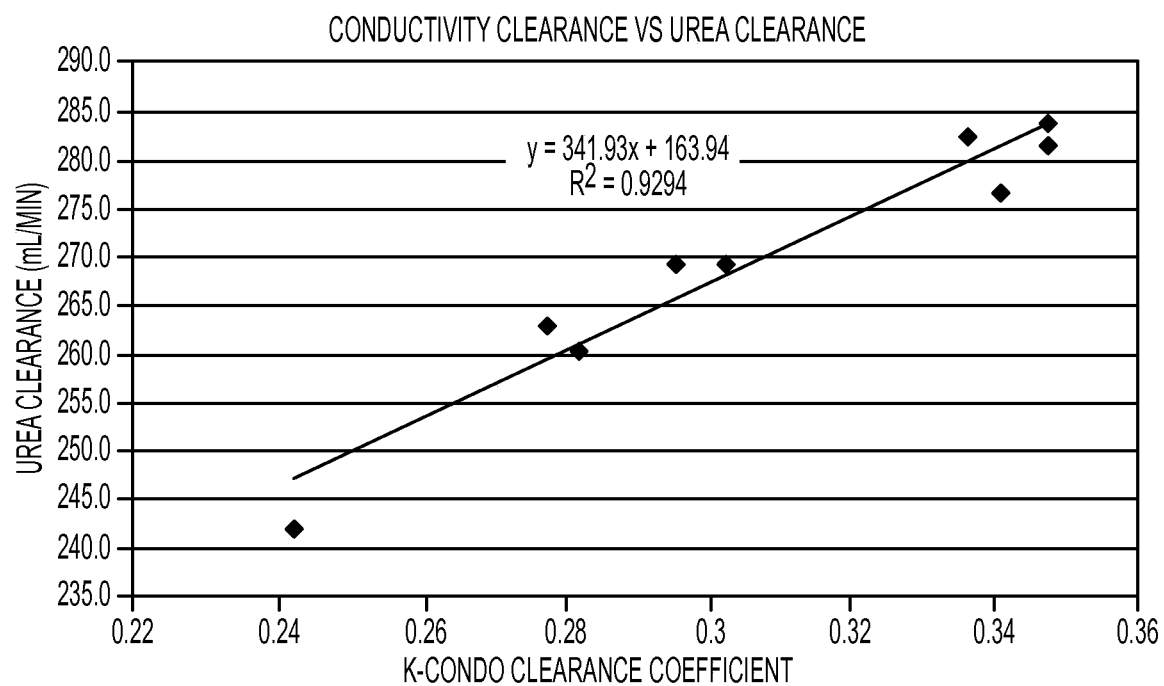
Figure 84:
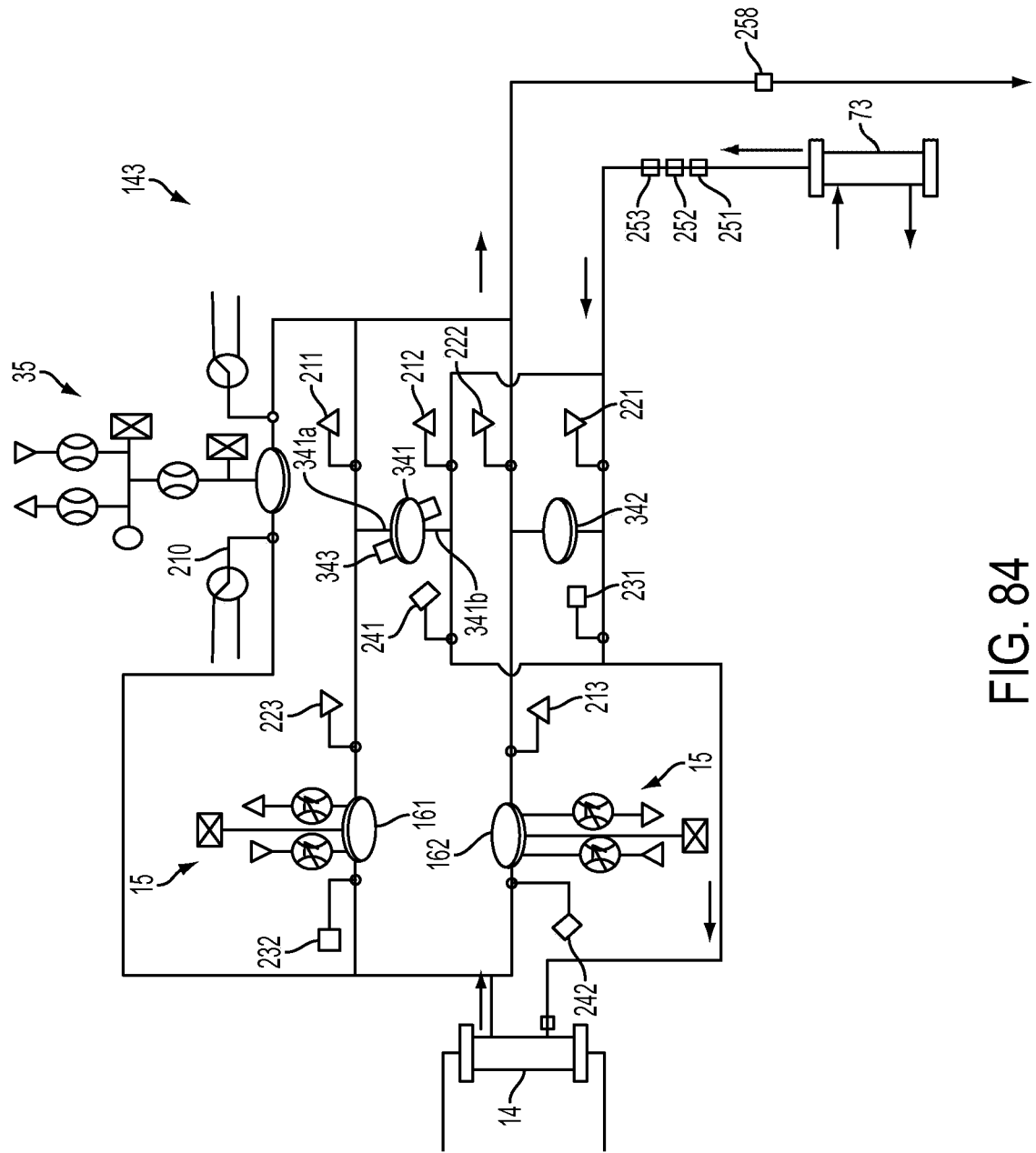
Figure 85:
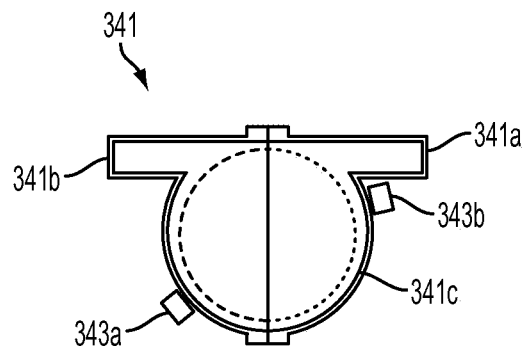
Figure 86:
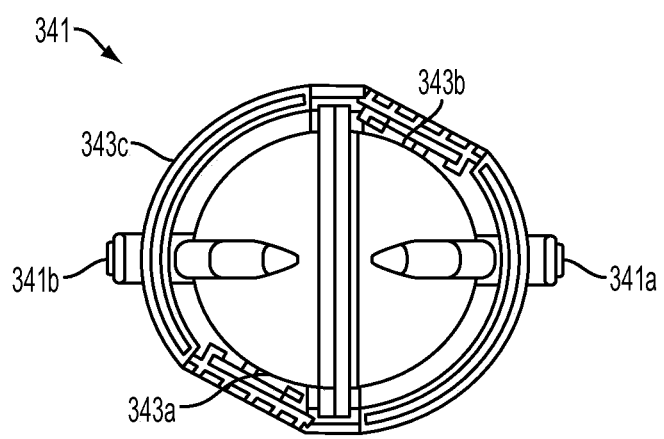
Figure 87:
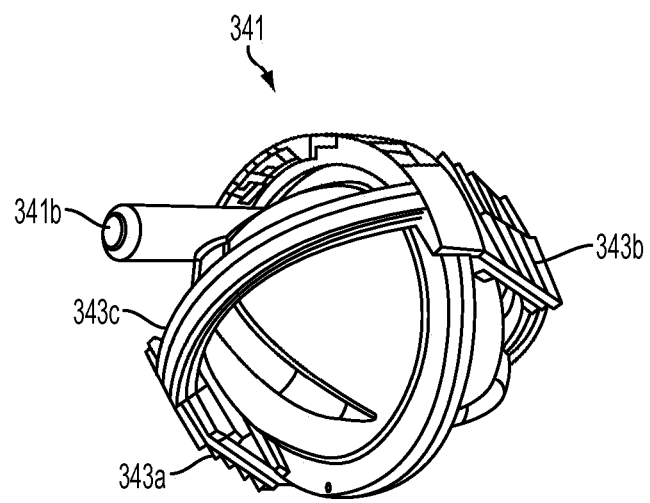
Figure 88:
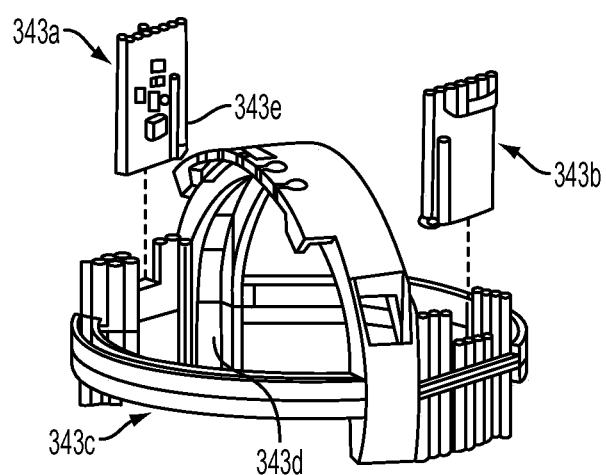
Figure 89:
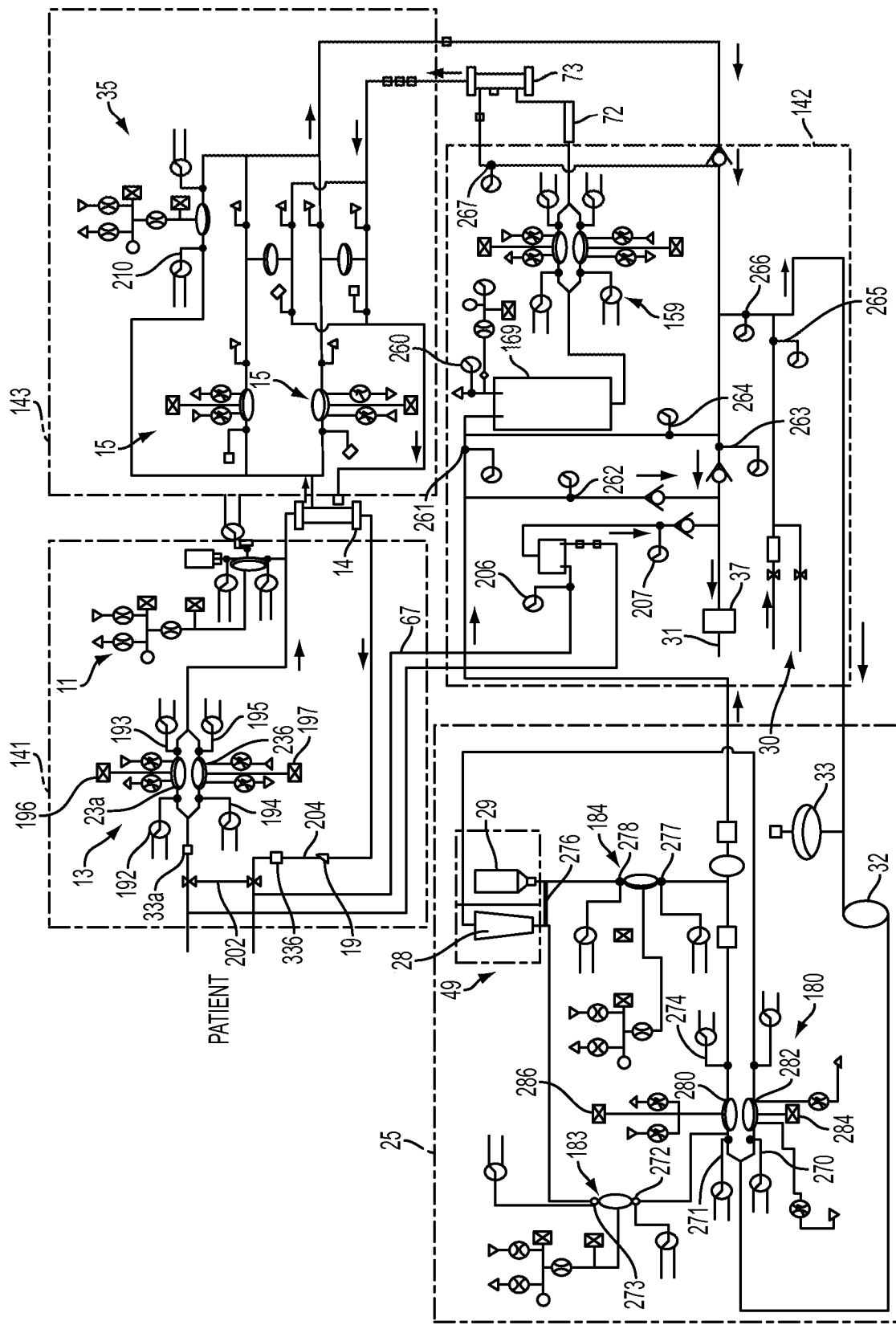
Figure 90:
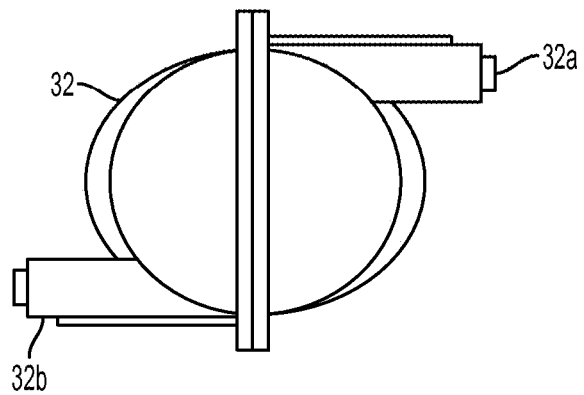
Figure 91:
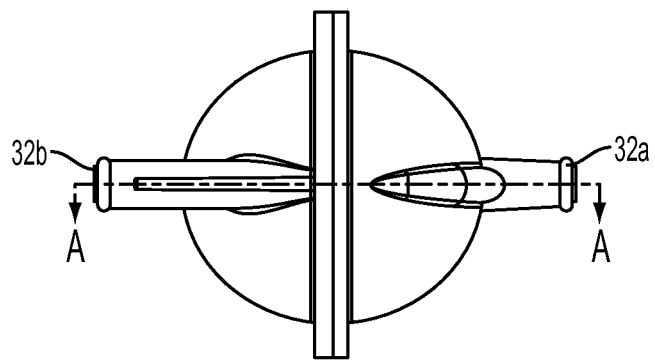
Figure 92:
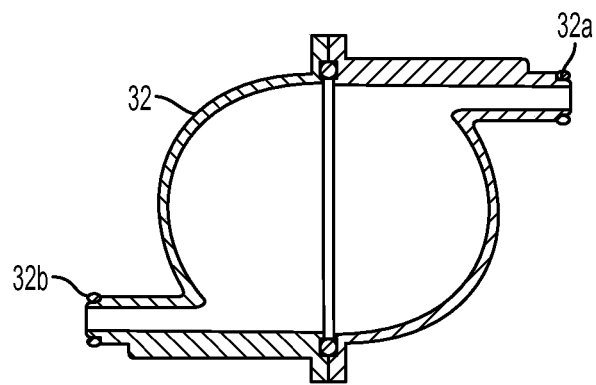
Figure 93:
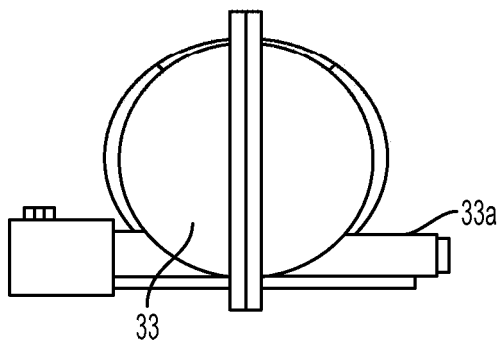
Figure 94:
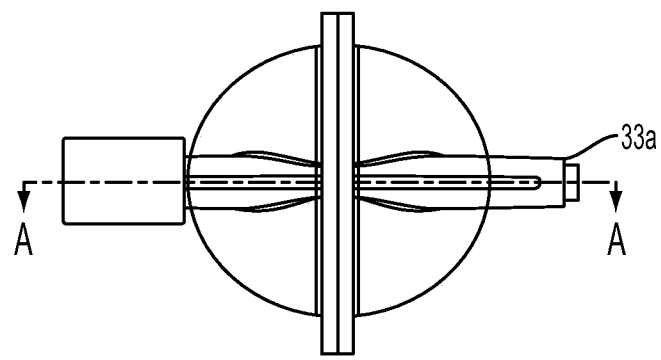
Figure 95:
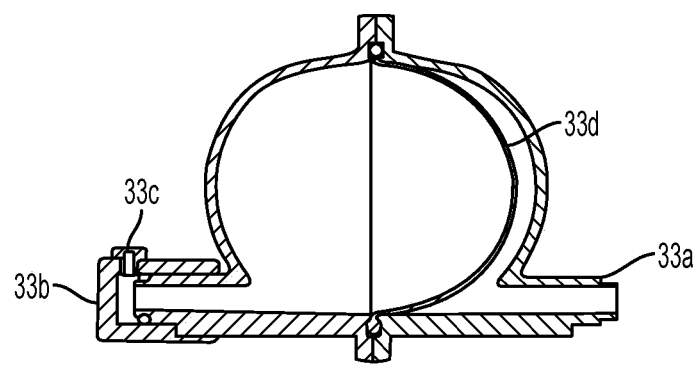
Figure 96:
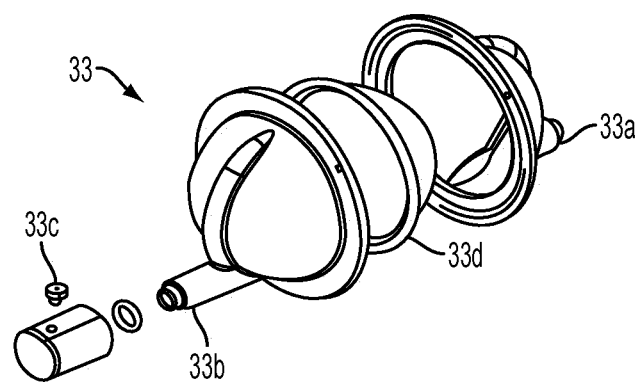
Figure 97:
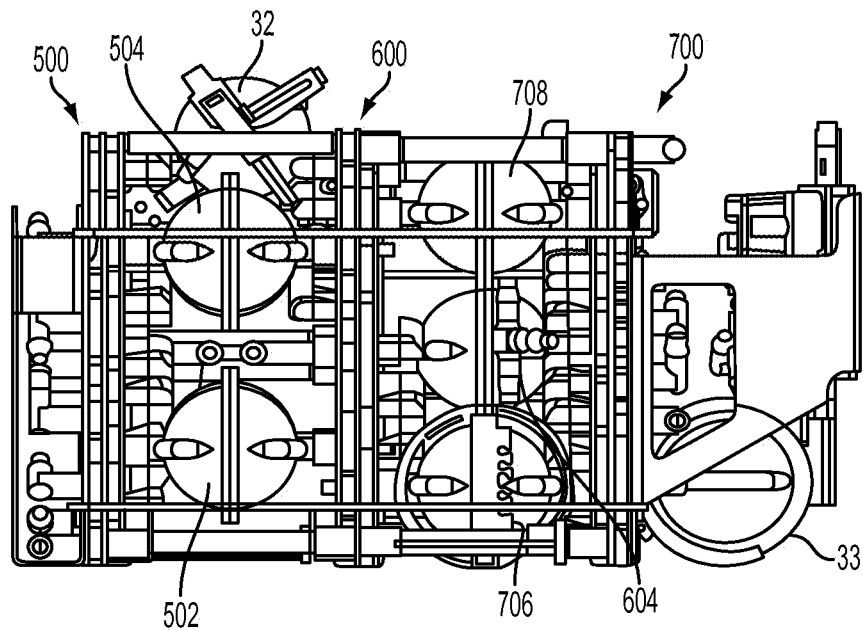
Figure 98:
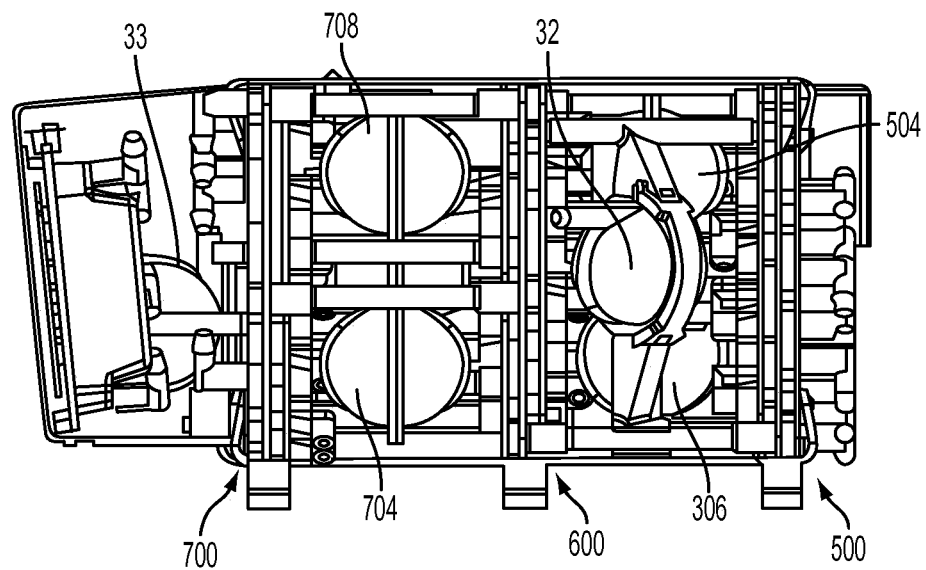
Figure 99:
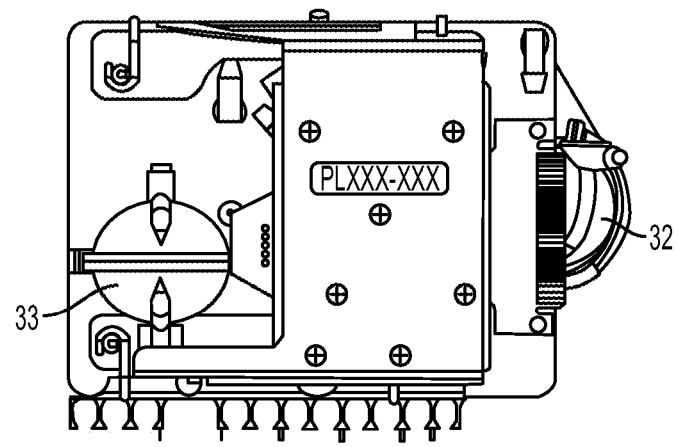
Figure 100:
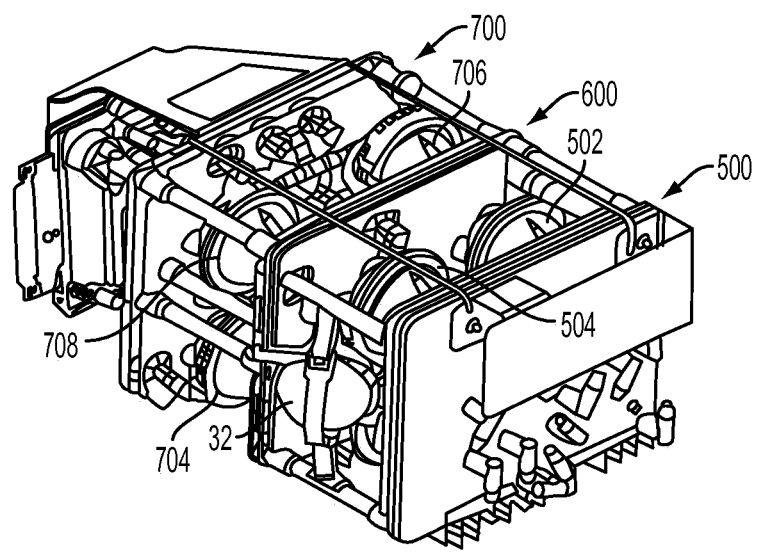
Figure 101A:
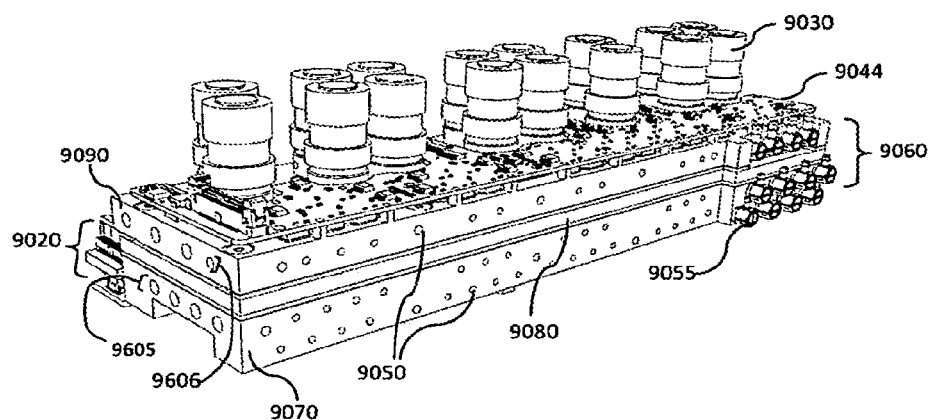
Figure 101B:
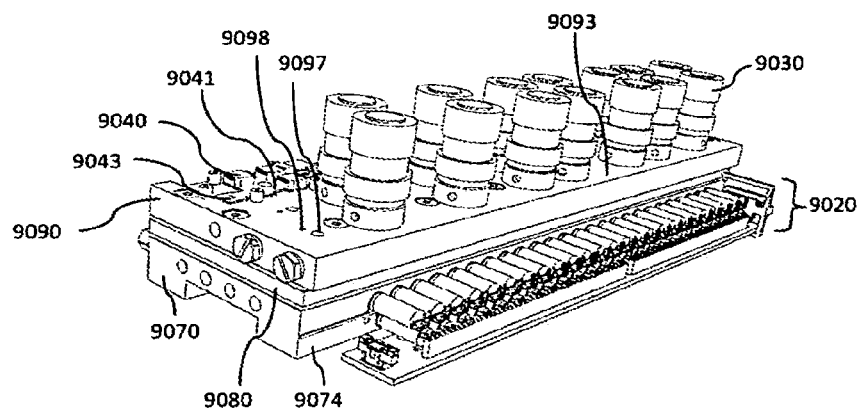
Figure 102:
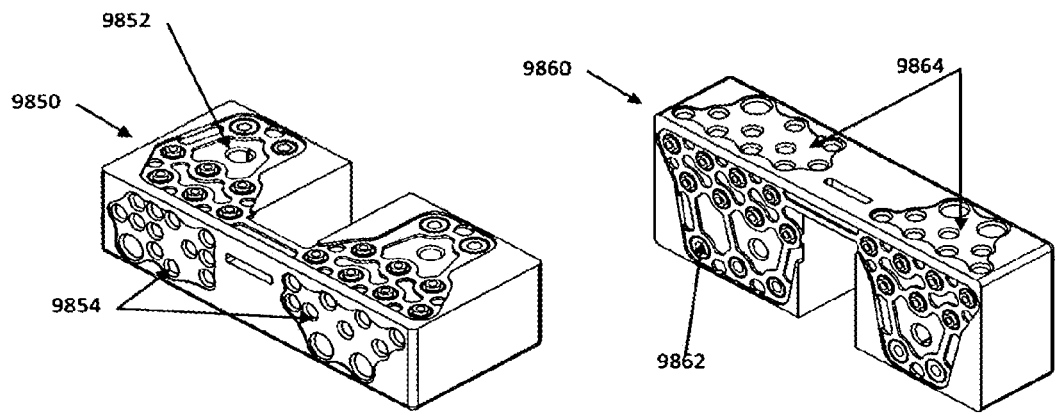
Figure 103:
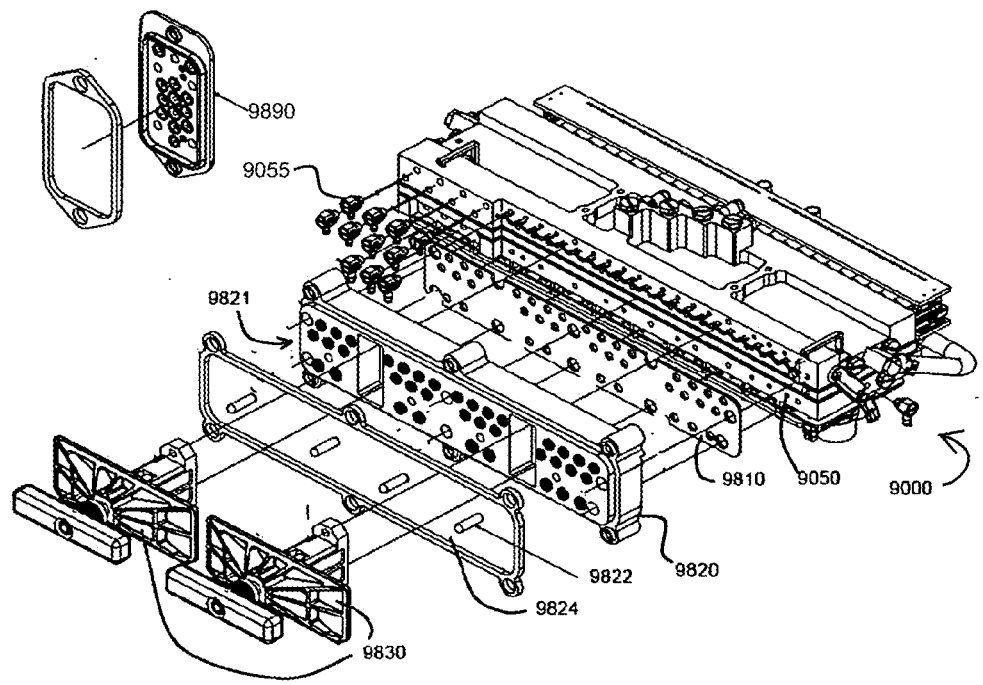
Figure 104:
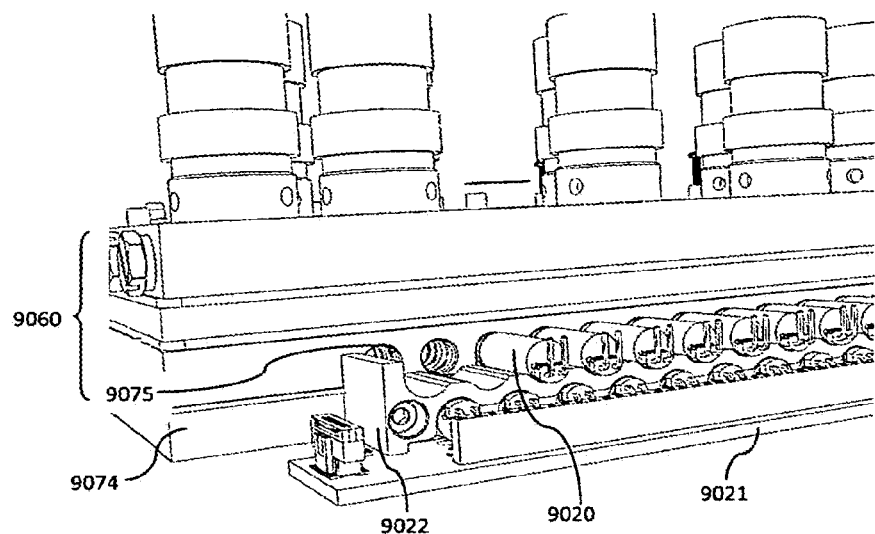
Figure 105:
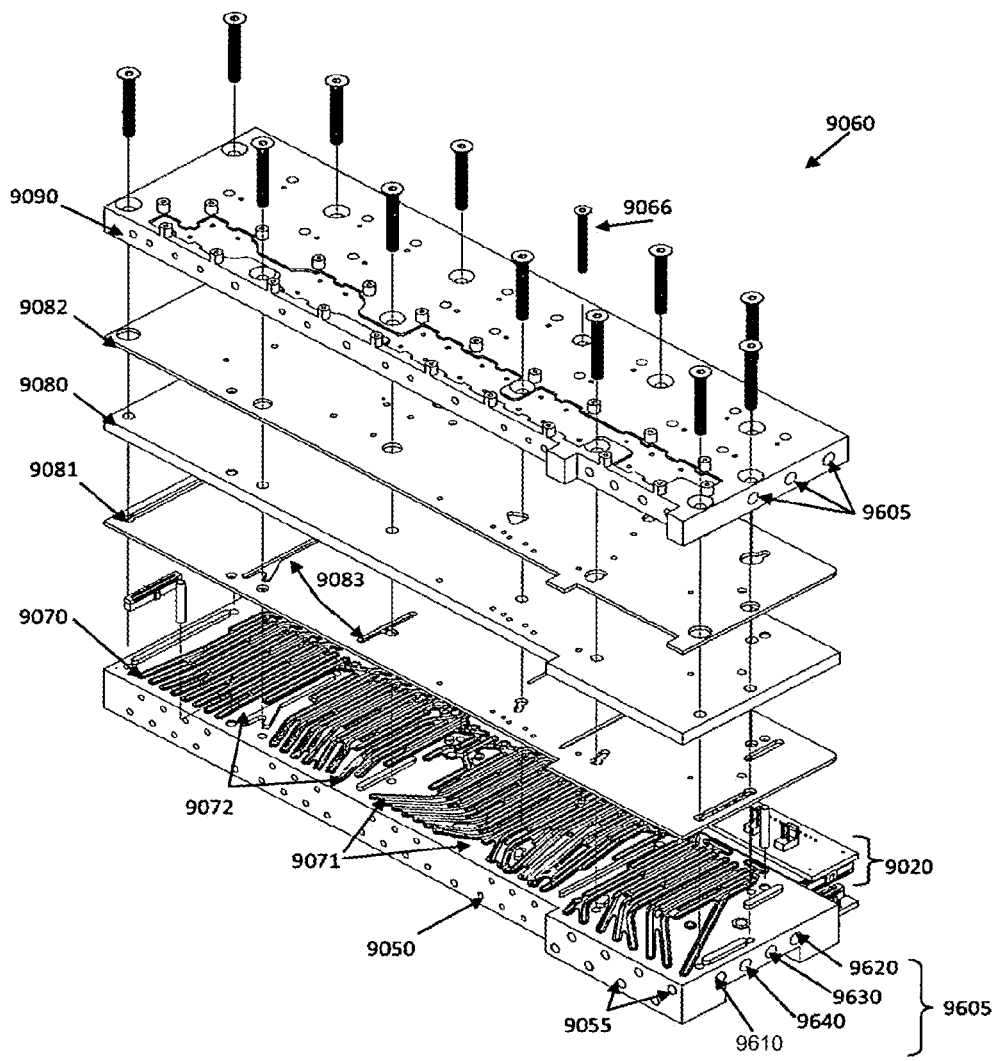
Figure 106:
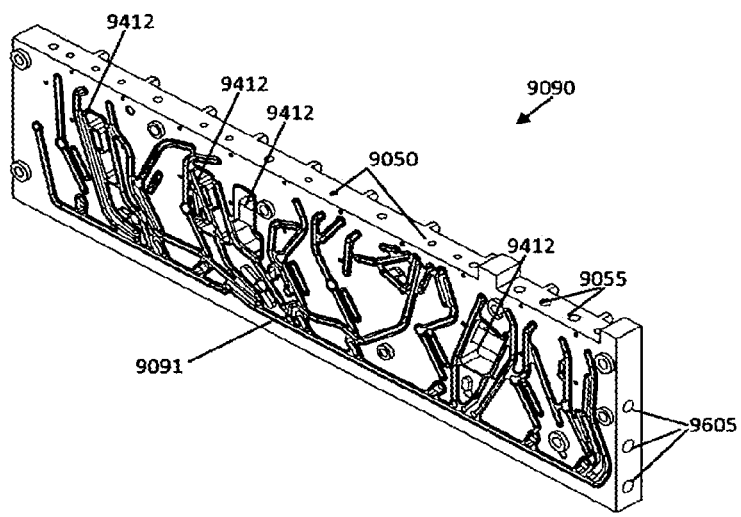
Figure 107:
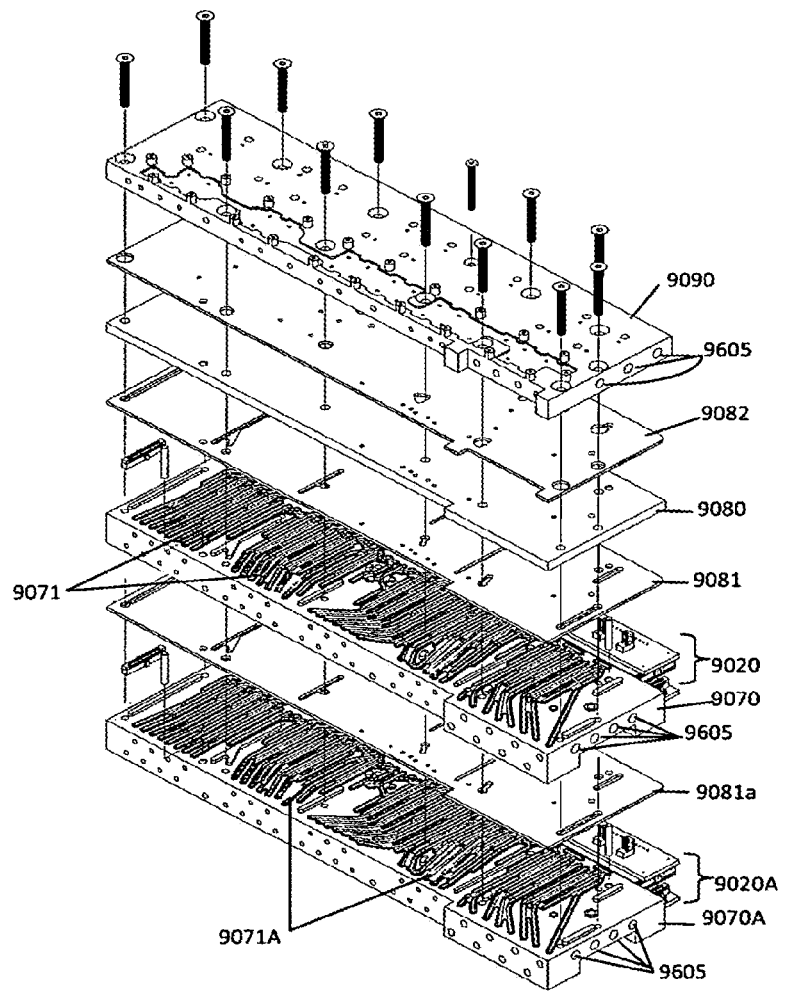
Figure 108:
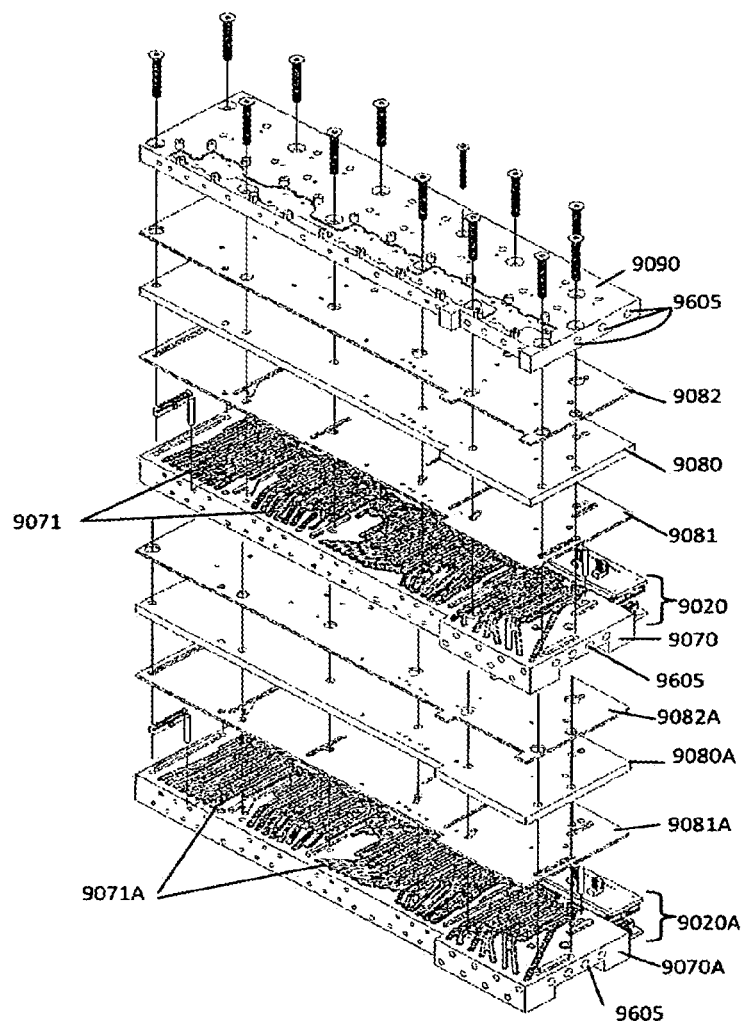
Figure 109:
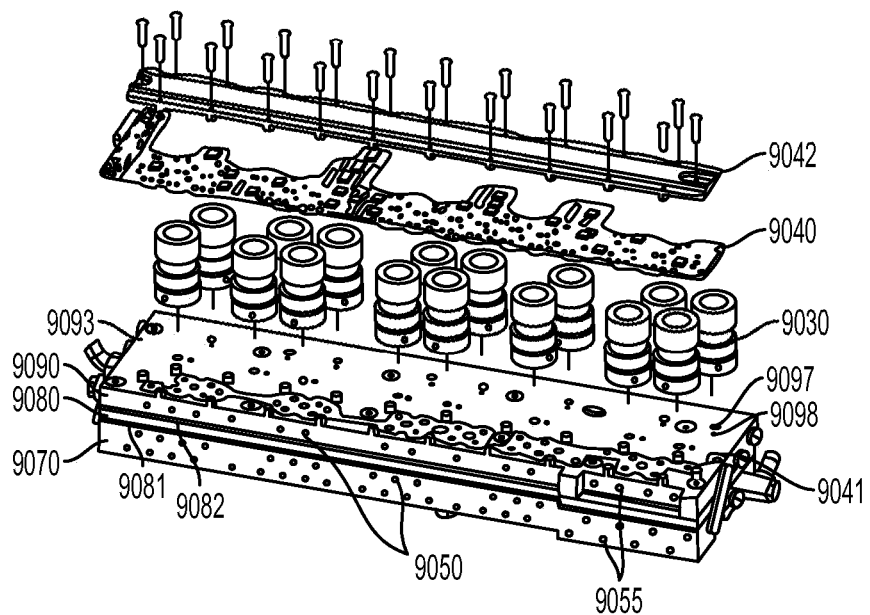
Figure 110:
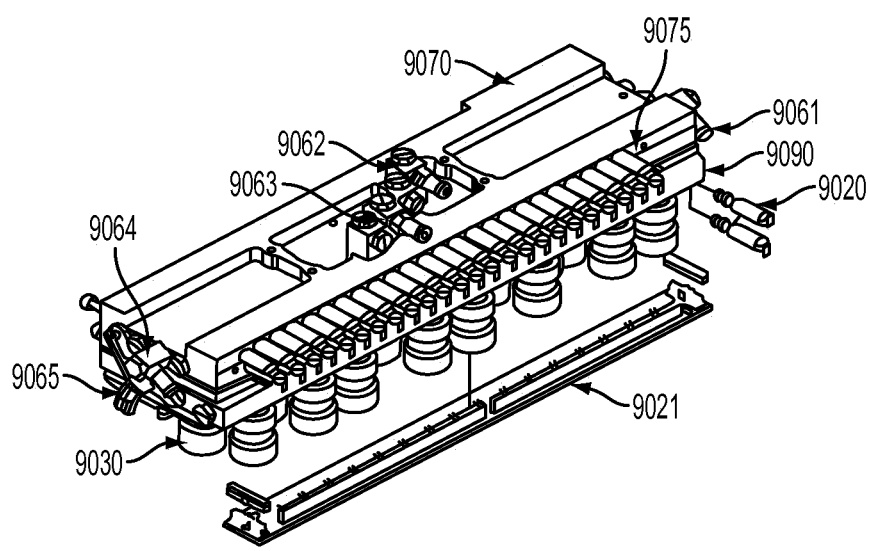
Figure 112:
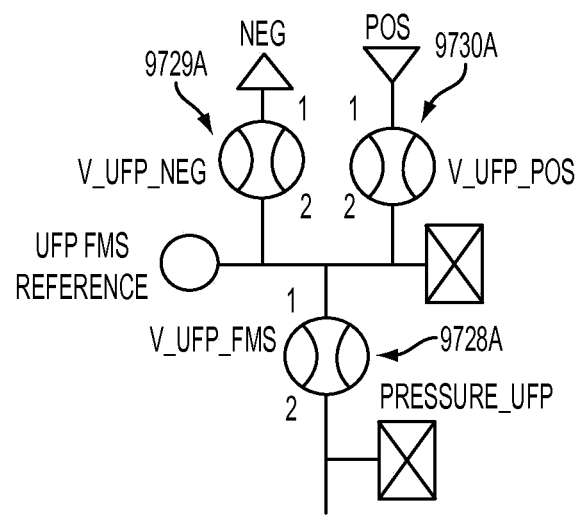
Figure 113:
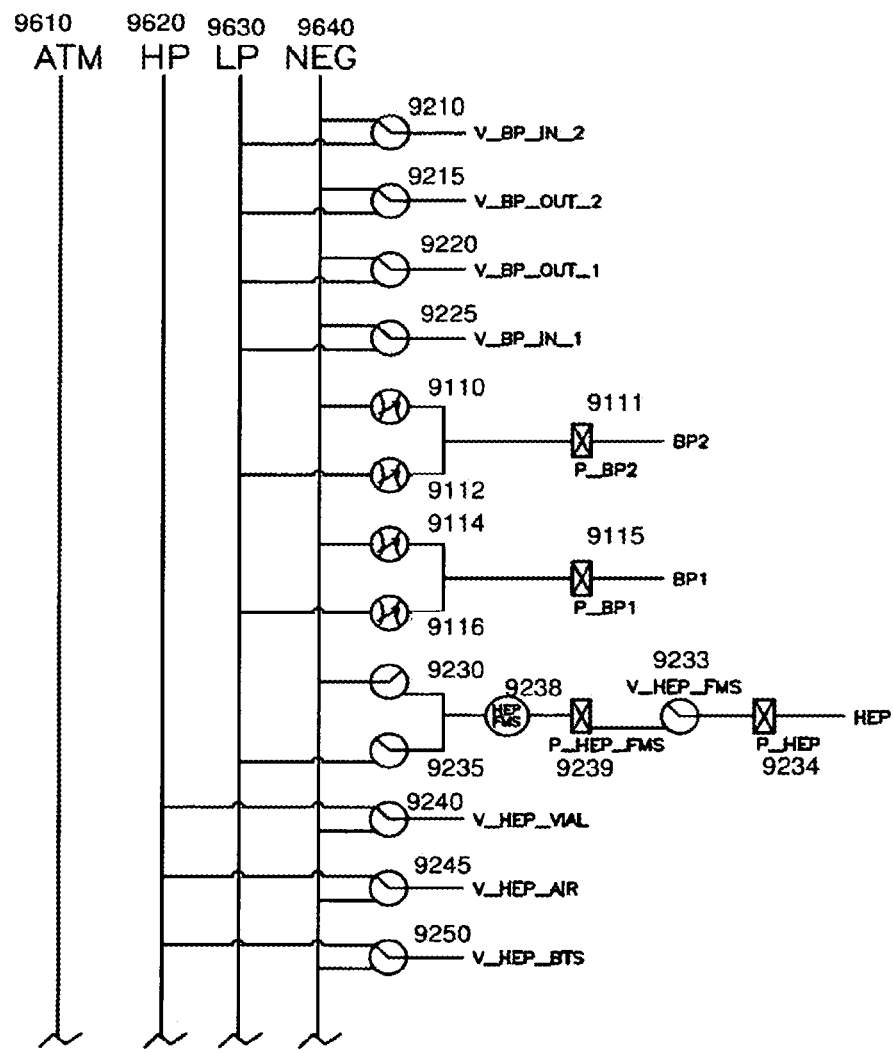
Figure 114:
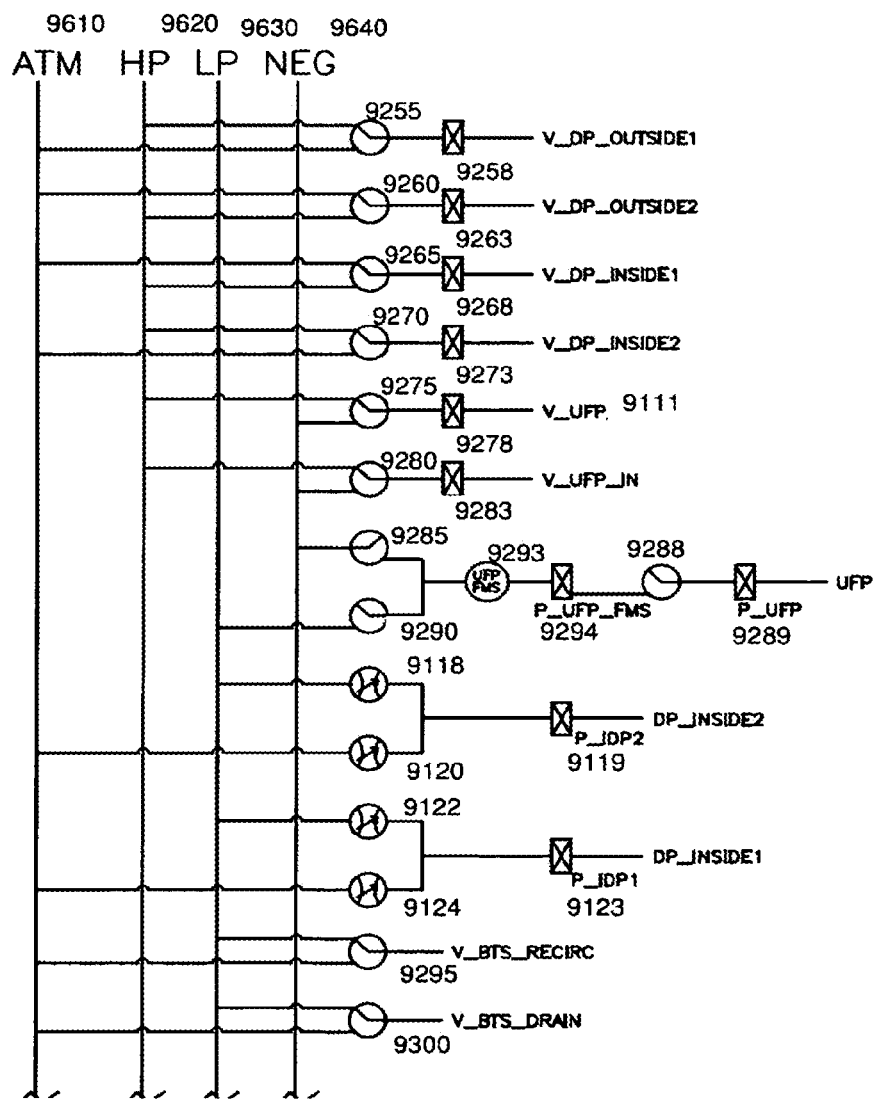
Figure 115:
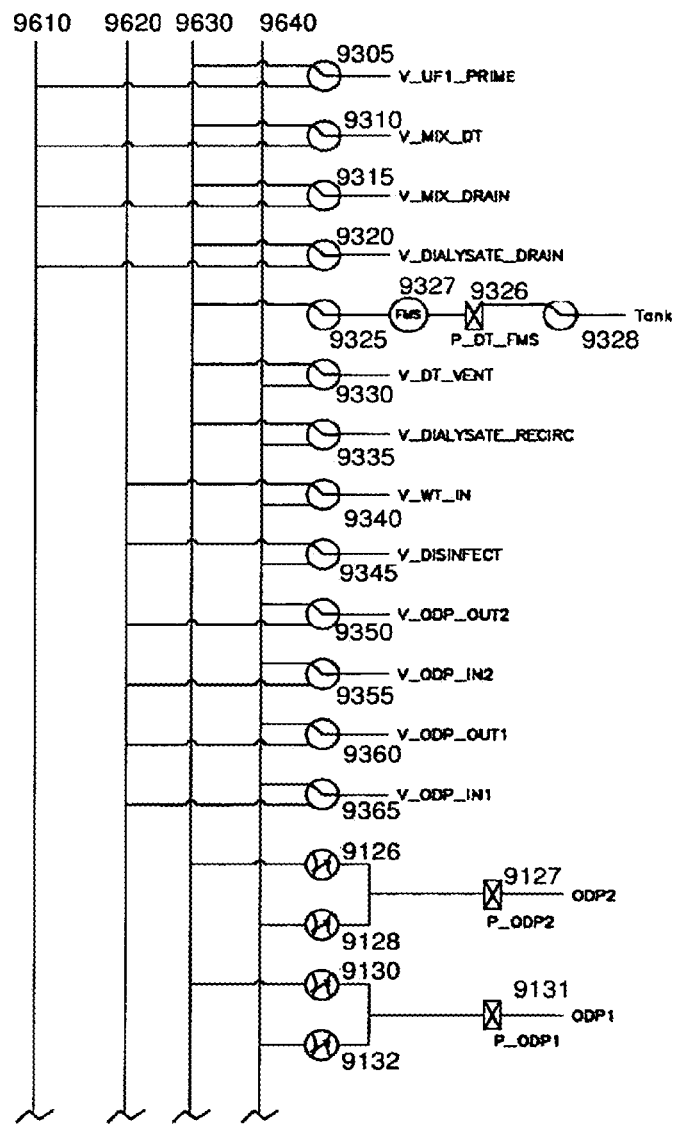
Figure 116:
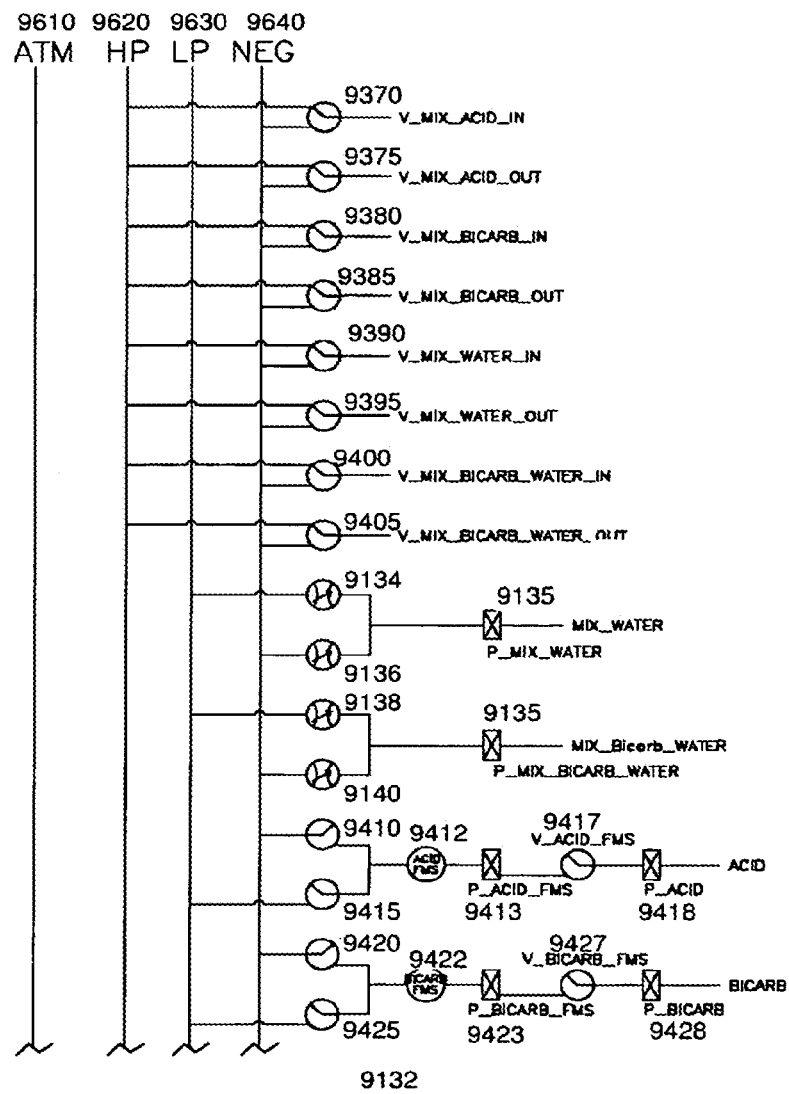
Figure 117:
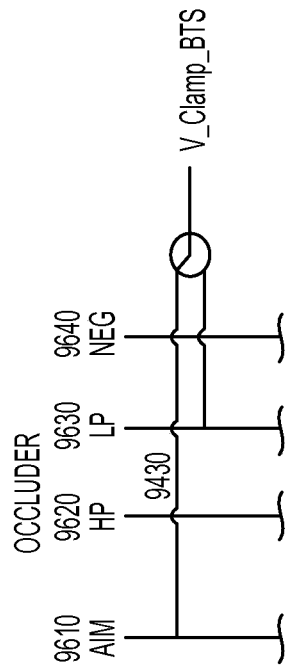
Figure 118:
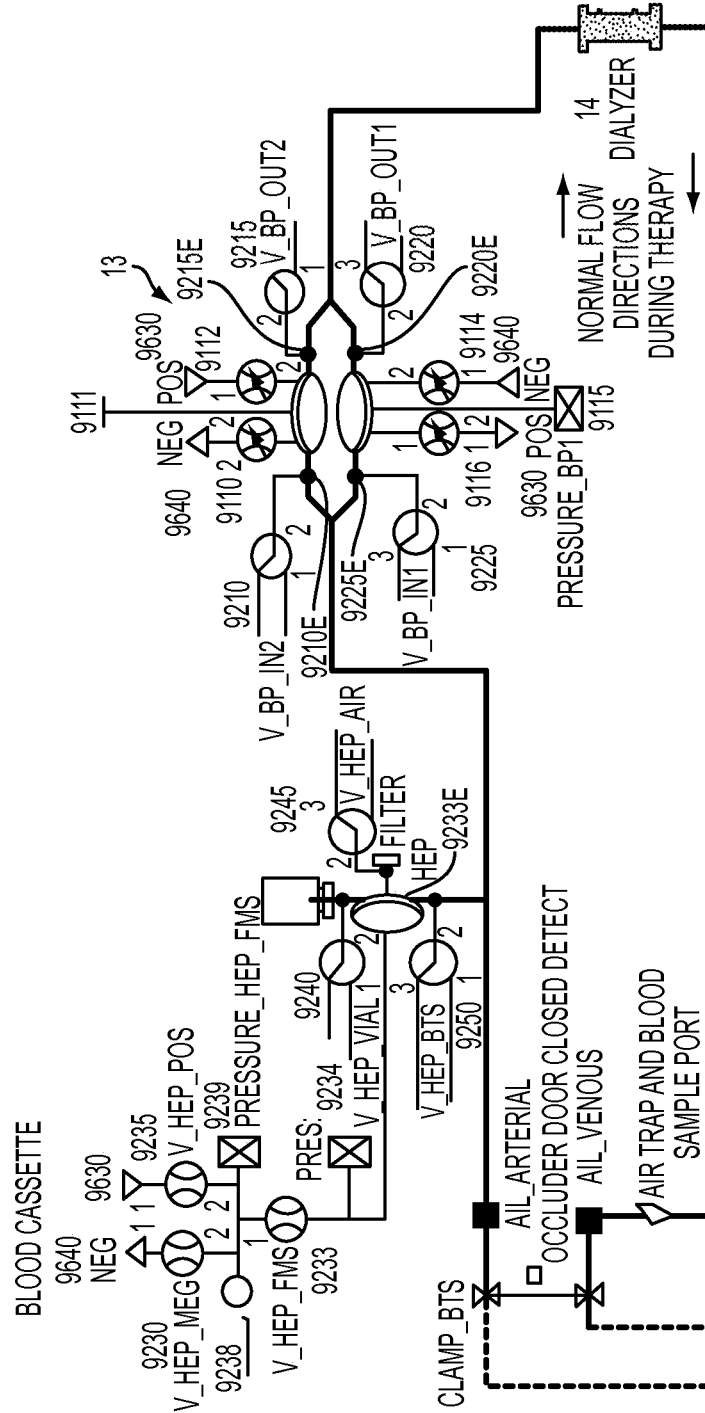
Figure 119:
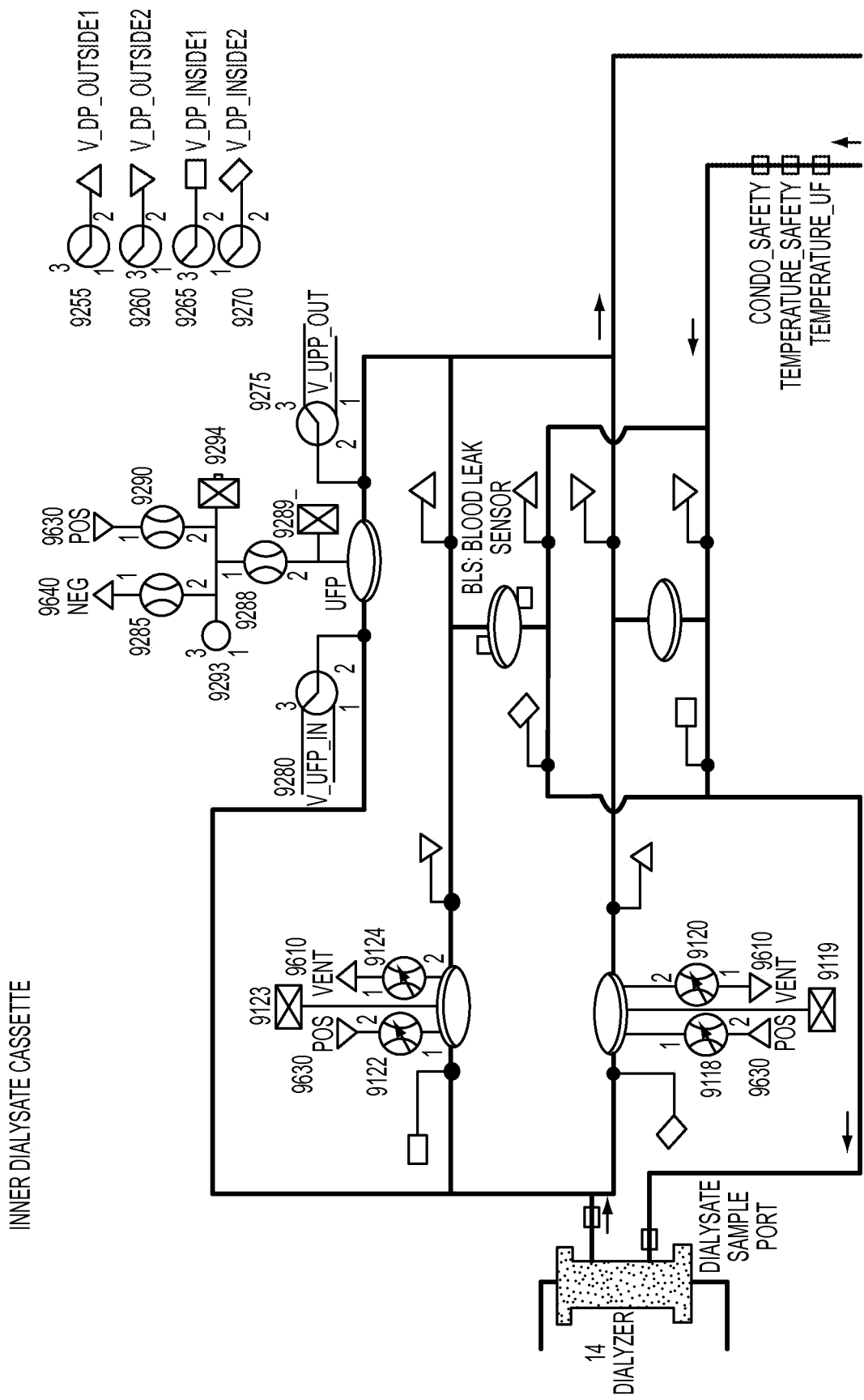
Figure 120:
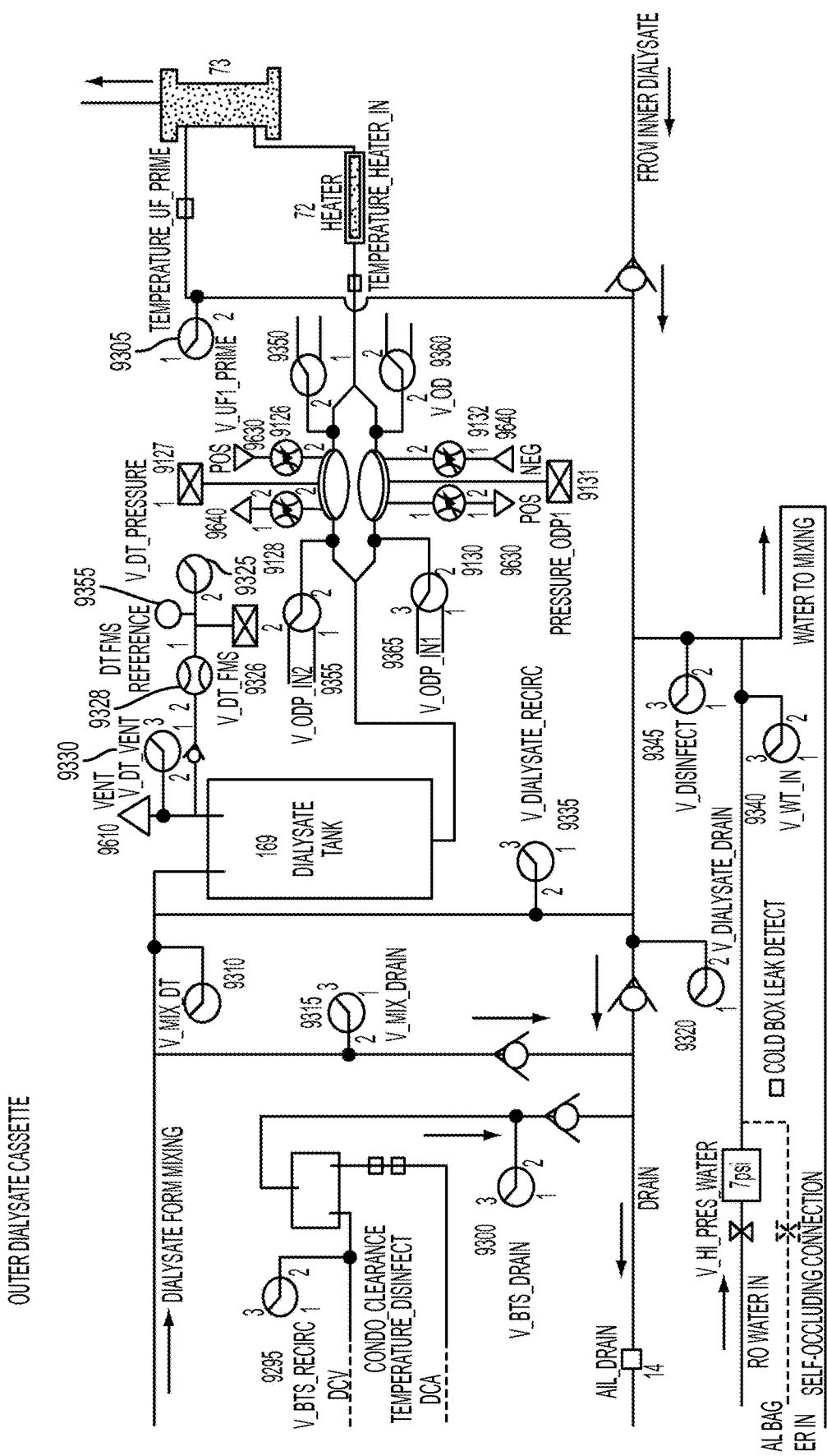
Figure 121:
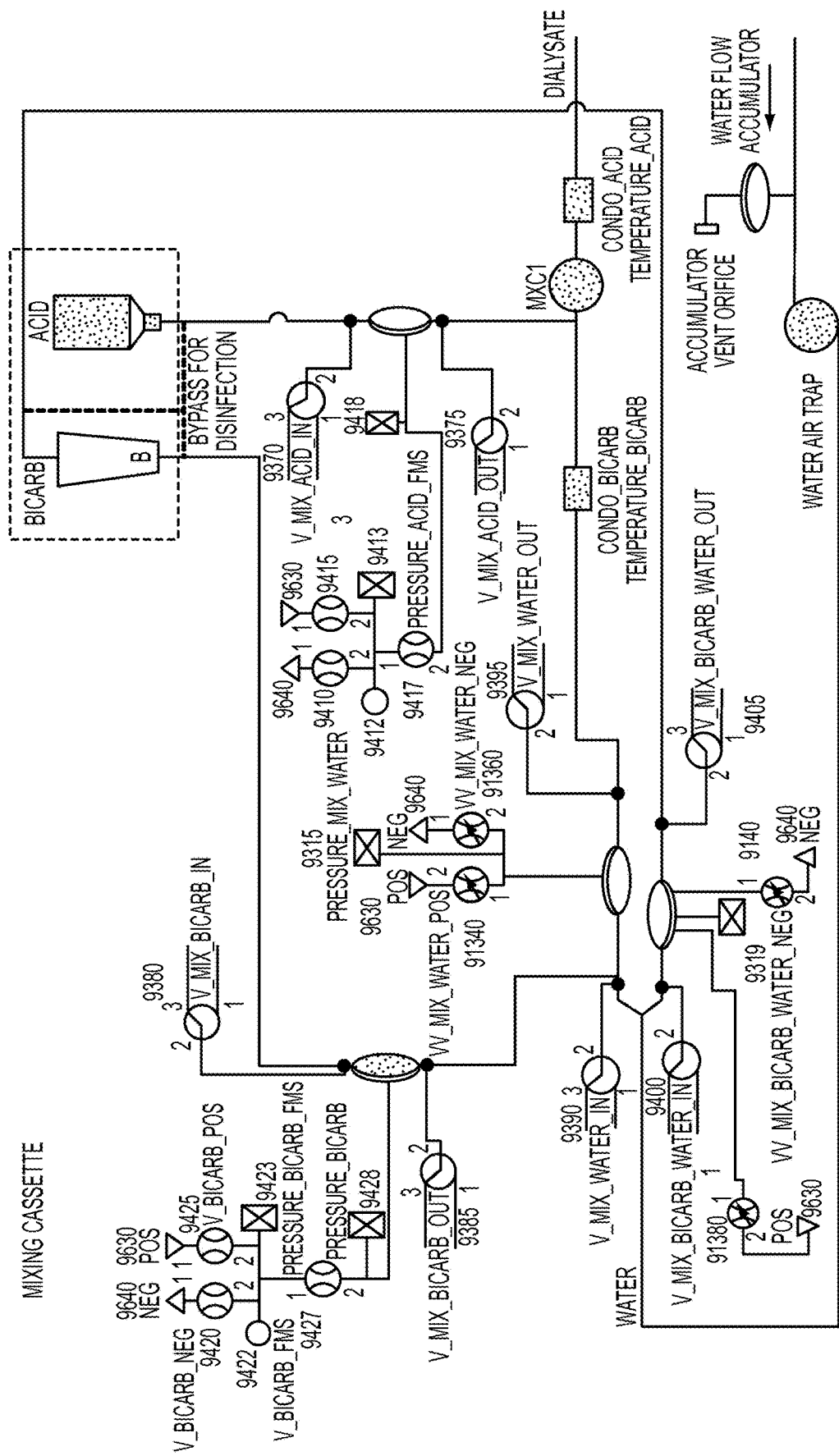
Figure 122:
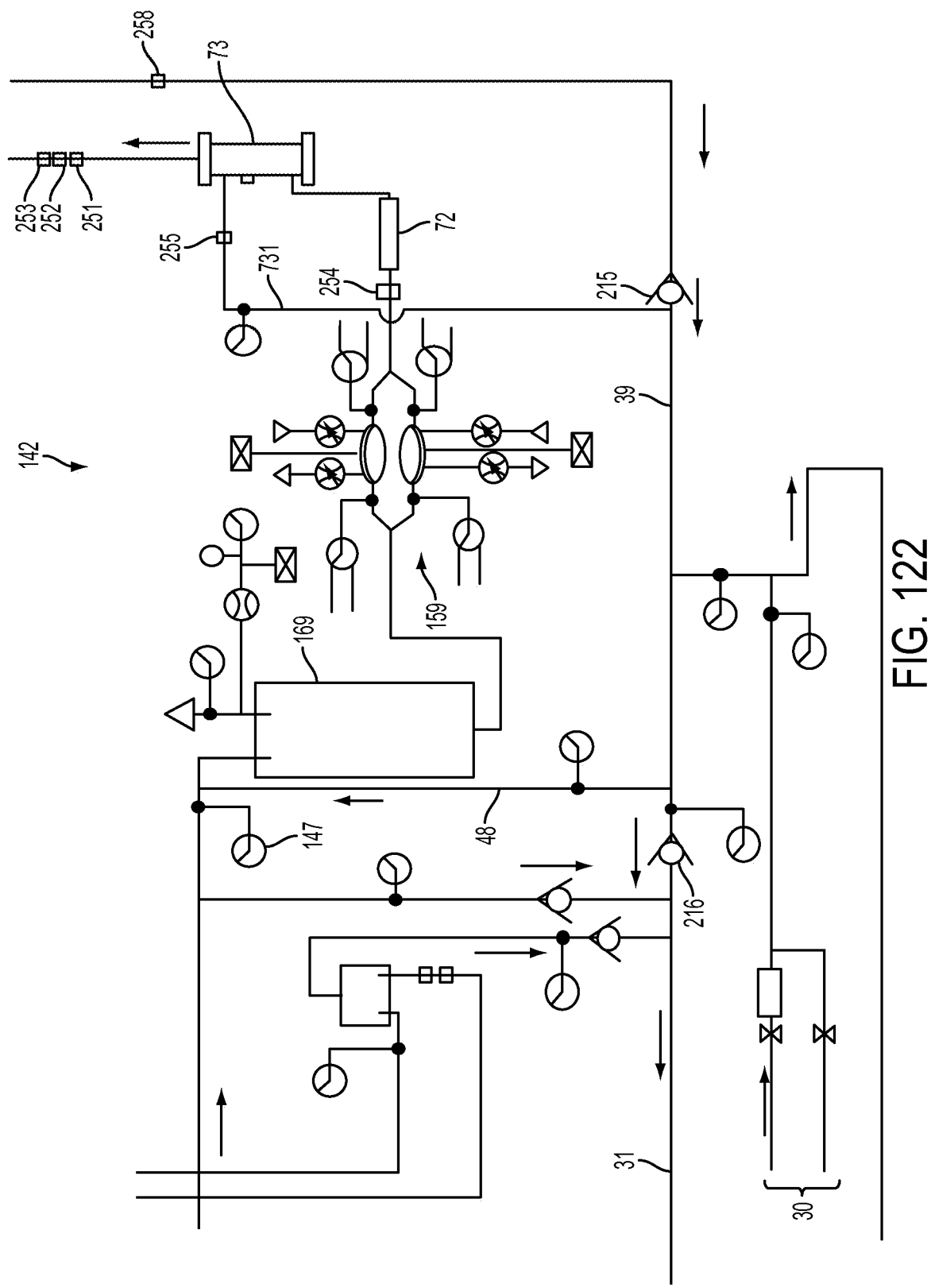
Figure 123C:
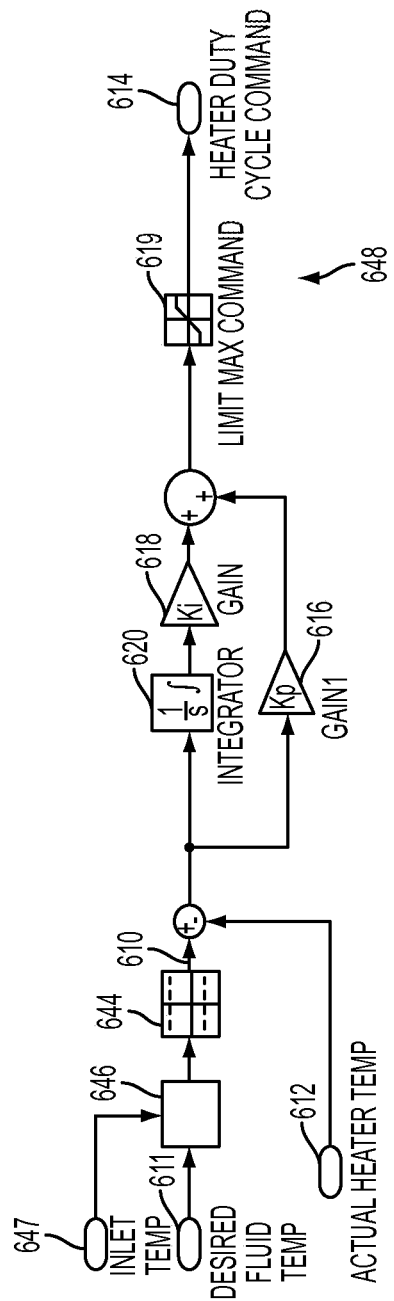

FIG. 76C graphically illustrates ultrafiltration fluid flow in one exemplary implementation of the hemodialysis apparatus;

FIG. 76D graphically illustrates ultrafiltration fluid flow including periodic backflushing of fluid across a dialyzer membrane in another exemplary implementation of the hemodialysis apparatus;

FIG. 76E graphically illustrates ultrafiltration fluid flow including other infusions or withdrawals of fluid from a patient during hemodialysis;

FIG. 76F illustrates a screen view for display on a graphical user interface to summarize the results of a hemodialysis therapy;

FIG. 77 is a schematic view showing shows an exemplary implementation of the Take Samples application;

FIGS. 78A-78C is a schematic view showing shows an exemplary implementation of the Replace Components application;

FIGS. 79A-79B are schematic views showing shows an exemplary implementation of the Install Chemicals application;

FIG. 80 shows, in the context of the hemodialysis system, a pathway between a pressurized air tank and a dialysate tank;

FIG. 81 is a fluid schematic of a hemodialysis system illustrating the blood side and dialysate side flow pathways used for measuring dialyzer clearance according to an embodiment of the invention;

FIG. 82 is a plot of measured and model conductivity data versus pump stroke number used in the determination of dialyzer clearance according to an embodiment of the invention;

FIG. 83 is a plot correlating a dialyzer parameter K determined from data such as that illustrated in FIG. 82 with measured urea clearance;

FIG. 84 shows a schematic diagram of a balancing circuit that includes a balancing chamber and an associated blood leak sensor;

FIG. 85 shows a cross sectional front view of a balancing chamber and blood leak sensor in an illustrative embodiment;

FIG. 86 shows a bottom view of the FIG. 85 embodiment;

FIG. 87 shows a lower left side perspective view of the FIG. 85 embodiment;

FIG. 88 shows a perspective view of a blood leak sensor bracket in this illustrative embodiment;

FIG. 89 shows a schematic diagram of a dialysis system including an air trap and accumulator in a water supply conduit in an illustrative embodiment;

FIG. 90 shows a front view of an air trap in an illustrative embodiment;

FIG. 91 shows a bottom view of the air trap of FIG. 90;

FIG. 92 shows a cross sectional front view of the air trap of FIG. 90;

FIG. 93 shows a front view of an accumulator in an illustrative embodiment;

FIG. 94 shows a bottom view of the accumulator of FIG. 93;

FIG. 95 shows a cross sectional front view of the air trap of FIG. 93;

FIG. 96 shows an upper front left perspective view of the air trap of FIG. 93;

FIG. 97 shows a top view of a cassette system in an illustrative embodiment;

FIG. 98 shows a rear view of the cassette system of FIG. 97;

FIG. 99 shows a right side view of the cassette system of FIG. 97;

FIG. 100 shows an upper right rear perspective view of the cassette system of FIG. 97;

FIG. 101A is an isometric view that shows the front of the pressure distribution module according to an embodiment of the invention;

FIG. 101B is an isometric view that shows the back of the pressure distribution module according to an embodiment of the invention;

FIG. 102 is an isometric view of left and right interface blocks for use with the pressure distribution module of FIG. 101A;

FIG. 103 is an exploded view showing how interface blocks are secured with respect to the pressure distribution module of FIG. 101B;

FIG. 104 is a detailed isometric view of the back of the pressure distribution module according to an embodiment of the invention;

FIG. 105 is an exploded view of an embodiment of a multi-part pneumatic manifold;

FIG. 106 is an isometric view showing the flow channels of the end-manifold block;

FIG. 107 is an exploded view of an alternative embodiment of the multi-part pneumatic manifold;

FIG. 108 is an exploded view of another alternative embodiment of the multi-part pneumatic manifold;

FIG. 109 is an isometric view of a pressure distribution module showing the vary-valves and pressure sensor PCB;

FIG. 110 is an isometric view of a pressure distribution module showing the cartridge-valves and the pressure supply fittings;

FIGS. 111A-111D are isometric views showing details of a mid-manifold blocks;

FIG. 112 is a schematic of exemplary pod pump with an FMS system;

FIG. 113 is a schematic of a pneumatic routing for a blood cassette;

FIG. 114 is a schematic of a pneumatic routing for an inner dialysate cassette;

FIG. 115 is a schematic of a pneumatic routing for an outer dialysate cassette;

FIG. 116 is a schematic of a pneumatic routing for a mixing cassette;

FIG. 117 is a schematic of a pneumatic routing for an occluder;

FIG. 118 is a flow schematic for a blood cassette;

FIG. 119 is a flow schematic for an inner dialysate cassette;

FIG. 120 is a flow schematic for an outer dialysate cassette;

FIG. 121 is a flow schematic for a mixing cassette;

FIG. 122 is a schematic representation of a directing circuit that may be used in a hemodialysis system;

FIG. 123A is a schematic of a heater temperature control loop;

FIG. 123B is a schematic of a heater temperature control loop nested inside a fluid temperature control loop;

FIG. 123C is a schematic of a heater power control loop;

FIGS. 124-129 show flow chart diagrams illustrating a method for communicating between a tablet and a base in accordance with an embodiment of the present disclosure.

Figure 130:
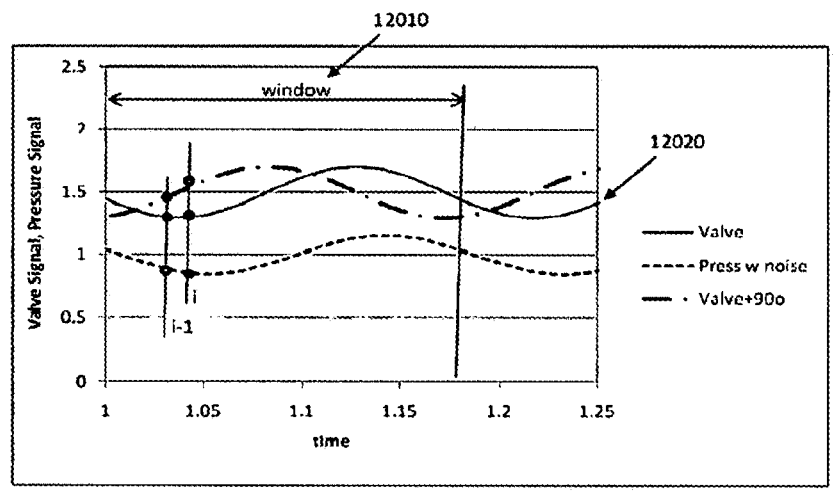

FIG. 130 is a plot of simulated valve command and pressure response used in cross-correlation calculations.

Figure 131:
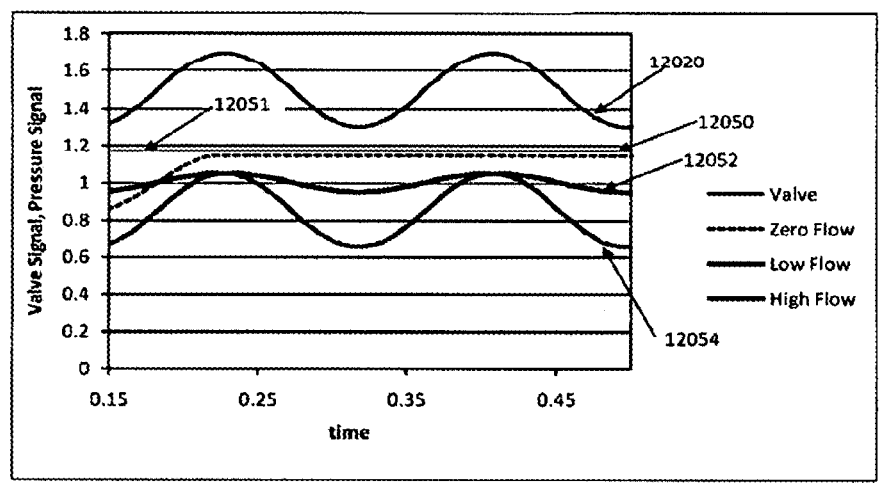

FIG. 131 is a plot of illustrative curves from cross-correlation calculations.

Figure 132:
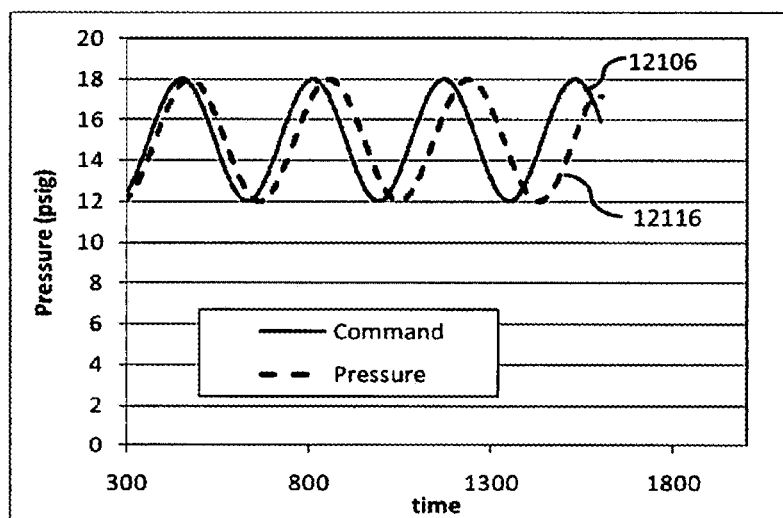

FIG. 132 is a plot of simulated valve commands and pressure response where the phase angle between the command and the pressure changes.

Figure 133:
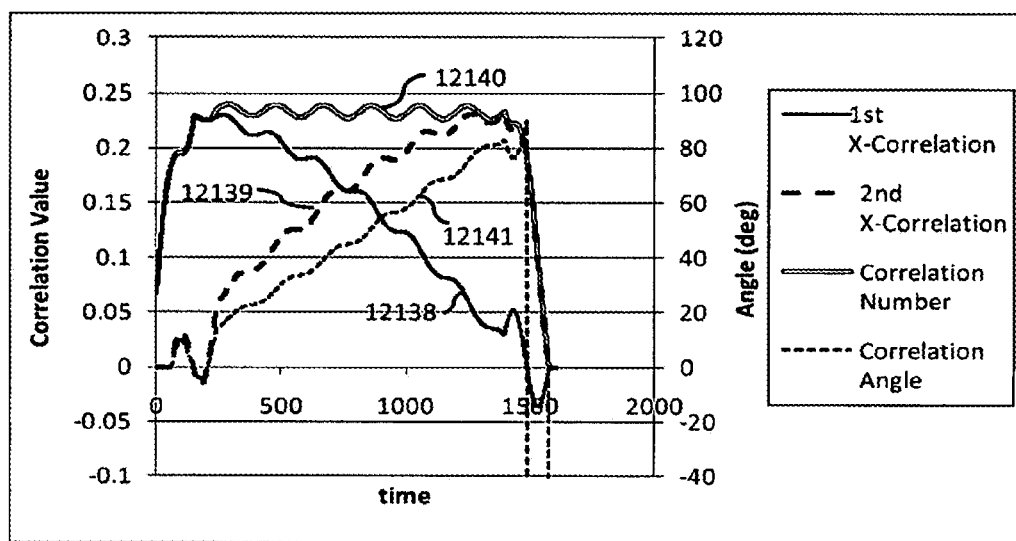

FIG. 133 is the a plot of cross-correlations results based on simulated valve command and response including a phase shift.

Figure 134:
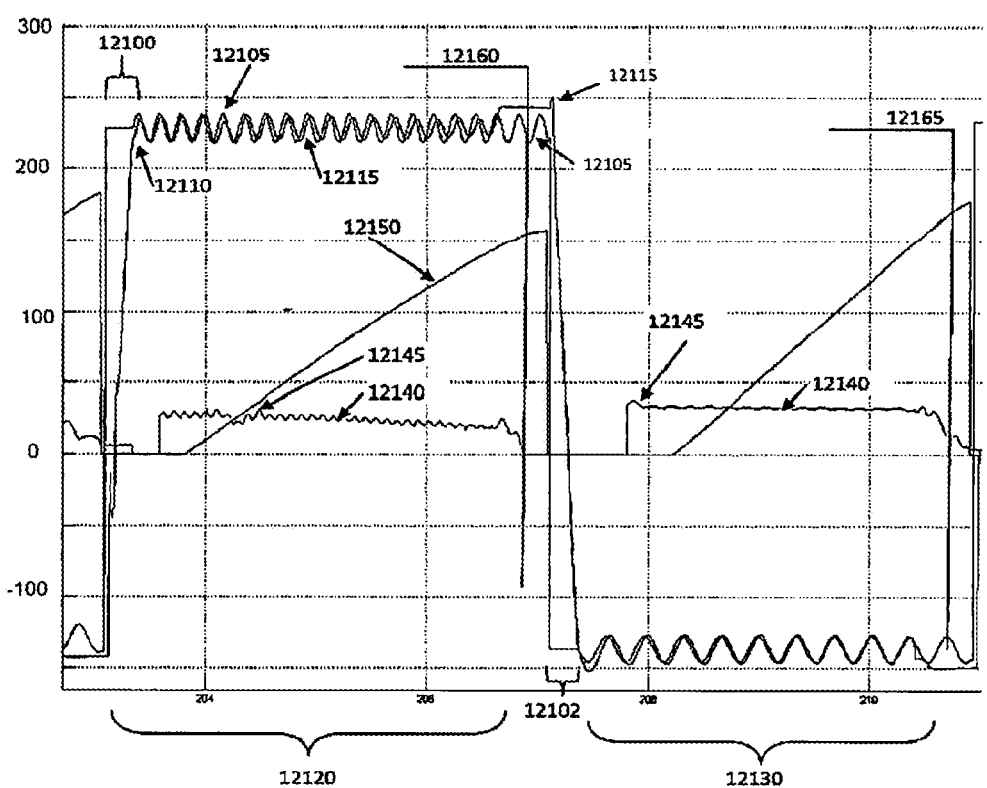

FIG. 134 is a plot of pressures and cross-correlations from a fill and deliver stroke.

Figure 135:
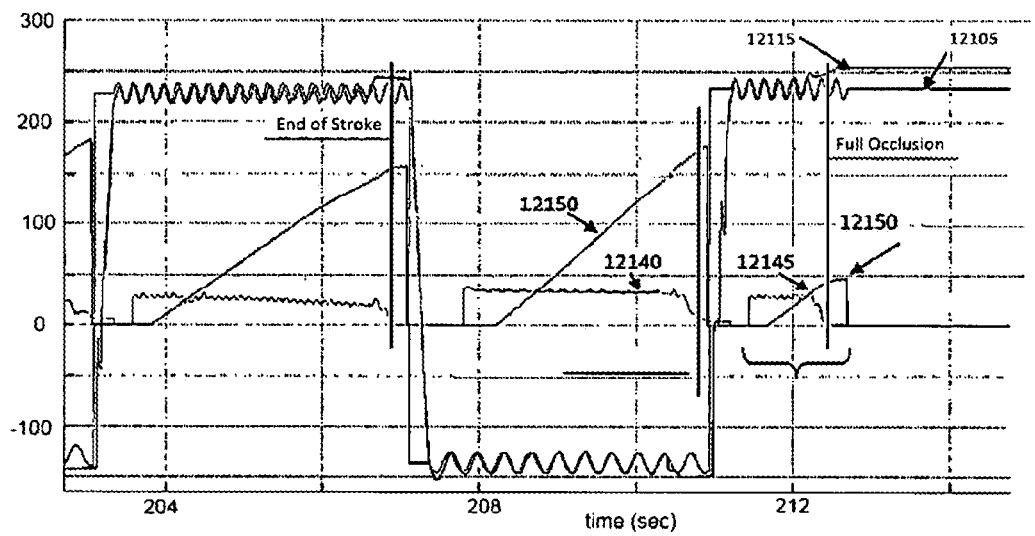

FIG. 135 is a plot of pressures and cross-correlations from a fill and deliver stroke with an occlusion.

Figure 136:
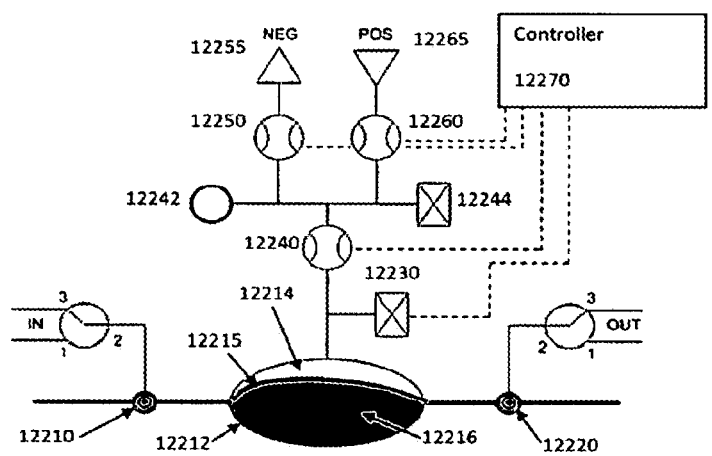

FIG. 136 is a schematic of a pressure driven diaphragm pump actuated by binary valves.

Figure 137:
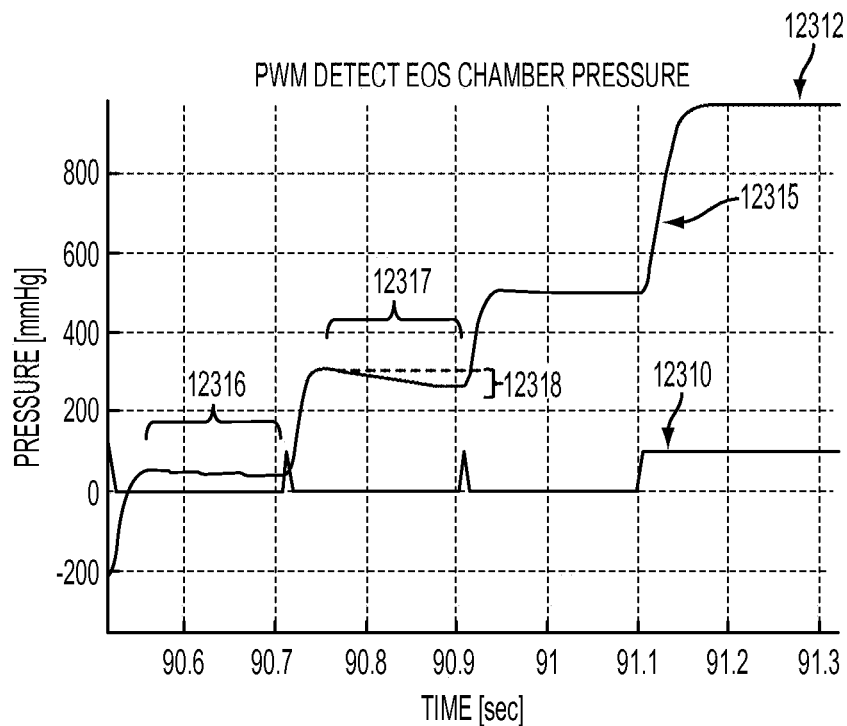

FIG. 137 is a plot of the valve actuation and the resulting pump pressure during a deliver stroke.

Figure 138:
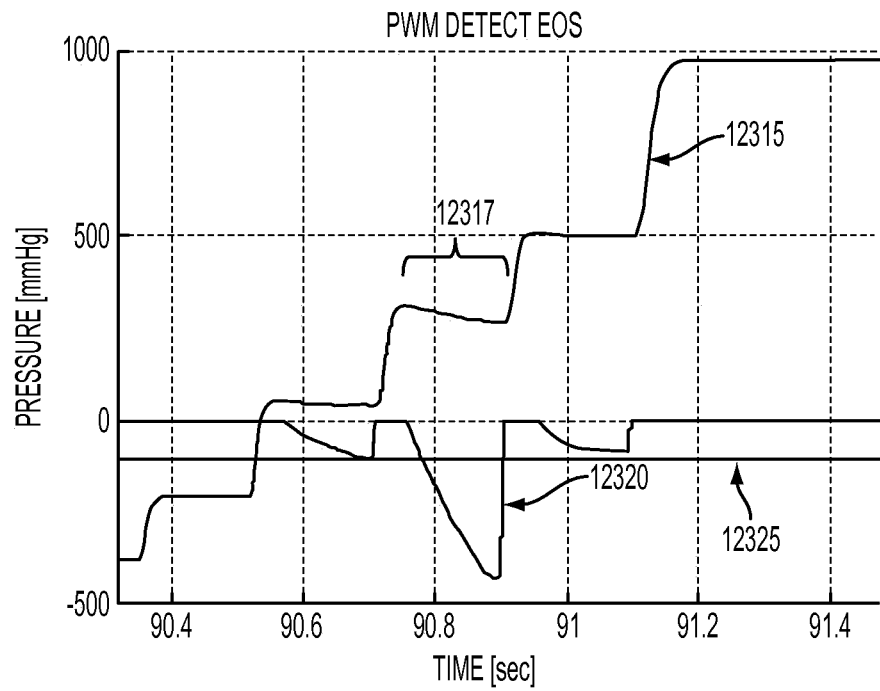

FIG. 138 is a plot of the pump pressure and integrated pressure change while valve is closed for a deliver stroke.

Figure 139:
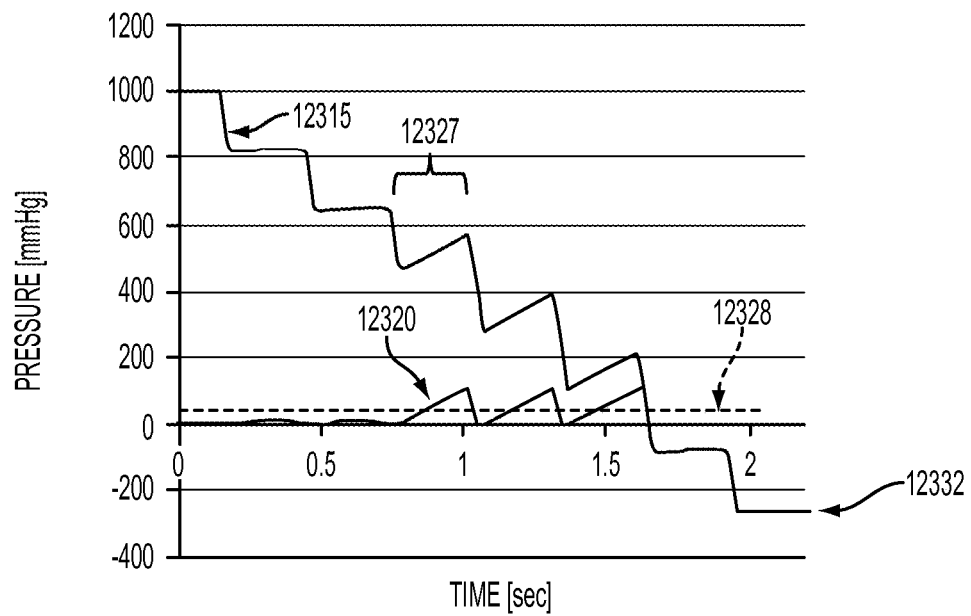

FIG. 139 is a plot of the pump pressure and integrated pressure change while valve is closed for a fill stroke.

Figure 140:
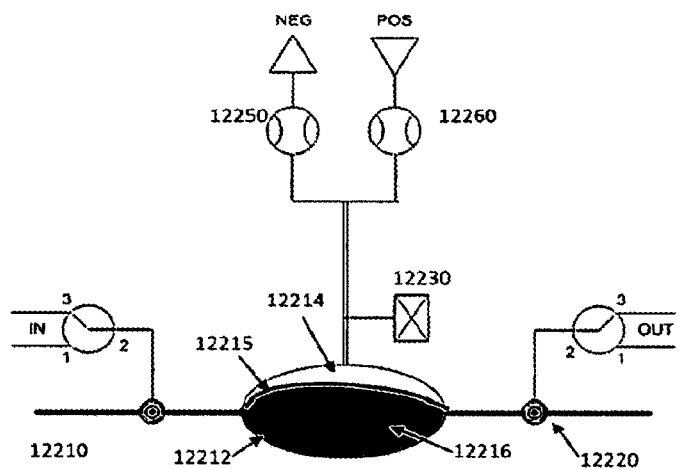

FIG. 140 is a schematic of a pressure driven diaphragm pump actuated by binary valves.

Figure 1:
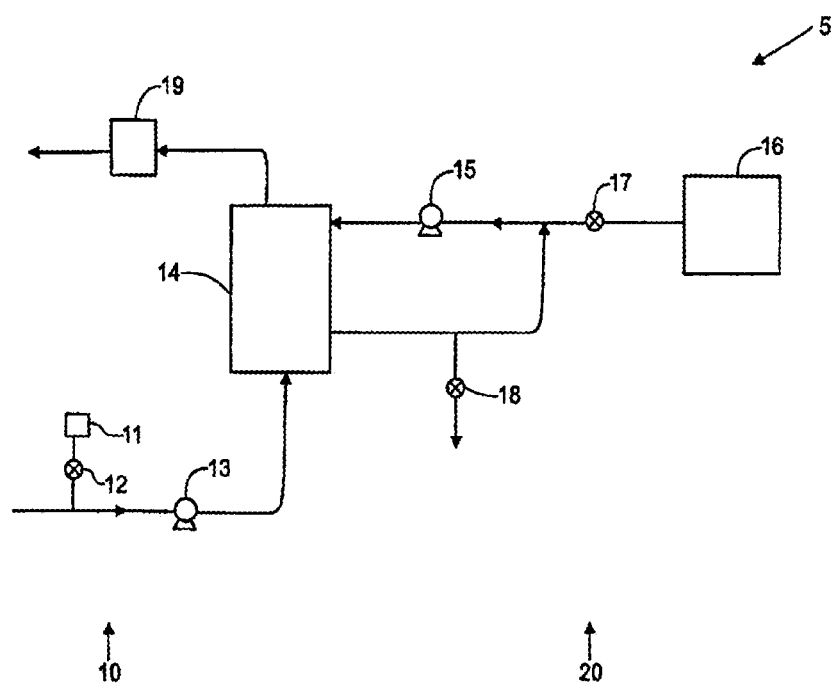
FIG. 1 is a schematic representation of a hemodialysis system.
Figure 141:
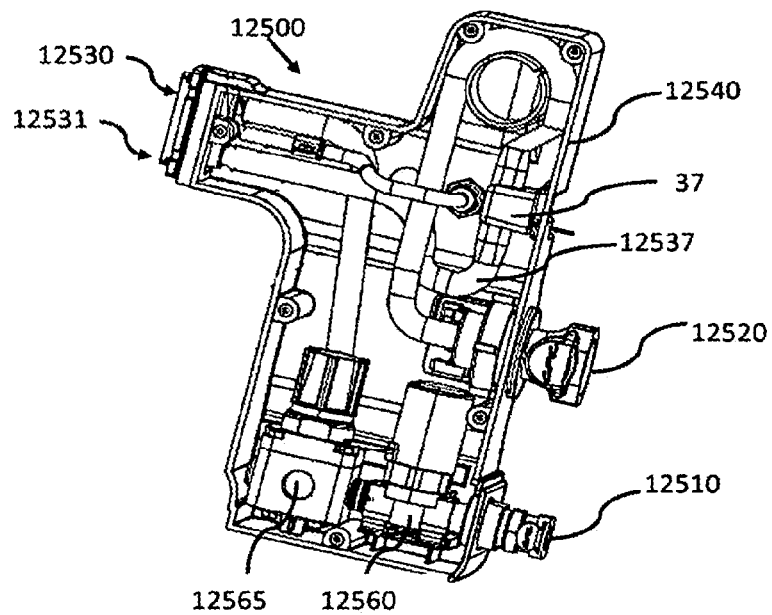
Figure 142:
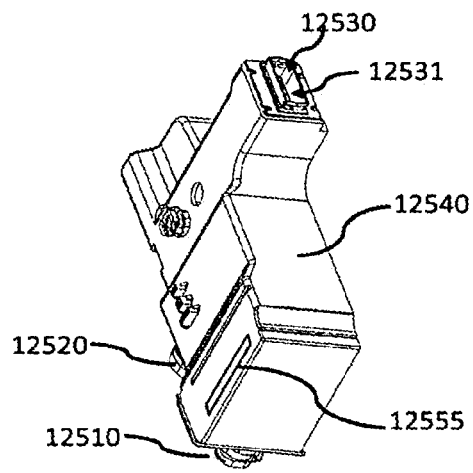
Figure 143:
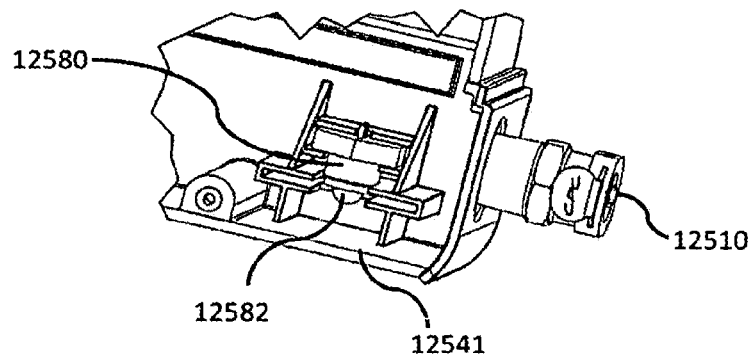
Figure 144:
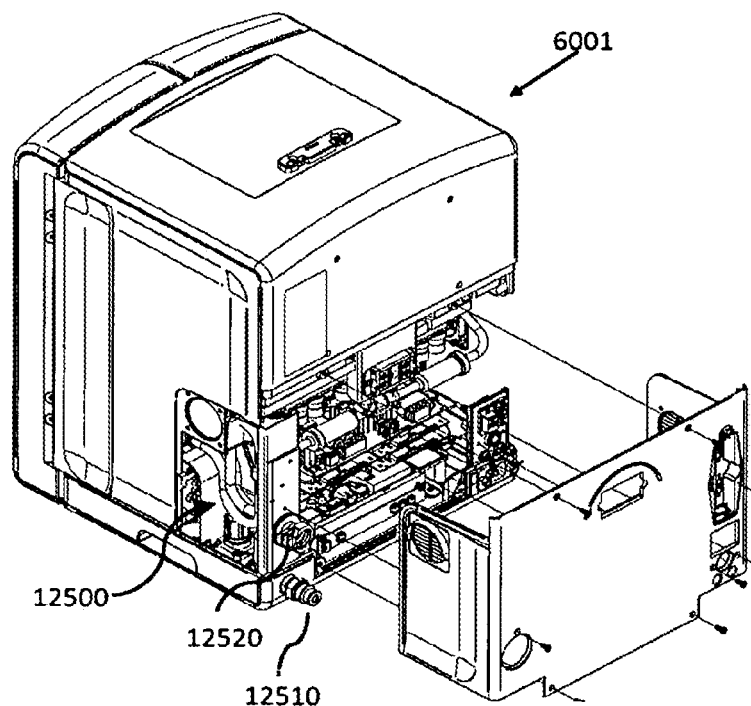
Figure 145A:
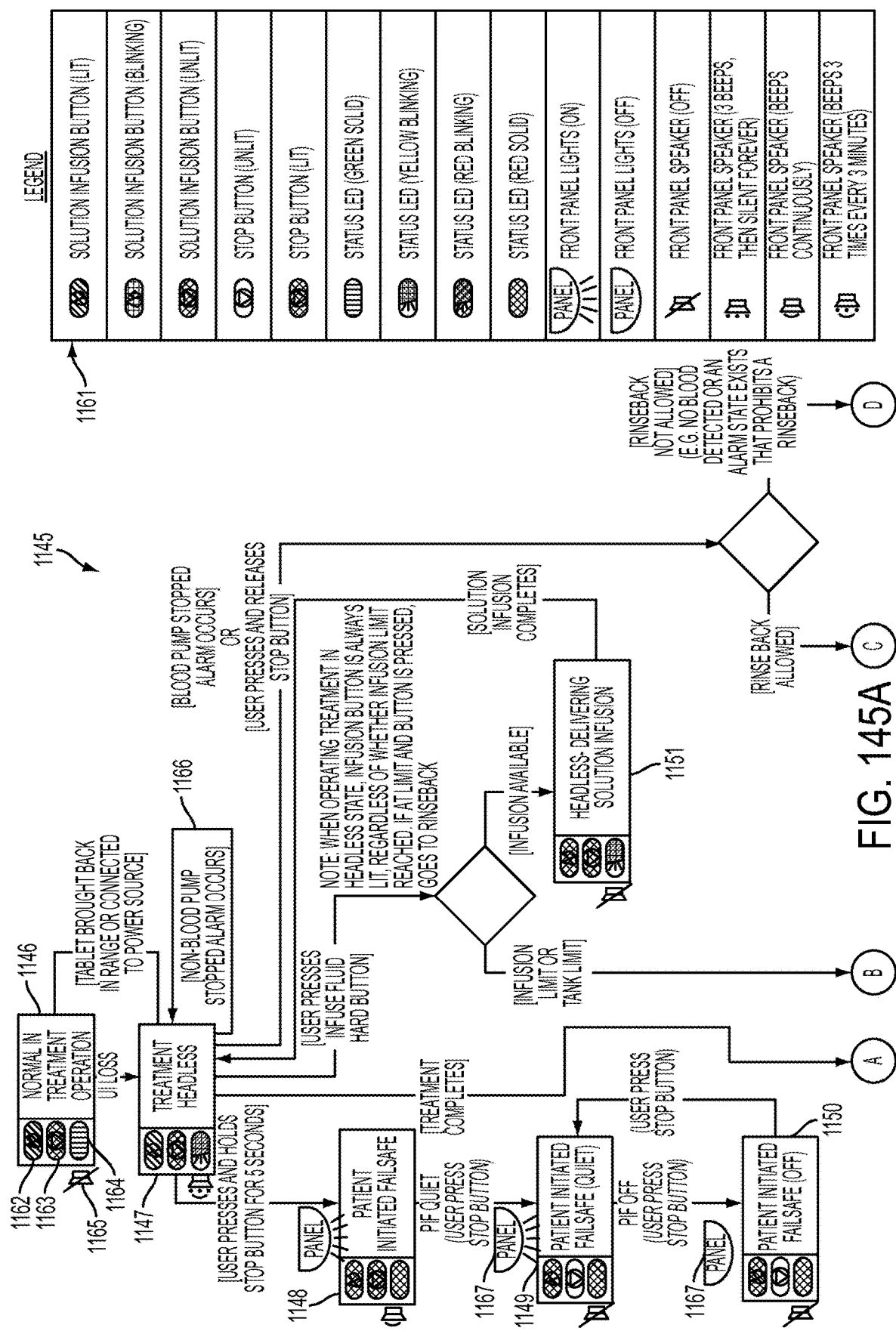
Figure 145B:
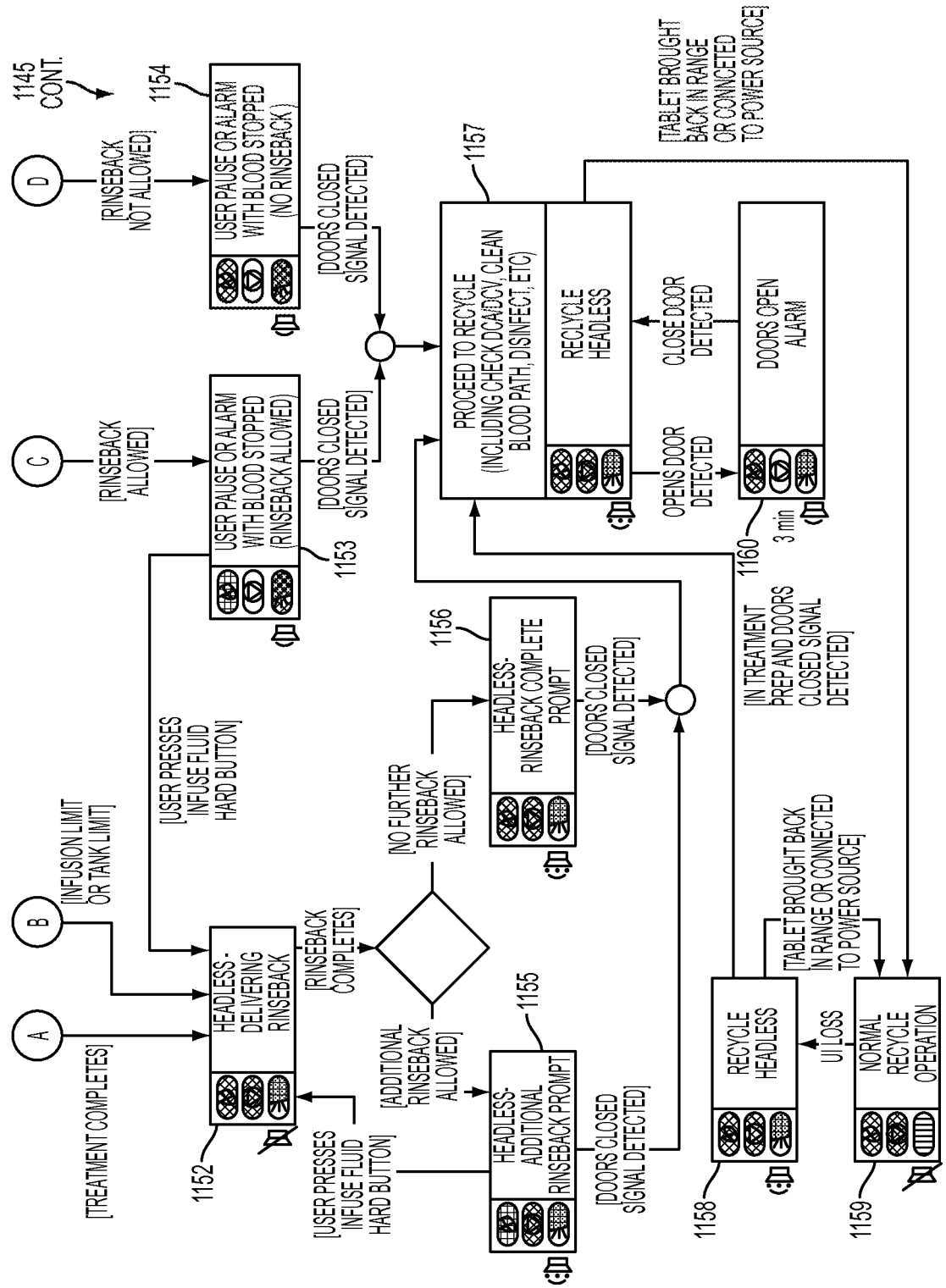
Figure 147A:
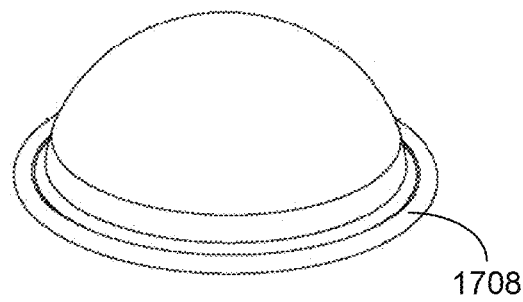
Figure 147B:
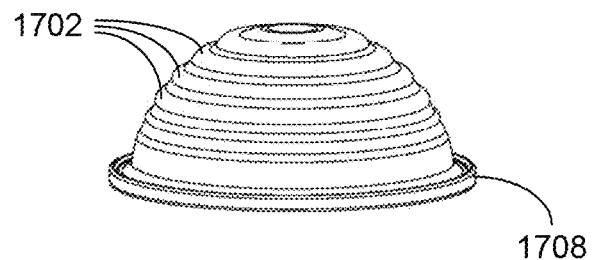
Figure 147C:
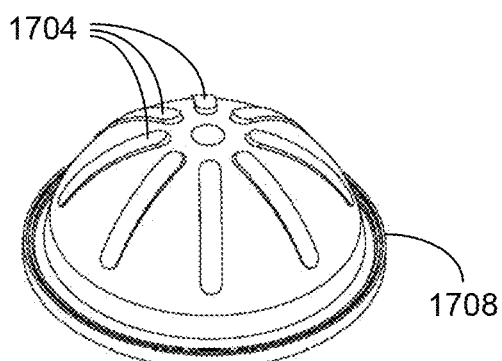
Figure 147D:
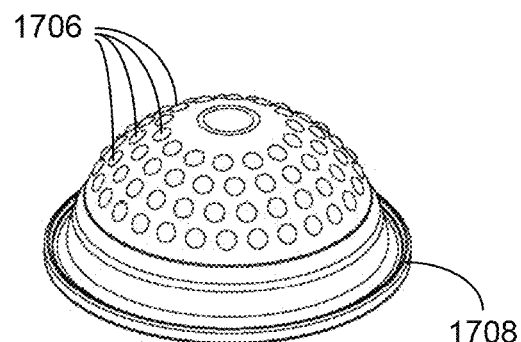
Figure 148A:
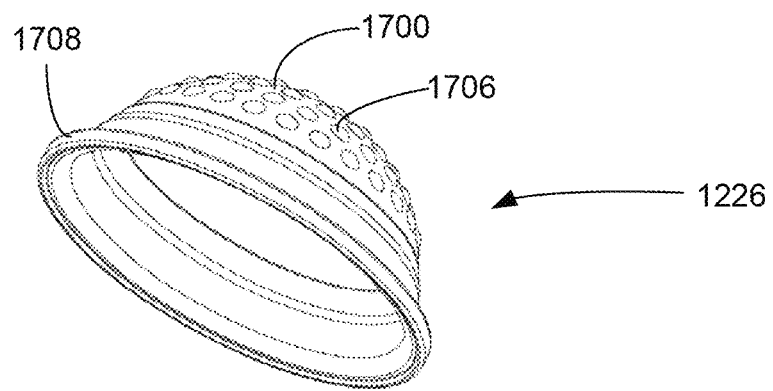
Figure 148B:
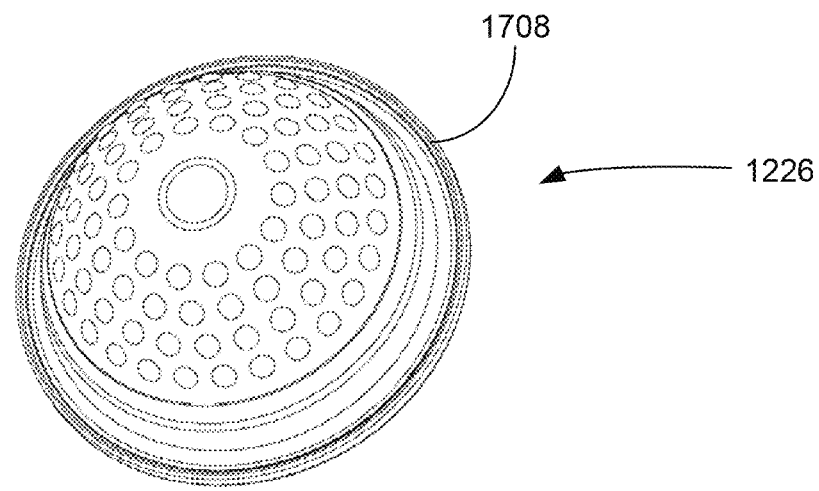
Figure 149A:
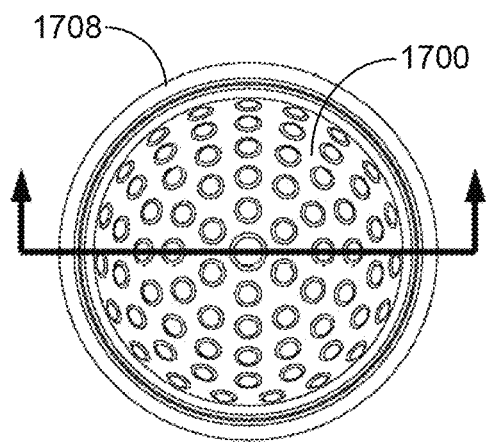
Figure 149B:
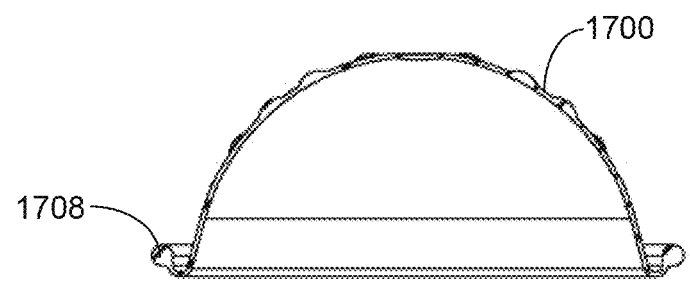
Figure 150:
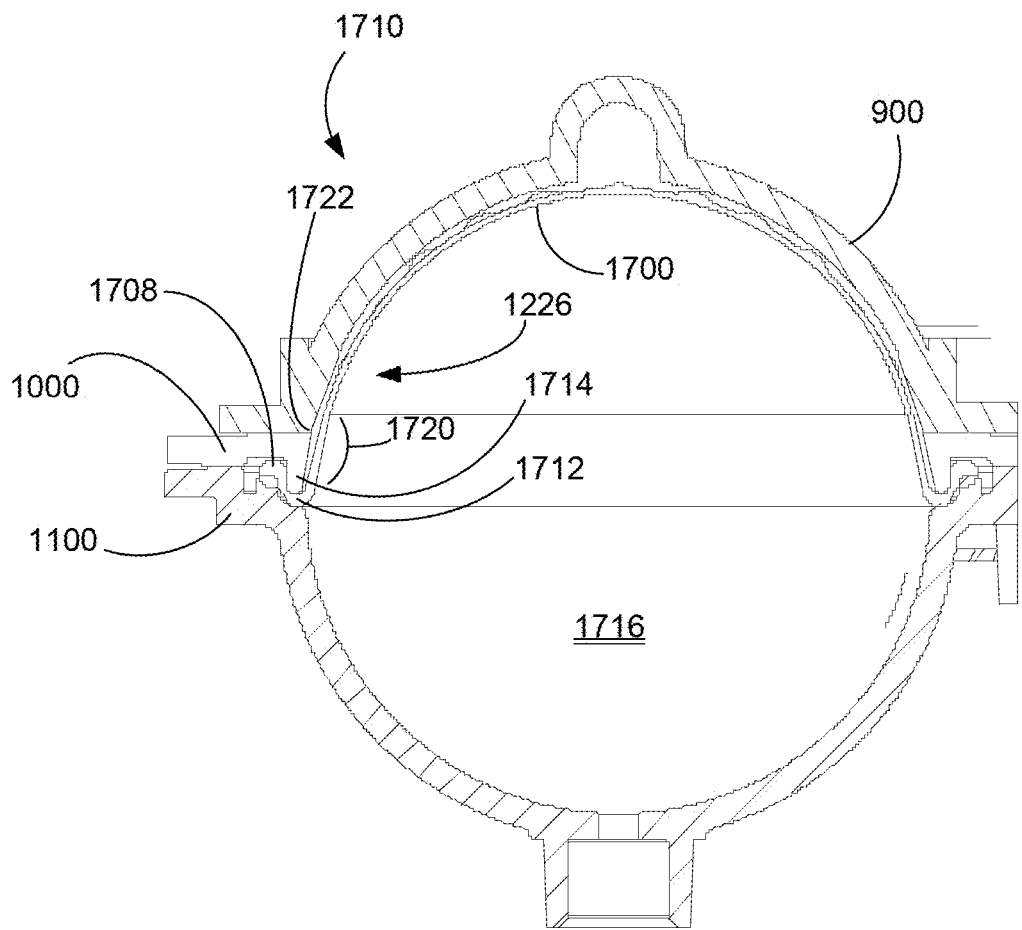
Figure 151:
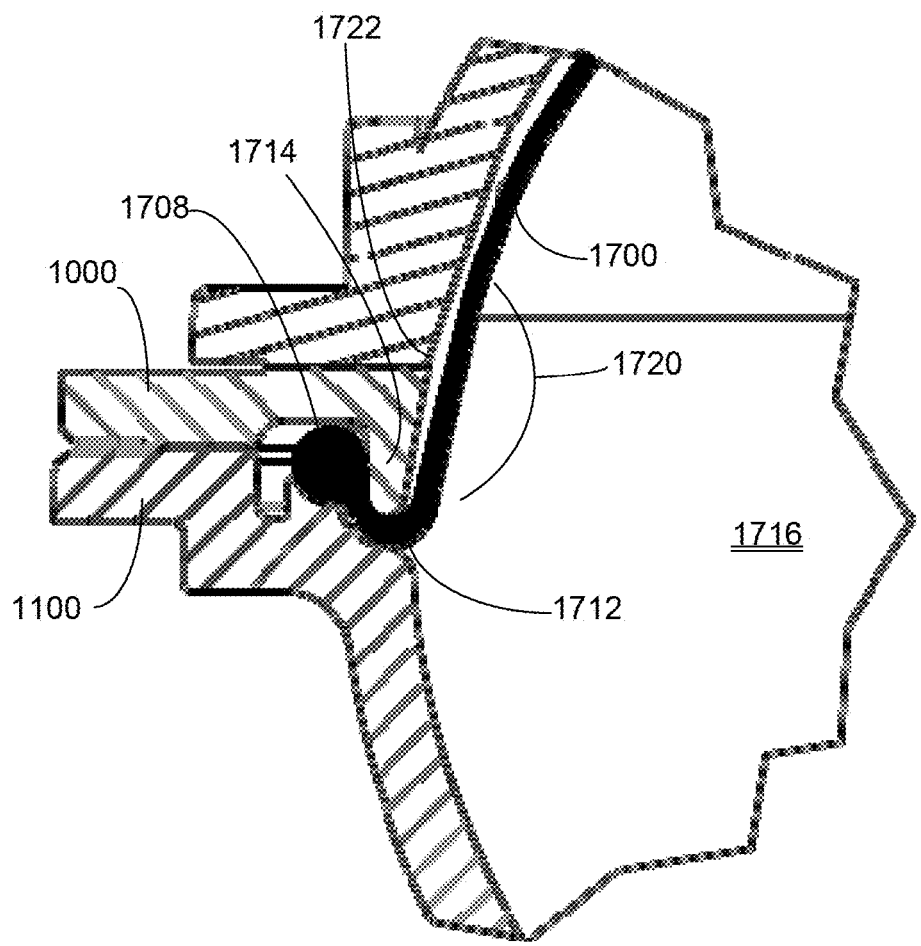
Figure 152A:
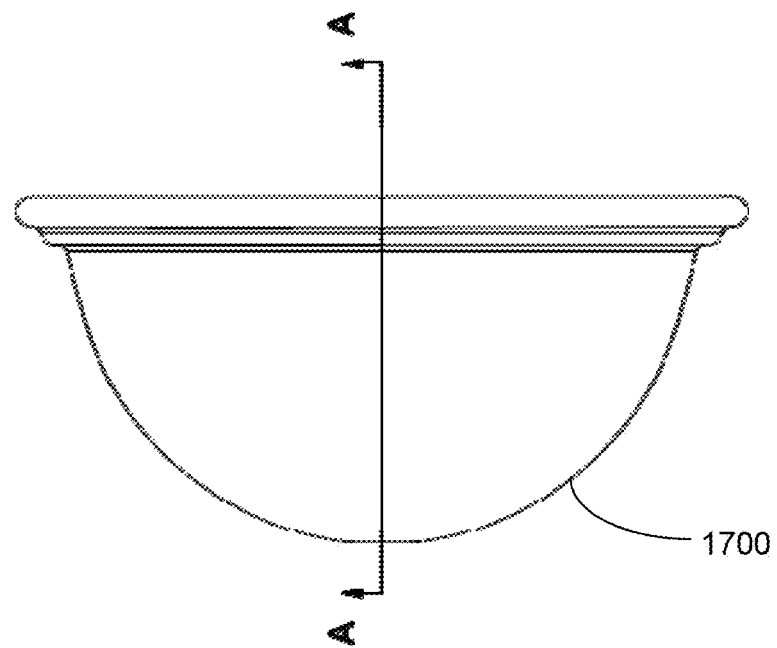
Figure 152B:
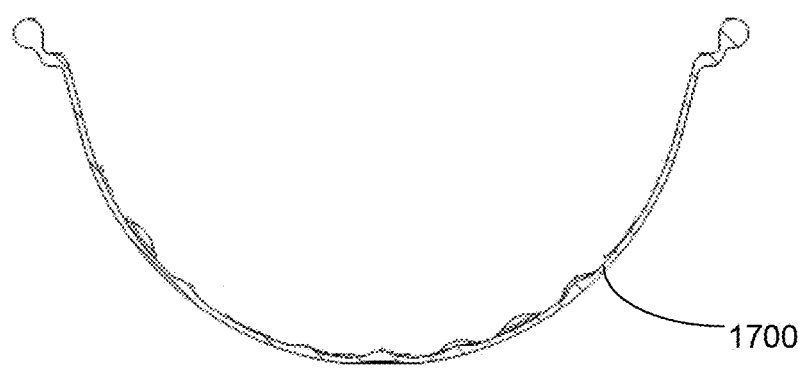
Figure 153:
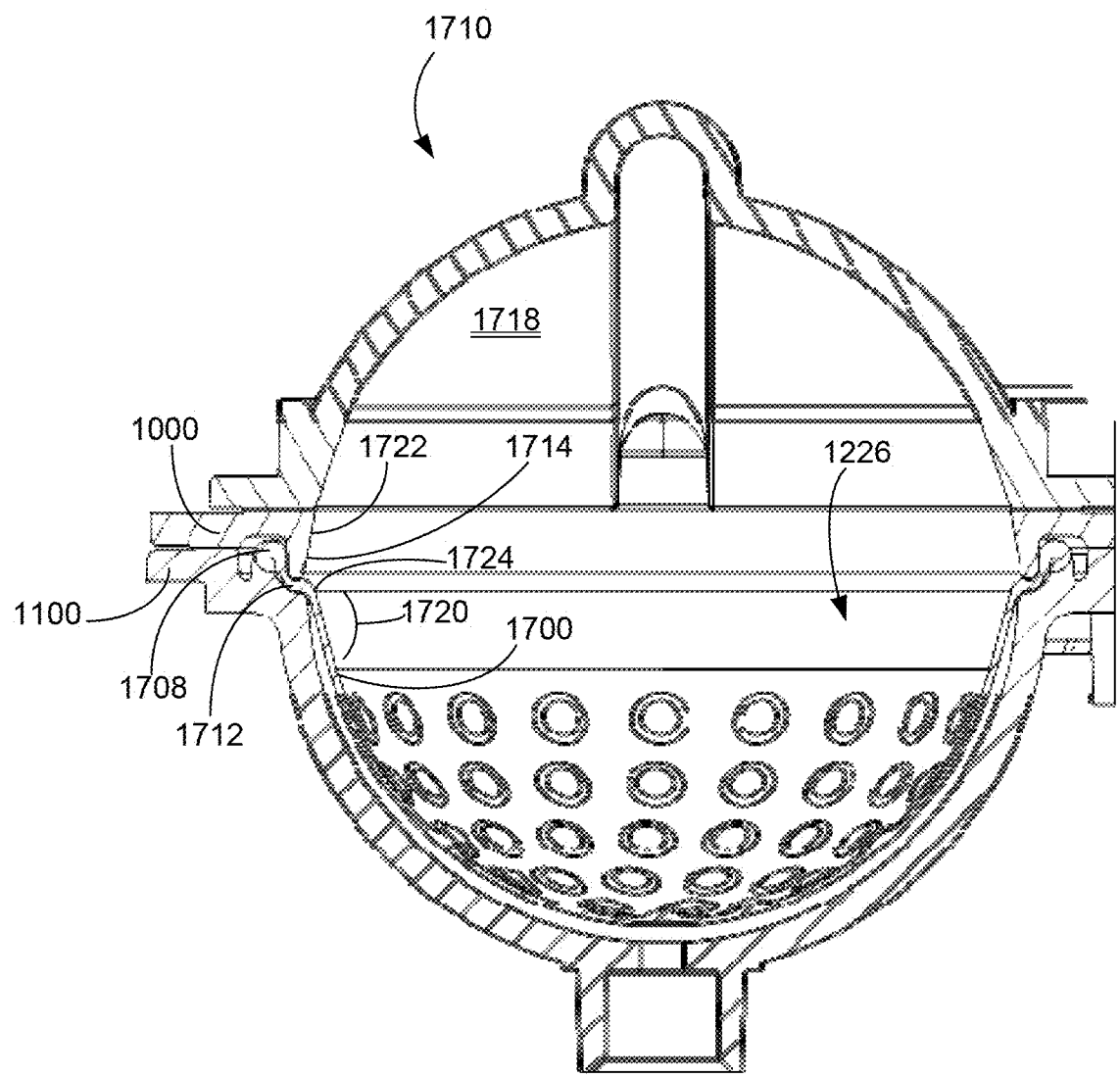
Figure 154:
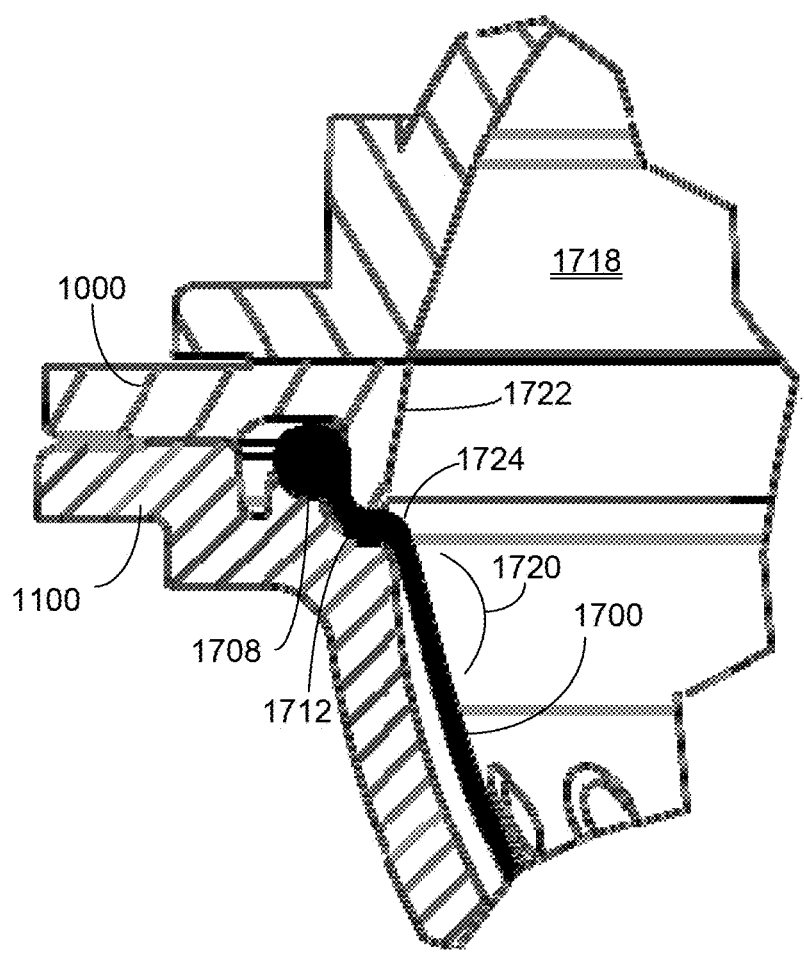
Figure 155:
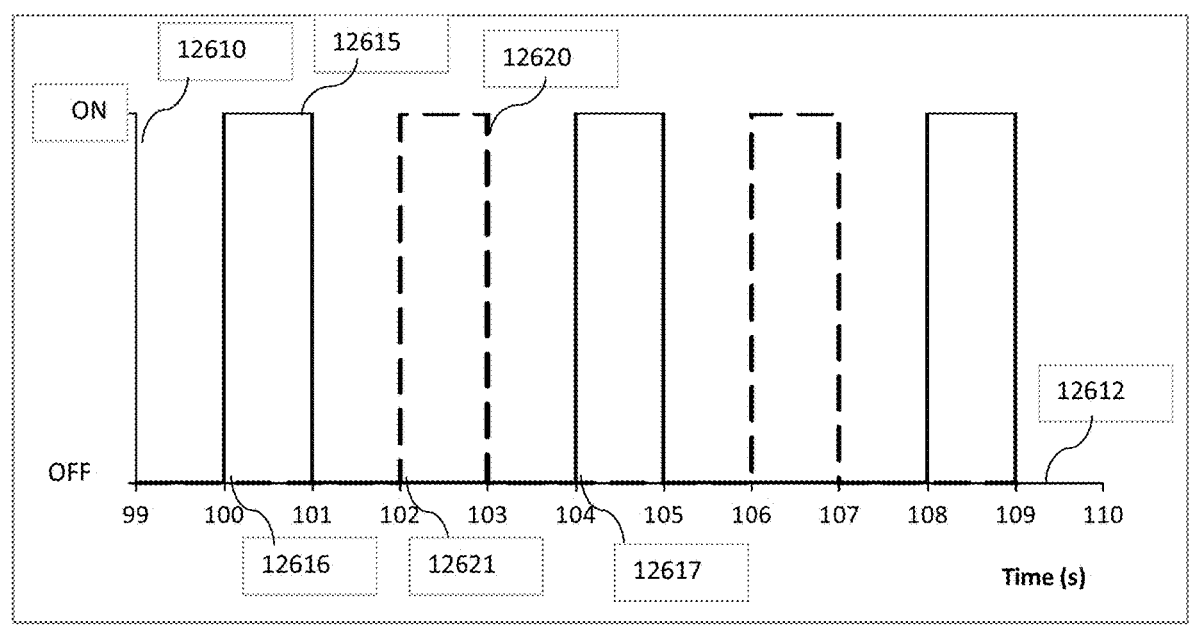
Figure 156:
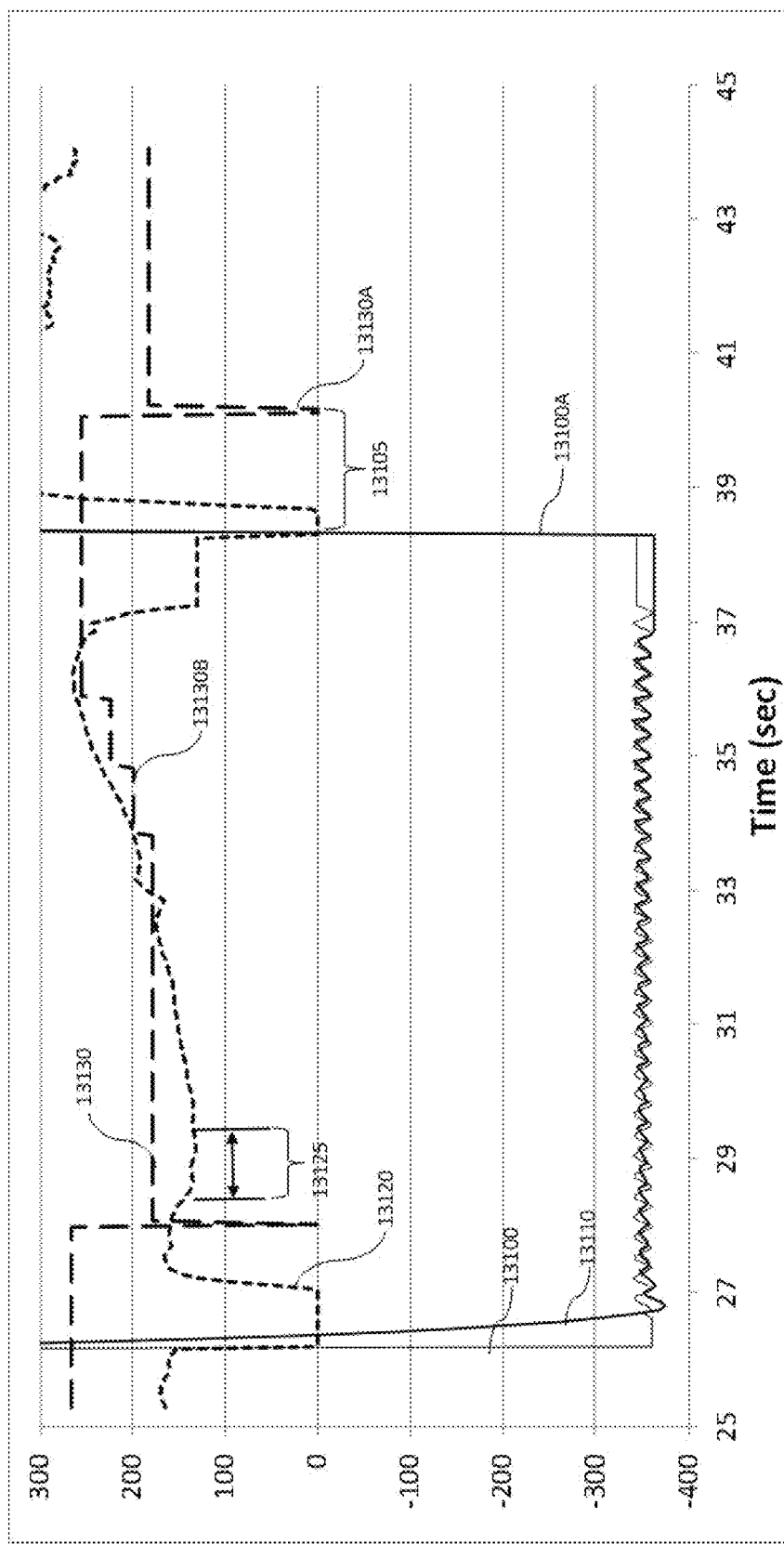
Figure 157A:
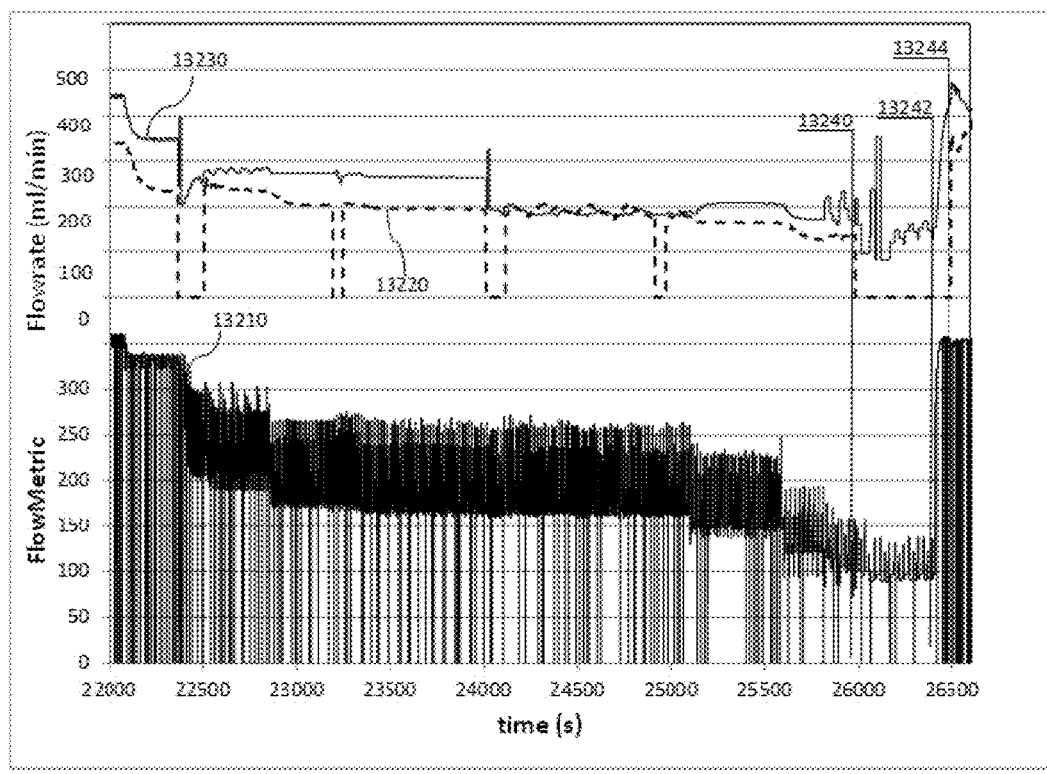
Figure 157B:
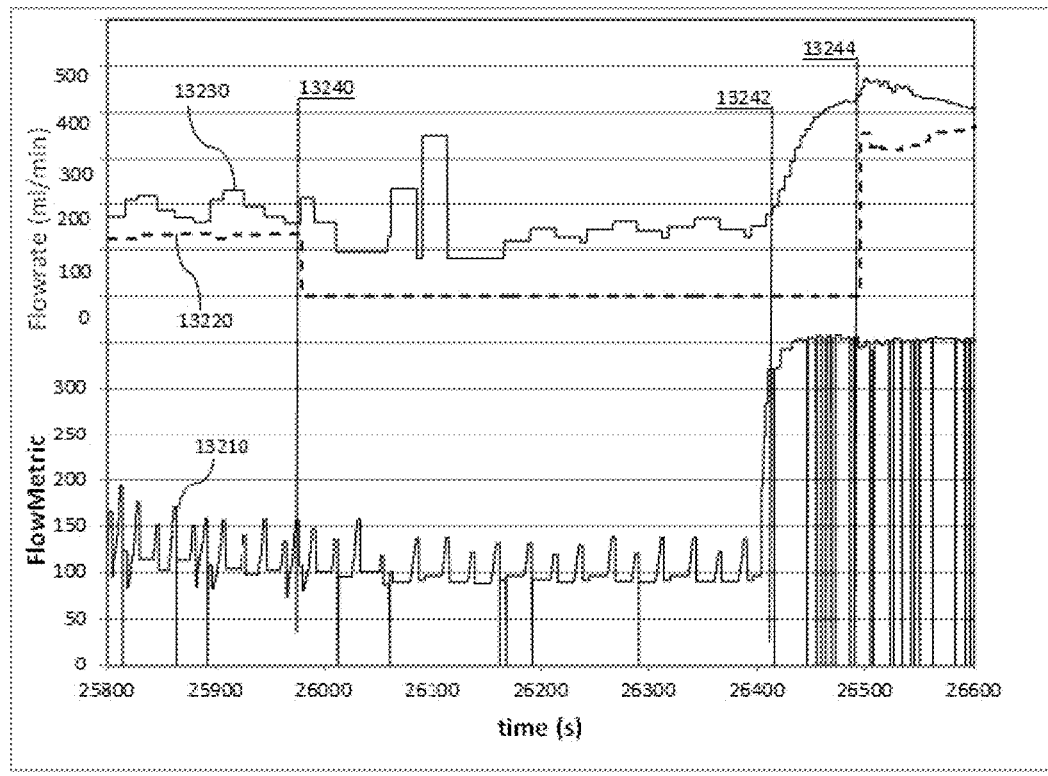

FIG. 141 is a cutaway view of a water inlet module used in a hemodialysis apparatus;

FIG. 142 is a perspective view of the water inlet module of FIG. 141;

FIG. 143 shows a water sensor used in the water inlet module of FIG. 141;

FIG. 144 shows a location for the water inlet module of FIG. 1 in a hemodialysis apparatus FIGS. 145A-145B show a state diagram that illustrates the operation of a dialysis apparatus when used with a tablet having a user interface for the dialysis apparatus in accordance with an embodiment of the present disclosure;

FIGS. 146A and 146B show an exemplary pump cassette, with FIG. 146B representing a cross sectional view of the pump cassette along the lines shown in FIG. 146A;

FIGS. 147A-147D show exemplary pump diaphragms;

FIGS. 148A and 148B show different views of a pump diaphragm having raised features or bumps on the pumping chamber side of the diaphragm;

FIGS. 149A and 149B show further views of a pump diaphragm with raised features or bumps on the body of the diaphragm, with FIG. 146B representing a cross sectional view of the diaphragm along the line shown in FIG. 146A;

FIG. 150 shows a cross sectional view of a diaphragm pump with its diaphragm disposed in the pumping chamber of the pump;

FIG. 151 shows a close-up cross sectional view of a peripheral region of the diaphragm of the pump of FIG. 150;

FIGS. 152A and 152B show an alternate embodiment of a pump diaphragm, with FIG. 152B representing a cross sectional view of the diaphragm along the line shown in FIG. 152A;

FIG. 153 shows a cross sectional view of a diaphragm pump with its diaphragm disposed in the control chamber of the pump;

FIG. 154 shows a close-up cross sectional view of a peripheral region of the diaphragm of the pump of FIG. 153;

FIG. 155 shows an exemplary plot of a dual heater arrangement in which two heater elements are controlled at 25% duty cycle;

FIG. 156 shows an exemplary pump control chamber pressure tracing and flow metric calculation of an applied and measured pressure signal during a pump fill-stroke;

FIGS. 157A and 157B show an exemplary pump control chamber pressure tracing, flow metric calculation and pump control operations during a period of progressive occlusion of a flow line connected to the inlet of a pump.

DETAILED DESCRIPTION

The present invention generally relates to hemodialysis and similar extracorporeal blood treatment systems, including a variety of systems and methods that would make hemodialysis more efficient, easier, and/or more affordable. One aspect of the invention is generally directed to new fluid circuits for fluid flow. In one set of embodiments, a hemodialysis system may include a blood flow path and a dialysate flow path, where the dialysate flow path includes one or more of a balancing circuit, a mixing circuit, and/or a directing circuit. Preparation of dialysate by the mixing circuit, in some instances, may be decoupled from patient dialysis. In some cases, the circuits are defined, at least partially, within one or more cassettes, optionally interconnected with conduits, pumps, or the like. In one embodiment, the fluid circuits and/or the various fluid flow paths may be at least partially isolated, spatially and/or thermally, from electrical components of the hemodialysis system. In some cases, a gas supply may be provided in fluid communication with the dialysate flow path and/or the dialyzer that, when activated, is able to urge dialysate to pass through the dialyzer and urge blood in the blood flow path back to the patient. Such a system may be useful, for example, in certain emergency situations (e.g., a power failure) where it is desirable to return as much blood to the patient as possible. The hemodialysis system may also include, in another aspect of the invention, one or more fluid handling devices, such as pumps, valves, mixers, or the like, which can be actuated using a control fluid, such as air. In some cases, the control fluid may be delivered to the fluid handling devices using an external pump or other device, which may be detachable in certain instances. In one embodiment, one or more of the fluid handling devices may be generally rigid (e.g., having a spheroid shape), optionally with a diaphragm contained within the device, dividing it into first and second compartments.

Various aspects of the present invention are generally directed to new systems for hemodialysis and the like, such as hemofiltration systems, hemodiafiltration systems, plasmapheresis systems, etc. Accordingly, although the various systems and methods described herein are described in relation to hemodialysis, it should be understood that the various systems and method described herein are applicable to other dialysis systems and/or in any extracorporeal system able to treat blood or other bodily fluids, such as plasma.

As discussed above, a hemodialysis system typically includes a blood flow path and a dialysate flow path. It should be noted that within such flow paths, the flow of fluid is not necessarily linear, and there may be any number of "branches" within the flow path that a fluid can flow from an inlet of the flow path to an outlet of the flow path. Examples of such branching are discussed in detail below. In the blood flow path, blood is drawn from a patient, and is passed through a dialyzer, before being returned to the patient. The blood is treated by the dialyzer, and waste molecules (e.g., urea, creatinine, etc.) and water are passed from the blood, through a semi-permeable membrane in the dialyzer, into a dialysate solution that passes through the dialyzer by the dialysate flow path. In various embodiments, blood may be drawn from the patient from two lines (e.g., an arterial line and a venous line, i.e., "dual needle" flow), or in some cases, blood may be drawn from the patient and returned through the same needle (e.g., the two lines may both be present within the same needle, i.e., "single needle" flow). In still other embodiments, a "Y" site or "T" site is used, where blood is drawn from the patient and returned to the patient through one patient connection having two branches (one being the fluid path for the drawn blood, the second the fluid path for the return blood). In an embodiment, a "Y" or "T" connection can be made with a single-lumen needle or catheter. In another embodiment, a "dual needle" flow effect can be obtained with the use of a single catheter or needle having dual lumens. The patient may be any subject in need of hemodialysis or similar treatments, although typically the patient is a human. However, hemodialysis may be performed on non-human subjects, such as dogs, cats, monkeys, and the like.

In the dialysate flow path, fresh dialysate is prepared and is passed through the dialyzer to treat the blood from the blood flow path. The dialysate may also be equalized for blood treatment within the dialyzer (i.e., the pressure between the dialysate and the blood are equalized), i.e., the pressure of dialysate through the dialyzer is closely matched to the pressure of blood through the dialyzer, often exactly, or in some embodiments, at least within about 1% or about 2% of the pressure of the blood. In some cases, it may be desirable to maintain a greater pressure difference (either positive or negative) between the blood flow path and dialysate flow path. After passing through the dialyzer, the used dialysate, containing waste molecules (as discussed below), is discarded in some fashion. In some cases, the dialysate is heated prior to treatment of the blood within the dialyzer using an appropriate heater, such as an electrical resistive heater. The dialysate may also be filtered to remove contaminants, infectious organisms, debris, and the like, for instance, using an ultrafilter. The ultrafilter may have a mesh or pore size chosen to prevent species such as these from passing therethrough. For instance, the mesh or pore size may be less than about 0.3 micrometers, less than about 0.2 micrometers, less than about 0.1 micrometers, or less than about 0.05 micrometers, etc. The dialysate is used to draw waste molecules (e.g., urea, creatinine, ions such as potassium, phosphate, etc.) and water from the blood into the dialysate through osmosis or convective transport, and dialysate solutions are well-known to those of ordinary skill in the art.

The dialysate typically contains various ions such as sodium chloride, bicarbonate, potassium and calcium that are similar in concentration to that of normal blood. In some cases, the bicarbonate, may be at a concentration somewhat higher than found in normal blood. Typically, the dialysate is prepared by mixing water from a water supply with one or more ingredients: an "acid" (which may contain various species such as acetic acid, dextrose, NaCl, CaCl, KCl, MgCl, etc.), sodium bicarbonate ($NaHCO_3$), and/or sodium chloride (NaCl). The preparation of dialysate, including using the appropriate concentrations of salts, osmolarity, pH, and the like, is well-known to those of ordinary skill in the art. As discussed in detail below, the dialysate need not be prepared at the same rate that the dialysate is used to treat the blood. For instance, the dialysate can be made concurrently or prior to dialysis, and stored within a dialysate storage vessel or the like.

Within the dialyzer, the dialysate and the blood typically do not come into physical contact with each other, and are separated by a semi-permeable membrane. Typically, the semipermeable membrane is formed from a polymer such as cellulose, polyarylethersulfone, polyamide, polyvinylpyrrolidone, polycarbonate, polyacrylonitrile, or the like, which allows the transport of ions or small molecules (e.g., urea, water, etc.), but does not allow bulk transport or convection during treatment of the blood. In some cases, even larger molecules, such as beta-2-microglobulin, may pass through the membrane. In other cases, convective transfer of fluid, ions and small molecules can occur, for example, when there is a hydrostatic pressure difference across the semi-permeable membrane.

The dialysate and the blood do not come into contact with each other in the dialyzer, and are usually separated by the membrane. Often, the dialyzer is constructed according to a "shell-and-tube" design comprising a plurality of individual tubes or fibers (through which blood flows), formed from the semipermeable membrane, surrounded by a larger "shell" through which the dialysate flows (or vice versa in some cases). Flow of the dialysate and the blood through the dialyzer can be countercurrent, or concurrent in some instances. Dialyzers are well-known to those of ordinary skill in the art, and are obtainable from a number of different commercial sources.

In one aspect, the dialysate flow path can be divided into one or more circuits, such as a balancing circuit, a mixing circuit, and/or a directing circuit. It should be noted that a circuit, in reference to fluid flow, is not necessarily fluidically isolated, i.e., fluid may flow into a fluid circuit and out of a fluid circuit. Similarly, a fluid may pass from one fluid circuit to another fluid circuit when the fluid circuits are in fluid communication or are fluidly connected to each other. It should be noted that, as used herein, "Fluid" means anything having fluidic properties, including but not limited to, gases such as air, and liquids such as water, aqueous solution, blood, dialysate, etc.

A fluid circuit is typically a well-defined module that receives a certain number of fluid inputs and in some cases performs one or more tasks on the fluid inputs, before directing the fluids to appropriate outputs. In certain embodiments of the invention, as discussed below, the fluid circuit is defined as a cassette. As a specific example, a dialysate flow path may include a balancing circuit, a directing circuit, and a mixing circuit. As another example, a blood flow path may include a blood flow circuit. Within the balancing circuit, dialysate is introduced into the balancing circuit and pumps operate on the dialysate such that the pressure of dialysate passing through the dialyzer balances the pressure of blood passing through the dialysate, as previously discussed. Similarly, within the directing circuit, fresh dialysate is passed from the mixing circuit to the balancing circuit, while used dialysate is passed from the balancing circuit to a drain. Within the mixing circuit, ingredients and water are mixed together to form fresh dialysate. The blood flow circuit is used to draw blood from the patient, pass the blood through a dialyzer, and return the blood to the patient. These circuits will be discussed in detail below.

Figure 2A:
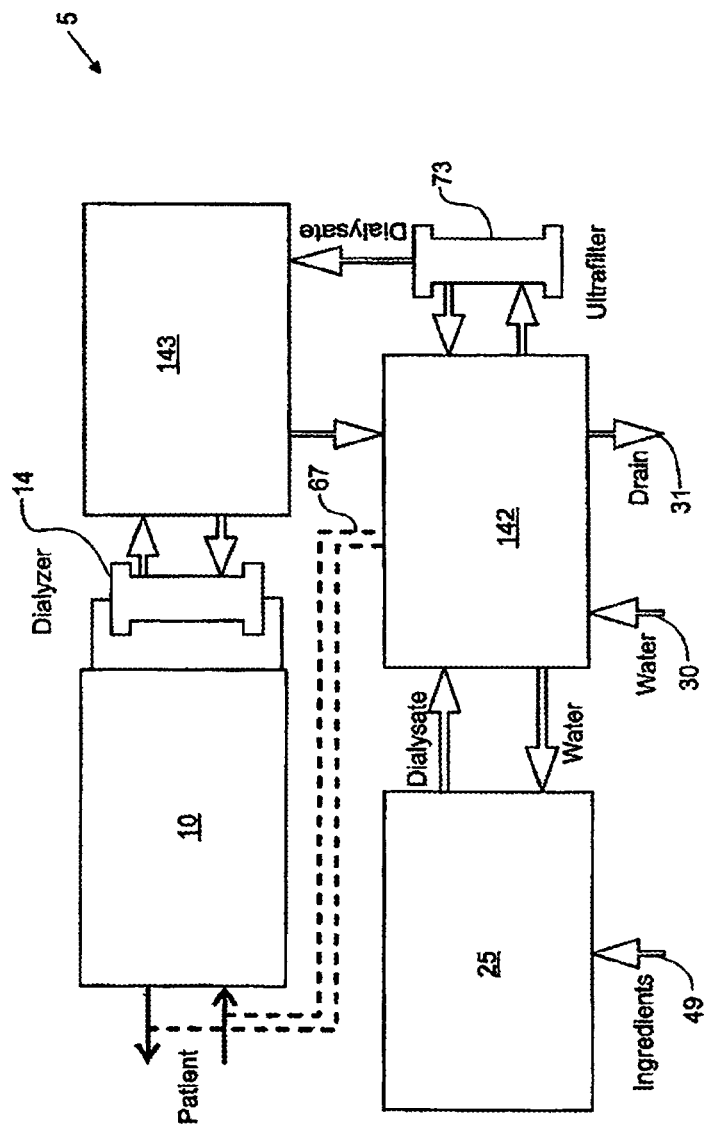
FIGS. 2A-2B are high-level schematics of various embodiments of a dialysis system.

An example of a hemodialysis system having such fluid circuits is illustrated schematically in FIG. 2A as a high-level overview. FIG. 2A illustrates a dialysis system 5 that includes a blood flow circuit 10, through which blood passes from a patient to a dialyzer 14, and through which treated blood returns to the patient. The hemodialysis system in this example also includes a balancing circuit 143 (part of an internal or inner dialysate circuit), which takes dialysate after it passes through an ultrafilter 73 and passes the dialysate through dialyzer 14, with used dialysate returning to balancing circuit 143 from dialyzer 14. A directing circuit 142 (part of an external or outer dialysate circuit) handles fresh dialysate before it passes through ultrafilter 73. A mixing circuit 25 prepares dialysate, for instance, on an as-needed basis, during and/or in advance of dialysis, etc., using various ingredients 49 and water. The directing circuit 142 can also receive water from a water supply 30 and pass it to mixing circuit 25 for preparation of the dialysate, and the directing circuit 142 can also receive used dialysate from balancing circuit 143 and pass it out of system 5 as waste via drain 31. Also shown, in dotted lines, are conduits 67 that can be connected between blood flow circuit 10, and directing circuit 142, e.g., for disinfection of the hemodialysis system. In one set of embodiments, one or more of these circuits (e.g., the blood flow circuit, the balancing circuit, the directing circuit, and/or the mixing circuit) may include a cassette incorporating the valves and pumps needed for controlling flow through that portion. Examples of such systems are discussed in detail below.

Figure 2B:
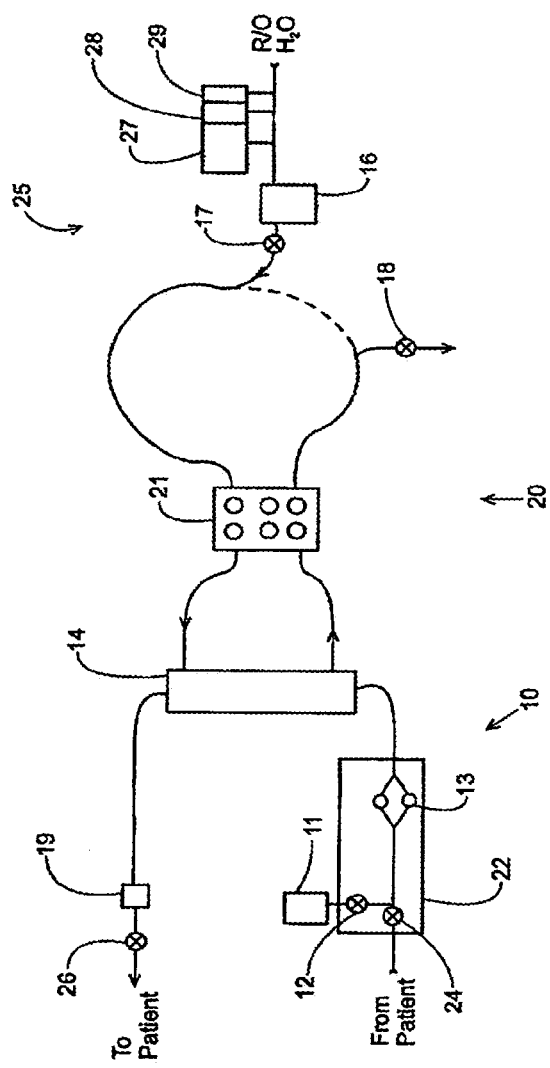

FIG. 2B is a schematic representation of a hemodialysis system according to one embodiment of the invention. In this schematic, a blood flow cassette 22 is used to control flow through the blood flow circuit 10, and a dialysate cassette 21 is used to control flow through the dialysate circuit. The blood flow cassette includes at least one inlet valve 24 (in other embodiments, more than one inlet valve is included) to control the flow of blood through cassette 22 as well as an anticoagulant valve or pump 12 to control the flow of anticoagulant into the blood, and a blood flow pump 13, which may include a pair of pod pumps in some cases. These pod pumps may be of the type (or variations of the type) as described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each of which is incorporated herein in its entirety. All the pumps and valves in this example system may be controlled by a control system, e.g., an electronic and digital control system, although other control systems are possible in other embodiments.

Providing two pod pumps may allow for a more continuous flow of blood through the blood flow circuit 10; however, a single pod pump, such as a single pod pump may be used in other embodiments. The pod pumps may include active inlet and outlet valves (instead of passive check valves at their inlets and outlets) so that flow in the blood flow circuit 10 may be reversed under some conditions. For instance, by reversing flow in the blood flow circuit, the hemodialysis system can check whether the outlet of the blood flow circuit is properly connected to the patient so that the treated blood is correctly returned to the patient. If, for example, the patient connection point has been disconnected, e.g., by falling out, reversing the blood flow pump would draw air rather than blood. This air can be detected by standard air detectors incorporated into the system.

In another embodiment, blood outlet valve 26 and air trap/filter 19, which are located downstream of the dialyzer, may be incorporated into blood flow cassette 22. The pod pumps and all the valves (including the valves associated with the pod pumps' inlets and outlets) in the blood flow cassette 22 may be actuated pneumatically. Sources of positive and negative gas pressure in one embodiment, are provided by a base unit holding cassette or other device holding the cassette. However, in other embodiments, the positive and negative gas pressure may be provided by an external device fluidly connected to the cassettes, or any device build into the system The pump chamber may be actuated in the manner described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," referred to hereinabove. For instance, the pumps may be controlled and the end of stroke detected in the manner described below. The blood flow cassette 22 may also contain an integrally formed spike for receiving a vial of anticoagulant.

The anticoagulant pump, in one embodiment, includes three fluid valves (which may be controlled with a control fluid) and a single pumping compartment (although there may be more than one pumping compartment in other embodiments. The valves may connect the compartment to a filtered air vent, to a vial of anticoagulant (or other anticoagulant supply, such as a bag or a bottle, etc.), or to the blood flow path. The anticoagulant pump can be operated by sequencing the opening and closing of the fluid valves and controlling the pressure in the pump compartment, e.g., via the control fluid. When the anticoagulant is removed from the vial it may be replaced with an equal volume of air, e.g., to keep pressure within the vial relatively constant. This replacement of anticoagulant volume with air may be accomplished, for example, by (i) opening the valve from the filtered air vent to the pump compartment, (ii) drawing air into the compartment by connecting the negative pressure source to the chamber, (iii) closing the air vent valve, (iv) opening the valve connecting the compartment to the vial, and (v) pushing air into the vial by connecting the positive pressure source to the compartment. The anticoagulant can be pumped from the vial into the blood flow path with a similar sequence, using the valves to the vial and the blood path rather than the valves to the air vent and the vial.

Figure 3A:
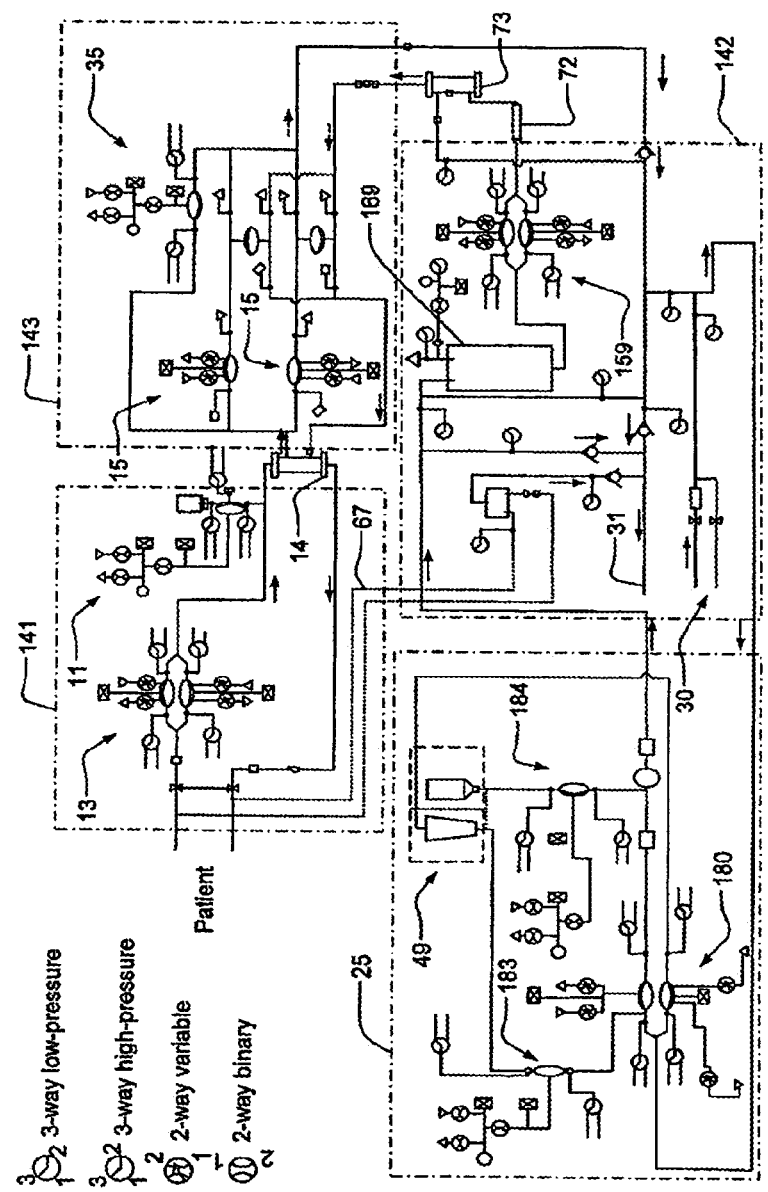
FIGS. 3A-3B are schematics showing an example of a fluid schematic for a dialysis system.

FIG. 3A is a schematic diagram showing a specific embodiment of the general overview shown in FIG. 2A. FIG. 3A shows, in detail, how a blood flow circuit 141, a balancing circuit 143, a directing circuit 142, and a mixing circuit 25 can be implemented on cassettes and made to interrelate with each other and to a dialyzer 14, an ultrafilter 73, and/or a heater 72, in accordance with one embodiment of the invention. It should be understood, of course, that FIG. 3A is only one possible embodiment of the general hemodialysis system of FIG. 2A, and in other embodiments, other fluid circuits, modules, flow paths, layouts, etc. are possible. Examples of such systems are discussed in more detail below, and also can be found in the following, each of which is incorporated herein by reference: U.S. Provisional Patent Application Ser. No. 60/903,582, filed Feb. 27, 2007, entitled "Hemodialysis System and Methods"; U.S. Provisional Patent Application Ser. No. 60/904,024, filed Feb. 27, 2007, entitled "Hemodialysis System and Methods"; U.S. patent application Ser. No. 11/871,680, filed Oct. 12, 2007, entitled "Pumping Cassette"; U.S. patent application Ser. No. 11/871,712, filed Oct. 12, 2007, entitled "Pumping Cassette"; U.S. patent application Ser. No. 11/871,787, filed Oct. 12, 2007, entitled "Pumping Cassette"; U.S. patent application Ser. No. 11/871,793, filed Oct. 12, 2007, entitled "Pumping Cassette"; or U.S. patent application Ser. No. 11/871,803, filed Oct. 12, 2007, entitled "Cassette System Integrated Apparatus."

The components in FIG. 3A will be discussed in detail below. Briefly, blood flow circuit 141 includes an anticoagulant supply 11 and a blood flow pump 13 which pumps blood from a patient to a dialyzer 14. The anticoagulant supply 11, although shown in the path of blood flowing towards the dialyzer, in other embodiments, may be instead located in the path of blood flowing towards the patient, or in another suitable location, such as upstream or downstream of blood flow pump 13. The anticoagulant supply 11 may be placed in any location downstream from blood flow pump 13. Balancing circuit 143 includes two dialysate pumps 15, which also pump dialysate into dialyzer 14, and a bypass pump 35. Directing circuit 142 includes a dialysate pump 159, which pumps dialysate from dialysate tank 169 through heater 72 and/or ultrafilter 73 to the balancing circuit. Directing circuit 142 also takes waste fluid from balancing circuit 143 and directs it to a drain 31. In some cases, the blood flow circuit 141 can be connected via conduits 67 to directing circuit 142, e.g., for disinfection, as discussed below. Dialysate flows into dialysate tank 169 from a dialysate supply.

In certain embodiments, the invention provides methods for making dialysate from water contained within or supplied to the system and at least one supply of solutes contained within or supplied to the system. For example, as is shown in FIGS. 3A, 3B, 7A and 7B the dialysate is produced in mixing circuit 25. Water from water supply 30 flows through directing circuit 142 into mixing circuit 25. Dialysate ingredients 49 (e.g., bicarbonate and acid) are also added into mixing circuit 25, and a series of mixing pumps 180, 183, 184 are used to produce the dialysate, which is then sent to directing circuit 142. This method, and the control thereof, to ensure acceptable dialysate quality is produced and maintained during treatment is described in more detail below.

In this example system, one of the fluid circuits is a blood flow circuit, e.g., blood flow circuit 141 in FIG. 3A. In the blood flow circuit, blood from a patient is pumped through a dialyzer and then is returned to the patient. In some cases, blood flow circuit is implemented on a cassette, as discussed below, although it need not be. The flow of blood through the blood flow circuit, in some cases, is balanced with the flow of dialysate flowing through the dialysate flow path, especially through the dialyzer and the balancing circuit.

Figure 4A:
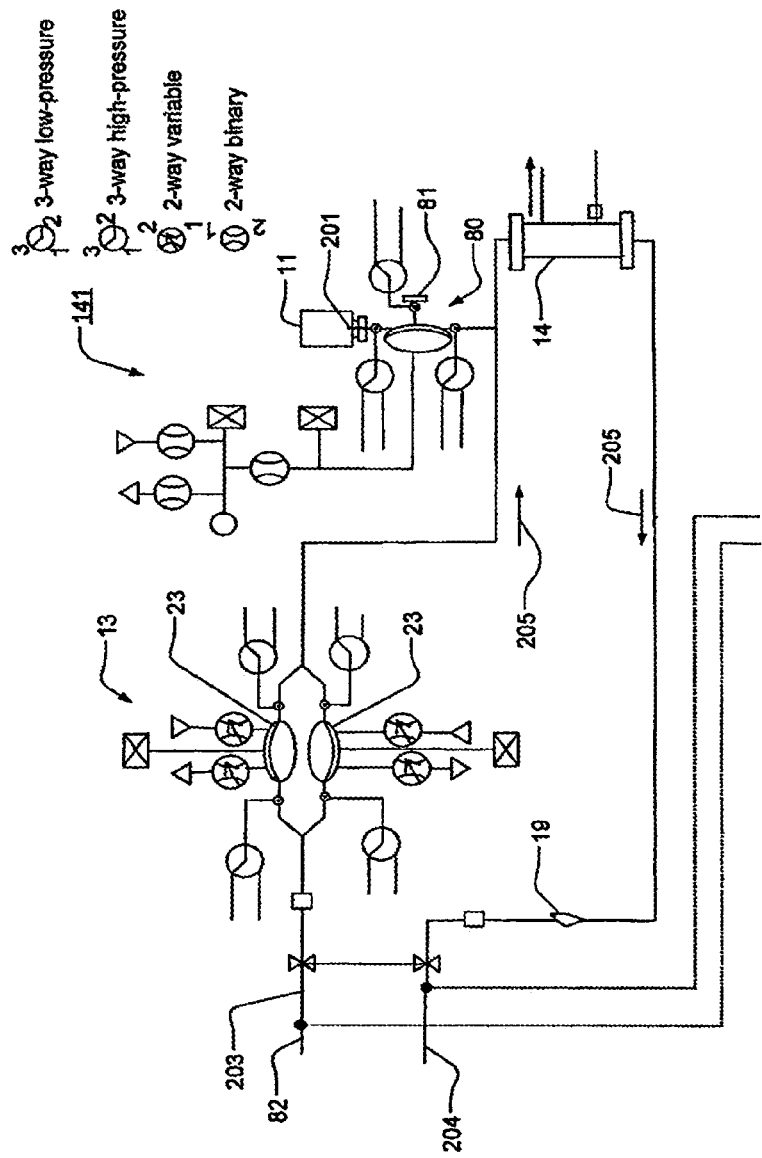
FIGS. 4A-4B are schematic representations of various embodiments of a blood flow circuit that may be used in a hemodialysis system.
Figure 4B:
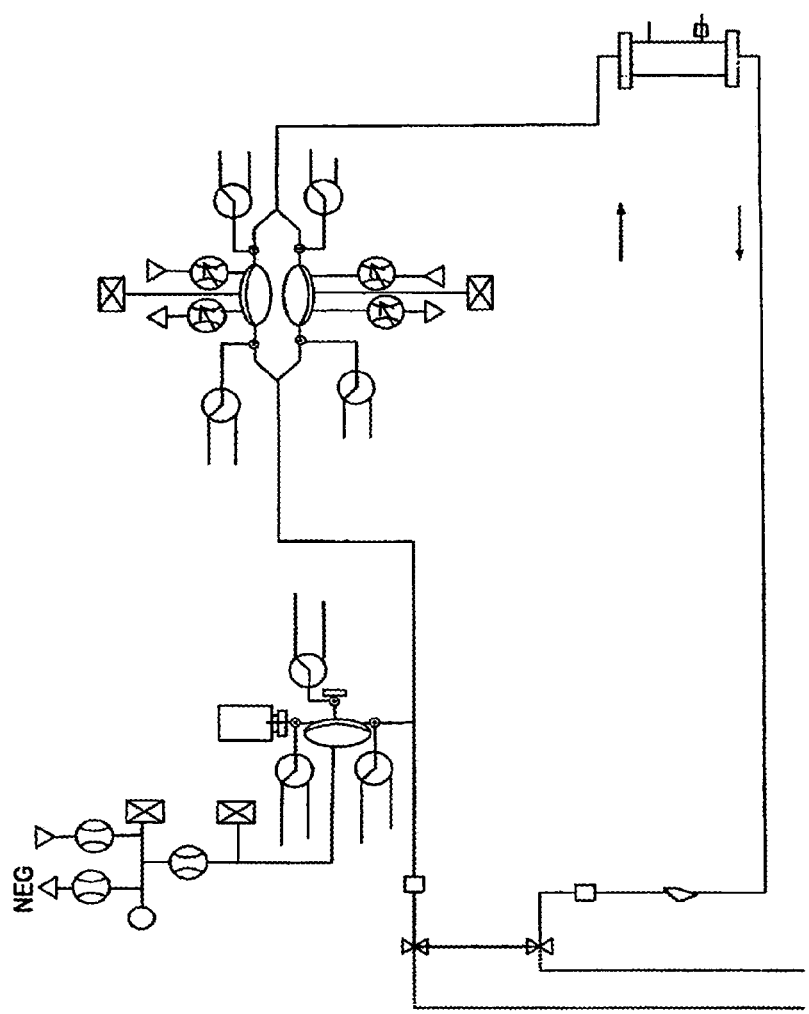

One example of a blood flow circuit is shown in FIG. 4A. Generally, blood flows from a patient through arterial line 203 via blood flow pump 13 to dialyzer 14 (the direction of flow during normal dialysis is indicated by arrows 205; in some modes of operation, however, the flow may be in different directions, as discussed below). Optionally, an anticoagulant may be introduced into the blood via anticoagulant pump 80 from an anticoagulant supply. As shown in FIG. 4A, the anticoagulant can enter the blood flow path after the blood has passed through blood flow pump 13; however, the anticoagulant may be added in any suitable location along the blood flow path in other embodiments. For example, in FIG. 4B, the anticoagulant enters the blood flow path before the blood has passed through blood flow pump 13. This may be useful, for example, if a blood pump cassette of the type shown in FIGS. 30C-33D is used, and blood flow is directed to cause blood to enter at the top of the cassette, and exit at the bottom of the cassette. The blood pump chambers can thus additionally serve to trap air that may be present in the blood before it is pumped to the dialyzer. In other embodiments, anticoagulant supply 11 may be located anywhere downstream from the blood flow pump. After passing through dialyzer 14 and undergoing dialysis, the blood returns to the patient through venous line 204, optionally passing through air trap and/or a blood sample port 19.

As is shown in FIG. 4A, blood flow cassette 141 also includes one or more blood flow pumps 13 for moving blood through the blood flow cassette. The pumps may be, for instance, pumps that are actuated by a control fluid, such as is discussed below. For instance, in one embodiment, pump 13 may comprise two (or more) pod pumps, e.g., pod pumps 23 in FIG. 4A. Each pod pump, in this particular example, may include a rigid chamber with a flexible diaphragm or membrane dividing each chamber into a fluid compartment and control compartment. There are four entry/exit valves on these compartments, two on the fluid compartment and two on the control compartment. The valves on the control compartment of the chambers may be two-way proportional valves, one connected to a first control fluid source (e.g., a high pressure air source), and the other connected to a second control fluid source (e.g., a low pressure air source) or a vacuum sink. The fluid valves on the compartments can be opened and closed to direct fluid flow when the pod pumps are pumping. Non-limiting examples of pod pumps are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Further details of the pod pumps are discussed below. If more than one pod pump is present, the pod pumps may be operated in any suitable fashion, e.g., synchronously, asynchronously, in-phase, out-of-phase, etc.

For instance, in some embodiments, the two-pump pumps can be cycled out of phase to affect the pumping cycle, e.g., one pump chamber fills while the second pump chamber empties. A phase relationship anywhere between 0° (the pod pumps act in the same direction, filling and emptying in unison) and 180° (the pod pumps act in opposite directions, in which one pod pump fills as the other empties) can be selected in order to impart any desired pumping cycle.

Figure 8A:
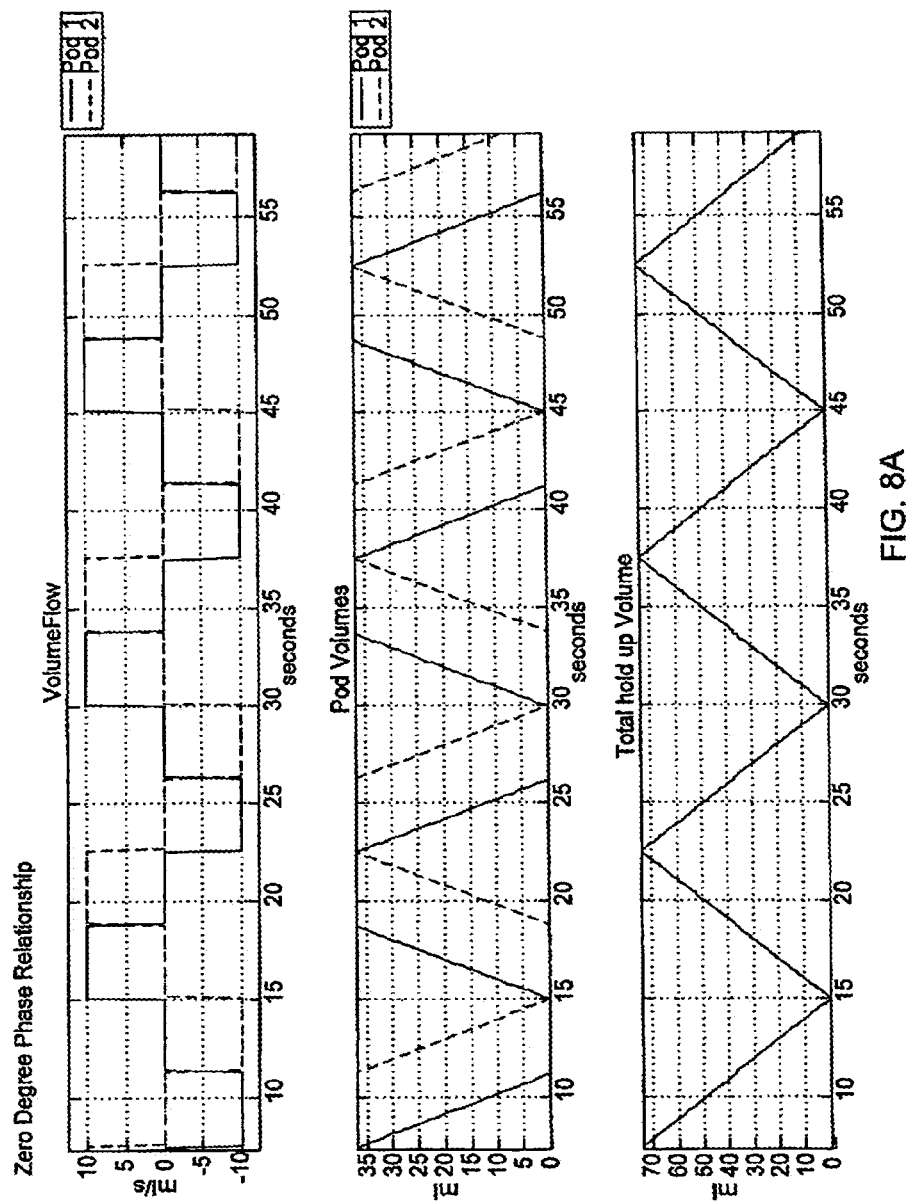
FIGS. 8A-8C are graphical representations of phase relationships.
Figure 8B:
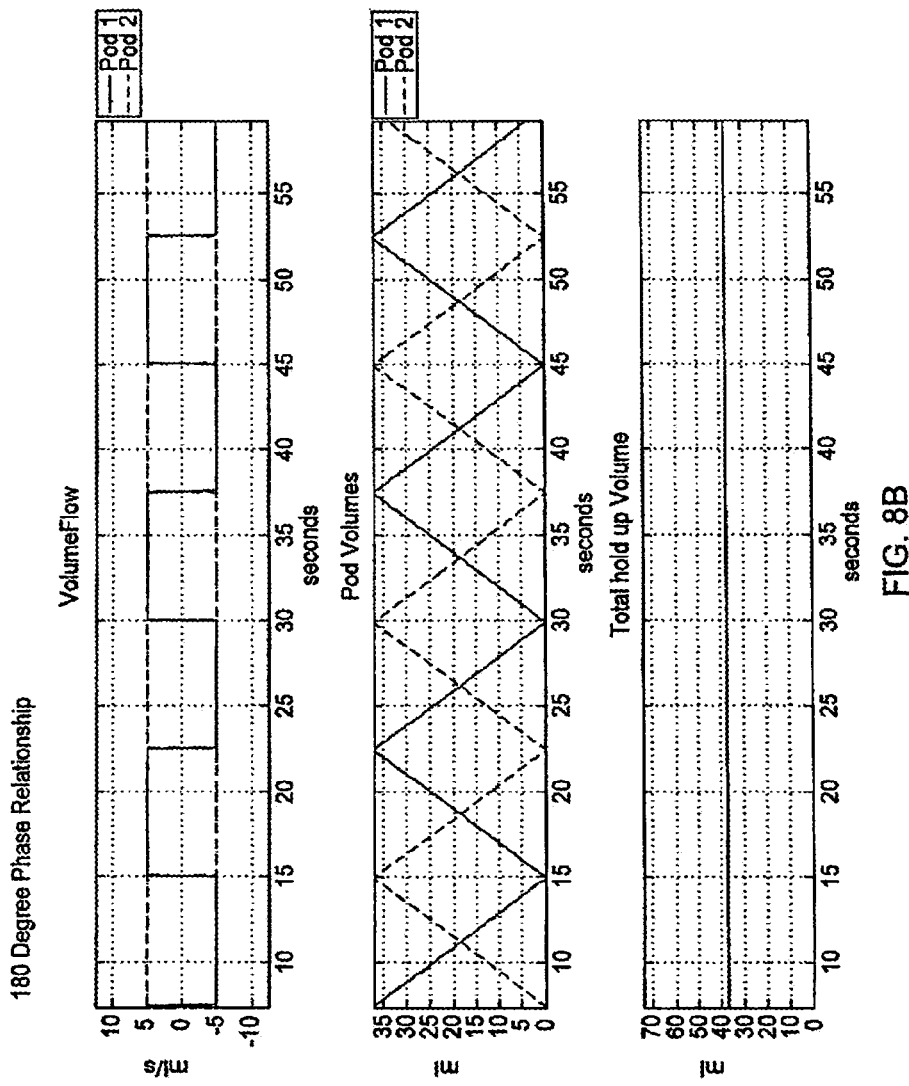
Figure 8C:
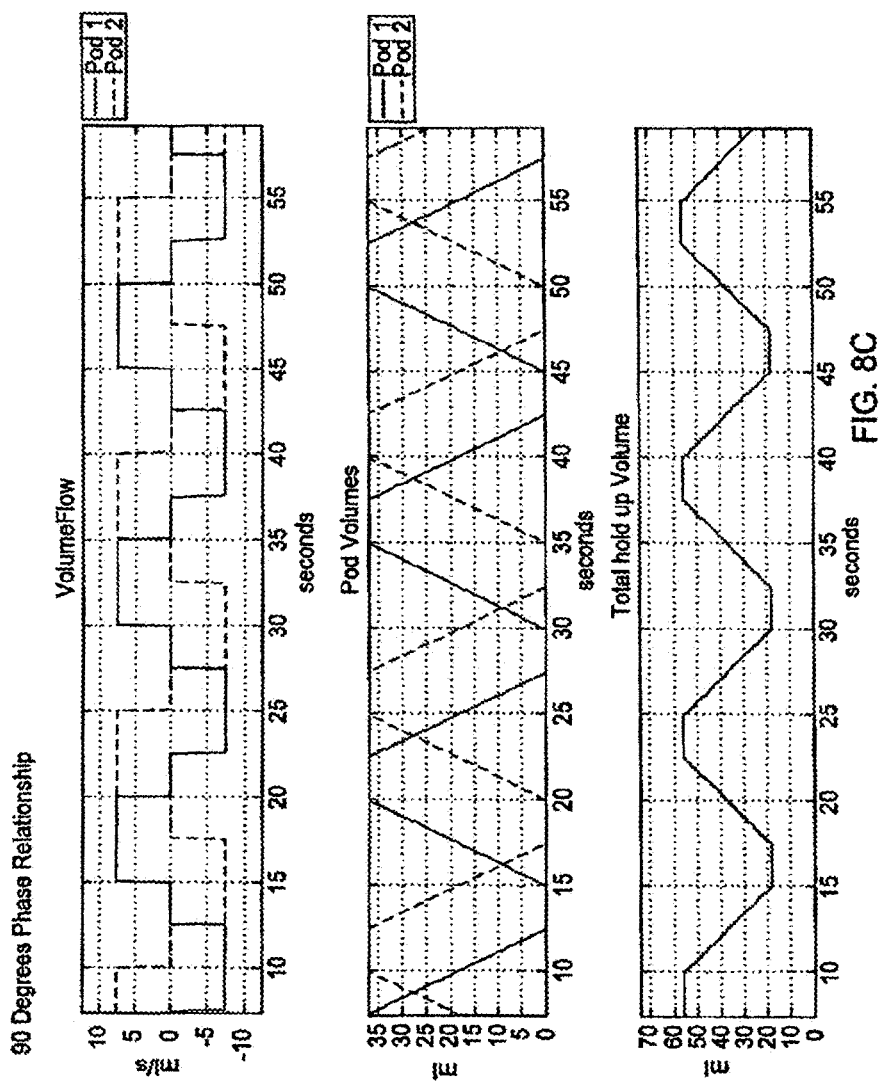

A phase relationship of 180° may yield continuous flow into and out of the pod pump cassette. This is useful, for instance, when continuous flow is desired, e.g., for use with dual needle flow or a "Y" or "T" connection. Setting a phase relationship of 0°, however, may be useful in some cases for single needle flow, in situations in which a "Y" or "T" connection is made with a single needle or single lumen catheter, or in other cases. In a 0° relationship, the pod pumps will first fill from the needle, then deliver blood through the blood flow path and back to the patient using the same needle. In addition, running at phases between 0° and 180° can be used in some cases, to achieve a push/pull relationship (hemodiafiltration or continuous back flush) across the dialyzer. FIGS. 8A-8C are graphical representations of examples of such phase relationships. In these figures, the volume or flow of each pod pump, the volumes of each pod pumps, and the total hold up volume of both pod pumps is shown as a function of time. These times and flow rates are arbitrarily chosen, and are presented here to illustrate the relationships between the pod pumps at different phasings. For instance, at a 180° phase relationship (FIG. 8B), the total hold up volume remains substantially constant.

Figure 14:
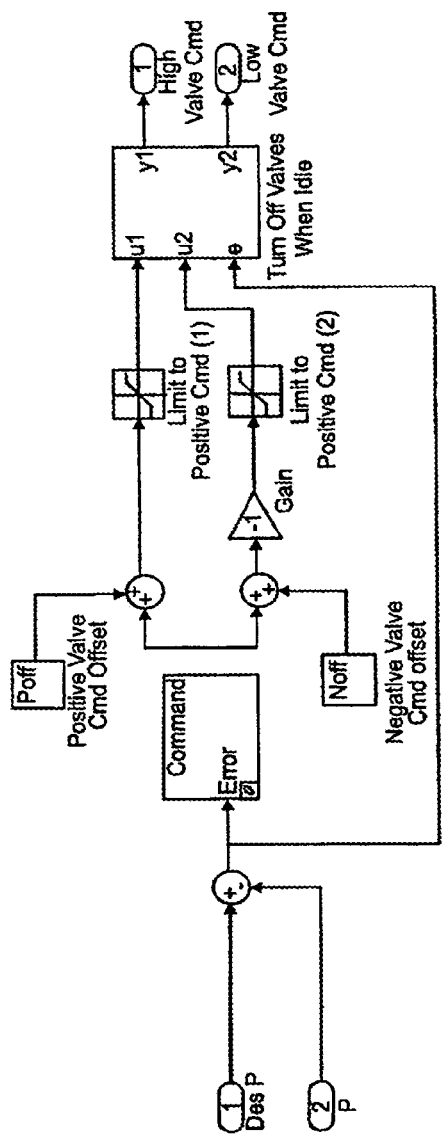
FIG. 14 is a diagram of one embodiment of a control algorithm.

In some cases, an anticoagulant (e.g., heparin, or any other anticoagulant known to those of ordinary skill in the art) may be mixed with the blood within blood flow cassette 141 as is shown in FIG. 14. For instance, the anticoagulant may be contained within a vial 11 (or other anticoagulant supply, such as a tube or a bag), and blood flow cassette 141 may be able to receive the anticoagulant vial with an integrally formed spike 201 (which, in one embodiment, is a needle) that can pierce the seal of the vial. The spike may be formed from plastic, stainless steel, or another suitable material, and may be a sterilizable material in some cases, e.g., the material may be able to withstand sufficiently high temperatures and/or radiation so as to sterilize the material. As an example, as is shown in FIG. 4A, spike 201 may be integrally formed with a blood flow cassette 141, and a vial 11 can be placed onto the spike, piercing the seal of the vial, such that anticoagulant can flow into blood flow cassette to be mixed with the blood in the blood flow path, or in some cases, mixed with dialysate as discussed below.

A third pump 80, which can act as a metering chamber in some cases, in blood flow cassette 141 can be used to control the flow of anticoagulant into the blood within the cassette. Third pump 80 may be of the same or of a different design than pump 13. For instance, third pump 80 may be a pod pump and/or third pump 80 may be actuated by a control fluid, such as air. For example, third pump 80 may be a membrane-based or diaphragm-based metering pump. For instance, as is shown in FIG. 4A, third pump 80 may include a rigid chamber with a flexible diaphragm dividing the chamber into a fluid compartment and a control compartment. Valves on the control compartment of the chamber may be connected to a first control fluid source (e.g., a high pressure air source), and the other compartment connected to a second control fluid source (e.g., a low pressure air source) or a vacuum sink. Valves on the fluid compartment of the chamber can be opened and closed in response to the control compartment, thus controlling the flow of anticoagulant into the blood. Further details of such a pod pump are discussed below. In one set of embodiments, air may also be introduced into the blood flow path through a filter 81, as discussed below.

Fluid Management System ("FMS") measurements may be used to measure the volume of fluid pumped through a pump chamber during a stroke of the membrane or diaphragm, or to detect air in the pumping chamber. FMS methods are described in U.S. Pat. Nos. 4,808,161; 4,826,482; 4,976,162; 5,088,515; and 5,350,357, which are hereby incorporated herein by reference in their entireties. In some cases, the volume of liquid delivered by an anticoagulant pump, a dialysate pump, or other membrane-based pump is determined using an FMS algorithm in which changes in chamber pressures are used to calculate a volume measurement at the end of a fill stroke and at the end of a delivery stroke. The difference between the computed volumes at the end of a fill and delivery stroke is the actual stroke volume. This actual stroke volume can be compared to an expected stroke volume for the particular sized chamber. If the actual and expected volumes are significantly different, the stroke has not properly completed and an error message can be generated.

If stroke volumes are collected with a scale, the calculation can be worked backwards to determine a calibration value for the reference chamber. FMS systems can vent to atmosphere for the FMS measurement. Alternatively, the system can vent to a high pressure positive source and a low pressure negative source for the FMS measurement. Doing so provides the following advantages, amongst others: (1) if the high pressure source is a pressure reservoir with a controlled pressure, there is an opportunity to do a cross check on the pressure sensors of the reservoir and chamber to ensure they are similar when the chamber is being vented to the reservoir. This can be used to detect a broken pressure sensor or a failed valve; (2) by using higher/lower pressures to vent, there are larger pressure differences for the FMS measurements so better resolution can be obtained.

Blood flow circuit 141 may also include an air trap 19 incorporated into blood flow circuit 141 in some cases. Air trap 19 may be used to remove air bubbles that may be present within the blood flow path. In some cases, air trap 19 is able to separate any air that may be present from the blood due to gravity. In some cases, air trap 19 may also include a port for sampling blood. Air traps are known to those of ordinary skill in the art.

Figure 4C:
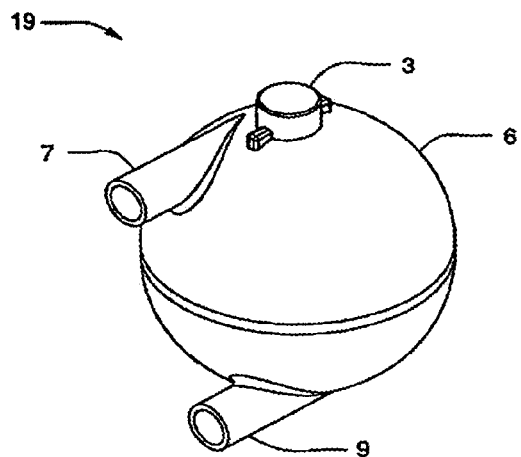
FIGS. 4C and 4D are perspective and side views, respectively, of the air trap shown in FIG. 4A.
Figure 4D:
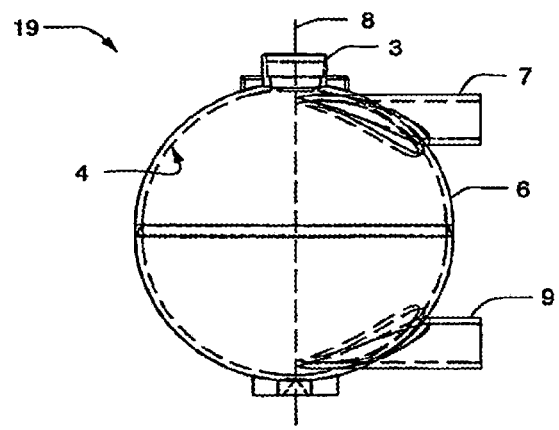

In accordance with another aspect of the invention, the air trap 19 is placed in the blood flow path after the blood exits the dialyzer and before it is returned to the patient. As shown in FIGS. 4C and 4D, air trap 19 may have a spherical or spheroid-shape container 6, and have its inlet port 7 located near the top and offset from the vertical axis of the container, and an outlet 9 at a bottom of the container. The curved shape of the inside wall 4 of the trap can thus direct the blood to circulate along the inside wall as the blood gravitates to the bottom of the container, facilitating the removal of air bubbles from the blood. Air present in the blood exiting the outlet 9 of the dialyzer 14 will enter at the top of the air trap 19 and remain at the top of the container as blood flows out the outlet at the bottom and to the venous blood line 204. By locating the inlet port 7 near the top of trap 19, it is also possible to circulate blood through the trap with minimal or no air present within the container (as a "run-full" air trap). The ability to avoid an air-blood interface for routine circulation of blood in the trap can be advantageous. Placing the inlet port 7 at or near the top of the container also allows most or all of the air present in the trap to be removed from the trap by reversing the flow of fluid through the blood tubing (i.e. from the bottom to the top of the trap 19, exiting through the inlet port of the trap 19). In an embodiment, a self-sealing port 3, such as a self-sealing stopper with a split septum or membrane, or another arrangement, is located at the top of the trap, allowing the withdrawal of air from the container (e.g., by syringe). The blood-side surface of the self-sealing membrane can be situated nearly flush with the top of the interior of the trap, in order to facilitate cleaning of the self-sealing port during disinfection. The self-sealing port 3 can also serve as a blood sampling site, and/or to allow the introduction of liquids, drugs or other compounds into the blood circuit. A sealed rubber-type stopper can be used if access with a needle is contemplated. Using a self-sealing stopper with split septum permits sampling and fluid delivery using a needleless system.

Additional fluid connections 82 may allow blood flow circuit 10 to also be connected to the patient, and/or to a fluid source for priming or disinfecting the system, including blood flow circuit 10. Generally, during disinfection, arterial line 203 and venous line 204 are connected directly to directing circuit 142 via conduits 67, such that a disinfecting fluid (e.g., heated water and in some embodiments, a combination heated water and one or more chemical agent) may be flowed through dialyzer 14 and blood flow circuit 141 back to directing circuit 142 for recirculation, this disinfection is similar to those shown in U.S. Pat. No. 5,651,898 to Kenley, et al., which is incorporated herein by reference. This is also discussed in more detail below.

The pressure within arterial line 203, to draw blood from the patient, may be kept to a pressure below atmospheric pressure in some cases. If a pod pump is used, the pressure within blood flow pump 13 may be inherently limited to the pressures available from the positive and negative pressure reservoirs used to operate the pump. In the event that a pressure reservoir or valve fails, the pump chamber pressure will approach the reservoir pressure. This will increase the fluid pressure to match the reservoir pressure until the diaphragm within the pod pump "bottoms" (i.e., is no longer is able to move, due to contact with a surface), and the fluid pressure will not exceed a safe limit and will equilibrate with a natural body fluid pressure. This failure naturally stops operation of the pod pump without any special intervention.

Figure 30A:
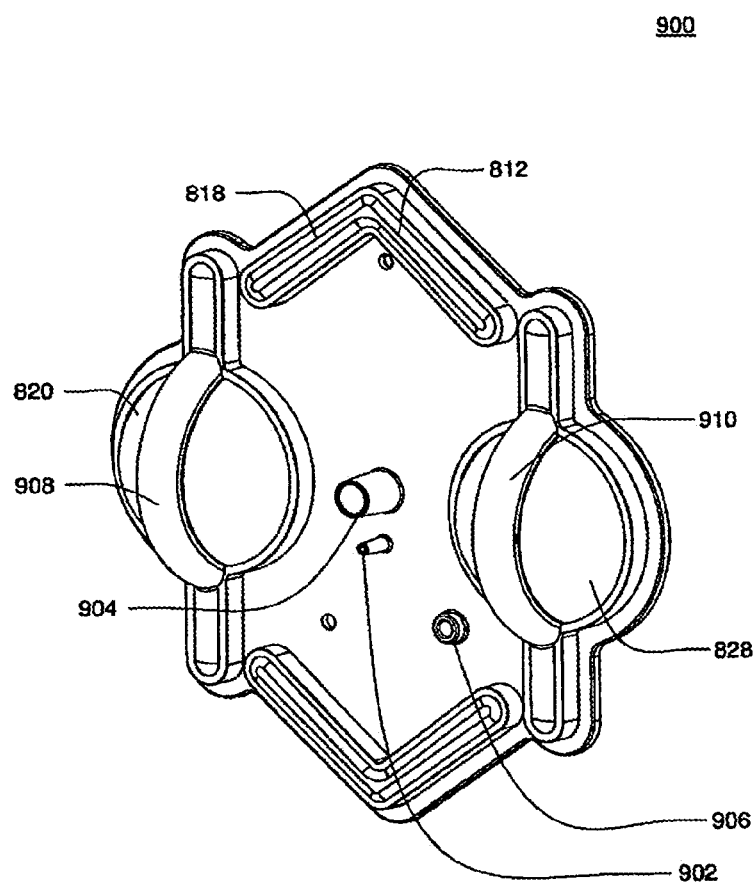
FIGS. 30A and 30B are isometric and top views of an outer top plate of an exemplary embodiment of the cassette.
Figure 30B:
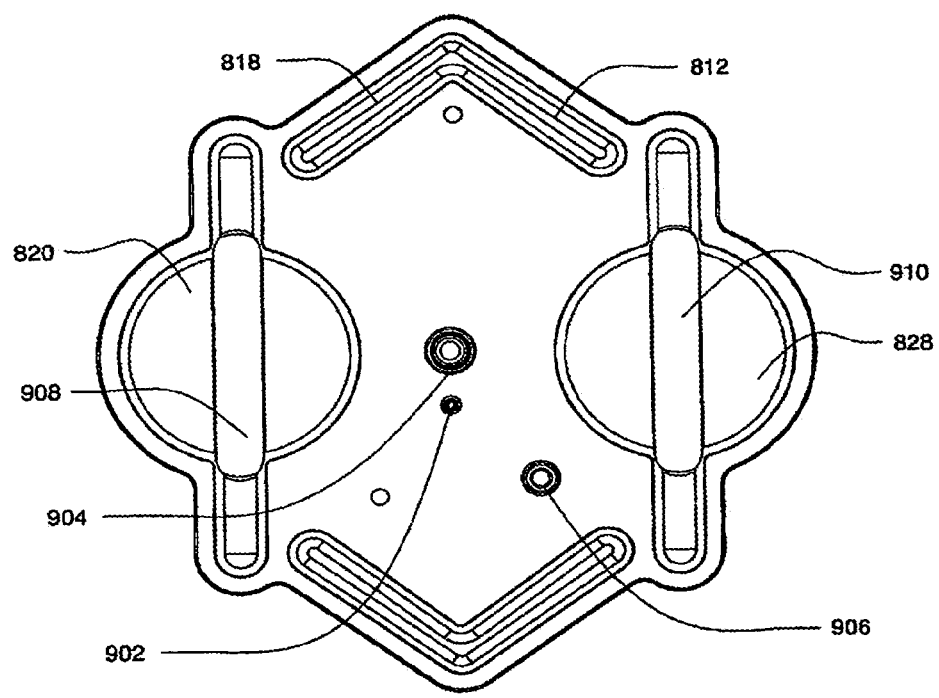

A specific non-limiting example of a blood flow cassette is shown in FIGS. 30A-33D. Referring now to FIGS. 30A and 30B, the outer side of the top plate 900 of an exemplary embodiment of the cassette is shown. The top plate 900 includes one half of the pod pumps 820, 828. This half is the liquid half where the source fluid will flow through. The two fluid paths 818, 812 are shown. These fluid paths lead to their respective pod pumps 820, 828.

The pod pumps 820, 828 include a raised flow path 908, 910. The raised flow path 908, 910 allows for the fluid to continue to flow through the pod pumps 820, 828 after the diaphragm (not shown) reaches the end of stroke. Thus, the raised flow path 908, 910 minimizes the diaphragm causing air or fluid to be trapped in the pod pump 820, 828 or the diaphragm blocking the inlet or outlet of the pod pump 820, 828, which would inhibit continuous flow. The raised flow path 908, 910 is shown in one exemplary embodiment having particular dimensions, and in some cases, the dimensions are equivalent to the fluid flow paths 818, 812. However, in alternate embodiments, the raised flow path 908, 910 is narrower, or in still other embodiments, the raised flow path 908, 910 can be any dimensions as the purpose is to control fluid flow so as to achieve a desired flow rate or behavior of the fluid. In some embodiments, the raised flow path 908, 910 and the fluid flow paths 818, 812 have different dimensions. Thus, the dimensions shown and described here with respect to the raised flow path, the pod pumps, the valves or any other aspect are mere exemplary and alternate embodiments. Other embodiments are readily apparent.

In one exemplary embodiment of this cassette, the top plate includes a spike 902 as well as a container perch 904. The spike 902 is hollow in this example, and is fluidly connected to the flow path. In some embodiments, a needle is attached into the spike. In other embodiments, a needle is connected to the container attachment.

Figure 30C:
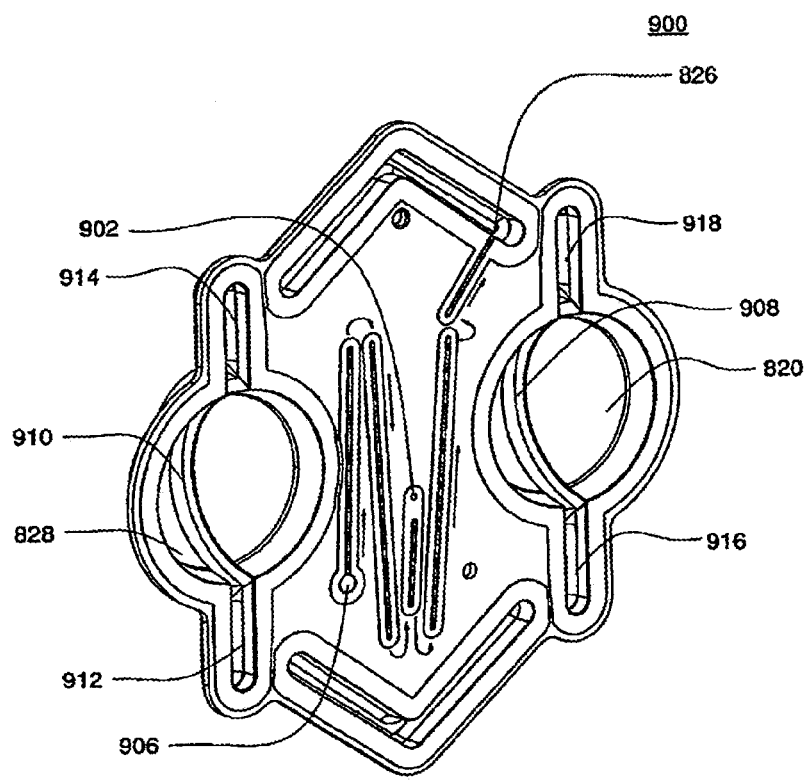
FIGS. 30C and 30D are isometric and top views of an inner top plate of an exemplary embodiment of the cassette.
Figure 30D:
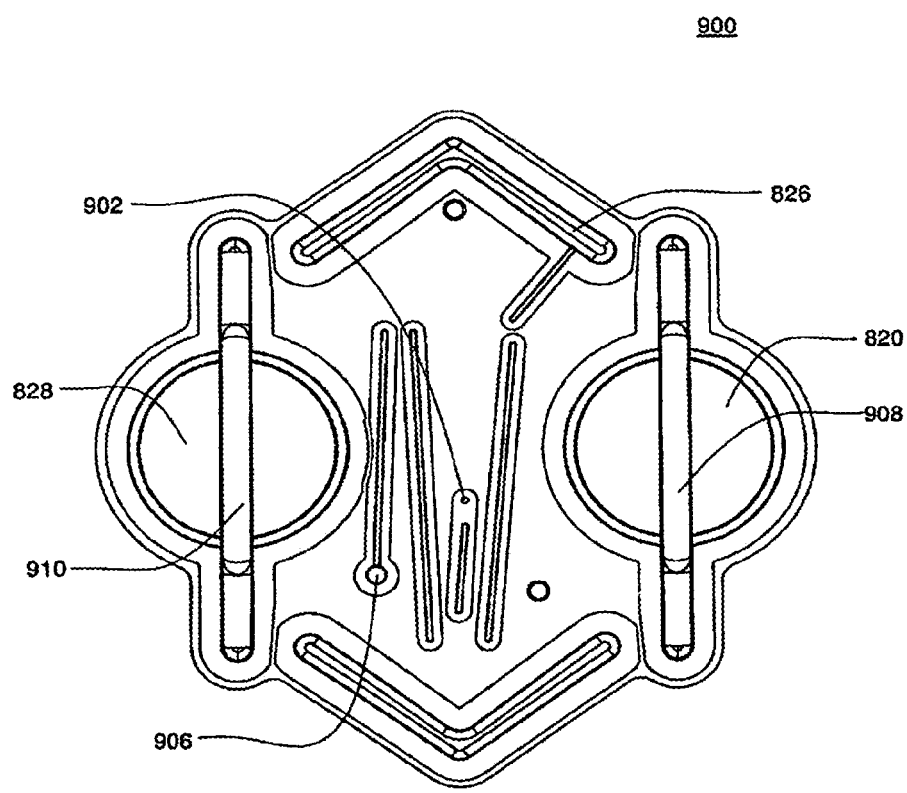
Figure 30E:
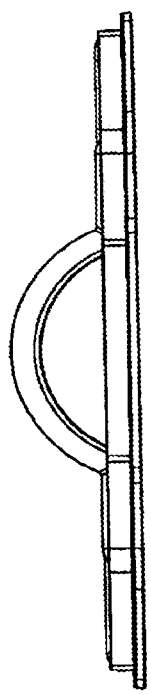
FIG. 30E is a side view of the top plate of an exemplary embodiment of an cassette.

Referring now to FIGS. 30C and 30D, the inside of the top plate 900 is shown. The raised flow paths 908, 910 connects to the inlet flow paths 912, 916 and outlet flow paths 914, 918 of the pod pumps 820, 828. The raised flow paths are described in more detail above.

The metering pump (not shown) includes connection to an air vent 906 as well as connection to the spike's hollow path 902. In one exemplary embodiment, the air vent 906 includes an air filter (not shown). The air filter may be a particle air filter in some cases. In some embodiments, the filter is a somicron hydrophobic air filter. In various embodiments, the size of the filter may vary, in some instances the size will depend on desired outcome. The metering pump works by taking air in through the air vent 906, pumping the air to the container of second fluid (not shown) through the spike's hollow path 902 and then pumping a volume of second fluid out of the container (not shown) through the spike's hollow path 902 and into the fluid line at point 826. This fluid flow path for the metering pump is shown with arrows on FIG. 30C.

Figure 31A:
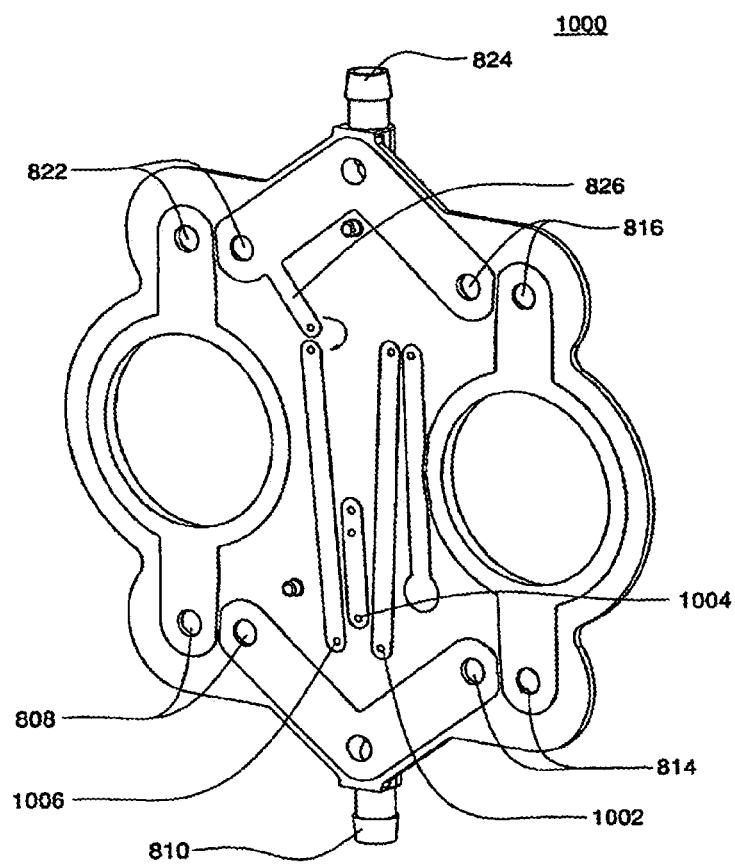
FIGS. 31A and 31B are isometric and top views of the liquid side of a midplate according to an exemplary embodiment of the cassette.
Figure 31B:
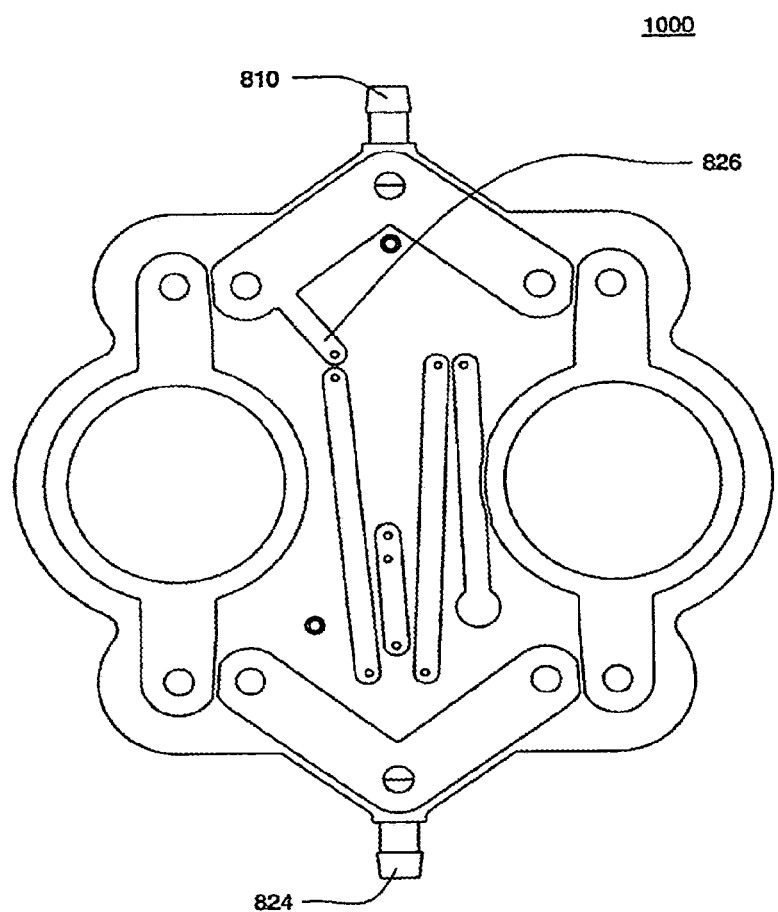

Referring now to FIGS. 31A and 31B, the liquid side of the midplate 1000 is shown. The areas complementary to the fluid paths on the inner top plate are shown. These areas are slightly raised tracks that present a surface finish that is conducive to laser welding, which is the mode of manufacture in one embodiment. The fluid inlet 810 and fluid outlet 824 are also shown in this view.

Figure 31C:
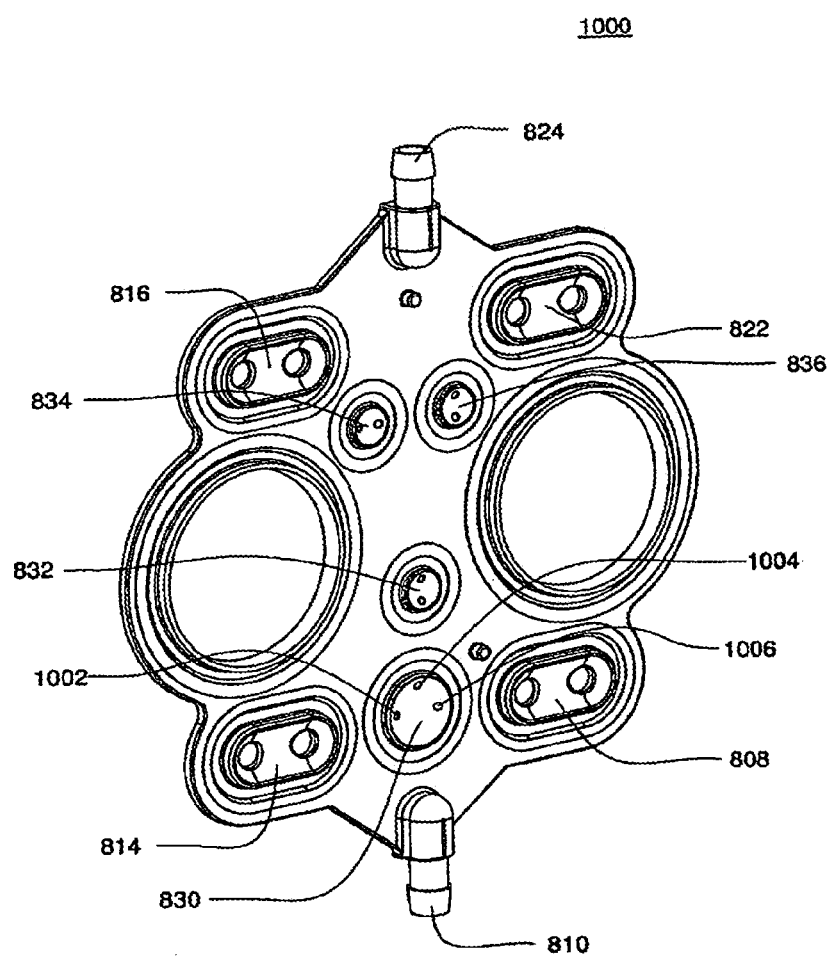
FIGS. 31C and 31D are isometric and top views of the air side of a midplate according to an exemplary embodiment of the cassette.
Figure 31D:
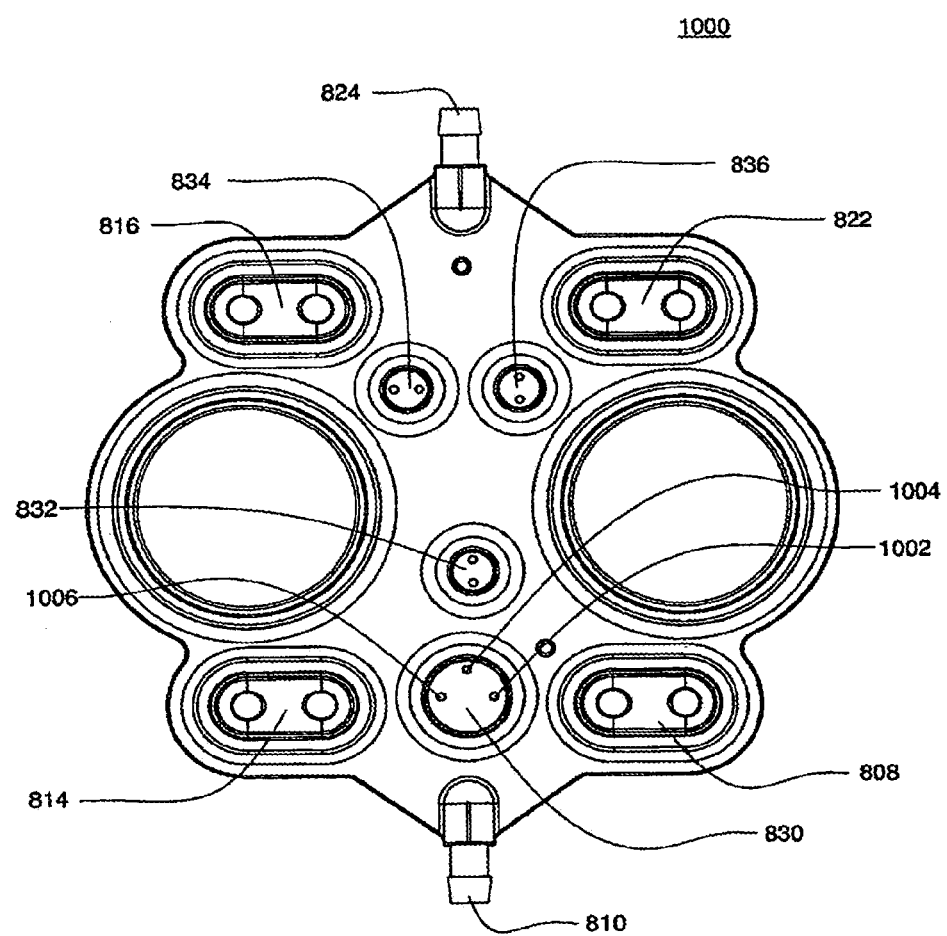

Referring next to FIGS. 31C and 31D, the air side of the midplate 1000 is shown according to one embodiment. The air side of the valve holes 808, 814, 816, 822 correspond to the holes in the fluid side of the midplate (shown in FIG. 31A). As seen in FIGS. 33C and 33D, diaphragms 1220 complete valves 808, 814, 816, 822 while diaphragms 1226 complete pod pumps 820, 828. The metering pump 830 is completed by diaphragm 1224. The valves 808, 814, 816, 822, 832, 834, 836 are actuated pneumatically, and as the diaphragm is pulled away from the holes, liquid is drawn in, and as the diaphragm is pushed toward the holes, liquid is pushed through. The fluid flow is directed by the opening and closing of the valves 808, 814, 816, 822, 832, 834, 836.

Referring to FIGS. 31A and 31C, the metering pump includes three holes, 1002, 1004, 1006. One hole 1002 pulls air into the metering pump, the second hole 1004 pushes air to the spike/source container and also, draws liquid from the source container, and the third hole 1006 pushes the second fluid from the metering pump 830 to the fluid line to point 826.

Valves 832, 834, 836 actuate the second fluid metering pump. Valve 832 is the second fluid/spike valve, valve 834 is the air valve and valve 836 is the valve that controls the flow of fluid to the fluid line to area 826.

Figure 32A:
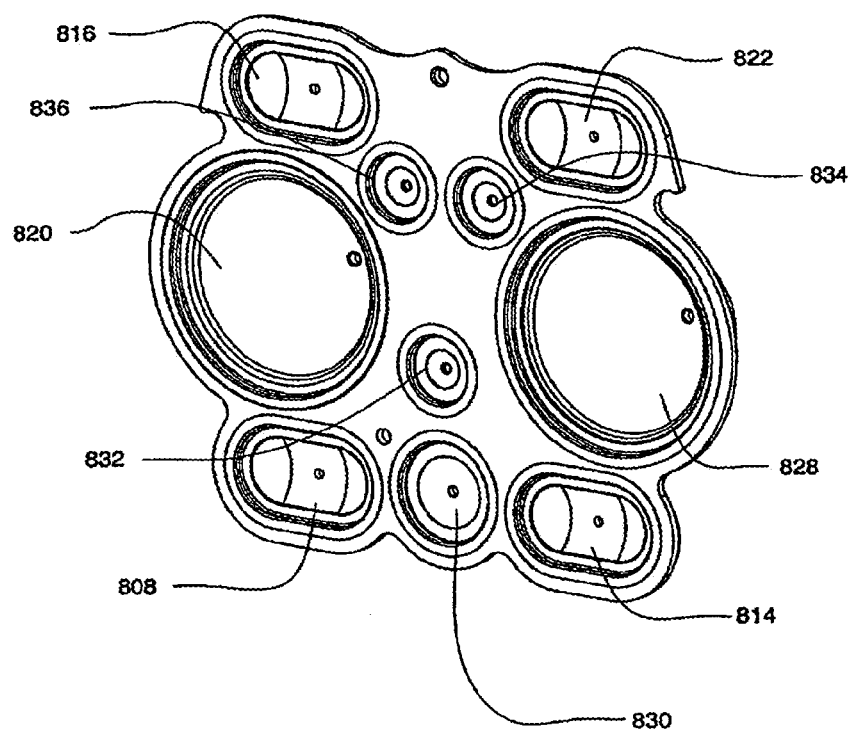
FIGS. 32A and 32B are isometric and top views of the inner side of a bottom plate according to an exemplary embodiment of the cassette.
Figure 32B:
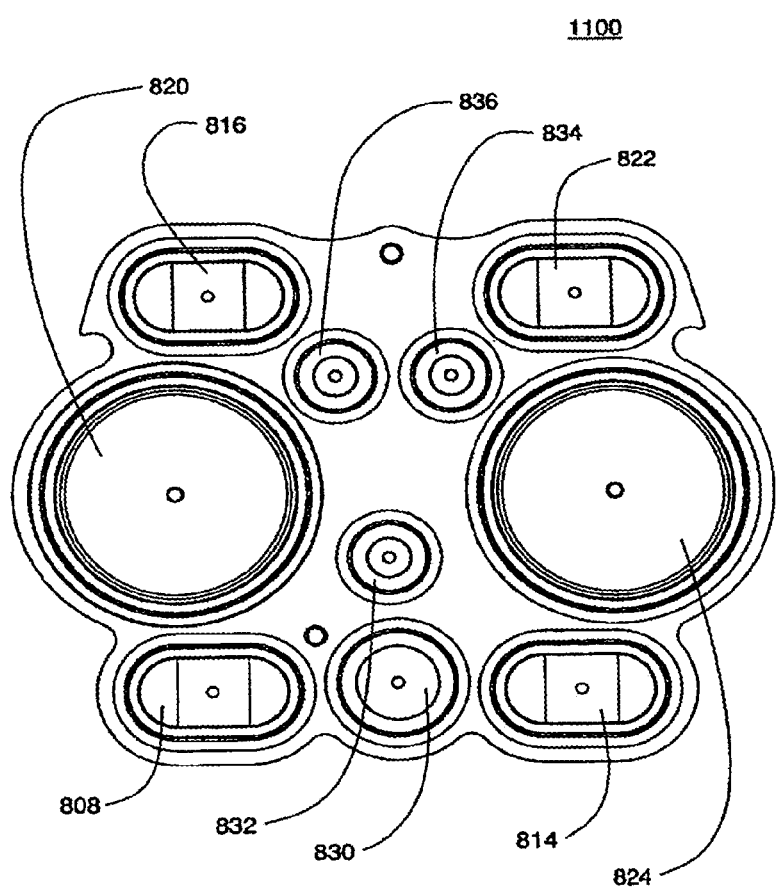
Figure 32C:
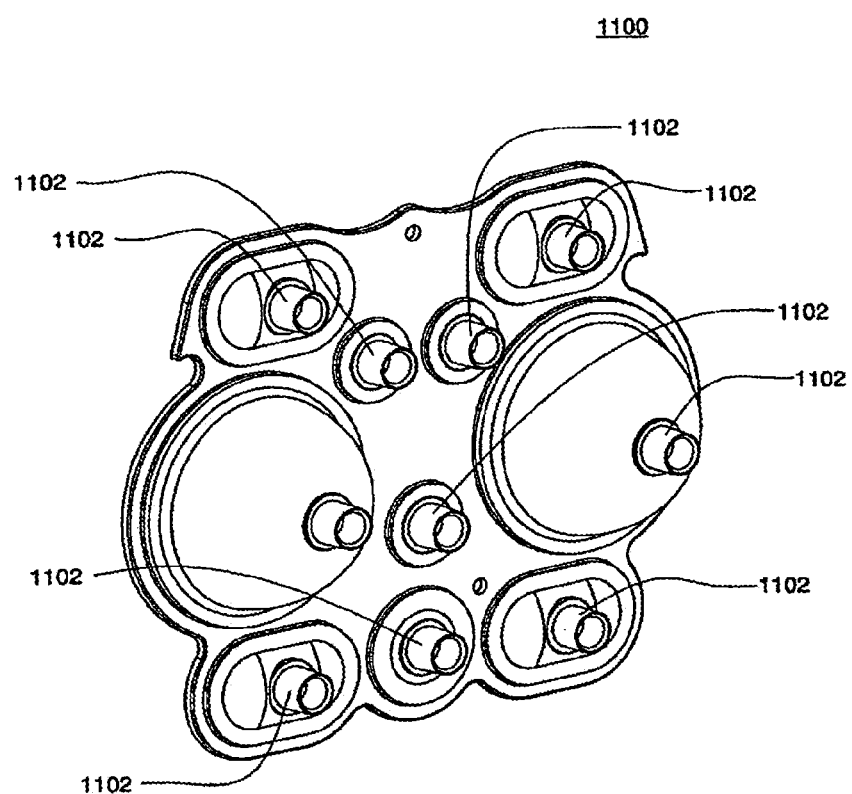
FIGS. 32C and 32D are isometric and top views of the outer side of a bottom plate according to an exemplary embodiment of the cassette.
Figure 32D:
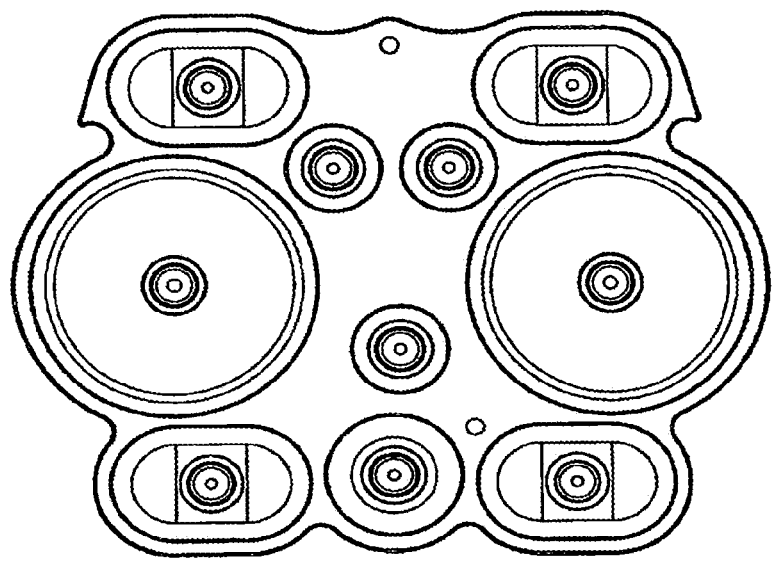
Figure 32E:
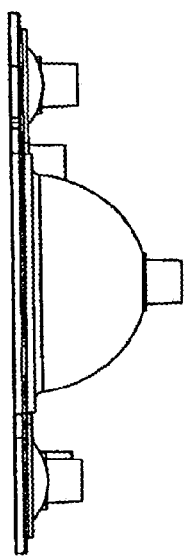
FIG. 32E is a side view of a bottom plate according to an exemplary embodiment of the cassette.

Referring next to FIGS. 32A and 32B, the inner view of the bottom plate 1100 is shown. The inside view of the pod pumps 820, 828, the metering pump 830 and the valves 808, 814, 816, 822, 832, 834, 836 actuation/air chamber is shown. The pod pumps 820, 828, metering pump 830 and the valves 808, 814, 816, 822, 832, 834, 836 are actuated by a pneumatic air source. Referring now to FIGS. 32C and 32D, the outer side of the bottom plate 1100 is shown. The source of air is attached to this side of the cassette. In one embodiment, tubes connect to the features on the valves and pumps 1102. In some embodiments, the valves are ganged, and more than one valve is actuated by the same air line.

Figure 33A:
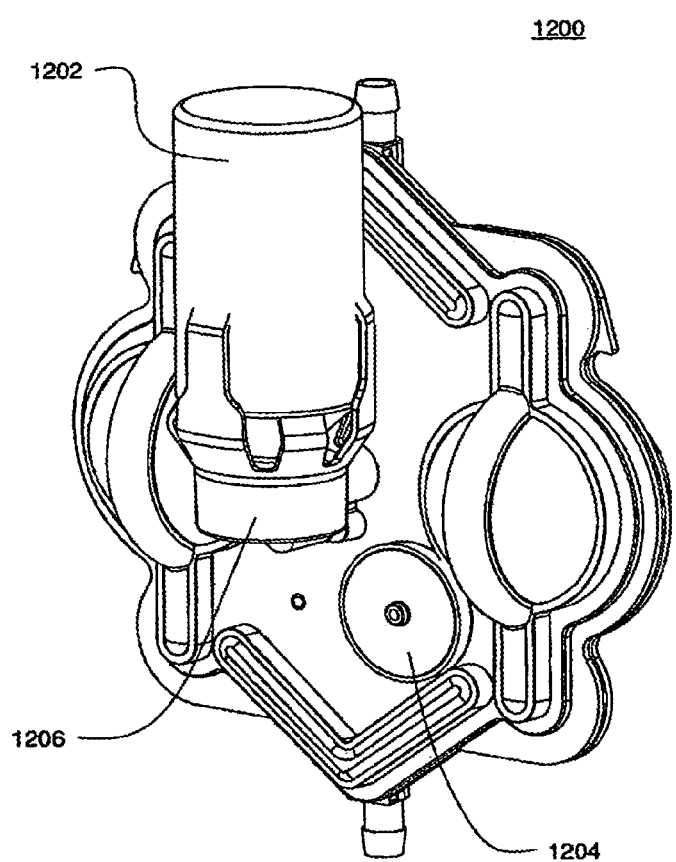
FIG. 33A is a top view of an assembled exemplary embodiment of a cassette with a vial attached.
Figure 33B:
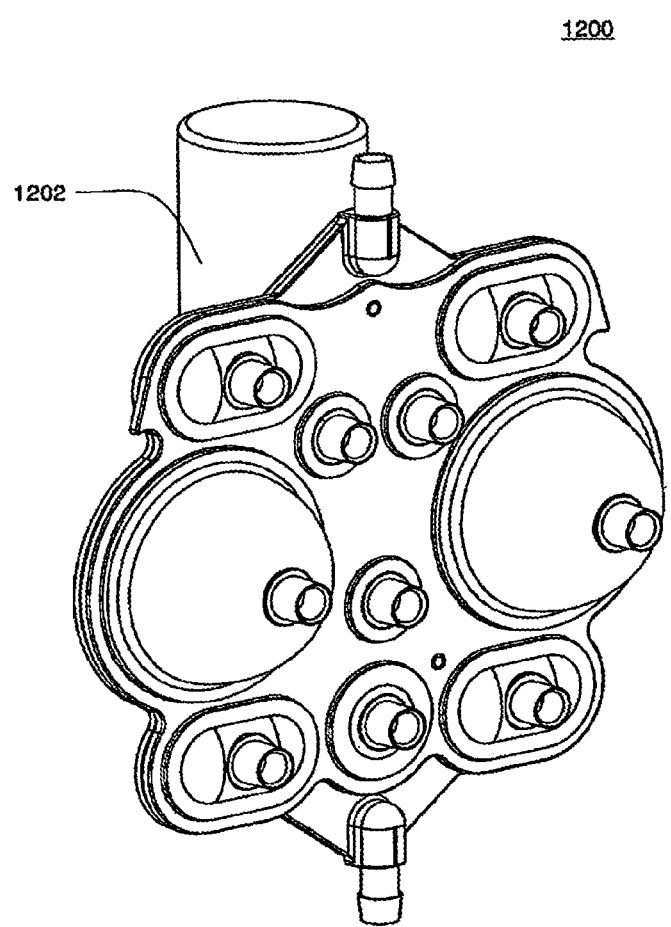
FIG. 33B is a bottom view of an assembled exemplary embodiment of a cassette with a vial attached.
Figure 33C:
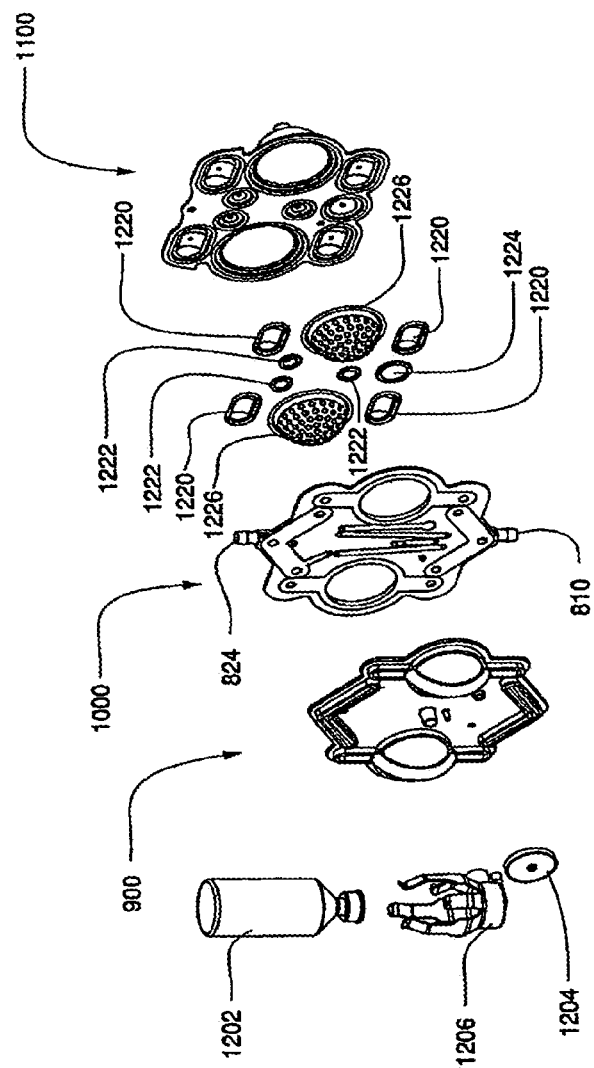
FIG. 33C is an exploded view of an assembled exemplary embodiment of a cassette with a vial.
Figure 34A:
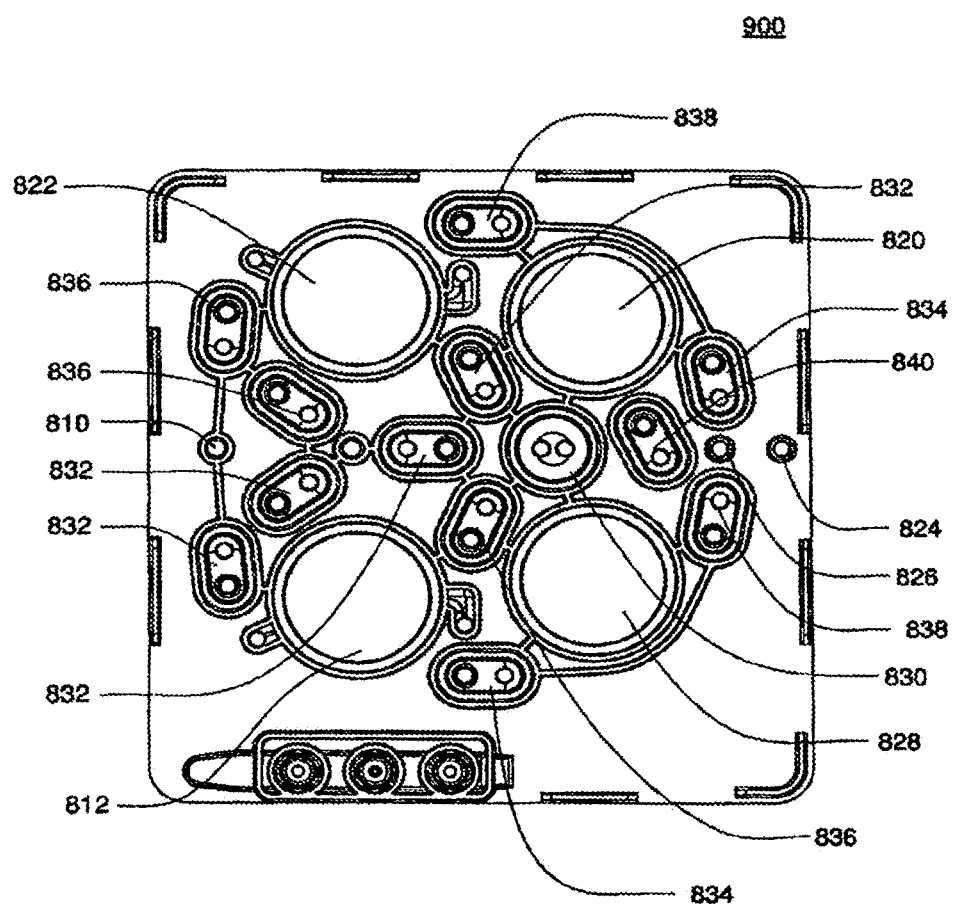
FIG. 34A is an isometric bottom view of an exemplary embodiment of the midplate of an exemplary embodiment of the cassette.
Figure 34B:
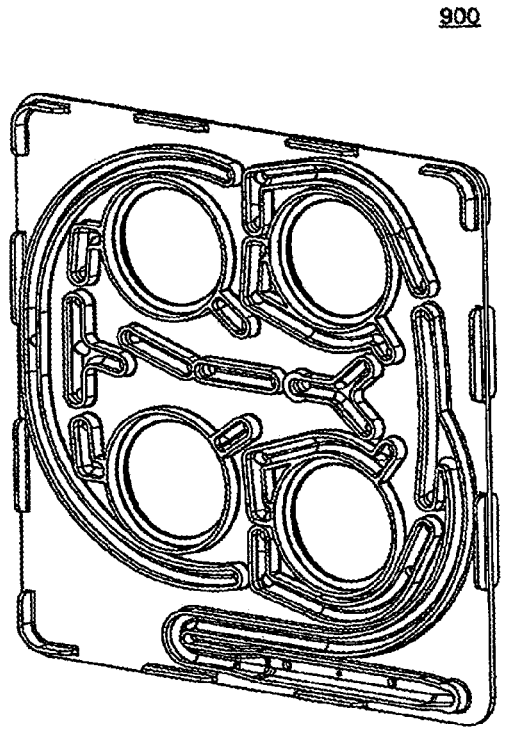
FIG. 34B is an isometric top view of the midplate of an exemplary embodiment of a cassette.
Figure 34C:
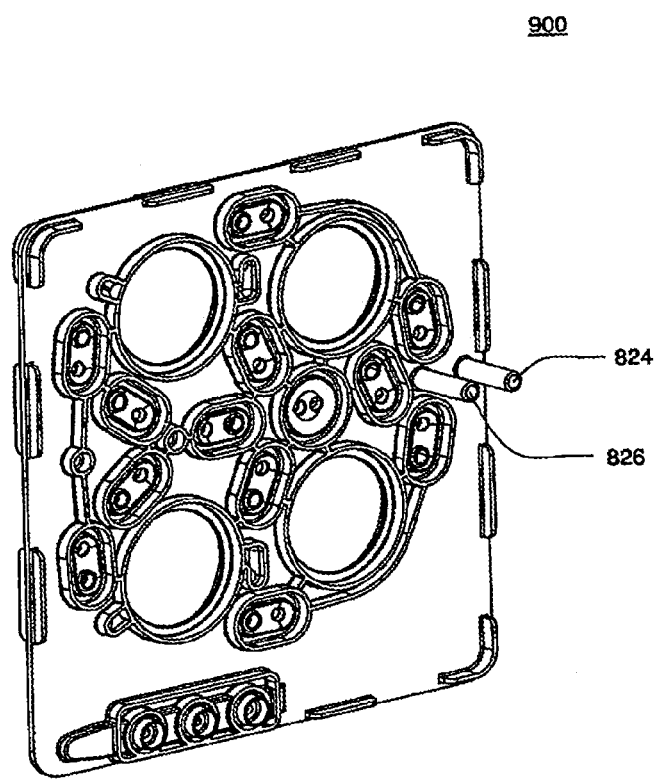
FIG. 34C is an isometric bottom view of an exemplary embodiment of the midplate of a cassette.
Figure 34D:
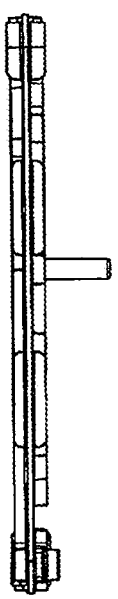
FIG. 34D is a side view of an exemplary embodiment of the midplate of a cassette.

Referring now to FIGS. 33A and 33B, an assembled cassette 1200 with a container (or other source) of a second fluid 1202 is shown, which, in this embodiment, may be an anticoagulant as described above, attached is shown. The container 1202 contains the source of the second fluid and is attached to a hollow spike (not shown) by a container attachment 1206. The spike may be situated within the container attachment 1206, directed upward to penetrate the top of the container 1202, which is held in an inverted position by the container attachment 1206. The spike is in fluid communication with a fluid channel similar to the hollow path 902 depicted in FIGS. 30C and 30D. The air filter 1204 is shown attached to the air vent (not shown, shown in FIG. 30A as 906). Although not visible in FIG. 33A, the container perch (shown in FIG. 30A as 904) is under the container attachment 1206.

In some cases, the metering pump is an FMS pump, associated with a reference chamber and capable of being monitored with a pressure transducer to determine the volume of fluid that it delivers. The FMS algorithm uses changes in pressures to calculate a volume measurement at the end of a fill stroke and at the end of a delivery stroke. The difference between the computed volumes at the end of a fill and delivery stroke is the actual stroke volume. This actual stroke volume can be compared to an expected stroke volume for the particular sized chamber. If the actual and expected volumes are significantly different, the stroke has not properly completed and an error message can be generated. FMS systems can vent to atmosphere for the FMS measurement. Alternatively, the system can vent to a high pressure positive source and a low pressure negative source for the FMS measurement. In one set of embodiments, the metering pump (e.g., the anticoagulant pump) is primed. Priming the pump removes air from the metering pump and the flow path, and ensures that the pressure in the fluid container (e.g., the anticoagulant vial) is acceptable.

The metering pump can be designed such that air in the pump chamber flows up into the vial. The test is performed by closing all of the metering pump fluid valves, measuring the external volume, charging the pump's FMS chamber with vacuum, opening valves to draw from the vial into the pumping chamber, measuring the external volume (again), charging the FMS chamber with pressure, opening the valves to push fluid back into the vial, and then measuring the external volume (again). Changes in external volume resulting from fluid flow should correspond to the known volume of the pumping chamber. If the pumping chamber cannot fill from the vial, then the pressure in the vial is too low and air must be pumped in. Conversely, if the pumping chamber cannot empty into the vial, then the pressure in the vial is too high and some of the anticoagulant must be pumped out of the vial. Anticoagulant pumped out of the vial during these tests can be discarded, e.g., through the drain.

During routine delivery of heparin or other medication to the blood path, the pressure in the vial can be measured periodically. If the vial pressure is approaching a predefined threshold value below atmospheric pressure, for example, the metering pump can first introduce air into the vial via the metering pump air vent, normalizing the pressure in the vial and helping to ensure the withdrawal of a reasonably precise amount of medication from the vial. If the vial pressure approaches a predefined threshold value above atmospheric pressure, the metering pump can forego instilling any further air into the vial before the next withdrawal of medication from the vial.

An exploded view of an assembled fluid pump cassette 1200 shown in FIGS. 33A and 33B is shown in FIGS. 33C and 33D. In some embodiments, this cassette may be adapted for pumping blood. In these views, an exemplary embodiment of the pod pump diaphragms or membranes 1226 is shown. The gasket or bead of the diaphragm locates the diaphragm between the pumping chamber and the control chamber of the pump, and provides a seal between the liquid chamber (in the pumping-side body or top plate 900) and the air/actuation chamber (in the control-side body or bottom plate 1100). The dimpled texture on the body or dome of diaphragms 1226 provide, amongst other features, additional space for air and liquid to escape the chamber at the end of stroke.

In an exemplary embodiment, the diaphragm 1226 has a curved, domed or semi-spheroid shape, to generally conform to the shape or geometry of the internal wall of the pump chamber and/or the control chamber of the pump portion of the pump cassette. Other diaphragm geometries are possible if the inner rigid wall of the pumping or control chamber has a different geometry. In a preferred embodiment, the diaphragm, which separates the pumping chamber from the control chamber of the pump, has a shape or contour that generally conforms to the particular curved contour of the inner wall of the pumping chamber and/or the control chamber of the pump portion of the pump cassette. If the rigid inner wall contour of the pump chamber matches that of the control chamber, then the diaphragm may be molded so as to have a contour that generally conforms to curved inner wall of the pumping chamber when it is extended into the pumping chamber during a fluid delivery stroke, and that generally conforms to the curved inner wall of the control chamber when it is extended into the control chamber during a fluid fill stroke.

In some embodiments, the body 1700 of the flexible diaphragm or membrane 1226 has a variable cross-sectional thickness, as shown in FIG. 146B. Thinner, thicker or variable thickness diaphragms may be used to accommodate the strength, flexural and other properties of the chosen diaphragm materials. Thinner, thicker or variable diaphragm wall thickness may also be used to manage the diaphragm thereby encouraging it to flex more easily in some areas than in other areas, thereby aiding in the management, of pumping action and flow of subject, fluid in the pump chamber. In this embodiment the diaphragm is shown having its thickest cross-sectional area closest to its center. However in other embodiments having a diaphragm with a varying cross-sectional thickness, the thickest and thinnest areas may be in any location on the diaphragm. Thus, for example, the thinner cross-section may be located near the center and the thicker cross-sections located closer to the perimeter of the diaphragm. Still other configurations are possible. Referring to FIGS. 147A-147D, some embodiments of a diaphragm are shown having various raised features on its surface, or surface embodiments, projections or protuberances. Other than a smooth surface (FIG. 147A), these raised features may include, for example, raised rings or partially or fully circumferential ridges 1702 (FIG. 147B), raised ribs or radial ridges 1704 (FIG. 147C), or a plurality of recessed dimples, raised dots, or bumps 1706 (FIG. 147D) of variable thickness and/or geometry located at various locations on the actuation and/or pumping side of the diaphragm. In one embodiment of the diaphragm, the diaphragm has a tangential slope in at least one section, but in other embodiments, the diaphragm is completely smooth or substantially smooth. Referring now to FIGS. 148A and 148B, one of the alternate embodiments of the diaphragm is shown. In this embodiment, the diaphragm has a dimpled or dotted surface. In a typical construction, the raised features, protuberances or dots 1706 are formed on the surface of the diaphragm facing the liquid pumping chamber of the pump. A convenient molding method has the pumping chamber side of the diaphragm formed convexly within a mold cavity, so that the body of the diaphragm is in a relaxed or non-stressed shape with respect to the periphery of the diaphragm (i.e. with respect to the bead, gasket or o-ring component 1708 of the diaphragm 1226) when the pumping chamber side of the diaphragm is in a convex configuration. Thus less force might be required to fully extend the diaphragm into the pumping chamber during pumping operations, with the diaphragm tending toward its molded or non-stressed state during a fluid delivery stroke.

The diaphragm may be made of any flexible material having a desired durability and compatibility with the subject fluid to be pumped. The diaphragm can be made from any material that may flex in response to fluid, liquid or gas pressure or vacuum applied to the actuation chamber. The diaphragm material may also be chosen for particular biocompatibility, temperature compatibility or compatibility with various subject fluids that may be pumped by the diaphragm or introduced to the chambers to facilitate movement of the diaphragm. In the exemplary embodiment, the diaphragm is made from high elongation silicone. However, in other embodiments, the diaphragm is made from any elastomer or rubber, including, but not limited to, silicone, urethane, nitrile, EPDM or any other rubber, elastomer or flexible material. The diaphragm may exhibit elastic properties when stretched beyond its relaxed, non-stressed, or molded shape.

The shape of the diaphragm is dependent on multiple variables. These variables include, but are not limited to: the shape of the chamber; the size of the chamber; the subject fluid characteristics; the volume of subject fluid pumped per stroke; and the means or mode of attachment of the diaphragm to the housing. The size of the diaphragm is dependent on multiple variables. These variables include, but are not limited to: the shape of the chamber; the size of the chamber; the subject fluid characteristics; the volume of subject fluid pumped per stroke; and the means or mode of attachment of the diaphragm to the housing. Thus, depending on these or other variables, the shape and size of the diaphragm may vary in various embodiments.

The diaphragm can have any thickness. However, in some embodiments, the range of thickness is between 0.002 inches to 0.125 inches. Depending on the material used for the diaphragm, the desired thickness may vary. In one embodiment, high elongation silicone is used in a thickness ranging from 0.015 inches to 0.050 inches. However in other embodiments, the thickness may vary.

In the exemplary embodiment, the diaphragm is pre-formed to include a substantially dome-shape or spheroid (or otherwise curved) shape in at least part of the area of the diaphragm, such as the body 1700 of the diaphragm 1226. One embodiment of the dome-shaped diaphragm is shown in FIGS. 149A and 149B. FIG. 149B shows a cross-sectional view along the lines indicated in FIG. 149A. Again, the dimensions of the dome may vary based on some or more of the variables described above. However, in other embodiments, the diaphragm may not include a pre-formed dome or curved shape.

In the exemplary embodiment, the diaphragm dome is formed using liquid injection molding. However, in other embodiments, the dome may be formed by using compression molding. In alternate embodiments, the diaphragm is substantially flat. In other embodiments, the dome size, width or height may vary.

In various embodiments, the diaphragm may be held in place by various means and methods. In one embodiment, the diaphragm is clamped between the portions of the cassette, and in some of these embodiments, the rim of the cassette may include features to grab a bead 1708 of the diaphragm. In others of this embodiment, the diaphragm is clamped to the cassette using at least one bolt or another device. In another embodiment, the diaphragm is over-molded with a piece of plastic and then the plastic is welded or otherwise attached to the cassette. In another embodiment the diaphragm is pinched between the mid-body or mid plate 1000 and the control-side body or bottom plate 1100 of a pump cassette 1710 (see, e.g., FIG. 146A, B). Although some embodiments for attachment of the diaphragm to the cassette are described, any method or means for attaching the diaphragm to the cassette can be used. The diaphragm, in one alternate embodiment, is attached directly to one portion of the cassette. In some embodiments, the diaphragm is thicker at the edge or periphery, where the diaphragm is pinched by the plates, than in other areas of the diaphragm. In some embodiments, this thicker area is a gasket, in some embodiments an O-ring, a bead element or ring, or any other shaped thickening suitable for capture by the compression or welding of the mid-pate 1000 to the bottom plate 1100, or of the mid-plate 1000 to a pumping-side body or top plate 900 of the pump cassette 1710. In some embodiments, more than one gasket or bead may provide the attachment point of the diaphragm to the cassette. In other embodiments, the diaphragm includes a single bead or gasket. Diaphragms with one bead or gasket 1708 are shown, for example, in the embodiments of FIGS. 147A-147D).

In some embodiments, the gasket, O-ring or bead 1708 at the periphery of the diaphragm is contiguous (or co-molded) with the body 1700 of the diaphragm. A transitional section between the gasket and the main portion or body of the diaphragm may be of a thickness that is intermediate between the thickness of the gasket or bead, and the thickness of the body of the diaphragm. Alternatively, the transition between the bead and body may have a uniform thickness matching the thickness of the body of the diaphragm. However, in other embodiments, the gasket or bead may be a separate part of the diaphragm. In some embodiments, the gasket or bead is made from the same material as the diaphragm. However, in other embodiments, the gasket or bead may be made of a material different from the diaphragm. In some embodiments, the gasket or bead is formed by over-molding a ring around the diaphragm. The gasket or bead can be any shape ring or seal desired so as to complement the pod pump housing embodiment. In some embodiments, the gasket or bead is a compression type gasket, acquiring a cross-sectional shape that conforms to the rigid shape of the cassette components that clamp the gasket or bead in place.

As shown in FIG. 150, a transitional portion 1712 of the diaphragm 1226 between the gasket 1708 of the diaphragm and the body 1700 of the diaphragm may be supported, pinched or clamped between the mid-body and the control-side body. In an embodiment, this is accomplished by a prominence or projection 1714 of the mid-body 1000 of the pump cassette 1710 along the perimeter of the opening of the mid-body, the opening formed to accommodate movement of the body 1700 of the flexible diaphragm 1226 between control chamber 1716 of the control-side body or bottom plate 1100 and the pumping chamber 1718 of the pumping-side body or top plate 900 of the cassette 1710. The clamping feature 1714 in this embodiment is formed from the mid-body or mid-plate 1000 of the cassette assembly, but a similar feature could equally effectively originate from the control-side body or bottom plate 1100 of the cassette assembly, functioning to pinch or clamp the transitional portion 1712 of the diaphragm 1226 between the mid-body and the control-side body.

As shown in FIG. 149A and FIG. 149B, the body 1700 of the diaphragm 1226 may be molded so as to have a relaxed or non-stressed configuration with the pumping chamber side of the diaphragm convex to the pumping chamber 1718 side of the pump cassette 1710. Thus, when installed in the pump, any elastic tension in the diaphragm is reduced when the pumping chamber side of the diaphragm assumes a convex shape, and/or is at a minimum when the diaphragm is extended into the pumping chamber. As shown in FIG. 150 and FIG. 151, in this case, the transitional region 1712 between the gasket 1708 of the diaphragm 1226 and the body 1700 of the diaphragm 1226 may be curved to wrap around the projection 1714 of the mid-body 1000, essentially draping the diaphragm 1226 into the pumping chamber 1718 region. Although this arrangement may have some advantages in allowing the diaphragm to fully deploy with minimal stretching against the pumping chamber wall during a delivery stroke, it has also unexpectedly been found to be associated with some degree of clotting of blood or the formation of fibrinous protein strands in the pumping chamber near the junction of the diaphragm and the mid-body against which it is pinched or clamped. Although other explanations may exist, there are two possible reasons that a typical diaphragm configuration (relaxed state convex to the pumping chamber side) may be associated with coagulation when pumping blood. First, the body 1700 of the diaphragm 1226 may or may not fully deploy into the control chamber 1716 when a negative pressure or vacuum is applied to the control chamber 1716 unless the transitional region 1712 is caused to stretch elastically, creating a discontinuity or gap between the diaphragm-contacting portion of the mid-body 1000 and the surface of the diaphragm near or at its transitional region 1712. Such a discontinuity or gap may serve as a site of attachment for blood elements, leading to stagnation of blood and the initiation of coagulation. Alternatively, as the diaphragm is deployed into the pumping chamber during a delivery stroke, a peripheral portion 1720 of the body 1700 of the diaphragm 1226 may trap some blood as the diaphragm naturally attempts to restore its non-stressed configuration into contact with the pumping chamber wall 1722 of either the mid-body 1000 or the pump-side body or top plate 900. Such blood trapping may lead to stagnation of blood elements and the initiation of coagulation. In either circumstance (or for other reasons), it appears that a diaphragm 1226 molded to naturally assume a non-stressed configuration that is convex toward the pumping chamber wall 1722 may facilitate the formation of fibrinous protein strands or blood clots.

Surprisingly, it has been found that blood clotting or the development of fibrinous protein strands in the pumping chamber of the pump cassette may be reduced by altering the design and configuration of the diaphragm 1226. As shown in FIG. 152A and FIG. 152B, in an alternate embodiment, the body 1700 of the diaphragm 1226 may be molded so that its relaxed or un-stressed state has the control surface of the diaphragm convex to the control chamber 1716 side of the pump cassette 1710, rather than having the pumping surface of the diaphragm convex to the pumping chamber side. Thus, when installed in the pump, any elastic tension in the diaphragm is reduced when the control chamber side of the diaphragm assumes a convex shape, and/or is at a minimum when the diaphragm is fully extended into the control chamber. In this case, the mold form in which the diaphragm is molded may have a plurality of recessed 'dimples' located on the convex portion of the form, rather than on the concave portion of the form. As shown in FIG. 153 and FIG. 154, in this case, the transitional region 1712 between the bead or gasket 1708 of the diaphragm 1226 and the body 1700 of the diaphragm 1226 may naturally curve away 1724 from the chamber-facing wall 1722 of the mid-body 1000 or pumping body or top plate 900 as the transitional region 1712 of the diaphragm 1226 emerges from contacting the clamping or pinching portions of the mid-body or mid-plate 1000 and the control-side body or bottom plate 1100. A possible advantage of this arrangement is that as a negative pressure is applied to the body 1700 of the diaphragm 1226 during a fill stroke, a peripheral portion 1720 of the diaphragm 1226 will have a tendency to naturally move away from the chamber-facing wall 1722 of the mid-body 1000. This may help to prevent stretching of the transitional region 1712 and the development of a discontinuity or gap between the transitional region 1712 of the diaphragm 1226 and the portion of the cassette with which it is in contact. Alternatively, during a delivery stroke, the elastic force of the diaphragm resisting its deployment into the pumping chamber may prevent a peripheral portion 1720 of the diaphragm from fully contacting the pumping chamber wall 1722, thus helping to avoid trapping and stagnation of blood in that region. Thus the elastic restoring force of a diaphragm molded to have a convex configuration toward the control chamber wall may inhibit the peripheral regions of the diaphragm from fully contacting the pumping chamber wall and potentially trapping any residual fluid in the pumping chamber. In some pump configurations, maintaining a potential space between the diaphragm 1226 and the pumping chamber wall in this peripheral region may be useful when pumping liquids containing proteinaceous materials, such as blood or plasma (or other relatively viscous liquids), because dissolved or suspended compounds will have less of a chance of aggregating, coalescing, polymerizing, or clotting in the pumping region adjacent the chamber-facing wall 1722 of the mid-body or pumping-side body of the pumping chamber 1718.

Alternative embodiments may also serve to discourage the formation of stagnant regions between the peripheral portion 1720 of the body 1700 of the diaphragm 1226 and the periphery 1722 of the pumping chamber 1718. For example, the diaphragm 1226 may be molded in a manner to extend the transitional region 1712 between the gasket 1708 and the body 1700 of the diaphragm 1226, so that when the diaphragm 1226 is seated within the pump cassette, the transitional region 1712 extends further into the chamber as it exits away from the gasket 1708 region and from contact with the clamping portion 1712 of the mid-body 1000 of the cassette 1710. In a relaxed state, the body 1700 of the diaphragm 1226 will thus have a tendency to elastically move away from contact with the chamber-facing side 1722 of the mid-body, (or more generally the periphery 1722 of the pumping chamber 1718 wall). Optionally, the transitional region 1712 of the diaphragm 1226 may be molded to have a thickened cross section to enhance its stiffness and resistance to flexing toward the chamber-facing side 1722 of the mid-body 1000 (or more generally the periphery 1722 of the chamber wall).

A system of the present invention may also include a balancing circuit, e.g., balancing circuit 143 as shown in FIG. 3A. In some cases, blood flow circuit is implemented on a cassette, although it need not be. Within the balancing circuit, the flow of dialysate that passes in and out of the dialyzer may be balanced in some cases such that essentially the same amount of dialysate comes out of the dialyzer as goes into it (however, this balance can be altered in certain cases, due to the use of a bypass pump, as discussed below).

In addition, in some cases, the flow of dialysate may also be balanced through the dialyzer such that the pressure of dialysate within the dialyzer generally equals the pressure of blood through the blood flow circuit. The flow of blood through the blood flow circuit 141 and dialyzer in some cases is synchronized with the flow of dialysate in the dialysate flow path through the dialyzer. Because of the potential of fluid transfer across the semi-permeable membrane of the dialyzer, and because the pumps of the balancing circuit run at positive pressures, the balancing circuit pumps can be timed to synchronize delivery strokes to the dialyzer with the delivery strokes of the blood pumps, using pressure and control data from the blood flow pumps.

Figure 5:
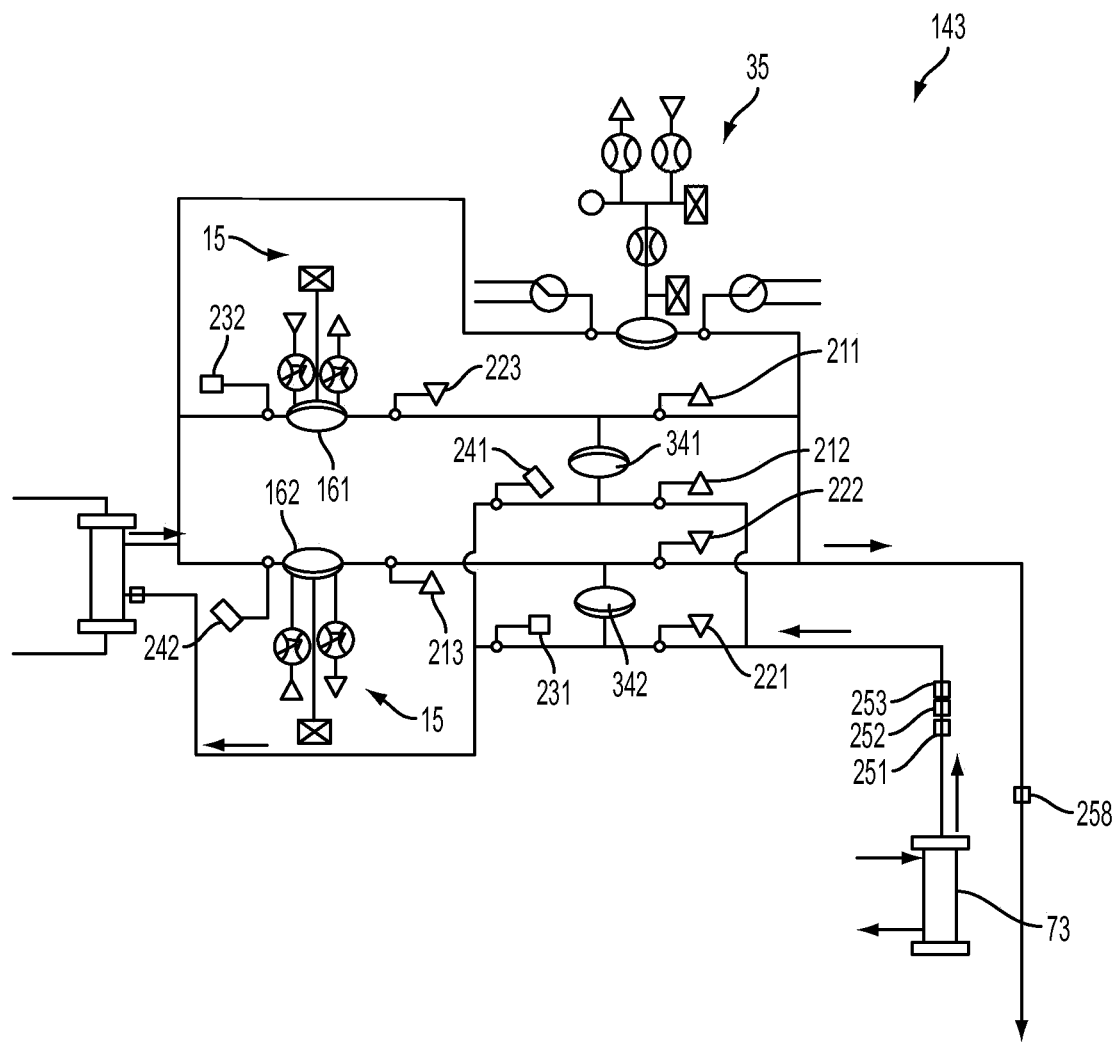
FIG. 5 is a schematic representation of one embodiment of a balancing circuit that may be used in a hemodialysis system.

A non-limiting example of a balancing circuit is shown in FIG. 5. In balancing circuit 143, dialysate flows from optional ultrafilter 73 into one or more dialysate pumps 15 (e.g., two as shown in FIG. 5). The dialysate pumps 15 in this figure include two pod pumps 161, 162, two balancing chambers 341, 342, and pump 35 for bypassing the balancing chambers. The balancing chambers may be constructed such that they are formed from a rigid chamber with a flexible diaphragm dividing the chamber into two separate fluid compartments, so that entry of fluid into one compartment can be used to force fluid out of the other compartment and vice versa. Non-limiting examples of pumps that can be used as pod pumps and/or balancing chambers are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Additional examples of pod pumps are discussed in detail below. As can be seen in the schematic of FIG. 5, many of the valves can be "ganged" or synchronized together in sets, so that all the valves in a set can be opened or closed at the same time.

Figure 18A:
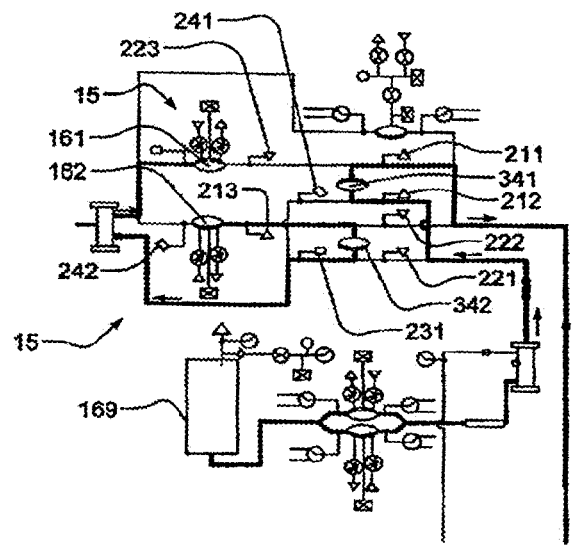
FIGS. 18A-18B illustrate the fluid flow of dialysate from a dialysate tank, through the dialyzer and out to drain in one embodiment of the invention.

More specifically, in one embodiment, balancing of flow works as follows. FIG. 5 includes a first synchronized, controlled together set of valves 211, 212, 213, 241, 242, where valves 211, 212, 213 are ganged and valves 241 and 242 are ganged, as well as a second synchronized, controlled together set of valves 221, 222, 223, 231, 232, where valves 221, 222, 223 are ganged, and valves 231 and 232 are ganged. At a first point of time, the first ganged set of valves 211, 212, 213, 241, 242 is opened while the second ganged set of valves 221, 222, 223, 231, 232 is closed. Fresh dialysate flows into balancing chamber 341 while used dialysate flows from dialyzer 14 into pod pump 161. Fresh dialysate does not flow into balancing chamber 342 since valve 221 is closed. As fresh dialysate flows into balancing chamber 341, used dialysate within balancing chamber 341 is forced out and exits balancing circuit 143 (the used dialysate cannot enter pod pump 161 since valve 223 is closed). Simultaneously, pod pump 162 forces used dialysate present within the pod pump into balancing chamber 342 (through valve 213, which is open; valves 242 and 222 are closed, ensuring that the used dialysate flows into balancing chamber 342). This causes fresh dialysate contained within balancing chamber 342 to exit the balancing circuit 143 into dialyzer 14. Also, pod pump 161 draws in used dialysate from dialyzer 14 into pod pump 161. This is also illustrated in FIG. 18A.

Figure 18B:
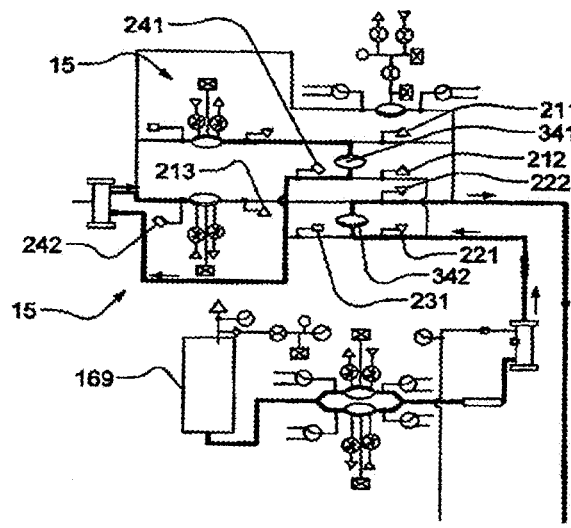

Once pod pump 161 and balancing chamber 341 have filled with dialysate, the first set of valves 211, 212, 213, 241, 242 is closed and the second set of valves 221, 222, 223, 231, 232 is opened. Fresh dialysate flows into balancing chamber 342 instead of balancing chamber 341, as valve 212 is closed while valve 221 is now open. As fresh dialysate flows into balancing chamber 342, used dialysate within the chamber is forced out and exits balancing circuit, since valve 213 is now closed. Also, pod pump 162 now draws used dialysate from the dialyzer into the pod pump, while used dialysate is prevented from flowing into pod pump 161 as valve 232 is now closed and valve 222 is now open. Pod pump 161 forces used dialysate contained within the pod pump (from the previous step) into balancing chamber 341, since valves 232 and 211 are closed and valve 223 is open. This causes fresh dialysate contained within balancing chamber 341 to be directed into the dialyzer (since valve 241 is now open while valve 212 is now closed). At the end of this step, pod pump 162 and balancing chamber 342 have filled with dialysate. This puts the state of the system back into the configuration at the beginning of this description, and the cycle is thus able to repeat, ensuring a constant flow of dialysate to and from the dialyzer. This is also illustrated in FIG. 18B. In an embodiment, the fluid (e.g. pneumatic) pressures on the control side of the balancing chamber valves are monitored to ensure they are functioning properly.

As a specific example, a vacuum (e.g., 4 p.s.i. of vacuum) can be applied to the port for the first ganged set of valves, causing those valves to open, while positive pressure (e.g., 20 p.s.i. of air pressure, 1 p.s.i. is 6.89475 kilopascals) is applied to the second ganged set of valves, causing those valves to close (or vice versa). The pod pumps each urge dialysate into one of the volumes in one of the balancing chambers 341, 342. By forcing dialysate into a volume of a balancing chamber, an equal amount of dialysate is squeezed by the diaphragm out of the other volume in the balancing chamber. In each balancing chamber, one volume is occupied by fresh dialysate heading towards the dialyzer and the other volume is occupied by used dialysate heading from the dialyzer. Thus, the volumes of dialysate entering and leaving the dialyzer are kept substantially equal.

It should be noted that any valve associated with a balancing chamber may be opened and closed under any suitable pressure. However, it may be advantageous to apply a lower or more controlled pressure to initiate and effect valve closure than the pressure ultimately used to keep the valve closed ("holding pressure"). Applying the equivalent of the holding pressure to effectuate valve closure may lead to transient pressure elevations in the fluid line sufficient to cause an already closed downstream valve to leak, adversely affecting the balancing of dialysate flow into and out of the dialyzer. Causing the dialysate pump and balancing chamber inlet and/or outlet valves to close under a lower or more controlled pressure may improve the balancing of dialysate flow into and out of the dialyzer. In an embodiment, this can be achieved, for example, by employing pulse width modulation ("PWM") to the pressure being applied in the fluid control lines of the valves. Without being limited to the following theories, the use of moderate or controlled pressure to 'slow-close' the valves may be effective for example, because: (1) it is possible that in some cases, the pressure in a balancing chamber can transiently exceed the holding pressure in the closed balancing chamber outlet valve (caused, for example by applying excessive pressure to close the balancing chamber inlet valve against the mass of fluid behind the valve diaphragm). The transient elevation of pressure in the fluid line can overcome the holding pressure of the closed outlet valve, resulting in a leak of fluid and an imbalance of fluid delivery between the two sides of the balancing chamber. (2) Also, the presence of air or gas between the balancing chamber and a balancing chamber valve, coupled with a rapid valve closure, could cause excess fluid to be pushed through the balancing chamber without being balanced by fluid from the opposite side of the balancing chamber.

As the diaphragms approach a wall in the balancing chambers (so that one volume in a balancing chamber approaches a minimum and the other volume approaches a maximum), positive pressure is applied to the port for the first ganged set of valves, causing those valves to close, while a vacuum is applied to the second ganged set of valves, causing those valves to open. The pod pumps then each urge dialysate into one of the volumes in the other of the balancing chambers 341, 342. Again, by forcing dialysate into a volume of a balancing chamber, an equal amount of dialysate is squeezed by the diaphragm out of the other volume in the balancing chamber. Since, in each balancing chamber, one volume is occupied by fresh dialysate heading towards the dialyzer and the other volume is occupied by used dialysate heading from the dialyzer, the volumes of dialysate entering and leaving the dialyzer are kept equal.

Also shown within FIG. 5 is bypass pump 35, which can direct the flow of dialysate from dialyzer 14 through balancing circuit 143 without passing through either of pod pumps 161 or 162. In this figure, bypass pump 35 is a pod pump, similar to those described above, with a rigid chamber and a flexible diaphragm dividing each chamber into a fluid compartment and a control compartment. This pump may be the same or different from the other pod pumps, metering pumps and/or balancing chambers described above. For example, this pump may be a pump as was described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Pod pumps are also discussed in detail below.

When control fluid is used to actuate this pump, dialysate may be drawn through the dialyzer in a way that is not balanced with respect to the flow of blood through the dialyzer. The independent action of the bypass pump 35 on the dialysate outlet side of the dialyzer causes an additional net ultrafiltration of fluid from the blood in the dialyzer. This may cause the net flow of liquid away from the patient, through the dialyzer, towards the drain. Such a bypass may be useful, for example, in reducing the amount of fluid a patient has, which is often increased due to the patient's inability to lose fluid (primarily water) through the kidneys. As shown in FIG. 5, bypass pump 35 may be controlled by a control fluid (e.g., air), irrespective of the operation of pod pumps 161 and 162. This configuration may allow for easier control of net fluid removal from a patient, without the need to operate the balancing pumps (inside and outside dialysate pumps) in a way that would allow for such fluid to be withdrawn from the patient. Using this configuration, it is not necessary to operate the inside dialysate pumps either out of balance or out of phase with the blood pumps in order to achieve a net withdrawal of fluid from the patient.

To achieve balanced flow across the dialyzer, the blood flow pump, the pumps of the balancing circuit, and the pumps of the directing circuit (discussed below) may be operated to work together to ensure that flow into the dialyzer is generally equal to flow out of the dialyzer. If ultrafiltration is required, the ultrafiltration pump (if one is present) may be run independently of some or all of the other blood and/or dialysate pumps to achieve the desired ultrafiltration rate.

To prevent outgassing of the dialysate, the pumps of the balancing circuit may be always kept at pressures above atmospheric pressure. In contrast, however, the blood flow pump and the directing circuit pumps use pressures below atmosphere to pull the diaphragm towards the chamber wall for a fill stroke. Because of the potential of fluid transfer across the dialyzer and because the pumps of the balancing circuit run at positive pressures, the balancing circuit pumps may be able to use information from the blood flow pump(s) in order to run in a balanced flow mode. The delivery strokes of the balancing circuit chambers to the dialyzer can thus be synchronized with the delivery strokes of the blood pumps.

In one set of embodiments, when running in such a balanced mode, if there is no delivery pressure from the blood flow pump, the balancing circuit pump diaphragm will push fluid across the dialyzer into the blood and the alternate pod of the balancing circuit will not completely fill. For this reason, the blood flow pump reports when it is actively delivering a stroke. When the blood flow pump is delivering a stroke the balancing pump operates. When the blood flow pump is not delivering blood, the valves that control the flow from the dialyzer to the balancing pumps (and other balancing valves ganged together with these valves, as previously discussed) may be closed to prevent any fluid transfer from the blood side to the dialysate side from occurring. During the time the blood flow pump is not delivering, the balancing pumps are effectively frozen, and the stroke continues once the blood flow pump starts delivering again. The balancing pump fill pressure can be set to a minimal positive value to ensure that the pump operates above atmosphere at minimal impedance. Also, the balancing pump delivery pressure can be set to the blood flow pump pressure to generally match pressures on either side of the dialyzer, minimizing flow across the dialyzer during delivery strokes of the inside pump.

In some cases, it may be advantageous to have the dialysate pump deliver dialysate to the dialyzer at a pressure higher than the delivery pressure of the blood pump to the dialyzer. This can help to ensure, for example, that a full chamber of clean dialysate can get delivered to the dialyzer. In an embodiment, the delivery pressure on the dialysate pump is set sufficiently high to allow the inside pump to finish its stroke, but not so high as to stop the flow of blood in the dialyzer. Conversely, when the dialysate pump is receiving spent dialysate from the dialyzer, in some cases it may also be advantageous to have the pressure in the dialysate pump set lower than the outlet pressure on the blood side of the dialyzer. This can help ensure that the receiving dialysate chamber can always fill, in turn ensuring that there is enough dialysate available to complete a full stroke at the balancing chamber. Flows across the semipermeable membrane caused by these differential pressures will tend to cancel each other; and the pumping algorithm otherwise attempts to match the average pressures on the dialysate and blood sides of the dialyzer.

Convective flow that does occur across the dialyzer membrane may be beneficial, because a constant and repeated shifting of fluid back and forth across the dialyzer in small increments—resulting in no net ultrafiltration—can nevertheless help to prevent clot formation within the blood tubing and dialyzer, which in turn may allow for a smaller heparin dosage, prolong the useful life of the dialyzer, and facilitate dialyzer cleaning and re-use. Backflushing has the additional benefit of promoting better solute removal through convection. In another embodiment, a form of continuous backflushing across the dialyzer membrane can also be achieved by making small adjustments to the synchronization of the delivery strokes of blood with the delivery strokes of dialysate through the dialyzer.

In certain embodiments, the pod pumps 15 (FIG. 89) of the inner dialysate cassette 143 may be phased to minimize occlusions in the blood side of the dialyzer 14. The inner dialysate pop pumps 15 may be phased to work with the blood pumps 13 to alternately flow liquid into the blood side of the dialyzer 14 and back to the dialysate side with each stroke of the inner dialysate pump 15. The timing of the pump strokes, valve openings, valve closings and pop pump actuation pressures may be controlled by the automatic computer 6106. The automatic computer may control the pumps, valves and receives pressure data via the pneumatic pressure distribution module 9000. Phasing the inner dialysate pumps to push the fluid back and forth across the dialyzer membrane has benefits including but not limited to improved removal of large molecule solutes from the blood and minimized occlusions of the dialyzer, The flows through the dialyzer 14 may be controlled by the pumps and valves shown schematically in FIG. 89. One example of the timing and function of the blood and dialysate pumps are plotted in FIGS. 8A-8C. The blood pumps pod pumps 23a, 23b may operating 180 degrees out of phase to provide a near continuous flow of blood to the dialyzer 14. Cleaned blood and some dialysate fluid may flow from the dialyzer to the venous line 204 in the BTS. Fresh dialysate may flow into the dialyzer from the balancing pod 342, while used dialysate and fluid from the blood side flow into a receiving pod pump 161. Clean dialysate may flow from the balance pod 342 as the other dialysate pump 162 forces used dialysate into the balancing pod 342. The used and clean dialysate are separated by a diaphragm. The other balancing pod 341 may be filled with fresh dialysate from the outer dialysate pump 159 in preparation for the next pump stroke.

The blood pump 23A may be caused to deliver blood to the dialyzer 14 by opening the downstream valve, closing the upstream valve and raising the pod pressure measured by 193. The blood pump 23b may be caused to fill from the arterial line by opening the upstream valve, closing the downstream line and reducing the pressure below ambient as measured by 197.

One exemplary sequence to push and pull fluid across the dialyzer membrane may begin at time 12411 with blood pump 23A delivering blood to the dialyzer, while blood pump 23b is filled. The measured pressures of the delivering and filling pumps are plotted as 12420 and 12430 respectively. The pressures 12420, 12430 may vary periodically in response to the vari-valves 198, 199 sinusoidally varying the size of the valve port. The automatic computer 6106 may monitor the pressure traces 12420 and 12430 to detect end-of-stroke in the blood pumps.

The pumps and valves of the inner dialysate may be controlled to allow fluid from the blood in the dialyzer 14 to flow into the receiving dialysate pump pod 161 between times 12411 and 12412. Valve 231 may be closed to prevent the flow of clean dialysate into the dialyzer 14. Valve 232 may be open and the pump pod pressure 12440 may be low to allow fluid from the blood to flow into the dialysate pump pod 161. The blood pump 13 may flow blood through the dialyzer during this period 12410.

The inner dialysate valves and pumps may be controlled between times 12412 and 12413 to flow dialysate through the dialyzer with zero or minimal flow across the dialyzer membrane. Valves 231 and 213 may be opened to allow the pneumatic pressure 12450 in pump pod 162 to force clean dialysate from the balancing pod 342 through the dialyzer 14 and into pump pod 162. Pump 162 may force clean dialysate from the balancing pod 342 by flowing used dialysate into back side of membrane 341C. The blood pump 13 may continue to flow blood through the dialyzer during this period. The pressures in pump pods 161 and 162 may vary periodically in response to the vari-valves 163, 164 sinusoidally varying the size of the valve ports. The automatic computer 6106 may monitor the pressure traces 12440 and 12450 to detect end-of-stroke in the dialysate pumps 15.

Dialysate may flow into the blood side of the dialyzer during the last part of the dialysate pump stroke. The receiving pump pod 161 may completely fill at time 12413, while the delivery pump 162 continues to pump fresh dialysate from the balancing pod 342 until time 12414. The dialysate from the balancing pod may not be able not enter the full pump pod 161 and may instead flow across the dialyzer membrane and enter the blood circuit. The blood pump 13 may continue to flow blood through the dialyzer during part or all of this period. Without wishing to be bound by any theory, it is believed that the dialysate flowing into the blood side of the dialyzer may dislodge the larger solutes from the pores, centers and ends of the membrane tubes. Once dislodged from the surface, the larger solutes are then more likely to flow through or across the membrane.

In one exemplary method the action of the dialysate pumps 161, 162 may be stopped, while the blood pump 13 switches from one pump pod to the other, if the receiving pump pod 161 is not full. The dialysate pumps may be stopped to avoid a false end-of-stroke due to pressure signals from the switching blood pumps. If the automatic computer 6106 detects an end-of-stroke condition on the blood pump 13 before the receiving pump pod 161 is full, then it may close the balancing chamber outlet valve 231 and the pump inlet valve 232. The valves 231 and 232 may be reopened once the blood pump restarts. If the blood pump pod completes a stroke after the receive pump pod 161 is full, then the blood pump will wait until the delivering pump pod 162 completes its stroke. The automatic computer may determine that pump pod strokes are complete or that the dialysate pump pod is full based on the correlation number to determine an end-of-stroke condition.

The pump pod pressures in the dialysate circuit may be optimally set to assure the desired direction of dialysate and blood flow without damaging the dialyzer membrane. The pressure in the deliver pod pump 162 may be set to 54 mmHg above the blood delivery pressure. The receiving pump pod 161 may be adjusted to the larger of 25 mmHg above ambient pressure or the blood delivery pressure minus the transmembrane pressure. The delivery pump pod pressure may be increased to the maximum transmembrane pressure of the dialyzer after the fill or receiving pump pod 162 is full.

In one exemplary method the vari-valves in the blood pump 198, 199 may be cycled at a different frequency than the vari-valves of the dialysate pump 163, 164 to allow the end-of-stroke detection of each pump to be separately measured. As described elsewhere, the restriction of the vari-valve on a pump pod is varied sinusoidally about a mean value. This small change in restriction produces a similar small change in the measure pressure in the activation chamber. The correlation filter described elsewhere produces a numerical measure of how well the pressure responds to the vari-valve variations. The resulting correlation number may be used to determine end-of-stroke. The pressure variations in the blood pump pod 23a may be detected by the sensor on the fill pump pod 161, which could produce false end-of-stroke readings. However, correlation filter rejects pressure signals that are at a different frequency than the vari-valve frequency. In order to isolate the pressure signals from the two pumps 161, 23a, the vari-valves may be dithered at a frequency that is 90% of the frequency at which the blood pump vari-valve is dithered.

In one exemplary method, the deliver pump delay 12410 is optimally adjusted to deliver the desired amount of dialysate into the blood circuit at the end of the dialysate stroke. A simple proportional closed loop controller varies the deliver pump delay 12410 to achieve the desired time for dialysate flow into the blood circuit 12416. The controller may adjust the pump delay time to adapt to changes in the flow impedances on the blood side and or the dialysate side of the flow circuit or changes in the transmembrane impedance of the dialyzer.

The sequence is then repeated, where pump pod 162 is now the receiving pump that begins the process by receiving fluid from the blood size of the dialyzer, while the delivering pump 161 is fixed. Then both pumps 161 and 162 move until the receiving pump 162 is full. At this time pump 161 continues and delivers dialysate to the blood side.

The method to create small periodic flows back and forth across the dialyzer with pumps, valves and balancing chambers is one exemplary method. Other methods and pump/valve embodiments are contemplated.

The described hardware of the inner dialysate and blood cassettes and the method of phasing the dialysate is one implementation. The same method of phasing one or more pumps on at least one side of a semi-permeable filter in order to periodically force fluid back and forth across filter could be applied to flows of liquid through other semi-permiable filters including but not limited to ultra filters.

It is generally beneficial to keep the blood flow as continuous as possible during therapy, as stagnant blood flow can result in blood clots. In addition, when the delivery flow rate on the blood flow pump is discontinuous, the balancing pump must pause its stroke more frequently, which can result in discontinuous and/or low dialysate flow rates.

However, the flow through the blood flow pump can be discontinuous for various reasons. For instance, pressure may be limited within the blood flow pump, e.g., to +600 mmHg and/or −350 mmHg to provide safe pumping pressures for the patient. For instance, during dual needle flow, the two pod pumps of the blood flow pump can be programmed to run 180° out of phase with one another. If there were no limits on pressure, this phasing could always be achieved. However to provide safe blood flow for the patient these pressures are limited. If the impedance is high on the fill stroke (due to a small needle, very viscous blood, poor patient access, etc.), the negative pressure limit may be reached and the fill flow rate will be slower than the desired fill flow rate. Thus the delivery stroke must wait for the previous fill stroke to finish resulting in a pause in the delivery flow rate of the blood flow pump. Similarly, during single needle flow, the blood flow pump may be run at 0° phase, where the two blood flow pump pod pumps are simultaneously emptied and filled. When both pod pumps are filled, the volumes of the two pod pumps are delivered. In an embodiment, the sequence of activation causes a first pod pump and then a second pod pump to fill, followed by the first pod pump emptying and then the second pod pump emptying. Thus the flow in single needle or single lumen arrangement may be discontinuous.

One method to control the pressure saturation limits would be to limit the desired flow rate to the slowest of the fill and deliver strokes. Although this would result in slower blood delivery flow rates, the flow rate would still be known and would always be continuous, which would result in more accurate and continuous dialysate flow rates. Another method to make the blood flow rate more continuous in single needle operation would be to use maximum pressures to fill the pods so the fill time would be minimized. The desired deliver time could then be set to be the total desired stroke time minus the time that the fill stroke took. However, if blood flow rate cannot be made continuous, then dialysate flow rate may have to be adjusted so that when the blood flow rate is delivering the dialysate flow is higher than the programmed value to make up for the time that the dialysate pump is stopped when the blood flow pump is filling. The less continuous the blood flow, the more the dialysate flow rate may have to be adjusted upward during blood delivery to the dialyzer. If this is done with the correct timing, an average dialysate flow rate taken over several strokes can still match the desired dialysate flow rate.

A non-limiting example of a balancing cassette is shown in FIGS. 34A-36E. In one structure of the cassette shown in FIG. 34A, the valves are ganged such that they are actuated at the same time. In one embodiment, there are four gangs of valves 832, 834, 836, 838. In some cases, the ganged valves are actuated by the same air line. However, in other embodiments, each valve has its own air line. Ganging the valves as shown in the exemplary embodiment creates the fluid-flow described above. In some embodiments, ganging the valves also ensures the appropriate valves are opened and closed to dictate the fluid pathways as desired.

In this embodiment, the fluid valves are volcano valves, as described in more detail herein. Although the fluid flow-path schematic has been described with respect to a particular flow path, in various embodiments, the flow paths may change based on the actuation of the valves and the pumps. Additionally, the terms inlet and outlet as well as first fluid and second fluid are used for description purposes only (for this cassette, and other cassettes described herein as well). In other embodiments, an inlet can be an outlet, as well as, a first and second fluid may be different fluids or the same fluid types or composition.

Figure 35A:
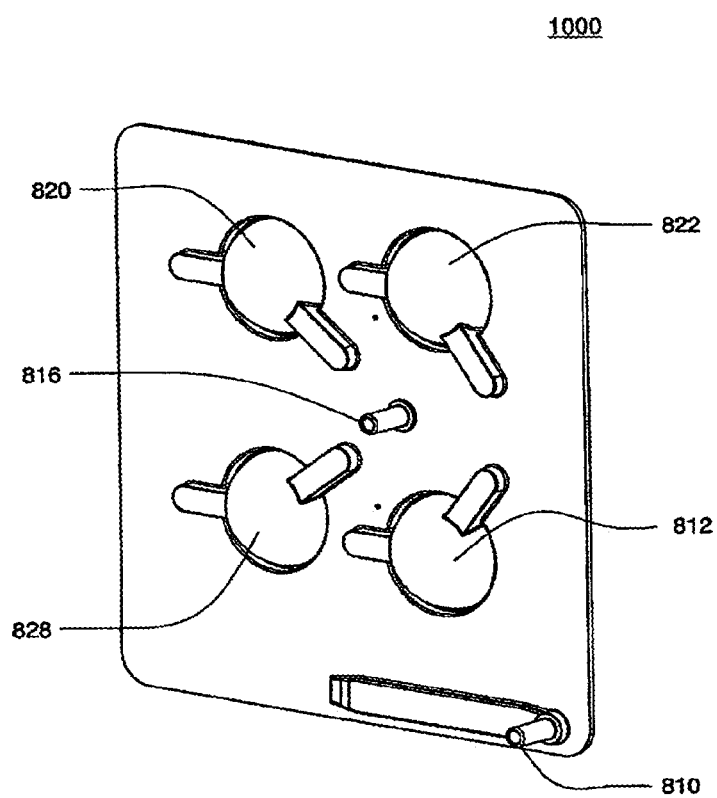
FIGS. 35A-35B are isometric and top views of an exemplary embodiment of the top plate of an exemplary embodiment of the cassette.
Figure 35B:
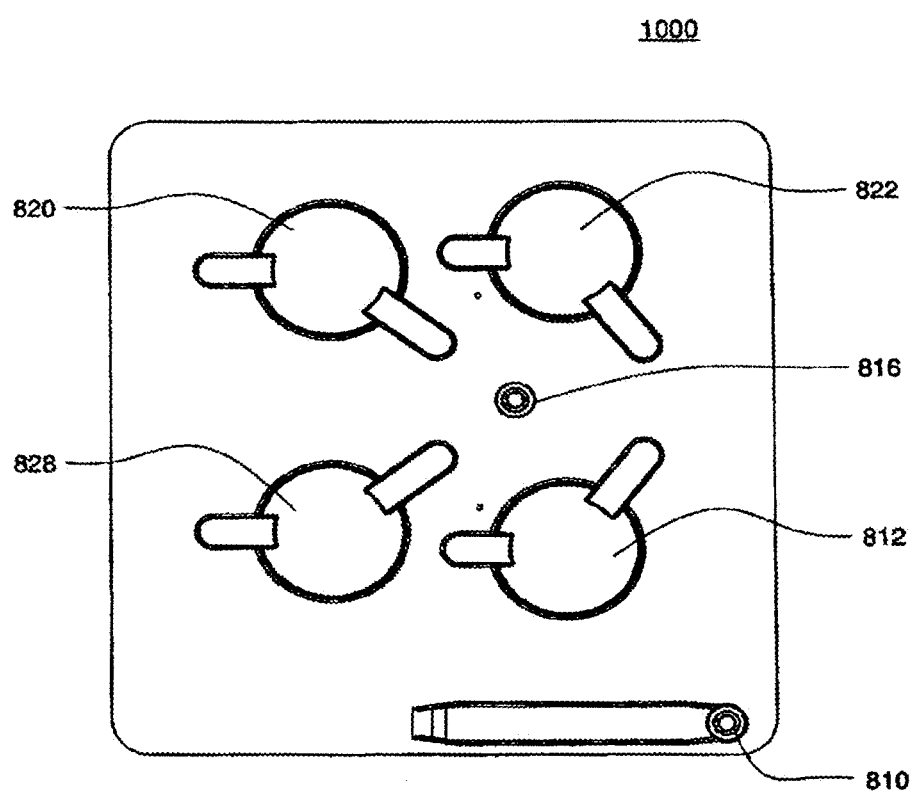

Referring now to FIGS. 35A-35E, the top plate 1000 of an exemplary embodiment of the cassette is shown. Referring first to FIGS. 35A and 35B, the top view of the top plate 1000 is shown. In this exemplary embodiment, the pod pumps 820, 828 and the balancing pods 812, 822 on the top plate, are formed in a similar fashion. In this embodiment, the pod pumps 820, 828 and balancing pods 812, 822, when assembled with the bottom plate, have a total volume of capacity of 38 ml. However, in various embodiments, the total volume capacity can be greater or less than in this embodiment. The first fluid inlet 810 and the second fluid outlet 816 are shown.

Figure 35C:
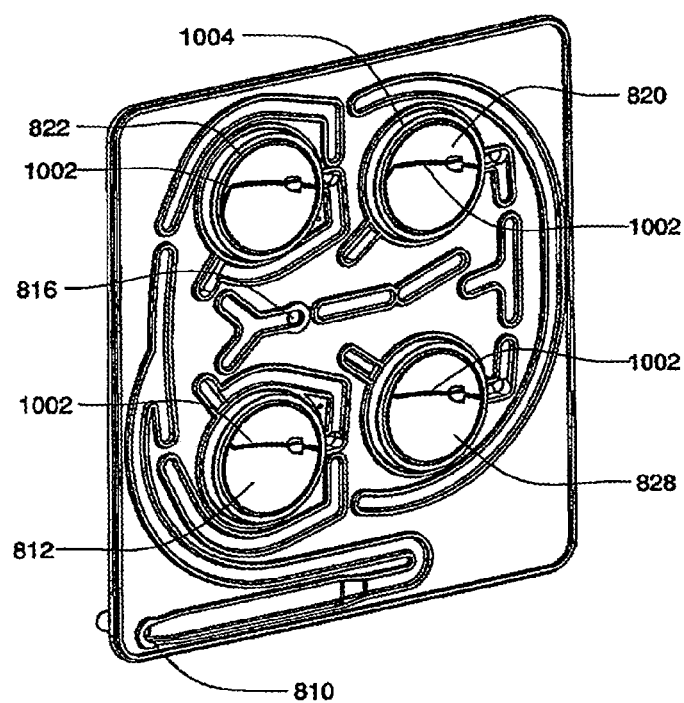
FIGS. 35C-35D are isometric views of an exemplary embodiment of the top plate of an exemplary embodiment of the cassette.
Figure 35D:
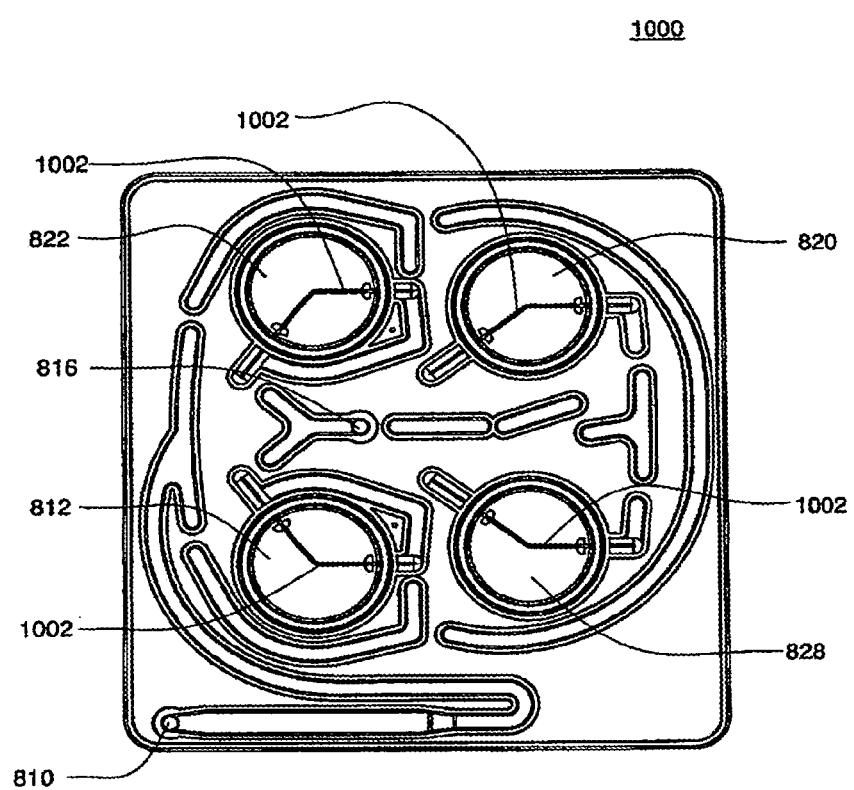

Referring now to FIGS. 35C and 35D, the bottom view of the top plate 1000 is shown. The fluid paths are shown in this view. These fluid paths correspond to the fluid paths shown in FIG. 34B in the midplate 900. The top plate 1000 and the top of the midplate form the liquid or fluid side of the cassette for the pod pumps 820, 828 and for one side of the balancing pods 812, 822. Thus, most of the liquid flow paths are on the top and midplates. The other side of the balancing pods' 812, 822 flow paths are located on the inner side of the bottom plate, not shown here, shown in FIGS. 36A-36B.

Still referring to FIGS. 35C and 35D, the pod pumps 820, 828 and balancing pods 812, 822 include a groove 1002. The groove 1002 is shown having a particular shape, however, in other embodiments, the shape of the groove 1002 can be any shape desirable. The shape shown in FIGS. 35C and 35D is an exemplary embodiment. In some embodiments of the groove 1002, the groove forms a path between the fluid inlet side and the fluid outlet side of the pod pumps 820, 828 and balancing pods 812, 822.

The groove 1002 provides a fluid path whereby when the diaphragm is at the end of stroke, there is still a fluid path between the inlet and outlet such that the pockets of fluid or air do not get trapped in the pod pump or balancing pod. The groove 1002 is included in both the liquid and air sides of the pod pumps 820, 828 and balancing pods 812, 822 (see FIGS. 36A-36B with respect to the air side of the pod pumps 820, 828 and the opposite side of the balancing pods 812, 822).

The liquid side of the pod pumps 820, 828 and balancing pods 812, 822, in one exemplary embodiment, include a feature whereby the inlet and outlet flow paths are continuous while the outer ring 1004 is also continuous. This feature allows for the seal, formed with the diaphragm (not shown) to be maintained.

Figure 35E:
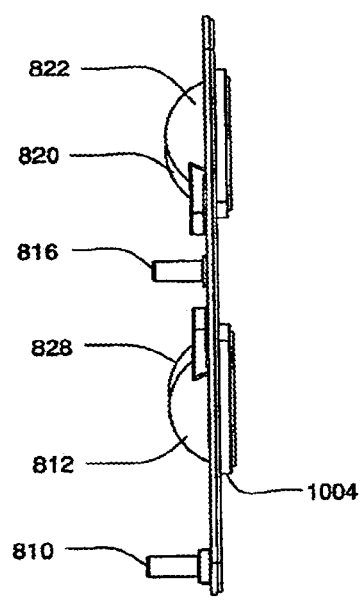
FIG. 35E is a side view of an exemplary embodiment of the top plate of a cassette.

Referring to FIG. 35E, the side view of an exemplary embodiment of the top plate 1000 is shown. The continuous outer ring 1004 of the pod pumps 820, 828 and balancing pods 812, 822 can be seen.

Figure 36A:
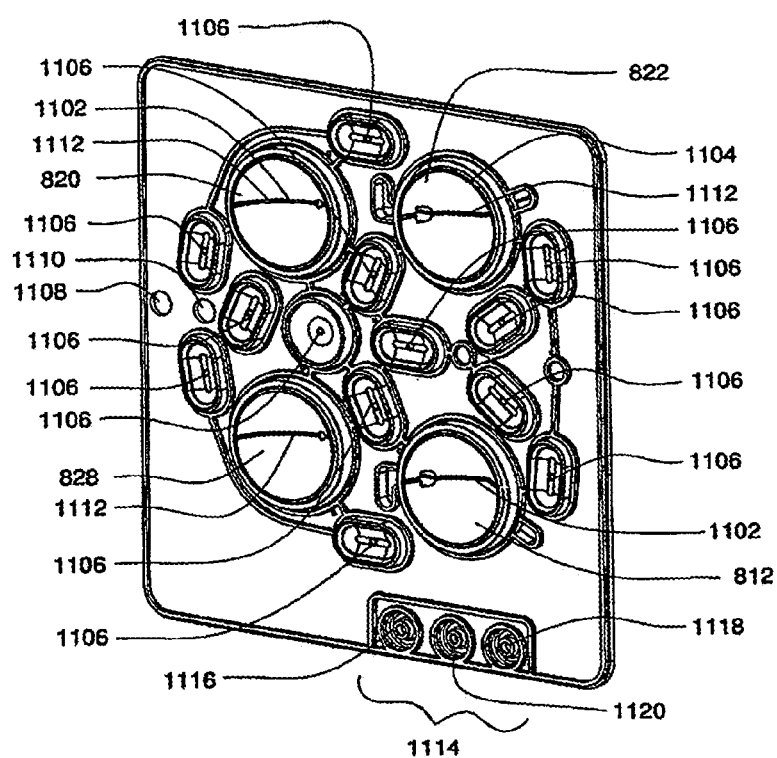
FIGS. 36A and 36B are isometric bottom views of an exemplary embodiment of the bottom plate of an exemplary embodiment of a cassette.
Figure 36B:
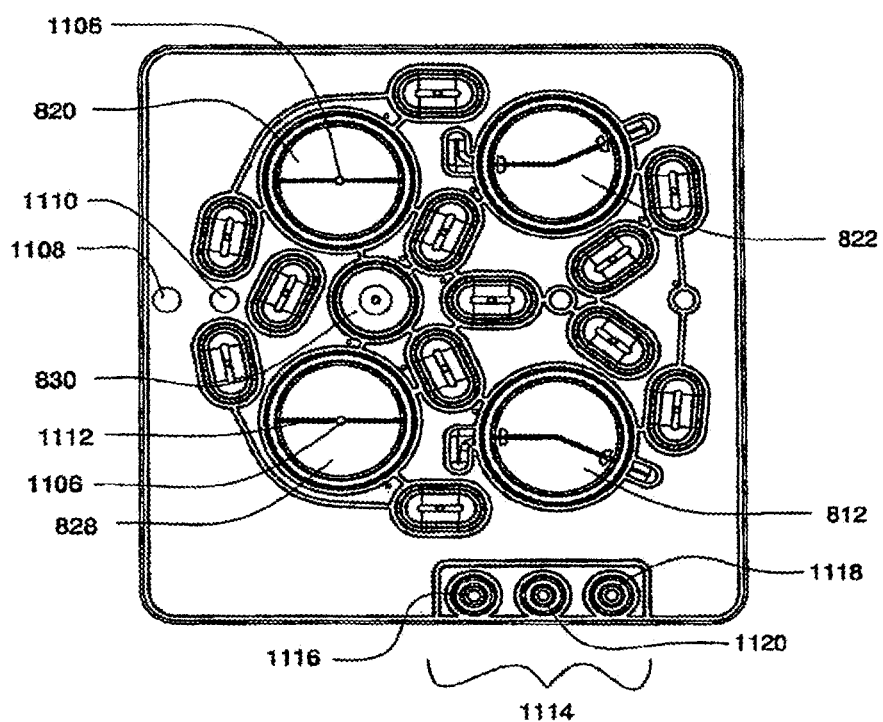

Referring now to FIGS. 36A-36E, the bottom plate 1100 is shown. Referring first to FIGS. 36A and 36B, the inside surface of the bottom plate 1100 is shown. The inside surface is the side that contacts the bottom surface of the midplate (not shown, see FIG. 34C). The bottom plate 1100 attaches to the air lines (not shown). The corresponding entrance holes for the air that actuates the pod pumps 820, 928 and valves (not shown, see FIG. 34C) in the midplate can be seen 1106. Holes 1108, 1110 correspond to the second fluid inlet and second fluid outlet shown in FIGS. 34C, 824, 826 respectively. The corresponding halves of the pod pumps 820, 828 and balancing pods 812, 822 are also shown, as are the grooves 1112 for the fluid paths. Unlike the top plate, the bottom plate corresponding halves of the pod pumps 820, 828 and balancing pods 812, 822 make apparent the difference between the pod pumps 820, 828 and balancing pods 812, 822. The pod pumps 820, 828 include an air path on the second half in the bottom plate, while the balancing pods 812, 822 have identical construction to the half in the top plate. Again, the balancing pods 812, 822 balance liquid, thus, both sides of the diaphragm, not shown, will include a liquid fluid path, while the pod pumps 820, 828 are pressure pumps that pump liquid, thus, one side includes a liquid fluid path and the other side, shown in the bottom plate 1100, includes an air actuation chamber or air fluid path.

In one exemplary embodiment of the cassette, sensor elements are incorporated into the cassette so as to discern various properties of the fluid being pumped. In one embodiment, the three sensor elements are included. In one embodiment, the sensor elements are located in the sensor cell 1114. The cell 1114 accommodates three sensor elements in the sensor element housings 1116, 1118, 1120. In an embodiment, two of the sensor housings 1116, 1118 accommodate a conductivity sensor element and the third sensor element housing 1120 accommodates a temperature sensor element. The conductivity sensor elements and temperature sensor elements can be any conductivity or temperature sensor elements in the art. In one embodiment, the conductivity sensor elements are graphite posts. In other embodiments, the conductivity sensor elements are posts made from stainless steel, titanium, platinum or any other metal coated to be corrosion resistant and still be electrically conductive. The conductivity sensor elements can include an electrical lead that transmits the probe information to a controller or other device. In one embodiment, the temperature sensor is a thermistor potted in a stainless steel probe. In alternate embodiments, there are either no sensors in the cassette or only a temperature sensor, only one or more conductivity sensors or one or more of another type of sensor. In some embodiments, the sensor elements are located outside of the cassette, in a separate cassette, and may be connected to the cassette via a fluid line.

Figure 36C:
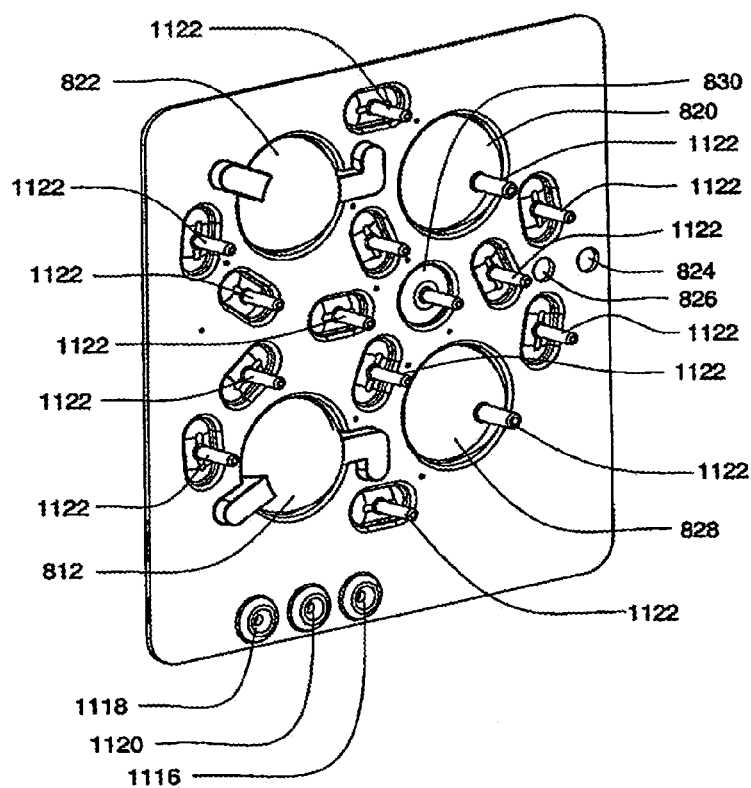
FIGS. 36C and 36D are isometric top views of an exemplary embodiment of the bottom plate of an exemplary embodiment of a cassette.
Figure 36D:
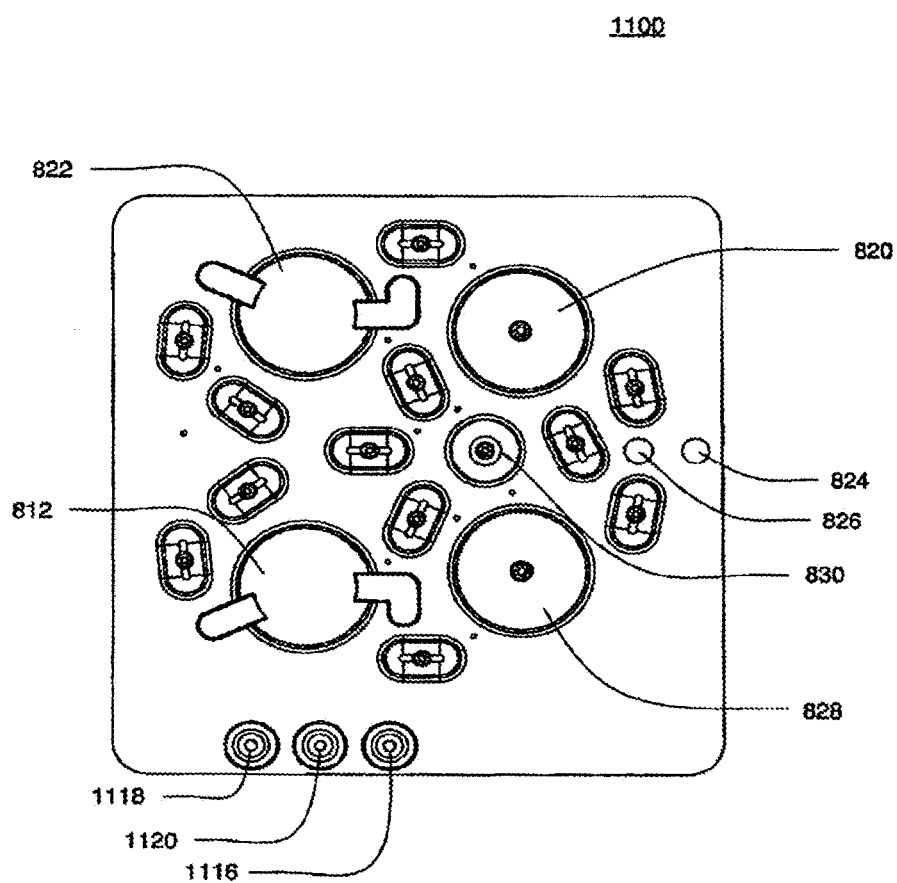

Still referring to FIGS. 36A and 36B, the actuation side of the metering pump 830 is also shown as well as the corresponding air entrance hole 1106 for the air that actuates the pump. Referring now to FIGS. 36C and 36D, the outer side of the bottom plate 1100 is shown. The valve, pod pumps 820, 828 and metering pump 830 air line connection points 1122 are shown. Again, the balancing pods 812, 822 do not have air line connection points as they are not actuated by air. As well, the corresponding openings in the bottom plate 1100 for the second fluid outlet 824 and second fluid inlet 826 are shown.

Figure 36E:
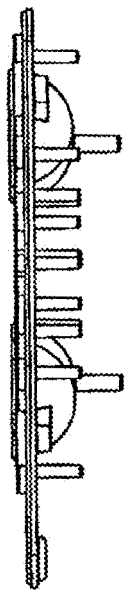
FIG. 36E is a side view of an exemplary embodiment of the bottom plate of an exemplary embodiment of a cassette.

Referring now to FIG. 36E, a side view of the bottom plate 1100 is shown. In the side view, the rim 1124 that surrounds the inner bottom plate 1100 can be seen. The rim 1124 is raised and continuous, providing for a connect point for the diaphragm (not shown). The diaphragm rests on this continuous and raised rim 1124 providing for a seal between the half of the pod pumps 820, 828 and balancing pods 812, 822 in the bottom plate 1100 and the half of the pod pumps 820, 828 and balancing pods 812, 822 in the top plate (not shown, see FIGS. 35A-35D).

As mentioned, dialysate flows from a directing circuit, optionally through a heater and/or through an ultrafilter, to the balancing circuit. In some cases, the directing circuit is implemented on a cassette, although it need not be. An example of a directing circuit can be seen in FIG. 3A as directing circuit 142. Directing circuit 142 is able to perform a number of different functions, in this example. For instance, dialysate flows from a dialysate supply (such as from a mixing circuit, as discussed below) through the directing circuit to a balancing circuit, while used dialysate flows from the balancing circuit to a drain. The dialysate may flow due to the operation of one or more pumps contained within the directing circuit. In some cases, the directing circuit may also contain a dialysate tank, which may contain dialysate prior to passing the dialysate to the balancing circuit. Such a dialysate tank, in certain instances, may allow the rate of production of dialysate to be different than the rate of use of dialysate in the dialyzer within the system. The directing circuit may also direct water from a water supply to the mixing circuit (if one is present). In addition, as previously discussed, the blood flow circuit may be fluidically connected to the directing circuit for some operations, e.g., disinfection.

Thus, in some cases, dialysate may be made as it is needed, so that large volumes of dialysate do not need to be stored. For instance, after the dialysate is prepared, it may be held in a dialysate tank 169. A dialysate valve 17 may control the flow of dialysate from tank 169 into the dialysate circuit 20. The dialysate may be filtered and/or heated before being sent into the dialyzer 14. A waste valve 18 may be used to control the flow of used dialysate out of the dialysate circuit 20.

Figure 6:
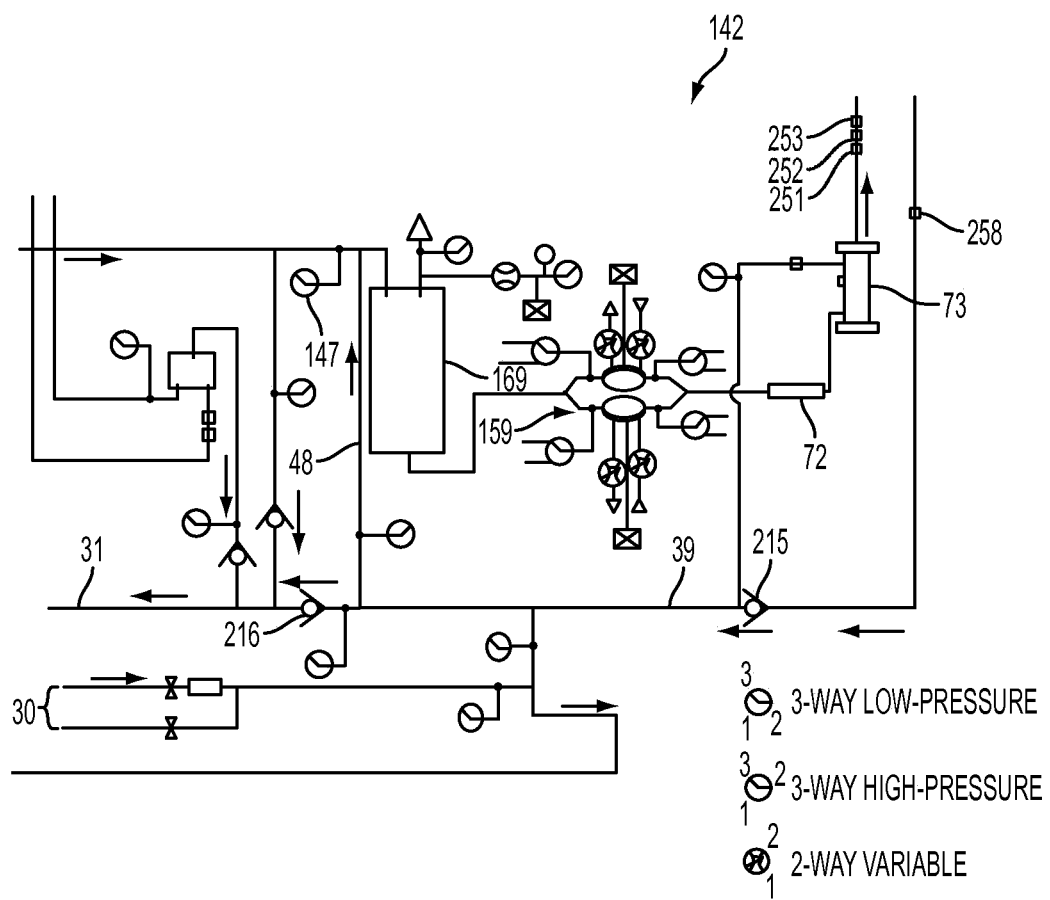
FIG. 6 is a schematic representation of a directing circuit that may be used in a hemodialysis system.

One non-limiting example of a directing circuit is shown in FIG. 6. In this figure, directing circuit 142 fluidically connects dialysate from a dialysate supply to a dialysate tank 169, then through dialysate pump 159, heater 72, and ultrafilter 73, before entering a balancing circuit, as previously discussed. It should be understood that although this figure shows that dialysate in the dialysate flow path flows from the dialysate supply to the dialysate tank, the pump, the heater, and the ultrafilter (in that order), other orderings are also possible in other embodiments. Heater 72 may be used to warm the dialysate to body temperature, and/or a temperature such that the blood in the blood flow circuit is heated by the dialysate, and the blood returning to the patient is at body temperature or higher. Ultrafilter 73 may be used to remove any pathogens, pyrogens, etc. which may be in the dialysate solution, as discussed below. The dialysate solution then flows into the balancing circuit to be directed to the dialyzer.

Dialysate tank 169 may comprise any suitable material and be of any suitable dimension for storing dialysate prior to use. For instance, dialysate tank 169 may comprise plastic, metal, etc. In some cases, dialysate tank may comprise materials similar to those used to form the pod pumps as discussed herein.

The flow of dialysate through directing circuit 142 may be controlled (at least in part) by operation of dialysate pump 159. In addition, dialysate pump 159 may control flow through the balancing circuit. For instance, as discussed above with reference to FIG. 5, fresh dialysate from the directing circuit flows into balancing chambers 341 and 342 on balancing circuit 143; pump 159 may be used as a driving force to cause the fresh dialysate to flow into these balancing chambers. In one set of embodiments, dialysate pump 159 includes a pod pump, similar to those described above. The pod pump may include a rigid chamber with a flexible diaphragm dividing each chamber into a fluid compartment and control compartment. The control compartment may be connected to a control fluid source, such as an air source. Non-limiting examples of pumps that may be used as pod pumps and/or balancing chambers are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Pod pumps are also discussed in detail below.

Heater

After passing through pump 159, the dialysate may flow to a heater, e.g., heater 72 in FIG. 6. The heater may be any heating device suitable for heating dialysate, for example, an electrically resistive heater as is known to those of ordinary skill in the art. The heater may be kept separated from the directing circuit (e.g., as is shown in FIG. 3A), or the heater may be incorporated into the directing circuit, or other circuits as well (e.g., the balancing circuit).

In one non-limiting example, the heater may comprise a heater cartridge, a metal tube providing a fluid path, a casting and one or more temperature sensors. The metal tube may be a coil of stainless steel tubing. The casting may be zinc or aluminum overmolded on the stainless steel coil and including a cavity to receive the heater cartridge. The temperature sensor may comprise a thermistor, a resistance temperature detector (RTD) or thermocouple, for example, that is wired to provide the heater temperature to a controller. A thermal switch or fuse may be mounted to the casing and wired in-series to the cartridge heater to provide hardware over-temperature protection. In one embodiment the cartridge heater may be designed to provide about 1 kW of thermal power operating at approximately 110 VAC. In another embodiment, the cartridge heater is designed to provide about 1 kW of thermal power operating at approximately 220 VAC.

In another embodiment, the cartridge heater may incorporate two or more heater elements that can be energized independently. For example, two 500 W heater elements may be included in a single heater cartridge. Power may be provided sequentially to a plurality of independent heater elements to reduce the magnitude of changes in electrical current through the heater as the heater elements are powered on or off. This may reduce voltage fluctuation in the electrical mains that supply other appliances on the same circuit, such as, for example, overhead lights. Providing heater power to a plurality of independent heater elements using sequential or out-of-phase activation may be helpful in meeting regulatory limitations of voltage fluctuations or flicker (see, e.g., International Electrotechnical Commission Standard on Electromagnetic compatibility (IEC 61000-3-3).

In some cases, the dialysate is heated to a temperature such that blood passing through the dialyzer is not significantly chilled. For instance, the temperature of the dialysate may be controlled such that the dialysate is at a temperature at or greater than the temperature of the blood passing through the dialyzer. In such an example, the blood may be heated somewhat, which may be useful in offsetting heat loss caused by the blood passing through the various components of the blood flow circuit, as discussed above. In addition, in some cases as discussed below, the heater may be connected to a control system such that dialysate that is incorrectly heated (i.e., the dialysate is too hot or too cold) may be recycled (e.g., back to the dialysate tank) or sent to drain instead of being passed to the dialyzer, for example, via line 31 (see, e.g., FIG. 3a, 6 or 122). The heater may be integrated as part of a fluid circuit, such as a directing circuit and/or a balancing circuit, or, as is shown in FIG. 3A, the heater may be a separate component within the dialysate flow path.

The heater may also be used, in some embodiments, for disinfection or sterilization purposes. For instance, water may be passed through the hemodialysis system and heated using the heater such that the water is heated to a temperature able to cause disinfection or sterilization to occur, e.g., temperatures of at least about 70° C., at least about 80° C., at least about 90° C., at least about 100° C., at least about 110° C., etc. In some cases, as discussed below, the water may be recycled around the various components and/or heat loss within the system may be minimized (e.g., as discussed below) such that the heater is able to heat the water to such disinfection or sterilization temperatures.

The heater may include a control system that is able to control the heater as discussed above (e.g., to bring dialysate up to body temperature for dialyzing a patient, to bring the water temperature up to a disinfection temperatures in order to clean the system, etc.).

A non-limiting example of a heater controller follows. The controller may be selected to be capable of dealing with varying inlet fluid temperatures as well as for pulsatile or varying flow rates. In addition the heater control must function properly when flow is directed through each of the different flow paths (dialyze, disinfect, recirculate etc). In one embodiment, the heater controller is used on SIP1 boards with an IR (infrared) temperature sensor on the ultra filter and an IR temperature sensor on the tank. In other embodiments, the board is in a box with less heat losses and to uses conductivity sensors for the inlet temperature sensor. Another embodiment of the controller uses a simple proportional controller using both tank (heater inlet) and ultrafilter (heater outlet) temperatures, e.g.:

$$\text{powerHeater} = \text{massFlow} * ((\text{tankPGain} * \text{errorTank}) + (\text{UFPGain} * \text{errorUF})),$$

where:
PowerHeater=heater duty cycle cmd (0-100%);
MassFlow=the fluid mass flow rate;
TankPGain=proportional gain for the tank or inlet temperature sensor;
ErrorTank=difference between the tank or inlet temperature sensor and the desired temperature;
UFPGain=proportional gain for the ultrafilter or outlet temperature sensor; and
ErrorUF=difference between the of or outlet temperature sensor and the desired temperature.

From the heater duty cycle command (0-100%) a PWM command is generated. In some embodiments, this controller may reduce the mass flow rate if the given temperature is not maintained and the heater is saturated.

Heater Controls

An alternative embodiment of the heater 72 in FIG. 122 may include a dialysate flow path through which, an electrical heater element and a heater temperature sensor are complemented by temperatures sensors located in the fluid path upstream and downstream of the heater. Temperature sensor 254 is located just upstream of the heater to provide information on the temperature of the entering fluid. Redundant temperature sensors 252 and 251 are located downstream of the ultrafilter 73 in order to measure the temperature of the dialysate entering inner dialysate cassette, which in turn may affect the temperature of the blood returning to the patient. A temperature sensor 255 may be located on line 731 in order to measure flow diverted from the inner cassette Referring to FIG. 89, in an exemplary embodiment, the fluid temperature may be measured at a variety of locations, such as the inlet of the heater 72, in the balancing or inner dialysate circuit 143, in the directing or outer dialysate circuit 142, in the ultrafiltration pump circuit 35, in the mixing circuit 25 and/or at the drain line 31. The heater controller may vary the power of the heater 72 based on the measured temperature from one or more of these temperature sensors. The particular fluid temperature sensor selected for control may be based on the existing fluid flow path of dialysate in use at a give time (e.g., during therapy, during paused therapy with continued dialysate recirculation through the ultrafilter 73, during dialysate production, etc.). For example, suspension or pausing of dialysis operations may include the controller closing valves in the inner dialysate circuit in order to stop the flow of dialysate through the balancing circuit and the dialyzer. In some cases, it may be advantageous to continue to flow dialysate from the dialysate tank through the outer dialysate pumps, to be re-circulated to the dialysate tank or optionally directed to drain. A temperature sensor may be placed in the recirculation or drain flowpath, or at least in an upstream flowpath common to each destination, but downstream from the heater 72, for feedback to the controller controlling the heater 72. This arrangement allows the heater 72 to maintain a pre-determined temperature for dialysate being drawn from the dialysate tank, or being re-circulated to the dialysate tank. Thus, upon resumption of dialysis operations, fresh dialysate fluid at the pre-determined or desired temperature is more quickly available for delivery to the balancing circuit and dialyzer. Furthermore, temperature feedback during continued flow of dialysate (optionally at a lower, maintenance flow rate) through the heater 72 helps to prevent over-heating of dialysate solution during suspension or a pause in dialysis operations. In certain embodiments, an ultrafilter optionally may be present within this recirculation or drain flow path, either upstream or downstream of the heater 72.

Referring to FIG. 123A, in an alternative embodiment, a 'Heater Control Mode' consists of a control loop 608 around the heater. In an embodiment, the Heater Control Mode uses a closed loop controller to simple proportional integral controller to bring the heater temperature 612 to the desired temperature 610 by outputting a duty cycle command to the heater 72. In another example the closed loop controller is a proportional controller. The heater temperature 612 is measured by the heater temperature sensor. The heater temperature sensor is in thermal contact with the flow conduit in the heater 72. The heater temperature sensor may also be embedded in the heater 72.

The duty cycle command may be converted to a pulse width modulation ('PWM') command with a base frequency of 1 Hz. The heater current may be controlled by the PWM command with SCR electronics that turn on and off at zero crossing. The heater current may also be controlled by a transistor switch (such as a FET, IGBT or BJT). Assuming a 60 Hz power line frequency, the 1 Hz PWM frequency allows a resolution of 1 in 60.

In another embodiment the PWM (pulse width modulation) command has a base frequency of ¼ Hz, so that the heater element is turned on for a fraction of the 4 second period, turned off for the rest of the 4 second period and the cycle is then repeated. In one embodiment in which more than one heater element is present, the controller may power the elements with different PWM signals. In one example, heater elements may be driven with the same frequency, but the signal may be delayed or phase-shifted to avoid turning more than one element on at a time. Applying power to less than all the heater elements at a given time minimizes the changes in current flow and thus reduces voltage variations in the AC mains.

In one example, two 500 W heater elements are located within the same heater 72. The duty cycle is commanded at 0.125 Hz, where the first heater is turned on at t=0 seconds and the second heater is delayed by 2 seconds. Thus the two heater elements are not switched on at the same time for any duty cycle. The two heater elements may be on at the same time, but both heaters preferably not switched on or off at the same time in order to reduce current fluctuations. In the present context, the term 'switched on' means a transition from a state in which no substantial current is flowing through the heater element to a state in which current is flowing through the heater element. An example of the control of two heater elements at 25% duty cycle is shown in FIG. 155 in which a 25% duty cycle is plotted for the first and second heaters. The on/off state of the first heater is plotted by line 12615 and the on/off state of the second heater element is plotted by line 12620 on a time axis against time 12612. The first heater is turned on at time marker 12616 for 1 second then off until time marker 12617 when it is turned on again for a 25% duty cycle. The second heater is turned on for the same duty cycle and frequency, but delayed by two seconds so that it turns on at time marker 12621. In more general terms, the second heater operates at the same frequency as the first heater but is delay by half a period, where a period is the inverse of the frequency. In more general terms for n heater elements where the heaters elements are numbered from 1 to n and referred to as heater element i: all the heater elements operate with the same frequency and duty cycle, but each heater element i is delayed by the period divided by n from the previous heater element i−1. The lower limit on heater duty cycle command may be zero. The heater may be configured to run at 100% duty cycle or at a reduced duty cycle. The maximum duty cycle may be limited by the electrical power available. In one embodiment, the maximum duty cycle for the heater may be 70% for a total current draw of 8 amps, allowing adequate power to run the balance of components in the Dialysis Machine 6001. In another embodiment, the maximum total current draw is 11 amps and the heat duty cycle is limited to 100%. The user or technician may set the maximum duty cycle of the heater controller and the maximum draw of the Dialysis Machine 6001 (represented in block form in FIG. 61) by selecting a high or low power setting via software. The lower power setting may allow the Dialysis Machine 6001 to be plugged into the same circuit as a machine to prepare water for the Dialysis Machine 6001. The maximum heater command may be limited by saturation block 619 shown in FIGS. 123A-123C. The maximum flow rate through the heater may be controlled based on the inlet temperature 254 and available power in order to produce dialysate that achieves the minimum allowed dialysate temperature as measured by sensors 251, 252.

The heater controller may be considered inherently non-symmetrical as it can increase the heater temperature by using more electrical power, but depends on heat loss to the ambient air or flowing dialysate to reduce the heater temperature.

Two control loops may be used to control temperature in the system. The first control loop operates on the heater itself, feeding back the internal heater temperature to generate a duty cycle command for the heater. The second control loop wraps a controller around the heater loop, computing the desired heater temperature based on the error between the desired and actual fluid temperatures. The fluid temperature sensor used to provide feedback can be selected based upon the desired or selected flow path. The controller can be run in a number of different modes. The inner loop on the heater can be run by itself, directly controlling the temperature of the heater, or the two loops can be run together, controlling the fluid temperature.

The control loop in FIG. 123A may be operated with different integral and proportional gains, 618, 616 to adapt to different levels of heat loss due to external factors, which include but are not limited to ambient temperatures, incoming dialysate temperature and dialysate flow rates.

Figure 62:
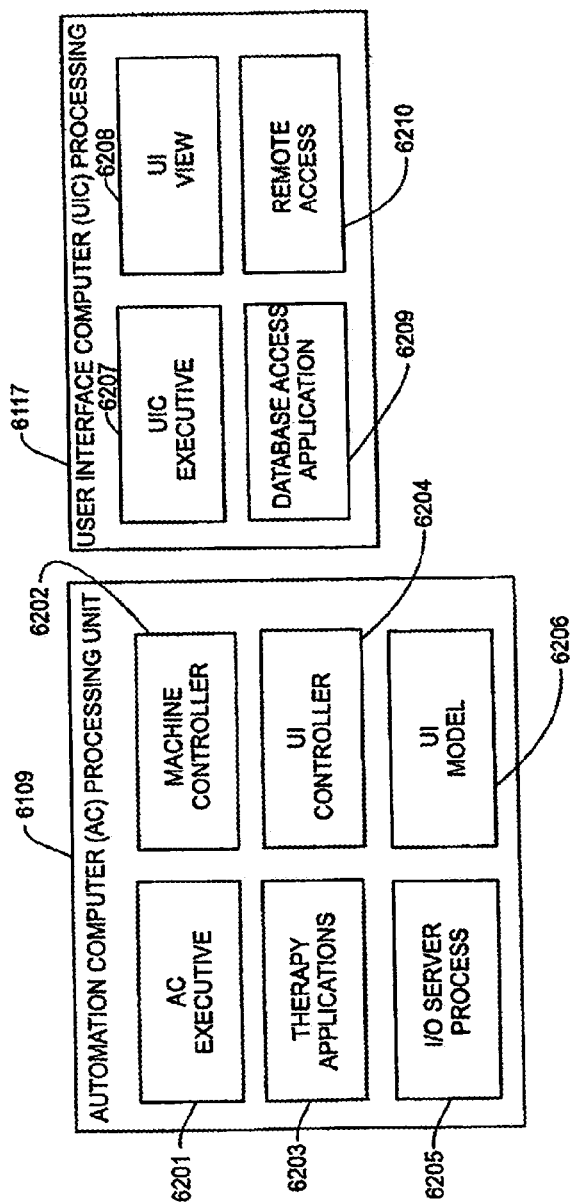
FIG. 62 is a schematic view showing exemplary software processes that may execute on the automation computer and user interface computer shown in FIG. 61.

The Heater Control Mode may select different gains depending on the operating mode selected in the Therapy Applications 6203 (FIG. 62). The gains 616, 618 may be set higher when an operating mode is selected that calls for high fluid flow through the heater. The gains 616, 618 may be set lower when an operating mode is selected that calls for low fluid flow through the heater. The gains may be set to minimum or zero values during modes when there is no flow through the heater in order to prevent temperature overshoot. The gains 616, 618 may be set low during a disinfect operating mode to prevent overshoot at high temperatures, as disinfection temperatures may be near the material temperature limits and the large temperature increases associated with thermal disinfection are more likely to produce temperature overshoots.

A saturation block 619 may limit the output 614 of the heater control loop 608 to that of the maximum heater duty cycle. In a preferred embodiment the maximum heater duty cycle is selectable between about 70% and about 100%.

In another embodiment, to avoid temperature overshoot, the value of an integrator 620 may be limited. If the heater command is at its upper limit, the integrator value 620 may not be allowed to increase until the heater command drops below its upper limit. The integrator value is allowed to decrease at all times.

In order to minimize heater temperature fluctuations when fluid flow through the heater is momentarily stopped, the Heater Control Mode may suspend the heater operation and save one or more control parameters in memory. In a preferred embodiment when fluid flow through the heater stops for a short period, the heater may be turned off and the integrator value 620 may be saved. The heater subsequently may be turned back on with the gains 616, 618 appropriate for the operating mode and with the integrator value reloaded from memory.

An alternative embodiment of the heater controller referred to as a 'Fluid Temp Control Mode' is shown in FIG. 123B. The Fluid Temp Control Mode may add an outer control loop 638 around the inner control loop 608 of the Heater Control Mode. The outer control loop 638 may bring the actual fluid temperature 632 to the desired fluid temperature 630 by varying the desired heater temperature 610. The Fluid Temp Control Mode supplies this desired heater temperature 610 to the inner control loop 608, which produces a signal 614 to control the heater as described above in the Heater Control Mode. The inner control loop may include changing the gains 616, 618 based on the operating mode of the dialysis unit, and limiting the integrator when the heater command reaches the maximum allowed value. The Fluid Temp Control Mode may include a feed-forward command (ffCmd) 642 based on the desired temperature 630, the inlet fluid temperature 254, the fluid flow rate and a gain factor:

$$\text{ffCmd} = T_{des} + (T_{des} - T_{in}) \times \dot{m} * \text{ffGain}$$

Where:
ffCmd is the feed forward command
$T_{des}$ is the desired temperature setpoint
$T_{in}$ is the temperature at the inlet of the heater
ṁ is the desired mass flow
ffGain is a gain applied to the calculation The outer control loop 638 may include a saturation block 644 that imposes on the feed-forward command 642 an upper and lower limit to values between the desired fluid temperature point 630 and a maximum allowed heater temperature. A second saturation block 639 may limit the output 610 of the outer control loop 638 to the maximum heater temperature. In a preferred embodiment the maximum temperature during dialysis may be set to about 70° C., and to about 112° C. during disinfection.

The Fluid Temp Control Mode may select different gains 636, 638 depending on the operating mode selected in the Therapy Applications 6203 (FIG. 62). The gains 636, 638 may be set higher when an operating mode calls for high fluid flow through the heater. The gains 636, 638 may be set lower when an operating mode calls for low flows of fluid through the heater 72. The gains may be set to minimum or zero values during modes when there is no flow through the heater 72 in order to prevent temperature overshoot.

Fluid Temp Control Mode may limit the integrator value 640 in order to avoid temperature overshoot. If either the heater command 614 or desired heater temperature 610 are at the maximum allowed values, then the integrator value 640 may not be allowed to increase until both the heater command and desired heater temperature drop below their upper limits. The integrator value is allowed to decrease at all times.

The Fluid Temp Control Mode is optionally able to change the dialysate flow rate from the outer pump 159 to maintain the dialysate within the desired temperature limits. If either the heater command 614 or desired heater temperature 610 are at the maximum allowed values for a predetermined minimum period of time, the dialysate flow rate may be reduced to a rate of, for example, about 30 ml/min/stroke. If both the heater command and desired heater temperature drop below their upper limits for a pre-determined minimum period of time, the desired flow rate may be ramped up at a rate of, for example, 30 ml/min until the flow rate returns to its original programmed value. In a preferred embodiment, the minimum period of time is set to the time to complete the current and previous strokes. The Fluid Temp Control Mode uses the minimum period of time to produce a smoother temperature response and reduce temperature overshoots. The flow through the heater may be limited to a pre-determined minimum value. In a preferred embodiment the minimum flow rate for dialysate through the heater as measured by the outer pump is set to about 100 ml/min.

In order to minimize heater temperature fluctuations when fluid flow through the heater is stopped for a short time, the Fluid Temp Control Mode is programmed to suspend the heater operation and save one or more control parameters in memory. The fluid flow may be stopped periodically as the dialysis unit performs functional checks that include dialysate levels, and performance of the fluid valves. In a preferred embodiment when fluid flow through the heater stops for a short period, the heater is turned off, while the preceding dialysate flow rate and the integrator values 640, 620 are saved in memory. When the flow restarts, the integrator values and dialysate flow rate are reloaded from memory, the heater is turned back on, and the gains 616, 618, 636, 638 are set as appropriate for the operating mode.

In an alternative embodiment, as shown in FIG. 123C, the heater controller has a 'Heater Only Power Mode,' consisting of a control loop 648 around the heater. The Heater Only Power Mode may use a simple proportional integral controller to bring the heater temperature 612 to the heater set point temperature 610 by outputting a duty cycle command to the heater 72. The heater set point temperature 610 may be the output of a feed-forward command 646 limited by a saturation block 644. The feed-forward command 646 may be based a number of parameters, such as the measured inlet fluid temperature 647, desired fluid temperature 611, assumed fluid mass flow and a gain factor. In a preferred embodiment, the feed-forward signal 646 may be calculated as:

$$\text{ffCmd} = T_{des} + (T_{des} - T_{in}) \times \dot{m} * \text{ffGain}$$

Where:
ffCmd is the feed forward command
$T_{des}$ is the desired temperature setpoint
$T_{in}$ is the temperature at the inlet of the heater
$\dot{m}_A$ is the assumed mass flow
ffGain is a gain applied to the calculation The feed-forward command 646 may be limited by a saturation block 644 to a range of values. In a preferred embodiment, the saturation block 644 limits the desired heater temperature 610 to values between the desired fluid temperature 611 and a maximum value, such as, for example, 41° C.

The heater temperature 612 may be measured by the heater temperature sensor. The inlet temperature is measured by sensor 254. The duty cycle command may be converted to a PWM command, which in one aspect has a base frequency of about 1 Hz. The heater current may be controlled by a PWM command with SCR electronics that turn on and off at zero crossing or a transistor switch such as a FET, IGBT or BJT. Assuming a 60 Hz power line frequency, the 1 Hz PWM frequency allows a resolution of 1 in 60.

The lower limit on heater duty cycle command can be set to zero. The heater may be configured to run at 100% duty cycle or at a reduced duty cycle. The maximum duty cycle may be limited by the electrical power available. In a preferred embodiment, the maximum duty cycle is set to about 70%, limiting the total current draw to 8 amps, which would allow power for running the balance of components in the Dialysis Machine 6001. Alternatively, the maximum total current draw is set to 11 amps and the heat duty cycle is limited to 100%. The user or technician may set the maximum duty cycle of the heater controller and the maximum draw of the Dialysis Machine 6001 by selecting via software a high or low power setting. The lower power setting may allow the Dialysis Machine 6001 to be plugged into the same electrical circuit as a machine that prepares water for the Dialysis Machine 6001. Depending on the available power, the maximum flow rate through the heater may be controlled by monitoring the inlet temperature 254 so that the dialysate produced achieves the minimum allowed dialysate temperature as measured at sensors 251, 252.

The Heater Only Power Mode may select different gains depending on the operating mode selected in the Therapy Applications 6203 (FIG. 62). The gains 616, 618 may be set higher when an operating mode is selected that calls for high fluid flow through the heater. The gains 616, 618 may be set lower when an operating mode is selected that calls for low fluid flow through the heater. The gains may be set to minimum or zero values during modes when there is no flow through the heater in order to prevent temperature overshoot. The gains 616, 618 may be set low during disinfect operating mode to prevent overshoot at high temperatures, as disinfection temperatures may approach material temperature limits, and the large temperature increases are more likely to produce temperature overshoots.

Another method to avoid temperature overshoot involves limiting the integrator value 620. If the heater command is at its upper limit, the integrator value 620 is not allowed to increase until the heater command drops below its upper limit. The integrator value is allowed to decrease at all times.

In order to minimize heater temperature fluctuations when fluid flow through the heater is momentarily stopped, the Heater Only Power Mode may suspend the heater operation and save one or more control parameters in memory. In a preferred embodiment, when fluid flow through the heater stops for a short period, the heater may be turned off and the integrator value 620 may be saved in memory. The heater may be turned back on by reloading the integrator value from memory with the gains 616, 618 set as appropriate for the operating mode.

In one embodiment of the heater controller a number of safety checks are performed during start up to confirm the functioning of the heater system, including heater function, temperature sensors, and control electronics. The startup safety checks may include checking that temperature sensor outputs are within an expected range. In an embodiment, the expected range for temperature sensors is 0° C. to 110° C. In order to verify that the heater can be turned on and off, the startup safety checks may include a heater system test that turns the heater on for a short period, while monitoring the heater temperature sensor during this on-period, and then for a longer off-period. The test may require that the heater sensor value increases during the on-period and does not continue to increase during the off-period. In a preferred embodiment with one heater element, the heater is turned on for about 5 seconds while the temperature sensor is monitored during the 5 second on-period and a subsequent 20 second off-period. In an embodiment, the test is passed if the heater temperature increases by at least about 1.0° C. and no less than about 6.0° C.

The start safety checks with multiple heater elements verifies the functioning of each heater element and associated control switch. The safety check may test one element at a time switching it on for a period and then turn it off while monitoring the heater temperatures. The safety check may repeat this process for each heater element and thereby verify that each element and control switch is operational. In order to pass the safety check, the monitored temperature must increase by greater than a first predetermined amount while the heat element is switched on and then must not increase by more than a second predetermined threshold during the off period. In one example, the safety check also requires that the temperature does not increased by more than a third predetermined threshold during the on period.

In a preferred embodiment with 2 heater elements, the first heater element or pre-heater element located distally from the temperature sensor on the heater body. The safety check turns the preheater on at 100% duty cycle for 15 seconds followed by a 45 second off period and the temperature increase is measured over a period of 60 seconds. The increase in temperature is monitored over the duration of the test. If at any time, the heater temperature increase is greater than 6 degrees, the heaters are turned off and the test fails. At the end of the 60 seconds, the heater temperature increase must be at least 0.5 degrees to pass the test. The safety check of the second heater element is turns the second heater element on at 100% duty cycle on for about 5 seconds while the temperature sensor is monitored during the 5 second on-period and a subsequent 20 second off-period. In an embodiment, the test is passed if the heater temperature increases by at least about 1.0° C. and no less than about 6.0° C.

In order to verify proper heater function during the operation of the dialysis unit, the heater temperature is monitored when the heater command 614 is at its maximum value. In order to pass this test, the heater temperature is expected to rise a pre-determined amount over a specified time period. In a preferred embodiment the heater temperature is expected to rise more than about 0.5° C. over a 1 minute period. This test may be run during operational modes when the patient is connected to the dialysis unit.

The safety tests may monitor the heater temperature during all operations to avoid excessive fluid temperatures. If the heater temperature 612 exceeds maximum allowed heater temperature for a given operating mode, the heater and heater controller are disabled. In a preferred embodiment, the maximum heater temperature during patient connected operations is set to about 70° C. The maximum heater temperature during disinfect mode may be set to a higher temperature, such as about 100-110° C. The heater may include a secondary safety system composed of a thermal fuse on the heater.

The safety tests may monitor two or more of the fluid temperature sensors and disable the heater 14 and heater controllers if any one of the temperature sensors exceeds a maximum disinfect fluid temperature. Preferably, all the fluid temperature sensors 251, 252, 254, 255 are monitored, with a maximum disinfect fluid temperature set to about 100° C. One benefit of this test is that protects against failures of a single fluid temperature sensor or failure of the heater temperature sensor.

The safety tests may include monitoring the outer pump 157 during Fluid Temp Control Mode, and disabling the heater 72 and heater controllers if fluid flow cannot be verified. The heater 72 and controllers may be disabled in Fluid Temp Control Mode if the outer pump controller detects an occlusion or a pneumatic leak.

It should be understood that the above-described heater controls are by way of example only, and that other heater control systems, and other heaters, are also possible in other embodiments of the invention.

The dialysate may also be filtered to remove contaminants, infectious organisms, pathogens, pyrogens, debris, and the like, for instance, using an ultrafilter. The filter may be positioned in any suitable location in the dialysate flow path, for instance, between the directing circuit and the balancing circuit, e.g., as is shown in FIG. 3A, and/or the ultrafilter may be incorporated into the directing circuit or the balancing circuit. If an ultrafilter is used, it may be chosen to have a mesh or pore size chosen to prevent species such as these from through the filter. For instance, the mesh or pore size may be less than about 0.3 micrometers, less than about 0.2 micrometers, less than about 0.1 micrometers, or less than about 0.05 micrometers, etc. Those of ordinary skill in the art will be aware of filters such as ultrafilters, and in many cases, such filters may be readily obtained commercially.

In some cases, the ultrafilter may be operated such that waste from the filter (e.g., the retentate stream) is passed to a waste stream, such as waste line 39 in FIG. 6. In some cases, the amount of dialysate flowing into the retentate stream may be controlled. For instance, if the retentate is too cold (i.e., heater 72 is not working, or heater 72 is not heating the dialysate to a sufficient temperature, the entire dialysate stream (or at least a portion of the dialysate) may be diverted to waste line 39, and optionally, recycled to dialysate tank 169 using line 48. Flow from the filter may also be monitored for several reasons, e.g., using temperature sensors (e.g., sensors 251 and 252), conductivity sensors (for confirming dialysate concentration, e.g., sensor 253), or the like. An example of such sensors is discussed below; further non-limiting examples can be seen in U.S. patent application Ser. No. 12/038,474 entitled "Sensor Apparatus Systems, Devices and Methods," filed on Feb. 27, 2008, and incorporated herein by reference.

It should be noted that the ultrafilter and the dialyzer provide redundant screening methods for the removal of contaminants, infectious organisms, pathogens, pyrogens, debris, and the like, in this particular example (although in other cases, the ultrafilter may be absent). Accordingly, for contaminants to reach the patient from the dialysate, the contaminants must pass through both the ultrafilter and the dialyzer. Even in the event that one fails, the other may still be able to provide sterility and prevent contaminants from reaching the patient's blood.

Directing circuit 142 may also be able to route used dialysate coming from a balancing circuit to a drain, e.g., through waste line 39 to drain 31 in FIG. 6. The drain may be, for example, a municipal drain or a separate container for containing the waste (e.g., used dialysate) to be properly disposed of. In some cases, one or more check or "one-way" valves (e.g., check valves 215 and 216) may be used to control flow of waste from the directing circuit and from the system. Also, in certain instances, a blood leak sensor (e.g., sensor 258) may be used to determine if blood is leaking through the dialyzer into the dialysate flow path. In addition, a liquid sensor can be positioned in a collection pan at the bottom of the hemodialysis unit to indicate leakage of either blood or dialysate, or both, from any of the fluid circuits.

The drain 31 (FIG. 89) may include an air-in-line detector (AIL) 37 to monitor the balancing and directing circuits for leaks and diaphragm ruptures. The dialysate that flows passed the AIL detector 37 has previously flowed through a pump in the directing cassette and a balancing chamber and pump in the balancing cassette as well as a number of valves. If any of the diaphragms on the valves or pod pumps leaked, then the leaked air would flow past the AIL detector in the drain 31. In addition, the AIL detector 37 may detect gas evolving from the dialysate possibly as it is heated In a preferred embodiment, the AIL detector 37 will be positioned on the drain 31, where the flow is upward. This potentially advantageous position facilitates detection of air bubbles flowing with the dialysate as the drain path (which may be made as long as suitable) provides ample opportunity for bubbles to consolidate prior to reaching the detector 37. The positioning of the AIL detector 37 on the drain 31 allows the detector to identify diaphragm rupture from air bubbles.

In addition, directing circuit 142 may receive water from a water supply 30, e.g., from a container of water such as a bag, and/or from a device able to produce water, e.g., a reverse osmosis device such as those that are commercially available. In some cases, as is known to those of ordinary skill in the art, the water entering the system is set at a certain purity, e.g., having ion concentrations below certain values. The water entering directing circuit 142 may be passed on to various locations, e.g., to a mixing circuit for producing fresh dialysate and/or to waste line 39. In some cases, as discussed below, valves to drain 31, various recycle lines are opened, and conduits 67 may be connected between directing circuit 142 and blood flow circuit 141, such that water is able to flow continuously around the system. If heater 72 is also activated, the water passing through the system will be continuously heated, e.g., to a temperature sufficient to disinfect the system. Such disinfection methods will be discussed in detail below.

Figure 41A:
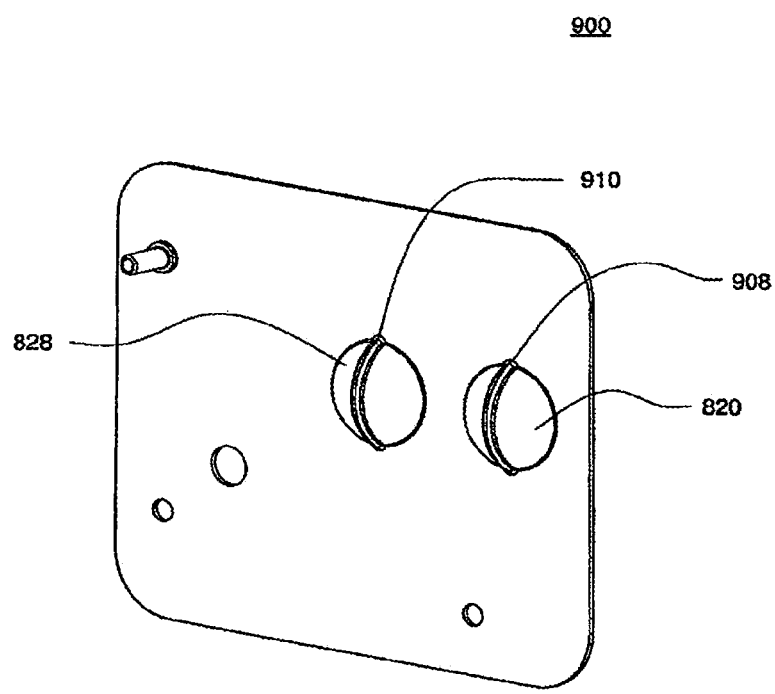
FIGS. 41A and 41B are isometric and front views of an exemplary embodiment of the outer top plate of an exemplary embodiment of a cassette.
Figure 41B:
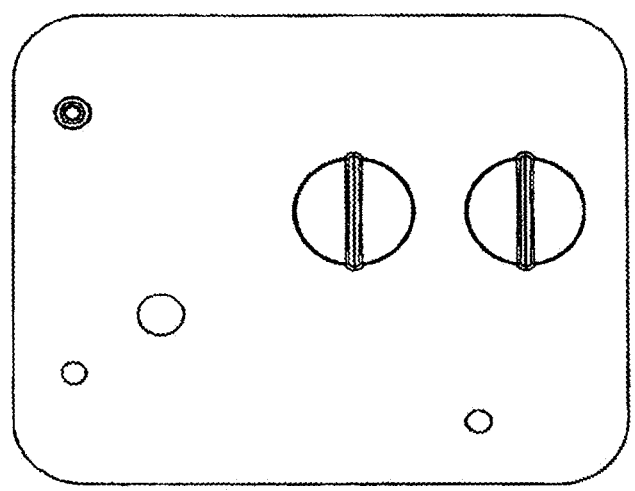

A non-limiting example of a directing cassette is shown in FIGS. 41A-45. Referring now to FIGS. 41A and 41B, the outer side of the top plate 900 of one embodiment of the cassette is shown. The top plate 900 includes one half of the pod pumps 820, 828. This half is the fluid/liquid half where the source fluid will flow through. The inlet and outlet pod pump fluid paths are shown. These fluid paths lead to their respective pod pumps 820, 828.

Figure 41C:
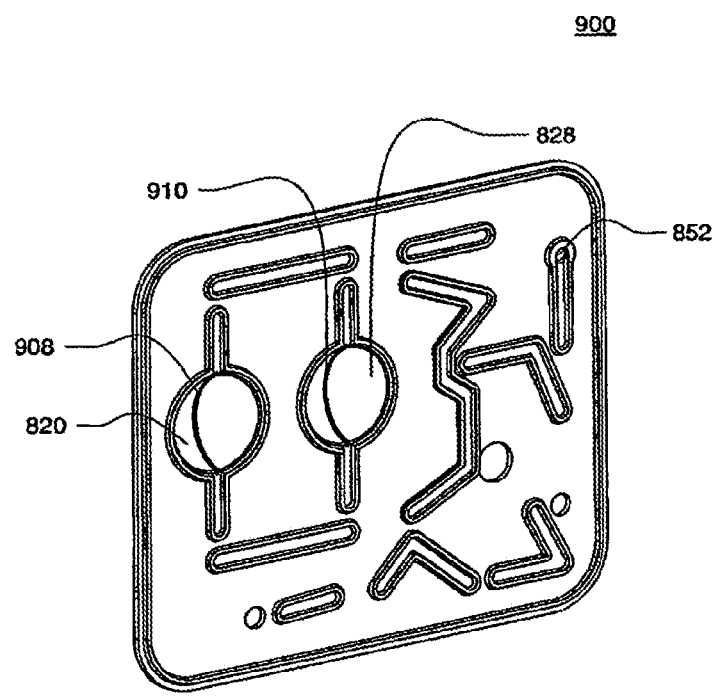
FIGS. 41C and 41D are isometric and front views of an exemplary embodiment of the inner top plate of a cassette.
Figure 41D:
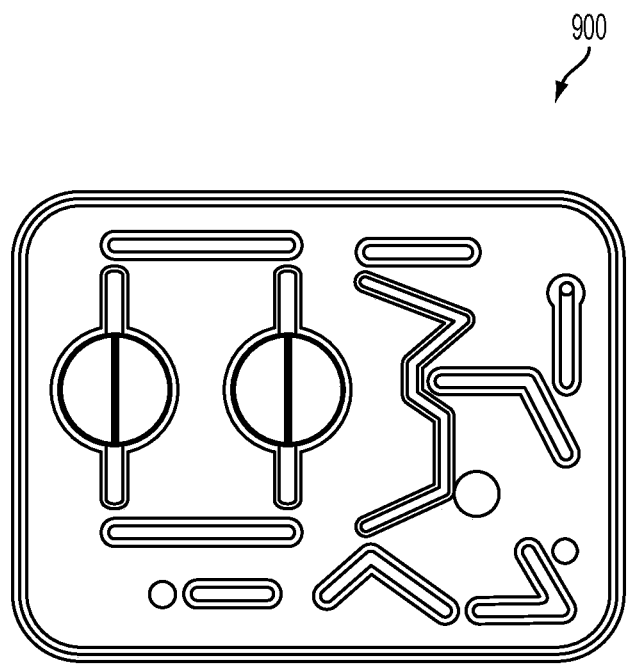
Figure 41E:
FIG. 41E is a side view of the top plate of an exemplary embodiment of a cassette.

The pod pumps 820, 828 can include a raised flow path 908, 910. The raised flow path 908, 910 allows for the fluid to continue to flow through the pod pumps 820, 828 after the diaphragm (not shown) reaches the end of stroke. Thus, the raised flow path 908, 910 minimizes the diaphragm causing air or fluid to be trapped in the pod pump 820, 828 or the diaphragm blocking the inlet or outlet of the pod pump 820, 828, which would inhibit flow. The raised flow path 908, 910 is shown in this embodiment having particular dimensions. In alternate embodiments, the raised flow path 908, 910 is larger or narrower, or in still other embodiments, the raised flow path 908, 910 can be any dimension as the purpose is to control fluid flow so as to achieve a desired flow rate or behavior of the fluid. Thus, the dimensions shown and described here with respect to the raised flow path, the pod pumps, the valves, or any other aspect are mere exemplary and alternate embodiments. Other embodiments are readily apparent. FIGS. 41C and 41D show the inner side of the top plate 900 of this embodiment of the cassette. FIG. 41E shows a side view of the top plate 900.

Figure 42A:
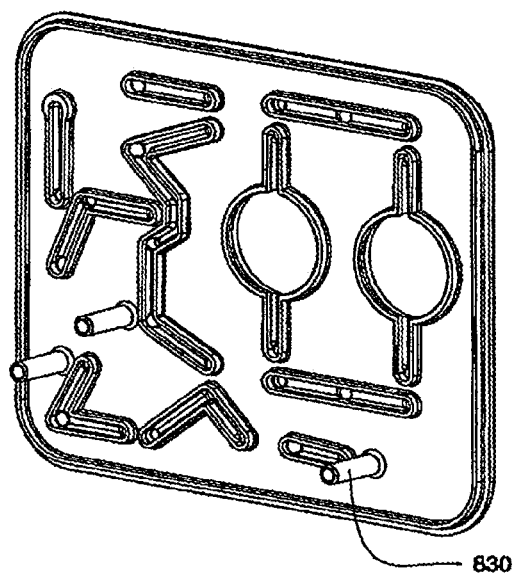
FIGS. 42A and 42B are isometric and front views of an exemplary embodiment of the liquid side of the midplate of a cassette.
Figure 42B:
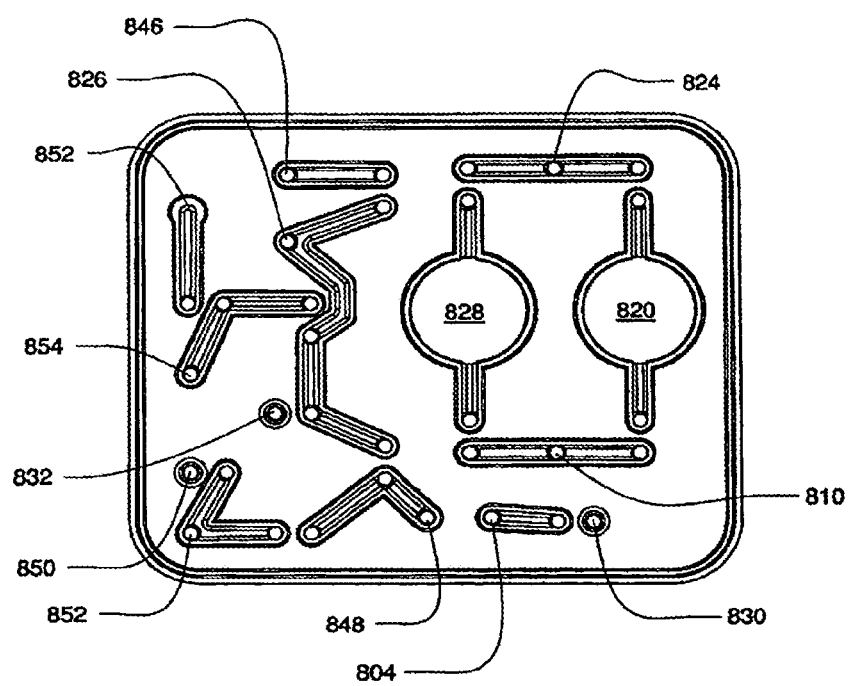

Referring now to FIGS. 42A and 42B, the fluid/liquid side of the midplate 1000 is shown. The areas complementary to the fluid paths on the inner top plate shown in FIGS. 41C and 41D are shown. These areas are slightly raised tracks that present a surface finish that is conducive to laser welding, which is one mode of manufacturing in this embodiment. Other modes of manufacturing the cassette are discussed above.

Figure 42C:
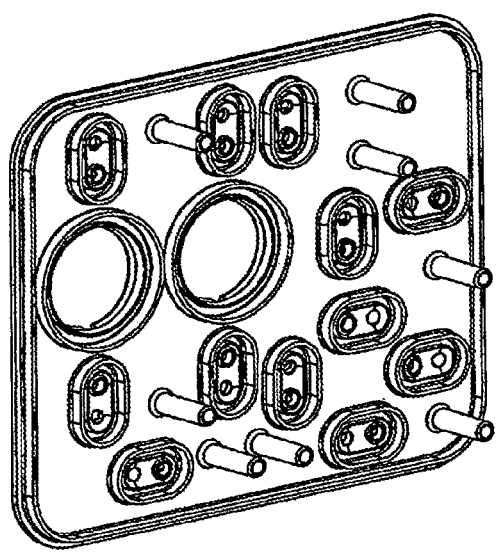
FIGS. 42C and 42D are isometric and front views of an exemplary embodiment of the air side of the midplate of a cassette.
Figure 42D:
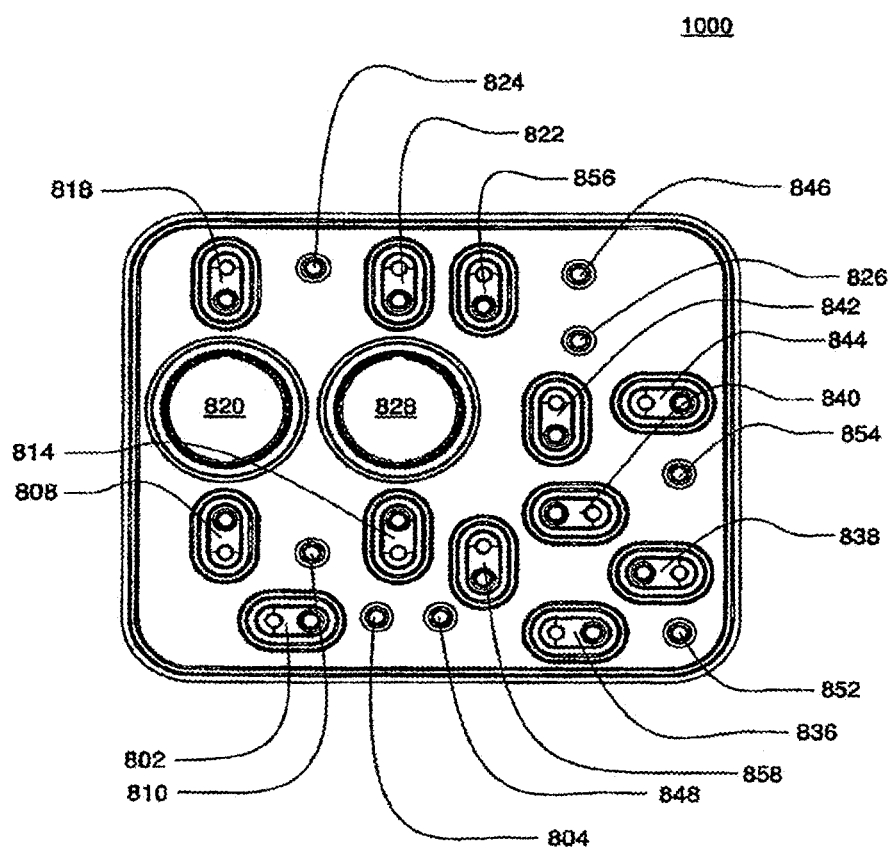
Figure 42E:
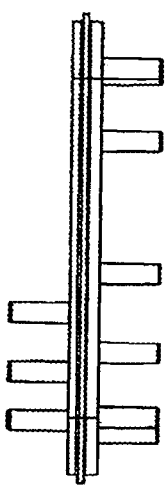
FIG. 42E is a side view of the midplate according to an exemplary embodiment of a cassette.
Figure 43A:
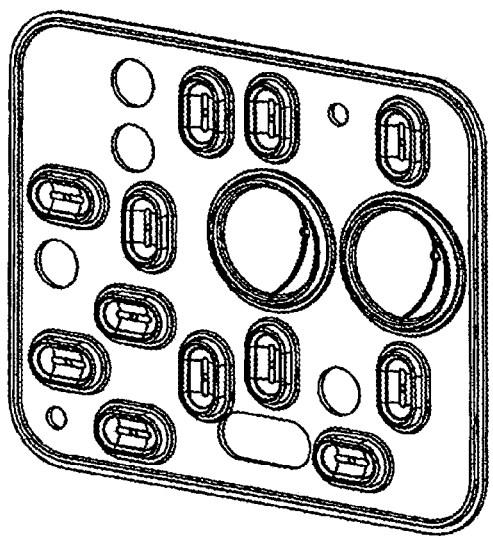
FIGS. 43A and 43B are isometric and front views of the inner side of a bottom plate according to an exemplary embodiment of a cassette.
Figure 43B:
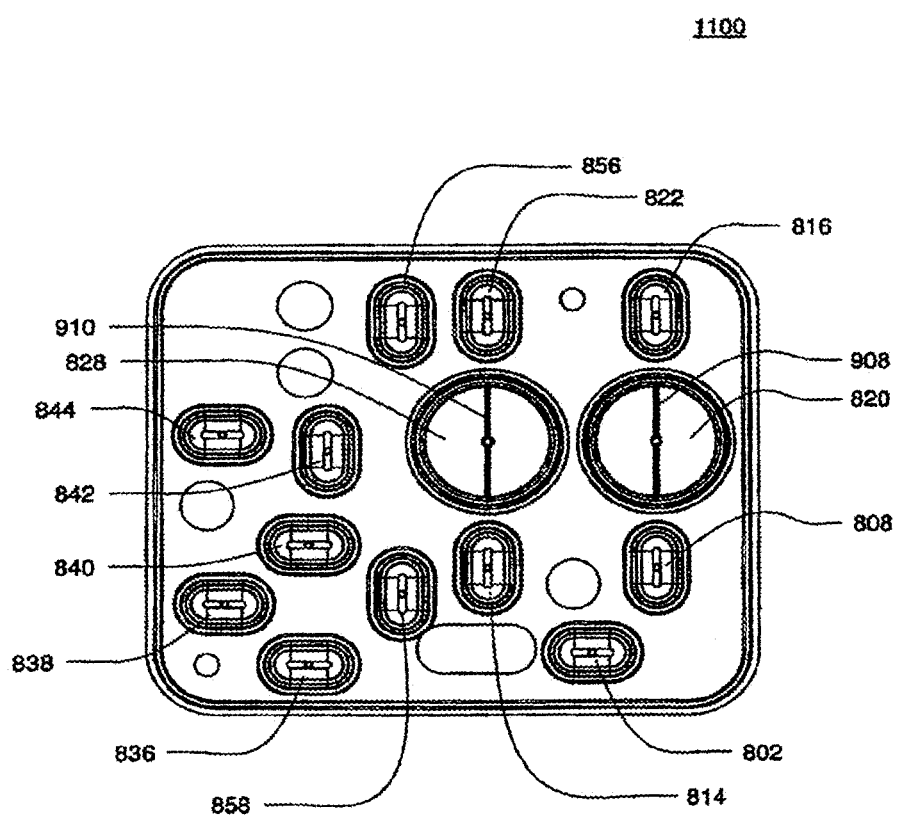
Figure 43C:
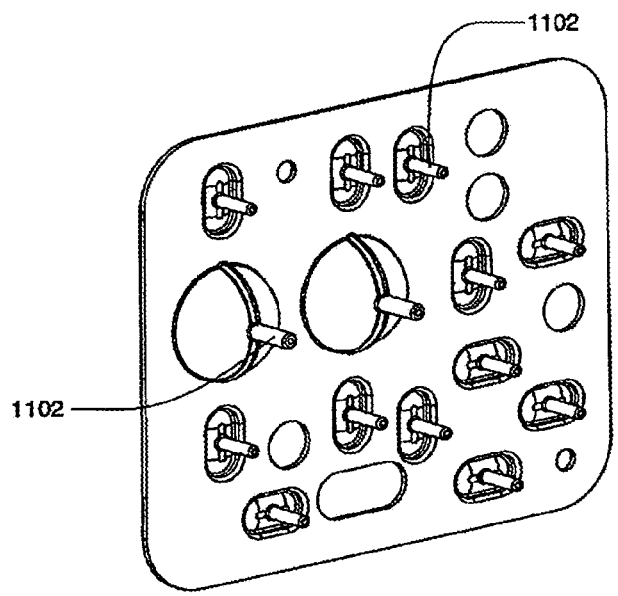
FIGS. 43C and 43D are isometric and front views of an exemplary embodiment of the outer side of the bottom plate of a cassette.
Figure 43D:
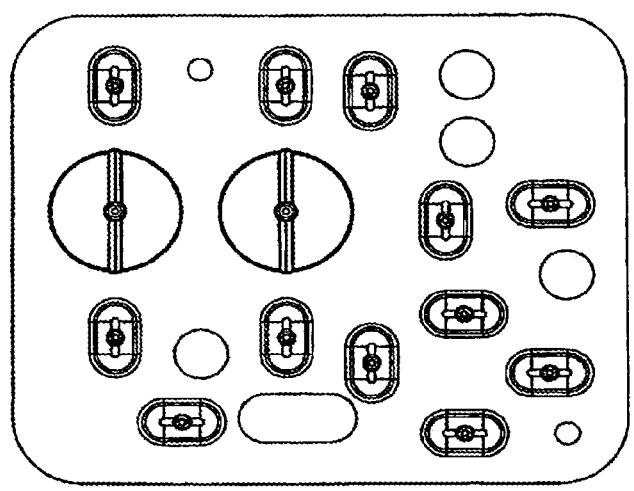
Figure 43E:
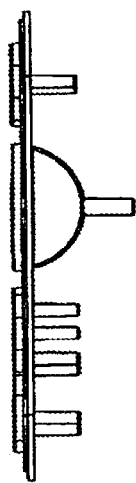
FIG. 43E is a side view of a bottom plate according to an exemplary embodiment of a cassette.

Referring next to FIGS. 42C and 42D, the air side, or side facing the bottom plate (not shown, shown in FIGS. 43A-43E) of the midplate 1000 is shown according to this embodiment. The air side of the valve holes 802, 808, 814, 816, 822, 836, 838, 840, 842, 844, 856 correspond to the holes in the fluid side of the midplate 1000 (shown in FIGS. 42A and 42B). As seen in FIGS. 44C and 44D, diaphragms 1220 complete pod pumps 820, 828 while diaphragms 1222 complete valves 802, 808, 814, 816, 822, 836, 838, 840, 842, 844, 856. The valves 802, 808, 814, 816, 822, 836, 838, 840, 842, 844, 856 are actuated pneumatically, and as the diaphragm is pulled away from the holes, liquid/fluid is allowed to flow. As the diaphragm is pushed toward the holes, fluid flow is inhibited. The fluid flow is directed by the opening and closing of the valves 802, 808, 814, 816, 822, 836, 838, 840, 842, 844, 856. Referring next to FIGS. 43A and 43B, the inner view of the bottom plate 1100 is shown. The inside view of the pod pumps 820, 828, and the valves 802, 808, 814, 816, 822, 836, 838, 840, 842, 844, 856 actuation/air chamber is shown. The pod pumps 820, 828, and the valves 802, 808, 814, 816, 822, 836, 838, 840, 842, 844, 856 are actuated by a pneumatic air source. Referring now to FIGS. 43C and 43D, the outer side of the bottom plate 1100 is shown. The source of air is attached to this side of the cassette. In one embodiment, tubes connect to the tubes on the valves and pumps 1102. In some embodiments, the valves are ganged, and more than one valve is actuated by the same air line.

Figure 44A:
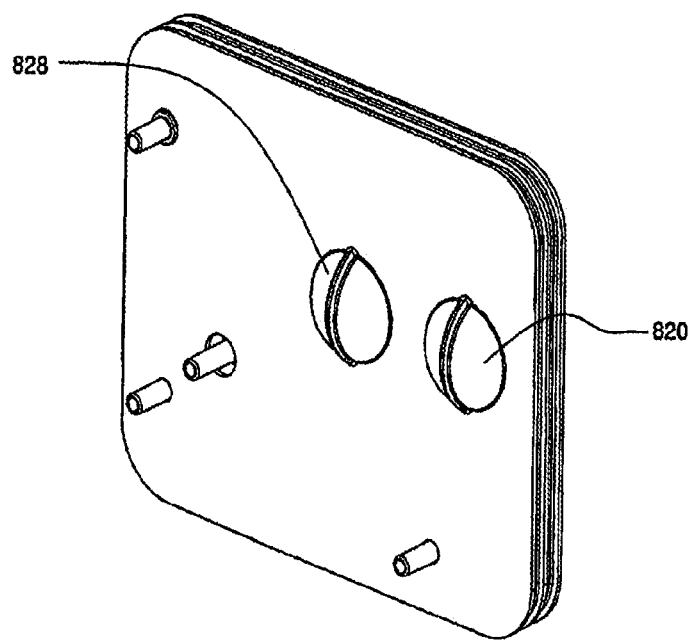
FIG. 44A is a top view of an assembled exemplary embodiment of a cassette.
Figure 44B:
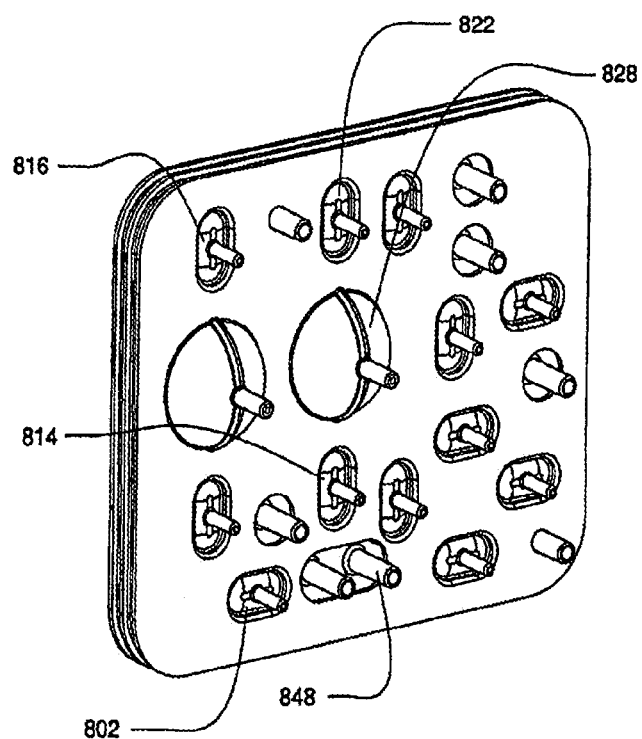
FIG. 44B is a bottom view of an assembled exemplary embodiment of a cassette.
Figure 44D:
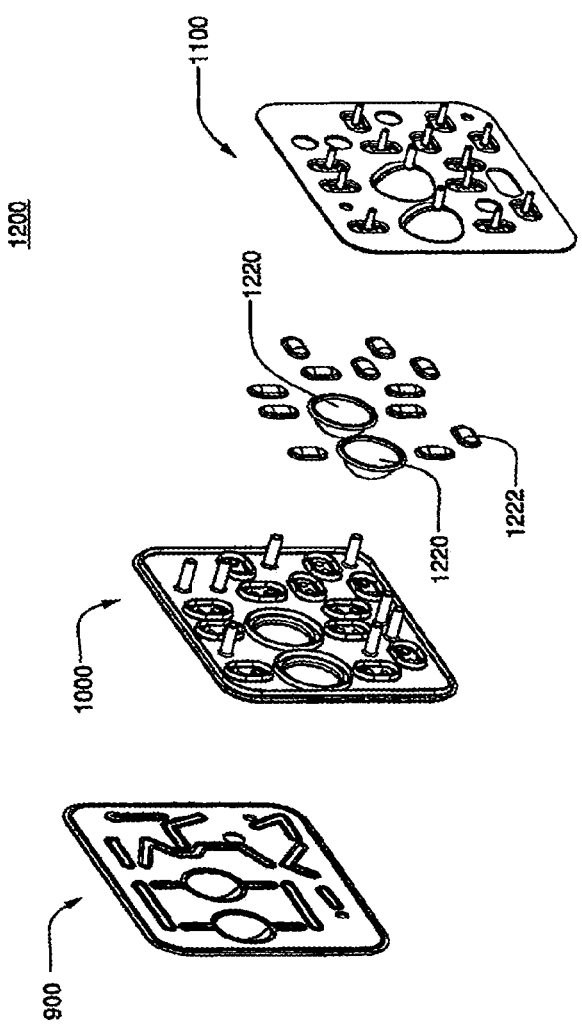
FIG. 44D is an exploded view of an assembled exemplary embodiment of a cassette.

Referring now to FIGS. 44A and 44B, an assembled cassette 1200 is shown. An exploded view of the assembled cassette 1200 shown in FIGS. 44A and 44B is shown in FIGS. 44C and 44D. In these views, the embodiment of the pod pump diaphragms 1220 is shown. The gasket of the diaphragm provides a seal between the liquid chamber (in the top plate 900) and the air/actuation chamber (in the bottom plate 1100). In some embodiment, texture on the dome of the diaphragms 1220 provide, amongst other features, additional space for air and liquid to escape the chamber at the end of stroke. In alternate embodiments of the cassette, the diaphragms may include a double gasket. The double gasket feature would be preferred in embodiments where both sides of the pod pump include liquid or in applications where sealing both chambers' sides is desired. In these embodiments, a rim complementary to the gasket or other feature (not shown) would be added to the inner bottom plate 1100 for the gasket to seal the pod pump chamber in the bottom plate 1100.

Figure 45:
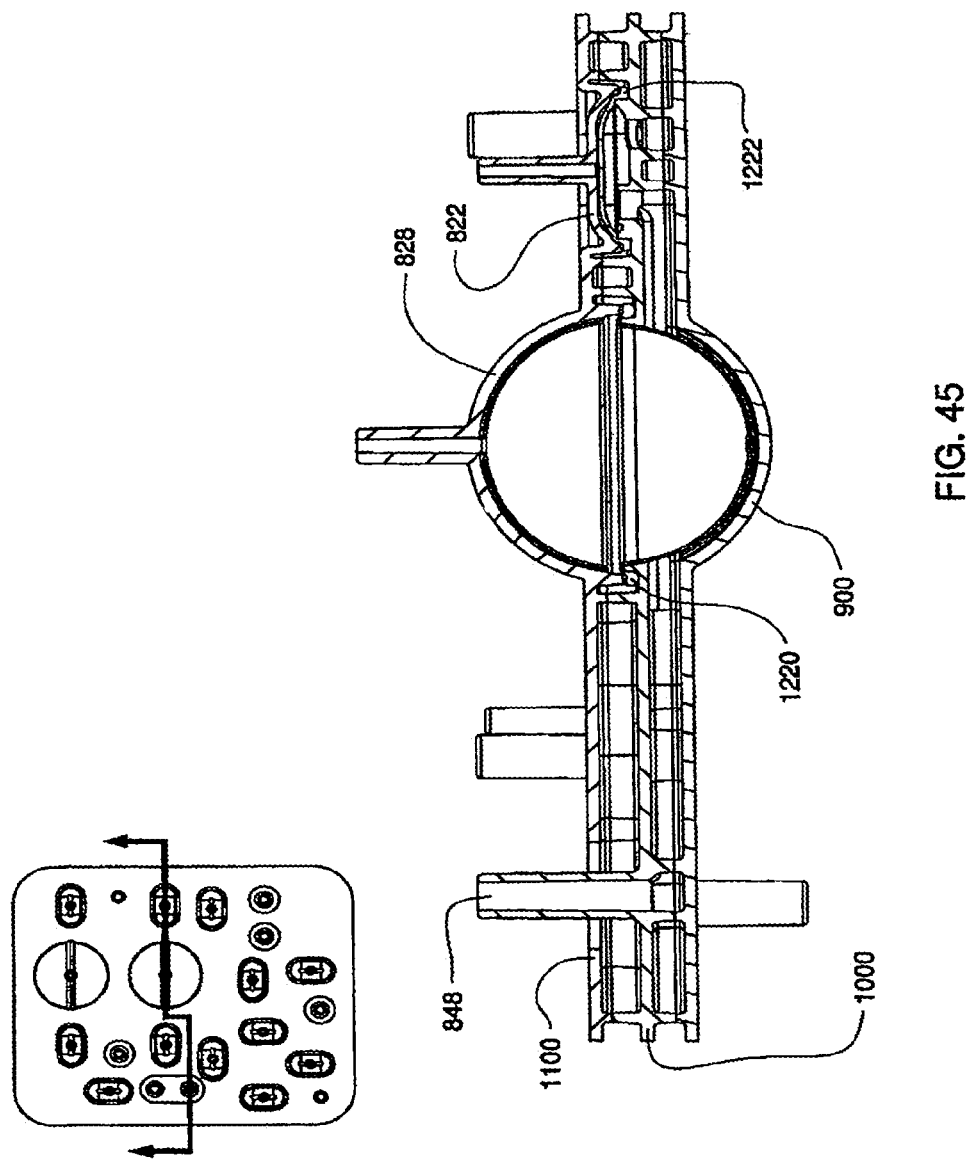
FIG. 45 shows a cross sectional view of an exemplary embodiment of an assembled cassette.

Referring now to FIG. 45, a cross sectional view of the pod pumps 828 in the cassette is shown. The details of the attachment of the diaphragm 1220 can be seen in this view. Again, in this embodiment, the diaphragm 1220 gasket is pinched by the midplate 1000 and the bottom plate 1100. A rim on the midplate 1000 provides a feature for the gasket to seal the pod pump 828 chamber located in the top plate 900.

Referring next to FIG. 45, this cross sectional view shows the valves 834, 836 in the assembled cassette. The diaphragms 1220 are shown assembled and are held in place, in this embodiment, by being sandwiched between the midplate 1000 and the bottom plate 1100. Still referring to FIG. 45, this cross sectional view also shows a valve 822 in the assembled cassette. The diaphragm 1222 is shown held in place by being sandwiched between the midplate 1000 and the bottom plate 1100.

In one set of embodiments, dialysate may be prepared separately and brought to the system for use in the directing circuit. However, in some cases, dialysate may be prepared in a mixing circuit. The mixing circuit may be run to produce dialysate at any suitable time. For instance, dialysate may be produced during dialysis of a patient, and/or prior to dialysis (the dialysate may be stored, for instance, in a dialysate tank. Within the mixing circuit, water (e.g., from a water supply, optionally delivered to the mixing circuit by a directing circuit) may be mixed with various dialysate ingredients to form the dialysate. Those of ordinary skill in the art will know of suitable dialysate ingredients, for instance, sodium bicarbonate, sodium chloride, and/or acid, as previously discussed. The dialysate may be constituted on an as-needed basis, so that large quantities do not need to be stored, although some may be stored within a dialysate tank, in certain cases.

Figure 7A:
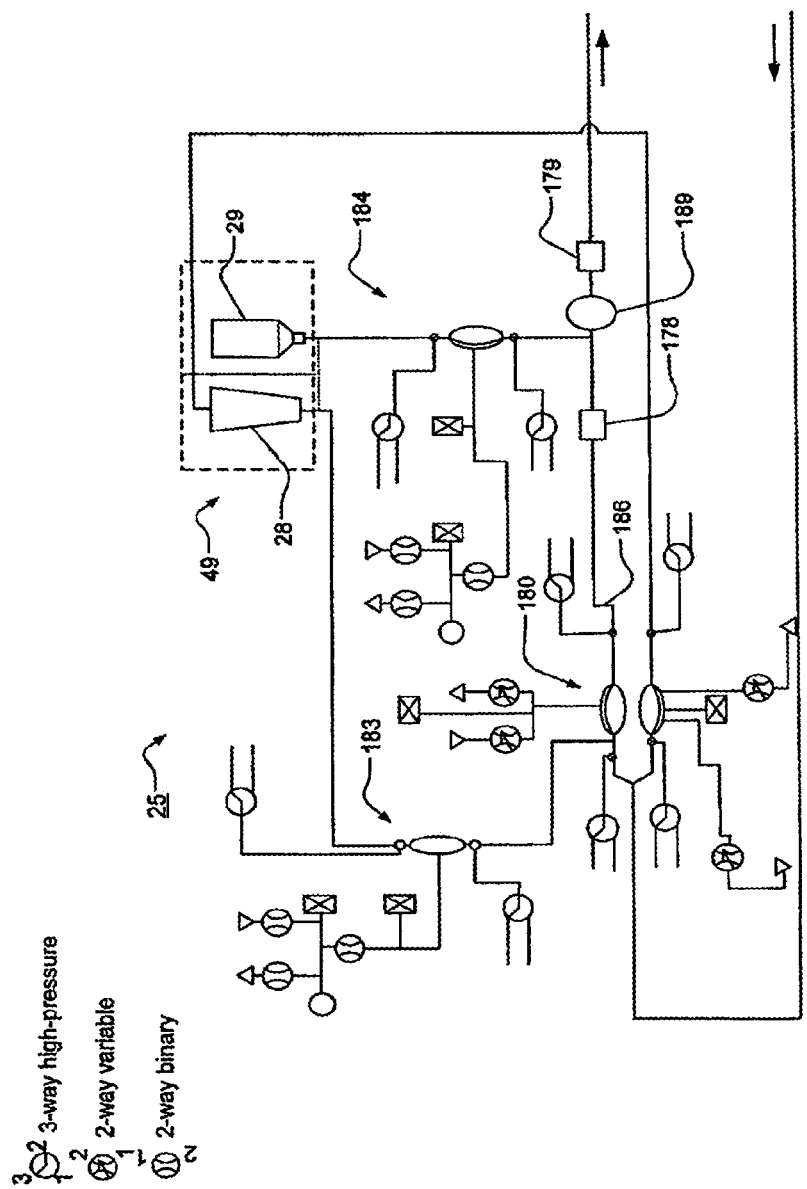
FIGS. 7A-7B are schematic representations of mixing circuits that may be used in a hemodialysis system.

FIG. 7A illustrates a non-limiting example of a mixing circuit, which may be implemented on a cassette in some cases. In FIG. 7A, water from a directing circuit flows into mixing circuit 25 due to action of pump 180. In some cases, a portion of the water is directed to ingredients 49, e.g., for use in transporting the ingredients through the mixing circuit. As shown in FIG. 7A, water is delivered to bicarbonate source 28 (which may also contain sodium chloride in some cases). The sodium chloride and/or the sodium bicarbonate may be provided, in some cases, in a powdered or granular form, which is moved through the action of water. Bicarbonate from bicarbonate source 28 is delivered via bicarbonate pump 183 to a mixing line 186, to which water from the directing circuit also flows. Acid from acid source 29 (which may be in a liquid form) is also pumped via acid pump 184 to mixing line 186. The ingredients (water, bicarbonate, acid, NaCl, etc.) are mixed in mixing chamber 189 to produce dialysate, which then flows out of mixing circuit 25. Conductivity sensors 178 and 179 are positioned along mixing line 186 to ensure that as each ingredient is added to the mixing line, it is added at proper concentrations. This method, and the control thereof, to ensure acceptable dialysate quality is produced and maintained during treatment is described in more detail below.

In one set of embodiments, pump 180 comprises one or more pod pumps, similar to those described above. The pod pumps may include a rigid chamber with a flexible diaphragm dividing each chamber into a fluid compartment and control compartment. The control compartment may be connected to a control fluid source, such as an air source. Non-limiting examples of pumps that can be used as pod pumps are described in U.S. Provisional Patent Application Ser. No. 60/792,073, filed Apr. 14, 2006, entitled "Extracorporeal Thermal Therapy Systems and Methods"; or in U.S. patent application Ser. No. 11/787,212, filed Apr. 13, 2007, entitled "Fluid Pumping Systems, Devices and Methods," each incorporated herein by reference. Similarly, in some cases, pumps 183 and/or 184 may each be pod pumps. Additional details of pod pumps are discussed below.

In some cases, one or more of the pumps may have pressure sensors to monitor the pressure in the pump. This pressure sensor may be used to ensure that a pump compartment is filling and delivering completely. For example, ensuring that the pump delivers a full stroke of fluid may be accomplished by (i) filling the compartment, (ii) closing both fluid valves, (iii) applying pressure to the compartment by opening the valve between the positive pneumatic reservoir and the compartment, (iv) closing this positive pressure valve, leaving pressurized air in the path between the valve and the compartment, (v) opening the fluid valve so the fluid can leave the pump compartment, and (vi) monitoring the pressure drop in the compartment as the fluid leaves. The pressure drop corresponding to a full stroke may be consistent, and may depend on the initial pressure, the hold-up volume between the valve and the compartment, and/or the stroke volume. However, in other embodiments of any of the pod pumps described herein, a reference volume compartment may be used, where the volume is determined through pressure and volume data.

The volumes delivered by the water pump and/or the other pumps may be directly related to the conductivity measurements, so the volumetric measurements may be used as a cross-check on the composition of the dialysate that is produced. This may ensure that the dialysate composition remains safe even if a conductivity measurement becomes inaccurate during a therapy.

Figure 7B:
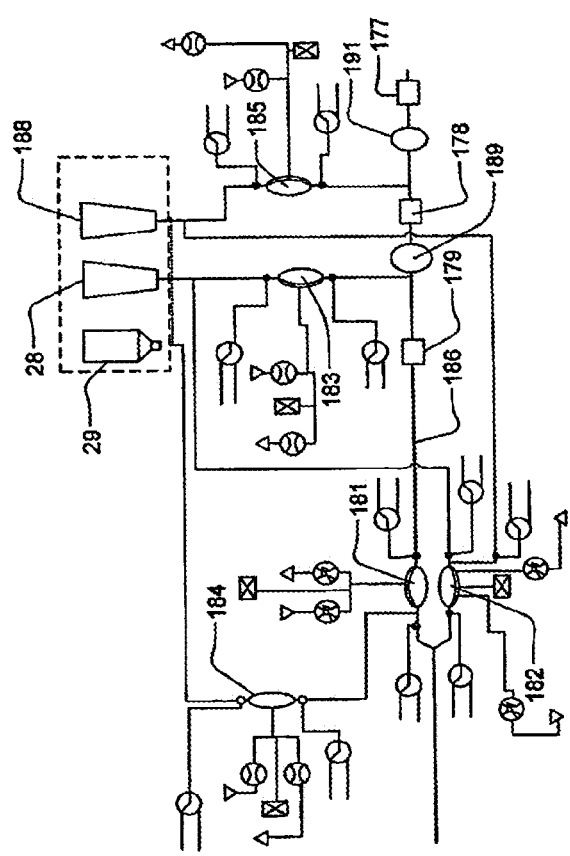

FIG. 7B is a schematic diagram showing another example of a mixing circuit, implementable on a cassette in certain cases. Mixing circuit 25 in this figure includes a pod pump 181 for pumping water from a supply along a line 186 into which the various ingredients for making the dialysate are introduced into the water. Another pump 182 pumps water from a water supply into source 28 holding the sodium bicarbonate (e.g., a container) and/or into source 188 holding the sodium chloride. A third pump 183 introduces the dissolved bicarbonate into mixing line 186 (mixed in mixing chamber 189), while a fourth pump 185 introduces dissolved sodium chloride into line 186 (mixed in mixing chamber 191). A fifth pump 184 introduces acid into the water before it passes through the first pump 181. Mixing is monitored using conductivity sensors 178, 179, and 177, which each measure the conductivity after a specific ingredient has been added to mixing line 186, to ensure that the proper amount and/or concentration of the ingredient has been added. An example of such sensors is discussed below; further non-limiting examples can be seen in U.S. patent application Ser. No. 12/038,474 entitled "Sensor Apparatus Systems, Devices and Methods," filed on Feb. 27, 2008, and incorporated herein by reference. This method, and the control thereof, to ensure acceptable dialysate quality is produced and maintained during treatment is described in more detail below.

Figure 3B:
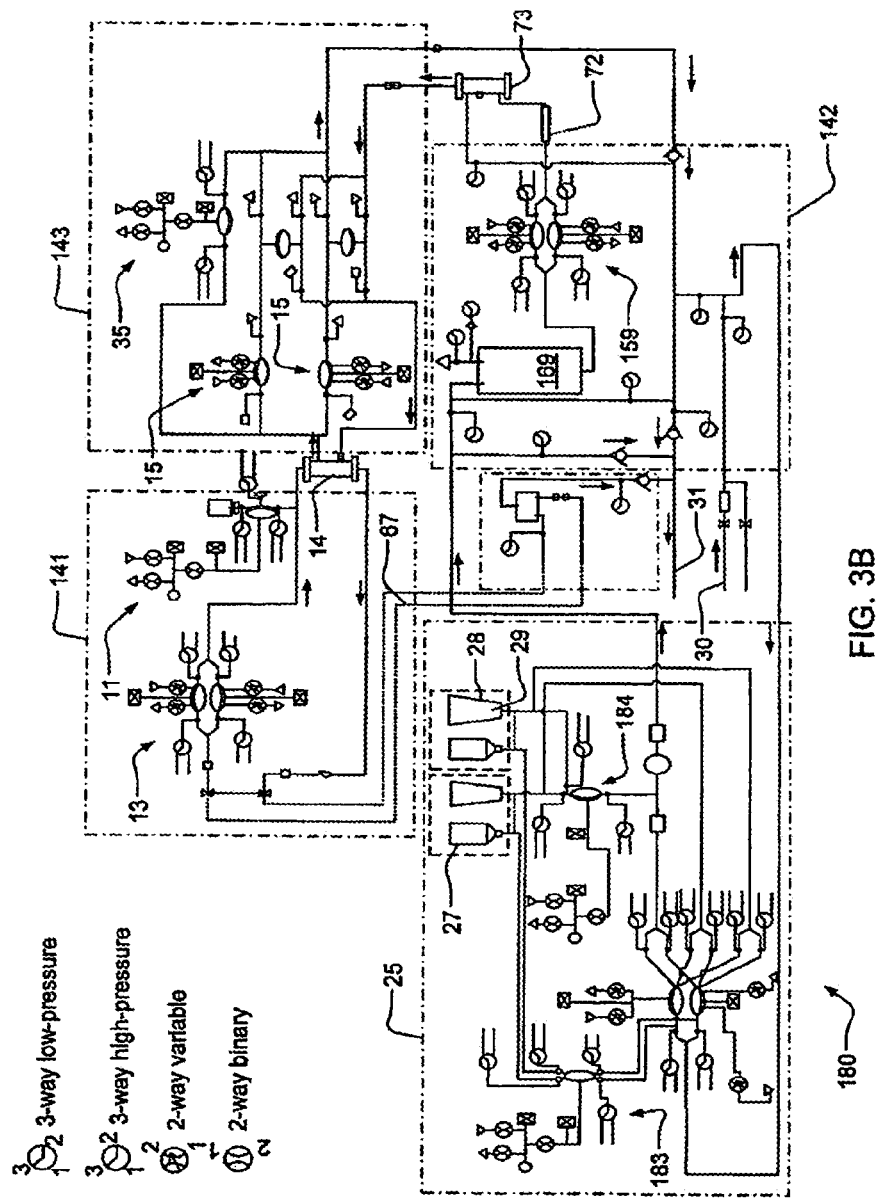

Referring now to FIG. 3B, in this embodiment, mixing circuit 25 constitutes dialysate using two sources: an acid concentrate source 27 and a combined sodium bicarbonate ($NaHCO_3$) and sodium chloride (NaCl) source. As shown in the embodiment shown in FIG. 3B, in some embodiments, the dialysate constituting system 25 may include multiples of each source. In embodiments of the method where the system is run continuously, the redundant dialysate sources allow for continuous function of the system, as one set of sources is depleted, the system uses the redundant source and the first set of sources is replaced. This process is repeated as necessary, e.g., until the system is shut down.

A non-limiting example of a balancing cassette is shown in FIGS. 34A-36E. In the exemplary fluid flow-path cassette shown in FIG. 37, valves are open individually. In this exemplary embodiment, the valves are pneumatically open. Also, in this embodiment, the fluid valves are volcano valves, as described in more detail elsewhere in this specification.

Figure 38A:
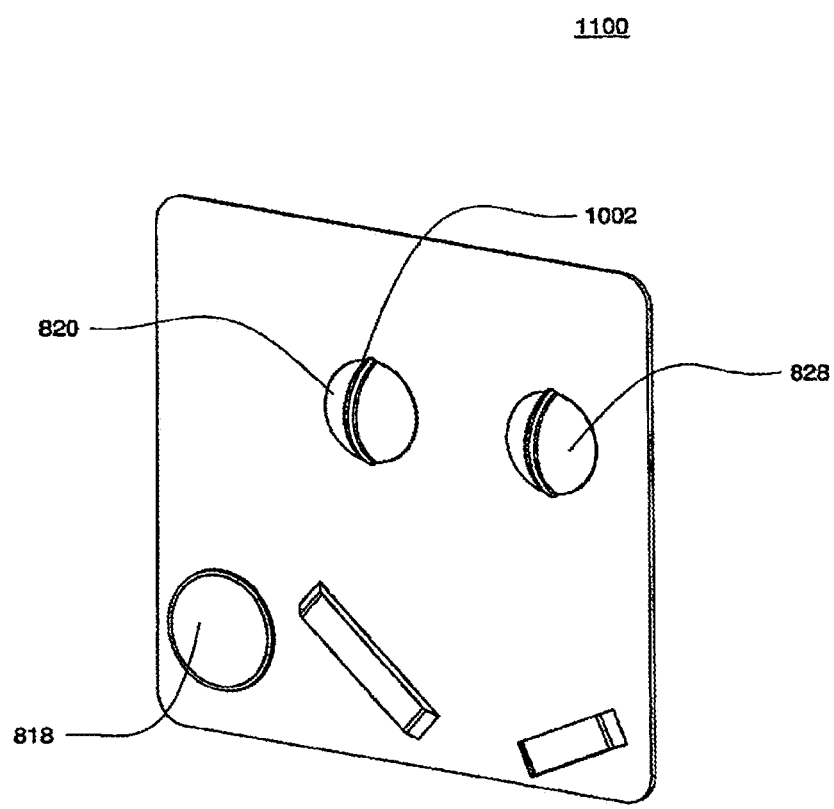
FIG. 38A is a view of an exemplary embodiment of the outer top plate of a cassette.
Figure 38B:
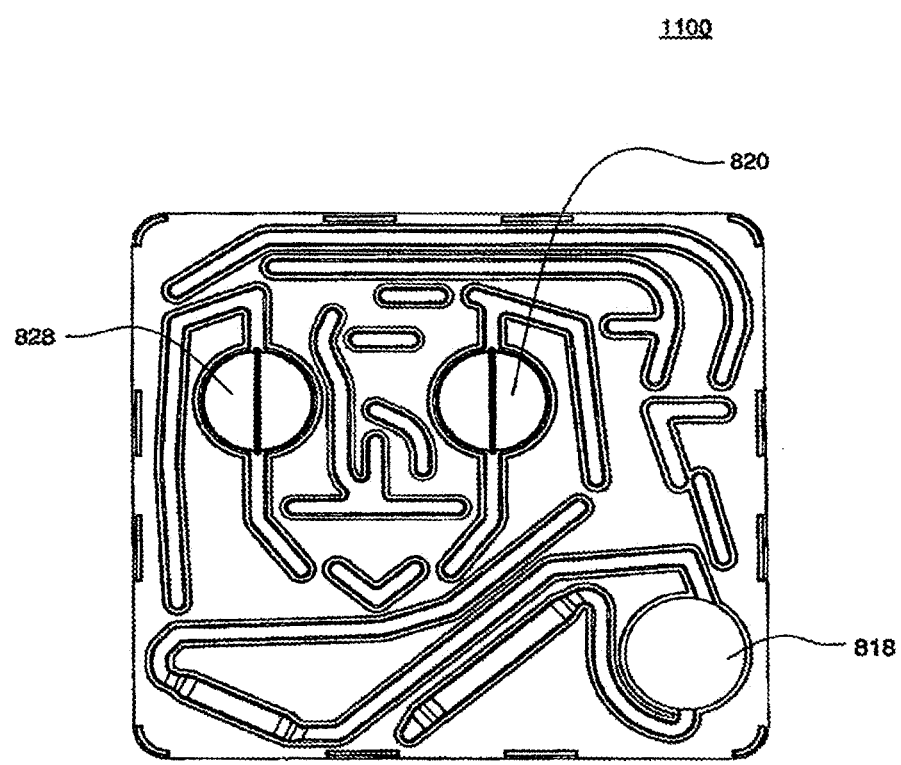
FIG. 38B is a view of an exemplary embodiment of the inner top plate of a cassette.

Referring now to FIGS. 38A-38B, the top plate 1100 of one exemplary embodiment of the cassette is shown. In this exemplary embodiment, the pod pumps 820, 828 and the mixing chambers 818 on the top plate 1100, are formed in a similar fashion. In this exemplary embodiment, the pod pumps 820, 828 and mixing chamber 818, when assembled with the bottom plate, have a total volume of capacity of 38 ml. However, in other embodiments, the mixing chamber may have any size volume desired.

Referring now to FIG. 38B, the bottom view of the top plate 1100 is shown. The fluid paths are shown in this view. These fluid paths correspond to the fluid paths shown in FIGS. 39A-39B in the midplate 1200. The top plate 1100 and the top of the midplate 1200 form the liquid or fluid side of the cassette for the pod pumps 820, 828 and for one side of the mixing chamber 818. Thus, most of the liquid flow paths are on the top 1100 and midplates 1200. Referring to FIG. 39B, the first fluid inlet 810 and the first fluid outlet 824 are shown.

Still referring to FIGS. 38A and 38B, the pod pumps 820, 828 include a groove 1002 (in alternate embodiments, this is a groove). The groove 1002 is shown having a particular size and shape, however, in other embodiments, the size and shape of the groove 1002 may be any size or shape desirable. The size and shape shown in FIGS. 38A and 38B is one exemplary embodiment. In all embodiments of the groove 1002, the groove 1002 forms a path between the fluid inlet side and the fluid outlet side of the pod pumps 820, 828. In alternate embodiments, the groove 1002 is a groove in the inner pumping chamber wall of the pod pump.

The groove 1002 provides a fluid path whereby when the diaphragm is at the end-of-stroke there is still a fluid path between the inlet and outlet such that the pockets of fluid or air do not get trapped in the pod pump. The groove 1002 is included in both the liquid/fluid and air/actuation sides of the pod pumps 820, 828. In some embodiments, the groove 1002 may also be included in the mixing chamber 818 (see FIGS. 40A-40B with respect to the actuation/air side of the pod pumps 820, 828 and the opposite side of the mixing chamber 818. In alternate embodiments, the groove 1002 is either not included or on only one side of the pod pumps 820, 828.

Figure 38C:
FIG. 38C is a side view of an exemplary embodiment of the top plate of a cassette.

In an alternate embodiment of the cassette, the liquid/fluid side of the pod pumps 820, 828 may include a feature (not shown) whereby the inlet and outlet flow paths are continuous and a rigid outer ring (not shown) is molded about the circumference of the pumping chamber is also continuous. This feature allows for the seal, formed with the diaphragm (not shown) to be maintained. Referring to FIG. 38C, the side view of an exemplary embodiment of the top plate 1100 is shown.

Figure 37:
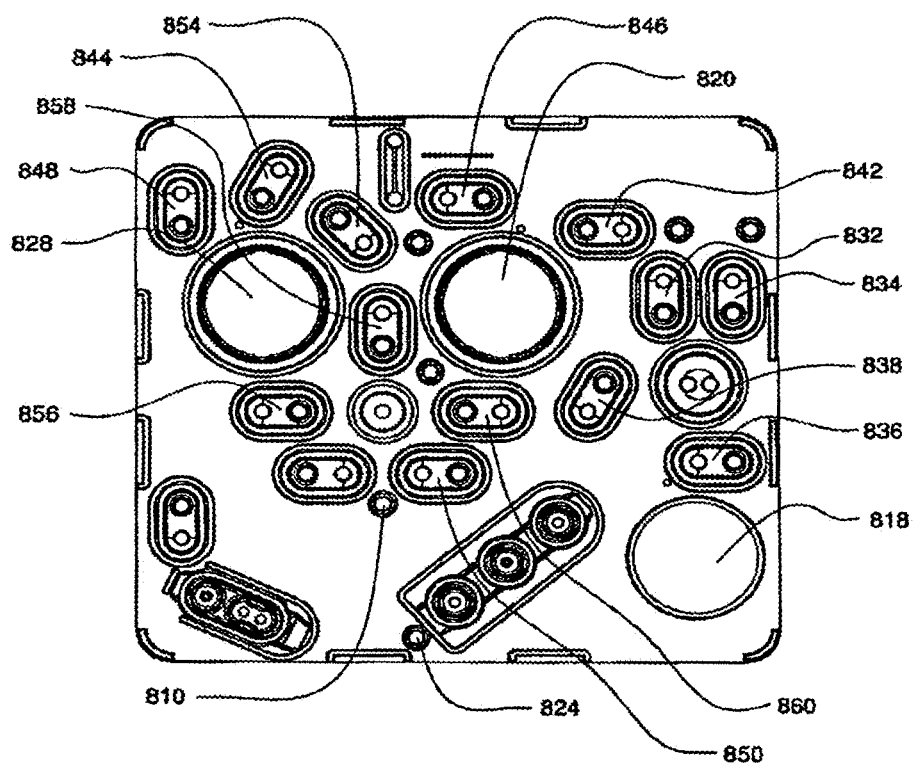
FIG. 37 is an isometric front view of an exemplary embodiment of the actuation side of the midplate of a cassette with the valves indicated corresponding to FIG. 36.
Figure 39A:
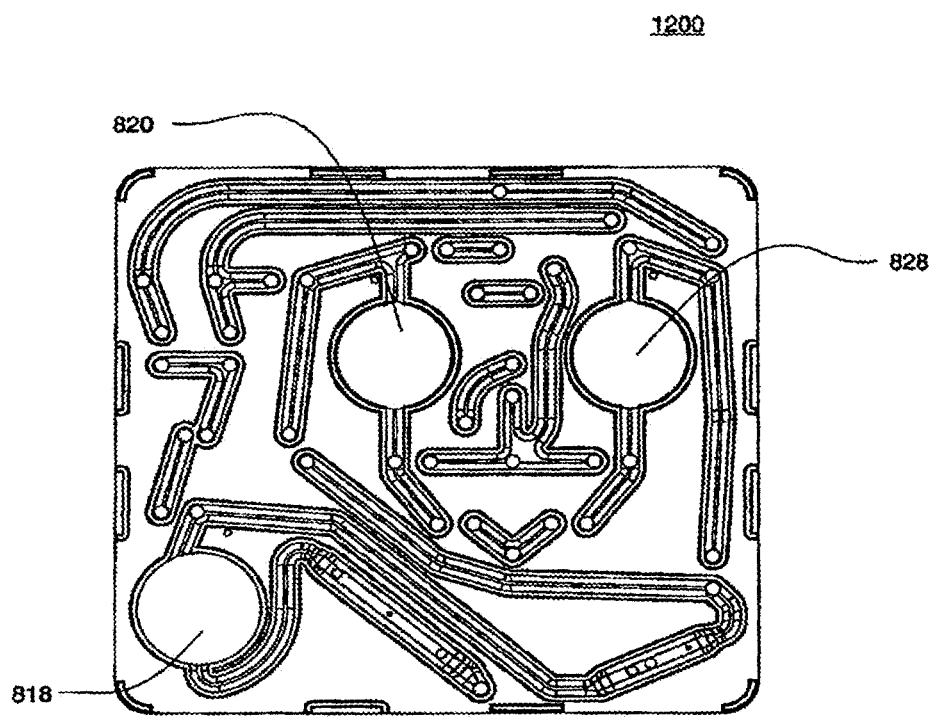
FIG. 39A is a view of an exemplary embodiment of the fluid side of the midplate of a cassette.
Figure 39B:
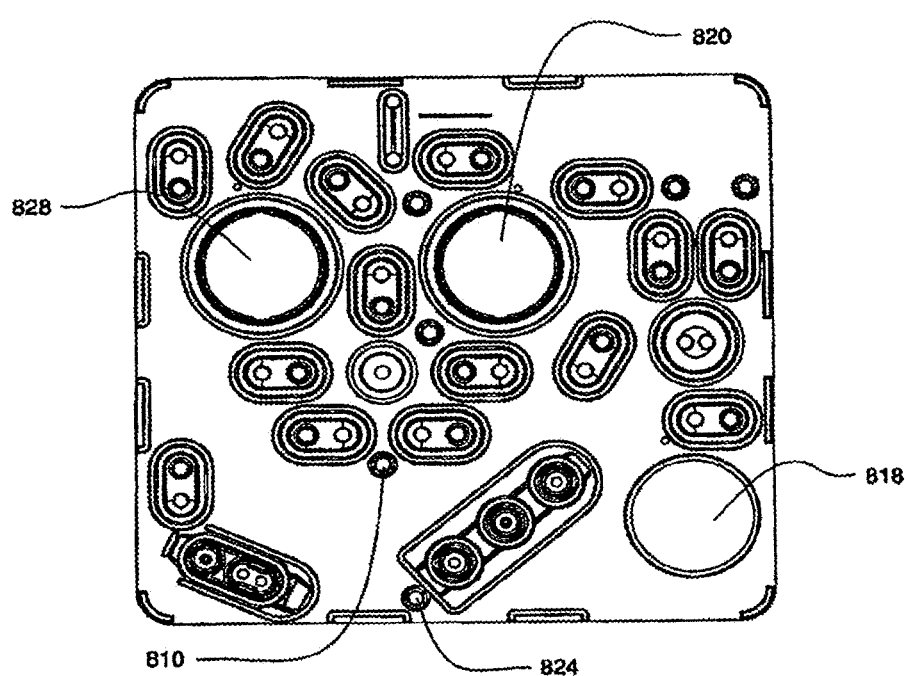
FIG. 39B is a front view of an exemplary embodiment of the air side of the midplate of a cassette.

Referring now to FIGS. 39A-39B, an exemplary embodiment of the midplate 1200 is shown. The midplate 1200 is also shown in FIG. 37, where this FIG. corresponds with FIGS. 39A-39B. Thus, FIG. 37 indicates the locations of the various valves and valving paths. The locations of the diaphragms (not shown) for the respective pod pumps 820, 828 as well as the location of the mixing chamber 818 are shown.

Referring now to FIG. 39A, in one exemplary embodiment of the cassette, sensor elements are incorporated into the cassette so as to discern various properties of the fluid being pumped. In one embodiment, three sensor elements are included. However, in this embodiment, six sensor elements (two sets of three) are included. The sensor elements are located in the sensor cell 1314, 1316. In this embodiment, a sensor cell 1314, 1316 is included as an area on the cassette for sensor(s) elements. In one embodiment, the three sensor elements of the two sensor cells 1314, 1316 are housed in respective sensor elements housings 1308, 1310, 1312 and 1318, 1320, 1322. In one embodiment, two of the sensor elements housings 1308, 1312 and 1318, 1320 accommodate conductivity sensor elements and the third sensor elements housing 1310, 1322 accommodates a temperature sensor element. The conductivity sensor elements and temperature sensor elements may be any conductivity or temperature sensor elements in the art. In one embodiment, the conductivity sensors are graphite posts. In other embodiments, the conductivity sensor elements are posts made from stainless steel, titanium, platinum or any other metal coated to be corrosion resistant and still be electrically conductive. The conductivity sensor elements will include an electrical lead that transmits the probe information to a controller or other device. In one embodiment, the temperature sensor is a thermistor potted in a stainless steel probe. However, in alternate embodiments, a combination temperature and conductivity sensor elements is used similar to the one described in a U.S. Patent Application entitled "Sensor Apparatus Systems, Devices and Methods," filed Oct. 12, 2007 (U.S. Patent Publication No. US-2008-0240929-A1).

In alternate embodiments, there are either no sensors in the cassette or only a temperature sensor, only one or more conductivity sensors or one or more of another type of sensor.

Figure 39C:
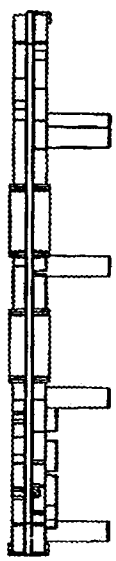
FIG. 39C is a side view of an exemplary embodiment of the midplate of a cassette.
Figure 40A:
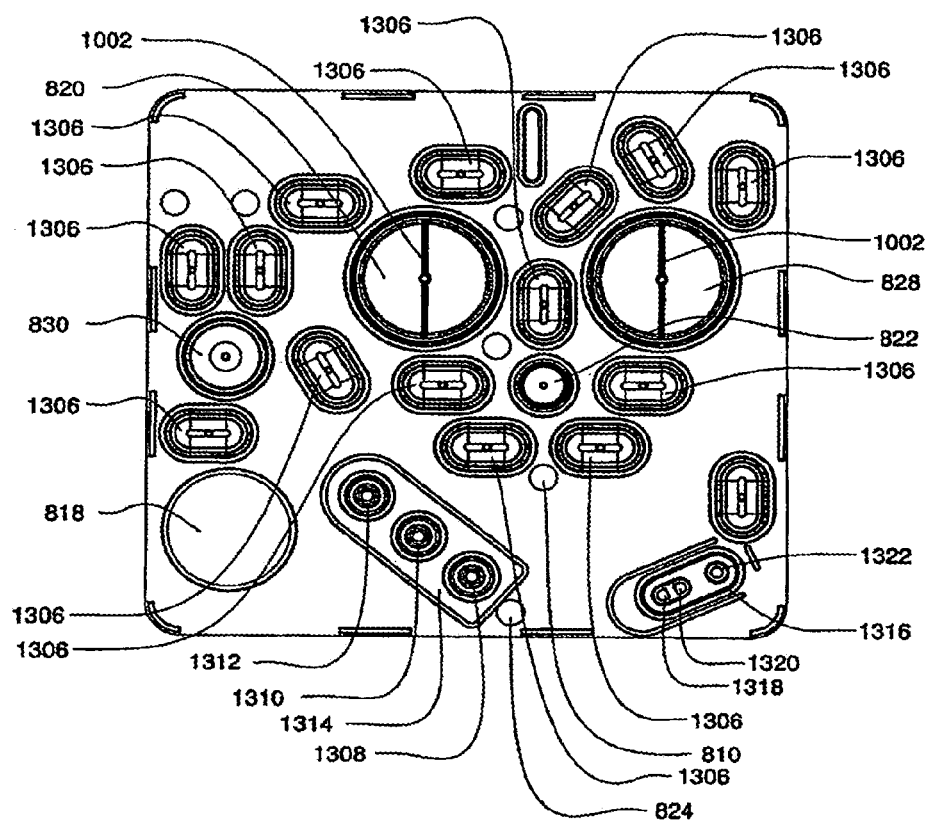
FIG. 40A is a view of an exemplary embodiment of the inner side of the bottom plate of a cassette.
Figure 40B:
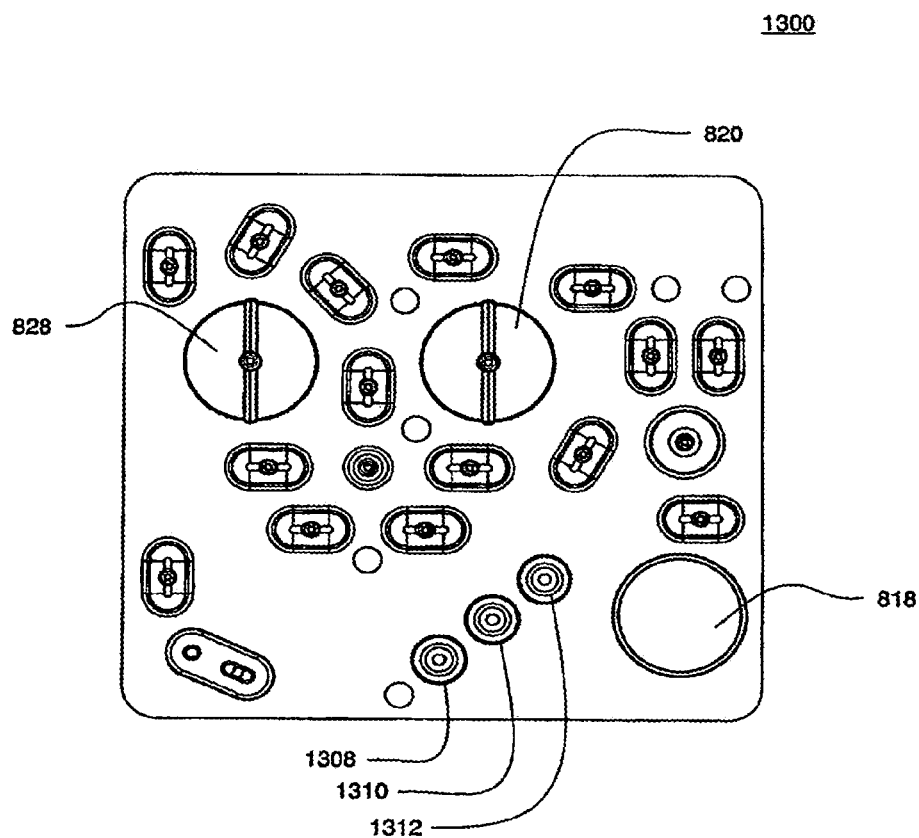
FIG. 40B is a view of an exemplary embodiment of the outer side of the bottom plate of a cassette.

Referring now to FIG. 39C, the side view of an exemplary embodiment of the midplate 1200 is shown. Referring now to FIGS. 40A-40B, the bottom plate 1300 is shown. Referring first to FIG. 40A, the inner or inside surface of the bottom plate 1300 is shown. The inner or inside surface is the side that contacts the bottom surface of the midplate (not shown). The bottom plate 1300 attaches to the air or actuation lines (not shown). The corresponding entrance holes for the air that actuates the pod pumps 820, 828 and valves (not shown, see FIG. 37) in the midplate 1200 can be seen. Holes 810, 824 correspond to the first fluid inlet and first fluid outlet shown in FIGS. 39B, 810, 824 respectively. The corresponding halves of the pod pumps 820, 828 and mixing chamber 818 are also shown, as are the grooves 1002 for the fluid paths. The actuation holes in the pumps are also shown. Unlike the top plate, the bottom plate 1300 corresponding halves of the pod pumps 820, 828 and mixing chamber 818 make apparent the difference between the pod pumps 820, 828 and mixing chamber 818. The pod pumps 820, 828 include an air/actuation path on the bottom plate 1300, while the mixing chamber 818 has identical construction to the half in the top plate. The mixing chamber 818 mixes liquid and therefore, does not include a diaphragm (not shown) nor an air/actuation path. The sensor cell 1314, 1316 with the three sensor element housings 1308, 1310, 1312 and 1318, 1320, 1322 are also shown.

Figure 40C:
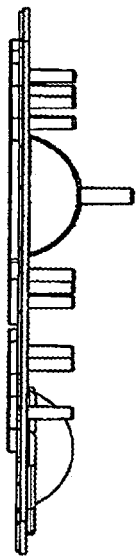
FIG. 40C is a side view of an exemplary embodiment of the midplate of a cassette.

Referring now to FIG. 40B, the actuation ports 1306 are shown on the outside or outer bottom plate 1300. An actuation source is connected to these actuation ports 1306. Again, the mixing chamber 818 does not have an actuation port as it is not actuated by air. Referring to FIG. 40C, a side view of the exemplary embodiment of the bottom plate 1300 is shown.

As described above, in various aspects of the invention, one or more fluid circuits may be implemented on a cassette, such as the blood flow circuit, the balancing circuit, the directing circuit, and/or the mixing circuit, etc. Other cassettes may be present, e.g., a sensing cassette as is disclosed in U.S. patent application Ser. No. 12/038,474 entitled "Sensor Apparatus Systems, Devices and Methods," filed on Feb. 27, 2008, and incorporated herein by reference. In some embodiments, some or all of these circuits are combined in a single cassette. In alternate embodiments, these circuits are each defined in respective cassettes. In still other embodiments, two or more of the fluid circuits are included on one cassette. In some cases, two, three, or more cassettes may be immobilized relative to each other, optionally with fluidic connections between the cassettes. For instance, in one embodiment, two cassettes may be connected via a pump, such as a pod pump as previously described. The pod pump may include a rigid chamber with a flexible diaphragm dividing each chamber into a first side and a second side, and the sides may be used for various purposes as noted above.

Non-limiting examples of cassettes that may be used in the present invention include those described in U.S. patent application Ser. No. 11/871,680, filed Oct. 12, 2007, entitled "Pumping Cassette"; U.S. patent application Ser. No. 11/871,712, filed Oct. 12, 2007, entitled "Pumping Cassette"; U.S. patent application Ser. No. 11/871,787, filed Oct. 12, 2007, entitled "Pumping Cassette"; U.S. patent application Ser. No. 11/871,793, filed Oct. 12, 2007, entitled "Pumping Cassette"; U.S. patent application Ser. No. 11/871,803, filed Oct. 12, 2007, entitled "Cassette System Integrated Apparatus"; or in U.S. patent application Ser. No. 12/038,648 entitled "Cassette System Integrated Apparatus," filed on Feb. 27, 2008. Each of these is incorporated by reference herein in their entireties.

A cassette may also include various features, such as pod pumps, fluid lines, valves, or the like. The cassette embodiments shown and described in this description include exemplary and various alternate embodiments. However, any variety of cassettes is contemplated that include a similar functionality. Although the cassette embodiments described herein are implementations of the fluid schematics as shown in the figures, in other embodiments, the cassette may have varying fluid paths and/or valve placement and/or pod pump placements and numbers and thus, is still within the scope of the invention.

In one example embodiment, a cassette may includes a top plate, a midplate and a bottom plate. There are a variety of embodiments for each plate. In general, the top plate includes pump chambers and fluid lines, the midplate includes complementary fluid lines, metering pumps and valves and the bottom plate includes actuation chambers (and in some embodiments, the top plate and the bottom plate include complementary portions of a balancing chamber or a pod pump).

In general, the diaphragms are located between the midplate and the bottom plate, however, with respect to a balancing chamber or a pod pump, a portion of a diaphragm is located between the midplate and the top plate. Some embodiments include where the diaphragm is attached to the cassette, either overmolded, captured, bonded, press fit, welded in or any other process or method for attachment, however, in the exemplary embodiments, the diaphragms are separate from the top plate, midplate and bottom plate until the plates are assembled.

The cassettes may be constructed of a variety of materials. Generally, in the various embodiments, the materials used are solid and non-flexible. In one embodiment, the plates are constructed of polysulfone, but in other embodiments, the cassettes are constructed of any other solid material and in exemplary embodiment, of any thermoplastic or thermoset.

In one exemplary embodiment, the cassettes are formed by placing diaphragms in their correct locations (e.g., for one or more pod pumps, if such pod pumps are present), assembling the plates in order, and connecting the plates. In one embodiment, the plates are connected using a laser welding technique. However, in other embodiments, the plates may be glued, mechanically fastened, strapped together, ultrasonically welded or any other mode of attaching the plates together.

In practice, the cassette may be used to pump any type of fluid from any source to any location. The types of fluid include nutritive, nonnutritive, inorganic chemicals, organic chemicals, bodily fluids or any other type of fluid. Additionally, fluid in some embodiments include a gas, thus, in some embodiments, the cassette is used to pump a gas.

The cassette serves to pump and direct the fluid from and to the desired locations. In some embodiments, outside pumps pump the fluid into the cassette and the cassette pumps the fluid out. However, in some embodiments, the pod pumps serve to pull the fluid into the cassette and pump the fluid out of the cassette.

As discussed above, depending on the valve locations, control of the fluid paths is imparted. Thus, the valves being in different locations or additional valves are alternate embodiments of this cassette. Additionally, the fluid lines and paths shown in the figures described above are mere examples of fluid lines and paths. Other embodiments may have more, less and/or different fluid paths. In still other embodiments, valves are not present in the cassette.

The number of pod pumps (if pod pumps are present within the cassette) described above may also vary depending on the embodiment. For example, although the various embodiments shown and described above include two pod pumps, in other embodiments, the cassette includes one pod pump. In still other embodiments, the cassette includes more than two pod pumps, or there may be no pod pumps present. The pod pumps may be single pumps or multiple pod pumps may be present that can work in tandem, e.g., to provide a more continuous flow, as discussed above. Either or both may be used in various embodiments of the cassette. However, as noted above, in some cases, there may be pod pumps not present on a cassette, but contained between two or more cassettes. Non-limiting examples of such systems can be seen in U.S. patent application Ser. No. 12/038,648 entitled "Cassette System Integrated Apparatus," filed on Feb. 27, 2008, and incorporated by herein reference.

The various fluid inlets and fluid outlets disclosed herein may be fluid ports in some cases. In practice, depending on the valve arrangement and control, a fluid inlet may be a fluid outlet. Thus, the designation of the fluid port as a fluid inlet or a fluid outlet is only for description purposes. The various embodiments have interchangeable fluid ports. The fluid ports are provided to impart particular fluid paths onto the cassette. These fluid ports are not necessarily all used all of the time; instead, the variety of fluid ports provides flexibility of use of the cassette in practice.

Figure 46A:
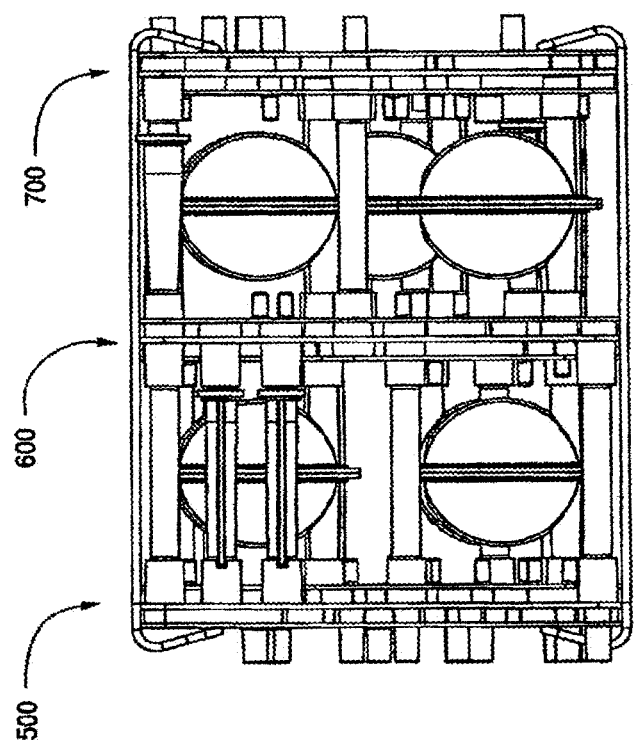
FIG. 46A is a front view of the assembled exemplary embodiment of the cassette system.
Figure 46B:
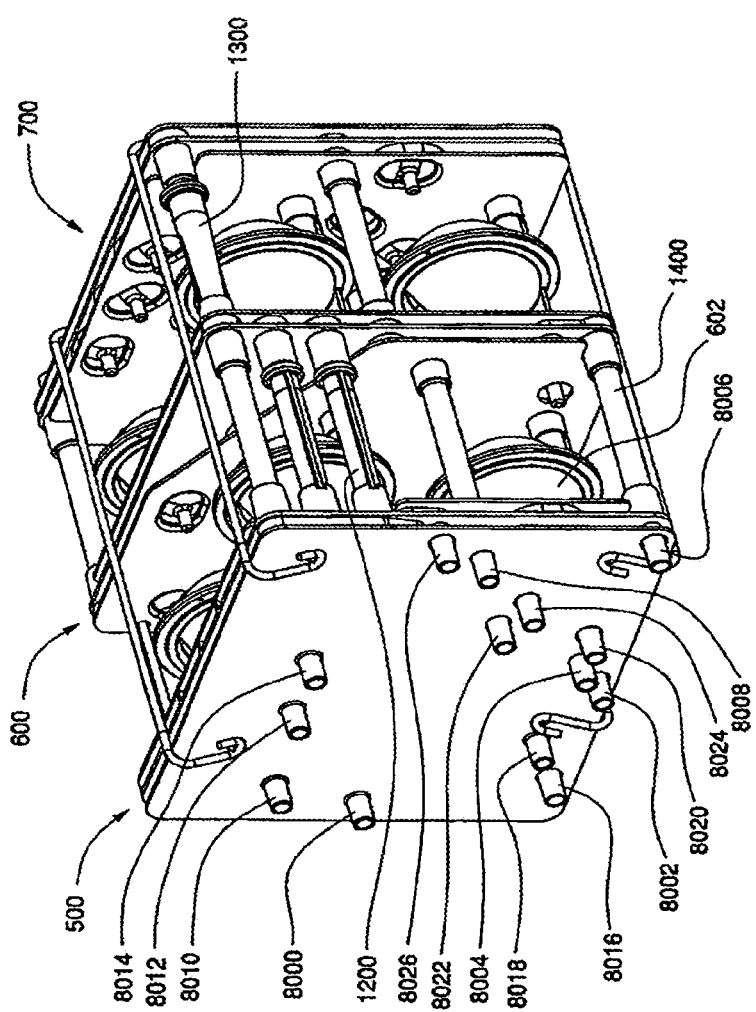
FIG. 46B is an isometric view of the assembled exemplary embodiment of the cassette system.
Figure 46C:
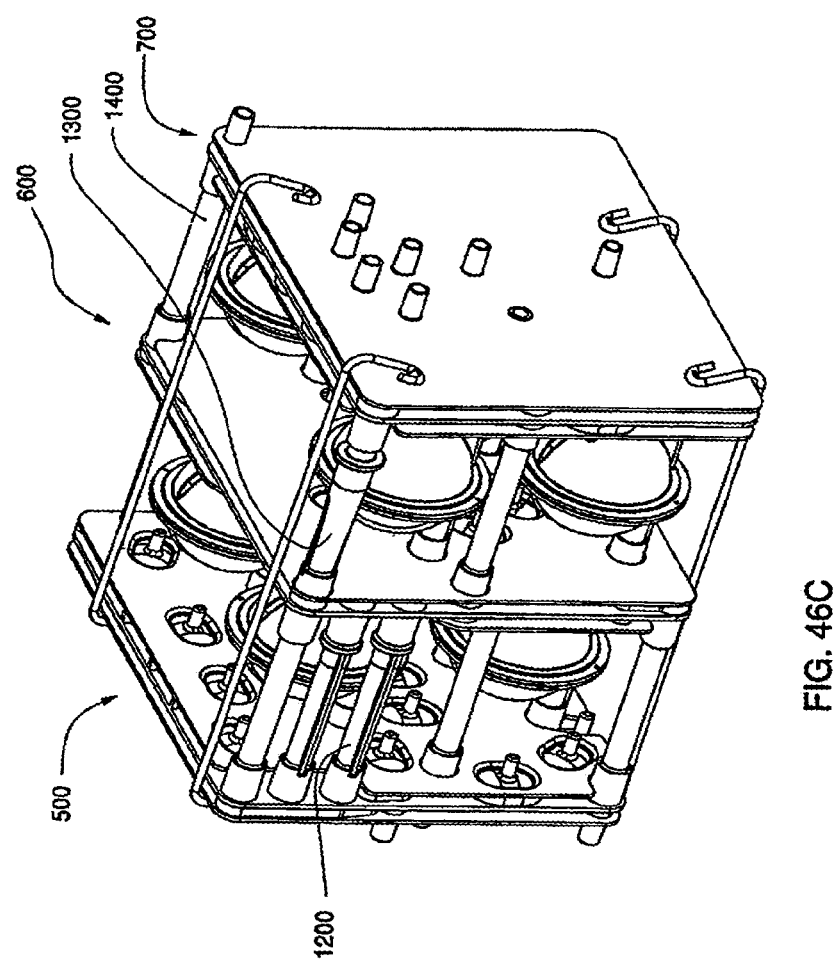
FIG. 46C is an isometric view of the assembled exemplary embodiment of the cassette system.
Figure 50A:
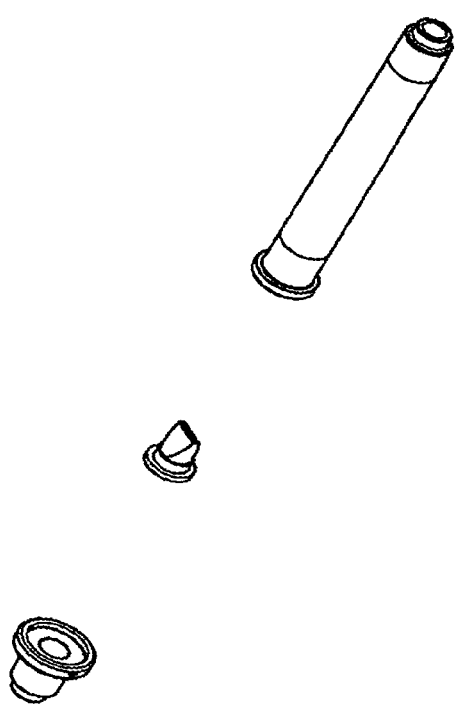
FIG. 50A is an exploded view of one embodiment of a check valve fluid line in the cassette system.
Figure 50B:
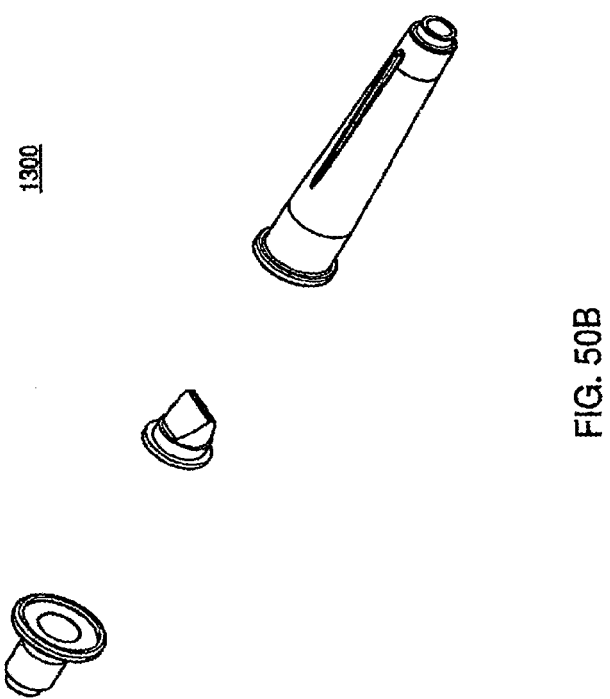
FIG. 50B is an exploded view of one embodiment of a check valve fluid line in the cassette system.
Figure 50C:
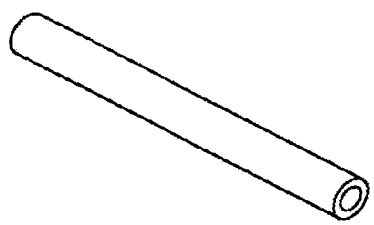
FIG. 50C is an isometric view of an exemplary embodiment of a fluid line in the cassette system.

Another non-limiting example of a cassette is shown with reference to FIGS. 46A-46E. Referring now to FIG. 46A, the assembled cassette system integrated is shown. The mixing cassette 500, middle cassette 600 and balancing cassette 700 are linked by fluid lines or conduits. The pods are between the cassettes. Referring now to FIGS. 46B and 46C, the various views show the efficiency of the cassette system integrated. The fluid lines or conduits 1200, 1300, 1400 are shown in FIG. 50A, FIG. 50B and FIG. 50C respectively. The fluid flows between the cassettes through these fluid lines or conduits. Referring now to FIGS. 50A and 50B, these fluid lines or conduits represent larger 1300 and smaller 1200 check valve fluid lines. In the exemplary embodiment, the check valves are duck bill valves; however, in other embodiments, any check valve may be used. Referring to FIG. 50C, fluid line or conduit 1400 is a fluid line or conduit that does not contain a check valve. For purposes of this description, the terms "fluid line" and "conduit" are used with respect to 1200, 1300 and 1400 interchangeably.

Figure 51A:
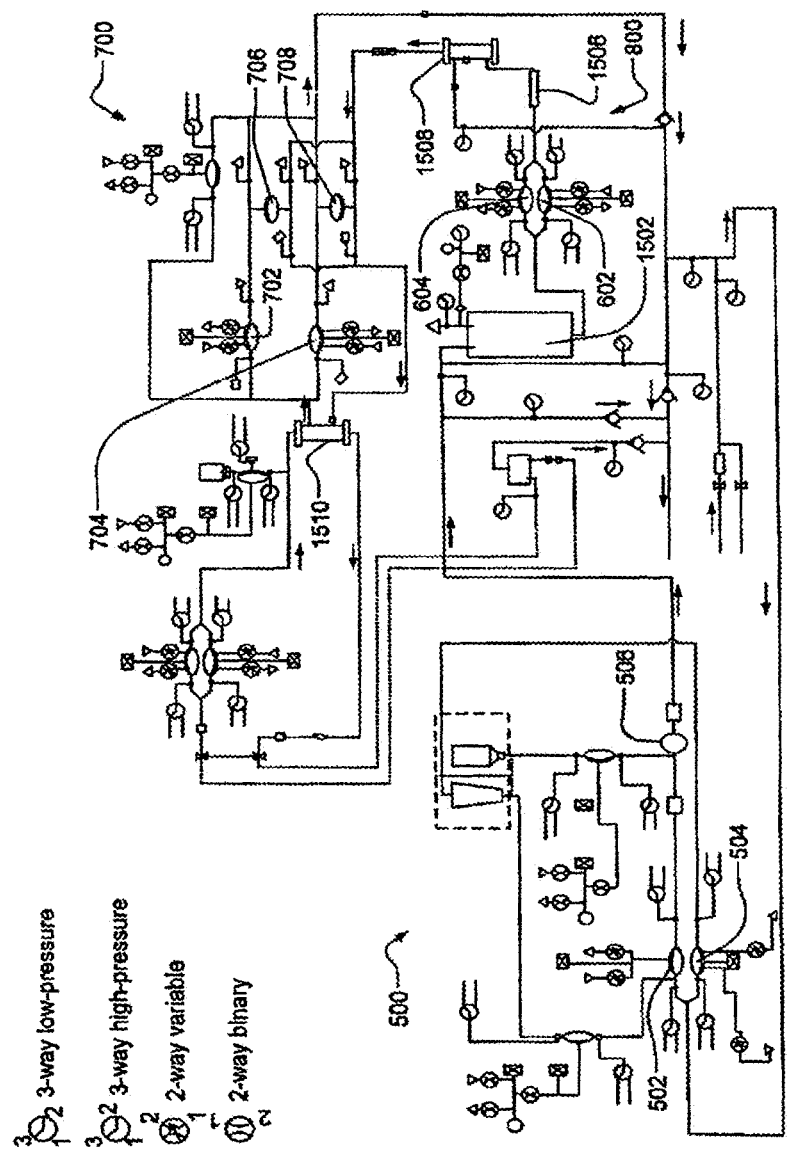
FIG. 51A is one embodiment of the fluid flow-path schematic of the cassette system integrated.

Referring now to FIGS. 46B and 46C, and FIG. 51A, the following is a description of one embodiment of the fluid flow through the various cassettes. For ease of description, the fluid flow will begin with the mixing cassette 500. Referring now to FIG. 46B and FIG. 51A, the fluid side of the mixing cassette 500 is shown. The fluid side includes a plurality of ports 8000, 8002, 8004, 8006, 8008 and 8010-8026 that are either fluid inlets or fluid outlets. In the various embodiments, the fluid inlets and outlets may include one or more fluid inlets for reverse osmosis ("RO") water 8004, bicarbonate, an acid, and a dialysate 8006. Also, one or more fluid outlets, including a drain, acid 8002 and at least one air vent outlet as the vent for the dialysate tank. In one embodiment, a tube (not shown) hangs off the outlet and is the vent (to prevent contamination). Additional outlets for water, bicarbonate and water mixture, dialysate mixture (bicarbonate with acid and water added) are also included.

Figure 46D:
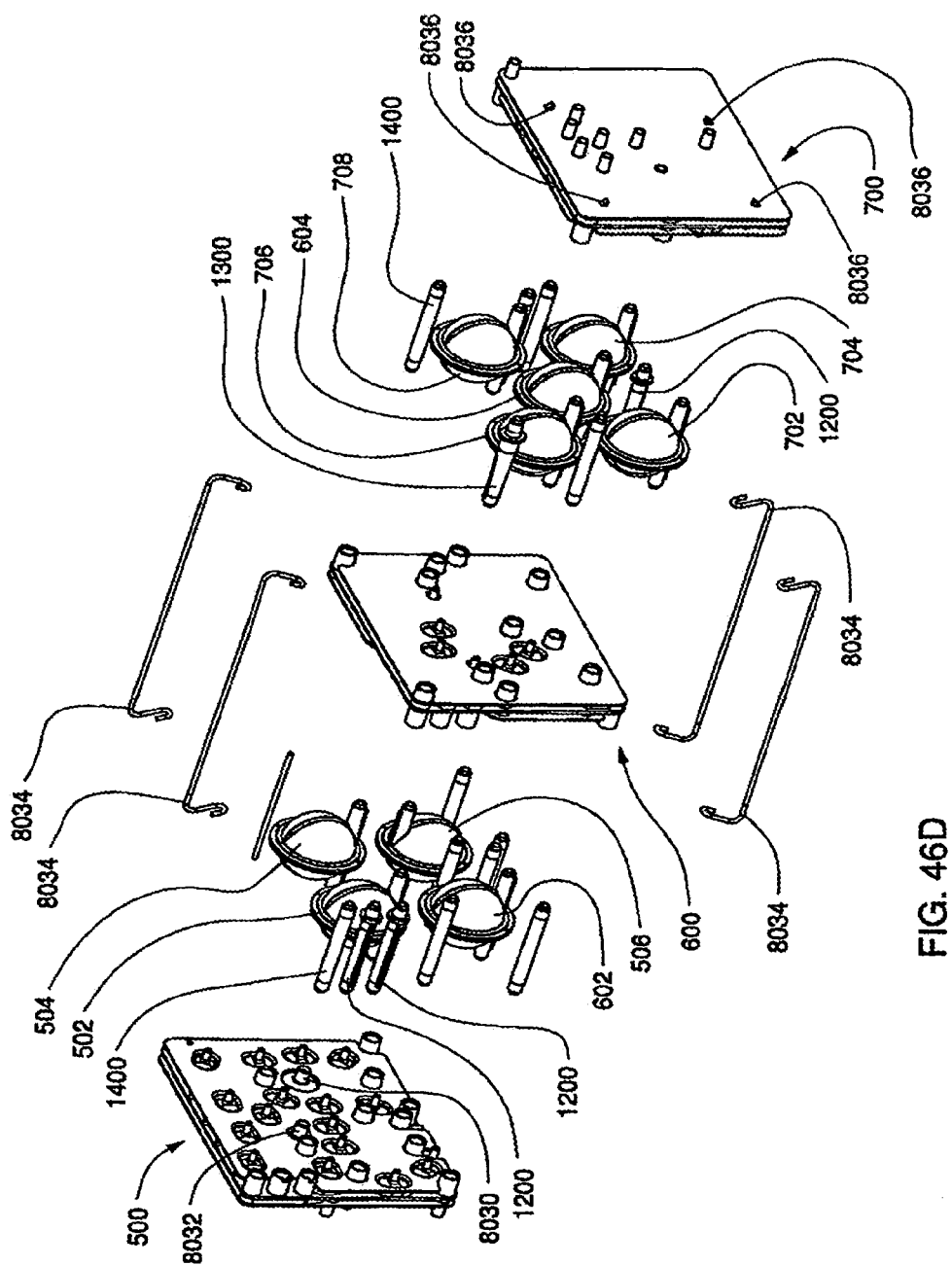
FIG. 46D is an exploded view of the assembled exemplary embodiment of the cassette system.
Figure 46E:
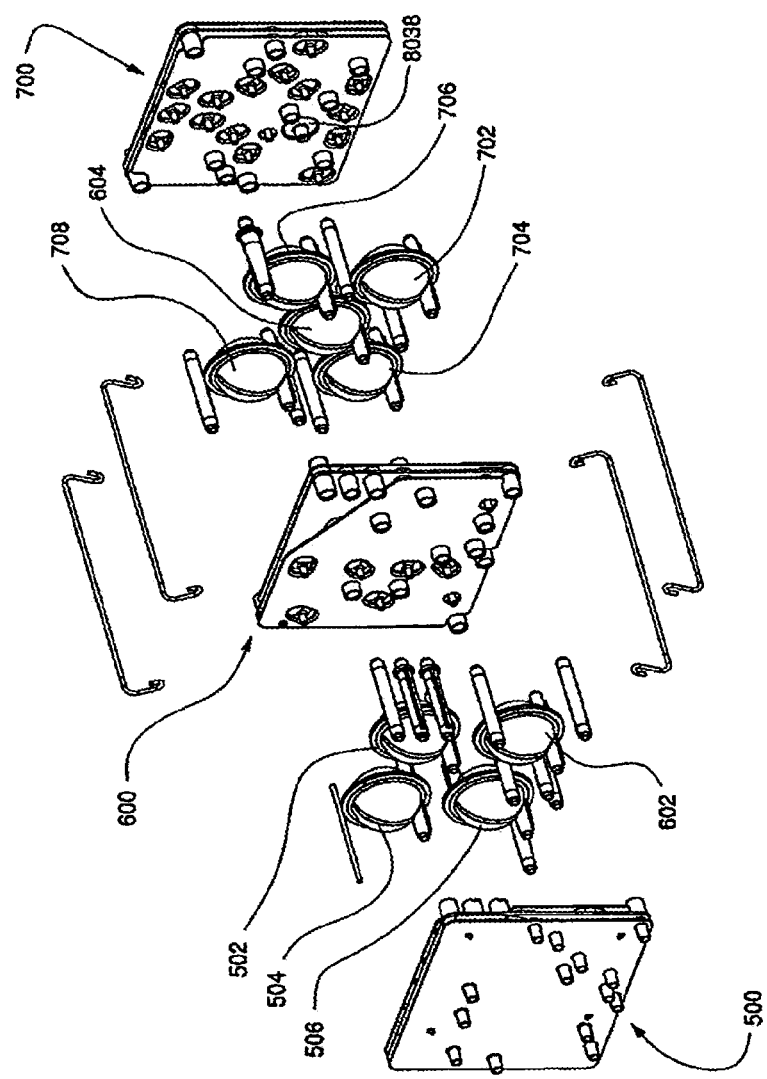
FIG. 46E is an exploded view of the assembled exemplary embodiment of the cassette system.

The dialysate flows out of the mixing cassette 500, to a dialysate tank (not shown, shown as 1502 in FIG. 51A) and then through a conduit to the inner dialysate cassette 700 (pumped by the outer dialysate cassette 600 pod pumps 602 and 604 (604 not shown, shown in FIGS. 46D and 46E). The fluid paths within the cassettes may vary. Thus, the location of the various inlet and outlets may vary with various cassette fluid paths.

Figure 51B:
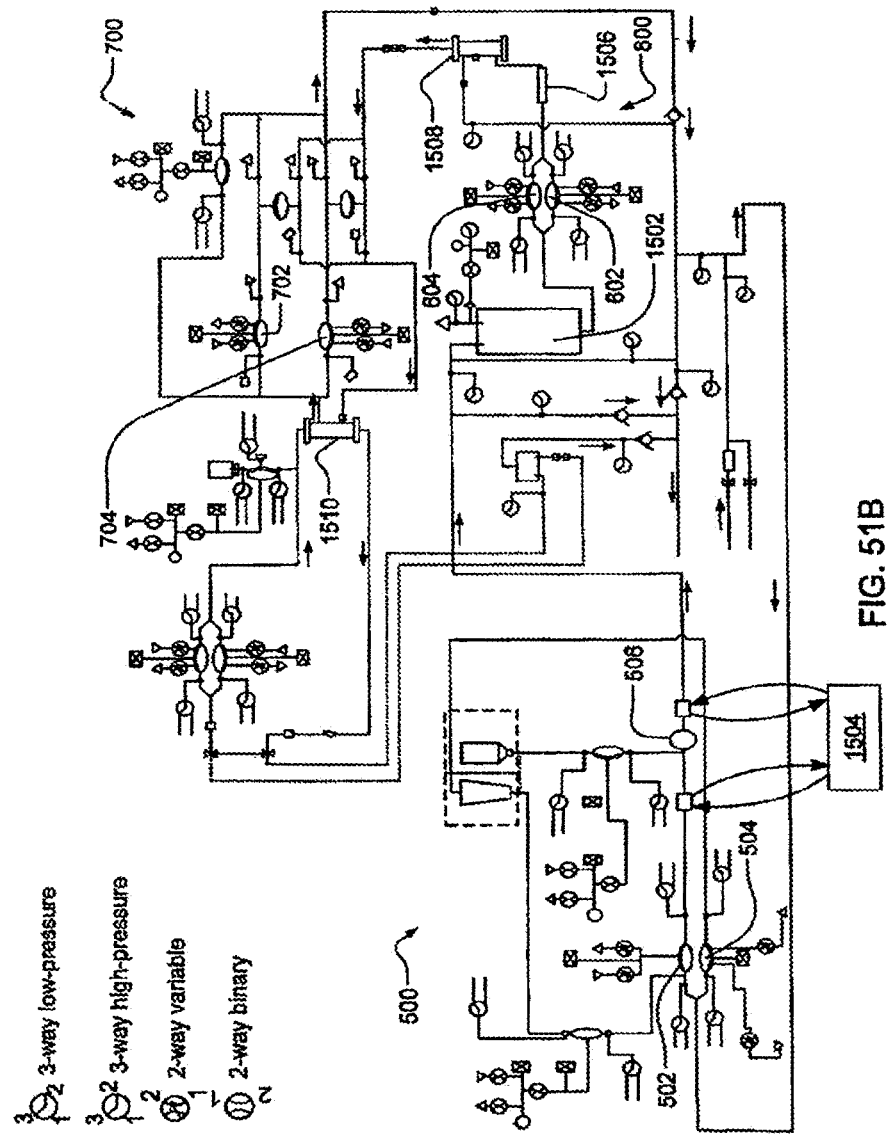
FIG. 51B is one embodiment of the fluid flow-path schematic of the cassette system integrated.

Referring now to FIG. 51B, in one embodiment of the cassette system, the condo cells, conductivity and temperature sensors, are included in a separate cassette 1504 outside of the cassette system shown in FIGS. 46A-46 C. This outside sensor cassette 1504 may be one of those described in U.S. patent application Ser. No. 12/038,474 entitled "Sensor Apparatus Systems, Devices and Methods," filed on Feb. 27, 2008, and incorporated herein by reference.

The fluid flow-path for this embodiment is shown in FIG. 51B. In this embodiment, during the mixing process for the dialysate, the bicarbonate mixture leaves the mixing cassette 500 and flows to an outside sensor cassette, and then flows back into the mixing cassette 500. If the bicarbonate mixture meets pre-established thresholds, acid is then added to the bicarbonate mixture. Next, once the bicarbonate and acid are mixed in the mixing chamber 506, the dialysate flows out of the cassette into the sensor cassette and then back to the mixing cassette 500. This method, and the control thereof, to ensure acceptable dialysate quality is produced and maintained during treatment is described in more detail below.

Referring now to FIG. 46D, the mixing cassette 500 include a pneumatic actuation side. In the block shown as 500, there are a plurality of valves and two pumping chambers 8030, 8032 build into the cassette 500 for pumping or metering the acid or bicarbonate. In some embodiments, additional metering pumps, or less metering pumps, are included. The metering pumps 8030, 8032 can be any size desired. In some embodiments, the pumps are different sizes with respect to one another, however, in other embodiments, the pumps are the same size with respect to one another. For example, in one embodiment, the acid pump is smaller than the bicarbonate pump. This may be more efficient and effective when using a higher concentration acid, as it may be desirable to use a smaller pump for accuracy and also, it may be desirable for control schemes to have a smaller pump so as to use full strokes in the control rather than partial strokes.

The conduits 1200, 1300 include a check-valve. These conduits 1200,1300 allow for one-way flow. In the exemplary embodiment, these conduits 1200, 1300 all lead to drain. Referring to the flow-path schematic FIG. 51A, the locations of these check-valve conduits are apparent. In the embodiment shown, any fluid that is meant for drain flows through the mixing cassette 500. Referring again to FIG. 46B, a fluid drain port 8006 is located on the fluid side of the cassette 500.

Once the dialysate is mixed, and after the dialysate flows to the sensor cassette (1504 in FIG. 51B) and it is determined that the dialysate is not within set parameters/thresholds, then the dialysate will be pumped back into the mixing cassette 500, through a plain conduit 1400 then to the outer dialysate cassette 600, then back through conduit a check valve conduit 1200 and then through the mixing cassette 500 to the drain fluid outlet.

Referring now to FIGS. 46D and 46E, the various pods 502, 504, 506, 602, 604, 702, 704, 706, 708 are shown. Each of the pod housings are constructed identically, however, the inside of the pod housing is different depending on whether the pod is a pod pump 502, 504 602, 604, 702, 704 a balancing chamber pods 706, 708 or a mixing chamber pod 504.

Referring now to FIGS. 46D and 46E, together with FIGS. 51A and 51B, the various pods are shown both in the fluid flow-path and on the cassette system. Pod 502 is the water pod pump and 504 is the bicarbonate water pod pump (sends water to the bicarbonate) of the mixing cassette 500. Pod 506 is the mixing chamber. Once the dialysate is mixed in the mixing chamber 506, and then flows from the mixing cassette 500 to the sensor cassette 1504, and it is determined that the dialysate qualifies as acceptable, then the dialysate flows to the dialysate tank 1502 through the mixing cassette dialysate tank outlet. However, if the dialysate is rendered unacceptable, then the fluid is pumped back into the cassette 500, then through a 1400 conduit, to the outer dialysate cassette 600 and then pumped through a 1200 check valve conduit, through the mixing cassette 500 and out the drain outlet.

Referring to FIGS. 46A-46C, together with FIGS. 51A-B, the outer dialysate cassette is shown 600 between the mixing cassette 500 and the inner dialysate cassette 700. Pod pumps 602, 604, pump the dialysate from the dialysate tank 1502 and send it to the balancing chambers 706,708 in the inner dialysate cassette 700 (driving force for the dialysate solution). The outer dialysate cassette 600 pushes the dialysate into the inner dialysate cassette (i.e., the pumps in the inner dialysate cassette 700 do not draw the dialysate in). Thus, from the outer dialysate cassette 600, the dialysate is pumped from the dialysate tank 1502, through a heater 1506 and through an ultrafilter 1508, and then into the inner dialysate cassette 700.

Still referring now to FIGS. 46D and 46E, together with FIGS. 51A-B, the inner dialysate cassette 700 includes a metering pod 8038 (i.e., an ultra filtration metering pod) and includes balancing pods 706, 708 and pod pumps 702, 704. The inner dialysate cassette 700 also includes fluid outlets and inlets. These inlets and outlets include the outlet to the dialyzer 1510, the inlet from the dialyzer 1510, and a dialysate inlet (the ultrafilter 1508 connects to a port of the inner dialysate cassette). Fluid inlets and outlets are also included for the DCA and DCV connections during priming and disinfection. Various conduits (1200,1300,1400) serve as fluid connections between the cassettes 500, 600, 700 and are used for dialysate fluid flow as well as fluid to pass through in order to drain through the mixing cassette 500. The largest check valve 1300 (also shown in FIG. 50B) is the largest check-valve, and is used during disinfection. This tube is larger in order to accommodate, in the preferred embodiment, blood clots and other contaminants that flow through the conduits during disinfection.

The valves and pumps of the cassette system are pneumatically actuated in the exemplary embodiment. The pneumatics attach to the cassettes via individual tubes. Thus, each pump, balancing pod, or valve includes an individual tube connection to a pneumatic actuation manifold (not shown). Referring now to FIGS. 52A-F, the tubes are connected, in the exemplary embodiment, to at least one block, 1600. In some embodiments, more than one block is used to connect the various tubes. The block 1600 is dropped into the manifold and then connected to the pneumatics actuators appropriately. This allows for easy connection of the pneumatic tubes to the manifold.

Referring again to FIG. 46D, the cassette system includes springs 8034, in one embodiment, to aid in holding the system together. The springs 8034 hook onto the mixing cassette 500 and inner dialysate cassette 700 via catches 8036. However, in other embodiments, any other means or apparatus to assist in maintaining the system in appropriate orientation may be used including, but not limited to, latching means or elastic means, for example.

Figure 47A:
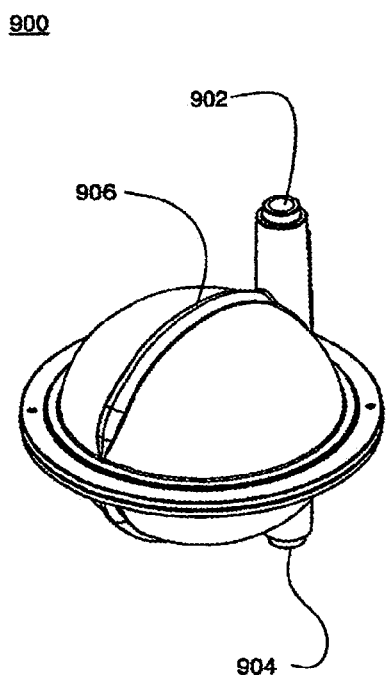
FIG. 47A is an isometric view of an exemplary embodiment of the pod of the cassette system.
Figure 47B:
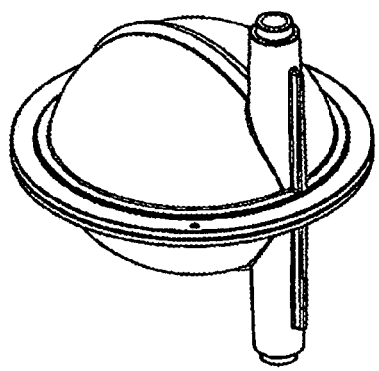
FIG. 47B is an isometric view of an exemplary embodiment of the pod of the cassette system.
Figure 47C:
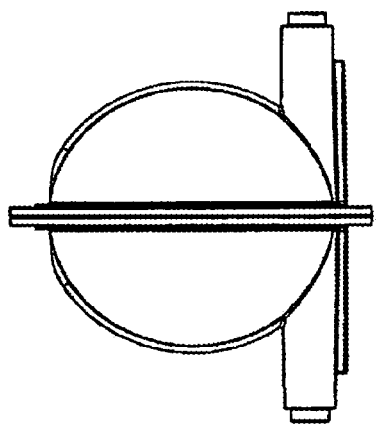
FIG. 47C is a side view of an exemplary embodiment of the pod of the cassette system.

Referring now to FIGS. 47A-47C, the exemplary embodiment of the pod is shown. The pod includes two fluid ports 902, 904 (an inlet and an outlet) and the pod may be constructed differently in the various embodiments. A variety of embodiments of construction are described in U.S. patent application Ser. No. 11/787,212, filed Apr. 13, 2007, and entitled "Fluid Pumping Systems, Devices and Methods," which is hereby incorporated herein by reference in its entirety.

Figure 47D:
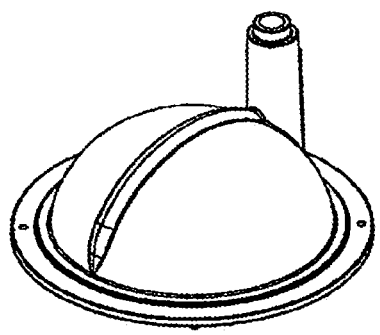
FIG. 47D is an isometric view of an exemplary embodiment of one half of the pod of the cassette system.
Figure 47E:
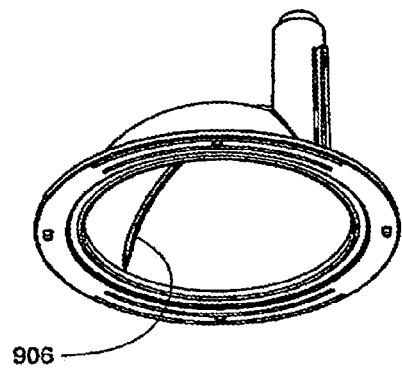
FIG. 47E is an isometric view of an exemplary embodiment of one half of the pod of the cassette system.

Referring now to FIGS. 47A, 47D and 47E the groove 906 in the chamber is shown. A groove 906 is included on each half of the pod housing. In other embodiments, a groove is not included and in some embodiments, a groove is only included on one half of the pod.

Figure 48A:
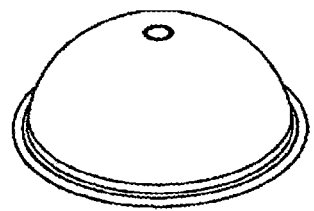
FIG. 48A is a pictorial view of the exemplary embodiment of the pod membrane of the cassette system.
Figure 48B:
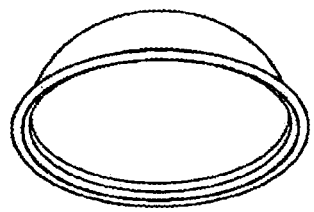
FIG. 48B is a pictorial view of the exemplary embodiment of the pod membrane of the cassette system.
Figure 49:
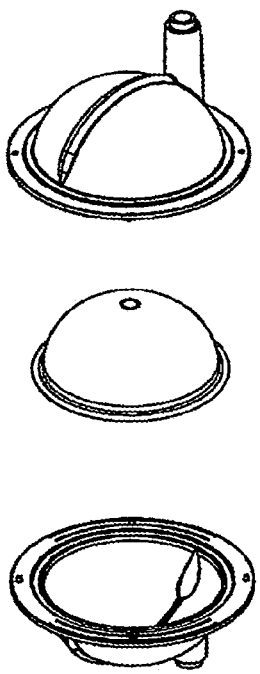
FIG. 49 is an exploded view of an exemplary embodiment of the pod of the cassette system.

Referring now to FIGS. 48A and 48B, the exemplary embodiment of the membrane used in the pod pumps 502, 504 602, 604, 702, 704 is shown. An exploded view of a pod pump according to the exemplary embodiment is shown FIG. 49.

Various aspects of the invention include one or more "pod pumps," used for various purposes. The structure of a general pod pump will now be described, although, as noted above, this structure may be modified for various uses, e.g., as a pump, a balancing chamber, a mixing chamber, or the like. In addition, a pod pump may be positioned anywhere in the system, for instance, on a cassette or between two or more cassettes, etc.

Generally, a pod pump includes a rigid chamber (which may have any suitable shape, e.g., spherical, ellipsoid, etc.), and the pod pump may include a flexible diaphragm dividing each chamber into a first half and a second half. In some cases, the rigid chamber is a spheroid. As used herein, "spheroid" means any three-dimensional shape that generally corresponds to a oval rotated about one of its principal axes, major or minor, and includes three-dimensional egg shapes, oblate and prolate spheroids, spheres, and substantially equivalent shapes.

Each half of the pod pump may have at least one entry valve, and often (but not always) has at least one exit valve (in some cases, the same port may be used for both entry and exit). The valves may be, for instance, open/closing valves or two-way proportional valves. For instance, valves on one side of a chamber may be two-way proportional valves, one connected to a high pressure source, the other connected to a low pressure (or vacuum) sink, while the valves on the other half may be opened and closed to direct fluid flow.

In some embodiments, the diaphragm has a variable cross-sectional thickness. Thinner, thicker or variable thickness diaphragms may be used to accommodate the strength, flexural and other properties of the chosen diaphragm materials. Thinner, thicker or variable diaphragm wall thickness may also be used to manage the diaphragm thereby encouraging it to flex more easily in some areas than in other areas, thereby aiding in the management of pumping action and flow of subject fluid in the pump chamber. In this embodiment, the diaphragm is shown having its thickest cross-sectional area closest to its center. However in other embodiments having a diaphragm with a varying cross-sectional, the thickest and thinnest areas may be in any location on the diaphragm. Thus, for example, the thinner cross-section may be located near the center and the thicker cross-sections located closer to the perimeter of the diaphragm. In one embodiment of the diaphragm, the diaphragm has a tangential slope in at least one section, but in other embodiments, the diaphragm is completely smooth or substantially smooth.

The diaphragm may be made of any flexible material having a desired durability and compatibility with the subject fluid. The diaphragm may be made from any material that may flex in response to fluid, liquid or gas pressure or vacuum applied to the actuation chamber. The diaphragm material may also be chosen for particular bio-compatibility, temperature compatibility or compatibility with various subject fluids that may be pumped by the diaphragm or introduced to the chambers to facilitate movement of the diaphragm. In the exemplary embodiment, the diaphragm is made from high elongation silicone. However, in other embodiments, the diaphragm is made from any elastomer or rubber, including, but not limited to, silicone, urethane, nitrile, EPDM or any other rubber, elastomer or flexible material.

The shape of the diaphragm is dependent on multiple variables. These variables include, but are not limited to: the shape of the chamber; the size of the chamber; the subject fluid characteristics; the volume of subject fluid pumped per stroke; and the means or mode of attachment of the diaphragm to the housing. The size of the diaphragm is dependent on multiple variables. These variables include, but are not limited to: the shape of the chamber; the size of the chamber; the subject fluid characteristics; the volume of subject fluid pumped per stroke; and the means or mode of attachment of the diaphragm to the housing. Thus, depending on these or other variables, the shape and size of the diaphragm may vary in various embodiments.

The diaphragm may have any thickness. However, in some embodiments, the range of thickness is between 0.002 inches to 0.125 inches (1 inch=2.54 cm). Depending on the material used for the diaphragm, the desired thickness may vary. In one embodiment, high elongation silicone is used in a thickness ranging from 0.015 inches to 0.050 inches. However in other embodiments, the thickness may vary.

In the exemplary embodiment, the diaphragm is pre-formed to include a substantially dome-shape in at least part of the area of the diaphragm. Again, the dimensions of the dome may vary based on some or more of the variables described above. However, in other embodiments, the diaphragm may not include a pre-formed dome shape.

In the exemplary embodiment, the diaphragm dome is formed using liquid injection molding. However, in other embodiments, the dome may be formed by using compression molding. In alternate embodiments, the diaphragm is substantially flat. In other embodiments, the dome size, width or height may vary.

In various embodiments, the diaphragm may be held in place by various means and methods. In one embodiment, the diaphragm is clamped between the portions of the cassette, and in some of these embodiments, the rim of the cassette may include features to grab the diaphragm. In others of this embodiment, the diaphragm is clamped to the cassette using at least one bolt or another device. In another embodiment, the diaphragm is over-molded with a piece of plastic and then the plastic is welded or otherwise attached to the cassette. In another embodiment, the diaphragm is pinched between a mid plate and a bottom plate. Although some embodiments for attachment of the diaphragm to the cassette are described, any method or means for attaching the diaphragm to the cassette may be used. The diaphragm, in one alternate embodiment, is attached directly to one portion of the cassette. In some embodiments, the diaphragm is thicker at the edge, where the diaphragm is pinched by the plates, than in other areas of the diaphragm. In some embodiments, this thicker area is a gasket, in some embodiments an O-ring, ring or any other shaped gasket.

In some embodiments of the gasket, the gasket is contiguous with the diaphragm. However, in other embodiments, the gasket is a separate part of the diaphragm. In some embodiments, the gasket is made from the same material as the diaphragm. However, in other embodiments, the gasket is made of a material different from the diaphragm. In some embodiments, the gasket is formed by over-molding a ring around the diaphragm. The gasket may be any shape ring or seal desired so as to complement the pod pump housing embodiment. In some embodiments, the gasket is a compression type gasket.

Due to the rigid chamber, the pod pump has a generally constant volume. However, within the pod pump, the first and second compartments may have differing volumes depending on the position of the flexible diaphragm dividing the chamber. Forcing fluid into one compartment may thus cause the fluid within the other compartment of the chamber to be expelled. However, the fluids are typically not able to come into direct contact with each other within the pod pump due to the presence of the flexible diaphragm.

Accordingly, in one embodiment, a pod pump used for pumping is constructed to receive a control fluid in a first compartment and a fluid to be pumped in a second compartment. The control fluid may be any fluid, and may be a liquid or a gas. In one embodiment, the control fluid is air. Drawing control fluid away from the pod pump (e.g., through a vacuum, or at least a pressure lower than the pressure within the pod pump) causes the pod pump to draw in fluid (e.g., blood, dialysate, etc.) into the other compartment of the pod pump. Similarly, forcing control fluid into the pod pump (e.g., from a high pressure source) causes the pod pump to expel fluid. By also controlling the valves of the second compartment, fluid may be brought in through a first valve and then expelled through a second valve due to action of the control fluid.

As another example, a pod pump may be used for fluid balancing, e.g., of dialysate as discussed above. In such cases, instead of a control fluid, a fluid may be directed to each compartment of the pod pump. As mentioned, the volume of the pod pump remains generally constant due to the rigid chamber. Accordingly, when a first volume of fluid is drawn into a first compartment of a balancing pod, an equal volume of fluid is expelled from the second compartment of the balancing pod (assuming the fluids to be generally incompressible under conditions in which the pod is operated). Thus, using such balancing pods, equal volumes of fluid can be moved. For instance, in FIG. 5, a balancing pod may allow fresh dialysate to enter a first compartment and used dialysate to enter a second compartment; the volumetric flows of fresh dialysate and used dialysate can be balanced against each other.

In some cases, a pod pump is used that does not contain a flexible diaphragm dividing the chamber. In such instances, the pod pump can be used as a mixing chamber. For instance, mixing chamber 189 in FIG. 7A may be such a pod pump.

Figure 9:
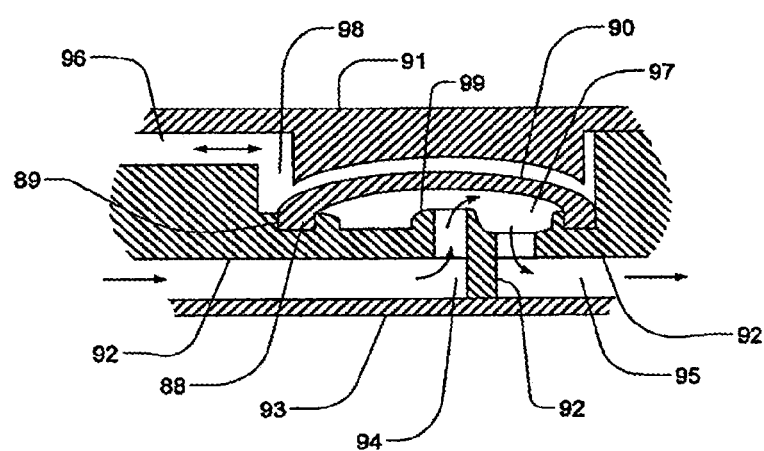
FIG. 9 is a sectional view of a valve that may be incorporated into embodiments of the fluid-control cassettes.

A non-limiting example of a pod pump is shown in FIG. 9. This figure is a sectional view of a pneumatically controlled valve that may be used in embodiments of the cassettes. "Pneumatic," as used herein, means using air or other gas to move a flexible diaphragm or other member. (It should be noted that air is used by way of example only, and in other embodiments, other control fluids, such as nitrogen ($N_2$), $CO_2$, water, an oil, etc. may be used). Three rigid pieces are used, a "top" plate 91, a middle plate 92, and a "bottom" plate. (The terms "top" and "bottom" only refer to the orientation shown in FIG. 9. The valve may be oriented in any direction in actual use.) The top and bottom plates 91, 93 may be flat on both sides, while the middle plate 92 is provided with channels, indentations and holes to define the various fluid paths, chamber and ports. A diaphragm 90, along with the middle plate 92, defines a valving chamber 97. Pneumatic pressure is provided through a pneumatic port 96 to either force, with positive gas pressure, the diaphragm 90 against a valve seat 99 to close the valve, or to draw, with negative gas pressure, the diaphragm away from the valve seat to open the valve. A control gas chamber 98 is defined by the diaphragm 90, the top plate 91, and the middle plate 92. The middle plate 92 has an indentation formed on it, into which the diaphragm 90 is placed so as to form the control gas chamber 98 on one side of the diaphragm and the valving chamber 97 on the other side.

The pneumatic port 96 is defined by a channel formed on the "top" surface of the middle plate 92, along with the top plate 91. By providing fluid communication between several valving chambers in a cassette, valves may be ganged together so that all the valves ganged together may be opened or closed at the same time by a single source of pneumatic pressure. Channels formed on the "bottom" surface of the middle plate 92, along with the bottom plate, define the valve inlet 94 and the valve outlet 95. Holes formed through the middle plate 92 provide communication between the inlet 94 and the valving chamber 97 (through the valve seat 99) and between the valving chamber and the outlet 95.

The diaphragm 90 is provided with a thickened rim 88, which fits tightly in a groove 89 in the middle plate 92. Thus, the diaphragm 90 may be placed in and held by the groove 88 before the top plate 91 is ultrasonically welded to the middle plate 92, so the diaphragm will not interfere with the ultrasonic welding of the two plates together, and so that the diaphragm does not depend on the two plates being ultrasonically welded together in just the right way to be held in place. Thus, this valve may be manufactured easily without relying on ultrasonic welding to be done to very tight tolerances. As shown in FIG. 9, the top plate 91 may include additional material extending into control gas chamber 98 so as to prevent the diaphragm 90 from being urged too much in a direction away from the groove 89, so as to prevent the diaphragm's thickened rim 88 from popping out of the groove 89.

Pressure sensors may be used to monitor pressure in the pods. For instance by alternating applied air pressure to the pneumatic side of the chamber, the diaphragm is cycled back and forth across the total chamber volume. With each cycle, fluid is drawn through the upstream valve of the inlet fluid port when the pneumatics pull a vacuum on the pods. The fluid is then subsequently expelled through the outlet port and the downstream valve when the pneumatics deliver positive pressure to the pods.

Figure 10:
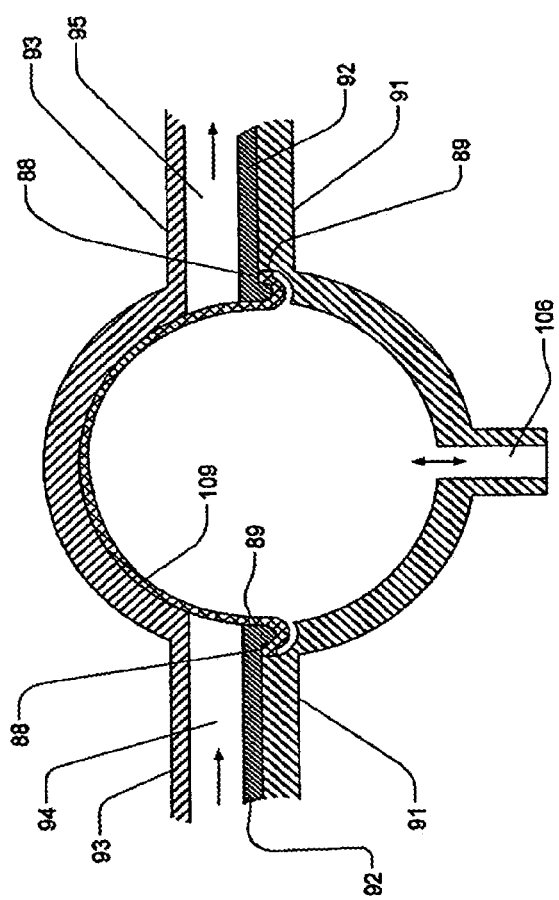
FIG. 10 is a sectional view of a pod-pump that may be incorporated into embodiments of the fluid-control cassettes.

FIG. 10 is a sectional view of one embodiment of a pod pump that may be incorporated into embodiments of the fluid-control cassettes. In some embodiments, the cassette would incorporate several pod pumps and several valves made in accordance with the construction techniques shown in FIGS. 9 and 10. In such embodiments, the pod pump of FIG. 10 is made from different portions of the same three rigid pieces used to make the valve of FIG. 9. These rigid pieces are the "top" plate 91, the middle plate 92, and the "bottom" plate. (As noted above, the terms "top" and "bottom" only refer to the orientation shown in FIG. 9.) To form the pod pump, the top and bottom plates 91, 93 may include generally hemispheroid portions that together define a hemispheroid pod pump.

A diaphragm 109 separates the central cavity of the pod pump into a chamber (the pumping chamber) that receives the fluid to be pumped and another chamber (the actuation chamber) for receiving the control gas that pneumatically actuates the pump. An inlet 94 allows fluid to enter the pumping chamber, and an outlet allows fluid to exit the pumping chamber. The inlet 94 and the outlet 95 may be formed between middle plate 92 and the bottom plate 93. Pneumatic pressure is provided through a pneumatic port 106 to either force, with positive gas pressure, the diaphragm 109 against one wall of pod pump's cavity to minimize the pumping chamber's volume (as shown in FIG. 10), or to draw, with negative gas pressure, the diaphragm towards the other wall of the pod pump's cavity to maximize the pumping chamber's volume.

In some embodiments of the pod pump, various configurations, including grooving on one or more plates exposed to the cavity of the pod pump, are used. Amongst other benefits, grooving can prevent the diaphragm from blocking the inlet or outlet (or both) flow path for fluid or air (or both).

The diaphragm 109 may be provided with a thickened rim 88, which is held tightly in a groove 89 in the middle plate 92. Thus, like in the valving chamber of FIG. 9, the diaphragm 109 may be placed in and held by the groove 89 before the top plate 91 is ultrasonically welded to the middle plate 92, so the diaphragm will not interfere with the ultrasonic welding of the two plates together, and so that the diaphragm does not depend on the two plates being ultrasonically welded together in just the right way to be held in place. Thus, this pod pump can be manufactured easily without relying on ultrasonic welding to be done to very tight tolerances.

Figure 11A:
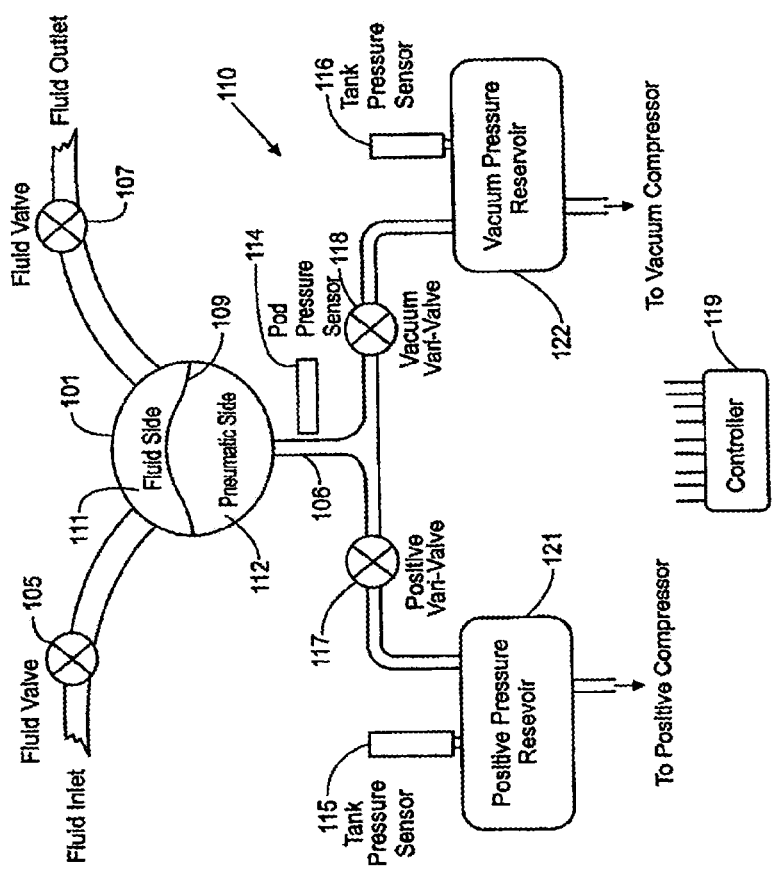

FIG. 11A is a schematic view showing an embodiment of a pressure actuation system 110 for a pod pump, such as that shown in FIG. 10. In this example, air is used as a control fluid (e.g., such that the pump is pneumatically driven). As mentioned, other fluids (e.g., water) may also be used as control fluids in other embodiments.

In FIG. 11A, pressure actuation system 110 alternately provides positive and negative pressurizations to the gas in the actuation chamber 112 of the pod pump 101. The pneumatic actuation system 110 includes an actuation-chamber pressure transducer 114, a variable positive-supply valve 117, a variable negative-supply valve 118, a positive-pressure gas reservoir 121, a negative-pressure gas reservoir 122, a positive-pressure-reservoir pressure transducer 115, a negative-pressure-reservoir pressure transducer 116, as well as an electronic controller 119.

The positive-pressure reservoir 121 provides to the actuation chamber 112 the positive pressurization of a control gas to urge the diaphragm 109 towards a position where the pumping chamber 111 is at its minimum volume (i.e., the position where the diaphragm is against the rigid pumping-chamber wall). The negative-pressure reservoir 122 provides to the actuation chamber 112 the negative pressurization of the control gas to urge the diaphragm 109 in the opposite direction, towards a position where the pumping chamber 111 is at its maximum volume (i.e., the position where the diaphragm is against the rigid actuation-chamber wall).

A valving mechanism is used in this example to control fluid communication between each of these reservoirs 121, 122 and the actuation chamber 112. In FIG. 11A, a separate valve is used for each of the reservoirs; a positive-supply valve 117 controls fluid communication between the positive-pressure reservoir 121 and the actuation chamber 112, and a negative-supply valve 118 controls fluid communication between the negative-pressure reservoir 122 and the actuation chamber 112. These two valves are controlled by an electronic controller 119. (Alternatively, a single three-way valve may be used in lieu of the two separate valves 117, 118.) In some cases, the positive-supply valve 117 and the negative-supply valve 118 are variable-restriction valves, as opposed to binary on-off valves. An advantage of using variable valves is discussed below.

The controller 119 also receives pressure information from the three pressure transducers shown in FIG. 11A: an actuation-chamber pressure transducer 114, a positive-pressure-reservoir pressure transducer 115, and a negative-pressure-reservoir pressure transducer 116. As their names suggest, these transducers respectively measure the pressure in the actuation chamber 112, the positive-pressure reservoir 121, and the negative-pressure reservoir 122. The controller 119 monitors the pressure in the two reservoirs 121, 122 to ensure they are properly pressurized (either positively or negatively). A compressor-type pump or pumps may be used to attain the desired pressures in these reservoirs 121, 122.

In one embodiment, the pressure provided by the positive-pressure reservoir 121 is strong enough, under normal conditions, to urge the diaphragm 109 all the way against the rigid pumping-chamber wall. Similarly, the negative pressure (i.e., the vacuum) provided by the negative-pressure reservoir 122 is preferably strong enough, under normal conditions, to urge the diaphragm all the way against the rigid actuation-chamber wall. In some embodiments, however, these positive and negative pressures provided by the reservoirs 121, 122 are within safe enough limits that even with either the positive-supply valve 117 or the negative-supply valve 118 open all the way the positive or negative pressure applied against the diaphragm 109 is not so strong as to harm the patient.

In one embodiment, the controller 119 monitors the pressure information from the actuation-chamber-pressure transducer 114 and, based on this information, controls the valving mechanism (valves 117, 118) to urge the diaphragm 109 all the way to its minimum-pumping-chamber-volume position and then after this position is reached to pull the diaphragm 109 all the way back to its maximum-pumping-chamber-volume position.

The pressure actuation system (including the actuation-chamber pressure transducer 114, the positive-pressure-reservoir pressure transducer 115, the negative-pressure-reservoir pressure transducer 116, the variable positive-supply valve 117, the variable negative-supply valve 118, the controller 119, the positive-pressure gas reservoir 121, and the negative-pressure gas reservoir 122) is located entirely or mostly outside the insulated volume (item 61 of FIG. 6). The components that come into contact with blood or dialysate (namely, pod pump 101, the inlet valve 105 and the outlet valve 107) may be located, in some cases, in the insulated volume so that they can be more easily disinfected.

Another example of a pressure actuation system 110 for a pod pump is illustrated in FIG. 11B. In this example, pod pump 101 includes a pumping chamber 111, an actuation chamber 112, and a diaphragm 109 separating the two sides. Fluid ports 102 and 104 allow access of fluid in and out of pumping chamber 111, e.g., through the use of fluid valves (not shown). Within pod pump 101, however, fluid ports 102 and 104 include a "volcano" port 126, generally having a raised shape, such that when diaphragm 109 contacts the port, the diaphragm is able to form a tight seal against the port. Also shown in FIG. 11B is a 3-way valve connecting pressure reservoirs 121, 122. The 3-way valve 123 is in fluid communication with actuation chamber 112 by a single port in this example.

It will be appreciated that other types of actuation systems may be used to move the diaphragm back and forth instead of the two-reservoir pneumatic actuation system shown in FIGS. 11A-11B.

As noted above, the positive-supply valve 117 and the negative-supply valve 118 in the pneumatic actuation system 110 of FIG. 11A are preferably variable-restriction valves, as opposed to binary on-off valves. By using variable valves, the pressure applied to the actuation chamber 112 and the diaphragm 109 can be more easily controlled to be just a fraction of the pressure in reservoir 121, 122, instead of applying the full reservoir pressure to the diaphragm. Thus, the same reservoir or set of reservoirs may be used for different pod pumps, even though the pressures for operating the pod pumps may differ from pod pump to pod pump. Of course, the reservoir pressure needs to be greater than the desired pressures to be applied to various pod pump's diaphragms, but one pod pump may be operated at, say, half of the reservoir pressure, and another pod pump may be actuated with the same reservoir but at, say, a quarter of the reservoir pressure. Thus, even though different pod pumps in the dialysis system are designed to operate at different pressures, these pod pumps may all share the same reservoir or set of reservoirs but still be actuated at different pressures, through the use of variable valves. The pressures used in a pod pump may be changed to address conditions that may arise or change during a dialysis procedure. For example, if flow through the system's tubing becomes constricted because the tubes get twisted, one or both of the positive or negative pressures used in the pod pump may be increased in order to over compensate for the increased restriction.

Figure 12:
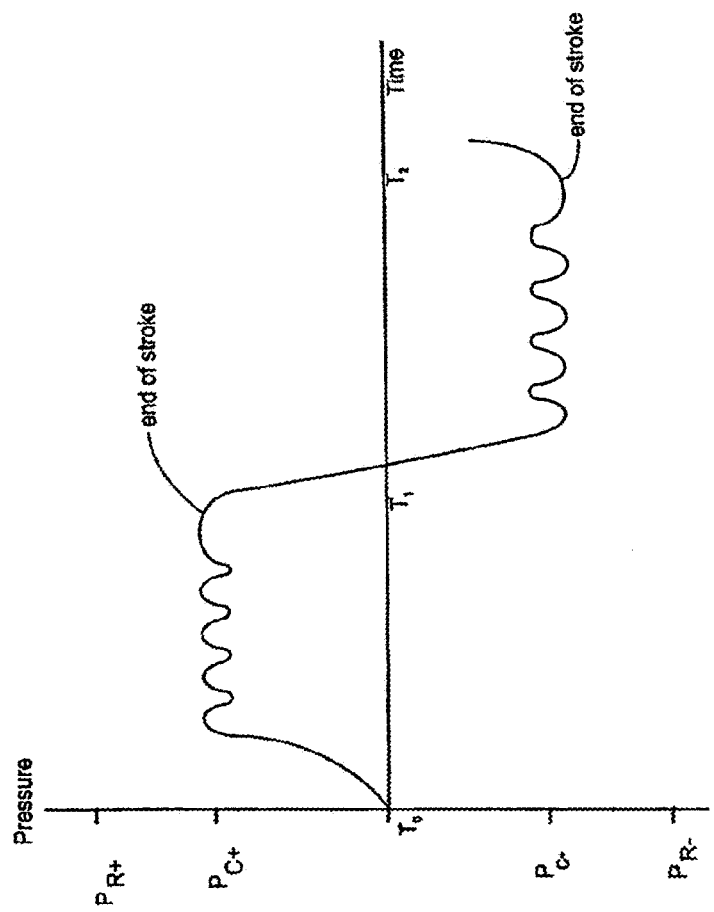
FIG. 12 is a graph showing how pressures applied to a pod pump may be controlled.

FIG. 12 is a graph showing how pressures applied to a pod pump may be controlled using variable valves. The vertical axis represents pressure with $P_{R+}$ and $P_{R-}$ representing respectively the pressures in the positive and negative reservoirs (items 121 and 122 in FIG. 11A), and $P_{C+}$ and $P_{C-}$ representing respectively the positive and negative control pressures acting on the pod pump's diaphragm. As can be seen in FIG. 12, from time $T_0$ to about time $T_1$, a positive pressure is applied to the actuation chamber (so as to force fluid out of the pumping chamber). By repeatedly reducing and increasing the flow restriction caused by the positive variable valve (item 117 in FIG. 11A), the pressure being applied to the actuation chamber can be held at about the desired positive control pressure, $P_{C+}$. The pressure varies, in a sinusoidal manner, around the desired control pressure. An actuation-chamber pressure transducer (item 114 in FIG. 11A) in communication with the actuation chamber measures the pressure in the actuation chamber and passes the pressure-measurement information to the controller (item 119 in FIG. 11A), which in turn controls the variable valve so as to cause the actuation chamber's pressure to vary around the desired control pressure, $P_{C+}$. If there are no fault conditions, the diaphragm is pushed against a rigid wall of the pumping chamber, thereby ending the stroke. The controller determines that the end of stroke has been reached when the pressure measured in the actuation chamber no longer drops off even though the restriction created by the variable valve is reduced. In FIG. 12, the end of the expelling stroke occurs around time $T_1$. When the end of stroke is sensed, the controller causes the variable valve to close completely so that the actuation chamber's pressure does not increase much beyond the desired control pressure, $P_{C+}$.

After the positive variable valve is closed, the negative variable valve (item 118 in FIG. 11A) is partially opened to allow the negative pressure reservoir to draw gas from the actuation chamber, and thus draw fluid into the pumping chamber. As can be seen in FIG. 12, from a time shortly after $T_1$ to about time $T_2$, a negative pressure is applied to the actuation chamber). As with the expelling (positive pressure), stroke described above, repeatedly reducing and increasing the flow restriction caused by the negative variable valve can cause the pressure being applied to the actuation chamber can be held at about the desired negative control pressure, PG (which is weaker than the pressure in the negative pressure reservoir). The pressure varies, in a sinusoidal manner, around the desired control pressure. The actuation-chamber pressure transducer passes pressure-measurement information to the controller, which in turn controls the variable valve so as to cause the actuation chamber's pressure to vary around the desired control pressure, $P_{C-}$. If there are no fault conditions, the diaphragm is pulled against a rigid wall of the actuation chamber, thereby ending the draw (negative pressure) stroke. As described above, the controller determines that the end of stroke has been reached when the partial vacuum measured in the actuation chamber no longer drops off even though the restriction created by the variable valve is reduced. In FIG. 12, the end of the draw stroke occurs around time $T_2$. When the end of stroke is sensed, the controller causes the variable valve to close completely so that the actuation chamber's vacuum does not increase much beyond the desired negative control pressure, $P_{C-}$. Once the draw stroke has ended, the positive variable valve can be partially opened to begin a new expelling stroke with positive pressure.

Thus, each pod pump in this example uses the two variable-orifice valves to throttle the flow from the positive-pressure source and into the negative-pressure. The pressure in the actuation chamber is monitored and a controller uses this pressure measurement to determine the appropriate commands to both valves to achieve the desired pressure in the actuation chamber. Some advantages of this arrangement are that the filling and delivering pressure may be precisely controlled to achieve the desired flow rate while respecting pressure limits, and that the pressure may be varied with a small sinusoidal signature command. This signature may be monitored to determine when the pump reaches the end of a stroke.

Another advantage of using variable valves in this way, instead of binary valves, is that by only partially opening and closing the variable valves the valves are subject to less wear and tear. The repeated "banging" of binary valves all the way opened and all the way closed can reduce the life of the valve.

Figure 13A:
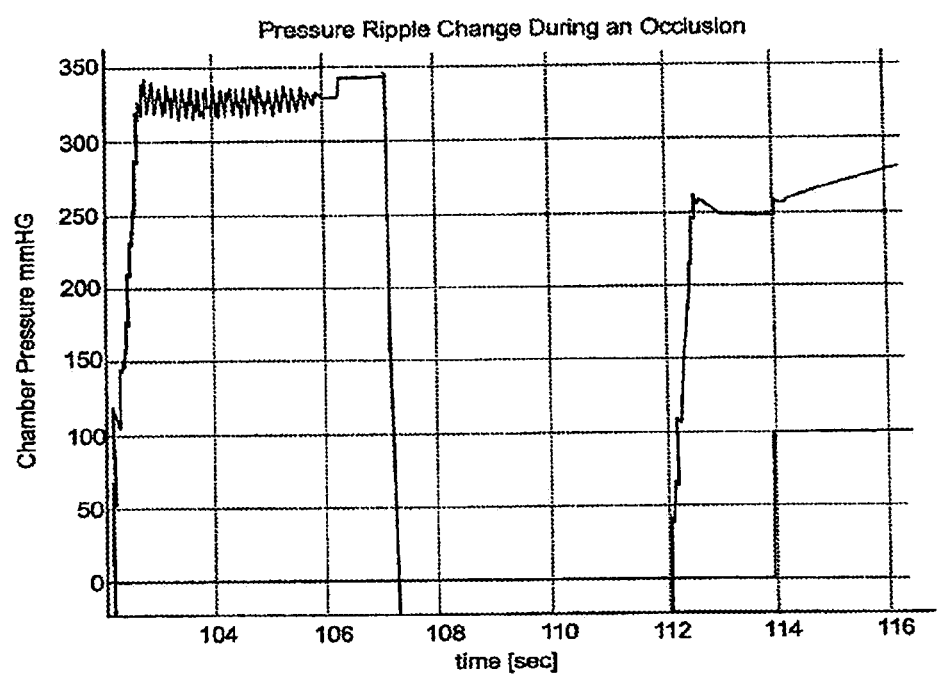
FIGS. 13A-13B are graphical representations of occlusion detection.
Figure 13B:
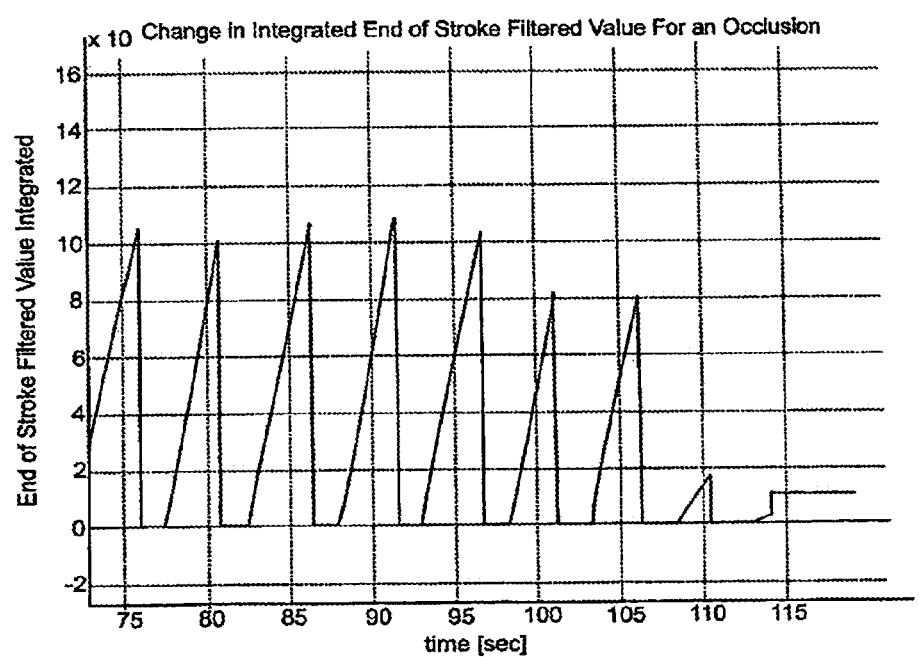

If the end of stroke is detected and the integrated value of the correlation function is very small, this may be an indication that the stroke occluded and did not complete properly. It may be possible to distinguish upstream occlusions from downstream occlusions by looking at whether the occlusion occurred on a fill or a delivery stroke (this may be difficult for occlusions that occur close to the end of a stroke when the diaphragm is near the chamber wall). FIGS. 13A-13B depict occlusion detection (the chamber pressure drops to 0 when an occlusion is detected).

Under normal operation, the integrated value of the correlation function increases as the stroke progresses. If this value remains small or does not increase the stroke is either very short (as in the case of a very low impedance flow or an occlusion) or the actual pressure may not be tracking the desired sinusoidal pressure due to a bad valve or pressure signals. Lack of correlation can be detected and used for error handling in these cases.

Under normal circumstances when the flow controller is running, the control loop will adjust the pressure for any changes in flow rate. If the impedance in the circuit increases dramatically and the pressure limits are saturated before the flow has a chance to reach the target rate, the flow controller will not be capable of adjusting the pressures higher to reach the desired flow rate. These situations may arise if a line is partially occluded, such as when a blood clot has formed in the circuit. Pressure saturation when the flow has not reached the target flow rate can be detected and used in error handling.

If there are problems with the valves or the pneumatics such as a leaking fluid valve or a noisy pressure signal, ripple may continue on the stroke indefinitely and the end of stroke algorithm may not see enough of a change in the pressure ripple to detect end of stroke. For this reason a safety check is added to detect if the time to complete a stroke is excessive. This information can be used for error handling.

In a dual pump, such as pump 13 in FIG. 3A, the two pump chambers may be cycled in opposite directions to affect the pumping cycle. A phase relationship from 0° (both chambers act in the same direction) to 180° (chambers act in opposite directions) can be selected. Phase movement may be modified somewhat in certain cases because it may not be possible to move both chambers in the same direction simultaneously; doing so could have both input or output valves open and end of stroke will not be detected properly.

Selecting a phase relationship of 180° yields continuous flow into and out of the pod. This is the nominal pumping mode when continuous flow is desired. Setting a phase relationship of 0° is useful for single needle flow. The pods will first fill from the needle and then deliver to the same needle. Running at phases between 0 and 180 degrees can be used to achieve a push/pull relationship (hemodiafiltration/ continuous back flush) across the dialyzer. FIGS. 8A-8C are graphical representations of such phase relationships.

The pod pumps may control flow of fluid through the various subsystems. For instance, a sinusoidal pressure waveform may be added to a DC pressure command to make up the commanded pressure signal for the pod pumps. When the diaphragm is moving, the pressure in the pods tracks the sinusoidal command. When the diaphragm comes in contact with the chamber wall and is no longer moving, the pressure in the pod remains constant and does not track the sinusoidal input command. This difference in the pressure signal command following of the pods is used to detect the end of a stroke. From the end of stroke information, the time for each stroke is calculated. Knowing the volume of the pods and the time to complete a stroke, a flow rate for each pod can be determined. The flow rate is fed back in a PI loop in order to calculate the required DC pressure for the next stroke.

The amplitude of the sinusoidal input may be selected such it is large enough for the actual pressure to reasonably track the command and small enough such that when it is subtracted from the minimum DC pump pressure and applied to the pod, the pressure is sufficient to cause the diaphragm to move under expected operating conditions of fluid viscosity, head height and fluid circuit resistance. The frequency of the sinusoidal input was selected empirically such that it is possible to reliably detect end of stroke. The more cycles of the sine wave per stroke, the more accurate the end of stroke detection algorithm.

At the end of a pump stroke, or during an occlusion in the outlet line of a pod pump, the measured pressure deviates from expected pressure. In an embodiment, to detect a deviation in the measured pressure of a pod pump from a commanded pressure, the commanded and measured pressure signals in the pods may be sent through a cross correlation filter. Preferably, the size of the sampling window for the cross correlation filter is equivalent to the period of the input sine wave. For every sample in the window, the commanded pressure signal is multiplied by the previous sample of the actual pressure and added to the previous correlation value. The window is then shifted by one frame and the process is repeated. In an embodiment, the resulting product is then differentiated and passed through a second order filter with a corner frequency the same as the input sine wave frequency and a damping ratio of one. The effect of this filter is to act as a band pass filter, isolating correlated signals at the input sinusoidal frequency. Optionally, the absolute value of the output of this filter may then be passed through a second order low pass filter with the same frequency of the sinusoidal frequency and a damping ratio of, for example, about 3.0. This second filter is used integrate the differentiated signal to and to reduce noise in the resulting signal. If the two signals are correlated, the resulting filtered value will be large. If the two signals are not correlated (for example at end of stroke), the resulting filtered value will be small. The end of stroke can be detected when the filtered cross correlation signal drops below a particular pre-determined threshold, or when the signal drops off a by a percentage of its maximum value throughout the stroke. To tune performance for a particular pumping scenario, this threshold or percent drop can be varied as a function of pressure or flow rate.

Because the end of stroke algorithm typically takes about one cycle of the sinusoidal ripple to detect end of stroke, minimizing this cycle time (maximizing the sine wave frequency) reduces the delay at the end of stroke. Low pressure, high frequency flows are not well tracked by the controller. Lower pressure strokes tend to have lower flow rates and thus the delay at the end of stroke is a lesser percentage of the total stroke time. For this reason, the frequency can be lower for low pressure strokes. The frequency of the sine wave can be adjusted as a linear or other function of the delivery pressures. This ensures minimum delays when the strokes short. When the frequency of the sine wave for the desired pressure is changed, the filters for the cross correlation function should also be adjusted. Filters are set up to continuously calculate the filter coefficients based on this changing frequency.

The pressure in the pod chambers may also be controlled using two variable solenoid valves; one connecting the plenum to a higher pressure source, the second connecting the plenum to a lower pressure (or vacuum) sink. Solenoid valves tend to have a large dead band region, so to compensate a non-linear offset term may be added to the algorithm of the controller.

Phase-Insensitive Cross-Correlation

A system controller 119 (FIG. 11A) can analyze in a number of ways the pressure response to changes in the flow restriction of the valves 117, 118 (such as vari-valves) operating pressure-driven reciprocating pumps 110. One technique is to use a cross-correlation filter that is insensitive to phase shifts in the pressure signal of the pump's actuation chamber 112 relative to the signals controlling the operation of the valves. Applying a phase-insensitive cross-correlation filter to the above pressure and valve signal data generates a set of values that herein will be referred to as the correlation numbers. The correlation numbers are a quantitative measure of the correlation between the pressure measured in the actuation chamber 112 and the periodically varying signal that operates the opening and closing of either the vari-valve 117 that supplies positive pressure to the pump actuation chamber or the vari-valve 118 that supplies negative pressure to the pump actuation chamber.

In an embodiment the signal that operates the vari-valves 117, 118 may be the output of a closed loop controller that varies the valve command signal in order to achieve a desired pressure in the actuation chamber 112. In this embodiment, the desired pressure is varied in a periodic manner and the controller varies the valve command signal to minimize the difference between the desired and measured pressure at each time increment. In this embodiment, the correlation number may be calculated between the desired pressure driving the valve controller and the measured pressure in the actuation chamber.

In an embodiment, the correlation number may be used to provide an estimate of the instantaneous flow rate of the liquid being pumped, as well as a number of other conditions including end-of-stroke, partial occlusions and complete occlusions. The correlation number may be calculated using a number of inputs including, but not limited to, pressure signals received from the pump pressure sensor 114, the amplitude of the electronic signal that operates valves 117, 118 (vari-valves in this example) and the frequency of a time-varying signal (e.g., a ripple wave-form) that is applied to the valve operating signal. In the exemplary embodiment, this correlation number can be used to describe various operating parameters of a pod-pump in hemodialysis machine 6001 (represented in block form in FIG. 61). It may also be used in other systems in which a liquid is pumped in or out of a pressure-driven reciprocating pump having a control or actuating chamber that is subjected to positive or negative fluid pressure (e.g., such as pneumatic pressure) through the operation of a variable valve fluidly connected to a positive and/or negative pressure source.

In one aspect, the correlation number may be considered to be the vector sum of the cross-correlation between the time-varying command signal to the supply valve and the responsive pump pressure signal, and a second cross-correlation between a delayed command signal and the unaltered pressure signal. This mathematical operation yields a correlation number that may be insensitive to the phase angle between the vari-valve signal and the signal associated with pressure changes in the pump actuation chamber. In one embodiment, the cross correlation is calculated for the pressure signal and the valve command signal, in which it has been delayed or shifted by a quarter of a period of the input sine wave.

The principle underlying the calculation of the correlation number is illustrated in FIG. 130. In this example, a vari-valve is used to supply positive or negative pneumatic pressure to a pressure-driven reciprocating pump. The size of the sampling window 12010 for the cross correlation filter is equivalent to the period of the vari-valve signal 12020. The vari-valve signal is preferably a DC signal onto which a sinusoidal wave-form has been superimposed. In other embodiments, other time-varying periodic signals may be applied to a DC signal, such as, for example, a triangular or square wave. The controller can calculate the cross-correlation between the vari-valve command signal and pressure signal by digitally sampling the vari-valve command signal and the pump pressure signal, and multiplying the AC component of the vari-valve signal with the AC component of the measured pressure signal for each sample in the sampling window. The products of the two AC signals for each sample point in the sampling window are then summed.

A second cross-correlation is calculated from the AC signals of the pressure and the vari-valve command signal which has been shifted in time one quarter period or 90 degrees. This second cross correlation is calculated by multiplying the AC component of the shifted vari-valve signal times the AC component of the measured pressure signal for each sample point in the sampling window. The products of the two AC signals for each sample point in the sampling window are then summed.

Next, the amplitude of the vector addition of these two cross-correlations is calculated by taking the square root of the sum of the squares of the first cross-correlation and the squares of the second correlation to yield the correlation number. One benefit of doing a vector addition of the first cross-correlation with the second cross-correlation at a quarter-period shift includes a reduction in the sensitivity of the correlation number to changes in the phase between the pressure and vari-valve signal. Finally, in order to reduce noise, the pressure signal may be passed through a second order filter having a cutoff frequency, which for example, can be equal to the vari-valve frequency.

A correlation angle may be calculated from the first and second cross-correlations by considering the first cross-correlation as a horizontal vector and the second cross-correlation as a vertical vector. The correlation angle is the angle of the summed vector relative to the first cross-correlation. The angle can be considered to be a measure the phase shift of the actuation chamber pressure relative to the valve driving signals.

A controller may be programmed in a number of ways to calculate the correlation number. For example, the AC component of each signal may be calculated by subtracting the average value of the signal from the sampled value. The average value of the vari-valve and pressure signal may be determined from the first several samples before the cross-correlation calculations begin. This method helps to reduce the effects of noise in the pressure signal. In a preferred embodiment the AC component of the vari-valve and pressure signals is determined by taking the derivative of the vari-valve and pressure signals with respect to time. The derivative calculation is relatively flexible and robust. One exemplary implementation of this calculation for the first cross-correlation (A) for the discrete sampled points of the vari-valve and pressure signals is given by Equation 1:

$$A(i) := \sum_{j=i-n}^{i} \left( \frac{V(j) - V(j-1)}{\frac{\tau}{n}} \cdot \frac{P(j) - P(j-1)}{\frac{\tau}{2}} \right) \quad \text{Equation 1}$$

Where V(j) and P(j) are the sampled vari-valve and pressure signals respectively for sample j, V(j−1) and P(j−1) are the vari-valve and pressure signals for the sample before sample j, n is the number of samples in the window and t is the window period. In one example, the width of the window, n, is one period of the input sine wave or imposed periodic valve command fluctuation. The value of the first correlation, A, may be calculated at each time step beginning, for example, 1.25*n time steps after the start of the stroke command, and continues to the end of the stroke command.

The same calculations may be repeated to calculate the second cross-correlation with the vari-valve signal shifted by a quarter period, as shown in Equation 2:

$$B(i) := \sum_{j=i-n}^{i} \left( \frac{V\left(j-\frac{n}{4}\right) - V\left(j-\frac{n}{4}-1\right)}{\frac{\tau}{n}} \cdot \frac{P(j) - P(j-1)}{\frac{\tau}{n}} \right) \quad \text{Equation 2}$$

The value of the second correlation, B, may be calculated at each time step beginning, for example, 1.25*n time steps after the start of the stroke command, and continues to the end of the stroke command.

The raw correlation number may be defined as the square root of the sum of squares of the first and second cross-correlation values, A and B, as shown in Equation 3:

$$\text{Raw}(i) := \sqrt{A(i)^2 + B(i)^2} \quad \text{Equation 3}$$

The correlation number may then be filtered by a $2^{nd}$ order low-pass filter with a cut-off frequency, for example, equal to the frequency of the varying valve signal, as shown in Equation 4.

$$\text{Corr}(i) = \text{Raw}(i-1) + \alpha^*[\text{Raw}(i) - \text{Corr}(i-1)] \quad \text{Equation 4}$$

where $\alpha$ is the smoothing factor $0 < \alpha < 1$.

The correlation angle may be calculated from the first and second cross correlation values as:

$$\theta(i) := \text{atan}\left(\frac{B(i)}{A(i)}\right) - \text{atan}\left(\frac{B(1)}{A(1)}\right) \quad \text{Equation 5}$$

where A(1)B(1) are the initial values of A(i) and B(i). The correlation angle may be considered to be a measurement of the phase shift between the valve command signal and the measured actuation pressure signal. The correlation angle may be indicative of the progress of a stroke or the relative location of the diaphragm 109 within the pumping chamber. One possible theory among others is that the correlation angle 12141 is small when the volume of the actuation chamber 112 is small and may increase with the volume of the actuation chamber 112.

Graphical representations of the first cross-correlation (A) 12138, the second cross-correlation (B) 12139, the phase insensitive cross-correlation 12140 and the phase insensitive cross-correlation angle 12141 are shown in FIG. 133. The cross-correlation results are calculated from the two sinusoidal sets of values 12106, 12116 plotted in FIG. 132. The phase difference between the two sinusoidal sets varies over time in a fashion that may be similar to the change in phase relationship between the vari-valve command signal 12105 (FIG. 134) and the actuation chamber pressure 12115 in a reciprocating positive-displacement pump. One possible theory on the changing phase angle between the vari-valve command signal 12105 and pressure signal is that as the pump chamber 111 fills or empties of liquid, the volume of the actuation chamber gets smaller or larger respectively which changes the responsiveness of the pressure to the valve command.

The phase insensitive cross-correlation 12140 is approximately constant despite changes in the phase angle between the two signals 12106, 12116. The first cross-correlation value 12138 and second cross-correlation value 12139 vary significantly as the phase angle changes between the two signals.

One exemplary use of this phase-insensitive correlation number is shown in FIG. 134, in which pressure data and correlation values are plotted for a deliver and fill stroke for a pressure-driven reciprocating pump using the hardware described in FIG. 11A. The deliver stroke may be initiated by controlling one or both the vari-valves 117, 118 to pressurize the actuation chamber 112 to the desired pressure as measured by the sensor 114. Once the pressure rises to the desired level 12110, the pressure is controlled by only the positive pressure vari-valve 117. The control signal to positive pressure vari-valve 117 may be a function of the vari-valve signals during pressurization and the currently measured pressure. The restriction or opening of the positive pressure vari-valve may be varied sinusoidally 12105 to produce a responsive variation in the measured pressure 12115. In an embodiment, the controller 119 may be programmed to begin the calculation of the correlation number (as described above) after a few cycles in order to allow the signals to stabilize.

A high correlation number 12140 may indicate that the measured pressure is tracking the vari-valve command signal and that the diaphragm is moving. The controller may store the maximum correlation number 12145 during the stroke. The integral of the correlation number over time 12150 may additionally provide a measure of the amount of liquid displaced by the pump 110.

In one exemplary method in a membrane-type pressure-driven reciprocating pump, the physical end of stroke on the deliver stroke may be defined as occurring when the membrane 109 has displaced all or most of the liquid in the pump 101 and has reached the limit of its excursion against the wall of the pump chamber. A designated end of stroke may be defined as a point in time at which the correlation number becomes approximately zero. At the physical end of stroke, the volume of the actuation or control chamber 112 becomes fixed and the pressure within the chamber may stop fluctuating in response to the valve command signal. At the designated end of stroke 12160, the correlation number 12140 drops toward zero within a short time after the pressure signal 12115 loses its periodicity. Although slightly delayed from the physical end of stroke, the designated end of stroke based on the correlation number provides a more reliable indication of the physical end of stroke, because the effects of signal noise and variations due to signal strength are reduced.

The fill stroke follows a similar process as the delivery stroke. The fill stroke begins when one or both vari-valves 117, 118 bring the actuation chamber 112 to a desired low pressure 12102. Once the pressure drops to the desired low pressure, the actuation pressure may be controlled by only the negative pressure vari-valve 118. The control signal to negative pressure vari-valve 118 may be a function of the vari-valve signals during pressurization and the currently measured pressure. The negative pressure vari-valve command signal may be varied sinusoidally to produce a responsive variation in the measured pressure. To improve reliability of the computation, the controller 119 may be programmed to begin the calculation of the correlation number (as described above) after a few cycles. In one exemplary method, in a membrane-type pressure-driven reciprocating pump, the physical end of stroke on the fill stroke may defined as occurring when the pump chamber is full of liquid and the membrane 109 has reached the limit of its excursion against the wall of the actuation chamber. A designated end of stroke may be defined as a point in time at which the correlation number becomes approximately zero. At the physical end of stroke, the volume of the actuation chamber 112 becomes fixed at near zero and the pressure within the chamber stops fluctuating in response to the valve command signal. At the designated end of stroke

12165, the correlation number 12140 will drop toward zero within a short time as the pressure signal loses its periodicity.

The dialyzer is permeable to pressure waves generated by the inner dialysate pumps and the blood pumps. The cross-correlation procedure tends to reject pressure signals in the dialysate pump, for example, that are at a sufficiently different frequency from the vari-valve command signal. The correlation number calculations for the inner dialysate pumps and blood pumps may therefore be isolated from one another by programming the controller to vary the vari-valve command signals of the dialysate and blood pumps at different frequencies.

The controller 119 may declare an end-of-stroke 12160, 12165 when the correlation number 12140 drops below a pre-determined fraction of the maximum correlation number 12145. In another exemplary implementation, the controller may declare an end-of-stroke 12160,12165 when the correlation number 12140 drops below a pre-determined fraction of the maximum correlation number 12145 and is not increasing with time. In other embodiments, the designated end of stroke may be declared when the correlation number 12140 drops below a pre-determined fraction of the average correlation number during a pre-determined interval of time during the pump stroke (with or without the further condition that the value is no longer increasing over a pre-determined period of time). In another exemplary implementation, the controller may declare an end-of-stroke 12160 when the correlation number 12140 drops below a pre-determined threshold value. In another exemplary implementation, the controller may declare an end-of-stroke 12160 when the correlation number 12140 drops below a pre-determined threshold value and is not increasing with time.

The instantaneous flow rate out of the pump may be determined from the correlation number during most of the pump stroke. The flow rate may be proportional to correlation number. FIG. 131 shows three exemplary pressure traces 12050, 12052, 12054 in the actuation chamber 112 in response to the sinusoidally varied restriction 12020 in valve 117. The pressure responses, 12050, 12052, 12054 in the actuation chamber 112 tend to track the varied restriction of the vari-valves 117, 118 when the actuation chamber volume is changing as the membrane 109 moves. Pressure trace 12050 is an example of the pressure response if flow from the liquid side of the chamber 111 stops during a delivery stroke. If the flow stops, the volume of the actuation chamber 112 becomes constant and the chamber fills until the pressure 12050 reaches the reservoir pressure 12051. If the volume of the actuation chamber 112 is constant, changes in the restriction of the inlet valve 117 can only change the rate of pressure increase. Pressure trace 12054 is an example of the pressure response when liquid flow from the pump is relatively unrestricted, in which the membrane may be moving quickly and the actuation chamber volume may be quickly increasing, so restricting the flow of air significantly reduces the pressure 12054 in the chamber 112. Pressure trace 12052 is an example of low flow, where the pressure 12052 in the chamber changes only slightly as the valve restriction 12020 varies. The correlation numbers are proportional to the amplitude of pressure waveforms for a given amplitude of vari-valve restriction. High amplitude pressure waves may indicate fast membrane movement and high flow rates of liquid into or out of the pump. Thus high correlation numbers may be proportional to flow rates. The benefits of this method of measuring the instantaneous flow include improved reliability of therapies, improved accuracy in the therapies, better flow control and lower cost instrumentation.

In another exemplary implementation, the controller may declare an end of stroke when the correlation value 12141 is undefined. The controller may calculate the progress of the stroked from the value of the correlation angle. The instantaneous flow rate may be calculated from the rate of change of the correlation angle 12141.

An occlusion is considered to be present when the liquid flow from or to a pump chamber is restricted. As shown in FIG. 135, partial and full occlusions may be detected based on the correlation number as calculated above. A partial occlusion may produce low correlation numbers and a low integrated correlation number. The controller 119 may compensate for the partial occlusion by commanding more pump strokes or increasing the maximum applied pressure. A full occlusion may resemble an end-of-stroke and produce similar responses in the correlation number, integrated correlation number and correlation angle. In an embodiment, the controller may monitor for occlusion detection by tracking the stroke-to-stroke correlation and integrated correlation numbers. A full occlusion may be declared, for example, if any of the maximum correlation number 12145, integrated correlation number 12150 or the absolute value of the correlation angle at end of stroke are reduced by a pre-determined amount from the previous full stroke values (such as, for example, a reduction to less than about 70% of the previous full stroke values). In another aspect, a full occlusion may be declared when the maximum correlation number, integrated correlation number, or the absolute value of the correlation angle at end of stroke are less than 90% of the full stroke values for 3 sequential strokes. The full stroke maximum correlation number, integrated correlation number, or the absolute value of the correlation angle at end of stroke may be taken from the most recent full stroke. In another aspect, a full occlusion may be declared if the maximum correlation number, integrated correlation number, or the absolute value of the correlation angle at end of stroke are less than a pre-determined minimum value for at least 2 strokes. This last test may be used, for example, to detect chambers that are occluded from the start, rendering stroke-to-stroke comparisons difficult at best.

Blood Flow Metric

In another aspect, the controller may determine a numerical value that represents the quality, adequacy or sufficiency of blood flow generated in the blood circuit of an extracorporeal blood flow system. This may be related to the responsiveness of the blood pump diaphragm in moving toward the control chamber wall during a fill-stroke of the blood pump. A hemodialysis system is an example of an extracorporeal blood flow system that may benefit from this feature. Determining the adequacy of filling of the blood pump during hemodialysis may be useful, in that the pressure on the blood side of the dialyzer may be affected by slow or inadequate blood delivery by the blood pump due to slow or inadequate filling of the blood pump. Blood pressure in the dialyzer should preferably be kept at a level sufficient to permit the dialysate pump connected to the dialysate outlet of the dialyzer to fill completely, or at least sufficiently to permit the dialysate flow balancing circuit to operate in a volumetrically balanced manner. Thus, it is advantageous for the system controller to be able to determine a blood flow value or metric associated with the blood circuit that can be compared to a pre-determined value or metric (derived, for example, from nominal operations), so that the dialysate pump operation may be adjusted, paused or stopped, either temporarily or otherwise, until sufficient blood flow and/or blood pressure in the dialyzer can be assured.

A blood flow metric may vary from one blood pump stroke to another, or even within the duration of a blood pump fill-stroke. In an embodiment, the controller is able to determine a blood flow metric in a continuous or periodic manner during a single blood pump fill-stroke. This may be useful during a hemodialysis therapy, because a user may have the opportunity to make adjustments to improve blood flow in the blood circuit before the controller issues a command to pause or stop dialysate pump operations. For example, a poor blood flow condition (generating a substandard blood flow metric) may arise at the vascular access site (e.g., clot formation in a fistula, lodging of a cannula orifice against a vessel or fistula wall, etc.), or it may arise in the blood tubing leading to or from the vascular access (e.g., bending or kinking of the blood tubing). In an embodiment, the controller may allow the blood pump to continue to operate to allow a user enough time to correct a poor blood flow condition. In one example, real time tracking or monitoring of a blood flow metric by the controller allows it to alert the user before a threshold value is reached that would otherwise initiate a suspension of the dialysate pump. In another example, the controller may allow a sub-standard blood flow metric to exist for two or more pump strokes, during which the user is alerted to the condition and is provided enough time to correct it. In one preferred embodiment, the controller defers adjustment or suspension of the dialysate pump until a sub-standard blood flow metric has persisted for three consecutive blood pump strokes.

A blood flow metric may be determined from the responsiveness of the blood pump diaphragm to a pressure signal generated by a system controller. Preferably, the blood flow metric is determined during a fill-stroke of the blood pump, during which a time-varying pressure waveform is applied during movement of the diaphragm toward the pump control chamber.

Thus, in a system for controlling the flow of fluid from a dialyzer, with a dialysate pump receiving fluid from the dialysate outlet, the blood pump receiving blood from the blood circuit for delivery to the dialyzer, a pressure sensor located in the control chamber of the blood pump, and a controller monitoring the pressure and controlling the application of pressure to the blood pump diaphragm, the controller may be configured to apply a time-varying pressure waveform to the diaphragm during a fill-stroke, and monitor the pressure response in the control chamber measured by the pressure sensor. If the magnitude of the measured pressure variation deviates from a pre-determined threshold value, the controller may initiate a procedure to adjust, pause or stop one or more dialysate pumps connected to a dialysate outlet of the dialyzer.

In an example system, as outlined in FIG. 11A, a pressure actuation system 110 alternately provides positive and negative pneumatic pressure to an actuation chamber 112 of a reciprocating diaphragm pump 101. In this example, the system 110 may include an actuation-chamber pressure transducer 114, a variable positive-supply valve 117, a variable negative-supply valve 118, a positive-pressure gas reservoir 121, a negative-pressure gas reservoir 122, a positive-pressure-reservoir pressure transducer 115, a negative-pressure-reservoir pressure transducer 116, as well as an electronic controller 119.

The positive-pressure reservoir 121 provides a source of positive pneumatic pressure for the control or actuation chamber 112 to urge the diaphragm 109 toward an opposing wall of the pumping chamber 111 to execute a fluid delivery-stroke. The negative-pressure reservoir 122 provides a source of negative pressure or vacuum for the control or actuation chamber 112 to urge the diaphragm 109 in a direction toward an opposing wall of the actuation chamber 112 to execute a fluid fill-stroke. A fluid inlet valve 106 of the pump is opened during a fill-stroke, while a fluid outlet valve 107 is closed. In a blood pump, the fluid for the fill-stroke originates from a vascular access of a patient via an arterial blood line connected to the fluid inlet of the pump. If the volume of blood available to the pump is limited by, for example, a narrowing of the blood line, a partially clotted vascular access, a partial occlusion of an orifice of a vascular cannula, etc., then the mechanical response of the diaphragm 109 to the application of negative pressure in the control chamber 112 may be impaired.

In an embodiment, the controller 119 monitors the pressure information from the actuation-chamber-pressure transducer 114 and, based on this information, can control the valving mechanism (valves 117, 118) to urge the diaphragm 109 all the way to its minimum-pumping-chamber-volume position and then after this position is reached to pull the diaphragm 109 all the way back to its maximum-pumping-chamber-volume position. The controller 119 can vary the control pressure in the actuation chamber 112 to produce a desired flow rate. In a further embodiment, the controller 119 may impose a time-varying or periodic control signal to the control valves 117, 118 (e.g., by electromechanical variation of the valve orifice) to produce a pressure that oscillates about the desired control pressure as shown in FIG. 12. If the diaphragm 109 fails to move toward the control chamber in an expected manner during a pressure signaling imposed by the controller during a fill-stroke, a measured pressure or pressure variation in the pump control chamber may deviate from an expected value or pressure variation, which is detectable by the controller 119.

Referring now to FIG. 156, a pressure tracing from a pump control chamber is shown in which the valve control signal 13100 oscillates about a negative pressure during a fill stroke when the actuation chamber is connected to the negative pressure reservoir via a control valve. The control signal 13100 is plotted as a desired, expected or nominal pressure in units of mmHg. The resulting measured actuation chamber pressure 13110 initially follows the control signal 13100 poorly as can be seen at 27 seconds. As the stroke progresses the measured chamber pressure 13110 follows the control signal more and more tightly until the end of the stroke at approximately 37 seconds.

A flow metric representing the quality, adequacy or availability of blood flow during a blood pump fill-stroke can be calculated by the controller by monitoring the measured actuation chamber pressure 13110. For example, the flow metric may be based on the peak-to-peak magnitude of the measured pressure 13110, and its variation during the course of a fill-stroke. In another embodiment, the measured peak-to-peak measured pressure variation may be normalized to an expected or desired peak-to-peak pressure variation, or one that has been obtained as a baseline during normal or full flow conditions. These values may be filtered by a low pass filter or smoothed using a sliding averaging window over the course of the fill-stroke to reduce signal noise.

In an embodiment, the flow metric is calculated from the cross-correlation of the control signal 13100 and the measured pressure 13110. In a preferred embodiment, the flow metric is based on the magnitude of the phase insensitive cross correlation number, which is calculated by the vector sum of a first cross-correlation of the control signal 13100 and the measured pressure 13110 and a second cross-correlation of the control signal phase shifted by 90° and the measured pressure 13110. These calculations are described in detail above. A correlation number 13120 can be derived from the low-pass filtered value of the magnitude of the phase insensitive cross-correlation. In the example illustrated by FIG. 156, the correlation number is initially zero until the measured pressure 13110 begins to track the control signal 13100 at about 27 seconds. The correlation number quickly rises to approximately 165 and then decays to approximately 135 at 29 seconds before rising steadily to a peak of 265 at 36 seconds before dropping to zero at the end of stroke at 37 seconds. In one embodiment the controller may set the flow metric equal to the correlation number while the diaphragm is moving and then hold at a value reached before an end-of-stroke occurs or is detected.

In another embodiment, as shown in FIG. 156, a flow metric 13130 may be set at the maximum average correlation number during a single pump stroke. The flow metric or maximum average correlation number may be calculated after waiting for an initial delay period after the correlation number first begins to increase. The delay period may include a first period allowing the correlation values to stabilize and a second period during which the correlation numbers are averaged. The initial value of the flow metric may be set to the average value during the second period of time during the pump stroke. In the example shown in FIG. 156, the flow metric 13130 is calculated after an initial period at the beginning of a pump stroke, and during a second period 13125 of about one second to set the initial flow metric value 13130. The controller may be programmed to calculate the average of the next second's worth of correlation numbers and updates the flow metric to the new average if the new average is higher than the current flow metric value. As shown in FIG. 156, the correlation number may drop initially, but the controller will keep the flow metric constant at its previous higher value, until correlation number 13120 begins to exceed the flow metric 13130 at about 33 seconds. The flow metric 13130 continues to increase in a stepwise fashion 131308 until about 36 seconds when the correlation number starts to drop. The flow metric 13130 is held constant at this maximum value until the first average of correlations numbers is calculated in the next stroke at 13130A (while excluding start-up transients 13105 at the beginning of the next fill-stroke). In the example shown, a two-pump system allows the controller to accumulate data from the next fill-stroke by analyzing the pressure data from a complementary pump of the two-pump system (as the first pump delivers, the second pump fills). In a one-pump system, the controller would wait until the next fill-stroke of the single pump to continue to analyze the fill-stroke pressure data.

The controller may be programmed to pause or stop the inner and/or outer dialysate pumps of the hemodialysis system if the calculated flow metric drops below a specified or pre-determined value. Such a value can be obtained, for example, by determining flow metric values during various pumping conditions in which the available blood flow from the blood line is varied in a controlled fashion. During some of these flow conditions, the blood flow or blood pressure in the dialyzer will be affected to the point of reducing the ability of a dialysate pump (e.g. an inner dialysate pump) to fill sufficiently to deliver a full stroke volume of dialysate. If this situation is allowed to persist, then dialysate flow balancing via the dialysate balancing circuit may be adversely affected. The flow metric associated with this condition can thus be used as a threshold value at which the controller may be programmed to pause or stop the dialysate pump(s) until the flow metric exceeds the threshold value.

In an embodiment, the controller may be programmed to provide a user of an extracorporeal or hemodialysis system an indication of the flow metric during the course of each pump fill-stroke. For example, a flow metric value may be transmitted to a graphical user interface, providing the user with an ongoing indication of the quality or adequacy of blood flow in the blood line during therapy. A user interface (such as, e.g. an electronic tablet) may provide the user with raw flow metric data. In another embodiment, the flow metric may be proportionally scaled to a range of 1 to 5, with the value '5' representing, for example, excellent flow, a value '3' representing adequate flow, and a value '1' poor flow. Thus a specified range of flow metric values may be mapped into each of a set value of '1' to '5,' simplifying a user's interpretation of the adequacy of blood flow in the blood line. In other embodiments, the flow metric may be displayed to the user graphically, such as a moving or expanding bar graph, a dial gauge, or a set of colored lights, for example.

In a preferred embodiment, a marginal or sub-optimal flow metric may cause the controller to alert the user, so that the user may attempt to improve blood flow in the blood line (e.g., reposition the line, straighten out the line, adjust the vascular access cannula, etc.). The controller may be programmed initiate a procedure to pause or stop the dialysate pump that includes signaling the user and providing sufficient passage of time before the pausing or stopping of a dialysate pump to allow the user to correct the condition. In an embodiment, the user may be alerted to the low-flow condition during a fill-stroke, so that a timely adjustment by the user allows the flow metric to be restored to an acceptable value before the end of the fill-stroke. In other embodiments, the controller may be programmed to require sub-optimal flow metric values for two or three (or more) consecutive fill-strokes before commanding the dialysate pump to stop. Thus a timely correction of the low-flow condition by the user may forestall the interruption of dialysate pumping operations, and possibly interruption of therapy. In an example, the controller may be programmed to pause or stop the dialysate pump if the flow metric remains below 150 for three consecutive fill-strokes, and may be programmed not to restart the dialysate pump until the flow metric exceeds 200 for five consecutive blood pump strokes. In some of these embodiments, the controller allows the blood pump to continue to operate while the dialysate pump has been suspended, so that the user has an opportunity to restore a blood flow condition that allows the dialysate pump to be restarted, thus avoiding early termination of therapy.

FIGS. 157A and 157B illustrate an example of the operation of a controller in evaluating and acting on flow metrics during a pumping operation. Shown is a plot of a flow metric 13210, blood pump flow 13230 and inner dialysate pump flow 13220 during a study in which the blood line was progressively obstructed with a clamp. In this example, the flow restriction was made to occur over many pump strokes, taking approximately an hour or more before the controller triggered a signal to stop the dialysate pumps. Shown in FIG. 157B is a time period during which the dialysate pumps were stopped. The flow metric 13210 steadily decreases from a value of over 300 at a time of about 22500 seconds (FIG. 157A) to less than 150 at time 25900 seconds (FIG. 157B). The blood pump flow 13230 and inner dialysate pump flow 13220 decrease during this time period. (The inner dialysate pump periodically stops completely during this period for pump control requirements unrelated to flow metric control). In FIG. 157B, at approximately 25900 seconds, the peak flow metric value dropped below 150 for 2 out of 3 strokes. In this example, this condition is sufficient to cause the controller at time marker 13240 (approx. time 25970 seconds) to stop the inner and outer dialysate pumps. The clamp on the blood line was removed at time marker 13242 (approximately 26400 seconds), and the flow metric quickly improved to ~400. The controller restarted the inner dialysate pumps at time marker 13244 (approximately 26500 seconds), with the dialysate flow rate subsequently returning to 400 ml/min.

Vari-Valve Calibration

The vari-valves may be calibrated to determine the minimum electrical current required to open the valve for a given pressure difference across the valve. The minimum current may be referred to as the cracking current. In some embodiments, the cracking current may vary linearly with the pressure difference between the actuation chamber 112 and the reservoir 121, 122. A mathematical relationship between the measured pump actuation chamber pressure 114 and the cracking current may be established through a calibration procedure. One example of a calibration procedure uses one or both vari-valves 117, 118 to establish a pre-determined back pressure in actuation chamber 112. After both valves are closed, the current to one valve is increased as the pressure in the actuation chamber is measured by the pressure sensor 114. The cracking current is the measured current when the measured pressure is found to increase as the current delivered to the valve gradually increases. The cracking current may be determined for two or more pre-determined back pressures and the controller may use this data to fit an equation that relates the cracking current of the valve to the existing back pressure in the pump actuation chamber. In an embodiment of the pump and valve system, the equation may be a linear equation.

In one aspect of the calibration procedure, the controller determines the cracking current at 4 initial back pressure values in the pump actuation chamber for each vari-valve associated with the pump. This determination may be repeated several times (e.g., 3 times, for a total of twelve measurements). The controller may be programmed to ignore outlier current values and to develop a linear equation of cracking current as a function of initial back pressure using the remaining data.

Mitigation of Fluid Imbalance Due to Gas Bubbles in the Dialysate

The outgassing of air or other gas from either fresh or used dialysate may cause a cumulative imbalance between the fresh dialysate volume pushed through the dialyzer by the balance chamber and the used dialysate volume in the balance chamber used to push the fresh dialysate. For example, if a gas bubble fails to be expelled from a passageway on the used dialysate side of the balance chamber, its alternating expansion and contraction may cause an additional amount of used dialysate to be expelled from the balance chamber that is unaccounted for by the fresh dialysate that is being pushed to the dialyzer. As the inner dialysate pump pushes used dialysate into the balance chamber, and as an equivalent volume of fresh dialysate is being pushed to the dialyzer, the gas bubble becomes compressed under the pressure of the pump. However, at the end of the pump stroke, as pressure within the balance chamber decreases, the gas bubble may expand, causing an additional small amount of used dialysate to be expelled from the balance chamber outlet. This small additional amount of used dialysate being expelled from the used dialysate side of the balance chamber cumulatively over many pump strokes may result in a significant imbalance between the fresh dialysate being pushed into the dialyzer and the fresh dialysate being expelled to drain. In an embodiment, this potential fluid imbalance may be mitigated by ensuring that gas bubble expansion at the end of an inner dialysate pump stroke pushes dialysate back toward the pump chamber, rather than toward the drain line. The procedure to mitigate this unaccounted fluid flow may be illustrated by considering a delivery stroke from pump 162 to balancing chamber 342 in FIG. 5. At the end of a pump stroke to fill balance chamber 342 with dialysate from pump 162, outlet (drain) valve 222 is closed. The balancing chamber 342 may then be fluid locked by closing valves 231, 221 while keeping delivery pump outlet valve 213 open. Next, the controller may release the pneumatic pressure on the delivery pump 162, which allows any gas bubbles in the fluid path to the balance chamber to expand. Any liquid displaced by the gas bubble expansion will be free to move back toward pump 162 rather than to drain. Finally, the controller may close the outlet valve 213 on the delivery pump, and open valve 222 to prepare for expulsion of the dialysate in balance chamber 342 to drain. This same procedure may be applied to pump 161 and balancing pump 341. In addition a similar procedure may be used on the fresh dialysate side of the balance chambers 341, 342. In that case, the controller may release the pressure in the outer dialysate pump at the end of its pump stroke to fill one of the balance chambers, while the valve between the outer dialysate pump and the balance chamber is still open. Any expanding gas bubble in the fluid path between the outer dialysate pump and the balance chamber will tend to displace dialysate back toward the pump, rather than downstream toward the dialyzer.

Short Strokes on Blood Pumps

The pod pumps 180 (FIG. 3A) in the blood cassette may execute shortened strokes to reduce damage to blood elements. Damage to blood elements may be reduced by stopping the membrane in a pod pump from fully touching the wall of the pumping chamber at the end of a pumping stroke. The blood pump may be short-stroked while a system controller monitors blood flow rate and monitors for occlusions. At the start of pumping, full strokes are performed in order to achieve steady state flow and determine parameters that are used to control short-stroking, including the required delivery pressure, required fill pressure and time to fill the pumping chamber. The flow rate may be determined from the time required to deliver a full chamber of fluid. Steady state flow conditions may be indicated by a) the average flow changing less than about 3 ml/min, b) the maximum pump flow rate is within about 15 ml/min of the target for both the fill and deliver pressures and c) the average chamber delivery flow rate is within about 10% of the pump flow rate at the minimum actuation pressure.

The blood pump may be short-stroked by having the controller reduce the delivery stroke to a pre-determined fraction (e.g, about 80%) of the delivery pressure determined during the steady state phase. The reduced pressure may cause the delivery stroke to be, for example, approximately 90% complete by the time the pump diaphragm turns around and the nearly empty chamber begins the pump fill stroke. The pump diaphragm turns around when the chamber executing the fill stroke reaches end of stroke. The fill stroke occurs at pressure that was determined by the controller during the steady state phase. The nature of the short stroke may be monitored by examining the maximum and integrated correlation number and time to end-of-stroke of the same chamber during the subsequent fill stroke. The controller 119 (FIG. 11*a*) may monitor the time to fill the pump using the end-of-stroke detection algorithm described above. The controller 119 may adjust the deliver pressure in the actuation chamber 112 so that the time to fill the chamber is 90% of the fill time that was determined during the steady state phase. Alternatively, the integrated correlation value may be monitored, and the end of fill is deemed to be, for example, 90% of the integrated correlation number corresponding to a complete end-of-stroke cycle.

The blood pump 101 and controller 119 may detect full occlusions either upstream or downstream of the pump during short-stroking using the correlation number during the fill stroke. A full occlusion downstream will result in more blood left in the chamber, which will shorten the fill time. The end-of-stroke may be detected by a large drop in the correlation number. The short fill time may be detected by a low integrated correlation number. Similarly, an occlusion upstream of the pump will produce a large drop in correlation number and a lower integrated correlation number.

The short stroking scheme assumes the delivery impedance is constant. However changes in flow resistance across the dialyzer 14 or blood lines or changes in the patient's access may cause the blood pump to do full strokes. This problem may be mitigated by relearning the required delivery pressure, fill pressure and fill time by returning to full strokes every 100 strokes. If the delivery and fill impedance have not changed, the check may not require more than 8 full strokes. In order to limit hemolysis, the controller 112 may end the therapy if an excessive number or percentage of the blood pump strokes are full strokes. In one example, the controller 112 will end therapy if more than 200 full strokes to occur or if 20% of the strokes after the initial steady state phase are full strokes.

EOS, Occlusion and Back Pressure Detection with PWM Valve

A positive or negative pressure source connected to the activation chamber of a pod pump via a pulsed valve and a pressure sensor coupled to the activation chamber of a pod pump may be used to determine pump operating parameters including the end-of-stroke, occlusions and fluid pressures upstream and downstream of the pump. One exemplary configuration is shown in FIG. 136. The binary valve 12260 may supply positive pressure via the FMS valve 12240 to the actuation chamber 12214 of the pod pump 12212 to order deliver fluid from pump through valve 12220. The FMS valve 12240 may rapidly open and close to incrementally increase the pressure in the actuation chamber 12214. A closely coupled pressure sensor 12230 may measure the pneumatic pressure in the chamber 12214 and transmits the pressure to a controller 12270. The FMS volume 12242 and FMS Pressure sensor 12244 may be present, but are not used to in this embodiment.

The controller may control the opening and closing of the FMS valve 12240 and record the pressure sensor 12230 data in order to produce the time history of the valve operation 12310 and the resulting pressure 12315 in the actuation chamber shown in FIG. 137. The valve may be pulsed in a periodic fashion with the frequency, duration of the open period and duration of the closed period controlled by the controller 12270. The duty frequency may be selected heuristically. The frequency may be low enough to differentiate between membrane movement and system compliance. The frequency may be selected to be low enough to allow fluid to be displace, but high enough to meet the maximum required flow rates.

The response of the membrane 12215 and flow from the pump 12212 may be analytically monitored by summing the pressure decrease during each pump step (FIG. 138). When the FMS valve 12240 is closed, the controller may calculate the change in pressure between each time step or sample and sums the differences over one closed valve period:

$$\Delta P_{CH} = \Sigma (P_i - P_{i-1})$$

The pressure data may be filtered to reject signal noise. The chamber pressure may be filtered with a low pass filter before calculating the pressure change. A positive pressure change may be rejected from the sum. The pressure summation 12320 may be reset to zero 12321 when the FMS valve 12240 opens. The controller 12270 may detect flow of fluid from the pump when the absolute value of the sum of pressure change 12320 exceeds a defined value 12325. The controller may detect an end of stroke on the first summation 12320 that does not meet the defined value 12325 after a summation that does exceed the defined value. The controller may command the FMS valve 12240 to be held open to assure that all fluid is expelled from the pod pump 12212. The FMS valve 12240 is held open to improve stroke to stroke repeatability, which in turn increases flow rate accuracy.

The hardware configuration in FIG. 138 and the pressure data in FIGS. 137 and 138 may provide information on the fluid pressure downstream of the pod pump. The fluid will not flow out of the pod pump until the pneumatic pressure in the actuation chamber 12214 is greater than the fluid pressure downstream of the pump 12212 and valve 12220. The controller 12270 may detect flow of fluid and movement of the membrane when the absolute value of the sum of the pressure change 12320 exceeds a defined value 12325 as occurs in step 12317. The controller may store the average the pressure 12315 during this step 12317 as the downstream pressure. Alternatively, the pressure at the end of step 12317 before the FMS valve is reopened may be stored as the downstream pressure.

Full occlusions downstream of the pod pump 12212 may determined with the hardware configuration in FIG. 136 and the pressure plots in FIGS. 137, 138. An occlusion downstream of the pump 12212 may be declared by the controller 12270 when no fluid flow or membrane movement is detected as the pressure in the actuation pressure is increased to the maximum pressure 12312. The controller determines that the fluid has not flowed, when the pressure summation 12320 does not exceed the given value 12325.

The hardware configuration in FIG. 138 and the pressure data in FIG. 139 may provide information on the fluid pressure upstream of the pod pump during a fill stroke. A fill stroke may begin by opening the binary valve 12250 to supply negative pressure via the FMS valve 12240 to the actuation chamber 12214 of the pod pump 12212 to order to draw fluid into the pump through valve 12210. The FMS valve 12240 may rapidly open and close to incrementally decrease the pressure in the actuation chamber 12214. A closely coupled pressure sensor 12230 may measure the pneumatic pressure in the chamber 12214 and transmits the pressure to a controller 12270. The controller may control the opening and closing of the FMS valve 12240 and record the pressure sensor 12230 data in order to produce the time history of the valve operation and the resulting pressure 12315 in the actuation chamber shown in FIG. 139.

Fluid will not flow into the pod pump until the pneumatic pressure in the actuation chamber 12214 is less than the fluid pressure upstream of the pump 12212 and valve 12210. The controller 12270 may detect flow of fluid and movement of the membrane when the sum of the pressure change 12320 exceeds a defined value 12328 as occurs in step 12327. The controller may store the average the pressure 12315 during the step 12327 as the upstream pressure. Alternatively, the pressure at the end of step 12327 before the FMS is valve is reopened may be stored as the downstream pressure.

Full occlusions up stream of the pod pump 12212 may determined with the hardware configuration in FIG. 136 and the pressure plot in FIG. 139. An occlusion upstream of the pump 12212 may be declared by the controller 12270 when no fluid flow or membrane movement is detected as the pressure in the actuation pressure is decreased to the minimum pressure 12332. The controller may determine that the fluid has not flowed, when the pressure summation 12320 does not exceed the given value 12328.

One exemplary hardware configuration is shown in FIG. 140. The valve 12260 may be used opened and closed rapidly to step-wise increase the pressure in the actuation chamber 12214. The rapid opening and closing of the binary valve 12260 may produce a pressure plot similar to FIGS. 137 and 138. The end of stroke, downstream pressure and downstream occlusions may may be determined by the same methods described above. The upstream pressure can be determined by closing valve 12260 and rapidly opening and closing valve 12250 to step wise decrease the pneumatic pressure in the actuation chamber 12214. The rapid opening and closing of valve 12250 may produce a pressure plot similar to FIG. 139. The upstream pressure and upstream occlusions may be determined in the same method described above.

Air Detection with FMS System

In some cases, the controller needs to know if air is present in the liquid side 12216 of the heparin metering pump 80 (FIG. 4A) because it pumps both liquid from and air into the heparin vial 11. In one exemplary method to detect air in the metering pumps, herein named the Air Detect procedure, the controller 12270 may execute a first FMS volume measurement using the positive pressure source 12265 followed by a second FMS volume measurement using the negative pressure source 12255. The difference in the calculated volume of the actuator-chamber 12214 may be named the Air Volume Metric. The controller 12214 may declare air is present in the liquid side 12216 of the metering pump if the Air Volume Metric exceeds the Air Volume Limit. The Air Volume limit may be determined separately by running the Air Detect procedure twice to determine the Air Volume Metric when the metering pump full of air, then repeating the procedure when the pump is full of liquid. The Air Detect Limit may be set at the average of the two Air Volume Metrics for the pump full of air and full of liquid. The procedure to determine the Air Detect Limit may be repeated if the two values of the Air Volume Metric are too close or if the Air Volume Metric for a liquid filled pump is larger than the Air Volume Metric for gas filled pump. The Air Volume limit may be determined for each metering pump. This method provides an accurate and reliable way to detect air without additional hardware and despite large changes in manifold temperature, tubing volume and flex, or machine to machine reference volume variation.

A diagram of an example control algorithm is shown in FIG. 14. The controller in this example is a standard discrete PI controller. The output of the PI controller is split into two paths; one for the source valve, one to the sink valve. An offset term is added to each of these paths to compensate for the valve dead band. The resulting command is then limited to valves greater than zero (after being inverted in the case of the sink valve).

The offset term is positive in the case of the source valve, and negative in the case of the sink valve. As a result, both valves will be active even as the error goes to zero. These offsets do improve the trajectory following and disturbance rejection ability of the controller, but can also result in leakage from both valves at steady state if the command offsets are slightly larger than the actual valve dead band. If this is the case, the valves will have equal and opposite leakage mass flows at steady state.

To eliminate this leakage mass flow when the control system is idle, a "power save" block can be added to turn off the valves if the absolute value of the error term remains small for a period of time. This is analogous to using mechanical brakes on a servomotor.

Figure 15:
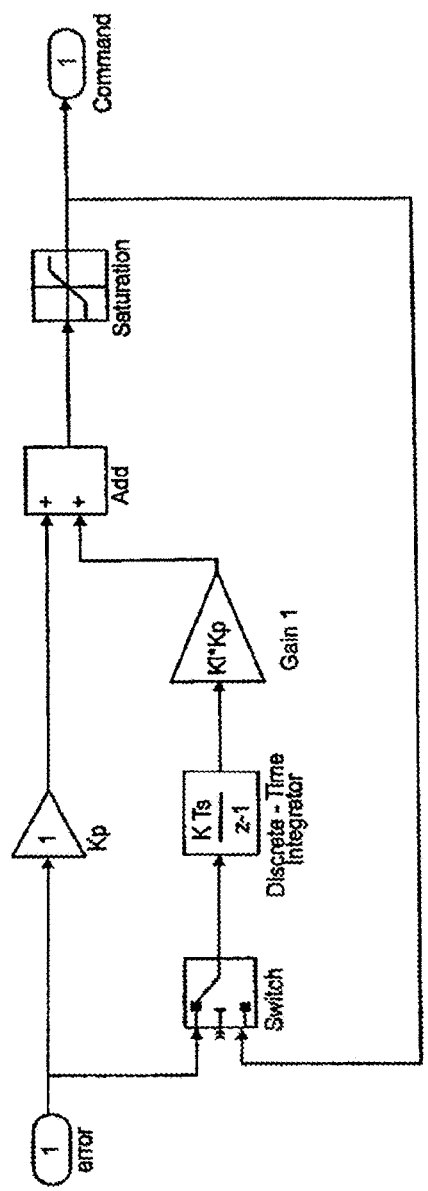
FIG. 15 is a diagram of one embodiment of the controller's standard discrete PI regulator.

Referring now to FIG. 15, the controller in this example uses a standard discrete PI regulator; a diagram of the PI regulator is shown. The integrator can be limited to prevent wind up when the commands are saturated. The integrator will always be capable of unwinding. Because there are different amounts of air in the pod for a fill and a deliver stroke, the response of the pod can be very different for a fill and deliver stroke. The proportional gain is adjusted differently for a fill and deliver stroke to better tune for the different pod responses.

The saturation limits chosen for the PI regulator should take into account the offset that will be added to the result. For example, if the valve saturates at 12V and a 5V fixed offset will be added after the PI loop, the saturation limit in the PI loop should be set to 7V. This positive and negative saturation limits will likely be different due to the different dead band in the source and sink valves.

During a fill stroke, the upstream fluid valve is closed and the down stream fluid valve is opened to allow fluid flow into the chamber. During a delivery stroke the upstream fluid valve is opened and the downstream fluid valve is closed to allow fluid flow out of the chamber. At the end of stroke, and until the next stroke starts, both fluid valves are closed.

As discussed, in certain aspects, a pod pump may be operated through action of a control fluid, for example, air, nitrogen, water, an oil, etc. The control fluid may be chosen to be relatively incompressible, and in some cases, chosen to be relatively inexpensive and/or non-toxic. The control fluid may be directed into the system towards the pumps using a series of tubes or other suitable conduits. A controller may control flow of control fluid through each of the tubes or conduits. In some cases, the control fluid may be held at different pressures within the various tubes or conduits. For instance, some of the control fluid may be held at positive pressure (i.e., greater than atmospheric pressure), while some of the control fluid may be held at negative pressures (less than atmospheric pressure) or even zero pressure (i.e., vacuum). As a specific, non-limiting example, a pod pump such as the one illustrated in FIG. 11A may be controlled through operation of the control fluid by the controller. As previously discussed, the controller (119) may open and close valves (e.g., valves 117 and 118) to expose the pneumatic side of the pod pump to a positive pressure (121) or a vacuum pressure (122) at different points during a pumping cycle.

In addition, in certain embodiments, the controller (typically electronic) may also be kept separate from the various fluid circuits, such that there is no electronic contact between the controller and the various fluid circuits, although the control fluid (e.g., air) is able to pass between the controller and the various pumps. This configuration has a number of advantages, including ease of maintenance (the controller and the various circuits can be repaired independently of each other). In one embodiment, the fluid circuits may be heated to disinfection temperatures and/or exposed to relatively high temperatures or other harsh conditions (e.g., radiation) to effect disinfection, while the electronic controller (which is typically more delicate) is not exposed to such harsh conditions, and may even be kept separate by an insulating wall (e.g., a "firewall") or the like.

Thus, in some embodiments, the system may include a "cold" section (which is not heated), and a "hot" section, portions of which may be heated, e.g., for disinfection purposes. The cold section may be insulated from the hot section through insulation. In one embodiment, the insulation may be molded foam insulation, but in other embodiments can be any type of insulation, including but not limited to a spray insulation or an insulation cut from sheets.

In some cases, the "hot" section may be heated to relatively high temperatures, e.g., the "hot" section may be heated to temperatures sufficient to sterilize components within the "hot" section. As many electronics can not go above 50° C. without failing or other adverse consequences, it may be advantageous in some embodiments to separate the electronics from other components that may be disinfected. Thus, in some cases, the components that may need to be disinfected are kept in the "hot" section, while components that cannot be heated to such temperatures are kept in the "cold" section. In one embodiment, the cold section includes a circulation system, e.g., a fan and/or a grid to allow air to flow in and out of the cold box.

All, or a portion of, the "hot" section may be encased in insulation. In some cases, the insulation may be extended to cover access points to the "hot" section, e.g., doors, ports, gaskets, and the like. For instance, when the "hot" section is sealed, the insulation may completely surround the "hot" section in some cases.

Non-limiting examples of components that may be present within the "cold" section include power supplies, electronics, power cables, pneumatic controls, or the like. In some cases, at least some of the fluids going to and from the "hot" section may pass through the "cold" section; however, in other cases, the fluids may pass to the "hot" section without passing through the "cold" section.

Non-limiting examples of components that may be present within the "hot" section include cassettes (if present), fluid lines, or the like. In some cases, some electrical components may also be included in the "hot" section. These include, but are not limited to, a heater. In one embodiment, the heater can be used to heat the hot box itself, in addition to fluid (see, e.g., heater 72 of FIG. 3A). In some embodiments, the heater heats the entire "hot" section to reach a desired temperature.

In one embodiment, the "hot" section includes some or all of the fluidic lines. In addition, in some cases, the "hot" section may include, but is not limited to, temperature and conductivity sensors, blood leak sensors, heaters, other sensors, switches, emergency lights, or the like.

In some cases, a manifold may transition from the "cold" section to the "hot" section, e.g., a manifold for air or another control fluid.

Separating the components into "hot" and "cold" sections may offer several advantages; those include, but are not limited to: longevity of electrical components, reliability, or efficiency. For example, by separating the components into hot and cold, the entire hot box may be heated. This may allows for more efficient use of heat which leads to a more energy efficient system. This also may allow for the use of standard, off the shelf electronics which leads to lower cost.

In some embodiments, the control fluid used for controlling the pumps, valves, etc. is air, and the air may be brought into the system through the operation of one or more air compressors. In some cases, the air compressor may be kept separate from the blood flow path and the dialysate flow path systems within the system, and air from the air compressor may be brought to the various pumps through various tubes, conduits, pipes, or the like. For example, in one embodiment, a pneumatic interface is used to direct air from the air compressor to a series of tubes or conduits fluidically connected with the various pumps or chambers.

Figure 16:
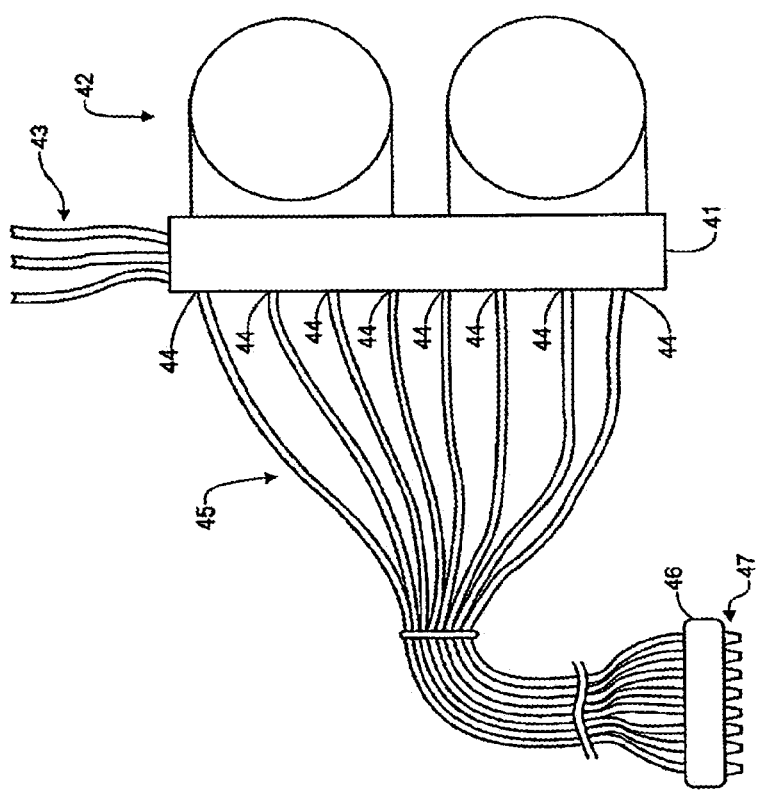
FIG. 16 is a schematic representation of a dual-housing cassette arrangement according to one embodiment.

A non-limiting example can be seen in FIG. 16, which shows a schematic representation of a dual-housing arrangement according to one embodiment. This arrangement may be advantageously used with cassettes that include many pneumatically actuated pumps and/or valves. If the number of pneumatically actuated pumps and/or valves in a cassette is large enough, the cassette containing these pumps and valves can become so large, and the pressures involved can become so great, that it may become difficult to properly seal and position all of the pumps and valves. This difficulty may be alleviated by using two or more different housings. The valves and pumps (such as pod pumps 42) are placed in a main housing 41, from which connecting tubes 45 lead from pneumatic ports 44. The main housing 41 also has inlet and outlet tubes 43, which allow liquid to flow into and out of the main housing. The connecting tubes 45 provide pneumatic communication between valves and pumps in the main housing 41 and a smaller, secondary tube-support housing 46, which is provided with a pneumatic interface 47 for each of the tubes. The proper positioning and sealing of all the pneumatic interfaces 47 against receptacles in the base unit can be accomplished more easily with the smaller tube-support housing 46 than it would be if the pneumatic actuation was applied to the larger main housing directly.

The control fluid (e.g., air) may be supplied to the system with one or more supply tanks or other pressure sources, in one set of embodiments. For instance, if two tanks are used, one supply tank may be a positive pressure reservoir, and in one embodiment, has a set point of 750 mmHg (gauge pressure) (1 mmHg is about 133.3 pascals). The other supply tank can be a vacuum or negative pressure reservoir, and in one embodiment, has a set point of −450 mmHg (gauge pressure). This pressure difference may be used, for instance, between the supply tanks and the required pod pressure to allow for accurate control of the variable valves to the pod pumps. The supply pressure limits can be set based on maximum pressures that can be set for the patient blood flow pump plus some margin to provide enough of a pressure difference for control of the variable valves. Thus, in some cases, the two tanks may be used to supply pressures and control fluids for the entire system.

In one embodiment, two independent compressors service the supply tanks. Pressure in the tanks can be controlled using any suitable technique, for instance, with a simple bang-bang controller (a controller that exists in two states, i.e., in an on or open state, and an off or closed state), or with more sophisticated control mechanisms, depending on the embodiment. As an example of a bang-bang controller, for the positive tank, if the actual pressure is less then the desired pressure minus a hysteresis, the compressor servicing the positive tank is turned on. If the actual pressure is greater then the desired pressure plus a hysteresis, the compressor servicing the positive tank is turned off. The same logic may be applied to the vacuum tank and control of the vacuum compressor with the exception that the sign of the hysteresis term is reversed. If the pressure tanks are not being regulated, the compressor is turned off and the valves are closed.

Tighter control of the pressure tanks can be achieved by reducing the size of the hysteresis band, however this will result in higher cycling frequencies of the compressor. If very tight control of these reservoirs is required, the bang-bang controller could be replaced with a PID controller and using PWM signals on the compressors. Other methods of control are also possible.

However, other pressure sources may be used in other embodiments, and in some cases, more than one positive pressure source and/or more than one negative pressure source may be used. For instance, more than one positive pressure source may be used that provides different positive pressures (e.g., 1000 mmHg and 700 mmHg), which may be used to minimize leakage. For example, high positive pressure can be used to control valves, whereas lower positive pressures can be used to control pumps. This limits the amount of pressure that can potentially be sent to the dialyzer or to the patient, and helps to keep actuation of the pumps from overcoming the pressures applied to adjacent valves. A non-limiting example of a negative pressure is −400 mmHg. In some cases, the negative pressure source may be a vacuum pump, while the positive pressure pump may be an air compressor.

Pressure Distribution Module

FIGS. 101A and 101B to 121 show the details of one embodiment of a pneumatic actuation manifold in the form of pressure distribution module 9000. The pressure distribution module connects the pod pumps and valves of the liquid handling cassettes of the system (e.g. as illustrated in FIGS. 30A-46E) to the pressure reservoirs (121,122 in FIG. 11A). The various pod pumps and valves of the system in various embodiments are controlled and driven by selective connection to one or more pressure reservoirs via digital and proportional valves, as described previously. These reservoirs may include a high positive pressure reservoir, a low positive pressure reservoir, a negative pressure or vacuum reservoir, and a vent to the atmosphere. Safe pressure limits may be defined for the patient at +600 mmHg and/or −350 mmHg. The low pressure reservoir may be maintained between atmospheric pressure and the high safe patient pressure. The high pressure reservoir may be maintained above the low pressure reservoir. The vacuum reservoir may be maintained between atmospheric pressure and the low safe patient pressure.

The pressure distribution module 9000 in FIGS. 101A and 101B may comprise a manifold 9060, cartridge valves 9020, surface-mount valves 9030, pressure sensors 9040, ports 9605 connected to pressure reservoirs and ports 9050, 9055 connected to corresponding port(s) on fluid handing cassettes such as those shown in FIGS. 30A-46E. The pneumatic module 9000 may be connected to the fluid handling cassettes (FIGS. 30A-46E) via pneumatic lines (not shown) that connect to/interconnect with the several ports 9050, 9055 via a connector. In one example, the pneumatic lines connect directly from the ports 9050, 9055 on the pressure distribution module 9000 to ports on fluid handling cassettes. In another example, a group of pneumatic lines connect ports on the fluid handing cassettes to corresponding ports on one or more interface blocks 9850, 9860 (FIG. 102) that can reversibly mate with the pressure distribution module 9000 via an interface block 9820 (FIG. 103) mounted to the output side of the pressure distribution module 9000.

The reservoirs, valves and ports are connected to a multi-part pneumatic manifold 9060. The valves 9020, 9030 are controlled in certain embodiments by electrical signals from a hardware interface board (see block 6111 in FIG. 61). The pressure sensors 9040 may be electrically connected to the interface board 6111. An automatic computer 6106 (FIG. 61) may be configured to control the flow of blood, dialysate, water, etc. through control of fluid valves and pumps in cassettes in the dialysis unit 6001 in FIG. 60 by opening and closing the pressure distribution valves 9020, 9030 based in part on the signals received from the pressure sensors 9040. The pod pumps and valves of the cassettes are pneumatically actuated by selective connection to the pressure reservoirs by the operation of electro mechanical valves comprising two-way and three-way digital valves and proportional valves on the pressure distribution module 9000. The digital valves have two positions. A two-way digital valve is either open or closed. A three-way digital valve connects a common port to either a first or second port. The proportional valves provide a variable resistance to flow that is controlled by a driving electrical signal having a variable current. In an example the proportional valves may achieve a variable resistance by varying the area of the minimum opening. In another example, the proportional valve varies the flow resistance by varying the fraction of the time that the valve is open while the valve rapidly moves between open and closed positions. In another example, a valve may oscillate between a more closed position and a more open position without fully closing. The flow resistance is varied by changing the fraction of time that the valve is commanded to be in the more open position.

In one embodiment, the surface-mount valves 9030 shown in FIGS. 101A, 101B and 109 may be proportional valves also referred to as "vari-valves". In the illustrated embodiment, the multiple surface-mount valves 9030 mount on the top face 9093 of end-manifold block 9090, the top face 9093 being parallel to the channeled face 9092. In certain embodiments, the first port of the surface-mount valve 9030 threads into a first port 9097 and connects the first port 9097 to the second port 9098 (see FIGS. 101B, 109). In some embodiments, the surface-mount valves 9030 may be any of a variety of commercially available variable valves, such as proportional solenoid valves; in one embodiment, the valves are Clippard Minimatic EV-PM-20-6025 valves available from Clippard Instrument laboratory, Inc., Cincinnati, Ohio. In another embodiment, the valve 9030 may be any digital two-way or three-way valve suitable for surface mounting, such as model 11-15-3-BV-12-P-0-0 from Parker Hannifin Corporation in Hollis, N.H. The surface mounted two-way or three-way valves may selectively connect ports 9097 and 9098 or a third port (not shown) on the surface of the top face 9093.

FIG. 101B, and 110 show an embodiment including a plurality of cartridge valves 9020 and the connections to the pressure reservoirs 9061-9064. A cartridge valve is inserted in a manifold port. Cavities 9075 are formed to accommodate seals on the outside of the cartridge valves 9020. The machined cavity may have a set of dimensions defined by the manufacturer of the valve to assure sealing and proper functioning of the cartridge valve 9020. In this embodiment, fifty cartridge valves 9020 mount on the back face 9074 of the mid-manifold block 9070. The back face 9074 is a side of the mid-manifold block 9070 perpendicular to the channeled face 9072. In certain embodiments, the cartridge valves are three-way valves, such as Lee LHDA Plug-In valves available from The Lee Company USA, Westbrook, Conn. The cartridge valves 9020 may be inserted into cavities 9075 and fixedly secured by backer plate 9022 (FIG. 104) that is mechanically connected to the manifold mid-plate 9070. The cartridge valves 9020 plug into circuit board 9021, as shown in FIG. 110.

As shown in FIG. 101B, the pressure sensors 9040 may be directly mounted to the top face 9093 of the end-manifold block 9090. The pressure sensors 9040 may be integrated circuits soldered to a printed circuit board (PCB) 9044. As shown in FIG. 101A, a printed circuit board 9044 including one or more pressure sensors 9040 may be mounted on the top face 9093 that is parallel to the channeled face of the manifold end-block 9090 with a gasket 9041 to pneumatically isolate each sensor, and with a plate 9042 to hold the PCB 9040 in place and compress the gasket 9041 enough to isolate each pressure sensor. In one example, the pressure sensor 9040 may be obtained from Freescale Semiconductor, Inc. in Tempe, Ariz. (part no. MPXH6250A). The PCB 9044 may be mounted as a unit to the end-manifold block 9090. The pressure sensing face of each pressure sensor 9040 may be fluidly connected via port 9043 (FIG. 101B) and channels 9091 (FIG. 106) to the desired pressure sources such as reference volumes 9412 (FIG. 106), or more remotely to the actuation chambers of pod-pumps, to dialysate reservoir tank 169, in many cases to monitor the liquid pressures in the liquid handling cassettes.

The pressure reservoirs described above may be fluidly connected to the pneumatic manifold via fittings on the mid-manifold block 9070 and the end-manifold block 9090. A reservoir of negative pneumatic pressure or vacuum may connect via fitting 9062 shown in FIG. 110. A high pressure reservoir may connect via fitting 9061. The low pressure reservoir may connect to both the mid-manifold block 9070 and the end-manifold block 9090. The low pressure reservoir may be connected to the mid-manifold block 9070 via fitting 9064. The low pressure reservoir may also be connected to the end-manifold block 9090 via fitting 9063. There is a flow path (not shown) from the digital-valve block through the mid-plate 9080 and the mid-plate gaskets 9081, 9082 to the end-manifold block 9090 (shown in FIG. 108). Both blocks 9070, 9090 have connections to ambient pressure or the atmosphere. Each connection or hole may be covered with a water guide 9065 that does not seal the hole, but directs any water in the manifold in a preferred direction. The pressure reservoirs to which the pressure distribution module 9000 may be connected are volumes maintained at specified or pre-determined pressures by pumps controlled by a system controller. In an embodiment, a high-pressure reservoir can be maintained at a pressure of about 1050 PSI, and a positive pressure reservoir can be maintained at a pressure of about 850 PSI. The pressures actually delivered to various pneumatically actuated pumps and valves may vary based on the pressure reservoir ported by the two-way, three-way and vari-valves on pressure distribution module 9000. Furthermore, intermediate pressures may also be delivered through a combination of rapid opening and closing of the on-off valves, or through a variation of the orifices of the vari-valves.

Manifold or Pressure Distribution Module

The manifold 9060 may comprise one or two end-manifold blocks 9090, one or more mid-manifold blocks 9070 and one or more mid-plates 9080 and gaskets 9081, 9082. An exploded view of a multi-part pneumatic manifold 9060 is shown in FIG. 105. The two manifold blocks 9090, 9070 may be clamped together with a gasketed mid-plate 9080 between them. The mid-plate 9080 may also be referred to as a backing plate, as it provides a rigid surface that forces the gasket to seal against multiple channels 9071, 9091. The channels 9091 on the underside of end-manifold block 9090 are visible in FIG. 106. Each manifold block 9070, 9090 may comprise at least one face 9072, 9092 with channels 9071, 9091 and various ports 9050, 9055 (FIG. 105), 9605 (FIG. 106), 9041 (FIG. 109), and 9370 (FIG Pneu 111A) on other faces. The channels 9071 (FIG. 108) and 9091 (FIG. 106) may be configured as a groove that includes a solid bottom and two side walls with an open top. The channel may be cut into one face 9072, 9092 of the manifold block or it may be formed with walls that extend above the surface of the manifold block face 9072, 9092. As shown in FIG. 107, the open top of the channels may be sealed by clamping a gasket 9081, 9082 backed by a rigid flat mid-plate 9080 against the channels. The mid-plate 9080 is a backing plate that forces the gasket 9081, 9082 to seal against all of the channels 9071, 9091. The channels 9071, 9091 are linked to pressure sources 9605, valves 9020, 9030, sensors 9040 and outlet ports 9050, 9055 that reside on other faces of the blocks. The manifold blocks 9070, 9090 may sandwich the gaskets 9081, 9082 and the mid-plate 9080 between them with mechanical fasteners 9066 to seal the multiple channels 9071, 9091 on the channeled faces 9072, 9092 of each of the manifold blocks. This sandwich construction allows the compact assembly of multiple manifold blocks with sets of channels 9071, 9091 on one face of each block 9090, 9070.

In some embodiments, there are ports or channels on five of the six faces of the manifold blocks. The end-manifold block 9090 may have channels 9091 on face 9092. Pressure sensors 9040 and surface mount valves 9030 may be attached to the top face 9093 of the end-manifold block 9093. The end-manifold block 9090 may include supply lines 9606, which run the length of the manifold block. The ports for the supply lines 9606 are at each end of the end-manifold block 9090. The ports 9050, 9055 that connect to the liquid handling cassettes may be on the front face 9096 (FIG. 103,105). The back face 9094 may include additional ports to connect to the liquid handling cassettes or cavities for cartridge valves.

The mid-manifold block 9070 may have channels on the top face 9072. Cartridge valves 9020 may mount on the back face 9074. The front face 9076 may include ports 9050, 9055 that connect to the liquid handling cassettes. Both end faces of the mid-manifold block include ports that connect to the supply lines 9605 that are cavities that run the length of the mid-manifold block 9070. In one embodiment, the bottom face (not shown) of mid-manifold block 9070 may include additional ports that connect to the supply lines 9605. In another embodiment, the bottom face (not shown) of mid-manifold block 9070 may be flat. In another embodiment, the bottom face (not shown) of mid-manifold block 9070 may include additional channels that provide fluid connections between some of the following, but not limited to, ports 9050, cartridge valves 9020 and supply lines.

In certain embodiments, the pneumatic channels 9071 (FIG. 105) connect many of the ports 9050, 9055 to a cartridge valve 9020 and many of the cartridge valves 9020 to one of the supply lines 9605. The supply lines 9605 may be in the form of long cavities that run the length, or a substantial portion thereof, of the manifold block. In the mid-manifold block the supply lines from the end faces 9076 may run generally perpendicular to the path of the channels 9071. Thus any channel 9071 may be connected to any one of the supply lines 9065. The channels also generally run from the front face 9074 to the back face 9075, thereby allowing connection between the ports to the liquid pumping cassettes and the cartridge valves. In a similar way the channels 9091 in end-manifold block 9090 allow connection to the supply lines 9065, ports 9055 and surface-mounted valves 9030. The three supply lines: high pressure 9620, low pressure 9630 and vacuum 9640 (FIG. 105) may be plumbed to one of the three pressure reservoirs. The fourth line 9610 may be vented to atmosphere. In certain embodiments, one or more of the channels 9071 connect a valve 9020 to a reference volume in the end-manifold block 9090, which is used to determine volume changes in remotely connected pneumatically actuated membrane pumps (via FMS techniques). The reference or FMS volumes 9412 in the end-manifold block 9090 are visible in FIG. 106.

Figure 111A:
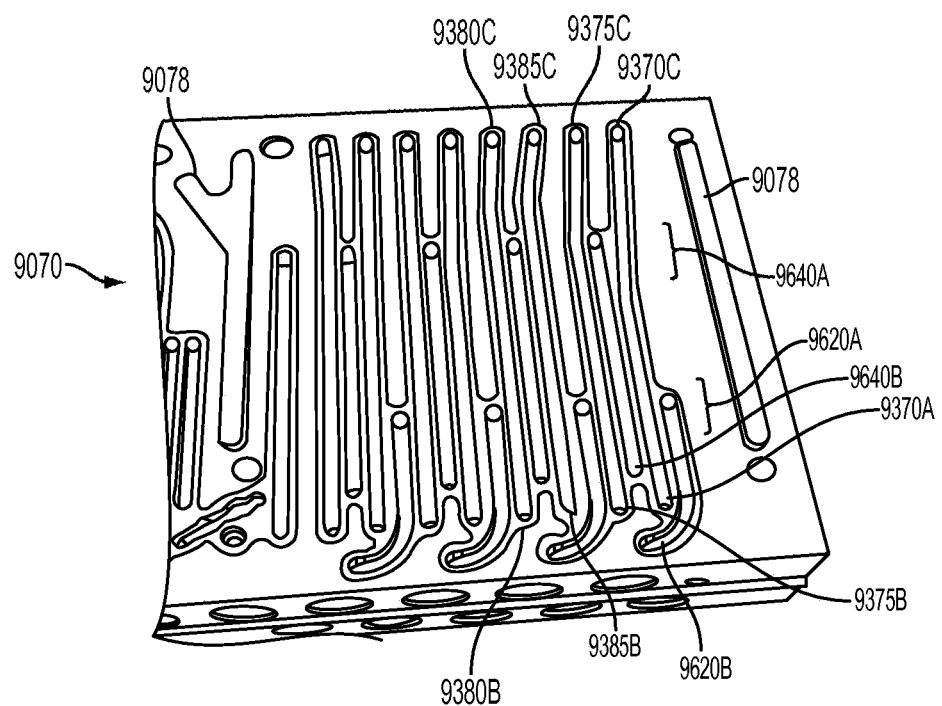
Figure 111B:
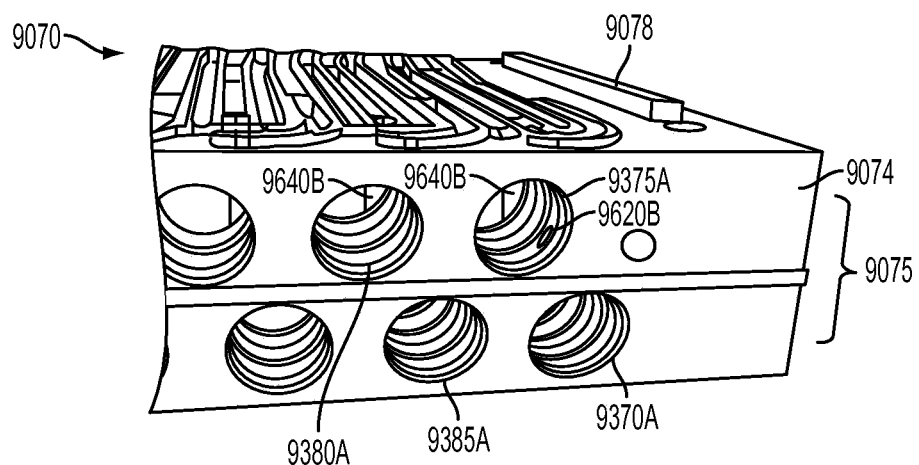
Figure 111C:
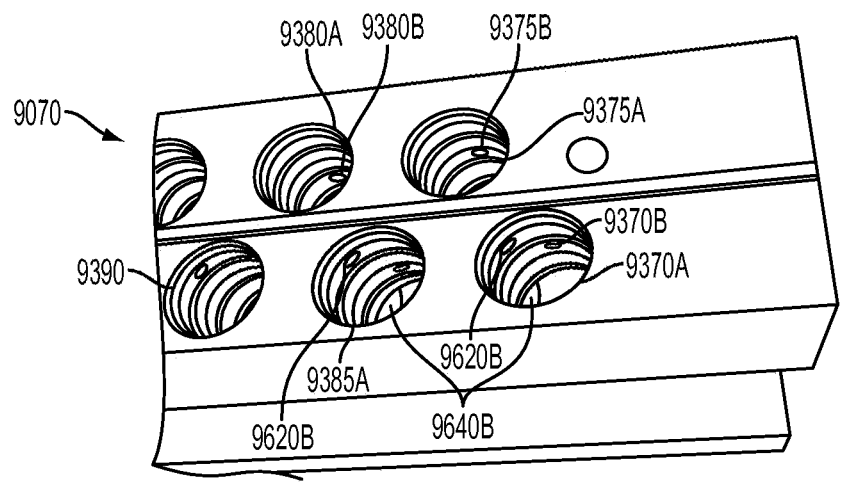

An example of the fluid connections to and from the channels 9071 (shown, e.g., in FIG. 105) are shown in FIG. 111A-111C, which present 3 views of the same part of the mid-manifold block 9070. The cartridge valve cavities 9075 (shown, e.g., in FIG. 104 and FIG. 110) may be connected to three channels via vertical holes from each of the three channels to the cartridge valve cavity 9075. The vertical holes may intersect the cartridge valve cavity at different axial depth from the back face 9074 so that a three way cartridge valve may connect the second hole to either the first or the third hole. The second hole may be connected to the liquid handling cassette where the pneumatic pressure will open or close a liquid valve or may actuate a pod pump. The first and third holes may be connected to pressure reservoirs.

An example of the connections between the pressure reservoirs and liquid valves in the liquid handling cassette can be seen in FIGS. 111A-111C. The cartridge valve cavity 90370A on the extreme right receives valve 9037. The cartridge valve cavity 90380A is connected to the vacuum reservoir via supply line 9620. The channel on the extreme right of FIG. 111A has a vertical hole 9620A that connects the channel to the supply line 9620 and a second hole 9620B that connects to the cartridge valve cavity 9370A. The second hold 9620B can be seen in FIG. 111C. The next channel connects the Mix Acid In valve 9370D (FIG. 120) in the mixing cassette to the cartridge valve 9370 via a vertical hole 9370C to a port 9050 and a vertical hole 9370B to the cartridge valve cavity 9370A. The cavity 9370A can be seen in FIG. 111A, 111C. The high pressure flows from supply line 9640 via hole 9640A, through the third channel and into the cartridge valve cavity 9370A via vertical hole 6940B. Similar connections are made for the next 4 valves 9375, 9380, 9385, and 9390. The cartridge valve cavities 9075 are formed in two rows with one row offset so that the cartridge valve cavities 9075 are staggered. The staggered arrangement allows two cartridge valve cavities 9370A and 9375A to share a single channel that supplies pressure. A single hole 9640B may supply high pressure to both cartridge valve cavities 9370A, 9370B by passing through both near the back of the cartridge valve cavities. The channel on the extreme right is in part aligned perpendicular to the supply lines and in part parallel to the supply lines to allow vertical hole 9620B to passes through both cartridge valve cavities 9375A and 9370A and to supply vacuum to both valves. The vertical holes 9620B, 9370B and 9640B intersect the cartridge valve cavities 9370A, 9375A at different distances from the back face 9074 of the manifold block 9070. The arrangement of vertical holes allows the cartridge valves 9370, 9375 to connect the liquid valves 9370E, 9375E on the mixing cassette to either the high pressure supply line 9640 or to the vacuum supply line 9620. The mid-plate 9080 and gaskets 9081, 9082 may include holes 9084 that connect channels 9071 in the mid-manifold block 9070 to any of number of elements in the end-manifold block 9090 including but not limited to channels 9091, pressure ports 9041, and surface mount valve ports 9097, 9098.

Figure 111D:
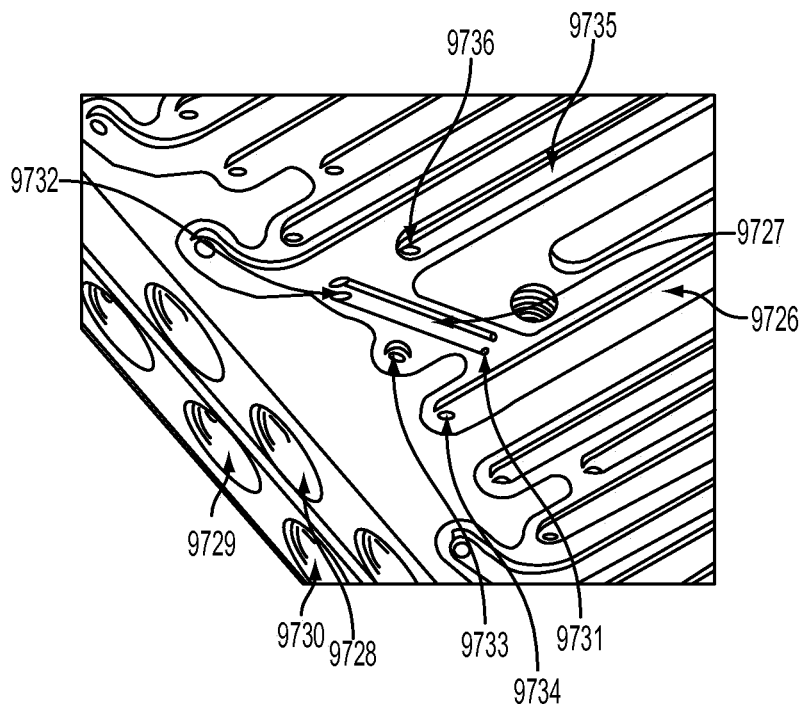

An exemplary description of manifold plumbing including a pump with an FMS system is presented in FIG. 111D and FIG. 112. The mid-manifold block 9070 incorporates channel features to implement different pneumatic control features. The channel 9726 carries a pneumatic pressure source to the hole 9734, which goes down to valve station 9730. The channel 9735 carries a different pneumatic pressure source to the hole 9736, which goes down to valve station 9729. Hole 9732 does down to a different port on station 9729, and channel 9727 carries this pneumatic signal over to hole 9731 which intercepts both valve stations 9728 and 9730. These features implement a portion of the pneumatic schematic (FIG. 112), with valves 9729A, 9730A, and 9728A corresponding to valve stations 9729, 9730 and 9728 respectively.

The channels 9071 are sealed with the gasket 9081 (see, e.g., FIG. 105), which is advantageously pressed essentially evenly against the channels by the mid-plate 9080. The manifold block and gasket can include features to assure an essentially even distribution of pressure on the gasket. The mid-manifold block 9070 may include raised sections 9078 (FIG. 111A, 111B) that fit through matching slots 9083 (FIG. 105) in the gasket 9081. The mid-plate 9080 sits on the raised features 9072 assuring essentially even compression of the gasket. In certain embodiments, screws 9066 (FIG. 105) are used to clamp the gaskets and mid-plate between the two manifold blocks 9070, 9090. The mid-plate 9080 provides a substantially smooth and rigid backing for the gaskets so that more than one manifold block may be assembled into the multi-part pneumatic manifold 9060.

The gaskets 9081, 9082 and mid plane 9080 include holes 9084 to allow pressure and flow communication between the mid-manifold block 9070 and the end-manifold block 9090. Some of the holes 9084 may allow flow from the mid-manifold block 9070 up to the surface mount valves 9030 and back. Some of the holes may allow pressure sensors 9040 to measure pressures in channels 9071 on the mid-manifold block 9070. Some of holes through the gasket 9081, 9082 and mid-plane 9080 may connect the supply lines 9605 in the mid-manifold block 9070 to supply lines 9066 in the end-manifold block 9090. The gaskets in one embodiment are made of ethylene propylene diene monomer (M-class) rubber (EPDM) with a 40 Shore A hardness or similar elastomer. The mid-plate 9080 is preferably a relatively stiff plate that provides a rigid and substantially planar surface to urge the gaskets against the grooves in both manifold blocks. In one embodiment, the mid-plate 9080 is 0.2 inch thick aluminum.

An alternative embodiment is presented in FIG. 106, where a third mid-manifold block 9070A is added. In this embodiment, the under-side of mid-manifold block 9070 (unseen in FIG. 107) is smooth with holes for communication between the second mid-manifold block 9070 and the third mid-manifold block 9070A. A gasket 9081A seals the channels 9071A of mid-manifold block 9070A. The channels of mid-manifold block 9070A serve the same function as 9071 and connect the exhaust ports 9050A, valves 9020A and supply ports 9605A. The second and third manifold blocks can be stacked because the cartridge valves 9020A are on the back face 9074A, the exhaust ports are on the front face 9075A and the supply ports are on the end faces 9076.

Further alternative embodiments of the pressure distribution system 9000 may comprise an end-manifold block and 2 or more mid-manifold blocks with channels on one face and a smooth surface on the opposite surface. The cartridge valves 9020 may be mounted on the back face 9074 on one side, while the exhaust ports may mount on the opposite face. The supply lines may extend the length of the manifold blocks. The smooth face 9073 of this embodiment of the mid-manifold block 9070 acts as the backing plate for the gasket 9081A that seals the channels 9071A on the second mid-manifold block 9070A. In other embodiments, multiple mid-manifold blocks can be added with gaskets 9081A between to create more channels and more output ports to control more complex pneumatically or fluidically driven systems.

In another alternative embodiment (FIG. 108), mid-manifold block 9070 has channels 9071 both on the top visible surface and on the lower (unseen) surface. The channels on the lower surface of 9070 may be sealed via both a gasket and a mid plate 9080 between 9070 and 9070A. Multiple mid-manifold blocks can stacked together with channels on both the upper and lower surfaces by placing gasketed mid-plates 9080 between each. In this way multiple mid-manifold blocks with channels on two surfaces can be combined to form more complex pneumatic supply systems.

In another example, the manifold 9060 may comprise one or more mid-manifold blocks 9070 between two end-manifold blocks 9090. Gasketed mid-plates 9080 may be placed between each pair of manifold blocks 9070, 9090 to create fluid channels.

The ports 9050, 9055 for the pneumatic lines that connect the pressure distribution manifold to the cassettes are visible on the front face in FIG. 109. In certain embodiments pneumatic lines from ports 9050 may connect to the integrated cassette system (e.g. that of FIGS. 46A-E) via interface blocks that quickly separate to allow the integrated cassette system to be easily replaced. The fixed interface block 9820 is shown in relation to the pressure distribution system 9000 in FIG. 103. Two removable interface blocks 9850, 9860 shown in FIG. 102 are clamped against 9820 by the two clamps 9830 against the front side 9821 of the fixed interface block. A gasket (not shown) on the face of the removable interface blocks 9852, 9862 provides an air tight seal. Alignment pins 9822 pressed into the fixed interface block 9820 align removable blocks 9850, 9860 so that the matching ports are aligned. The removable interface blocks 9850, 9860 can be located within the 'hot box' cavity of the dialysis unit within which the fluid pumps and valves are located. This cavity may be subject to a high temperature environment during disinfection of the dialysate-carrying pumps and valves. In contrast, the fixed interface block 9820 may be located in a section of the dialysis unit ('cold box' section) that is thermally segregated from the hot box section to protect the temperature sensitive elements of the dialysis system (electronic and electromechanical components).

The integrated cassette system, e.g. of FIGS. 46A-E, may be connected via flexible lines to the two removable interface blocks 9850, 9860. Alternatively, the integrated cassette system may be equipped with raised rigid ports spatially arranged to connect and form sealing engagements with mating ports on either fixed interface block 9820 or the removable interface blocks 9850, 9860. The flexible lines are secured to the ports 9854, 9864 at the top of the blocks. The blocks may be fabricated from polysulfone, or another tough thermoplastic with good stability at high temperatures. The integrated cassette system may be connected to the pneumatic controls of the dialysis machine 6001 by placing the removable blocks 9850 and 9860 against the fixed block 9820 and then turning the handles of the clamps 9830 to secure the removable blocks. The removable blocks provide a reliable and quick design to align and seal the many connections between the integrated cassette system and the pressure distribution module 9000. They provide for rapid connection to and disconnection from the pressure distribution module, greatly increasing the efficiency with which the integrated cassette system is periodically replaced.

The fixed interface block 9820 thermally isolates the pressure distribution system 9000 in the ambient temperature part of the dialysis machine 6001 to reduce heat flow from the insulated hot box where the heated dialysate/disinfection fluid flows through the integrated cassette system. In certain embodiments, the fixed interface block 9820 is fabricated from polysulfone, or another tough thermoplastic material with good stability at high temperatures. In certain embodiments, the fixed interface block 9820 may be bolted to pressure distribution system 9000 and the 9050 ports may be sealed with a gasket 9810, which may also aid in thermally insulating the pressure distribution module from the ambient temperatures in the hot box section of the dialysis unit.

Ports 9055 connect the pressure distribution system 9000 to the blood cassette e.g. of FIGS. 30A-34D and the FMS reservoir for the dialysate tank (not shown). The twelve ports 9055 shown in FIG. 101A are connected via flexible tubes to plate 9890 on the surface of the hot box of the dialysis machine. A second plate with flexible tubes is bolted to the first plate at the surface of the hot box. The second plate (not shown) is connected via flexible tubes to the FMS volume for the dialysate tank and to the control port assembly (not shown). The control port assembly has pneumatic receptacles that connect to the ports on the bottom plate of blood cassette 1100 (FIG. 33D).

The manifold block can be fabricated in advance and customized by the installer or product developer, if desired. A mass produced manifold block may be fabricated without the vertical holes connecting the channels 9071 and the supply lines 9605, and then configured for a particular application by connecting a given channel to a specific supply line.

Pneumatic Schematic of Pressure Distribution Module

The detailed plumbing schematic of an embodiment of the vary-valve manifold and digital valve manifold is described in the pneumatic schematics FIGS. 113-117 and with corresponding flow schematics of the blood, dialysate and mixing cassettes shown in FIGS. 118-121. In the pneumatic schematics the supply lines 9610, 9620, 9630, 9640 are represented as vertical lines. The three way valves, for example 9210, may be plumbed to two different supply lines and to a liquid valve 9210E in the liquid handling cassettes 25, 141, 142, 143. The three-way valve 9210 for a blood pump may connect the liquid valve 9210E to the vacuum supply line 9640 when not powered. In the non-powered position, the liquid valve 9210E is preferably in a default open position so that the blood is not trapped during a loss of power. In the powered position, the liquid valve 9210E is connected to the low pressure supply line 9630 to close the liquid valve. The blood pumps 13 may be actuated by a pair of proportional valves, for example 9110, 9112, that connect to a low pressure supply line 9630 and vacuum supply line 9640. The pressure supplied to the blood pump 13 may be monitored by a pressure sensor 9111. Some pneumatic circuits for pumps may include a FMS chamber to allow accurate measurement of the volume pumped. One example is a drug metering or heparin pump 11 actuated by valves 9230 and 9235 connected to the vacuum and high pressure lines respectively. The actuating fluid path is connected to an FMS chamber 9238 and flows through a third valve 9233 toward the heparin pump 9233E. Pressure sensors 9239, 9234 may monitor the pressure up and down stream of valve 9233.

The pressure supply lines and default valve positions may be selected to achieve safe conditions in the event of a failure. The liquid valves 9210E, 9215E, 9220E, 9225E and pumps 13 that handle blood in the blood cassette 141 may be powered by the vacuum supply line 9640 and the low pressure supply line 9630. The low pressure plumbing may be elected for the pumps or valves that handle blood elements to avoid the possibility of exposing the biological fluid and thereby the patient's vascular system to pressures in excess of the low pressure reservoir. In the inner dialysate cassette 143, the dialysate pumps 15 may be connected to the low pressure supply line 9630 and the ambient pressure line 9610. The inner dialysate pumps 15 preferably are not be connected to the vacuum supply line 9640 to avoid lowering the dialysate pressure below ambient and therein minimizing the amount of gas evolving out of the dialysate solution. In this case, the outer dialysate pump 159 may supply positive pressure to the dialysate entering the inner dialysate cassette 143, thereby filling the inner dialysate pumps 15 when the upstream valves 9270, 9265 are open.

The un-powered positions of the three-way valves in the pressure distribution system 9000 may be selected to provide a safe condition during power loss or failure of the controller or FPGA safety system. The blood pump valves 9210, 9215, 9220, 9225, the ODP valves 9350, 9355, 9360, 9365 and the BTS clamp 9430 default to a vacuum connection which opens the liquid valves allowing blood to be pushed out of the blood cassette. The unpowered position for the heparin pump valves 9230, 9235, ultrafiltration pump valves 9285, 9290, acid pump valves 9410, 9415 and the bicarbonate pump valves 9420, 9425 disconnects the pump from the pressure reservoirs so they do not pump any fluid. The balance of the valves may default to connecting high and low pressure to the liquid valves so that the liquid valves close when power is lost. Rinseback of blood to the patient is possible in a power failure scenario through the default positioning of the valves leading from the low (or high) positive pressurized tank, through the pressure distribution manifold valve 9325, and into the dialysate tank 169 via valve 9328, for example. Pressure applied to the dialysate fluid in the dialysate tank 169 can be directed to the blood side of the dialyzer through the outer dialysate pumps and valves, the ultrafilter, and the inner dialysate fluid path to the dialyzer, with the appropriate distribution manifold valves being arranged in either a default open position for the pathway to the dialyzer, or a default closed position for other dialysate pathways ultimately leading to drain. The dialysate fluid may thus be transferred to the blood side of the dialyzer membrane through hydrostatic pressure, which allows the blood in the blood tubing set to be rinsed back to the patient's vascular system.

Certain aspects of the invention include various sensors. For example, in various embodiments of the inventions described herein, fluid handling may include sensor apparatus systems comprising a sensor manifold. The sensor manifold may be arranged to include most of the fluid sensors used in the system, including, for example, dialysate conductivity and dialysate temperature sensors. A sensor manifold may include other types of sensors. Examples of such embodiments may include systems and methods for the diagnosis, treatment, or amelioration of various medical conditions, including embodiments of systems and methods involving the pumping, metering, measuring, controlling, and/or analysis of various biological fluids and/or therapeutic agents, such as various forms of dialysis, cardiac bypass, and other types of extracorporeal treatments and therapies. Further examples include fluid treatment and preparation systems, including water treatment systems, water distillation systems, and systems for the preparation of fluids, including fluids used in diagnosis, treatment, or amelioration of various medical conditions, such as dialysate.

Examples of embodiments of the inventions described herein may include dialysis systems and methods. More specifically, examples of embodiments of the inventions described herein may include hemodialysis systems and methods of the types described in U.S. patent application Ser. No. 11/871,680, filed Oct. 12, 2007 entitled "Pumping Cassette"; or U.S. patent application Ser. No. 12/038,648 entitled "Cassette System Integrated Apparatus," filed on Feb. 27, 2008, each of which is incorporated herein by reference.

In such systems and methods, the utilization of one or more sensor manifolds may allow subject media to be moved from one environment to another environment that is more conducive to obtaining sensor readings. For example, the cassette manifold may be contained in an area that is less subject to various types of environment conditions, such as temperature and/or humidity, which would not be preferable for sensor apparatus such as a sensing probe. Alternatively, sensing apparatus and sensing apparatus system may be delicate and may be more prone to malfunctions than other components of a system. Separating the sensor apparatus and the sensor apparatus systems from other components of the system by use of a sensor manifold may allow the sensing apparatus and sensing apparatus systems to be checked, calibrated, repaired or replaced with minimal impact to other components in the system. The ability to check, calibrate, repair or replace the sensor manifold with minimal impact to the remainder of the system may be advantageous when utilized in connection with the integrated cassette systems and methods described in U.S. patent application Ser. No. 12/038,648 entitled "Cassette System Integrated Apparatus," filed on Feb. 27, 2008. Alternatively, the sensor manifold may be replaced either more or less frequently than other components of the system.

With reference to FIGS. 53-58, various embodiments of an exemplary sensor manifold are shown. One or more subject media, e.g., a liquid in these exemplary embodiments, may be contained in or flow through cassette manifold 4100. For example, one subject media may enter cassette manifold 4100 via pre-molded tube connector 4101 and exit the cassette manifold via pre-molded tube connector 4102. Between tube connector 4101 and 4102, there is a fluid path though the cassette (best shown as fluid path 4225 in FIG. 54) Likewise, fluid paths (shown as fluid paths 4223, 4220, 4222, 4224, and 4221 respectively in FIG. 54) extend between sets of tube connectors 4103 and 4104; 4105 and 4106; 4107, 4108, and 4109; 4110 and 4111; and 4112 and 4113. In certain embodiments, each fluid path may contain subject media of different composition or characteristics. In other embodiments, one or more fluid paths may contain the same or similar subject media. In certain embodiments, the same subject media may be flowed through more than one flow path at the same time to check and/or calibrate the sensor apparatus systems associated with such fluid paths.

Figure 54:
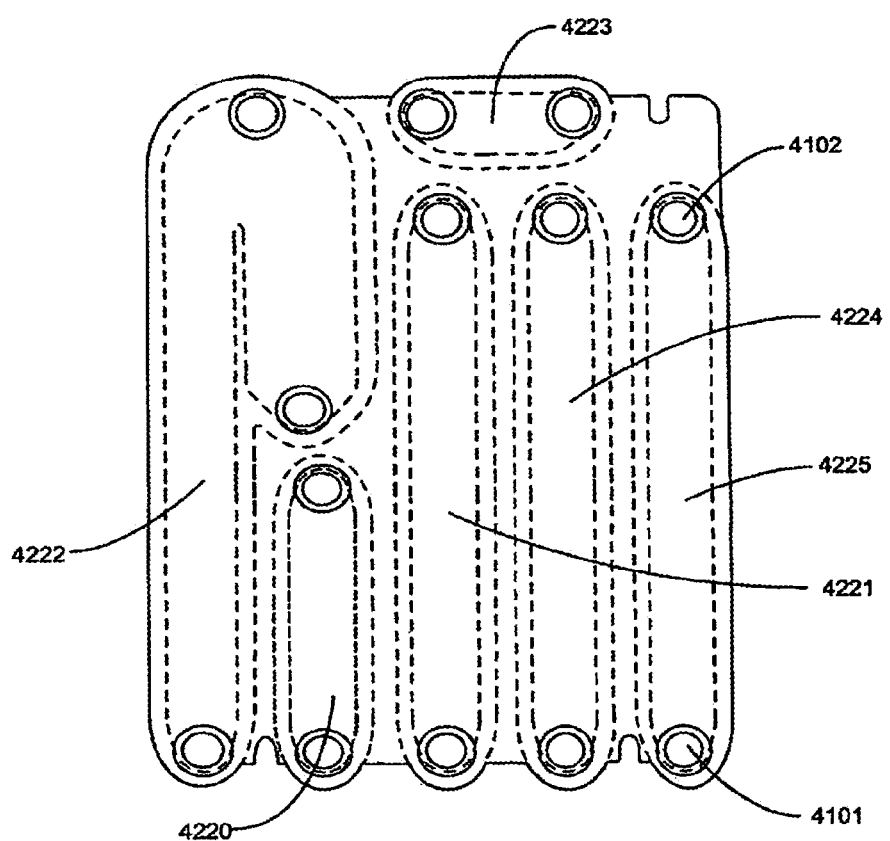
FIG. 54 is a view of the fluid paths within the exemplary sensor manifold shown in FIG. 53.
Figure 55:
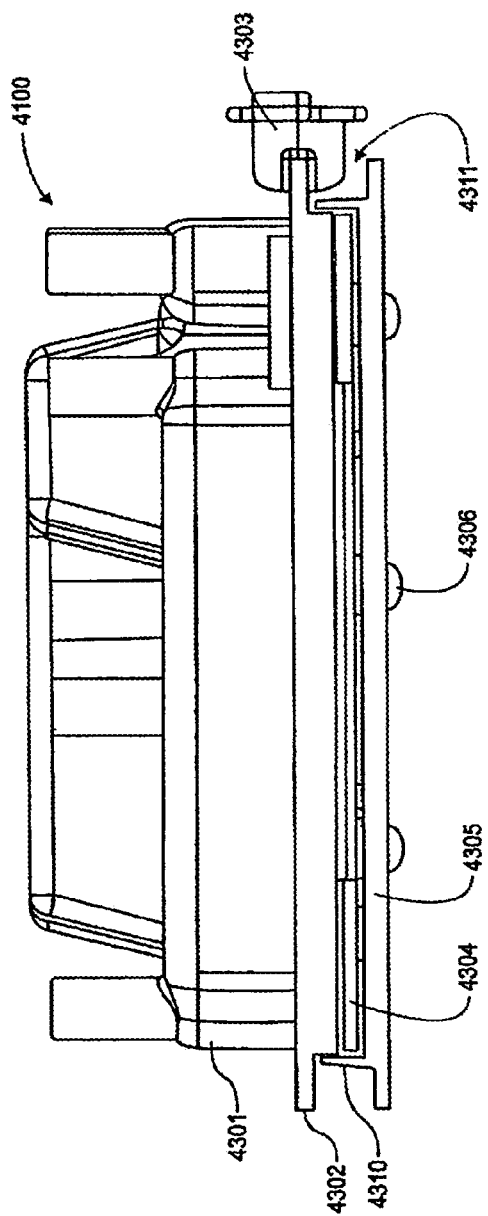
FIG. 55 is a side view of the exemplary sensor manifold shown in FIG. 53.
Figure 56:
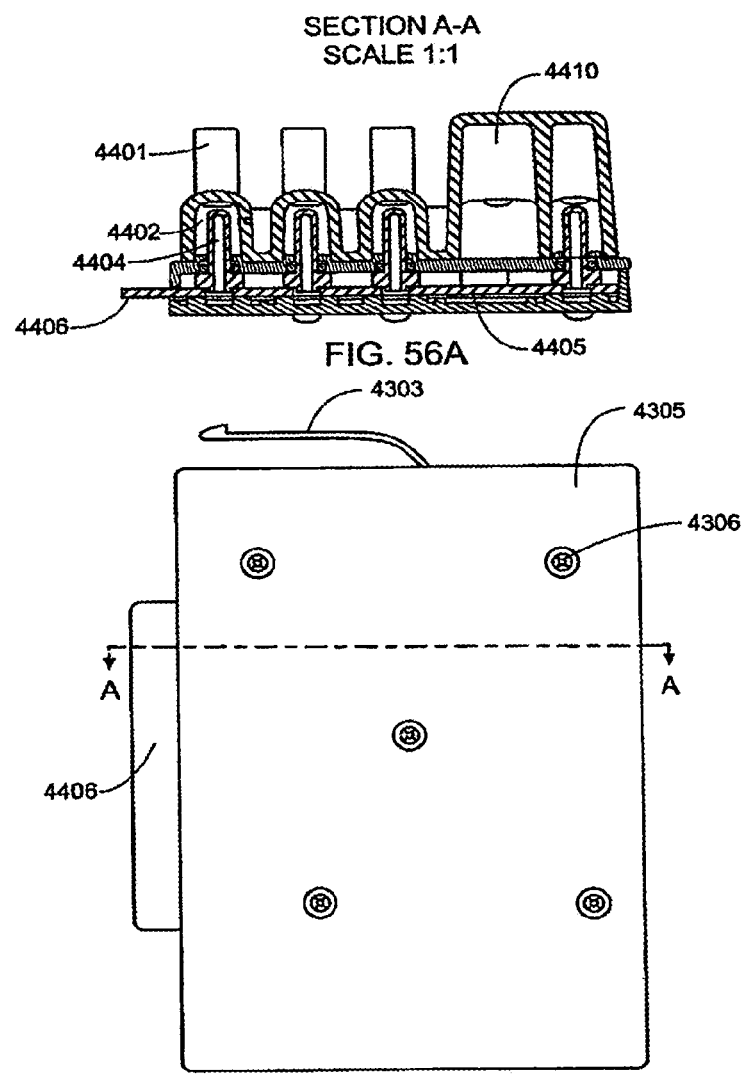
FIG. 56A is a cross sectional view of the exemplary sensor manifold shown in FIG. 53 at cross section A-A of FIG. 56B.
FIG. 56B is a front view of the exemplary sensor manifold shown in FIG. 53.

Referring now to FIG. 55, in these exemplary embodiments of sensor manifold 4100 that may be used in conjunction with the sensor apparatus and sensor apparatus systems described herein, the cassette includes a top plate 4302 and a base 4301. Fluid paths, such as the fluid path 4225 (as shown in FIG. 54) extending between tube connectors 4101 and 4102 extend between the base and top plate. The cassettes may be constructed from a variety of materials. Generally, in the various exemplary embodiment, the materials used are solid and non flexible. In the preferred embodiment, the plates are constructed of polysulfone, but in other embodiments, the cassettes are constructed of any other solid material and in exemplary embodiments, of any other thermoplastic. Some embodiments of sensor manifold 4100 may be fabricated utilizing the systems and methods described in U.S. patent application Ser. No. 12/038,648, entitled "Cassette System Integrated Apparatus," filed on Feb. 27, 2008.

Figure 57:
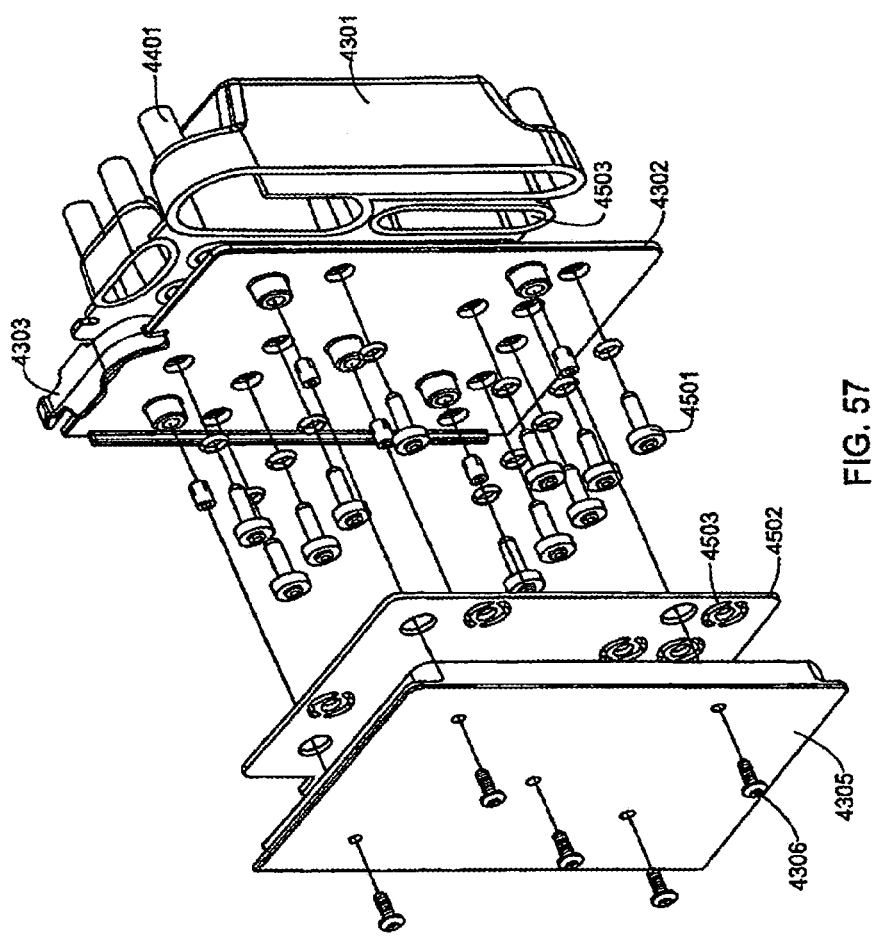
FIG. 57 is an exploded view of the exemplary sensor manifold shown in FIG. 53.
Figure 58:
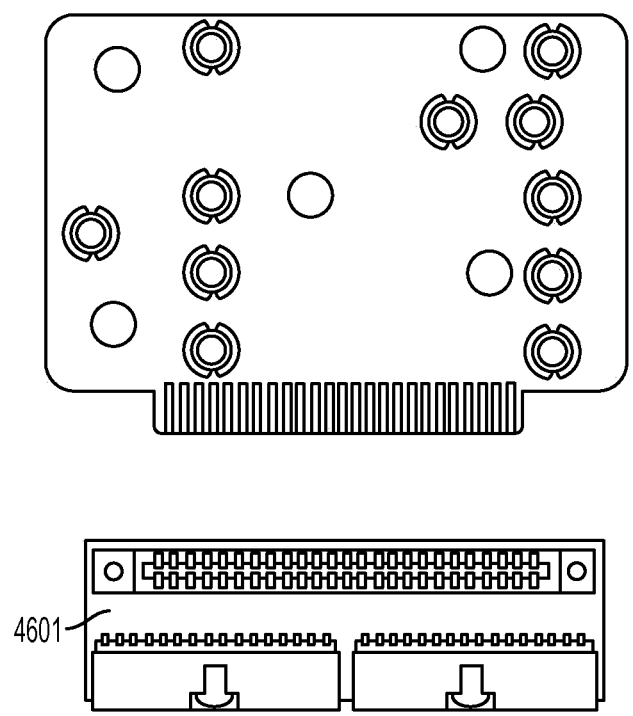
FIG. 58 is a view of a printed circuit board and media edge connector in accordance with the exemplary sensor manifold shown in FIG. 53.

Referring again to FIG. 55, in these exemplary embodiments of sensor manifolds that may be used in conjunction with the sensor apparatus and sensor apparatus systems described herein, the sensor manifold 4100 may also include printed circuit board (PCB) 4304 and a PCB cover 4305. Various embodiments may also include connector 4303 (also shown in FIGS. 53 and 56B) which may be utilized to mechanically connect the cassette manifold 4100 to the system, such as a hemodialysis system. Cassette manifold 4100 may also utilize various methods to hold the layers of sensor manifold 4100 together as a unit. In various embodiments, as shown in FIG. 57, connectors 4306 (also shown in FIG. 56B), which in one embodiment is a screw, but in other embodiments may be any means for connection, are utilized, but any means known to one of skill in the art, such as other types of screws, welds, clips, clamps, and other types of chemical and mechanical bonds may be utilized.

Referring now to FIG. 56A, in exemplary embodiments of the sensor manifold 4100, tube connectors, such as tube connector 4401, is utilized to bring subject media into or remove subject media from fluid path 4402. Sensing probes, such as sensing probe 4404 extending into fluid path 4402, are incorporated into sensor manifold 4100 so as to determine various properties of the subject media contained in or flowing through the particular fluid path in the sensor manifold. In various embodiments one sensing probe may be utilized to sense temperature and/or other properties of the subject media. In another embodiment, two sensing probes may be utilized to sense temperature and/or conductivity and/or other properties of the subject media. In yet further embodiments, three or more sensing probes may be included. In some embodiments, one or more combination temperature and conductivity sensing probes of the types generally described herein may be utilized. In other embodiments, the conductivity sensors and temperature sensor can be any conductivity or temperature sensor in the art. In one embodiment, the conductivity sensor elements (or sensor leads) are graphite posts. In other embodiments, the conductivity sensors elements are posts made from stainless steel, titanium, or any other material of the type typically used for (or capable of being used for) conductivity measurements. In certain embodiments, the conductivity sensors will include an electrical connection that transmits signals from the sensor lead to a sensor mechanism, controller or other device. In various embodiments, the temperature sensor can be any of the temperature sensors commonly used (or capable of being used) to sense temperature.

Figure 53:
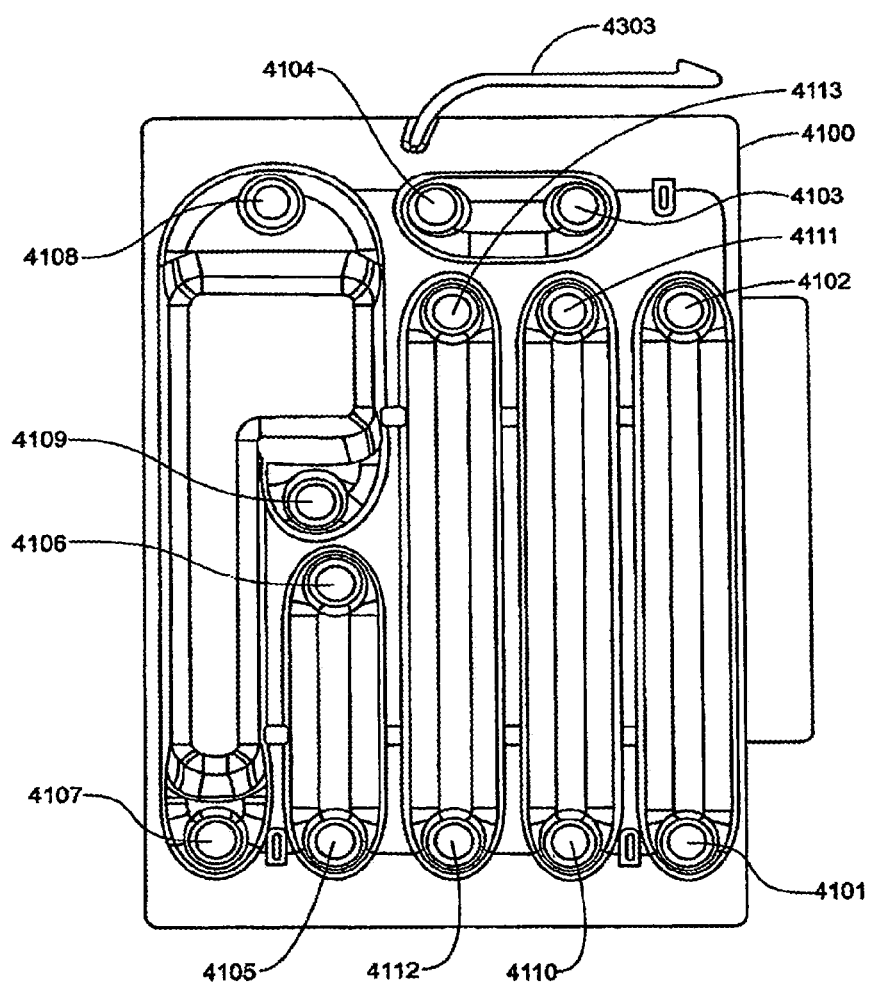
FIG. 53 is a view of another exemplary sensor manifold.

Referring again to FIG. 56A, sensing probe 4404 is electrically connected to PCB 4405. In certain embodiments, an electrically conductive epoxy is utilized between sensor element 4404 and PCB 4405 to ensure appropriate electrical connection, although other methods known to those of skill in the art may be used to obtain an appropriate electrical connection between sensor element 4404 and PCB 4405. PCB 4405 is shown with edge connector 4406. In various embodiments, edge connector 4406 may be used to transmit sensor information from cassette manifold 4100 to the main system. Edge connector 4406 may be connected to a media edge connector (such as media edge connector 4601 shown in FIG. 58). In various embodiments, media edge connector 4601 may be installed in a hemodialysis machine (not shown). In such embodiments, guide tracks 4310 and 4311 (as shown in FIG. 55) may be utilized to assist in the connection of edge connector 4406 and media edge connector 4601. Various embodiments may also include connector 4303 (as shown in FIGS. 53, 55 and 56B) which may be utilized to mechanically connect the cassette manifold 4100 to the system, such as a hemodialysis system.

Referring again to FIG. 56A, air trap 4410 is shown. In certain embodiments, an air trap, such as air trap 4410, may be utilized to trap and purge air in the system. As may be best shown in FIG. 54, subject media may flow through fluid path 4222 between tube connectors 4107 and 4109 in sensor manifold 4100. As the flow of the subject media is slowed around the turn in fluid path 4222 (near tube connector 4108), air may be removed from the subject media through connector 4108.

Referring now to FIG. 56B, PCB cover 4305 is shown. PCB cover 4305 may be connected to sensor manifold 4100 by connectors 4306. Edge connector 4406 is also shown.

In accordance with certain embodiments, sensor manifold 4100 is passive with respect to control of the fluid flow. In such embodiments, sensor manifold 4100 does not contain valves or pumping mechanisms to control the flow of the subject media. In such embodiments, the flow of the subject media may be controlled by fluid control apparatus external to sensor manifold 4100. In other embodiments, the sensor manifold may include one or more mechanical valves, pneumatic valves or other type of valve generally used by those of skill in the art. In such embodiments, the sensor manifold may include one or more pumping mechanisms, including pneumatic pumping mechanisms, mechanical pumping mechanisms, or other type of pumping mechanisms generally used by those of skill in the art. Examples of such valves and pumping mechanisms may include the valves and pumping mechanisms described in U.S. patent application Ser. No. 11/871,680, filed Oct. 12, 2007 entitled "Pumping Cassette"; or U.S. patent application Ser. No. 12/038,648, entitled "Cassette System Integrated Apparatus," filed on Feb. 27, 2008.

Referring now to FIG. 57, tube connector 4401 is shown in base 4301. Top plate 4302 is shown, along with connector 4303. Sensing probes, such as sensing probe 4501, extend through top plate 4302 into fluid path 4503. Sensing probe 4501 may be various types of sensors, including the embodiments of sensing probes generally discussed herein.

The sensing probes, such as sensing probe 4501, may be all the same, may be individually selected from various sensors based on the type of function to be performed, or the same probe may be individually modified based on the type of function to be performed. Similarly, the configuration of the fluid paths, such as the length of the fluid path and the shape of the fluid path, may be selected based on the function to be performed. By way of example, to detect the temperature of the subject media in a fluid path, a temperature sensor, such as a thermistor, may be used. Again, by way of example, to measure the conductivity of the subject media, one sensing probe configured to measure temperature and conductivity, and one sensing probe configured only to measure conductivity may be utilized. In other embodiments, two or more sensing probes configured to measure both temperature and conductivity may be utilized. In various embodiments of such configurations, by way of example, the second temperature sensor may be present but not utilized in normal operation, or the second temperature may be utilized for redundant temperature measurements, or the or the second temperature may be utilized for redundant temperature measurements.

Referring again to FIG. 57, PCB 4502 is shown with electrical connection 4503. As further shown in FIG. 58, PCB 4602 is shown with electrical connection 4603 for connection to a sensing probe (shown as 4501 in FIG. 45). PCB 4602 also contains opening 4604 for attachment to top plate (shown as 4305 in FIG. 57). In certain embodiments, electrical connection 4603 is mounted onto, or manufactured with, PCB 4602 with air gap 4606. In such embodiments, air gap 4606 may be utilized to provide protection to the electrical connection between sensing probe 4501 and PCB 4602 by allowing shrinking and expansion of the various components of sensor manifold 4100 with lesser impact to PCB 4602.

Referring again to FIG. 58, PCB 4602 is also shown with edge connector 4605. As described herein, edge connector 4605 may interface with edge connector receiver 4601, which may be connected to the system, such as the hemodialysis system, to which sensor manifold 4100 interfaces.

Figure 59:
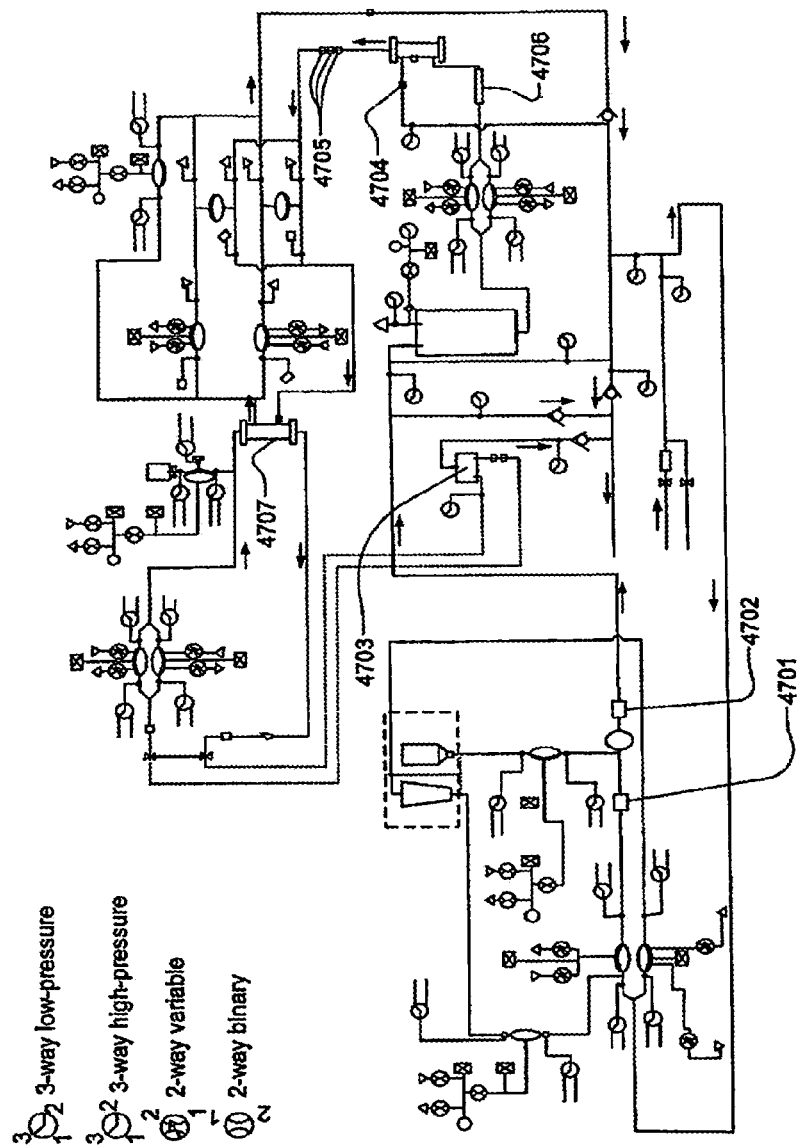
FIG. 59 is an exemplary fluid schematic of a hemodialysis system.

Various embodiments of exemplary sensor manifold 4100 shown in FIG. 53-58 may be utilized in conjunction with hemodialysis systems and methods described in U.S. patent application Ser. No. 11/871,680, filed Oct. 12, 2007 entitled "Pumping Cassette"; or U.S. patent application Ser. No. 12/038,648, entitled "Cassette System Integrated Apparatus," filed on Feb. 27, 2008. In certain embodiments, sensor manifold 4100 contains all of the temperature and conductivity sensors shown in FIG. 59. FIG. 59 depicts a fluid schematic in accordance with one embodiment of the inventions described in the patent applications reference above.

By way of example, in various embodiments, the temperature and conductivity of the subject media at position 4701 as shown in FIG. 59 may be determined utilizing sensor manifold 4100. In such embodiments, subject media flows into tube connector 4105 (as shown in FIG. 53) through fluid path 4220 (as shown in FIG. 54) and exits at tube connector 4106 (as shown in FIG. 53). The conductivity of the subject media is measured by two sensing probes (not shown) extending into fluid path 4220, at least one of which has been configured to include a temperature sensing element, such as a thermistor. The conductivity measurement or the temperature measurement of the subject media may be utilized to determine and/or correlate a variety of information of utility to the hemodialysis system. For example, in various embodiments at position 4701 in FIG. 59, the subject media may be comprised of water to which a bicarbonate-based solution has been added. Conductivity of the subject media at position 4701 may be utilized to determine if the appropriate amount of the bicarbonate based solution has been added prior to position 4701. In certain embodiments, if the conductivity measurement deviates from a predetermined range or deviates from a predetermined measurement by more than a predetermined amount, then the subject media may not contain the appropriate concentration of the bicarbonate based solution. In such instances, in certain embodiments, the hemodialysis system may be alerted.

Again, by way of example, in various embodiments, the conductivity of the subject media at position 4702 as shown in FIG. 59 may be determined utilizing sensor manifold 4100. In such embodiments, subject media flows into tube connector 4112 (as shown in FIG. 53) through fluid path 4221 (as shown in FIG. 54) and exits at tube connector 4113 (as shown in FIG. 53). The conductivity of the subject media is measured by two sensing probes (not shown) extending into fluid path 4221, at least one of which has been configured to include a temperature sensing element, such as a thermistor. The conductivity measurement or the temperature measurement of the subject media may be utilized to determine and/or correlate a variety of information of utility to the hemodialysis system. For example, in various embodiments at position 4702 in FIG. 59, the subject media may be comprised of water to which a bicarbonate-based solution and then an acid based solution has been added. Conductivity of the subject media at position 4702 may be utilized to determine if the appropriate amount of the acid based solution (and the bicarbonate based solution in a previous step) has been added prior to position 4702. In certain embodiments, if the conductivity measurement deviates from a predetermined range or deviates from a predetermined measurement by more than a predetermined amount, then the subject media may not contain the appropriate concentration of the acid based solution and the bicarbonate based solution. In such instances, in certain embodiments, the hemodialysis system may be alerted.

By way of further example, in various embodiments, the temperature and conductivity of the subject media at position 4703 as shown in FIG. 59 may be determined utilizing sensor manifold 4100. In such embodiments, subject media may flow into or out of tube connector 4107 (as shown in FIG. 53) through fluid path 4222 (as shown in FIG. 54) and may flow into or out of tube connector 4109 (as shown in FIG. 53). As described herein, air may be removed from the subject media as it moves past the turn in fluid path 4222. In such instances, a portion of the subject media may be removed through tube connector 4108 to the drain, bringing with it air from the air trap. The conductivity of the subject media is measured by two sensing probes (not shown) extending into fluid path 4222, at least one of which has been configured to include a temperature sensing element, such as a thermistor. The conductivity measurement or the temperature measurement of the subject media may be utilized to determine and/or correlate a variety of information of utility to the hemodialysis system. For example, in various embodiments, the conductivity measurement at position 4703 in FIG. 59 may be utilized to correlate to the clearance of the dialyzer. In such instances, in certain embodiments, this information may then be sent to the hemodialysis system.

Again, by way of further example, in various embodiments, the temperature of the subject media at position 4704 as shown in FIG. 59 may be determined utilizing sensor manifold 4100. In such embodiments, subject media flows into tube connector 4103 (as shown in FIG. 53) through fluid path 4223 (as shown in FIG. 54) and exits at tube connector 4104 (as shown in FIG. 53). The temperature of the subject media is measured by one or more sensing probes (not shown) extending into fluid path 4223. The temperature measurement of the subject media at position 4704 may be utilized to determine and/or correlate a variety of information of utility to the hemodialysis system. For example, in various embodiments at position 4704 in FIG. 59, the temperature of the subject media is determined down stream of a heating apparatus 4706. If the temperature deviates from a predetermined range or deviates from a predetermined measurement by more than a predetermined amount, then the hemodialysis system may be alerted. For example in certain embodiments, the subject media may be re-circulated through the heating apparatus 4706 until the temperature of the subject media is within a predetermined range.

Again, by way of further example, in various embodiments, the temperature and conductivity of the subject media at position 4705 as shown in FIG. 59 may be determined utilizing sensor manifold 4100. In such embodiments, subject media flows into tube connector 4110 (as shown in FIG. 53) through fluid path 4224 (as shown in FIG. 54) and exits at tube connector 4111 (as shown in FIG. 53). The conductivity of the subject media is measured by two sensing probes (not shown) extending into fluid path 4224, at least one of which has been configured to include a temperature sensing element, such as a thermistor. The conductivity measurement or the temperature measurement of the subject media may be utilized to determine and/or correlate a variety of information of utility to the hemodialysis system. For example, the temperature and conductivity measurement at position 4705 may be used as a further safety check to determine if the temperature, conductivity, and, by correlation, the composition of, the subject media is within acceptable ranges prior to the subject media reaching the dialyzer 4707 and, thus, the patient. In certain embodiments, if the temperature and/or conductivity measurement deviates from a predetermined range or deviates from a predetermined measurement by more than a predetermined amount, then the hemodialysis system may be alerted.

For the various embodiments described herein, the cassette may be made of any material, including plastic and metal. The plastic may be flexible plastic, rigid plastic, semi-flexible plastic, semi-rigid plastic, or a combination of any of these. In some of these embodiments the cassette includes one or more thermal wells. In some embodiments one or more sensing probes and/or one or more other devices for transferring information regarding one or more characteristics of such subject media are in direct contact with the subject media. In some embodiments, the cassette is designed to hold fluid having a flow rate or pressure. In other embodiments, one or more compartments of the cassette is designed to hold mostly stagnant media or media held in the conduit even if the media has flow.

In some embodiments, the sensor apparatus may be used based on a need to separate the subject media from the sensing probe. However, in other embodiments, the sensing probe is used for temperature, conductivity, and/or other sensing directly with subject media.

Another aspect of the invention is generally directed to methods and operations of the systems as discussed herein. For instance, a hemodialysis system may be primed, flow-balanced, emptied, purged with air, disinfected, or the like.

Figure 17A:
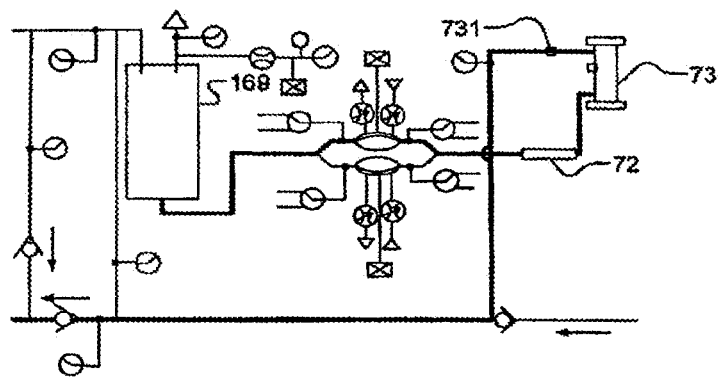
FIGS. 17A-17C are schematics relating to the priming of a portion of a system, in one embodiment of the invention.

One set of embodiments is generally directed to priming of the system with a fluid. The fluid to be primed is first directed to a dialysate tank (e.g. dialysate tank 169). Ultrafilter 73 is then first primed by pushing fluid from dialysate tank 169 to ultrafilter 73, and caused to exit line 731 through waste line 39 to the drain, as is shown by the heavy black lines in FIG. 17A. Any air present in ultrafilter 73 naturally rises to the priming port and is flushed to the drain.

Figure 17B:
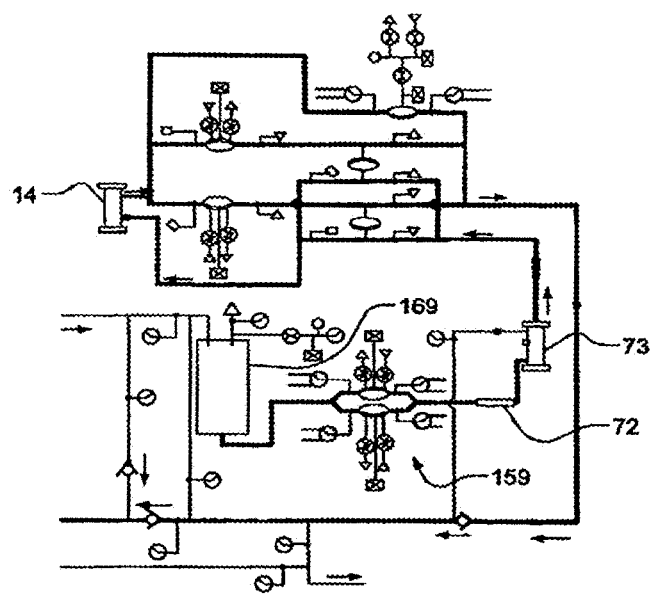

Next, as is shown in FIG. 17B, the balancing circuit and pump 159 of the directing circuit are primed by pushing fluid through the ultrafilter 73, through the balancing circuit, and out to the drain. Pump 159 is primed by running fluid forwards (through the ultrafilter to the drain). Air entering dialyzer 14 bubbles to the top of the dialyzer and leaves through the dialyzer exit to the drain.

Figure 17C:
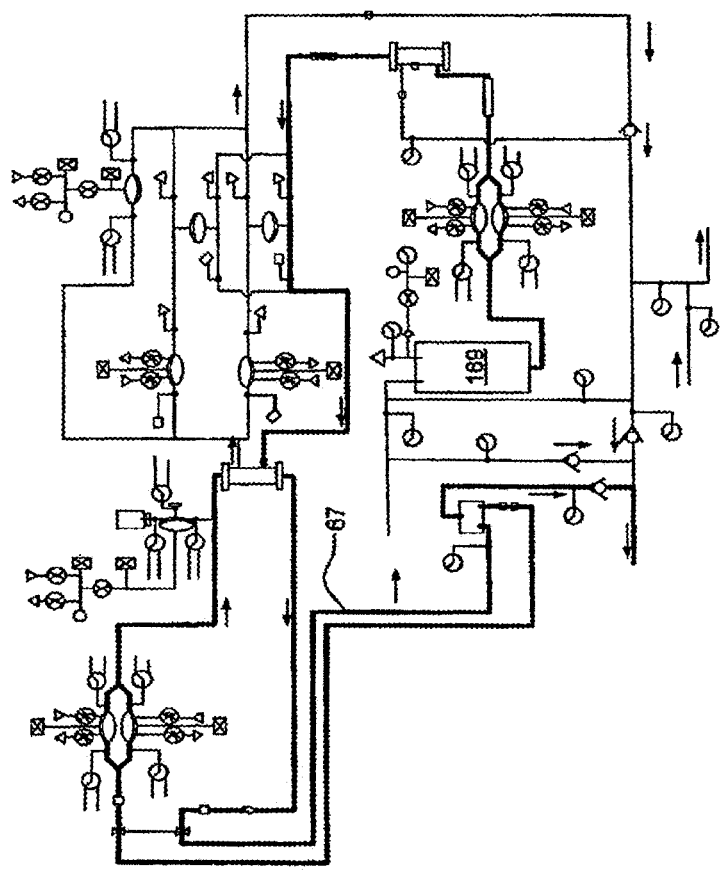

Next, the blood flow pump and tubing are primed by circulating fluid through the blood flow circuit and the air trap back to the directing circuit via conduit 67. As can be seen in FIG. 17C, fluid passes through the ultrafilter and dialyzer, forcing flow through the air trap and down the drain. The air trap traps air circulating in the blood flow circuit and sends it to the drain. Priming can be stopped when the air sensors stop detecting air (and some additional fluid has been passed through the system, as a safety margin).

Figure 19:
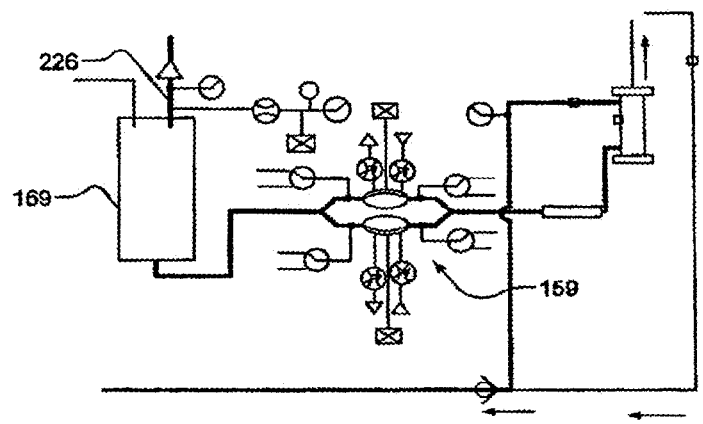
FIG. 19 illustrates emptying of a dialysate tank, in another embodiment of the invention.

Another set of embodiments is directed to adding air to the system, e.g., to empty the system of various fluids. For example, in one operation the dialysate tank is emptied. Vent 226 on dialysate tank 169 is opened, and pump 159 is used to pump fluid from the dialysate tank to the drain until air is detected in pump 159 (discussed below). This is shown in FIG. 19.

Figure 20:
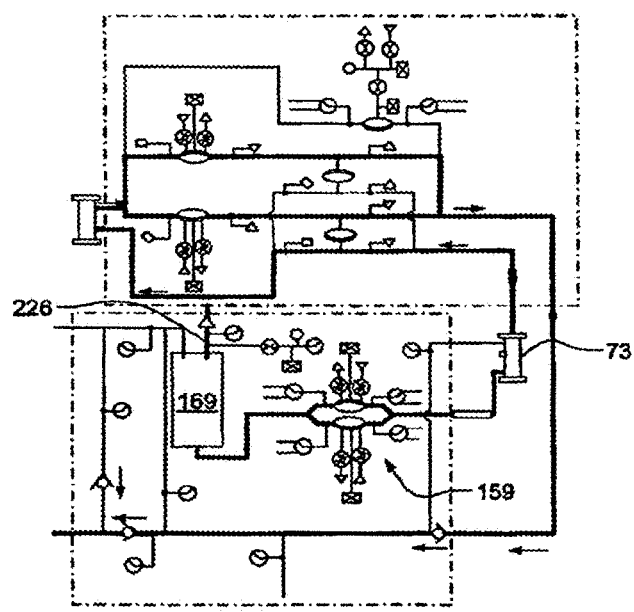
FIG. 20 illustrates the purging of the system with air at the end of treatment according to one embodiment of the invention.

Air may also be pumped into the balancing circuit in certain embodiments. This is shown in FIG. 20. Vent 226 on dialysate 16 is opened so that air may enter the dialysate tank. Pump 159 is used to pump air through the outside of ultrafilter 73. This air pressure displaces fluid outside the ultrafilter to the inside, then it flows through the dialyzer and down the drain. During this operation, pump 159 and the outside of the ultrafilter will fill with air.

Figure 21A:
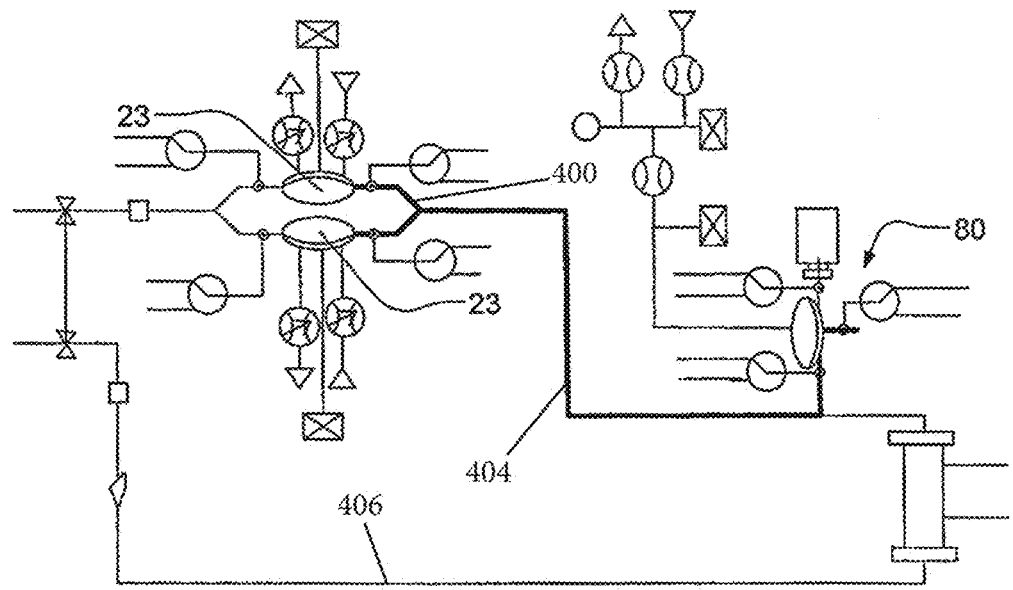
FIGS. 21A-21C illustrate the drawing of air in an anticoagulant pump, in still another embodiment of the invention.

In addition, air can be drawn in through the anticoagulant pump 80 into the blood flow circuit, as is shown in FIG. 21A. The air is first brought into pod pumps 23 (FIG. 21A), then may be directed from the pod pumps to the arterial line 203 and down the drain (FIG. 21B), or to the venous line 204 (through dialyzer 14) and down the drain (FIG. 21C).

In one set of embodiments, integrity tests are conducted. As the ultrafilter and the dialyzer may be constructed with membrane material that will not readily pass air when wet, an integrity test may be conducted by priming the filter with water, then applying pressurized air to one side of the filter. In one embodiment, an air outlet is included on one of the blood flow pumps and thus, the pumping chamber may be used to pump air for use in the integrity test. This embodiment uses the advantage of a larger pump. The air pressure pushes all of the water through the filter, and the air flow stops once the water has been displaced. However, if the air flow continues, the membrane is ruptured and must be replaced. Accordingly, the system is primed with water. First, the mixing circuit is primed first to eliminate air prior to the dialysate tank. Then the outside of the ultrafilter is primed next, as the ultrafilter will not pass water to the balancing circuit until the outside is primed. The balancing circuit and the dialyzer are primed next. Finally, water is pushed across the dialyzer to prime the blood flow circuit.

Figure 22A:
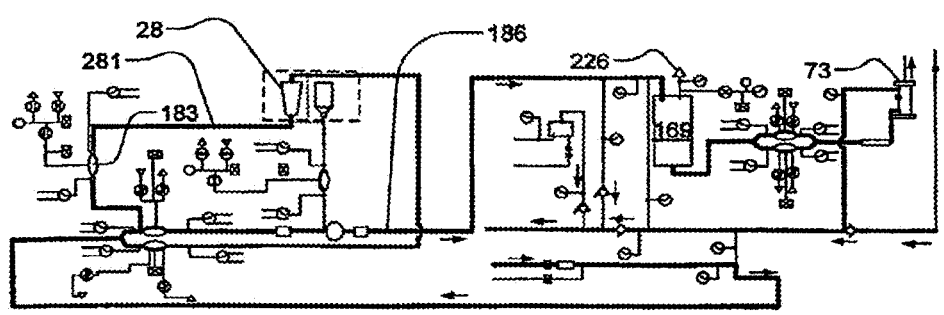
FIGS. 22A-22D illustrate integrity tests according to certain embodiments of the invention.
Figure 22B:
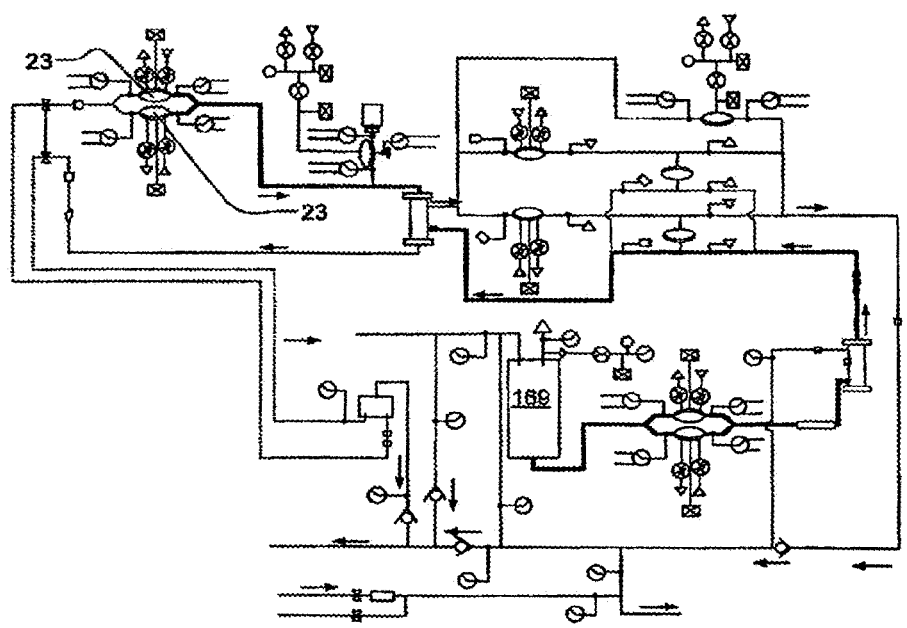
Figure 22C:
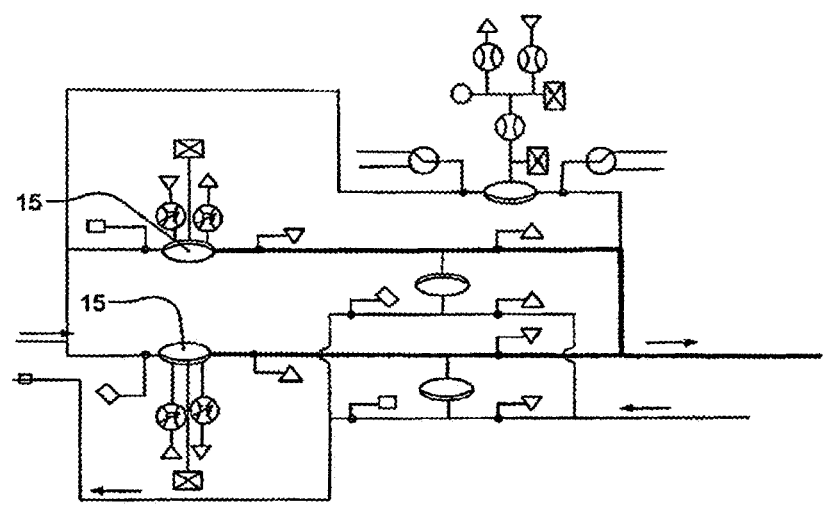

The mixing circuit is primed by first pushing water with pump 183, through line 281 and bicarbonate source 28, then through each of the pumps and through line 186 to dialysate tank 169. Dialysate tank 169 is vented so air that is pushed through bubbles to the top and leaves through vent 226. Once air has been primed out of dialysate tank 169, the tank is filled with water, then the priming flow continues from the dialysate tank through ultrafilter 73 to the drain. This can be seen in FIG. 22A. Water is then primed as previously discussed (see FIGS. 17A-17C). Next, the blood flow pod pumps 23 are filled with water from dialysate tank 169, as is shown in FIG. 22B, while balancing pumps 15 are emptied, as is shown in FIG. 22C.

Figure 22D:
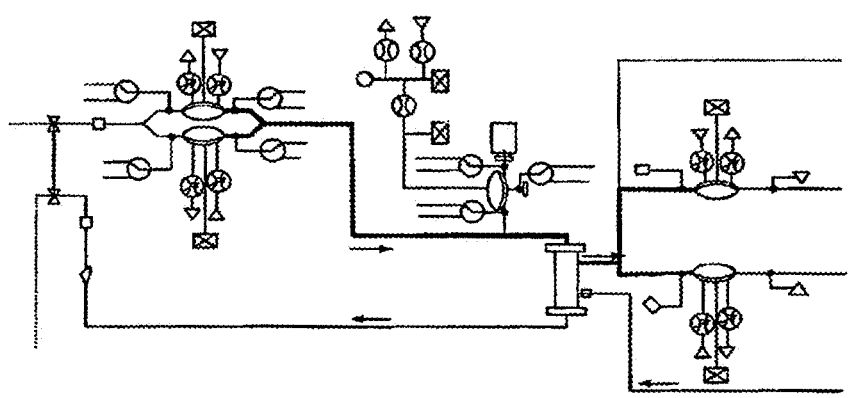

The test is conducted by using the blood flow pump to push each chamber of water across dialyzer 14 to balancing pump chambers 15, which start empty (FIG. 22C) and are vented to the atmosphere so that they are present at atmospheric pressure on the dialysate side of dialyzer 14. See FIG. 22D. Each of the blood flow circuit chambers delivers using a specific pressure and the end-of-stroke is determined to determine the flow rate.

Another integrity test is the ultrafilter flow test. In this test, the dialysate tank is filled with water, the ultrafilter is primed by pumping water from the dialysate tank through the ultrafilter and out line 731, and water is pumped through the ultrafilter, controlling flow rate, monitoring the delivery pressure required to maintain flow.

Another set of embodiments are directed to disinfection and rinsing of the system. This process removes any material which may have accumulated during therapy, and kills any active pathogens. Typically, heat is used, although in some cases, a disinfectant may be added. Water is maintained using the dialysate tank and replenished as necessary as water is discharged.

Figure 23:
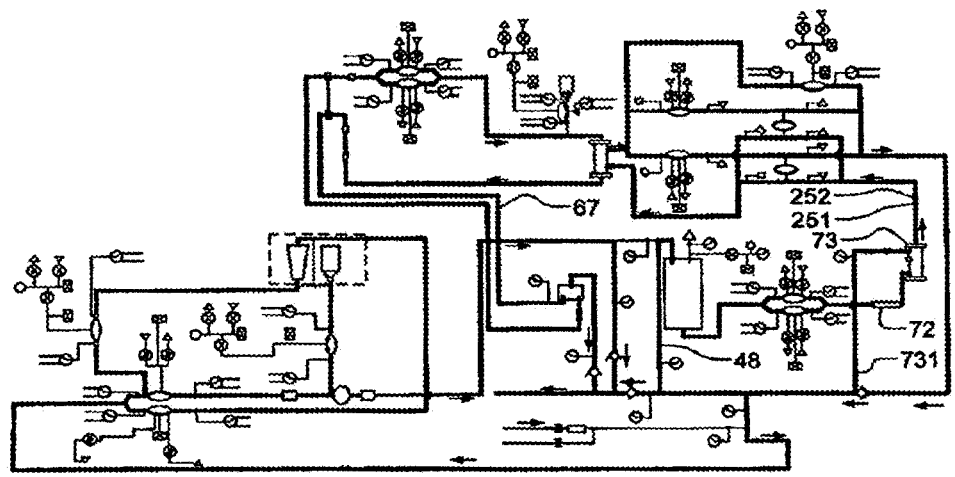
FIG. 23 illustrates a recirculating flow path, in another embodiment of the invention.

A recirculating flow path is shown in FIG. 23. The flow along this path is essentially continuous, and uses conduits 67 to connect the blood flow circuit with the directing circuit. The main flow path is heated using heater 72, which is used to increase the water temperature within the recirculating flow path, e.g., to a temperature that can kill any active pathogens that may be present. Most of the water is recirculated, although some is diverted to drain. Note that lines 48 and 731 are kept open in this example to ensure that these lines are properly disinfected. In addition, the flow paths through ultrafilter 73 can be periodically selected to purge air from the ultrafilter, and/or to provide recirculating flow through this path. Temperature sensors (e.g., sensors 251 and 252) can be used to ensure that proper temperatures are met. Non-limiting examples of such sensors can be seen in U.S. patent application Ser. No. 12/038,474, entitled "Sensor Apparatus Systems, Devices and Methods," filed on Feb. 27, 2008, and incorporated herein by reference.

Figure 24A:
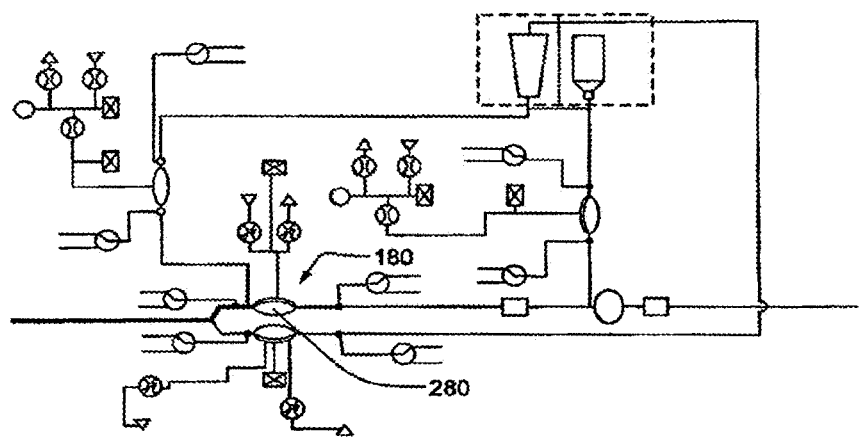
FIGS. 24A-24D illustrate the priming of a system with dialysate, in yet another embodiment of the invention.
Figure 24B:
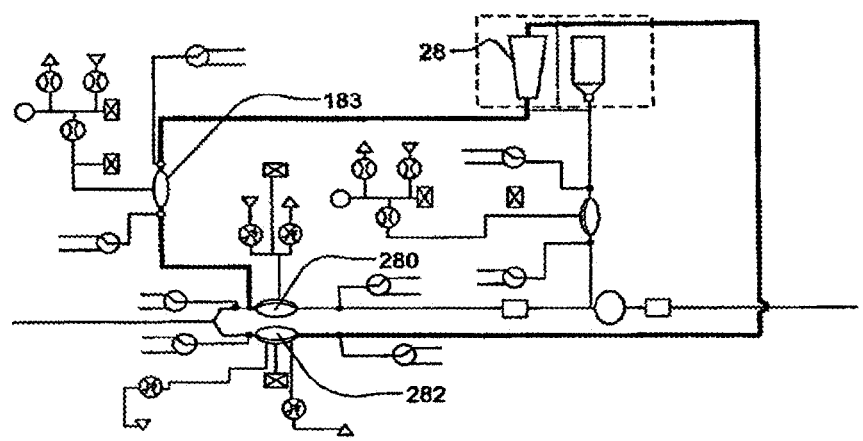
Figure 24D:
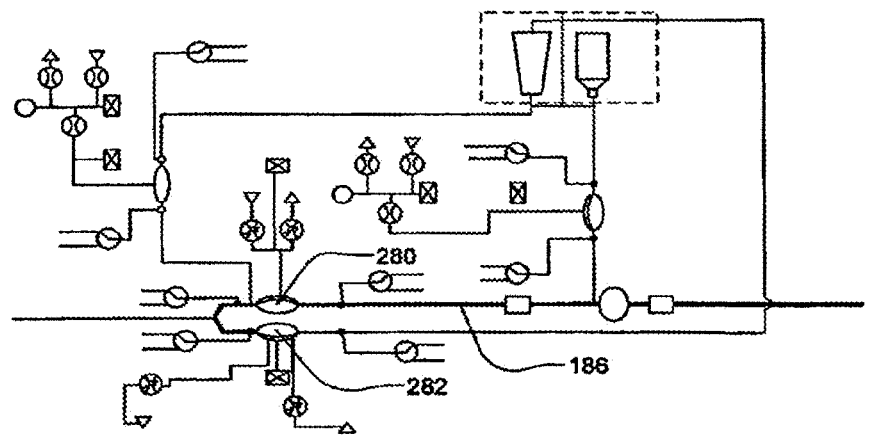

In one set of embodiments, the ingredients 49 of the mixing circuit 25 may be primed as follows. Initially and as shown schematically in FIG. 24A, a mix water pod pump 280 is filled with water, which is pushed backwards through a bicarbonate pump 183 and into a bottom of the bicarbonate source 28 so that air is expelled from the top of bicarbonate source 28 and into a line leading to a bicarbonate water supply pump 282. As a result, air in the bicarbonate source 28 is collected in the bicarbonate water supply pump 282. See FIG. 24B. The air in pump 282 is then transferred to the mix water pump 280, which moves the air into the line 186 toward the dialysate tank 169. See FIG. 24D. Air pushed by the mix water pump 280 may be moved into the dialysate tank 169, where a vent 226 in the dialysate tank 169 is opened to release the air from the system, or the air can be pushed toward the drain 31 through suitable valve control. See FIG. 3A. The process of moving water backwards from the mix water pump 280, through the bicarbonate pump 183, the bicarbonate source 28, the bicarbonate water supply pump 282 and to the mix water pump 280 may be repeated as many times as necessary to remove air from the flow path and thoroughly wet the bicarbonate supply 28 as needed. Also, by pushing the air and priming liquid from the mix water pump 280 to the drain 31 instead of the dialysate tank 169, the system may avoid adding improperly mixed bicarbonate/water material to the tank 169.

With the bicarbonate supply 28 and related circuitry (the bicarbonate path) primed in reverse, the bicarbonate path may be primed in the forward direction. That is, water may be moved by the bicarbonate water supply pump 280 into the bicarbonate source 28, through the bicarbonate pump 183 and to the mix water pump 280 as needed to remove any remaining air and prepare the bicarbonate path for providing bicarbonate at a suitable concentration to the water mix pump 280 for dialysate preparation. Liquid delivered to the water mix pump 280 during forward priming of the bicarbonate path may be directed by the pump 280 to the drain 31.

Figure 24C:
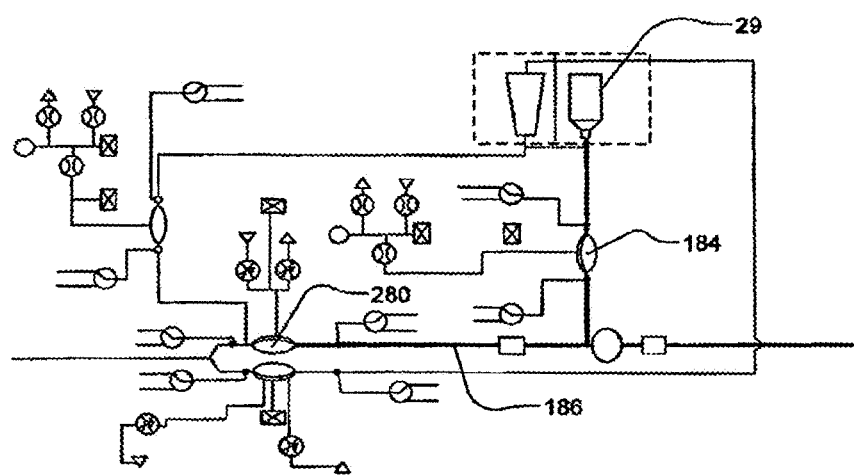

To prime the acid path, i.e., the circuit portion including the acid supply 29 and the acid pump 184, the acid pump 184 may be operated to deliver liquid to the mix water pump 280, which can subsequently direct the priming liquid to the drain 31. See FIG. 24C. This can be repeated as necessary until the acid path is suitably primed. Typically, the acid supply 29 will be in liquid form ready for use (unlike the bicarbonate supply 28), but if not, the mix water pump 280 can be used to direct water in reverse direction through the acid pump 184 and into the acid supply 29. (Any needed air venting may be performed at the acid supply 29, e.g., through a valve or opening in an acid container.) After priming is complete, the mix water pump 280 may direct water through the line 186 to drain 31 to clear the line 186 and other components of any remaining air or other materials.

The acid and bicarbonate solutions (and sodium chloride solution, if a separate sodium chloride source is present) are then metered with incoming water to prepare the dialysate. Sensors 178 and 179 are used to ensure that the partial mixtures of each ingredient with water is correct. Dialysate that does not meet specification is emptied to the drain, while good dialysate is pumped into dialysate tank 14.

As discussed above in the context of FIGS. 7A, 7B, 24A-D, 46 D-E and 51B, the present invention in certain embodiments provides methods and control systems configured for making dialysate "in system" from a water supply and one or more supplies of concentrated sources of solutes (e.g. bicarbonate source 28 and acid source 29). Described below are exemplary embodiments for implementing and controlling such methods the incremental assembly of the dialysate to ensure that the specifications on concentration remain within acceptable quality criteria.

Referring to mixing circuit 25 of FIG. 7A, in certain embodiments, a hemodialysis system of the invention is configured to make dialysate for hemodialysis therapy using standard, commercially available 45X acid concentrate (e.g. from acid concentrate supply 29). In other embodiments, any of a variety of other standard or custom recipes may be implemented using the methods described herein. Sodium bicarbonate is drawn from a flow-through cartridge 28 (e.g. a Baxter Altracart cartridge or similar). Essentially pure water is pumped into the top of this cartridge and concentrated solution is drawn from the bottom. The strength of the concentrated solution varies with the temperature of the cartridge and may also be affected by any channeling through the powder that develops while the cartridge is in use.

Water is drawn into the mixing water pump 180. The concentrated sodium bicarbonate solution is metered into the water stream by the bicarbonate pump 183 as the chamber of pump 180 is filling. This gives the water/bicarb mixture a chance to mix in the pumping chamber. This partial mixture of water and sodium bicarbonate is pumped out of the pump 180 and through the conductivity measurement cell 178 for conductivity measurement. The target conductivity of this partial mixture in one embodiment is approximately 3.7 mS/cm, so, in such an embodiment, conductivity measurement cell 178 may be optimized for measurements near this value. The acid pump 184 then meters acid concentrate solution (e.g. 45X acid concentrate) into the partial mixture. This flow proceeds through mixing chamber 189 and then to the conductivity measurement cell 179. The final conductivity to yield a target dialysate concentration in one embodiment is approximately 14 mS/cm, so, for such an embodiment, the conductivity measurement cells for measuring dialysate conductivity (e.g. cells 179 and 253 (see e.g. FIG. 6)) may be optimized for measurements near this value.

In certain embodiments, because the conductivity measurement cells 178 and 179 measure solutions that may not be homogenous—there still may be significant variations in concentration of the solutions as they pass through these sensors, to get a more accurate value for the conductivity, a plurality of individual measurements are taken and these measurements are averaged at high speed (e.g. 200 Hz), only while the solution is flowing through the conductivity measurement cells. The resulting averaged measurement has been found to correlate well with a measurement obtained by collecting the solution in a container and mixing it thoroughly prior to measuring conductivity.

Because the conductivity of these solutions may be highly dependent on temperature, e.g. changing about 2% per degree C., in certain embodiments, to improve the accuracy of conductivity measurements, a temperature correction may be applied. In certain cases, the effect of temperature change on change in measured conductivity is almost linear, but the nonlinear characteristic may in certain cases be significant enough that a second or third-order curve fit of conductivity-vs-temperature data may provide a significant benefit in the context of performing temperature correction. In certain embodiments, two conductivity-vs-temperature curves are utilized, one for correction of conductivity measurements of the sodium bicarbonate solution and another for conductivity measurements of the final dialysate solution. These corrections may be expressed as a multiplier to be chosen based on temperature. By convention, conductivity is normally expressed at 25 C. The correction curves thus may be constructed to yield a value of 1.0 for 25 C with a correction factor other than 1.0 at different measurement temperatures. The correction factors derived from the curves for the bicarbonate solution correction and the dialysate correction can be slightly different due to the different compositions, but they both vary, in typical embodiments, from about 0.6 at 5 C to about 1.3 at 40 C.

Conductivity is a strong function of the ion density in solution, so the amount of sodium bicarbonate in the first solution and the amount of sodium chloride and other ions in the final solution may be inferred or directly determined from conductivity measurements, if desired, in certain embodiments Like the temperature corrections, the relationships between measured conductivity and solute concentration may be nearly linear, but the non-linear characteristic may be significant enough that a second or third-order curve fit of conductivity vs. concentration data to use as a correlation standard may provides a significant benefit in determining concentrations from measured conductivity data.

The desired amount of sodium bicarbonate in the final dialysate may be specified in grams per liter (or equivalently, milligrams per milliliter). To compute the compositions from conductivity, the conductivity measurement made by sensor 178 may first be corrected for temperature as described above, and then the composition may be computed using the conductivity vs. concentration data curve fits described above. The determination of an actual concentration from conductivity data can be beneficial, for certain embodiments, for at least two reasons: it puts the composition into the correct units for concentration, allowing the controller to focus on the relevant measurement; and it facilitates prediction of the composition on a pump stroke-by-pump stroke basis, which can facilitate a safety check that prevents off-spec dialysate from being added to the dialysate tank 169 (as described in more detail below). The acid concentrate contains multiple ingredients, with sodium chloride being the dominant contributor to the additional conductivity. With the sodium bicarbonate already in solution at measurement cell 179, the relevant conductivity measurement for determining just the contribution of the added acid concentrate is the difference between the conductivity measured by sensor 189 and the conductivity of the bicarbonate mixture measured by sensor 178.

In certain embodiments, a control system for controlling mixing and production of the dialysate may be configured and implemented as described below. An inner control loop may be configured to operate the pumps to deliver the concentrated solutions into the mix stream (e.g. to mixing chamber 189). At this control level, the target mix fractions may be specified in the target number of pump strokes of each concentrate to be added for each water pump stroke. For each water pump 180 stroke, the meter pumps 183, 184 may deliver the closest integer number of strokes to the respective target number and carry the leftover fraction forward to the next water pump stroke. This can allow the control system to adjust the ratios as floating-point quantities, even though they are implemented as integers.

In certain embodiments, a control system may be configured so that the conductivity measurements are used as the primary guidance function to make dialysate that meets a dialysate concentration quality control criteria, e.g. is within an acceptable range of concentration surrounding a prescription recipe. The strength of the concentrated ingredients may vary somewhat during the therapy. The stroke volume delivered by the water pump 180 may vary from stroke to stroke to a degree. Volume metering via use of conductivity feedback can ensure that these effects are mitigated and the dialysate comes out as close to the specified composition as possible or desirable. A bicarbonate control loop of the overall control protocol may be provided that uses the composition of the sodium bicarbonate partial mixture determined as described above as the an input measurement and determined the number of strokes of the bicarbonate pump per stroke of the water pump for subsequent dialysate mixing as its output. Similarly, an acid concentrate control loop may be configured to use the measured conductivity change as a result of adding the acid (as described above) as the input measurement and the number of strokes of the acid pump per stroke of the water pump for subsequent dialysate mixing as its output.

The control loops described above can be configured to correct for and handle routine variations in pump delivery volume, reagent concentration, etc. that may affect the dialyate composition. Additional safety features may be configured into the system design and/or control system to mitigate/account for significant disturbances and special circumstances that could lead to substantially off-spec dialysate. The dialysate stored in the tank must be within a certain percentage of a target composition to ensure patient safety, e.g. in one embodiment, the dialysate is maintained within 2.5% of the prescription/target composition at all times. For example, with such a safety criteria for an exemplary embodiment in which one complete stroke of the water pump 180 is 50 ml, and the minimum volume of dialysate maintained in the dialysate tank 169 is 1 liter, (i.e. a pump stroke volume in such case is 1/20 or 5% of the minimum one liter volume in the tank), one stroke of pure water inadvertently added to the tank could pull the dialysate composition off spec by 5%. To prevent such an occurrence from happening, the tubing hold-up volume between conductivity sensor 179 and the valve positioned just upstream of the dialysate tank (e.g. valve 147 in FIG. 6) is sized to hold a complete stroke of the mixing water pump 180. In general, if the measured composition of any stroke is determined by to be off-spec by enough to compromise the acceptability of the concentration of dialysate in the tank, should it be added to the tank, that stroke is diverted to drain (e.g. 31 in FIG. 6).

In one particular example, the following three safety checks are performed by the system and must all succeed before adding newly mixed dialysate to the tank: (1) the mix composition for the stroke bolus being measured, as determined by conductivity measured by sensor 179, must approximately match the target stroke composition for the volume of water and concentrate added—since, as described above, in certain embodiments, these quantities are quantized to full strokes, the target composition of a given stroke may be significantly different than the prescribed composition of the dialysate in the dialysate tank; (2) the running average composition for the previous 20 mixing strokes (1 liter for a pump stroke volume of 50 ml) must be within an acceptable percentage of the target prescription dialysate composition, e.g. within 2%; and (3) the calculated/projected composition of dialysate in the tank after adding the newly mixed but not yet added stroke bolus must be within an acceptable percentage of the target prescription dialysate composition, e.g. within 2%.

The control and safety system may also be configured in certain embodiments, to prevent hazards created by certain user error. For example, for embodiments in which conductivity is used as a parameter to determine solute concentration in mixed dialysate, there is a risk that a user mistakenly use a container that does not contain the proper acid concentrate called for in the therapy and expected by the system (e.g. 45X acid concentrate) and attempt to start a therapy with such incorrect reagents. With an unlimited conductivity feedback system, there is a significant risk that whatever material is drawn into mixing circuit could be mixed with water to make the expected conductivity for dialysate. To minimize the possibility of this happening, the control system may be configured to enforce pre-set limits on the water/acid concentrate mixing ratio. Both the pump 180 and the acid concentrate pump 184 are, in preferred embodiments, reasonably accurate volumetric pumps. The pre-set limits on the water/acid concentrate mixing ratio may be chosen to facilitate therapy in the face of normal variations while prohibiting therapy if it appears that the acid concentrate is not that called for by the therapy protocol (e.g. standard 45× concentrate).

In another set of embodiments, the anticoagulant pump is primed. Priming the pump removes air from the heparin pump and the flow path, and ensures that the pressure in the anticoagulant vial is acceptable. The anticoagulant pump can be designed such that air in the pump chamber flows up into the vial. The test is performed by closing all of the anticoagulant pump fluid valves, measuring the external volume, charging the FMS chamber with vacuum, opening valves to draw from the vial into the pumping chamber, measuring the external volume (again), charging the FMS chamber with pressure, opening the valves to push fluid back into the vial, and then measuring the external volume (again). Changes in external volume that result from fluid flow should correspond to the known volume of the pumping chamber. If the pumping chamber cannot fill from the vial, then the pressure in the vial is too low and air must be pumped in. Conversely, if the pumping chamber cannot empty into the vial, then the pressure in the vial is too high and some of the anticoagulant must be pumped out of the vial. Anticoagulant pumped out of the vial during these tests can be discarded, e.g., through the drain.

In yet another set of embodiments, the system is rinsed with dialysate while the patient is not connected. This can be performed before or after treatment. Prior to treatment, dialysate may be moved and a portion sent to the drain to avoid accumulating sterilant in the dialysate. After treatment, this operation rinses the blood path with dialysate to push any residual blood to the drain. The flow paths used in this operation are similar to the flow paths used with water, as discussed above.

Figure 25:
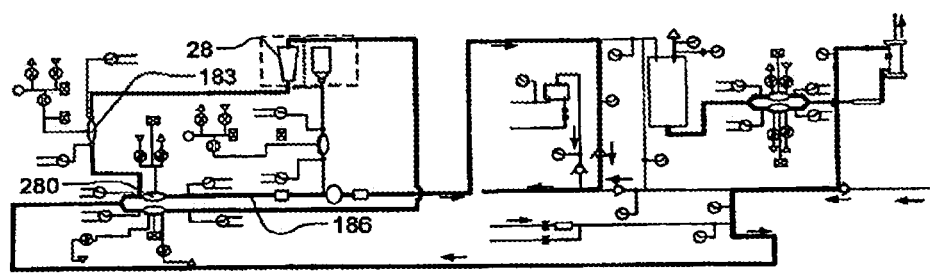
FIG. 25 illustrates the priming of an anticoagulant pump, in still another embodiment of the invention.

Acid concentrate may be pumped out of the mixing chamber. Pump 184 is activated so that pod pump 280 can draw out acid from pump 184 and acid source 29, to be mixed in line 186 and sent to the drain. Similarly, bicarbonate may be pumped out of the mixing chamber as is shown in FIG. 25. Pump 183 is used to draw water from bicarbonate source 28, then pod pump 280 is used to pass the water into line 186 to the drain.

Figure 26A:
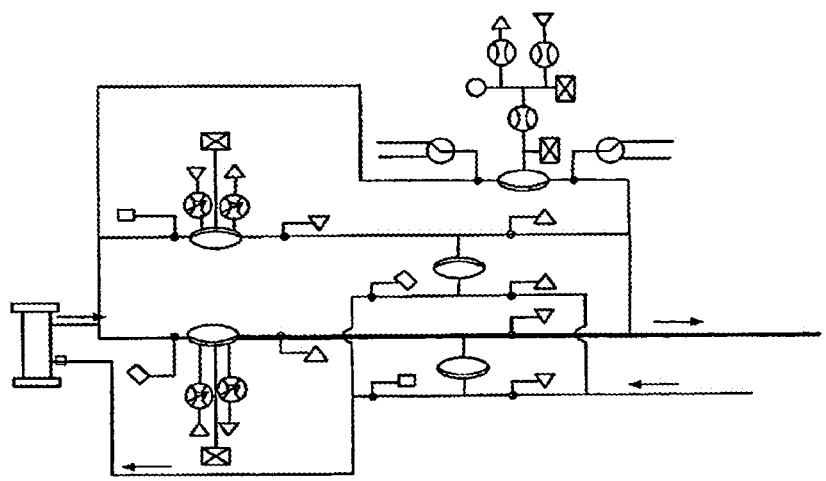
FIGS. 26A-26F illustrate the removal of dialysate from a blood flow circuit, in one embodiment of the invention.
Figure 26B:
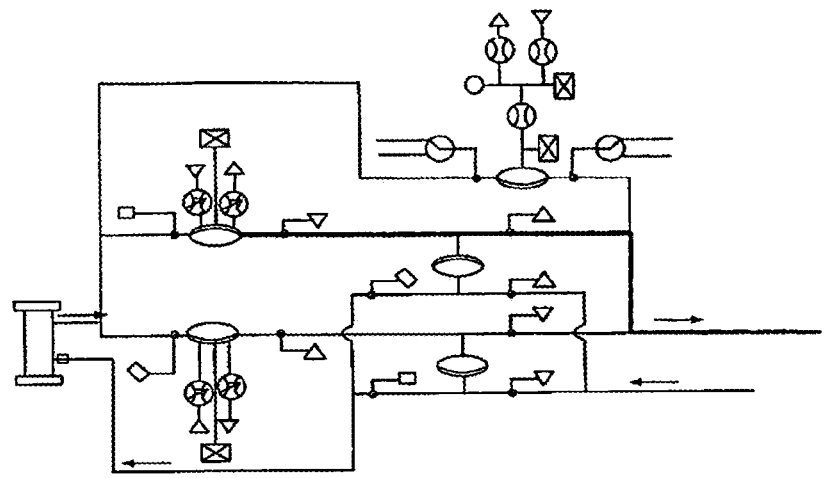
Figure 26C:
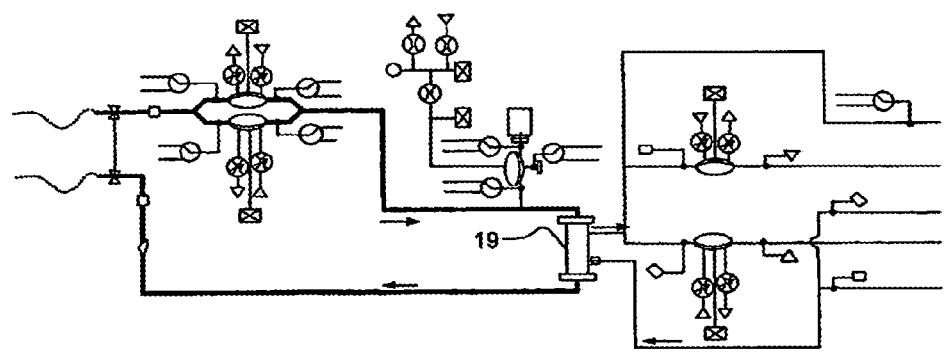
Figure 26D:
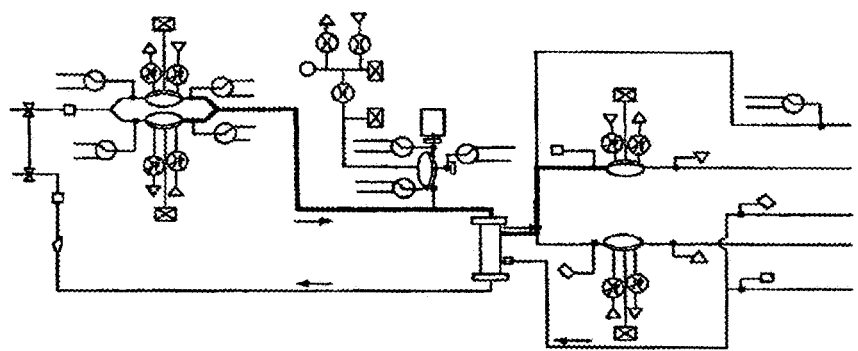
Figure 26E:
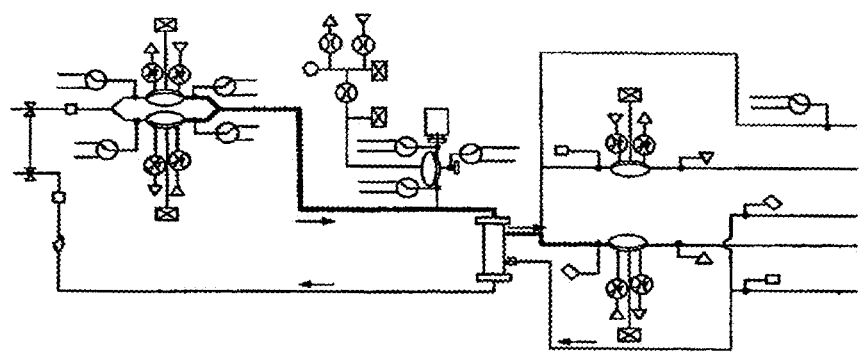
Figure 26F:
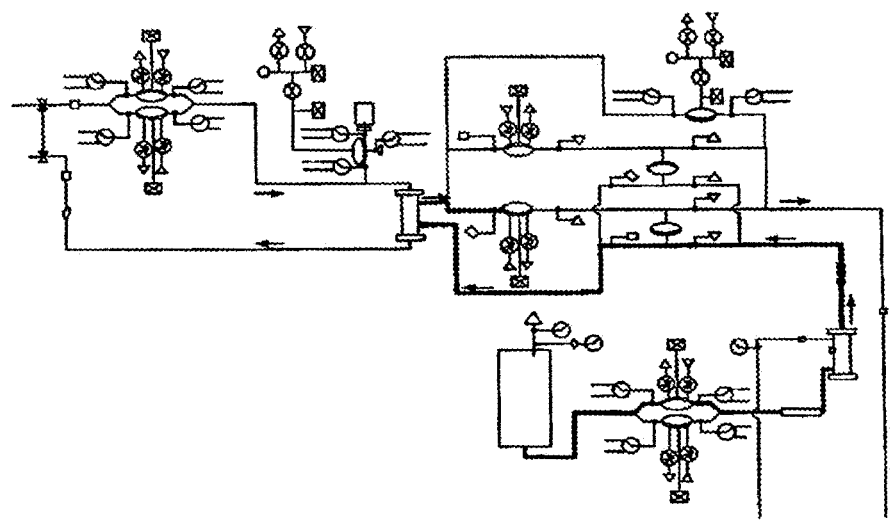

In still another set of embodiments, dialysate prime is removed from the blood flow circuit, to avoid giving the patient the priming fluid. FIGS. 26A and 26B show fluid leaving each of the balancing pump chambers and being expelled to the drain. Next, the dialysate side of dialyzer 14 is closed, while blood is drawn into the blood flow path from the patient (FIG. 26C). The patient connections are then occluded while the blood flow pump chambers 23 push the priming fluid across the dialyzer to the balancing circuit (FIGS. 26D and 26E). This fluid is then pushed to drain, as previously discussed. This operation can be repeated as necessary until sufficient priming fluid has been removed. Afterwards, the balancing pumps are then refilled with fresh dialysate, keeping the patient connections occluded, as is shown in FIG. 26F.

Figure 27A:
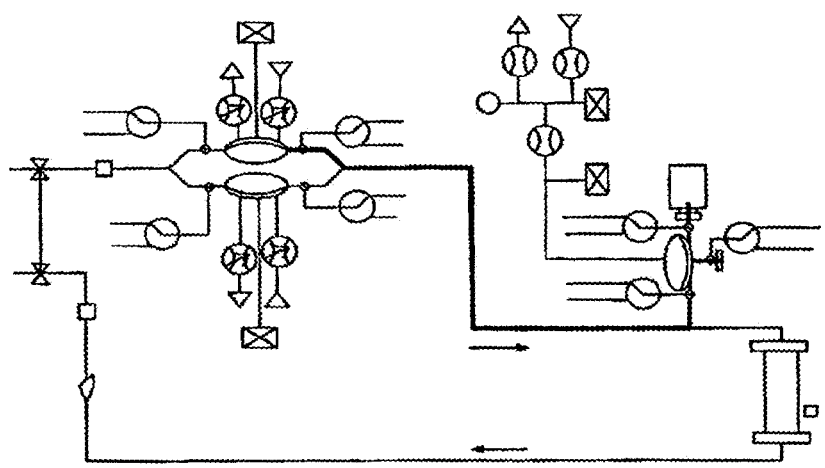
FIGS. 27A-27C illustrate the delivery of a bolus of anticoagulant to a patient, in another embodiment of the invention.
Figure 27B:
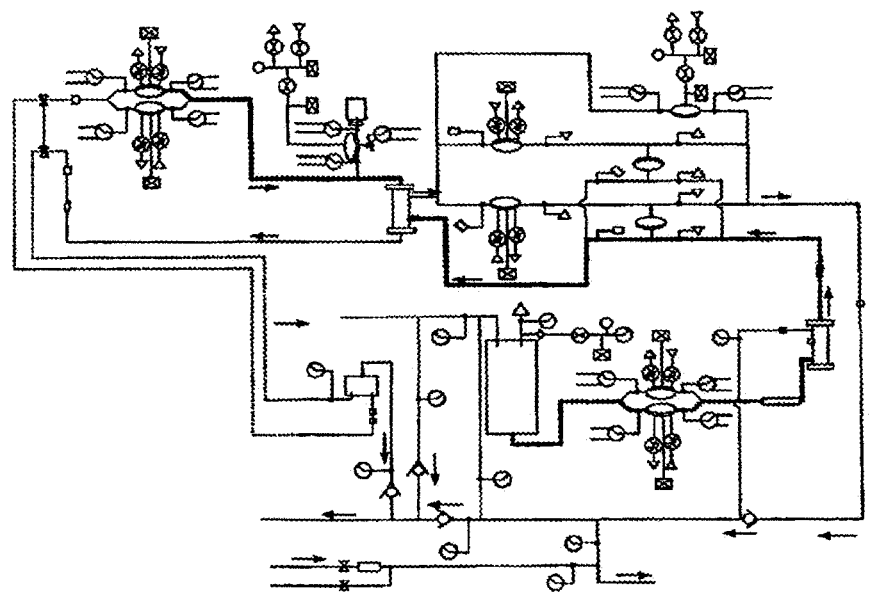
Figure 27C:
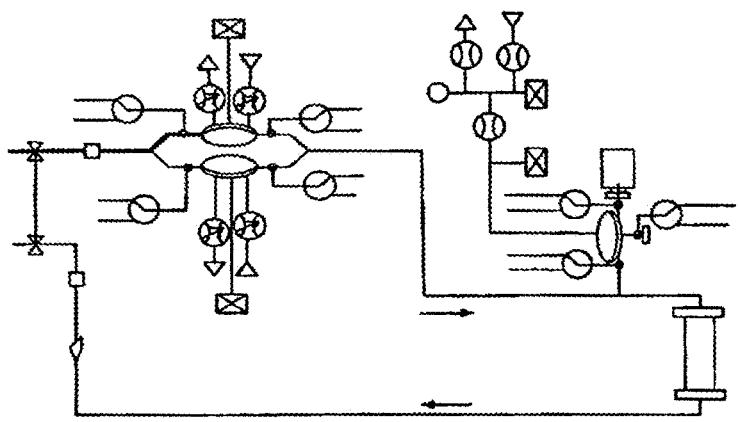

In yet another set of embodiments, a bolus of anticoagulant may be delivered to the patient. Initially, a bolus of anticoagulant is pumped from the vial (or other anticoagulant supply) to one chamber of pump 13, as is shown in FIG. 27A. The anticoagulant pump alternates between pumping air into the vial and pumping anticoagulant out of the vial, thereby keeping the pressure relatively constant. The remaining volume is then filled with dialysate (FIG. 27B). The combined fluids are then delivered to the patient down arterial line 203, as shown in FIG. 27B. In some cases, the same pump chamber may be refilled with dialysate again (see FIG. 27B), and that volume delivered to the patient also, to ensure that all of the anticoagulant has been properly delivered.

If air is detected by the air-in-line detector 33$a$ during the arterial bolus delivery, the bolus may be delivered via the venous line 204 (see FIG. 89). The air detected in the arterial line may be pulled back into the pump chamber 13 along with the heparin bolus. The heparin bolus may next be sent to the patient by delivering the chamber containing heparin in pump 13 toward the dialyzer 14 followed by delivering the $2^{nd}$ chamber of pump 13 toward the dialyzer. The heparin bolus and dialysate then flow through the air trap 19 to remove the air and past the venous air-in-line detector 33$b$ to the patient. The path from the pump 13 to the patient via the venous line 204 has a larger hold-up volume. The heparin bolus may be flushed into the patient with additional dialysate delivered from the outer dialysate pump 159 through the dialyzer 14.

In still another set of embodiments, the system may perform push-pull hemodiafiltration. In such cases, blood flow pump 13 and balancing pumps 15 can be synchronized to pass fluid back and forth across the dialyzer. In hemodiafiltration, hydrostatic pressure is used to drive water and solute across the membrane of the dialyzer from the blood flow circuit to the balancing circuit, where it is drained. Without wishing to be bound by any theory, it is believed that larger solutes are more readily transported to the used dialysate due to the convective forces in hemodiafiltration.

Figure 28:
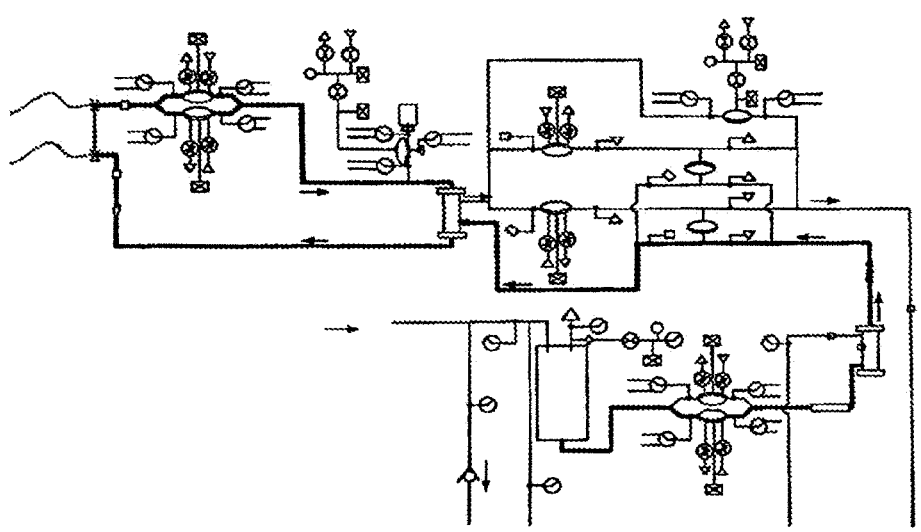
FIG. 28 illustrates solution infusion, in one embodiment of the invention.

In one set of embodiments, solution infusion may be used to delivery fluid to the patient. As is shown in FIG. 28, pump 159 in the directing circuit is used to push fluid across dialyzer 14 into the blood flow circuit, which thus causes delivery of fluid (e.g., dialysate) to the patient.

According to another set of embodiments, after repeated use, the dialyzer can lose its efficiency or even the ability to function at all as a result of compounds adhering to and building up on the membrane walls in the dialyzer. Any standard measure of dialyzer clearance determination may be used. However, as noted below, in certain embodiments, inventive methods of determining dialyzer clearance may be employed.

In one aspect, the invention involves methods for measuring the clearance of a dialyzer in a hemodialysis system to determine if the dialyzer has degraded to the point where it should no longer be used. While the inventive methods for determining the clearance of a dialyzer are described herein in the context of the illustrated blood treatment systems and methods described herein in the context of other aspects of the present invention, the inventive methods of determining a measure of dialyzer clearance are not limited to use only with the presently described systems and could be employed in essentially any hemodialysis system using a membrane-based dialyzer. Also described below are inventive data reduction methods for determining a dialyzer clearance parameter related to a measured small molecule (e.g. ion) clearance of a dialyzer and for determining an equivalent urea clearance of the dialyzer from such data. In certain embodiments, the dialyzer clearance measurement is determined by measuring the passage of ions in solution through the semipermeable membrane(s) separating a blood side of the dialyzer from a dialysate side of the dialyzer. Conveniently, the ions in solution used for such methods may be the same as those present in the acid concentrate contained in acid concentrate source 27 used to form dialysate during operation of the system for treatment protocols. In certain embodiments, such as described below, acid concentrate source 27 is used as the source for the ions whose passage through the dialysis membrane is determined. The acid concentrate typically comprises an aqueous solution of electrolytes, NaCl, CaCl, and other salts at a concentration several times (e.g., 40-45×) concentrated over that of the dialysate that is used for treatment. $Na^+$ and $Cl^-$ are the major ions in solution that contribute to the measurements made in the methods described herein for determining dialyzer clearance; however, in typical embodiments described below, it is the total ion clearance that is measured. In other embodiments, specific ions, such as Nat, or any other ion choice, may be added individually in solution for measurement of specific ion clearance, if desired. Described below are several exemplary embodiments of inventive dialyzer clearance measurement techniques, which are useful in the context of the present hemodialysis system and which also may be used in other hemodialysis systems and methods not specifically described herein.

In certain embodiments, in one method of measuring how much build-up has accumulated on the dialyzer membrane, i.e., how much the dialyzer's clearance has deteriorated, a gas is urged into the blood side of the dialyzer, while a liquid is held on the dialysate side of the dialyzer. By measuring the volume of gas in the dialyzer, the clearance of the dialyzer may be calculated based on the volume of gas measured in the dialyzer.

Alternatively, in another embodiment, because of the pneumatic aspects of the present system, clearance may be determined as follows. By applying a pressure differential along the dialyzer membrane and measuring the flow rate of liquid through the membrane (i.e. flux) of the dialyzer, the clearance of the dialyzer may then be correlated/determined or calculated, based on the pressure differential and the flow rate. For example, based on a known set of correlations or pre-programmed standards including a correlation table or mathematical relationship. For example, although a look-up table may be used, or a determined mathematical relationship may also be used.

The dialyzer's clearance can also be measured using a conductivity probe in the blood tube plug-back recirculation path and/or in the dialysate flow pathway. After treatment the patient connects the blood tubes back into the disinfection ports. The fluid in the blood tubes and dialyzer may be recirculated through these disinfection port connections, and the conductivity of this solution may be measured as it passes through the conductivity measurement cell in this recirculation path. Various implementation examples of this method are described in more detail below.

To measure the dialyzer clearance in certain embodiments, substantially pure water may be circulated through the dialysate path and the conductivity of the fluid flowing through the blood recirculation path may be continuously monitored. The pure water takes ions from the solution in the blood flow circuit recirculation path at a rate which is proportional to the concentration gradient and the clearance of the dialyzer. The clearance of the dialyzer may be determined by measuring the rate at which the conductivity of the solution in the blood flow circuit recirculation path changes and/or by measuring the rate at which the conductivity of the solution in the dialysate flow path changes.

In certain embodiments, the dialyzer's clearance can be measured by circulating pure water on one side and dialysate on the other, and measuring the amount of fluid passing through the dialyzer using conductivity.

In certain embodiments, and advantageously, a hemodialysis system of the present invention is configured to test small molecule clearance (e.g., ion clearance) of a dialyzer of the system prior to each usage of the system for a therapy treatment protocol. The dialyzer clearance test may be conducted after a user of the system provides new acid and bicarbonate concentrates for an upcoming therapy, and while the blood tubes of the blood tubing set are still plugged into the disinfection ports on the dialyzer machine (e.g. at a point in which the blood flow tubing is interconnected with the directing circuit via conduit 67 (see e.g., FIG. 17C)).

In certain embodiments, the method for measuring the clearance of the dialyzer involves creating flow of one liquid through the blood flow circuit/pathway of the hemodialysis system while creating a flow of a second liquid through the dialysate flow circuit/pathway. In certain embodiments, small molecules, such as ions (or salts yielding ions in solution) are added to either or both of the liquids in the blood flow pathway and the dialysate flow pathway to create a time varying change in the ionic strength of the liquid on one side of the dialysis membrane with respect to the other side. The liquid may then be pumped through the dialyzer and a parameter indicative of the concentration of ions in either or both of the liquid circulating through the blood flow path and the dialysate flow path may be measured to enable determination of the clearance of the dialyzer.

In certain such embodiments, the ions are added only to one of the liquid flow pathways (i.e., either to the liquid flowing in the blood flow pathway or the liquid flowing in the dialysate flow pathway), while essentially pure water is initially added to and circulated in the other flow pathway. In such embodiments, the measurement of the conductivity of the liquid in either or both of the blood flow pathway and dialysate flow pathway can provide a measure of the passage of ions across the dialysis membrane from the flow path to which the ions have been added to the flow path initially charged with essentially pure water. Although conductivity is a convenient means to determine a measure of the ionic strength of the liquid in the liquid flow pathway(s) for determination of dialyzer clearance, it should be understood that in other embodiments, other measures of ion concentration could be used and/or small molecules other than those that are ionic or charged species could be used for measurement of clearance.

In certain embodiments, ions are added to one of the flow paths and the liquid of such flow path is pumped through the dialyzer in a manner such that there is a change in the ionic strength of the liquid flowing through the dialyzer over the time period in which the dialyzer clearance is determined. As described in more detail below, in certain such embodiments, a concentrated ion or salt containing solution may be added in one or more pulses or boluses to water supplied to such flow path of the system in order to create one or more boluses or pulses of liquid having a higher ionic strength flowing through such flow path to facilitate measurement of conductivity and determination of dialyzer clearance.

In certain embodiments, for example, for those described immediately above wherein the change, such as a bolus or pulse of high ionic strength solution is added to a flow path of the system, it may be desirable for such flow path to be configured to be non-recirculating and pass through the dialyzer a single time. In certain such embodiments, it may be further advantageous for the flow path in fluid communication with the other side of the dialysate membrane to be continuously recirculating. For example, in one such embodiment, the dialysate flow path is the one to which one or more pulses of high ionic strength solution are added (e.g., by an acid concentrate source), and the dialysate flow pathway is configured for once-through flow through the dialyzer, while the blood flow circuit is configured for continuous recirculation of liquid through the blood side of the dialyzer and is initially primed with essentially pure water, as described in further detail below.

Advantageously, in certain embodiments in which a change in ionic strength with time is created in the liquid flowing on at least one side of the dialyzer during measurement of clearance, and especially in embodiments wherein one flow path is configured to be non-recirculating while the flow path in communication with the opposite side of the dialyzer membrane is configured to be continuously recirculating, conditions are created within the dialyzer wherein the ionic strength of the fluid on one side of the dialysis membrane with respect to the other side will change in magnitude with respect to time such that, in certain embodiments, ion passage through the dialysate membrane will, during certain periods of the test, move from the dialysate flow pathway across the membrane to the blood flow pathway while, during other periods of the test will move from the blood flow pathway across the dialysate membrane to the dialysate flow pathway.

As mentioned above, and as described in more detail below, a convenient, but not exclusive, means for measuring small molecule (e.g., ion) clearance of the dialyzer membrane is afforded by measuring the conductivity of one or both of the liquid streams flowing in the dialysate flow pathway and the blood flow pathway during the course of the dialysate clearance measurement. Described below in a specific example employed in the context of an embodiment of the present dialysis system as illustrated, for example, in FIGS. 3A-3B. In this exemplary embodiment, conductivity measurements are made for both the liquid flowing through the dialysate flow pathway and the liquid flowing through the blood flow pathway, and both sets of conductivity measurement data are used in determining dialyzer clearance. However, in alternative embodiments, conductivity could alternatively be measured only for one of the fluid pathways and/or multiple measurements of conductivity could be made at different points in the fluid circuit than illustrated in the system shown in FIG. 3A-3B and FIG. 81. So long as the location and number of conductivity measurement points enables detection of a change in conductivity resulting from passage of ions across the dialysis membrane during the test, such a configuration of measurement may be used in order to obtain a measure of dialyzer clearance. For example, referring to FIG. 81, in the specific exemplary protocol for determining dialyzer clearance discussed below, conductivity of the liquid flowing in the blood side flow pathway of the dialysis system is measured at point 4703 by conductivity probe 8002, while conductivity of the liquid flowing in the dialysate flow pathway is measured at position 4705 by conductivity probe 8004. In alternative embodiments, more or fewer conductivity measurements could be made and/or the conductivity probes could be differently positioned. For example, in one alternative embodiment, instead of using conductivity probe 8002 on the blood side circuit, an additional conductivity probe on the dialysate flow circuit positioned downstream of dialyzer 4707 could be used to measure ion concentration of the liquid both entering and exiting dialyzer 4707, thereby providing a measure of the ions passing through the dialyzer membrane during the test.

The following is a description of one exemplary embodiment of an inventive conductivity-based dialyzer clearance test according to the invention. Reference is made to FIG. 81, which reproduces the embodiment of the dialysis system of FIG. 3B with the fluid lines and equipment corresponding to the setup used for performing the dialyzer clearance test highlighted with thickened lines. In the figure, the dialysate flow pathway is shown in solid lines, while the blood flow pathway is shown in dashed lines. In summary, in the present example, flow pathways of the system are first primed with essentially pure water all the way through the blood set, which is interconnected for recirculation at location 4703 as shown. The test is conducted while the dialysate and blood flow circuits contain liquid flowing at a specific flow rate, which may be chosen to be similar to that used during dialysis treatment protocols (e.g., between about 250 ml/min-500 ml/min in certain embodiments, and in one particular example at about 350 ml/min). In certain embodiments, the flow rate of liquid through the dialysate flow circuit is maintained to be essentially the same as the flow rate recirculating in the blood flow circuit. During the test, the conductivity of the liquid in the blood flow pathway is measured using conductivity probe 8002, while the conductivity of the liquid flowing in the dialysate flow pathway is measured using conductivity probe 8004. During the test, as is described in more detail below, one or more pulses or boluses of higher conductivity dialysate are generated by the mixing circuit (e.g., see FIG. 7A) and added to the liquid pumped through the dialysate flow circuit, and the transfer of ions across the membrane in dialyzer 4707 to the blood side results in a corresponding pulse of higher conductivity fluid flowing through the blood flow circuit. After passage of the pulse, the conductivity of the liquid returns toward lower values and may approach zero in certain instances, as the liquid supplied by the mixing circuit switches from concentrated dialysate to water. The small molecule (e.g., ion) clearance of the dialyzer may be computed by analyzing a transfer function of ion passage from the dialysate side to the blood side of the dialyzer measured during passage of the pulse of higher conductivity liquid. The dialyzer clearance test may be used to verify that the dialyzer is capable of providing adequate clearance for additional therapy sessions in certain embodiments. Certain methods described herein measuring dialysate clearance based on conductivity measurements are useful in approximating urea clearance, which is a clinically conventional means for determining and expressing dialyzer clearance. As described in more detail below, one aspect of the present invention also involves techniques and algorithms for converting conductivity-based dialyzer clearance measurements into estimated urea clearance determinations.

As noted previously, in certain embodiments, the dialyzer clearance test occurs prior to conducting a treatment protocol, but after a user has connected the acid concentrate and bicarbonate reagents to the system. At this point in time, the lines of the system typically will contain a certain amount of water with residual disinfectant and a certain amount of air. As an initial step, water may be supplied to the system via water supply line 8006 (see FIG. 81) to fill the lines with water and prime both the dialysate flow pathway and the blood flow pathway as illustrated, for example, in FIGS. 17A-17C and FIG. 22A and described above in the context of those figures.

Water may be supplied via supply inlet 8006 to water pump 180 and is pumped to the outer dialysate/directing circuit to dialysate tank 169. The dialysate tank is filled and the water is pumped from the dialysate tank to the balancing circuit via pumps 159, the water in transit passing through ultrafilter 73. The water then flows into dialyzer 4707 as shown and through the dialyzer to fill the dialyzer and to fill the remaining portions of the dialysate flow pathway, as illustrated. During at least a portion of the prime sequence, flow exiting the dialysate pathway via drain 8008 may be restricted to force water through the dialyzer membrane and into the blood flow pathway. The blood flow pathway may be initially directed to drain until it is completely primed with water and residual air and disinfectant has been removed. At the conclusion of the priming, the dialyzer flow pathway is configured so that liquid entering the pathway makes a single loop around the dialysate flow circuit and exits the system via drain 8008. By contrast, the blood flow pathway is configured for continuous recirculation, as illustrated. It should be understood, that in alternative embodiments, the blood flow pathway could be configured for non-recirculating flow, while the dialysate flow pathway is configured for recirculating flow or both flow pathways could be either recirculating or non-recirculating. At the conclusion of the priming sequence, all of the lines, the dialysate tank, ultrafilter 73, and dialyzer 4707 should be completely filled with water and substantially free of air.

After priming with water, the system can be prepared for performing the clearance test. In certain embodiments, to reduce the degree of dilution of the high conductivity pulse added to the dialysate side fluid, dialysate tank 169 is emptied (see, e.g., FIG. 19 and associated discussion for process to do so) and then only partially refilled with water so that it contains enough water to perform the test but not so much to dilute the high concentration pulse(s) to an undesirable degree—e.g., for an embodiment in which the dialysate tank 169 has a capacity of about 2 liters, it may be filled at this stage with 100 milliliters to a few hundred milliliters of water. A small portion of this liquid may, prior to taking measurements, be pumped to drain as illustrated in FIG. 19, in order to re-prime ultrafilter 73.

To perform the test, the blood flow pathway is configured for continuous recirculation and the dialysate flow pathway is configured to pump once through to drain, as described previously. In certain embodiments in which the blood flow pathway flow rate is matched to the dialysate flow pathway flow rate, each of the pumps operating on the blood side and dialysate side circuits in the system, (e.g., pumps 180, 159, 161, 162 and 23) are operated in concert to provide a desired matched flow rate on the dialysate side and blood side of dialyzer 4707. In order to create the bolus(es)/pulse(s) of high concentration dialysate, during certain strokes of water pump 180, acid from acid source 29 is pumped into the dialysate flow pathway via acid pump 184, described previously. For example, in one particular embodiment, the acid pump 184 supplies 2-3 full strokes of acid concentrate for every 20-40 strokes of water supplied via water pump 181.

In certain embodiments, the flow direction of the recirculating flow in the blood flow pathway is counter-current to the flow direction of liquid in the dialysate flow pathway. In other embodiments, the flow may be circulated in a co-current fashion. The bolus(es)/pulse(s) of high conductivity liquid formed by the mixing circuit passes to the outer dialysate/directing circuit into partially filled dialysate tank 169 and is pumped from there through dialyzer 4707. During the pumping of the liquids through the dialysate side and blood side pathways during the test, during each pump stroke of the aforementioned pumps utilized for creating fluid motion, a plurality of conductivity measurements may be made by blood side conductivity probe 8002 and dialysate side conductivity probe 8004 and, for each pump stroke, the plurality of conductivity measurements (e.g., 100-200+ measurements) may be averaged to produce an average conductivity for the particular pump stroke number. Such measurements continue to be made during some or all of the course of the testing.

In certain embodiments, the test comprises passage of a single bolus/pulse of high conductivity/high-ionic strength dialysate through the dialysate flow pathway (the results of such a test are shown and described below in the context of FIG. 82). However, in other embodiments, multiple pulses may be added to create more complex conductivity versus time/pump stroke number functions. In yet other embodiments, instead of spiking the dialysate flow pathway with high concentration dialysate, such addition of concentrated solution may be made to the blood side flow pathway instead of, or in addition to, spiking of the liquid circulating in the dialysate flow pathway. Accordingly, if desired, a wide variety of functional forms of conductivity versus time/pump stroke number may be generated for analysis. For example, in certain embodiments, the conductivity versus time/pump stroke number data may take the form of a sine wave or other periodic function.

An example of data generated by the above-described exemplary dialysate clearance test, in which a single bolus/pulse of concentrated dialysate was passed through the dialysate flow pathway and dialyzer against a recirculating blood flow pathway containing water is shown in FIG. 82. The graph in this figure plots the measured conductivity versus pump stroke number, which correlates to the time of measurement and the total volume that has passed through the dialyzer during the test. Each data point for pump stroke number represents the average of a plurality of individual conductivity measurements made during the test, as described above. The plot showing the conductivity of the dialysis side liquid as measured by conductivity probe 8004 is shown by line 8050, while the plot of the conductivity measured in the blood side recirculating liquid as measured by conductivity probe 8002 is shown by line 8052.

As is apparent from the graph, the reactive conductivity measured on the blood side compared to the stimulus conductivity measured on the dialysate side is characterized both by having a lower maximum conductivity amplitude and by a measurement time lag (i.e., the maximum conductivity occurs at a later pump stroke number). The time lag displacement of the data is believed to be, in the system illustrated in FIG. 81, caused primarily by hold-up volume effects in the system, as opposed to being primarily caused by the kinetics of ion transport across the dialyzer membrane. In other embodiments, one or both of conductivity probes 8004 and 8002 could be placed in closer proximity to dialyzer 4707 in order to reduce or minimize the illustrated phase lag behavior. It is believed that the difference in amplitude between the dialysate side conductivity measurements and the blood side conductivity measurements is a factor that is primarily related to the dialyzer clearance. In certain embodiments, the measured amplitude difference and, optionally, the phase lag/phase shift, can be used directly as a measure of clearance and may be employed by the control circuitry/software of the system as a parameter by which to determine suitability of the dialyzer for continued use. However, in certain embodiments, and as described in more detail below, it may be desirable to develop a mathematical model correlated to the transfer function and fitting the measured blood side conductivity data, so that a single, optionally dimensionless, parameter may be derived from the data that may be utilized or further manipulated to determine a parameter used as the measure of dialyzer clearance by the system. Depending on the functional form of the data and the desired number and type of fitting parameters, it will be apparent to those skilled in the art that a very wide variety of statistical and mathematical data fitting protocols and algorithms could be potentially used for fitting the data and deriving a parameter indicative of dialyzer clearance. In certain embodiments, however, an inventive method and protocol are used to derive a single coefficient K, representing a dimensionless ion clearance, which parameter is substantially linearly related to measured urea clearance for the same dialyzer. In certain such embodiments, the model may be based on a weighting function and may have the functional form given below in Equation 0:

$$\text{Model}[i]=(1-K)*\text{Average}(\text{Model}[i-n:i-1])+K*\text{CondDialysate}[i-m] \quad \text{(Equation 0)}$$

In the above equation, K is a dimensionless fitting constant indicative of the ion clearance of the dialyzer membrane. i is a selected time interval (e.g., pump stroke number), Model[i] is a calculated value of a conductivity measured in the blood flow pathway liquid at time interval i (plotted in FIG. 82 as curve 8054), Average(Model[i−n:i−1]) is the average value of previous values of Model[i] determined over a range of intervals from i−n to i−1, CondDialysate[i−m] is a measured value of the conductivity of the dialysate side fluid determined at a time m intervals prior to interval i (e.g., the average of measured conductivity values that particular pump stroke number as described above), wherein n is greater than or equal to 2 and m is greater than or equal to zero. K is determined by fitting the equation for Model[i] to CondBloodSide[i] data (i.e. curve 8052) over the tested range of measurement intervals. The portion of the equation indicated by (K*CondDialysate[i−m]) represents a correction due to the phase shift behavior discussed above, and the value of m may be selected such that the phase of the measured dialysate side conductivity 8050 curve is approximately aligned with that of the measured blood side conductivity curve 8052. For the illustrated data shown in FIG. 82, m may be chosen for this purpose to be about 7. In certain embodiments, n is chosen to be greater than m. In one particular embodiment, n=m+1. In certain embodiments, data over the entire range of measured pump stroke number may by utilized for fitting the model; however, in certain embodiments, it may only be necessary or desirable to fit data bracketing the maximum peak amplitude (e.g., data for pump stroke numbers between about 30 and about 45 in the graph shown in FIG. 82).

The model form shown above in Equation DC-1 is fitted to the data, in certain embodiments, by determining the value of K which minimizes, to a desirable degree, the total error between the model calculation Model[i] and the measured values of conductivity for blood side liquid over the range of data analyzed (i.e. the data represented by curve 8052). As mentioned above, there are a number of statistical and curve-fitting algorithms that may be used for determining an optimal value for K. In one particular method, an iterative process is used in which a pair of model estimates for K are calculated and it is determined which of the two model estimates yields a lower error between the observed data points and the model. For example, a first pair of model estimates may use a value of K=0.0 and a value of K=1.0. Whichever model is closer to the actual measured data point is next used to narrow the range of possible values of K. Thus, if a better fit is obtained with a value of K=1.0, the next set of model estimates may be K=0.5 and K=1.0. If this set of estimates shows the optimum value of K to be closer to 0.5, the next set of model estimates may use K=0.5 and K=0.75. This procedure may be repeated until the two estimates of K chosen are equal to each other within, for example, three decimal places.

In one aspect of the invention, it has been determined that the coefficient K (a dimensionless clearance coefficient related to ion clearance) is essentially linearly related to urea clearance of the dialyzer. This linear relationship may be used to transform clearance coefficient K into an estimated urea clearance for a desired combination of blood and dialysate flow rate for a particular dialyzer. The graph shown in FIG. 83 shows data comparing the clearance coefficient K determined as described previously on the X axis versus measured urea clearance of the same dialyzer tested using a commercially available device used for quantitatively measuring urea clearance (Baxter). This substantially linear relationship may be used to transform the dimensionless conductivity based clearance coefficient K into an estimated urea clearance. This may be advantageous in that clinicians and patients are typically familiar with the concept of urea clearance. The system controller and software may then be configured to suggest that the user replace the dialyzer after the next therapy if such estimated urea clearance is below a clinician's settable percentage of the nominal urea clearance for a new dialyzer of the particular model being utilized.

In one set of embodiments, in case of a power failure, it may be desirable to return as much blood to the patient as possible. Since one embodiment of the hemodialysis system uses compressed gas to actuate various pumps and valves used in the system, a further embodiment takes advantage of this compressed gas to use it in case of power failure to return blood in the system to the patient. In accordance with this procedure and referring to FIG. 29A, dialysate is pushed across the dialyzer 14, rinsing blood residing in the blood flow circuit 10 back to the patient. Compressed gas (which in a preferred embodiment is compressed air) can be used to push dialysate across the dialyzer 14. A valve 77 releases the compressed air to initiate this function. This method may be used in situations where electrical power loss or some other failure prevents the dialysis machine from rinsing back the patient's blood using the method normally employed at the end of treatment.

As compressed air is used to increase the pressure on the dialysate side of the dialyzer 14 and force dialysate through the dialyzer to the blood side, thereby pushing the patient's blood back to the patient, the patient, or an assistant, monitors the process and clamps the tubes between the blood flow circuit and the patient once adequate rinse back has been achieved.

In one embodiment, a reservoir 70 is incorporated into the hemodialysis system and is filled with compressed air prior to initiating treatment. This reservoir 70 is connected to the dialysate circuit 20 through a manually actuated valve 77. When the treatment is finished or aborted, this valve 77 is opened by the patient or an assistant to initiate the rinse-back process. The membrane of the dialyzer 14 allows dialysate to pass through, but not air. The compressed air displaces dialysate until the patient tubes are clamped, or the dialysate side of the dialyzer is filled with air.

In another embodiment, a reservoir containing compressed air is provided as an accessory to the dialysis machine. If the treatment is terminated early due to a power failure or system failure of the dialysis machine, this reservoir may be attached to the dialysate circuit on the machine to initiate the rinse-back process. As in the previous embodiment, the rinse-back process is terminated when the patient tubes are clamped, or the dialysate side of the dialyzer is filled with air.

Figure 29A:
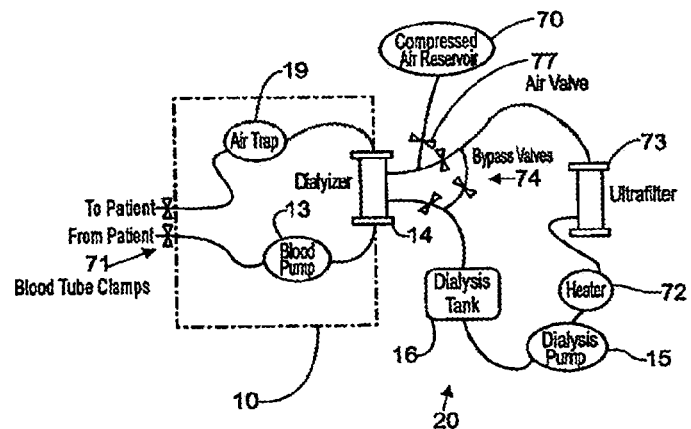
FIGS. 29A-29B are schematic representations showing how an emergency rinse-back procedure can be implemented.
Figure 29B:
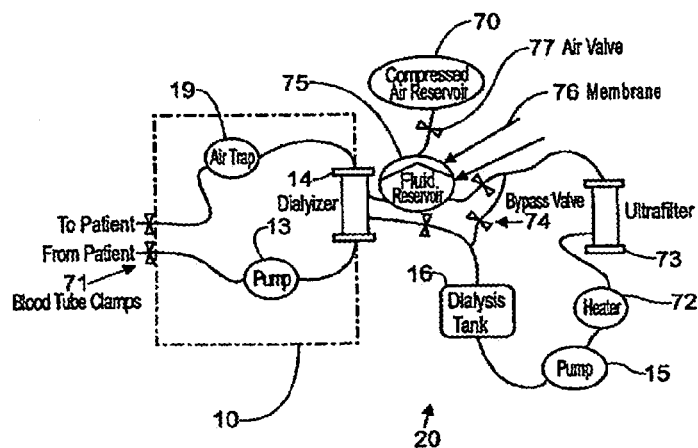

In yet another embodiment shown in FIG. 29B, an air reservoir 70 is incorporated into the system and attached to a fluid reservoir 75 with a flexible diaphragm 76 separating the air from the dialysate fluid. In this case, the compressed air pushes the diaphragm 76 to increase the pressure in the dialysate circuit 20 rather than having the compressed air enter the dialysate circuit. The volume of the dialysate that is available to be displaced is determined by the volume of the fluid chamber 75. The rinse-back process is terminated when the patient tubes are clamped, or when all of the fluid is expelled and the diaphragm 76 bottoms out against the wall of the fluid chamber 75.

In any of these embodiments, the operation of the systems or methods may be tested periodically between treatments by running a program on the dialysate machine. During the test the user interface prompts the user to actuate the rinse-back process, and the machine monitors the pressure in the dialysate circuit to ensure successful operation.

In the systems depicted in FIGS. 29A and 29B, blood is drawn from the patient by the blood flow pump 13, pushed through the dialyzer 14 and returned to the patient. These components and the tubing that connects them together make up the blood flow circuit 10. The blood contained in the blood flow circuit 10 should be returned to the patient when the treatment is finished or aborted.

The dialysate solution is drawn from the dialysate tank 169 by the dialysate pump 159, and passed through the heater 72 to warm the solution to body temperature. The dialysate then flows through the ultrafilter 73 which removes any pathogens and pyrogens which may be in the dialysate solution. The dialysate solution then flows through the dialyzer to perform the therapy and back to the dialysate tank.

The bypass valves 74 may be used to isolate the dialyzer 14 from the rest of the dialysate circuit 20. To isolate the dialyzer 14, the two valves connecting the dialysate circuit 20 to the dialyzer are closed, and the one shunting dialysate around the dialyzer is opened.

This rinse-back procedure may be used whether or not the dialyzer 14 is isolated and is used when the treatment is ended or aborted. The dialysate machine is turned off or deactivated so the pumps are not running. When the patient is ready for rinse-back, air valve 77 is opened by the patient or an assistant. The air in the compressed air reservoir 70 flows toward the dialysate circuit 20, increasing the pressure on the dialysate side of the dialyzer 14. This increase in pressure may be achieved by allowing the air to enter the dialysate circuit directly, as shown in FIG. 29A or indirectly by pushing on the diaphragm 76 shown in FIG. 29B.

The air pressure on the dialysate side of the dialyzer forces some dialysate solution through the dialyzer 14 into the blood flow circuit. This dialysate solution displaces the blood, rinsing the blood back to the patient. The patient or an assistant can observe the rinse process by looking at the dialyzer 14 and the blood tubes. The dialysate solution starts in the dialyzer, displacing the blood and making it appear much clearer. This clearer solution progresses from the dialyzer toward the patient. When it reaches the patient the blood tube clamps 71 are used to pinch the tubing to terminate the rinse-back process. If one line rinses back sooner than the other the quicker line may be clamped first and the slower line may be clamped later.

Once the rinse-back is completed and the blood lines are clamped the patient may be disconnected from the dialysis machine.

The implementation of one embodiment of the system and method is shown in FIG. 29A takes advantage of the hydrophilic nature of the material used to make the tiny tubes in the dialyzer 14. When this material is wet, the dialysate solution can pass through but air cannot. Where the embodiment shown in FIG. 29A is implemented, air may enter the dialyzer 14 but it will not pass across to the blood flow circuit 10.

In either implementation, the volume of dialysate that may be passed through the dialyzer 14 is limited. This limitation is imposed by the size of the compressed air reservoir 70, the volume of dialysate solution contained in the dialyzer 14 and in the case of the implementation shown in FIG. 7B the size of fluid reservoir 75. It is advantageous to limit the volume of dialysate that may be pushed across the dialyzer because giving too much extra fluid to the patient counteracts the therapeutic benefit of removing fluid during the therapy.

In another embodiment, in a loss of power, the air pressure to move dialysate from the dialysate circuit through the dialyzer can be derived from a pressurized air reservoir that normally powers the membrane pumps and also provides a pressure source for FMS measurements. As shown in FIG. 80, for example, this source of air pressure can be accessed via the FMS pathway 170 used to monitor the dialysate tank 169. In an embodiment, the manifold valves that direct air pressure or vacuum to the various pumps and valves in the liquid flow paths of the hemodialysis machine are electrically operated. In some embodiments, the valves in the liquid flow paths of the hemodialysis machine can themselves be electrically actuated. In the absence of electrical power, they can be chosen or pre-set to have default open or closed positions. If the default position of a manifold valve is closed, for example, then no air pressure (or vacuum) can be transmitted to its target. Similarly, if the default position of a manifold valve is open, then the pressure or vacuum source to which it is connected can pressurize the downstream device (such as a membrane-based pump, a membrane-based valve, or another type of valve). If a valve that directly controls flow in a liquid flow path is itself electrically actuated, the valve can be chosen to have a default position either to close off or to open its respective flow path. In the example illustrated in FIG. 80, by configuring the manifold valve 170a and the FMS valve 170b to have a default open position, for example, pressure from a pressurized air tank can be transmitted to the dialysate tank 169. By configuring various other manifold valves to the appropriate default positions, the corresponding flow path valves controlled by the manifold valves can be made to open a pathway from the dialysate tank 169, through the outer dialysate pump circuit 159, the ultrafilter 73, a portion of the balancing circuit 143, and ultimately to the dialyzer 14. Thus, in the absence of electrical power, and if the blood flow side of the dialyzer 14 offers no impedance, dialysate from the dialysate tank 169 can be made to flow to the dialyzer 14, allowing for rinseback of blood. During normal dialysis, the control software can ensure that there is a sufficient supply of dialysate in the dialysate tank 169 to allow for the rinseback of all of the blood residing in the blood tubing set.

In alternative embodiments, if the valves that directly control flow in the dialysate flow paths between the dialysate tank and the dialyzer are themselves electrically actuated, they can be chosen to have an open default position. Conversely, other valves that control flow in pathways that divert flow away from the dialyzer can be selected to have a default closed position.

For example, in FIG. 80, the default configuration for the appropriate manifold valves can cause the inlet and outlet valves 171 of the outer dialysate pump circuit 159, and the balancing circuit valves 172 to remain in an 'open' position, providing a flow path to the dialyzer 14. Conversely, the inlet feed valve 173a and the recirculation valve 173b of the dialysate tank 169, and the drain valve 174 of the ultrafilter 73 can be made to have 'closed' default positions in an unpowered state, to prevent the dialysate from being pushed to drain. In addition, the inlet valves 175 of the inner dialysate pump circuit 15 and the inlet valve 176 of the bypass or ultrafiltration pump circuit 35 can be made to have 'closed' default positions to prevent dialysate flow into those pathways from the dialyzer 14 in an unpowered state.

In order to avoid uncontrolled rinseback, the arterial supply and venous return lines of the blood tubing set can be compressed by an occluder mechanism that maintains a default 'occluded' position in the absence of power, and that is moved to an 'unoccluded' position during normal dialysis. The occluder can be positioned to simultaneously occlude both the arterial line before it reaches the blood pump cassette, and the venous line after exiting from the dialyzer or an air bubble trap. In a preferred embodiment, before rinseback is allowed, a patient, operator or assistant withdraws the arterial line from the patient's vascular access site when a rinseback is planned or a power-loss related rinseback is initiated. A suitable connector (such as a needle or needle-less spike, or Luer lock connector) is placed on the end of the arterial line, and is then connected to an air trap (such as air trap 19) in the venous return line. This helps to prevent any air caught in the blood flow path at the top of the blood pump cassette or the top of the dialyzer from being inadvertently rinsed back toward the patient's vascular access. Once the arterial line is connected to the air trap, the patient, operator or assistant may then manually move the occluder to an 'unoccluded' position, decompressing the venous return line and allowing the pressurized dialysate from the dialysate circuit to push the blood in the blood tubing set toward the patient's vascular access. If the patient observes air in the venous line downstream from the air trap, he or she may simply re-engage the occluder and stop the rinseback process.

Although the above rinseback procedures are described with dialysate as the solution that ultimately moves the blood in the blood flow path toward the patient's vascular access, any electrolyte solution that is physiologically compatible and can safely be mixed with blood can be used in a rinseback procedure. Furthermore, rinseback technology need not be limited to a dialysis system. Any system that circulates a patient's blood extracorporeally could potentially benefit from an emergency rinseback system and method. It would therefore be possible to introduce a filter having a semipermeable membrane (such as a dialyzer or ultrafilter) into the blood flow path of the extracorporeal system. The other side of the semipermeable membrane would then be exposed to an electrolyte solution in a flow path that can be pressurized by a compressed gas source with which it is in valved communication.

In one aspect of the invention, a dialysis system may include a chamber, such as a balancing chamber in a dialysate circuit, that has a membrane which is movable in the chamber and fluidly separates a first portion of the chamber from a second portion of the chamber. One such balancing chamber is discussed above with reference to FIG. 5 and reference numbers 341 and 342. The chamber may include a first inlet to the first portion and a second inlet to the second portion, e.g., so that fluid may enter and exit the chamber via the first inlet to fill the first portion of the chamber, and may enter and exit the chamber via the second inlet to fill the second portion of the chamber. The first and second portions and the membrane may be arranged so that a volume of fluid provided into the first portion displaces a corresponding volume of fluid in the second portion, and vice versa. Thus, when the first chamber is substantially filled, the second chamber may be substantially empty, and vice versa.

A blood leak sensor may be associated with the chamber and arranged to detect blood (either red blood cells, hemoglobin, other cellular constituents or other proteins, among other elements) in the first portion of the chamber. For example, the blood leak sensor may include a light emitter and detector arranged to measure an amount of light that is absorbed, attenuated or otherwise operated on by fluid in the chamber, which may be indicative of the presence of blood or its constituent elements in the chamber. In one embodiment, the light emitter may introduce light having a wavelength of about 570 nm, which is generally absorbed or otherwise attenuated by hemoglobin and/or other blood components. Thus, by determining a light level of illumination transmitted through the first portion of the chamber, and comparing it to a reference level of illumination, a determination may be made whether blood is present in the chamber or not.

In one arrangement, the first inlet may be fluidly coupled to receive used dialysate from a dialyzer so that used dialysate may be introduced into the chamber. Since the used dialysate is received from the dialyzer, this may allow the blood leak sensor to make a determination whether blood is present in used dialysate exiting the dialyzer, e.g., whether the dialyzer is leaking blood or blood components across the dialyzer membrane. It is also possible to have the second inlet connected to receive clean dialysate, e.g., which is to be provided to the dialyzer. Thus, the blood leak sensor may be operated to determine a reference level of signal detection associated with clean dialysate, thereby allowing the blood leak sensor to continually or periodically compare the signal transmission characteristics of used dialysate to clean (blood-free) dialysate, holding substantially all other variables affecting the signal transmission constant, since the only variation in the transmission media will be attributable to the unique characteristics of the used dialysate. That is, optical and other characteristics of clean dialysate, as well as portions of the balancing chamber optionally involved in blood detection such as the transparent or translucent portions of the walls of the balancing chamber and/or of the chamber membrane, may vary during treatment, which may in some cases affect the operation of the blood leak sensor. For example, chamber structures may become increasingly opacified over the course of a single treatment, multiple treatments, or disinfection processes, and may attenuate detection light. However, by allowing the blood leak sensor to operate alternately on clean and used dialysate in the same chamber during the treatment process, the blood leak sensor may be desensitized to variations other than those attributable to the used dialysate itself, allowing the sensor to reliably and accurately detect the presence of blood in dialysate flowing from the dialyzer.

Although in the embodiments discussed above the blood leak sensor detects optical characteristics of fluid to determine a presence or absence of blood, the blood leak sensor may detect other characteristics that may indicate a defect in the dialyzer membrane, such as chemical characteristics (such as binding of blood components to an antibody or other receptor), electrical characteristics (such as changes in fluid conductivity), the effects of leaked large proteins on the turbidity of the used dialysate, and others. Moreover, the blood leak sensor may also be used to detect the presence of other non-blood compounds that may affect the transmission of a signal from emitter to detector. Therefore, aspects of the invention are not necessarily limited to detecting optical characteristics of a fluid to determine the presence of blood, or to its sole use as a blood sensor where other compounds may affect signal transmission through the fluid.

In one embodiment, the blood leak sensor may be arranged to measure the transmission of a signal associated with a blood level (a first measurement) in fluid occupying the first portion of the chamber and to measure the transmission of a similar signal in blood-free fluid (a second measurement) occupying the second portion of the chamber for comparison of the first and second measurements to each other. By comparing the first and second measurements (e.g., where the first measurement is associated with used, potentially blood-contaminated dialysate and the second measurement is associated with clean blood-free dialysate), any confounding or biasing effects on light transmission and detection may be eliminated from blood detection. The blood leak sensor may be arranged to make a first measurement of the blood level with the first portion substantially full of fluid (e.g., of used dialysate) and the second portion substantially empty of fluid, and may be arranged to make a second measurement with the first portion substantially empty of fluid and the second portion substantially full of fluid (e.g., of clean dialysate).

In one embodiment, the blood leak sensor may be arranged to measure a first level in the first portion of the chamber and a second level in the second portion of the chamber for comparison of the first and second levels to each other. By comparing the first and second levels (e.g., where the first level is associated with used dialysate and the second level is associated with clean dialysate), any affect of dialysate variation may be eliminated from blood detection. The blood leak sensor may be arranged to measure the first level with the first portion substantially full of fluid (e.g., of used dialysate) and the second portion substantially empty of fluid, and may be arranged to measure the second level with the first portion substantially empty of fluid and the second portion substantially full of fluid (e.g., of clean dialysate).

The chamber may include a wall that defines an interior volume of the chamber, and the membrane may be arranged to contact a chamber wall when the first and second portions are substantially full of fluid. For example, the membrane may be arranged so that fluid may be introduced into the first portion so that the membrane moves to expel fluid from the second portion until the second portion is substantially empty and the membrane is in contact with one aspect of the chamber wall. Conversely, fluid may be introduced into the second portion so that the membrane moves to expel fluid from the first portion until the first portion is substantially empty and the membrane is in contact with another aspect of the chamber wall (e.g., on an opposite side of the chamber). Thus, the chamber may be alternately substantially filled with clean or used dialysate, allowing the blood leak sensor to operate to detect a signal associated with the presence of blood while the first portion is substantially full of used dialysate and to detect a signal associated with the absence of blood when the second portion is substantially full of clean dialysate.

The blood leak sensor may include a light emitter arranged to emit light into the chamber and a light detector arranged to detect light emitted by the light emitter. For example, the light emitter and light detector may be arranged on opposed sides of the chamber so that a straight light path extends from the light emitter to the light detector. As a result, the emitter may emit light that passes through fluid in the chamber and is received at the light detector. In one embodiment, the light emitter and the light detector may be arranged so that light emitted by the light emitter and received by the light detector passes through the membrane. For example, the membrane and suitable portions of the chamber wall may be transparent, or have a transparent or otherwise suitably translucent portion, so that light may pass through the first portion of the chamber, through the membrane and through the second portion of the chamber. Thus, the same emitter/detector pair may be used to detect the transmission of the emitter signal in both the first and second chambers. In one embodiment, the light emitter and the light detector may be arranged so that light emitted by the light emitter and received by the light detector passes through a wall of the chamber. Thus, the blood leak sensor may include a light emitter positioned outside of the chamber and a light detector positioned outside of the chamber so that light passes through the wall of the chamber and into the chamber interior space. In one arrangement, the blood leak sensor may be arranged to detect blood in a dialysate solution where the blood has a hematocrit of 40% and is in a concentration of about 0.4375 ml blood per liter or more. In another arrangement, the blood leak sensor may be arranged to detect blood in a dialysate solution where the blood has a hematocrit of 40% and is in a concentration of about 0.2 ml blood per liter or more. In other arrangements, the blood leak sensor may be arranged to detect blood in a dialysate solution where the blood is in a concentration equal to or less than half the threshold concentration specified by international standards setting organizations for dialysis equipment.

In another aspect of the invention, a method for detecting blood in a dialysate circuit of a dialysis system includes transmitting light through a first portion of a chamber having a movable membrane that separates the first portion of the chamber from a second portion of the chamber, and determining a presence of blood in liquid in the first portion based on a light level detected for light transmitted through the first portion. For example, the chamber may be a balancing chamber in the dialysate circuit, and the first portion of the balancing chamber may be fluidly coupled to receive used dialysate from the dialyzer. Attenuation or other effect on light transmitted through the first portion may be detected and represent a presence of blood components (or other compounds) in the used dialysate. In one arrangement, a first light level may be detected for light transmitted through fluid in the first portion of the chamber, and a second light level may be detected for light transmitted through fluid in the second portion of the chamber. A presence of blood in the first portion may be determined based on a comparison of the detected first and second light levels. For example, the first light level may be determined by filling the first portion of the chamber with used dialysate and transmitting light through the first portion of the chamber while the first portion is substantially filled with used dialysate. Similarly, the second light level may be determined by filling the second portion with clean dialysate and transmitting light through the second portion of the chamber while the second portion is substantially filed with clean dialysate. As a result, a single emitter/detector pair may be used to measure blood or turbidity levels in the used dialysate volume, using the second light level as a reference measurement associated with blood-free or turbidity-free fluid.

In another aspect of the invention, a method for detecting blood in a dialysate circuit of a dialysis system includes providing a chamber having a movable membrane that separates the first portion of the chamber from a second portion of the chamber, providing used dialysate received from a dialyzer into the first portion of the chamber, and determining whether blood is present in the used dialysate in the first portion based on a detected characteristic of the used dialysate in the first portion. For example, a characteristic of the used dialysate detected may include an absorption of light by the used dialysate, which may indicate the presence of blood. As also discussed above, clean dialysate for delivery to the dialyzer may be provided into the second portion of the chamber, and a characteristic of the clean dialysate in the second portion may be measured, e.g., based on impairment of light transmission by the clean dialysate, the chamber walls and the membrane in the chamber as represented by a light level detected for light transmitted through the clean dialysate. The detected characteristics of the used dialysate and the clean dialysate may be compared, and any difference may be used to determine a presence of blood in the used dialysate. The characteristic of the used dialysate may be detected with the first portion substantially filled with used dialysate and the second portion substantially empty (e.g., with the membrane in contact with the chamber wall on one side of the chamber), and the characteristic of the clean dialysate, the chamber and the membrane may be detected with the second portion substantially filled with clean dialysate and the first portion substantially empty (e.g., with the membrane in contact with the chamber wall on another side of the chamber).

In another aspect of the invention, a method for detecting blood in a dialysate circuit of a dialysis system includes providing a blood leak sensor associated with a chamber having a membrane that separates a first portion of the chamber from a second portion of the chamber. The chamber may be a balancing chamber used to balance inflow of clean dialysate with outflow of used dialysate with respect to a dialyzer. The blood leak sensor may determine a blood-free reference measurement by detecting a characteristic of clean dialysate in the second portion of the chamber, such as by detecting an absorption or attenuation of light passing through the clean dialysate (as well as potentially through other elements such as the membrane and/or chamber wall) from a light emitter to a light detector. Determining a reference level for use in blood detecting may be as simple as detecting and storing a light level at a light detector, or may involve other processes, such as adjusting a detector sensitivity, calculating a correction value to be applied to measured light values, determining a concentration of light absorbing constituents in the clean dialysate, and so on. Additionally, the blood-sensing operation may include adjusting the radiant output of the light emitter in order for the detector to receive a reference signal sufficient to discriminate between blood-contaminated dialysate and clean dialysate. A controller may be used to continually or periodically adjust the radiant output of the light emitter to allow a reference signal of pre-determined strength to be received by the detector. For example, the reference signal may be adjusted to be at a high end of the operating range of the detector, so that a degradation of the received signal intensity will more likely remain within the operating range of the detector.

The reference signal-adjusted blood leak sensor may be used to determine whether blood is present in used dialysate in the first portion of the chamber. For example, the blood leak sensor may be used to measure light attenuation or other characteristics of used dialysate in the first portion of the chamber which is received from the dialyzer. The detected light level or other characteristic may be compared to a light level or other characteristic detected for clean dialysate in the same chamber with the same membrane, and a difference between the two values used to determine whether blood is present in the used dialysate. As discussed above, the light level or other characteristic of the clean dialysate may be detected for a condition in which the second portion of the chamber is substantially filled with clean dialysate, and the characteristic of the used dialysate may be detected for a condition in which the first portion of the chamber is substantially filled with used dialysate.

In another aspect of the invention, a method for detecting blood in a dialysate circuit of a dialysis system includes operating the dialysis system to provide dialysis treatment to a patient by, at least in part, circulating dialysate through a dialysate circuit including a balancing chamber and a dialyzer. A blood leak sensor may be provided which is arranged to determine a presence of blood in used dialysate flowing from the dialyzer. In one embodiment, the blood leak sensor may be used to measure a characteristic of clean dialysate while the dialysis system is in operation to provide the dialysis treatment to the patient. For example, the blood leak sensor may measure light absorption or attenuation by clean dialysate in a balancing chamber while the system is in operation during a treatment. This characteristic may be used to determine whether blood is present in used dialysate. For example, the blood leak sensor may be arranged to detect light attenuation—or the absorption of light within a specified frequency range—caused by blood present in the used dialysate in the balancing chamber. Thus, the blood leak sensor may employ a potentially variable reference measurement representing blood-free dialysate by causing the blood leak sensor to operate to determine the amount of light transmitted through clean dialysate in a chamber while the dialysis system is in operation to provide the dialysis treatment to the patient. That is, the blood leak sensor may repeatedly make a reference measurement during normal system operation when providing dialysis treatment for a patient. This arrangement may provide for accurate measurement of blood in used dialysate occupying the same chamber, potentially reducing false positive or other erroneous operation of the blood leak sensor. Moreover, the repeated reference measurement process may make the blood sensor insensitive to changes in clean dialysate used in the treatment process, or in changes in the transparency or translucency of portions of the chamber wall or of the flexible membrane.

In one embodiment, the dialysis system may be operated so as to alternately substantially fill the balancing chamber with clean dialysate and with used dialysate. As will be understood from the discussion of the operation of the balancing chamber herein, the balancing chamber may be operated during treatment so that the balancing chamber alternately fills with clean dialysate and used dialysate, with the membrane in the chamber moving to maintain separation of the clean and used dialysate. When the balancing chamber is substantially filled with clean dialysate, the blood leak sensor may be operated to determine a signal associated with transmission through a blood-free or tubidity-free balancing chamber. Since no blood is present in clean dialysate, a characteristic of the clean dialysate detected by the blood leak sensor can provide a baseline or reference value which can be used in subsequent measurements of used dialysate to determine if blood is present.

In one aspect of the invention, a blood leak sensor may be used to determine whether blood is passing or has passed across the dialyzer membrane from the blood flow circuit 10 to the balancing circuit 143 or other dialysate circuit in a dialysis system. The ability to detect such blood leakage is required for hemodialysis systems, and has previously been done using an optical detector (e.g., like the sensor 258 shown in FIG. 5) associated with a piece of translucent tubing through which spent dialysate passes when moving to the drain. Some such detection techniques have suffered from problems with accuracy and reliability, e.g., as the drain tube with which the sensor is associated becomes dirty or opacified or otherwise affects the optical transmission of light, necessitating frequent re-calibration or adjustment.

In one illustrative embodiment, blood may be detected at a balancing chamber in the balancing circuit 143 or other dialysate flow path. One potential advantage of detecting blood in a balancing chamber is that the sensing system can be continually or periodically adjusted in relation to known clean dialysate at any desired frequency, such as for every filling and emptying cycle of the balancing chamber. That is, since a balancing chamber will alternately fill with clean dialysate, then fill with used dialysate, followed by another fill of clean dialysate, and so on, a sensor used to detect blood in the balancing chamber can determine a baseline or reference blood-free measurement level when the chamber is filled with clean dialysate and compare the reference level with a detected level sensed when the chamber is filled with used dialysate. As a result, it is possible to effectively adjust the blood sensor for every dialysate inflow and outflow cycle during patient treatment, although less frequent adjustment frequencies can be used. The sensor used to detect blood in the balancing chamber can operate on the same or similar principles used by prior blood sensors, e.g., the sensor can include a light emitter that introduces light into liquid in the balancing chamber and a detector that detects light transmitted through the liquid. However, other sensors may be used to determine the presence of blood, such as chemical detectors that detect the presence of blood proteins or other compounds, and be subject to similar re-adjustment with respect to repeated determinations of a reference measurement using clean dialysate.

FIG. 84 shows a schematic diagram of an alternate balancing circuit 143 that may be used in a hemodialysis system such as that having circuitry like that shown in FIG. 3A. The balancing circuit 143 in FIG. 84 is nearly identical to that of FIG. 5, with the difference being that a blood leak sensor 343 is provided with one of the balancing chambers 341. Although in this embodiment a blood leak sensor 343 is provided for only one balancing chamber 341, a sensor 343 may be provided for both chambers 341 and 342, or only with the balancing chamber 342. Also, as will be apparent from the detailed description below, a blood leak sensor may be used with one or both of the pod pumps 161 or 162, if desired, since these pumps 161, 162 may alternately fill with used dialysate and fill with air. While determining a measured blood baseline level using air as a reference fluid instead of clean dialysate may not be as desirable as using clean dialysate (e.g., because the optical properties of the clean dialysate may vary during treatment without having any effect on the dialysate's ability to remove impurities from blood), air or other fluid used to drive the pod pumps 161, 162 may provide a suitable reference representing a zero blood level in the pump 161, 162. As discussed in more detail below, a system controller may use the detected blood level in controlling the system operation, such as stopping or otherwise modifying treatment if blood is detected in the balancing circuit 143.

FIG. 85 shows a cross sectional view of an illustrative embodiment of a balancing chamber 341 associated with a blood leak sensor 343. While in this embodiment the balancing chamber 341 has a general arrangement like that of the pod shown in FIGS. 47A to 49, other arrangements for a balancing chamber 341 are possible. In this embodiment, the balancing chamber 341 has a used dialysate port 341a and a clean dialysate port 341b. As will be understood from FIG. 84, the used dialysate port 341a is fluidly coupled to an outlet of a pod pump 161, 162 and the drain 31, and the clean dialysate port 341b is fluidly coupled to the line between the ultrafilter 73 and the dialyzer 14 inlet. A membrane 341c separates the used dialysate port 341a and the clean dialysate port 341b from each other, and is arranged to move as fluid enters and exits the ports 341a, 341b. The membrane 341c may have any suitable arrangement, such as having a hemispherical shell shape like that shown in FIGS. 48A and 48B. As a result, flow caused by the pump 161 can cause the balancing chamber 341 to substantially fill with used dialysate that enters through the used dialysate port 341a (thereby displacing any clean dialysate in the chamber and discharging the clean dialysate through the clean dialysate port 341b), and/or substantially fill with clean dialysate that enters through the clean dialysate port 341b (thereby displacing any used dialysate in the chamber and discharging the used dialysate through the used dialysate port 341a). When the balancing chamber 341 is filled with used dialysate, the membrane 341c will be moved to the left as shown in FIG. 85 (shown in dashed line), and in some cases, will be pressed into contact with the wall of the balancing chamber 341. Alternately, when the balancing chamber 341 is filled with clean dialysate, the membrane 341c will be moved to the right as shown in FIG. 85 (shown in dotted line), and in some cases, will be pressed into contact with the wall of the balancing chamber 341.

The blood leak sensor 343 in this embodiment includes a light emitter assembly 343a (including, e.g., a light emitting diode (LED)) that emits a suitable wavelength or set of wavelengths of light into the balancing chamber 341 in the direction of a light detector assembly 343b (including, e.g., a photodiode or other suitable detecting element). The light emitted by the emitter assembly 343a may be suitably arranged to be absorbed or otherwise altered by blood components in the fluid in the chamber 341, but generally not be affected, or least affected less, by dialysate that is free of blood. For example, the light may be generally green in color (e.g., include light having a wavelength of around 570 nm), which is an approximate peak absorption wavelength for hemoglobin. Of course, other wavelengths or sets of wavelengths may be used, e.g., to exploit other optical characteristics of blood components, as desired. In this embodiment, the blood leak sensor 343 can detect the presence of blood in used dialysate based on attenuation of light passing through the used dialysate. That is, light emitted by the emitter assembly 343a passes through the membrane 341c and used dialysate (or clean dialysate depending on the measurement cycle) to the detector assembly 343b. If hemoglobin or other suitable blood components are present in the used dialysate, those components will absorb, scatter or otherwise reduce the amount of light that reaches detector assembly 343b. The detected light levels for used and clean dialysate volumes may be used, e.g., compared to each other, to determine whether blood is present in the used dialysate.

The intensity of the illuminating element in emitter assembly 343a (e.g., an LED) can be controlled to provide enough light to obtain a clear and unambiguous signal intensity at the receiving detector assembly 343b. For example, the intensity of an LED output can be controlled by having a controller adjust the current flow through the LED using pulse-width modulation. This may allow the blood leak sensor 343 to continue to provide optimal functionality if the optical pathway is degraded for any reason. The current to the LED can be set when clean dialysate is present in the chamber and in the light path, and then left at this value when used dialysate is introduced into the chamber and the light path. The current may be set such that the intensity observed by the detector assembly 343b is toward the high end of its range of sensitivity for clean dialysate. This makes most of the range of sensitivity available to observe the attenuation caused by the transition to used dialysate.

In this illustrative embodiment, the membrane 341c and the wall of the balancing chamber 341 are made of a transparent material (or at least transparent to light emitted by the emitter assembly 343a). Thus, light from the emitter assembly 343a may pass through the chamber wall and the membrane to the detector assembly 343b. However, other arrangements are possible. For example, the chamber wall may be made of an opaque material, and the emitter assembly and detector assembly 343a, 343b may be embedded in the wall (e.g., co-molded with the wall) so that light emitter/detector sections are exposed to the interior of the chamber 341. In another embodiment, the chamber wall may be formed to have a transparent window, light tube, or other path through which the emitter assembly and detector assembly 343a, 343b are exposed to the chamber 341 interior.

In other embodiments, the membrane 341c may be opaque and include one or more windows or other portions in suitable locations on the membrane 341c that are transparent to the light used by the blood leak sensor 343. Alternately, the emitter assembly and detector assembly 343a, 343b may be arranged to transmit light through portions of the chamber 341 without passing light through the membrane 341c. For example, a first emitter assembly and detector assembly pair 343a, 343b may be positioned on one side of the membrane 341c (e.g., on a used dialysate side) and a second emitter assembly and detector assembly pair 343a, 343b may be positioned on the other side of the membrane 341c (e.g., on a clean dialysate side). While this arrangement may not be ideal, e.g., because the emitter assembly and detector assembly pairs use different light paths in the chamber 341, the pairs may be suitably calibrated relative to each other at the time of manufacture of the hemodialysis system (e.g., by making measurements with each pair using identical solutions in the respective chamber 341 portions), or at other times (such as by circulating clean dialysate through the balancing circuit 143 prior to providing treatment to a patient). In another embodiment, a single emitter assembly and detector assembly pair 343a, 343b may be used to measure the presence of blood in the chamber 341 without passing light through the membrane 341c, e.g., by using a suitable light pipe arrangement (e.g., having a "Y" shape) that splits light from a single emitter assembly 343a to opposite sides of the membrane 341c and directs the two light beams into the chamber 341, and another suitable light pipe arrangement that receives the two light beams on an opposite side of the chamber 341 and conducts the light beams to a single detector assembly 343b.

While in the embodiments discussed above, light from an emitter assembly 343a traverses a portion of the chamber 341 to an opposed detector assembly 343b, other arrangements are possible. For example, light emanating from an emitter assembly 343a may traverse the chamber 341, and be reflected by the opposite chamber wall and/or a portion of the membrane 341c so the reflected beam transits to a detector assembly 343b located on a same side of the chamber 341 as the emitter assembly 343a. This arrangement may provide advantages, such as allowing electrical and other connections to the emitter assembly and detector assembly 343a, 343b on a same side of the chamber 341. In addition, or alternately, transiting the light beam through a dialysate volume two or more times may increase the sensitivity of the blood leak sensor 343, e.g., by allowing the sensor 343 to detect the presence of relatively small concentrations of blood components.

As described above, when dialysate is circulated through the dialyzer 14, the pod pumps 161, 162 pull used dialysate from the dialyzer 14 and push the used dialysate to the drain 31 via the balancing chambers 341, 342. That is, the pod pumps 161, 162 essentially drive (with coordinated control of the valves 211, 212, 213, 221, 222, 223, 231) the balancing chambers 341, 342 to act as pumps themselves so that the balancing chambers 341, 342 alternately substantially fill completely with used dialysate, followed by a substantial fill with clean dialysate. The blood leak sensor 343 operation may be timed so that the emitter assembly 343a emits light, and the detector assembly 343b detects light while the respective balancing chamber 341 is substantially filled with either used dialysate or clean dialysate. During each of these stages, which may be momentary, the membrane 341c may be pressed into contact with the chamber wall so that little or no fluid is between the membrane 341c and the adjacent emitter or sensor 343a, 343b. Thus, the membrane 341c may have little or no effect on light used to detect a blood component level in the chamber 341.

A light level measurement made while the chamber 341 is filled with clean dialysate may be compared to a light level measurement made while the chamber 341 is filled with used dialysate, and a difference, if any, between the two signals may be used to determine if blood is included in the used dialysate. For example, if a difference between the two measurement signals exceeds a suitable threshold, the presence of blood may be determined, and the system control may take suitable action. Blood presence detection may be performed by comparing light level measurements for consecutive balancing chamber fill operations, or each light level measurement for used dialysate may be compared to a different stored threshold. Comparison of a light level measurement made for a balancing chamber filled with clean dialysate to a stored threshold may be used to determine whether the threshold should be changed (e.g., replacement of the stored threshold with the recent light level measurement for clean dialysate or some other adjustment). On the other hand, comparison of a light level measurement made for a balancing chamber filled with used dialysate to a stored threshold may be used to determine whether sufficient blood is present in the used dialysate to trigger an alarm condition. However the light measurements are used, the system may be able to update or otherwise verify suitable measurement discrimination of the blood leak sensor 343 by the regular measurement of light transmission in the chamber when filled with clean dialysate. Thus, if the optical characteristics of the chamber, membrane or clean dialysate change during a treatment, the blood level sensor 343 may take such changes into account on a ongoing basis, and avoid false positive blood detections or other problems due to improper sensor reference level.

While the embodiments described above detect the presence and/or absence of blood based on absorption of light by blood components, other optical characteristics or properties may be exploited. For example, the blood leak sensor 343 may determine the presence of blood based on scattering or reflection of light by blood components, by light emission from blood components (e.g., caused by an excitation illumination), etc. Alternately, or in addition, the blood leak sensor 343 may include other sensor types than, or in addition to, an optical detector. For example, one or more sensors associated with a balancing chamber 341 may use a chemical detector to sense the presence of blood components, e.g., by the binding of a blood protein with a suitable receptor. Thus, aspects of the invention are not necessarily limited to optical detection of blood, but rather may employ any suitable sensor to detect the presence and/or absence of blood components in used dialysate.

FIGS. 86 and 87 show a bottom view and a lower left side perspective view of a balancing chamber 341 having a blood leak sensor 343 mounted to the chamber 341. The balancing chamber 341 has the same general arrangement like that of the pod shown in FIGS. 47A to 49, and the blood leak sensor 343 may include a bracket 343c that carries both the emitter assembly and detector assembly 343a, 343b and that is attached to the balancing chamber 341. The bracket 343c, which is shown in isolation in FIG. 88, may engage with the balancing chamber 341 in any suitable way, such as being molded as a single unitary piece with a portion of the chamber 341, being adhered or otherwise fastened to the chamber 341, engaged with the balancing chamber 341 by a friction or interference fit, and so on. Thus, the bracket 343c may be removable from the chamber 341, or may be permanently attached to the chamber 341. In this embodiment, the bracket 343c includes a pair of opposed slots 343d (see FIG. 88) that receive the annular mating rib of the balancing chamber 341 (i.e., the rib formed at the joint between the two hemispherical wall portions when joined together). The emitter assembly and detector assembly 343a, 343b may be mounted to the bracket 343c and arranged so that light emitting and receiving areas, respectively, are appropriately oriented with respect to the internal volume of the balancing chamber 341 and are appropriately oriented with each other, e.g., are diametrically opposed on opposite sides of the chamber 341. In this embodiment, the emitter assembly and detector assembly 343a, 343b are mounted to the bracket 343c and to the balancing chamber 341 so that the light emitting and receiving regions may be placed close to or into contact with the wall of the balancing chamber 341. While not necessarily required, an optically coupling material, such as a grease, glue, or other, may be provided to optically couple the emitter assembly and detector assembly 343a, 343b to the chamber wall. This may help reduce optical losses and/or help prevent dirt or other materials from potentially interfering with optical communication of the emitter assembly and detector assembly 343a, 343b with the balancing chamber 341.

As shown in FIG. 88, the emitter assembly and detector assembly 343a, 343b may be removably mounted to the bracket 343c. Although other arrangements are possible, in this embodiment, the emitter assembly and detector assembly 343a, 343b each include a generally planar body, which may conveniently be the circuit board to which optical, electronic and other components are mounted, and which is received in a corresponding slot of the bracket 343c. The planar body (e.g., circuit board) of the emitter assembly and detector assembly 343a, 343b may also include a cutout, forming a flexible or spring-like tab 343e with a distal jog that keeps the emitter assembly and detector assembly 343a, 343b engaged with the bracket 343c. Manufacturing a circuit board to include a cutout to create a spring tab may obviate the need to attach additional parts to the emitter and detector assemblies 343a and 343b in order to mount them reliably and accurately onto bracket 343c. To remove the emitter and/or detector assembly 343a, 343b, the spring tab 343e may be depressed to release the jog, allowing the emitter assembly and detector assembly 343a, 343b to be removed from its slot on the bracket 343c. This arrangement may allow for the replacement of a damaged or otherwise faulty emitter assembly and detector assembly 343a, 343b, as needed.

Although not shown, the emitter assembly and detector assembly 343a, 343b may include any suitable optical, electrical or other components as needed to perform desired functions. For example, the emitter assembly 343a may include a suitable LED light source, a filter to remove unwanted light frequencies from light emitted into the chamber 341, a lens (e.g., to focus, collimate, disperse, or otherwise operate on the emitted light in a desired way), electronic drive circuitry (such as a circuit capable of using PWM or other technique to control the intensity, timing or other characteristics of light emitted by the LED), electronic circuitry for communication with a system controller, and so on. The detector assembly 343b may likewise include any suitable light detector (such as a photodiode or other light sensitive device), an optical filter and/or lens, suitable circuitry to smooth, sample, or otherwise process signal data from the optical sensor, circuitry for communication with the system controller, and so on.

The blood leak sensor 343 may be arranged to detect any suitable blood concentration where the blood has a hemocrit percentage at any suitable level. For example, the blood leak sensor 343 may be arranged to be capable of detecting a leak rate across the dialyzer of 0.35 ml/min or more (or less) of blood having a hematocrit of 25% where the flow rate of dialysate out of the dialyzer is at a rate of about 1 L per minute. Thus, in one embodiment, the blood leak sensor 343 may need to be configured to detect a concentration of 25% hematocrit blood equivalent to about 0.35 ml blood per liter of clean fluid, such as a saline solution. In another embodiment, the blood leak sensor may be arranged to detect blood having a 40% hematocrit at a concentration of about 0.2 ml per 1 L of fluid. In other embodiments, the blood leak sensor may be arranged to determine the signal strength associated with dialysate having a pre-determined concentration of blood relative to a reference signal strength associated with blood-free fluid (e.g. clean dialysate). This relative or differential signal strength may be chosen as the threshold measurement that triggers an alarm condition. As the reference signal strength varies over time, the threshold value for triggering an alarm will also change to maintain the pre-determined relative or differential signal strength associated with the presence of blood at the specified concentration. In some arrangements, the blood leak sensor is capable of reliably discriminating between blood-free clean dialysate and used dialysate having a blood concentration less than half that specified by international standards setting organizations for hemodialysis equipment (e.g. ANSI/AAMI-RD5-2003 section 4.2.4.7). Moreover, a controller may be programmed to adjust the current to the emitter element (e.g. LED) in order to generate a pre-determined minimum reference signal strength received by the detector. This may help to prevent the reference signal strength received by the detector from becoming too weak to permit reliable signal strength discrimination between used dialysate and clean dialysate.

In another aspect of the invention, a dialysis system may include a water supply air trap arranged to remove air from water that is provided to the dialysis system, e.g., for use in making dialysate for treatment. The removal of air from water may help improve system performance, e.g., by reducing the interference of air with conductivity or other measurements made to confirm that dialysate has been properly formed. For example, air that is released from or otherwise present in dialysate may attach to an area between electrodes used to make a conductivity measurement of the dialysate. These air bubbles may cause an artificially low conductivity measurement, or otherwise faulty measurement, which may lead the system to improperly determine that the dialysate was not properly made and/or cause the system to improperly adjust the dialysis production process. That is, the dialysis system controller may use conductivity readings of dialysate to control amounts of acid, bicarbonate or other ingredients that are subsequently added to water to form dialysate. Faulty conductivity readings may cause the system to add improper amounts of such ingredients, causing the system to create unusable dialysate, or may cause the system to discard good dialysate that was identified as improperly made because of the faulty conductivity reading. Although improperly formed dialysate may be identified by another sensor, such as a safety conductivity sensor in the balancing circuit downstream of the ultrafilter, the improperly formed dialysate may cause a disruption in patient treatment as the unusable dialysate is cleared and replacement dialysate made and supplied.

Air bubbles can cause other problems as well, such as disrupting the system's ability to balance an amount of clean dialysate supplied to a dialyzer with an amount of used dialysate received from the dialyzer. This balance can be important, e.g., to ensure that a patient receives no excess fluids during the dialysis process, or when operating the system to remove fluids from the patient during treatment. For example, air bubbles out-gas sing from the clean dialysate being delivered to the dialyzer after leaving the clean dialysate side of a balance chamber may be transported to the used dialysate side of the balance chamber, ultimately causing more liquid to be delivered to the dialyzer than is being pulled from the dialyzer.

As will be appreciated from the above, air may be present in water provided to the dialysis system in at least two possible ways, e.g., as air bubbles in the water flowing from the water supply and/or as dissolved gas that is carried in the water and released to form bubbles within the mixing circuit or other locations in the system. Aspects of the invention may involve the removal of air bubbles in water supplied to the system and/or removal of dissolved air from water supplied to the system. Thus, aspects of the invention may not only remove air bubbles, but also dissolved gas from a water supply.

In one illustrative embodiment, a dialysis system may include a mixing circuit arranged to combine at least water and one ingredient to form dialysate used in a dialysis treatment, a water supply arranged to provide water to the mixing circuit via a water supply conduit, and a water supply air trap arranged to trap air in the water supply conduit. The air trap may be provided in fluid communication with a water supply conduit that is fluidly coupled between the water supply (such as a bag or other container of water, a reverse osmosis filtration system or other suitable arrangement) and a mixing circuit of the dialysis system. In one embodiment, the air trap may include a chamber having an inlet near a top of the air trap and an outlet near a bottom of the air trap. Thus, the air trap may capture air at the top of the chamber and release only liquid at the bottom of the chamber to the outlet, thereby removing air from the water as it passes from the water supply to the mixing circuit.

It should be understood that aspects of the invention are not necessarily limited to use in systems that include a water supply and mixing circuit. For example, aspects of the invention involved with air removal may be used in systems that include a dialysate supply (such as a reservoir of dialysate ready for use in treatment) and a directing circuit or other dialysate circuit that receives the dialysate from the dialysate supply and provides the dialysate to a dialyzer. In this case, aspects of the invention may be used to remove air from dialysate supplied from the dialysate supply. Thus, in one aspect, a dialysis system may include a liquid supply arranged to provide liquid for use in dialysis treatment, a liquid supply conduit fluidly coupled between the liquid supply and a directing circuit or other dialysate circuit of the dialysis system, and a water supply air trap arranged to trap air in the water supply conduit. The liquid supply may be a water supply or dialysate supply, and may provide the liquid (whether water or dialysate) in any suitable way.

In one embodiment, a relatively low pressure may be present, at least during some periods, in the water supply conduit that tends to release dissolved gas from the water. This gas, once released from dissolution, may be captured by the air trap. For example, the water supply may include a pressure regulator, flow restrictor, vent, or other arrangement to provide a suitable supply pressure for water provided to the water supply conduit. In addition, or alternatively, the water supply conduit itself and/or other components may be arranged, e.g., with a suitably small cross sectional size for its flow path, flow restrictor, etc., that helps to provide a relatively low pressure in the water supply conduit to help release dissolved gas from the water.

The mixing circuit may include one or more pumps that draw water from the water supply conduit, such as pumps that intermittently draw water from the water supply conduit. For example, the mixing circuit may include one or more pod pumps like those discussed above, a reciprocating piston pump, a syringe pump or other arrangement that intermittently draws fluid from the water supply conduit. This arrangement may allow the mixing circuit to periodically create a relatively low (negative) pressure in the water supply conduit to cause the release of dissolved gas without necessarily requiring constant flow in the water supply conduit. (A negative pressure may be a pressure below that experienced by the water or dialysate in the water supply and/or elsewhere in the dialysis system. In some embodiments, the negative pressure may be a pressure below atmospheric pressure.) Of course, other arrangements are possible, such as peristaltic or other pumps in the mixing chamber that provide an approximately constant draw of water from the water supply conduit. Alternately, a gang of two or more pod pumps or other intermittent-type pumps may be operated to provide a constant or approximately constant draw of water from the water supply conduit. In contrast to the pumps of the mixing circuit (at least in some embodiments), the water supply may be arranged to provide water on a continuous basis. The water supply may do this by using a continuous flow pump, a connection to city water or other plumbed connection, a water storage reservoir or other.

The air trap may be arranged to trap any suitable volume of air, e.g., up to about 1.5 ml of air or more, depending on requirements. For example, the air trap may be arranged to trap air at a rate of up to about 10 ml/hour with a flow of water of about 1200 ml/minute through the air trap. Other capture rates for the same or different water flow rates may be used, depending on system requirements. Air in the air trap may be purged in any suitable way, such as reversing flow in the water supply conduit so as to force air from the air trap into the water supply, into a drain line, or other suitable location. A controller may actuate one or more valves in the fluid path to allow diversion of reversed flow through the air trap to a drain line. Placing the inlet of the air trap at or near the top of the air trap helps to ensure that most or all of the air within it is preferentially pushed to drain. Alternately, the air trap may have a discharge port that can be opened to vent the trapped gas.

In another aspect of the invention, a method for operating a dialysis system includes receiving water from a water supply at a mixing circuit via a water supply conduit, and trapping air in the water at an air trap in communication with the water supply conduit. As discussed above, the step of receiving water may include drawing water from the water supply conduit using one or more pumps in the mixing circuit. For example, the one or more pumps may be operated to intermittently draw water from the water supply conduit. In one embodiment, a negative pressure may be created in the air trap during at least a portion of a period in which the mixing chamber receives water from the water supply conduit. The negative pressure may cause air in the water to be released from the water and be trapped in the air trap. The negative pressure may be created in any suitable way, such as, at least in part, by one or more pumps of the mixing circuit drawing water from the water supply conduit. In some embodiments, valves or other flow control elements may also cooperate with the pump operation to create a desired negative pressure in the air trap. For example, the water supply or water supply conduit may include a flow regulator, valve or other element that slows or otherwise adjusts flow of water during a period when the mixing circuit draws water from the water supply conduit. This reduced flow in water supply conduit may cause a negative pressure to be produced in the water supply conduit.

Water Inlet Module

A function of the water inlet module 12500 (FIG. 141) may be to connect the water ports 30,31 (FIG. 3A) on the cassette system to the water ports 12510, 12520 on the outside of the hemodialysis machine 6001 while protecting the electronics in the cold section from water leaks. The water inlet module 12500 may be located in the cold section of the hemodialysis machine 6001 with connections 12530 and 12531 to connect to the water supply 30 and drain 31 of the cassette system. The external ports 12510 and 12520 may extend through the exterior of the hemodialysis machine 6001 (FIG. 144). The tubing and connections between the ports are all contained in a case 12540 with a cover (not shown) that directs any leaked fluid to exit out the drain slot 12550 (FIG. 142). Water exiting the drain slot may collect in the bottom of the cold section away from the electronics. The water inlet module 12500 may include a water detector 12560 placed a given distance above the bottom of the case 125410 and able to discriminate between condensation and a significant leakage.

A number of functional elements are located in the water inlet module 12500 including, but not limited to, a water supply valve 12560, a water supply pressure regulator 12560, drain air-in-line detector 37 or a pneumatic line from dialysate tank 12570. The water supply valve 12560 may be a normally closed electro-mechanical valve that may prevent the flow of water through the dialysate circuit in the event of a power failure. In one example, the water supply valve 12560 may be located immediately downstream of the supply port 12510. The regulator 12566 may limit the water pressure supplied to the liquid handling cassettes shown in FIGS. 30A-46E to pressures against which the liquid valves can close. In one example, the regulator 12565 may be located immediately downstream of the water supply valve 12560. In an example regulator 12565 and valve 12560 may be hard plumbed together and to the inlet port 12510 without flexible lines. The drain air-in-line 37 may be located on a vertical portion of the drain line downstream of a p-trap 12537. The p-trap 12537 followed by a vertical section may serve to collect gas bubbles and allow them to coalesce in order to improve the detectability of the bubbles by the AIL sensor 37.

In order to protect the electronics in the cold section from water damage it is important to detect water leaks or breaks in the lines, components and fittings between the external ports 12510, 12520 and the hot box ports 12530, 12531. When a water leak is detected, the AC processing unit 6109 may close the water supply valve 12560 and initiate a shutdown procedure to minimize the amount of water entering the cold section. It is also important to only signal the AC processing unit 6109 when a significant leak has occurred. In the event of operating in a humid ambient environment, the cold water flow through line 12512 may condense significant amounts of water that may migrate to the bottom of the case. The water sensor 12580 (FIG. 143) may be a liquid level sensor that signals the AC processing unit 6109 when the tip 12581 is immersed in water. One example water sensor is the LLE105000 sensor from Honeywell Sensing and Control in Golden Valley, Minn., USA. The water sensor 12580 may be mounted a given distance above the base 12541 next to the drain slot 12550. The water sensor 12580 may detect water if the leak of water is larger than the allowable flow out the drain slot 12550. Smaller leaks and condensation may not trigger the water sensor 12580, but will drain out and evaporate in the hemodialysis machine 6001.

In another aspect of the invention, a dialysis system may include an accumulator arranged to receive and release water in fluid communication with the water supply conduit. The accumulator may be arranged, for example, so that when a negative pressure is present in the water supply conduit, the accumulator may release water into the water supply conduit, e.g., at a rate that helps to maintain a negative pressure in the water supply conduit to cause dissolved gas to be released from the water. In addition, the accumulator may be arranged so that when a positive pressure is present in the water supply conduit, water may be received into the accumulator. Thus, an accumulator may be used with an air trap, e.g., in cooperation to help establish and maintain, at least temporarily, a negative pressure in the water supply conduit and/or the air trap, to help remove dissolved gas from the water. Alternately, an accumulator may be used without an air trap, e.g., to help smooth a pressure or flow rate in the water supply conduit when the mixing circuit includes an intermittently operating pump to draw water from the water supply conduit.

As with aspects of the invention related to an air trap and/or removal of dissolved gas from a liquid for use in dialysis treatment, aspects of the invention related to an accumulator may be used with any liquid provided to a dialysis system for use in treatment. For example, a dialysis system may employ the use of an accumulator in a supply conduit that provides dialysate from a dialysate supply to a directing circuit or other dialysate circuit of the dialysis system. Accordingly, aspects of the invention relating to an accumulator may be equally applicable to systems that do not include a water supply or mixing circuit, but instead use a pre-prepared dialysate supply.

In one embodiment, the accumulator may include a moveable diaphragm that separates a liquid side of the accumulator from a gas side of the accumulator. For example, the accumulator may include a spherical chamber with a diaphragm that has a hemispherical shape and is movable to accommodate variable volumes of water in the liquid side of the accumulator. The gas side of the accumulator may be vented to atmospheric pressure or otherwise have a static or variable pressure in the gas side to provide a desired pressure or other flow affect on the water supply conduit. The accumulator may be arranged to store a volume of water of any suitable size, such as equal to about 27 ml. In one embodiment, the volume of liquid capable of being stored in the accumulator may be equal to about half or more of a stroke volume of a pod pump used by the mixing circuit to draw water from the water supply conduit. Thus, the accumulator may be arranged to receive and hold water from the water supply conduit during periods when the mixing circuit is not drawing water from the water supply conduit, and be arranged to supply water to the water supply conduit during periods when the mixing circuit is drawing water from the water supply conduit.

In another aspect of the invention, a method for operating a dialysis system includes receiving water from a water supply at a mixing circuit via a water supply conduit, providing water from an accumulator into the water supply conduit when the mixing circuit draws water from the water supply conduit, and receiving water from the water supply conduit in the accumulator when the mixing circuit does not draw water from the water supply conduit. In one embodiment, a water supply may provide water to the water supply conduit at a pressure that is greater than a maximum negative pressure that is used by the mixing circuit to draw water from the water supply conduit. As a result, when the mixing circuit draws water from the water supply circuit, the accumulator may provide water to the supply circuit, and when the mixing circuit stops drawing water, the accumulator may receive water from the water supply. This arrangement may smooth and/or help maintain a negative pressure in the water supply circuit, e.g., to help remove dissolved gas from the water for trapping in an air trap, if present. The mixing circuit may intermittently draw water from the water supply circuit where, for example, the mixing circuit includes one or more pod pumps or other similar device to draw water from the water supply circuit. Thus, the accumulator may provide water to the water supply conduit when a negative pressure is present in the conduit (e.g., when the mixing circuit draws water from the water supply conduit), and may receive water from the water supply conduit when a positive pressure is present in the conduit (e.g., when the mixing circuit does not draw water from the water supply). In one embodiment, the water supply may be arranged to provide water to the water supply conduit at a flow rate that is less than an instantaneous flow rate employed by the mixing circuit when drawing water from the water supply conduit. In this case, the accumulator may provide water to the water supply conduit to make up for a flow rate deficiency of the water supply. Water may be provided from the accumulator in a way that helps to maintain a negative pressure in the water supply conduit, e.g., the gas side of the accumulator may be vented to provide a desired total amount of liquid to the water supply conduit.

FIG. 89 shows a schematic block diagram of a dialysis system that is very similar to that in FIG. 3A with the difference being that the system in FIG. 89 includes an accumulator 33 and an air trap 32 in a water supply conduit between the water supply 30 and the pumps 180 of the mixing circuit 25. As discussed above, although the dialysis system in this illustrative embodiment includes both an air trap and accumulator, the dialysis system may be arranged to have only an accumulator 33 or only an air trap 32. However, combining the accumulator 33 and air trap 32 together may provide operating advantages for the system.

In this embodiment, the water supply 30 may include any suitable source of water, such as a reverse osmosis filtration system connected to a plumbed water line (e.g., "city water"), a bag or other container of water, and/or others. The water source 30 may be arranged to provide water to the water supply conduit at a desired pressure, such as about 7 psi, and/or at a desired flow rate, so that a desired negative pressure may be created in the water supply conduit, such as in the air trap 32. For example, the pumps 180 may be operated to draw water from the water supply conduit and into the mixing circuit 25, e.g., for use in making dialysate and or supplying water to the ingredients 49 as needed. The negative pressure created by the pumps 180 in the water supply conduit may be greater, in an absolute sense and at least momentarily, than a positive pressure provided by the water supply 30 to provide water to the water supply conduit. As a result, the pump 180 may generate a desired negative pressure in the air trap 32 or other locations, e.g., a pressure below atmospheric pressure or other suitable reference level pressure. For example, a suitable reference level pressure may be a lowest pressure that the water or dialysate experiences when coursing through the dialysis system. Accordingly, the water supply may provide water to the water supply conduit at a positive pressure that is less (in an absolute sense) than a negative pressure used by the mixing circuit to draw water from the water supply conduit.

The negative pressure created in the water supply conduit, e.g., a pressure below atmospheric pressure, may help to release dissolved gas from the water. Various components of the system may cooperate with the pump 180 operation to create a desired negative pressure, such as closing or otherwise controlling valves leading from the water supply 30 to control a flow rate of water from the water supply, providing flow restrictors or other components in the water supply conduit, venting or otherwise controlling a gas side of the accumulator 33 so as to help maintain a negative pressure induced by the pump 180, and others. For example, the accumulator 33 may be arranged to store a volume of water equal to about half or more of a volume drawn by the pump 180 in a single stroke. At some point before or during the draw stroke of the pump 180, a valve leading from the water supply 30 may be closed, allowing the pump 180 to develop a negative pressure in the water supply conduit and drawing water from the accumulator 33. (In other embodiments, a valve leading from the water supply 30 need not be closed, but may be left open and other elements, such as a flow restrictor, may allow a suitable negative pressure to be developed at the accumulator 33.) The accumulator 33 gas side may be vented to atmospheric pressure with a suitably sized orifice so that air may enter the gas side of the accumulator 33 at a rate that allows a desired negative pressure to be established and maintained over a period of time at the accumulator 33 and in the air trap 32. This sustained period of negative pressure may help bring dissolved gases in the water out of solution, which can then be trapped in the air trap 32.

Once the pump 180 stops drawing water from the water supply conduit, e.g., because a pump membrane has bottomed out, the positive pressure of water supplied by the water supply 30 may cause water to flow into the accumulator 33, causing air in the gas side of the accumulator 33 to be vented and the accumulator 33 to be filled with water in preparation for a next draw stroke of the pump 180. Thus, the pump 180, the water supply conduit (e.g., by way of a flow restrictor, cross sectional size of a portion of the water supply conduit, etc.), the accumulator 33, and/or the water supply 30 (e.g., including one or more valves, pressure regulators, etc.) may be arranged to provide a suitable negative pressure to release dissolved gases for removal from the water. Of course, not all of these elements need be specially arranged, or even provided, to provide a negative pressure in the water supply conduit. For example, the accumulator 33 may be omitted and a negative pressure established in the air trap 32 and/or in other regions of the water supply conduit by the pump 180 and operation of a valve or pressure regulator in the water supply 30. In other arrangements, the accumulator 33 may be operated to provide a negative pressure, e.g., by exposing the gas side of the accumulator 33 to a suitably low pressure.

While the discussion above mainly relates to the release of dissolved gases from water in the water supply conduit, the air trap 32 may function to trap air bubbles that are already present in the water provided from the water supply 30. Thus, the dialysis system may include an air trap 32 that is arranged to trap air, and yet not necessarily operate to establish a negative pressure in the water supply conduit or elsewhere to help liberate dissolved gases from the water. Also, aspects of the invention may be used with systems that receive prepared dialysate for use in treatment. For example, the water supply 30 may actually provide prepared dialysate (e.g., from a reservoir), and the mixing circuit 25 may be eliminated from the system. Thus, the air trap 32 and/or accumulator 33 may be provided in a supply conduit between the water supply 30 (dialysate supply) and the directing circuit 142 or other dialysate circuit of the system.

FIGS. 90-92 show a side view, bottom view and cross sectional view of an air trap 32 in one illustrative embodiment. The air trap 32 in this embodiment includes an inlet 32a for connection to the water supply 30 and an outlet 32b for connection to the mixing circuit 25. As can be seen in FIG. 91, the air trap 32 has a generally cylindrical shape, but may be arranged to have other shapes, such as a cylinder, a box, and others. The air trap 32 may generally be oriented with the inlet 32a positioned above the outlet 32b so that any air introduced into the air trap 32 or liberated in the air trap 32 may remain at a top of the air trap 32, while air-free water at the bottom of the air trap 32 may exit the outlet 32b. Of course, other arrangements are possible, such as having the inlet 32a and outlet 32b at a same level, or different levels, with suitable baffles, serpentine flow arrangements or other features in the air trap to help prevent air from being conducted to the outlet 32b. As can be seen in the cross sectional view of FIG. 92, the air trap 32 may be formed of two parts, e.g., each having a generally hemispherical shape, that are joined together, e.g., using an O-ring seal or other engagement to help prevent leaking at the joint.

Air collected in the air trap 32 may be removed in any suitable way. For example, the air trap 32 of FIG. 90 may have the air removed by reversing the flow of water from the outlet 32b to the inlet 32a, which may cause air to exit the inlet 32a and travel in the water supply conduit toward the water supply 30. The air may be forced to the drain 31 (e.g., by suitable control of valves), to the water supply 30 (where the air may be released, for example, into a reservoir), or may be released via a vent or other feature, whether in the air trap 32 or another location in the water supply conduit. Reversed flow of water in the air trap 32 may be caused by the pump 180 of the mixing circuit 25 reversing operation so as to push water toward the water supply 30.

Referring to FIG. 89, for example, a controller may periodically reverse through air trap 32 by first opening valves 265 and 271, and having pump 280 fill with water. Then valve 265 may be closed, and valves 266 and 263 opened. The chamber of pump 280 may then be delivered backward to drain by closing alternative flow paths, for example, by ensuring that valves 270, 272, 274, and 264 remain closed. Preferably, the inlet of air trap 32 is located above the fluid inlet of accumulator 33, as shown in 98 and 99.

The air trap 32 may have any suitable volume, such as an arrangement to trap an air volume of up to 1.5 ml or more. In one embodiment, the air trap 32 may be arranged to trap air at a rate of up to 10 ml/hour when experiencing water flows of up to about 1200 ml/minute. Of course, other air volume and/or air trapping rates may be used for the air trap 32.

FIGS. 93-96 show an illustrative embodiment of an accumulator. The accumulator 33 in this example includes an approximately spherical body with a liquid side port 33a to a liquid side of the accumulator 33. The port 33a may be fluidly coupled to the water supply conduit so that water may flow between the accumulator 33 and the water supply conduit. As can be seen in FIG. 95, a diaphragm 33d separates the liquid side of the accumulator 33 from a gas side. A gas side port 33b of the accumulator 33 includes an orifice 33c arranged to allow air to pass into and out of the gas side of the accumulator 33 depending on whether water is flowing into or out of the liquid side of the accumulator. While in this embodiment the orifice 33c is open to atmospheric pressure, the orifice 33c may communicate with any suitable static or variable pressure source. In addition, the orifice 33c may include a valve that can be controllably opened or closed, as desired. As discussed above, the orifice 33c may be arranged to help provide a suitable negative pressure in the air trap 32 or elsewhere in the water supply conduit. For example, the orifice 33c may be sized so that when the pump 180 draws water from the water supply conduit, the orifice 33c allows air to flow into the gas side of the accumulator at a suitably slow rate so as to help maintain a negative pressure in the water supply conduit. In other embodiments, the accumulator 33 itself may provide a desired negative pressure, e.g., by exposing the orifice to a suitable vacuum that induces a drop in pressure in the water supply conduit.

While in some embodiments the accumulator 33 may be arranged to help provide a negative pressure in the water supply conduit, the accumulator 33 need not be so arranged, and instead may function to help maintain a relatively constant positive pressure in the water supply conduit. For example, the gas side of the accumulator 33 may be charged with a positive pressure so that when the pump 180 draws water from the water supply conduit, the accumulator 33 expels water from the port 33a to help maintain a positive pressure in the water supply conduit.

The accumulator 33 may have any suitable volume, such as a capability to store at least 27 ml of water, or up to half or more of a volume drawn from the water supply conduit by a single stroke of the pump 180. Of course, the accumulator may be arranged to store smaller or larger volumes of water, if desired. Also, while the orifice 33c in one embodiment has a size of about 0.004 inches, the orifice 33c may have other sizes or arrangements, such as including a controllable valve that is operated to provide a desired flow rate into/out of the gas side of the accumulator 33. The diaphragm 33d may have an arrangement like that used for the membrane in the pod pumps discussed above. Thus, the diaphragm 33d may have a hemispherical shell arrangement and be made of a flexible material, such as a silicone rubber. Again, the diaphragm 33d may be arranged in any suitable way.

FIGS. 97-100 show various views of a cassette assembly that is nearly identical to that shown and described with reference to FIGS. 46A to 46E. Two of the major differences between the embodiment of FIGS. 97-100 and that of FIGS. 46A-46E is that the embodiment of FIGS. 97-100 includes an air trap 32 and accumulator 33. Accordingly, the cassette assembly of FIGS. 97-100 may be arranged to have a flow path like that shown in FIG. 89. As can be seen in FIGS. 97-100, an air trap 32 like that shown in FIGS. 90-92 is added to the cassette assembly between the outer dialysate cassette 600 and the inner dialysate cassette 700 on a rear side of the cassette assembly. Also, an accumulator 33 like that shown in FIGS. 93-95 is added at a right side of the cassette assembly, adjacent the inner dialysate cassette 700. Although fluidic connections (e.g., made by silicone rubber tubing) are not shown for clarity, the air trap 32 and accumulator 33 are fluidly coupled to each other, and to a water supply 30 and to the mixing cassette 500 (for connection to the mixing circuit pumps 502 and 504). In addition, FIGS. 97-100 show that one of the balancing chambers 706 may include a blood leak sensor like that described with reference to FIGS. 85-88. Other than these additions and changes, the cassette assembly operates in the same way as that described with respect to FIGS. 46A to 46E.

Another aspect of the invention is generally directed to a user interface for the system. The user interface may be operated by an individual, such as the patient, a family member, assistant, professional care provider, or service technician, to input options, such as treatment options, and to receive information, such as information about the treatment protocol, treatment status, machine status/condition, and/or the patient condition. The user interface may be mounted on the treatment device and controlled by one or more processors in the treatment device. In another embodiment, the user interface may be a remote device that may receive, transmit, or transmit and receive data or commands related to the treatment protocol, treatment status, and/or patient condition, etc. The remote device may be connected to the treatment device by any suitable technique, including optical and/or electronic wires, wireless communication utilizing Bluetooth, RF frequencies, optical frequencies, IR frequencies, ultrasonic frequencies, magnetic effects, or the like, to transmit and/or receive data and/or commands from or to the treatment device. In some cases, an indication device may be used, which can indicate when data and/or a command has been received by the treatment device or the remote device. The remote device may include input devices such as a keyboard, touch screen, capacitive input device, or the like to input data and/or commands to the treatment device.

In some embodiments, one or more processors of the treatment device may have a unique identification code, and the remote device may include the capability to read and learn the unique identification code of the treatment. Alternatively, the user can program in the unique identification code. The treatment device and the remote device may use a unique identification code to substantially avoid interference with other receivers, including other treatment device.

In one set of embodiments, the treatment device may have one or more processors that are connected to a web-enabled server and the user interface device may be run on this web-enabled server. In one embodiment, the device uses an external CPU (e.g., a GUI, graphical user interface) to communicate via Internet protocol to the embedded web server in or connected to the treatment device. The web page may be served up inside the device and the GUI may communication directly via 802.11b or other such wired or wireless Ethernet equivalent. The GUI may be operated by an individual, such as the patient, a family member, assistant, professional care provider, or service technician, to input options, such as treatment options, and to receive information, such as information about the treatment protocol, treatment status, machine status/condition, and/or the patient condition.

In another embodiment, the embedded web server in or connected to the treatment device may communicate to an appropriate site on the Internet. The Internet site may require a password or other user identification to access the site. In another embodiment, the user may have access to different information depending on the type of user and the access provider. For example, a patient or professional caregiver may have full access to patient treatment options and patient information, while a family member may be given access to certain patient information, such as the status and duration remaining for a given treatment or frequency of treatments. The service technician, dialysis center, or treatment device provider may access other information for troubleshooting, preventive maintenance, clinical trials, and the like. Use of the web-enabled server may allow more than one individual to access patient information at the same time for a variety of purposes.

The use of a remote device, e.g., via wired or wireless communication, Internet protocol, or through an Internet site utilizing a web enabled server, could allow a dialysis center to more effectively monitor each patient and/or more efficiently monitor a larger number of patients simultaneously. In some embodiments, the remote device can serve as a nocturnal monitor or nocturnal remote alert to monitor the patient during nocturnal dialysis treatment and to provide an alarm if the patient's condition does not meet certain parameters. In some cases, the remote device may be used to provide alarms to the patient, a family member, assistant, professional care provider, or service technician. These alarms could alert an individual to certain conditions such as, but not limited to, a fluid leak, an occlusion, temperature outside normal parameters, and the like. These alarms may be audible alarms, visual alarms, and/or vibratory alarms.

Figure 60:
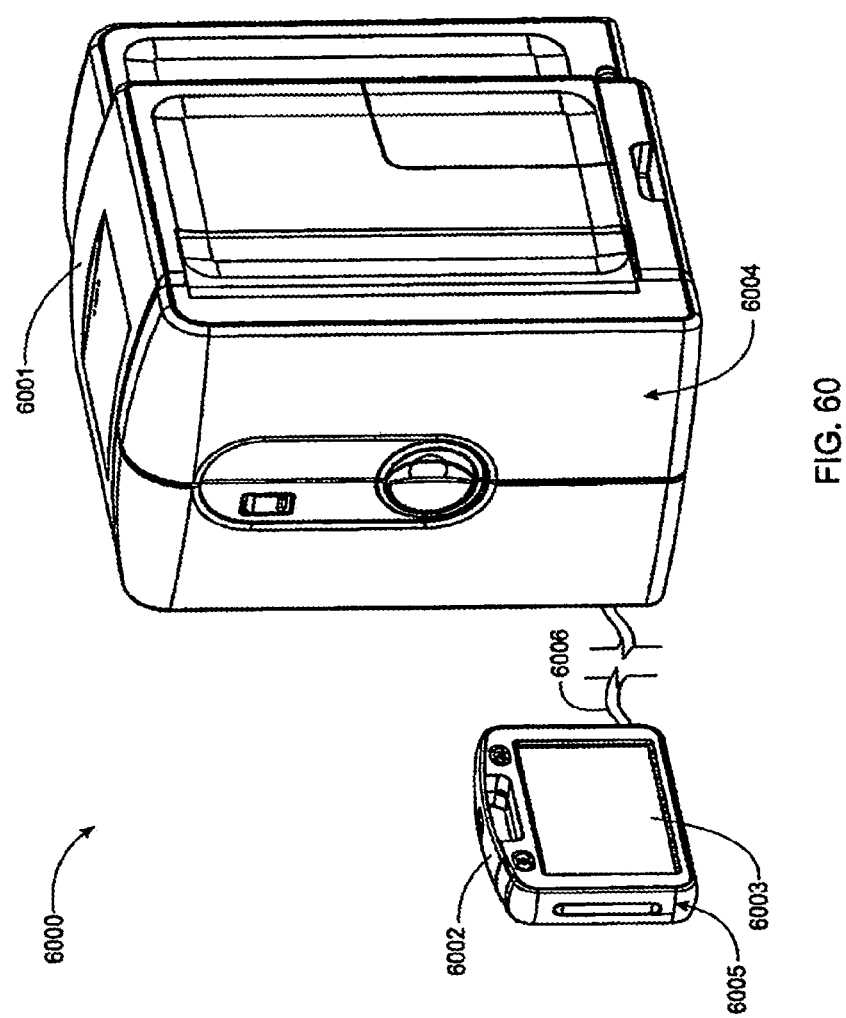
FIG. 60 is a perspective view of an exemplary embodiment of a user interface/treatment device combination.

An exemplary embodiment of a user interface/treatment device combination is shown in FIG. 60. In particular, FIG. 60 shows a perspective view of an exemplary hemodialysis system 6000 comprising a dialysis unit 6001 and a user interface unit 6002. In this embodiment, the dialysis unit 6001 comprises a housing 6004 that contains suitable components for performing hemodialysis. For example, the dialysis unit 6001 may include the mixing circuit 25, blood flow circuit 10, balancing circuit 143 and external or outer dialysate circuit 142 described, for example, in connection with FIG. 2A. The dialysis unit 6001 may also include all patient access connections and dialysate fluidic connections needed for operation of the system 6000.

The user interface unit 6002 comprises a user interface 6003 that a user, such as a hemodialysis patient, may use to control operation of the dialysis unit 6001 via a connection 6006. The connection 6006 may comprise any suitable data connection such as a bus, a wireless connection, a connection over a local area network (e.g., an Ethernet local area network), and/or a connection over a wide area network (e.g., the Internet). The user interface unit 6002 further comprises a housing 6005 that contains components for enabling operation of the user interface. In the example of FIG. 60, the user interface 6003 comprises a display screen with a touch sensitive overlay to allow touch control and interaction with a graphical user interface presented on the screen. However, many other types of user interfaces are possible, such as a screen with a separate input mechanism, such as a keyboard and/or pointing device. The user interface 6002 may also include other features, such as push buttons, a speaker, a microphone for receiving voice commands, and so on.

Wireless Communications with a User Interface

FIGS. 124-129 show flow chart diagrams illustrating a method 1 for communicating between a tablet and a base in accordance with an embodiment of the present disclosure. For example, the method 2001 may be a method for communicating between a tablet and a hemodialysis apparatus.

Method 2001 can facilitate communications between a tablet and a base by using a wired connection to establish a wireless connection through a pairing protocol. For example, the tablet may be physically connected to the base through a USB cable which is used pair the two devices together using the Bluetooth protocol; after pairing, the devices can communicate with each other wirelessly using the Bluetooth protocol. The tablet may provide the user interface to the base. For example, an interface program running on the tablet may provide an interface to a hemodialysis apparatus to control and/or monitor a dialysis treatment of a patient.

Method 2001 may be implemented by an operative set of processor executable instructions configured for execution by one or more processors. The one or more processors may be on the base and/or on the tablet. The operative set of processor executable instructions may be stored in a non-transitory processor-readable memory, such as a random-access memory, a read-only memory, a disk memory, an EEPROM, an optical-based drive, or other memory. The memory may be in the base, in the tablet, and/or the base and the tablet may each have a respective memory and one or more respective processors. The one or more processors may be in operative communication with the memory to read the operative set of processor executable instructions from the memory. The one or more processors can execute the instructions to perform the method 2001 of FIGS. 124-129.

The one or more processors may be one or more of a microprocessor, a microcontroller, an assembly-based processor, a MIPS processor, a RISC processor, a CISC processor, a parallel or multi-core processor, a CPLD, a PLA, a FPGA, a virtual processor, the like, or some combination thereof.

In some embodiments of the present disclosure, method 2001 includes acts 2002-2015. Act 2002 determines if a tablet is connected to a base through a physical connection. For example, a tablet may be connectable to a hemodialysis apparatus through a dock, a cable, a wire, a fiber optic link, or the like. The tablet and/or the base may determine that the tablet and the base are physically connected to each other through a USB connection, for example. Act 2003 establishes a first communications link between the tablet and the base through the physical connection. For example, act 2003 may establish the appropriate software interfaces and/or may perform handshaking between the tablet and the base such that data may be communicated therebetween.

Figure 126:
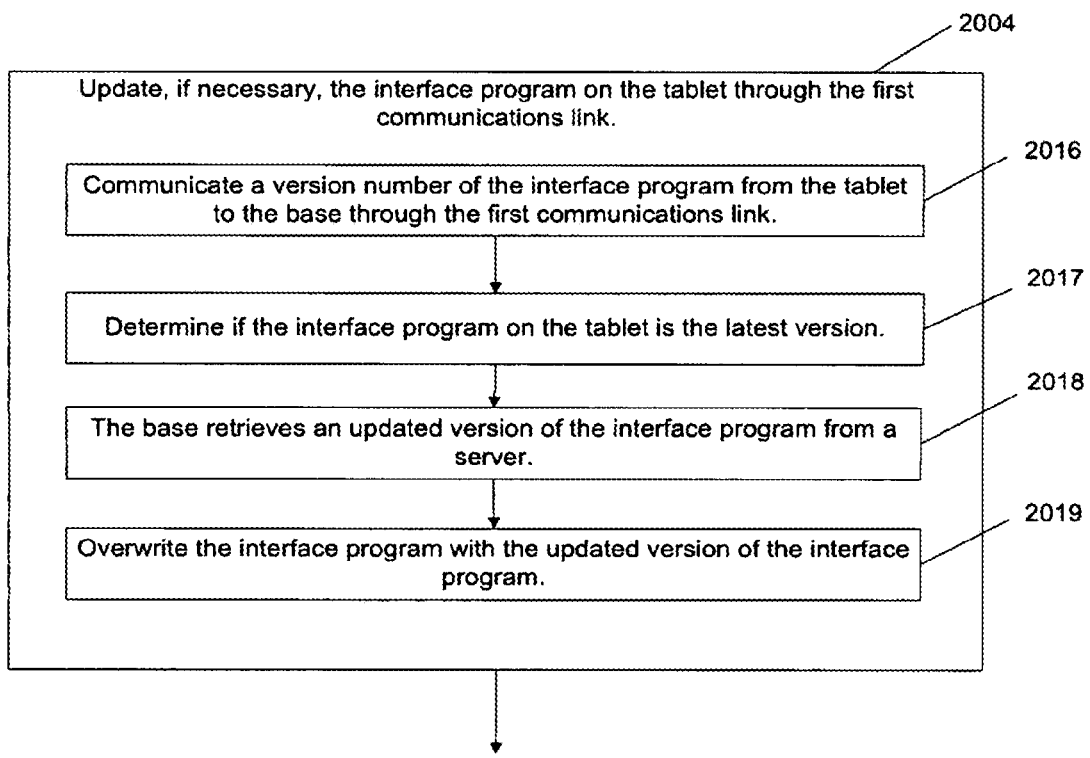

Act 2004 updates, if necessary, the interface program on the tablet through the first communications link. FIG. 126 illustrates one specific embodiment of act 2004 and is described below. Act 2004 may, for example, determine if the tablet includes the latest version of the interface program. If the tablet does not include the latest version of the interface program, the base and/or the tablet downloads (e.g., from a server) the latest version of the interface software which replaces (e.g., overwrites) the old version of the interface software. The interface software on the tablet provides a user interface (e.g., a touchscreen, a keyboard, and/or a microphone to receive voice commands) and functionality for a user to communicate with the base using the tablet.

Figure 127:
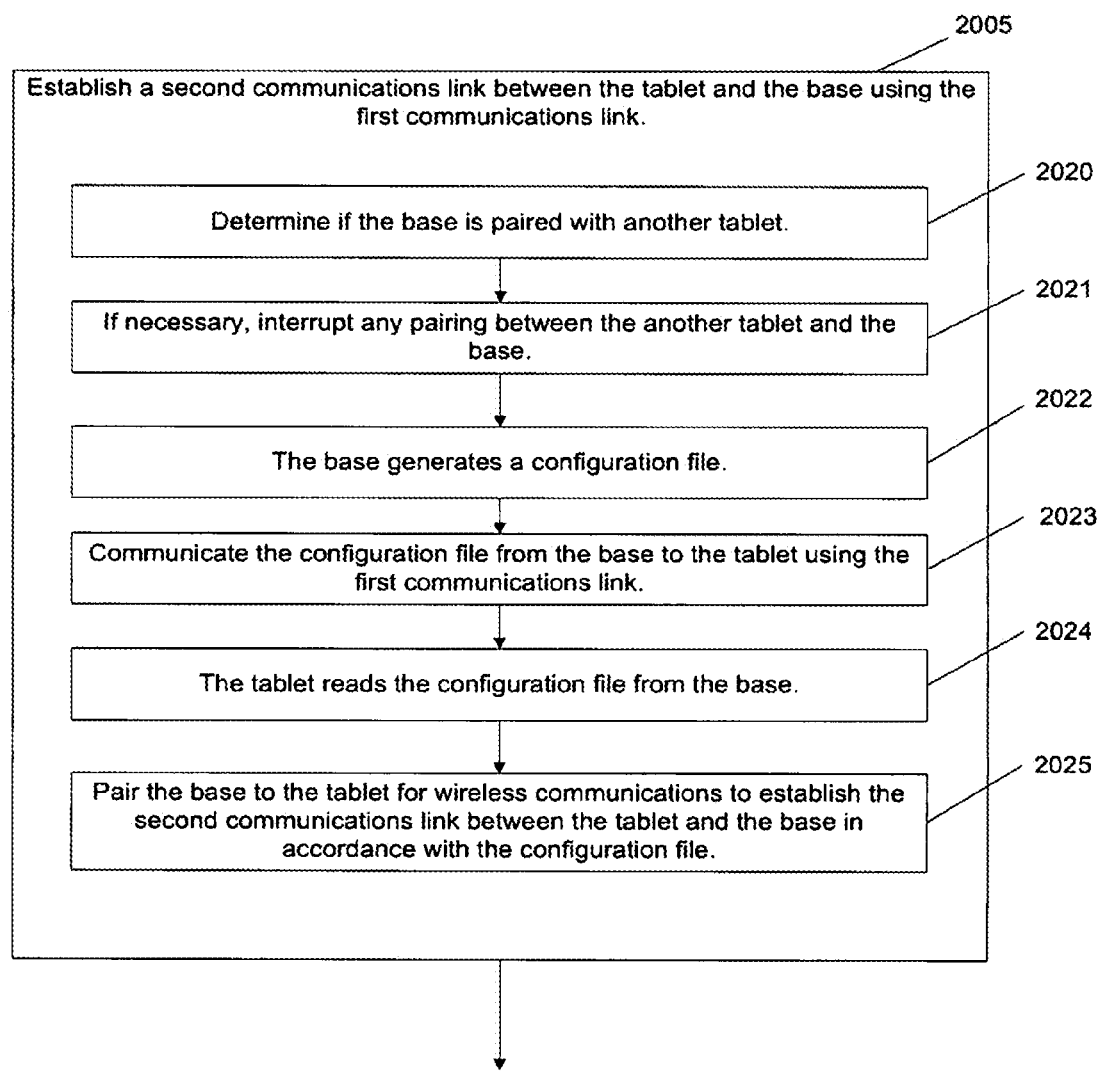

Act 2005 establishes a second communications link between the tablet and the base using the first communications link. FIG. 127 illustrates one embodiment of act 2005 and is described below. In one specific embodiment, act 2005 establishes a second communications link by pairing the tablet and the base together using a Bluetooth protocol. After pairing, data may be communicated using the second communications link. The data may be communicated over the second communication link using any know encryption algorithm, include symmetrical encryption, asymmetrical encryption, public-key infrastructure encryption, and the like. Act 2006 transmits data from the base to the tablet using the second communications link. The data may include information concerning the treatment progress of the base, the operation of the base, and/or any error messages from the base. Act 2007 displays data on the tablet in accordance with the data communicated from the base. Act 2008 initializes treatment of a patient using the tablet. For example, a user may select treatment parameters for treating a patient using the base, e.g., hemodialysis parameters. The treatment parameters may be communicated via the first or second communications link. In some embodiments, the treatment parameters may be communicated using a predetermined preferred one of the first and second communications link. For example, the second communications link may communicate the treatment parameters when the first communications link is unavailable. However, in another specific embodiment, treatment parameters are always communicated via the second communications link.

In act 2009, the base proceeds to operate. For example, the base may be a hemodialysis apparatus and the tablet communicates a start command to the hemodialysis apparatus. In another exemplary embodiment, a start button on the hemodialysis apparatus may be pressed to commence treatment of a patient. In yet additional embodiments, the user is not required to commence operation and the base automatically starts to operate.

Act 2010 removes the physical connection between the tablet and the base. For example, a user may disconnect or undock the physical connection between the tablet and the base. Act 2011 communicates data between the tablet and the base as long as a link quality value of the second communications link is above a threshold. Act 2012 enters into a headless state if the link quality value falls below the threshold. The headless state is described below with reference to FIGS. 128 and 129. The tablet and the base may both or individually enter into a headless state when the link quality value falls below a threshold. The link quality value may be part of the Bluetooth standard, may be based upon a bit error rate, a throughput rate, signal strength, or may use any metric known to one skilled in the relevant art.

In act 2013, the tablet and/or the base remain in the headless state as long as the link quality value remains below the threshold. Act 204 determines if the link quality value returns above the predetermined threshold and act 2015 exits the headless state when the link quality value returns above the predetermined threshold. In some embodiments, once the tablet or the base enter into a headless state, a second link quality value greater than the first link quality value causes the tablet and/or the base exit the headless state.

Figure 124:
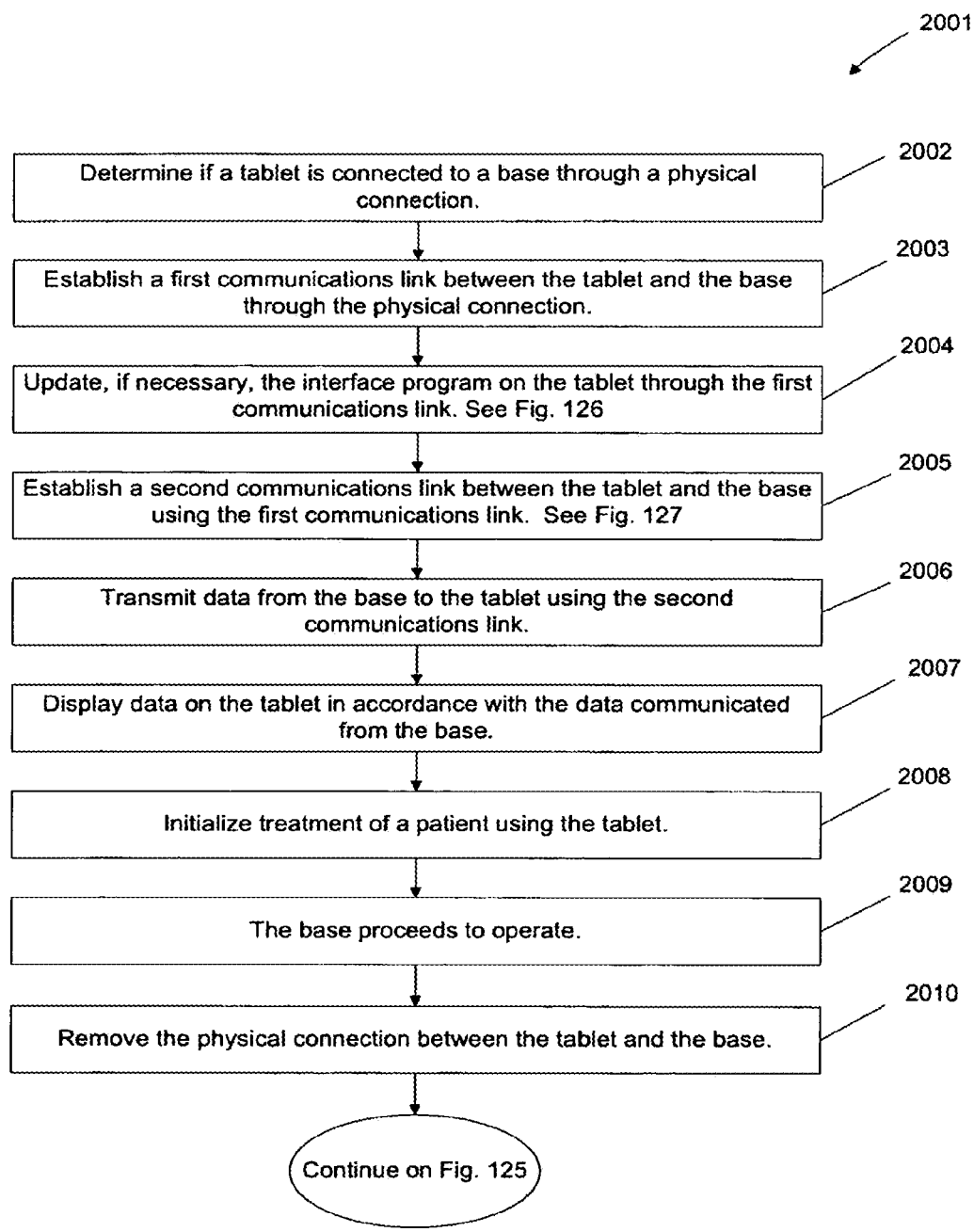

FIG. 126 shows a flow chart diagram of an embodiment of act 2004 of FIG. 124. Act 2004 includes acts 2016-2019. Act 2016 communicates a version number of the interface program from the tablet to the base through the first communications link. Act 2017 determines if the interface program on the tablet is the latest version. For example, the base may communicate with a server to determine what version number is the newest version of the interface program. In act 2018, the base retrieves an updated version of the interface program from a server, e.g., if there is an updated version of the interface program. Act 2019 overwrites the interface program with the updated version of the interface program. For example, the tablet 19 may include a program which can retrieve the updated interface program from the base and overwrite the previous interface program with the updated interface program.

FIG. 127 shows a flow chart diagram of an embodiment of act 2005 of FIG. 124. Act 2005 of FIG. 127 includes acts 2020-2025. Act 2020 determines if the base is paired with another tablet. Act 2021, if necessary, interrupts any pairing between the other tablet and the base. For example, in act 2021, any other pairing between another tablet and the base is interrupted so that the tablet that is physically connected to the base can be paired to the base. In act 2022, the base generates a configuration file which is communicated from the base to the tablet in act 2023 using the first communications link. In act 2024, the tablet reads the configuration file which is used in act 2025 to pair the base to the tablet for wireless communications to establish the second communications link between the tablet and the base in accordance with the configuration file.

Figure 125:
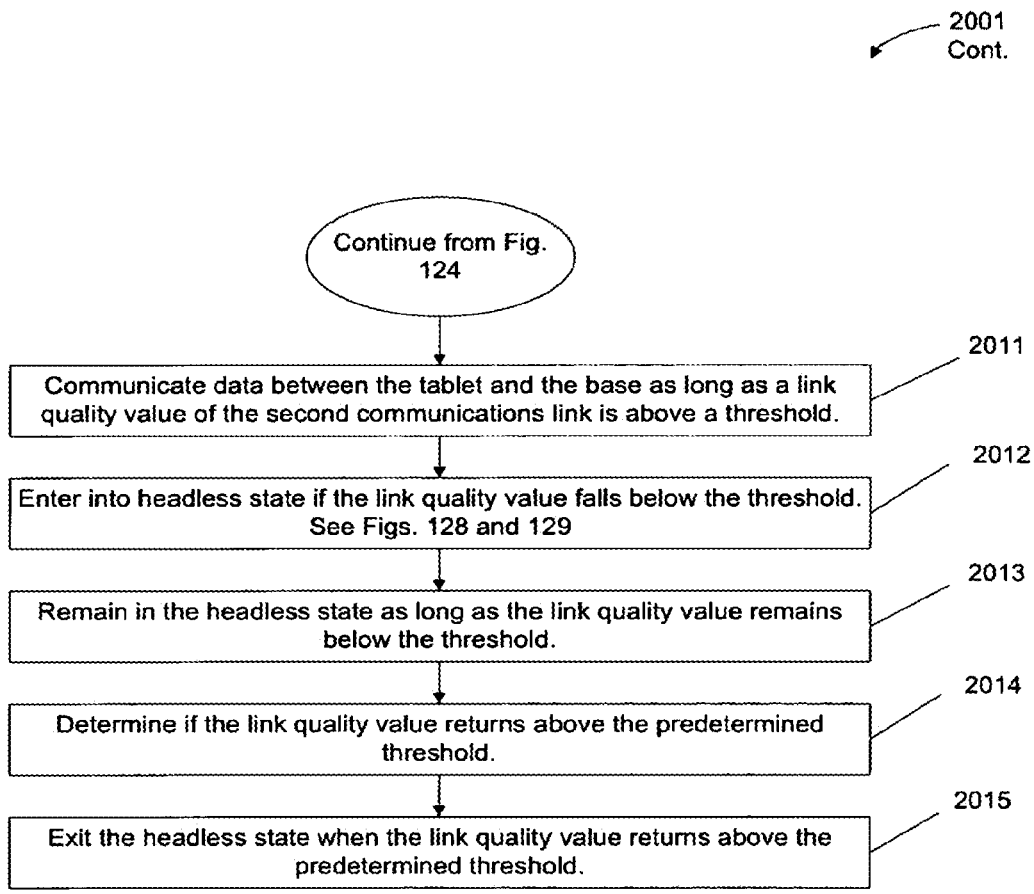
Figure 128:
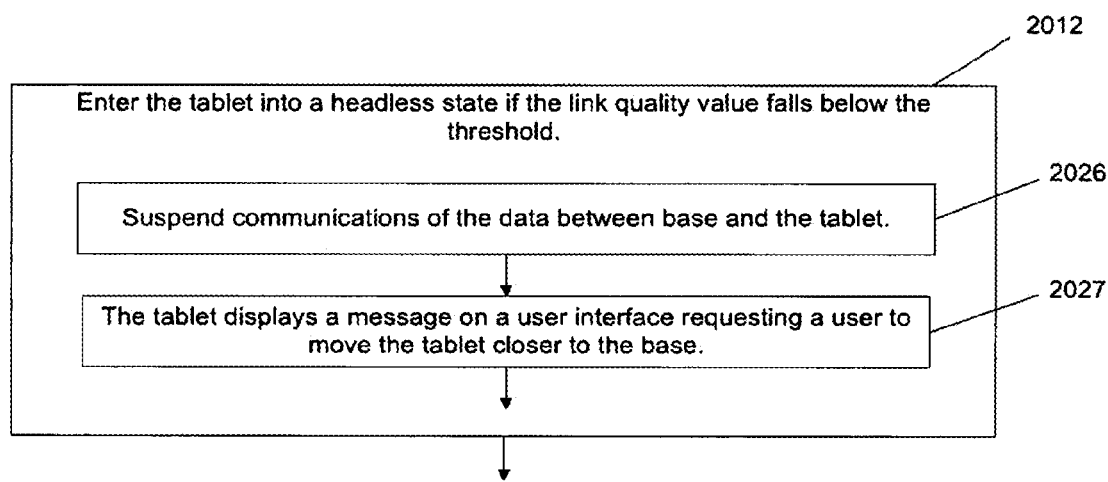
Figure 129:
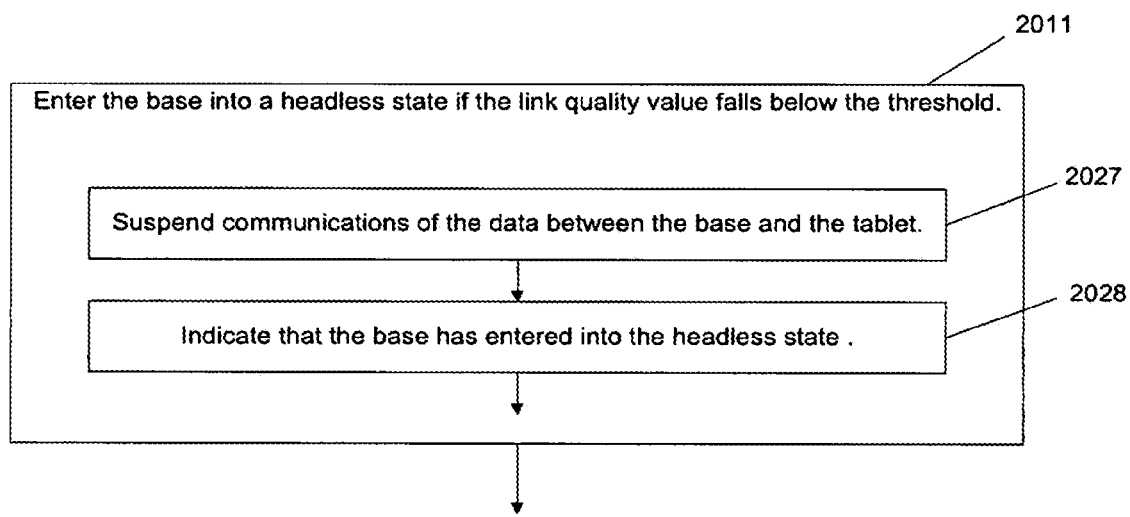

FIG. 128 shows a flow chart diagram illustrating an embodiment of act 2011 of FIG. 125. Act 2011 of FIG. 128 includes acts 2026-2027. Act 2026 suspends communications of the data between base and the tablet. In act 2027, the tablet displays a message on a user interface requesting a user to move the tablet closer to the base. FIG. 129 shows a flow chart diagram illustrating an embodiment of act 2012 of FIG. 125. Act 2012 of FIG. 128 includes acts 2027-2028. Act 2027 suspends communications of the data between the base and the tablet. Act 2028 indicates that the base has entered into the headless state. For example, the base may flash an indicator light and cause a speaker to beep.

FIGS. 145A-145B show a state diagram 1145 that illustrates the operation of a dialysis apparatus when used with a tablet having a user interface for the dialysis apparatus in accordance with an embodiment of the present disclosure. The state diagram 1145 includes states 1146-1160.

In FIG. 145A, a legend 1161 is shown to facilitate understanding of the state diagram 1145. The legend displays the operation of each of the buttons 1162, 1163, and a status light 1164 on the dialysis apparatus for each of the states 1146-1160, including the operation of a respective backlighting LED for the buttons 1162, 1163 and the status light 1164. Additionally, the legend 1161 may be used in conjunction with each of the states 1146-1160 to determine the state of a speaker 1165 of the dialysis apparatus. Circles with the letters "A," "B," "C," or "D" therein are used to link the states of FIG. 145A with the states of FIG. 145B. For example, the arrow leading into the circle designated "A" shown in FIG. 145A continues from the circle designated "A" in FIG. 145B. That is, each letter designation within each circle is used to link two states where one state is in FIG. 145A and the other state is in FIG. 145B.

As previously mentioned, the state diagram 1145 illustrates the states that a dialysis apparatus (e.g., a hemodialysis apparatus) may exists in when used with a tablet having a user interface. The tablet may be used to: (1) monitor the operation of the dialysis apparatus, (2) control the operation of the dialysis apparatus, (3) receive error conditions from the dialysis apparatus, (4) monitor the operation of the dialysis apparatus to determine if any error conditions exits, (5) monitor the operation of the dialysis apparatus to determine if an unsafe condition exists, (6) store an error or operating parameter for transmission to a server, (7) store an error or operating parameter for transmission to the dialysis apparatus for storage therein or for relaying to a server, (8) and/or provide the patient entertainment (e.g., video games, movies, music, or web browsing) while receiving treatment.

In some embodiments of the present disclosure, the tablet is used with a dialysis apparatus having a redundant user interface coupled thereto, such as a redundant, graphical user interface. In yet additional embodiments of the present disclosure, the tablet includes a graphical user interface and the dialysis apparatus includes buttons and lights, but no graphical user interface.

The state diagram 1145 may be implemented as a method or process. Additionally, a machine may be configured to exist in the states of the state diagram 1145. For example and as previously mentioned, a hemodialysis apparatus may be configured to exist in states 1146-1160 in accordance with the state diagram 1145 of FIGS. 145A-145B.

The state diagram 1145 of FIGS. 145A-145B may implemented by an operative set of processor executable instruction configured for execution by one or more processors (e.g., a method implemented by a processor). The one or more processors may be on the dialysis apparatus. The operative set of processor executable instruction may be stored in a memory, such as a non-transitory processor-readable memory, a random-access memory, a read-only memory, a disk memory, an EEPROM, an optical-based drive, or other memory. The memory may be in the dialysis apparatus. The one or more processors may be in operative communication with the memory to read the operative set of processor executable instructions from the memory. The one or more processors can execute the instructions to perform the state diagram 1145 of FIGS. 145A-145B.

The one or more processors may be one or more of a microprocessor, a microcontroller, an assembly-based processor, a MIPS processor, a RISC processor, a CISC processor, a parallel or multi-core processor, a CPLD, a PLA, a FPGA, a virtual processor, the like, or some combination thereof.

Referring again to FIGS. 145A-145B, in state 1146, the dialysis apparatus is in a treatment operation and communication between the dialysis apparatus and the tablet is occurring. That is, in state 1146, the dialysis apparatus is treating a patient and the tablet is in sufficient communication with the dialysis apparatus. The communications between the dialysis apparatus may be through a wireless link, such as a Bluetooth link. The protocol of the wireless link may require pairing between the dialysis apparatus and the tablet. The pairing may be configured or initiated utilizing a wired link, such as through a USB connection. In some embodiments, the wireless communications may be one of Bluetooth LE, WiFi, Zigbee, X-bee, ultra-wideband communication, wideband communication, code-division multiple access, time-division multiplexing, carrier-sense multiple-access multiplexing with or without collision avoidance, space-division multiplexing, frequency-division multiplexing, circuit-mode wireless multiplexing, wireless statistical multiplexing, orthogonal frequency-division multiplexing, or the like.

When a link quality indicator that described the quality of the wireless link between the tablet and the dialysis apparatus falls below a predetermined threshold, the dialysis apparatus enters into state 1147. In state 1147, the dialysis apparatus continues to treat a patient and ignores communications from the tablet. When an alarm occurs, as long as the alarm is not a blood-pump-stop level alarm, the state diagram 1145 will continue to operate in state 1147 (e.g., if an alarm occurs that is not a "stop pump" level alarm, the dialysis apparatus will re-enter state 1147 as is shown by the loop-back arrow 1166).

If the link quality value returns to above the predetermined threshold, the dialysis will return to state 1146. However, state 1147 may go to states 1148, 1152, 1151, 1153, or 1154. The dialysis apparatus will enter into state 1148 if a user presses and holds the stop button 1163 for 5 seconds. If the treatment completes prior to leaving state 1147, the dialysis apparatus will enter into state 1152 (see FIG. 145B). If while in state 1147, the user presses the infuse fluid button 1162, the hemodialysis apparatus will enter into one of state 1152 (if the infusion limit or tank limit have been reached) or into state 1151 when additional infusion fluid is available (e.g., neither of the infusion limit nor the tank limit has been met). The infusion limit is a limit on the amount of fluid that may be infused into a patient during a treatment session. The tank limit is a threshold amount of fluid (e.g., about 1 to 1.1 liters) that may be removed from the tank. After the tank limit has been reached, an infusion of fluid into the patient's blood is not permitted because there needs to be sufficient fluid to perform the rinseback operation. If the a blood-pump-stop level alarm has occurred, the dialysis apparatus will enter into one of state 1153 if a rinseback flag indicates that a rinseback is allow or into state 1154 if the rinseback flag indicates that a rinseback is not allowed.

If the dialysis apparatus enters into state 1148, it is because the patient or user has requested from the dialysis apparatus (using the stop button 1163) to stop treatment. State 1148 is an entryway into a trap formed by states 1149 and 1150 form "trap" states for the dialysis apparatus. That is, once the dialysis apparatus enters into state 1148, the dialysis apparatus can only enter into one of state 1149 or 1150 thereafter. A reset or reboot of the dialysis apparatus is the only way to leave this trap. State 1148 is a patient initiated failsafe ("PIF"). In state 1148, the speaker 1165 will audibly beep. If the user presses the stop button 1163 again, the dialysis apparatus will enter into state 1149, in which case the dialysis apparatus is in a PIF state, but the speaker 1165 is not beeping. If the patient or user presses the stop button 1163 yet again, the dialysis apparatus will enter into state 1150 and turn off the front panel light 1167. An additional stop button 1163 press will return the dialysis apparatus to state 1149 which will turn the front panel light 1167 back on.

As previously mentioned, if the dialysis apparatus is in state 1147, and the user presses the infuse fluid button 1162, the dialysis apparatus will enter into state 1151 if there is additional fluid available to deliver across the dialyzer's membrane and into the patient's blood. If in state 1151, after the fluid infusion has been infused into the patient's blood, the dialysis apparatus returns to state 1147.

In state 1147, if an alarm that is predetermined to be a stop-blood-pump level alarm, the dialysis apparatus enters from state 1147 into one of states 1153 and 1154; State 1153 is entered into when the rinseback flag indicates that rinseback is allowed, and state 1154 is entered into by the dialysis apparatus if the rinseback flag indicates that rinseback is not allowed.

Referring again to state 1152, the dialysis apparatus enters into state 1152 when either the treatment completes from state 1147 or when the user presses the infuse fluid button 1162 and one of the infusion limit or the tank limit has been reached. In state 1152, the dialysis apparatus performs a rinseback operation. In the rinseback operation, a blood pump of the dialysis apparatus is stopped and fluid is infused into the dialyzer to displace the blood from the dialyzer such that blood is returned back into the patient via both of the arterial and venous blood tubes.

After rinseback has completed in state 1152, the dialysis apparatus enters into state 1155 if additional rinseback is allowed or state 1156 if no further rinseback is allowed. A rinseback-allowed flag may be used to indicate whether or not a rinseback is allowed.

If a further rinseback is allowed, the dialysis apparatus enters into state 1155, at which time the use can press the infuse fluid button 1162 to return to state 1152 if a user closes the door which in turns causes the dialysis apparatus to enter into state 1157.

If no further rinseback is allowed and the dialysis apparatus enters into state 1156 from state 1152, the front panel speaker 1165 will beep 3 times every 3 minutes to notify the user that the rinseback operation completed. From state 1156, when the door is shut the dialysis apparatus enter into state 1157. A closed door prevents the patient from being connected to the arterial or venous tubes.

The dialysis apparatus may transition from state 1153 into state 1152 if the user presses the infuse fluid button 1162 to perform additional rinseback. Otherwise, the dialysis apparatus will leave state 1153 and enter into state 1157.

In state 1154, the dialysis apparatus will enter into state 1157 when the door is closed. When the dialysis apparatus is in state 1157, various routines are performed within the dialysis apparatus including self-test, checks to determine if the arterial drain connector is coupled to the arterial tube (e.g., a patient has disconnected this tube from themselves), check to determine if the venous drain connector is coupled to the venous tube, cleaning the blood path, disinfect the fluid pathways, and the like. While in state 1157, if the door is opened, the dialysis apparatus will enter into state 1160 to issue a door open alarm by beeping the front panel speaker 1165 continuously until the door is shut where the dialysis apparatus returns to state 1157.

If the communications link between the tablet and the dialysis apparatus has a link quality value that returns above the predetermined threshold while in state 1157, the dialysis apparatus will enter into state 1159 for normal recycle operation which commences communication between the tablet and the dialysis apparatus. If while in state 1159, the tablet again has the link quality that is below a predetermined threshold, the dialysis apparatus will enter into state 1158, which may return back to state 1159 if the link quality returns to above the predetermined threshold. States 1158 and 1159 continue the recycle operation. While in state 1158, if the treatment is still preparing for a treatment and the door closed signal is detected, the apparatus will return to state 1157.

While the hemodialysis system 6000 of FIG. 60 comprises a user interface unit 6002 remote from and physically coupled to a dialysis unit 6001, many alternative arrangements are possible. For example, the user interface unit 6002 may be mounted to or within dialysis unit 6001. For convenience, a user interface unit 6002 so mounted may be moveable from its mount for use in different locations and positions.

Figure 61:
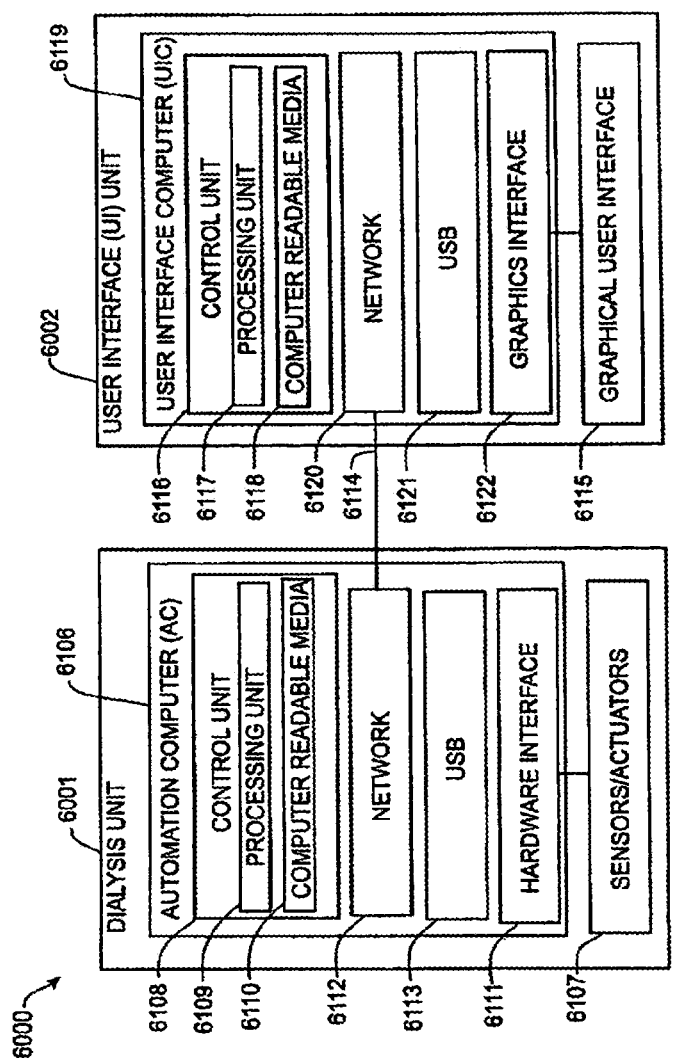
FIG. 61 is a schematic view of an exemplary hardware configuration for each of the dialysis unit and the user interface unit shown in FIG. 60.

FIG. 61 shows an exemplary hardware configuration for each of the dialysis unit 6001 and the user interface unit 6002. Each of these is controlled by a separate CPU, allowing for the separation of time and safety critical software from the user experience software. Once a therapy has begun, it can be completed even if the user interface computer fails or is disconnected. This can be supported by having some physical control buttons and indicator lights redundant to those implemented by the user interface unit 6002 and connected to the control processor of the dialysis unit 6001. The dialysis unit 6001 comprises an automation computer (AC) 6106 that controls hardware actuators and sensors 6107 that deliver and monitor hemodialysis-related therapy. The automation computer 6106 comprises a control unit 6108 that includes a processing unit 6109 and computer readable media 6110. The processing unit 6109 comprises one or more processors that may execute instructions and operate on data stored on the computer readable media 6110. The data may, for example, relate to hemodialysis processes that have been or may be performed on a patient. The system architecture provides the automation computer 6106 with software accessible safety sensors 6107 and the ability to command a fail-safe state (allowing for suspension or discontinuation of therapy in a safe manner). A parallel independent semiconductor device-based system can perform checks similar to those controlled by the software in order to provide a redundant safety system. This can be implemented, for example in a field-programmable gate array ("FPGA"), and it can also command a fail-safe state independently of the software system if one or more safety checks is not satisfied. The integrity of the pneumatic, hydraulic and electrical systems can be checked both during and between treatment sessions. The instructions may comprise, for example, an operating system (e.g., Linux), application programs, program modules, and/or other encoded instructions that perform particular processes.

The computer readable media 6110 may comprise any available media that can be accessed by the processing unit 6109. For example, computer readable media 6110 may comprise computer storage media and/or communication media. Computer storage media may include any one or more of volatile and/or nonvolatile memory and removable and/or non-removable media implemented in any method or technology for storage of information, such as computer readable instructions, data structures, program modules or other data. Examples of such computer storage media includes, but is not limited to, RAM, ROM, solid state disks, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by the processing unit 6109. Communication media typically embodies computer readable instructions, data structures, program modules or other data in a modulated data signal, such as a carrier wave or other transport mechanism, and includes any information delivery media. The term "modulated data signal" means a signal that has one or more of its characteristics set or changed in such a manner as to encode information in the signal. By way of example, communication media may include wired media, such as a wired network or direct-wired connection, and/or wireless media, such as acoustic, RF, infrared and other wireless media.

The various components of the automation computer 6106, including the computer readable media 6110 and the processing unit 6109, may be electrically coupled via a system bus. The system bus may comprise any of several types of bus structures including a memory bus or memory controller, a peripheral bus, and a local bus using any of a variety of bus architectures. By way of example, such architectures may include Industry Standard Architecture (ISA), Micro Channel Architecture (MCA), Enhanced ISA (EISA), Video Electronics Standards Associate (VESA), and Peripheral Component Interconnect (PCI).

The automation computer 6106 may further include a universal serial bus (USB) interface 6113 so that various input and/or output devices may be coupled to the control unit 6108. Examples of such input and/or output devices include a monitor, speakers, a printer, a keyboard, a pointing device (e.g., a mouse), a scanner, personal digital assistants, a microphone and other peripheral devices. USB is merely one exemplary type of interface that may be used to connect peripheral devices. Other interfaces may alternatively be used.

As discussed above, dialysis unit 6001 includes components for performing and monitoring hemodialysis processes. Such components include sensors and actuators 6107. To couple the control unit 6108 to the sensors and actuators 6107, the automation computer may include a hardware interface 6111. The hardware interface 6111 may provide inputs to and receive outputs from the sensors and actuators 6107.

Automation computer 6106 may further comprise a network interface 6112 to allow the computer to connect with networked devices, such as those within a local area network (LAN) and/or a wide area network (WAN). For example, the network interface 6112 may allow the dialysis unit 6001 to exchange data with the user interface unit 6002 over a network 6114, which may comprise a LAN, such an Ethernet LAN, and/or a WAN, such as the Internet, and may be wired or wireless. Of course, the dialysis unit 6001 may alternatively or additionally exchange data with the user interface unit 6002 over a bus or other data connection.

The user interface unit 6002 comprises a user interface computer 6119 that controls a user interface, such as graphical user interface 6115 that displays information to and receives inputs from the user. Like the automation computer 6106, the user interface computer 6119 comprises a control unit 6116 having a processing unit 6117 and computer readable media 6118, a USB interface 6121 and a network interface 6120, each of which may be the same as or similar to their counterparts in the automation computer 6119. In addition, the user interface computer 6119 may include a graphics interface 6122 to couple the control unit 6116 to the graphical user interface 6115. In a preferred implementation, the user interface computer 6119 software is not tasked to interpret data received from the automation computer 6106, but rather is tasked to display the data in a user-friendly manner.

FIG. 62 schematically shows various exemplary software processes that may execute on the processing units 6109 and 6117 of automation computer 6106 and user interface computer 6119, respectively. The processes shown may be launched and monitored by an executive process. For example, the AC processing unit 6109 and UIC processing unit 6117 may respectively include AC Executive 6201 and the UIC Executive 6207 to launch the processes within the given processing unit and provide a communications mechanism to determine the running status of the child processes. The executives monitor each child process to ensure that each starts as expected and continues to run. In particular, the AC Executive 6201 and the UIC Executive 6207 may detect hung processes. When a child process terminates or fails, each executive process may take appropriate action to ensure that the system continues to operate in a safe manner. This may involve terminating processes and informing the UIC executive 6207, leading to system shutdown, or restarting processes that are not safety-critical. On the UIC processor, this may entail informing the operator and allowing the treatment to be completed using the hard-keys. The AC Executive 6201 and the UIC Executive 6207 may use a Linux parent-child process relationship to receive notifications from the operating system about the termination of child processes. This allows handling of anomalous process terminations as well as expected terminations during a power-off sequence. The automation computer 6106 and the UIC Executives 6201 and 6207 may have a message interface between them to share information about their running processes. The status information may be shared on a periodic basis to allow a coherent view of state of all system processes on both processor units 6109 and 6117. The AC executive 6201 controls a watchdog signal to the electronics, allowing it to place the machine in a fail-safe state when any child process becomes unresponsive or requests a fail-safe state. Preferably, this control does not require an Input/Output server, but can occur directly via a hardware register.

As shown in the example of FIG. 62, the AC processing unit 6109 includes an I/O Server Process 6205. The I/O Server Process 6205 directly accesses hardware, such as sensors and actuators, of the dialysis unit, and provides an interface to allow other processes to request read and write operations. For example, the I/O Server Process 6205 may provide an interface for the Machine Controller 6202 to read from and write to the sensors and actuators, thereby isolating the Machine Controller from the details of the hardware. In the embodiment described, only the Machine Controller 6202 may communicate with the I/O Server Process 6205. The interface may be a synchronous message queue.

The Machine Controller 6202, mentioned above, serves as an interface for controlling machine operations and reporting machine operational status. In particular, the Machine Controller 6202 implements controllers that read sensors and set actuators via the I/O Server Process 6205. These controllers are designed to allow functions (e.g., pumping and heating) to be programmed with a variety of parameters (e.g., flow rates, phases, pressures, and temperatures) in order to support the various hemodialysis therapies that may be performed. The configuration of the controllers may be established by state machines that implement high-level machine functions, such as priming and disinfection. The state machines configure flow paths and controller set points based on the capabilities of the machine and the high level commands received from the Therapy Applications 6203, described below. The Machine Controller 6202 may also perform safety cross checks on various sensors to maintain a safe, effective therapy. Machine status and health information may be recorded by the Machine Controller 6202 to a database.

The Therapy Applications 6203 drive the patient's therapy by commanding the Machine Controller 6202 to perform individual operations relating to hemodialysis processes. In particular, the Therapy Applications 6203 may run state machines that implement therapies and control the modes of the system. The state machines may, for example, control priming the system with dialysate, connecting the patient to the machine, dialyzing the patient, rinsing the patient's blood back to their body, cleaning the machine, disinfecting the machine, running tests on the machine components, replacing old or worn out components, and waiting for the patient to return for their next treatment. The Therapy Applications 6203 issue commands to and request status information from the Machine Controller 6202 in order to implement the therapy operations. In order to obtain patient, therapy and machine information the Therapy Applications 6203 may interface with a database to access information and store treatment status information. The Therapy Applications 6203 may be used as an interface by the User Interface Model 6206 process, discussed below, to forward user selections and report therapy status back to the user interface. The Therapy Applications 6203 implements state machines that include treatment preparation, patient connection, dialysis, solution infusion, patient disconnect, recycle preparation, disinfect, rinse, and disposable replacement. The Therapy Applications 6203 process also contains a master control module responsible for sequencing the activity of all other therapy applications that prepare for and deliver daily treatment.

Like the Therapy Applications 6203, the User Interface (UI) Model 6206 runs on the AC processing unit 6109. The UI Model 6206 aggregates information describing the current state of the system and patient, and supports changes to the state of the system via operator input. The UI Model 6206 separates the content of the user interface display from non-content related aspects (e.g., presentation) by allowing the content of the user interface to change without affecting the underlying software that controls the user interface display. Thus, changes to the UI Model 6206 may be made without affecting the visual experience provided by the user interface. The UI Model 6206 does not have a display directly associated with it; rather, it commands the GUI 6115 of the user interface unit 6002 (FIG. 61) to display screens and return information. For example, when a user navigates to a new screen, the UI Model 6206 may send information to the user interface unit 6002 to be used in generating the new screen. The UI Model 6206 may also validate user data received from the user interface unit 6002 and, once validated, and forward the user data or commands based thereon to the Therapy Applications 6203.

To create the interactive displays for the GUI 6115 of the user interface unit 6002 (FIG. 61), the UI View Process 6208 runs on the UI processor 6117 of the user interface computer. The UI View Process 6208 need not keep track of screen flow or therapy state. Instead the UI View Process 6208 may receive from the UI Model 6206 running on the AC processing unit 6109 information specifying what and how to display the current state of a treatment to the user, as well as what may be input. As a result, the GUI 6115 may terminate and restart without impacting the system's operation. In addition, the GUI 6115 need not be responsible for validating user inputs. All inputs and commands received by the UI View 6208 may be sent to and validated by the UI Model 6206. Thus, all safety-critical aspects of the user interface may be handled by the UI Model 6206. Certain processes, such as those not safety-related, do not require the participation of the UI Model 6206. For example, allowing access to information stored in a database on the user interface computer may not require any functions to be performed by the UI Model 6206.

Also running on the UI processor 6117, a Remote Access Application 6210 provides an interface for external equipment. For example, the Remote Access Application 6210 may provide an interface for therapy monitoring, remote service, online assistance, and other external services, when authorized by a user. The Remote Access Application 6210 may be responsible for initiating a remote connection, validating the access, and supporting the communication from the remote site to the UI Model 6206.

A Database Access Application 6209 stores data to and retrieves data from one or more databases which may, for example, be located on the user interface computer 6119 (FIG. 61). The Database Access Application 6209 allows for record storage and retrieval, and provides a common access point for information required by the system, such as prescription, schedule, and history information. The Database Access Application 6209 may also manage database files to ensure they are backed up periodically.

As discussed in connection with FIG. 62, the functionality of the user interface software may be divided between the AC processing unit 6109 and the UIC processing unit 6117. The UI Model 6206 and UI Controller 6204 may cooperate to isolate the control of the UI data and state information on the automation computer 6106 so that software and screen design changes to the UI View 6208 will only affect the non-safety-critical software on the user interface computer 6119. Thus, while the UI Model 6206 may be tested and run at a safety-critical level, the UI View 6208 may run as a non-safety-critical process.

In general, therapy and machine state information displayed on the user interface computer 6119 originates only from the UI Model 6206. According to one exemplary embodiment, all data displayed on the user interface computer 6119 originates from the UI Model 6206, is taken directly from a database layer, or is temporary editing data entered by a user. The only local state information displayed or stored in the UI View 6208 may be this temporary editing data and details that allow for the local rendering of the information. In this manner, the UI Model 6208 may maintain and control the display of all validated data. Non-safety related data may be handled solely by the UI View 6208, if desired. For example, changes in the display language, or other display changes that do not impact safety-related content, may be performed using the UI View 6208 without any effect on the UI Model 6206.

It should be appreciated that the software processes shown in FIG. 62 and their association with processing units 6109 and 6117 represents just one example of a software configuration for performing the functions described above. The processes may be distributed in various alternative manners among processing units 6109 and 6117 and/or other local or remote processors. Further, not all processes may be required in the hemodialysis system. Certain processes may be omitted or modified while maintaining the functionality of a hemodialysis system.

Figure 62A:
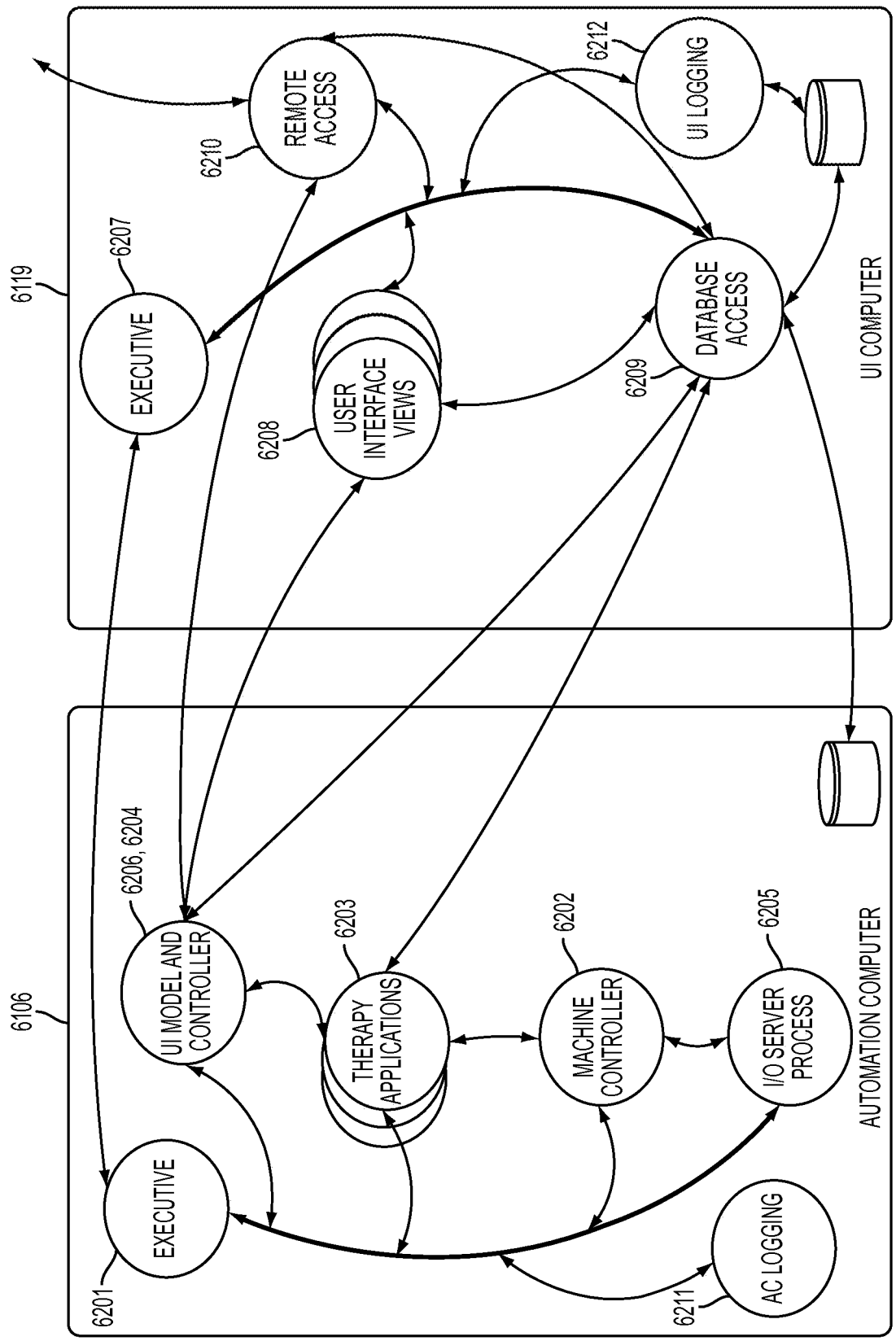
FIG. 62A is a schematic view showing the interactions of the software processes described in connection with FIG. 62.
Figure 62B:
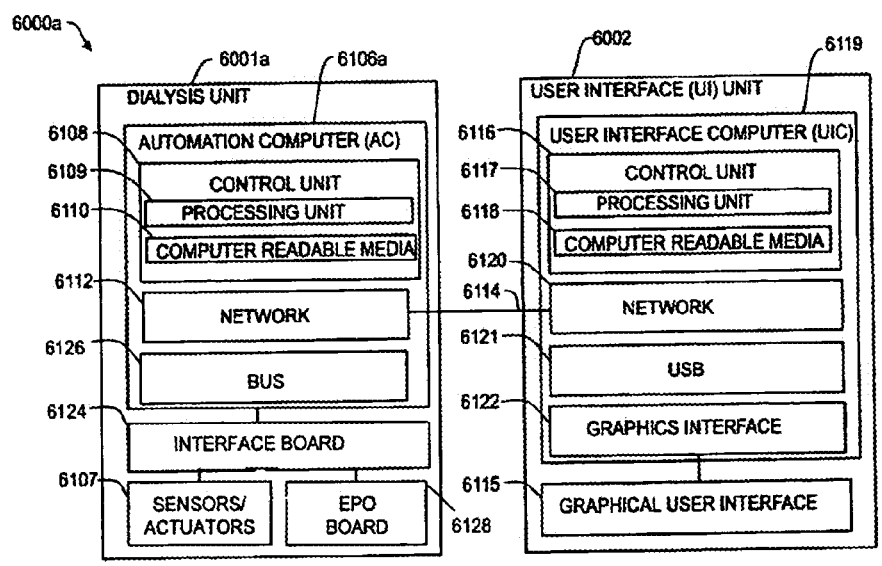
FIG. 62B is a schematic view showing an alternative hardware configuration the dialysis unit of FIG. 61 including a hardware interface board having a field programmable gate array (FPGA) safety system.

FIG. 62A schematically shows the interactions of the software processes described in connection with FIG. 62 in the context of the automation computer 6106 and the user interface computer 6119. In addition to the processes shown in FIG. 62, FIG. 62B shows an AC Logging Process 6211 and a UI Logging Process 6212, which handle logging functions. In particular, the AC Logging Process 6211 may be configured to allow messages from the automation computer 6106 to be logged to a log file created on a user interface file system. The AC Logging Process 6211 may also be configured to allow engineering logging and black box logging. The UI Logging Process 6212 may be configured to log system messages from the automation computer 6106 and user interface computer 6119 processes to create the message logs. Additionally, the UI Logging Process 6212 may be configured to receive and log engineering and black box data from the automation computer 6106 processes.

Referring again to FIG. 61, an exemplary hardware configuration for the dialysis unit 6001 and the user interface unit 6002 is shown wherein the automation computer 6106 of the dialysis unit includes a hardware interface 6111 that provides inputs to and receives outputs from sensors/actuators 6107. According to an alternative implementation, a hardware interface may be provided separate from the automation computer 6106. This interface may provide an alternative safety system or a redundant safety system, as discussed in connection with FIG. 61.

FIG. 62B shows an exemplary dialysis unit 6001*a* wherein sensor and hardware control signals pass between sensor/actuators 6107 and an interface board 6124 that is separate from the automation computer 6106*a*. In alternative embodiments, the interface board 6124 may be master board with one or more daughter boards. The interface board 6124 may be connected by a data bus 6126 to the AC processing unit 6109. The data bus may, for example, be a Serial Peripheral Interface (SPI) bus, which provides a low cost, fast and reliable connection.

The interface board 6124 may include a safety system independent of the automation computer 6106*a*. For example, the interface board 6124 can command a fail-safe condition if any of a set of electrical signals is outside of an acceptable range. The safety system may be programmed at the start of each therapy by the I/O Server Process 6205 of the AC processing unit 6109 described in connection with FIG. 62. The I/O Server Process 6205 may set the acceptable ranges of values for selected sensors, and the acceptable ranges for these sensors may be read back to the I/O Server Process 6205 to confirm that they were correctly transmitted and stored. According to one exemplary implementation, the interface board 6124 communicates with only the automation computer 6106*a* of the dialysis unit 6001*a* so that the dialysis unit enters a fail-safe condition when unsafe conditions occur, regardless of the automation computer, the UI computer 6119, or the state of the control software.

FPGA Safety Board

In one embodiment, the interface board 6124 includes Field Programmable Gate Arrays (FPGAs). The I/O Server Process 6205 of the AC processing unit 6109 may load patient or dialysate formula specific limits, including acceptable conductivity levels, for selected sensor signals. The use of patient or dialysate formula specific safety levels in a gate-array safety system may allow the safety system to be customized for each patient or dialysate formula, while providing the robustness, independence and speed of a safety system operating substantially independently from a main system processor.

The FPGA safety system on the interface board 6124 may monitor one or more of the following measurements dialysate temperature and conductivity, ultrafiltrate flow rate, valve states, door, front panel, and Occluder door switches, air leaks, fluid leaks, and/or the absence of communication from the AC processing unit 6109. The FPGA may enter a fail-safe state if one or more measurement exceeds its pre-programmed acceptable value or range of values indicating the presence of an unsafe condition. The FPGA safety system on the interface board 6124 may command a fail-safe state that allows manual rinse-back of blood to the patient for a first set of measurement values that are outside of their acceptable ranges. For a second set of measurement values that are further outside their acceptable ranges or indicative of unsafe fluid conditions, the interface board 6124 may command a fail-safe state in which blood cannot be rinsed back. The integrity of the FPGA safety system may be checked via operational tests that expose the sensors to physical conditions that produce measurements that may be outside the allowed range of acceptable conditions, and in which the entry into a fail-safe state is verified by the automatic computer. The automatic computer may reset the FPGA by writing to two or more registers within a given time limit.

In one example, the conditions that may generate a fail-safe state without rinse-back in the FPGA safety system include but are not limited to: conductivities more than about 7% outside the nominal conductivity specified by the formula for a period of seven seconds while the patient is connected; temperature exceeds 41.5° C., air at the AIL_Venous or AIL_Arterial and the patient is connected and the occluder does not close within 200 ms; the heprarin BTS valve and the heparin Vial valve are both open; or the heparin BTS valve and the heparin Air valve are both open.

The FPGA safety system may be programmed to enter a fail-safe state when the patient is connected if the measured conductivity of fluid (e.g., dialysate) falls outside a range predefined by a formula programmed into the device (the calculated range of acceptable conductivity being determined by, for example, the temperature of the fluid, or the stage of dialysate production). In one example the allowable range for final conductivity is 13.6 to 14.6 mS/cm. In some conditions, the AC processing unit 6109 may alert the user of a potentially unsafe condition and work with the user to resolve the condition. One example of an unsafe condition that the AC processing unit 6109 works with the user to resolve is air in the blood lines. The FPGA safety system will only initiate a fail-safe state if the AC processing unit 6109 does not react properly. In the example of air in the blood lines, the AC processing unit 6109 should close the occluder. The FPGA safety system will initiate a fail-safe state if it does not detect a closed occluder.

In an embodiment, the FPGA calculations are limited to integer calculations to improve the processing speed and reduce the cost and complexity of the interface board 6124. The I/O Server Process 6205 of the AC processing unit 6109 may be responsible for performing the calculations to convert conductivities, temperatures and/or pressures into analog-to-digital (A-D) values. Acceptable values, such as for the various conductivities, temperatures, and/or pressures, may be stored as A-D converted integer values.

The safety shutdown functionality of the FPGA safety system may be tested prior to every therapy by intentionally exposing the sensors to conditions that should trigger safety shutdown (also referred to as a fail-safe state). The verification of the safety shutdown functionality is performed by the AC processing unit 6109, while the patient is not connected. In one example, the AC processing unit 6109 sets the patient connected status to yes, and pumps fluid from the dialysate that does not have the correct conductivity through the condo safety sensor at position 4705 (FIG. 59), and verifies that the safety monitor enters a fail-safe state. In another example the AC processing unit 6109 sets the patient connected status to yes, and pumps dialysate that has been heated to 42° C. and that does not have the correct conductivity past the Temperature Safety sensor at position 4705, and verifies that the safety monitor enters a fail-safe state. In another example the AC processing unit 6109 sets the patient connected status to yes, sets the ultrafiltration or UF pump rate register to 60 ml/hr, operates the UF pump at 120 ml/hr and verifies that the safety monitor enters a fail-safe state. In another one of several possible examples, the AC processing unit 6109 sets the patient connected status to yes, and opens the outlet valves of both inner dialysate pumps to drain (i.e., the DP_Outside1 9255 and the DP_Outside2 9260 valves shown in FIG. 118) and verifies that the safety monitor enters a fail-safe state. In another example the AC processing unit 6109 sets the patient connected status to yes, and ensures that air is present in at the AIL_Venus and AIL_Arterial sensors, sets the occluder open and verifies that the safety monitor enters a fail-safe state.

The AC processing unit 6109 may reset the FPGA safety circuit in order to perform the next checkout test or to arm the FPGA safety circuit for use when a patient is connected to the dialysis unit. The the AC processing unit 6109 may reset the FPGA safety circuit by writing to two registers within a given time frame. In one example the AC processing unit 6109 toggles a first signal from a first value to a second value and then back to a first value, while a second signal is held constant at given value. Then the second signal is toggled from a first value to a third value and back to the first value within a pre-determined period of time.

Conductivity, Temperature and Valve State Checks

The electrical conductivity of heated dialysate and partially mixed dialysate may be measured in connection with a dialysis treatment. The conductivity of the fluid may indicate the concentration of acid, bicarbonate and other additives in the dialysis solution. Although allowable concentrations for a given patient or dialysate formula may be known, the electrical conductivity changes as a function of temperature. The FPGA safety system may be programmed with a table of high and low acceptable conductivities for a plurality of temperatures. The high and low conductivity limits for different temperatures may be specific to selected dialysate formulae. A user or clinician may select a dialysate formula and the AC processing unit 6109 may download the corresponding high and low conductivity limits to the FPGA. These high and low conductivity limits may be stored as A-D counts for each temperature range in order to minimize computing time and demand on computing resources. In one embodiment, these temperatures are selected to be about 1° C. apart. Temperatures may be measured next to each of the conductivity sensors. The FPGA safety system may compare the measured conductivity to the high and low acceptable conductivity values corresponding to the measured temperature. In an exemplary implementation, the electrical conductivity of the media may be determined at positions 4701, 4702 and/or 4705 described in connection with FIG. 59. Temperatures may be measured in the vicinity of these positions.

The temperature of the dialysate leaving the ultrafilter may be monitored. In one embodiment, a fail-safe state is trigged if this temperature is outside an acceptable temperature set by the I/O Server Process 6205 of the AC processing unit 6109. A fail-safe state may also be triggered if an unacceptable combination of valves is commanded open and or closed. This safety mechanism may prevent the balancing circuit from getting into a hydraulic lock and/or prevent unsafe flows in the blood and dialysate circuits.

The FPGA safety system may include logic to monitor the average flow rate through the ultrafiltration pump and enter a fail-safe state if the average flow is too high. The maximum allowed ultrafiltration flow rate can be fixed, or it can be one of the parameters that is programmable on the FPGA, being either therapy-specific or patient-specific, or both. A challenge of calculating the average flow rate is that flow through the ultrafiltration pump may be intermittent, only occurring during set time intervals. Thus, a cumulative average flow rate may be very low until the UF pump is activated, at which point the high instantaneous flow rate will quickly exceed a maximum allowed flow rate. In one example, the logic of the FPGA safety system calculates the average flow rate by creating a register with a maximum value (either fixed or programmable), and initializing the register at a second intermediate value. The register value is decreased by one for each ultrafiltration pump stroke and increased by one for each pre-determined time period when the pump can be active. If the register value either drops to zero or increases to the maximum value, the interface board 6124 may command a fail-safe state.

Certain fail-safe states can be implemented through commands from the interface board 6124. In one example, the fail-safe state with manual rinse back may be achieved by commanding pneumatic manifold valves 6020 with the interface board 6124 to close the occluder, turning off the binary pneumatic valves 6020, and holding the high pressure valve closed. The pneumatic valves 6020 in the pressure distribution module 9000 may be selected to be either normally-closed or normally-open so that in the powered down condition, manual rinse-back can be achieved. In another example, the fail-safe state without rinse back may be achieved by commanding the pneumatic manifold valves 6020 with the interface board 6124 to close the occluder, and de-pressurizing the positive pressure supply reservoir (either by venting it, or by opening a positive pressure valve to a negative pressure valve on the pressure distribution manifold) so that there is no pneumatic pressure available to the dialysate tank to push dialysate across the dialyzer membrane, and blood in the blood tubing set toward the patient. The pneumatic valves may also be unpowered during a fail-safe state without rinse back.

FIG. 62B also shows an Emergency Power Off (EPO) board 6128 coupled to the interface board 6125 within the dialysis unit 6001*a*. It should be appreciated that while the interface board 6124 and EPO board 6128 are shown within dialysis unit 6001*a* and separate from the automation computer 6106*a*, alternative configurations are possible. The EPO board 6128 may be configured to enable lighting and alarming in the case of a power outage. In particular, the EPO board 6128 may include a microcontroller and embedded software configured to sound a buzzer, illuminate warning lights and/or illuminate flood lights in response to a loss of power. Such light and alarm systems may be electrically coupled to the EPO board. In the event of a loss of power, the EPO board may be commanded on by a signal from the IO Server Process 6205 of the AC processing unit 6109. Other exemplary functions of the EPO board 6128 include reporting "stop" and "infuse" button states to the AC control unit 6108, illuminating lights (e.g., button, warning, and flood light LEDs) in response to commands from the AC processing unit 6109, and reporting a battery voltage level when requested by the AC processing unit 6109.

Figure 63:
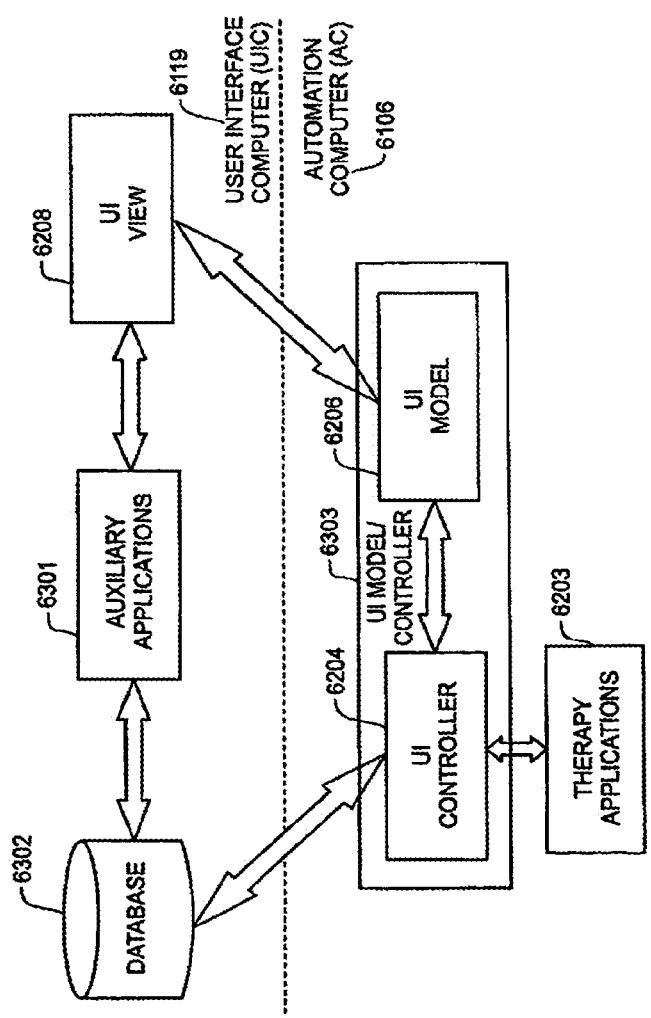
FIG. 63 is a schematic view showing an exemplary flow of information between and among the hardware and software components of the user interface computer and automation computer.

FIG. 63 shows an example of how information relating to the user interface may flow between and among the hardware and software components of the user interface computer 6119 and automation computer 6106. Information may flow and be handled so that safety-critical information is processed only at or below the UI Model layer. Safety-critical information relates to operations of the hemodialysis system. For example, safety-critical information may comprise a state of a dialysis process, a screen state of the graphical user interface, and/or the algorithms for implementing or monitoring therapies. In some cases, safety-critical information may be displayed by the graphical user interface. In such cases, the safety-critical information may comprise content that is material to the operations of the hemodialysis system. Non safety-critical information displayed by the user interface may comprise aspects of the display that relate to visual presentation and are not material to the operations of the hemodialysis system.

As shown in FIG. 63, the UI Model 6206, UI Controller 6204 and Therapy Applications 620, discussed in the connection with FIG. 62, run on the automation computer 6106. The UI View 6208 runs on the user interface computer 6119, along with Auxiliary Applications 6301. A database 6302, or an interface thereto (e.g., a database server) may also reside on the user interface computer 6119. The UI Model 6206 aggregates the information describing the current state of the system and patient, and commands the graphical user interface to display screens and return information. It validates and forwards user data and commands to the therapy applications in order to give the user control over the system. The UI Model 6206 keeps the content of the user interface independent from the display. The graphical user interface preferably does not maintain machine state information, allowing the user interface to be changed or temporarily disconnected without affecting the underlying software. Although the graphical user interface is not responsible for validating user inputs, it may constrain ranges of various inputs, the validation being the responsibility of the UI Model 6206.

Considering first the flow of information between the UI View 6208 and UI Model 6206, the UI View operates as a client of the UI Model, as explained below. The UI View 6208 requests the current screen state from the UI Model

6206, and the UI Model answers the request. The answer dictates the major screen state of the UI View 6208. The UI Model 6206 may publish data and state information in sufficient detail so that the UI View 6208 can present various subsets of display information according to a level of detail requested by a user. For example, the UI View 6208 could present the same therapy state as either a summary or a step-by-step guide using the same information from the UI Model 6206. The presentation of the information may be based, for example, on a mode selected by a user (e.g., "expert" or "novice"). The UI Model 6206 may provide the ability for the UI View 6208 to record sub-state information, such as a current presentation mode, in the UI Model. This allows the GUI to resume operation in its prior state in the event of a user interface computer 6119 reset.

The UI Model 6206 may accept user-input data and requests, such as a request to start a therapy, from the UI View 6208. Data integrity of any information submitted via the UI View 6208 may be enhanced or ensured in several ways, such as by sending data submitted via the UI View 6208 through the UI Model 6206 for verification. That is, while data may be edited locally in the UI View 6208, the accepted data may be transferred to the UI Model 6206 to be verified and recorded into database 6302 and/or sent to the Therapy Applications 6203. Verification may comprise, for example, verifying that entered data is within an expected range. Any entered information may be then read back from the database 6302 by the UI Model 6206, and sent to the UI View 6208 for display to the user. This process may be used to ensure that data stored in the database 6302 is correct or as a user intended. Data integrity may also be enhanced by requesting verification, by the user or another party, of entered data.

As shown in FIG. 63, direct authority to control the Therapy Applications 6203 in response to inputs received from the user interface, and thereby affect machine state, may be limited to the UI Model/UI Controller 6303 running on the automation computer 6106. In addition, direct authority to change information in the database 6302 may be limited to the UI Model/UI Controller 6303. In this case, the UI View 6208 and Auxiliary Applications 6301 may have read access to the database for actions such a viewing a log, but may not have write access to the database 6302, at least under most circumstances. In this way, actions that could have safety-critical implications may be isolated on the automation computer 6106. Of course, in some situations, it may be desirable to allow the UI View 6208 and Auxiliary Applications 6301 to have limited write access to the database 6302, such as to write to a particular portion of the database or to write non safety-related data to the database. In addition, in some embodiments, it may be desirable to allow the UI View 6208 to directly control aspects of the Therapy Applications 6203.

The Auxiliary Applications 6301, discussed above, may comprise log or documentation viewers, for example. These Applications 6301 may run on the user interface computer 6119 and operate in their own process space. However, to enable the UI View 6208 to control these applications, the Auxiliary Applications 6301 may be clients of the UI View 6208. This allows the UI View 6208 to communicate with the applications in a standard manner and allows the UI View to monitor these processes.

The UI Controller 6204 may comprise a table-based hierarchical state machine (HSM) that determines the state of the screens displayed by the UI View 6208 based on data polled from the Therapy Applications 6203, local timeouts, and command requests or data received from the UI View 6208. As represented in FIG. 63, the UI Controller 6204 may access and write data to the database 6302 as required. The state of the HSM in the UI Controller 6204 may determine the major state of the set of screens displayed by the UI View 6208.

Figure 64:
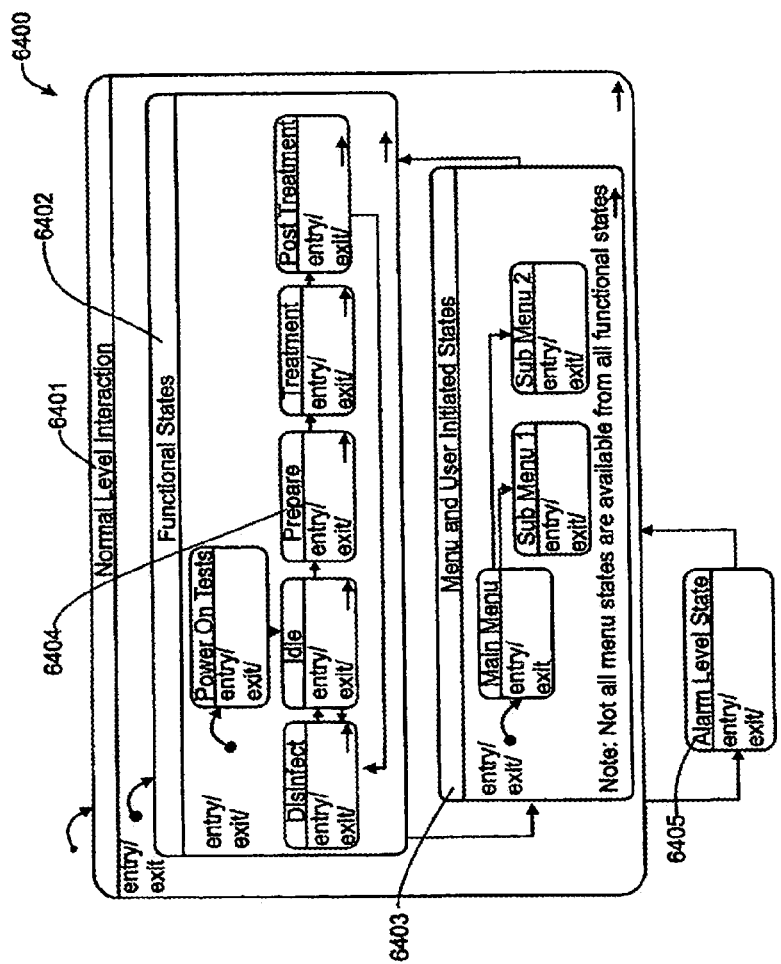
FIG. 64 is a schematic view of an exemplary hierarchical state machine (HSM) that may be used by the UI Controller shown in FIG. 63.

An exemplary HSM that may be used by the UI Controller 6204 to determine the state of the screens displayed by the UI View 6208 is schematically shown in FIG. 64. As shown, the HSM 6400 determines the state of "normal" (i.e., non-alarm) level interactions 6401, including the current functional state 6402 of the user interface and the current menu state 6403. The HSM 6400 shown in FIG. 64 is merely exemplary, and may be implemented in a much more detailed manner. For example, the state designated "Prepare" 6404 may involve several states relating to preparation for treatment, including a "gather supplies" state, an "install chemicals" state, the entering of patient information, and a validation screen. The validation screen gives the user the opportunity to return to any of the prior data entry screens so that inaccurate information can be corrected before the "Prepare" state is exited. The HSM 6400 also shows an alarm state 6405 that may be triggered. The alarm state is described in connection with FIG. 65.

Figure 65:
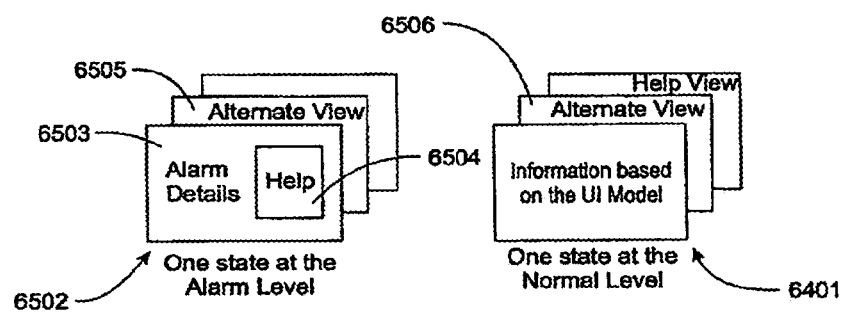
FIG. 65 is a schematic view of normal screen displays and alarm screen displays that may be displayed by the user interface shown in FIG. 61.

The UI View 6208 may have the ability to take over the screen display at any time in order to display alarms. An alarm condition may be triggered in certain circumstances to notify a user or other individual of an abnormal or otherwise noteworthy condition, such as a fluid leak, an occlusion, or an out-of-range temperature. When an alarm condition occurs, the state of the UI Controller 6204 may change. As shown in FIG. 65, when the UI View 6208 polls the UI Model 6206 for the current state, the UI View will change the display view from a normal state 6501 to an alarm state 6502 displaying alarm information 6503. When in an alarm condition, the UI View 6208 may prevent other information from blocking the display of the alarm. However, even during an alarm condition, the display may be configured such that a user may activate a "help" button to access additional information. In this case, help information 6504 may be laid out so that the help information covers only a portion of the view. Safety-critical logic of the alarm display, such as silencing logic, may be controlled in the automation computer 6106. For example, if a user would like an alarm to be silenced, an indication of the silencing request may be relayed back to the UI Model/UI Controller 6303, which can allow the audible alert to be silenced temporarily. In each of the alarm state and the normal state, alternate views 6505 and 6506, respectively, may be possible.

As explained above, when an alarm occurs, the normal UI View state is terminated so that the alarm state information can be displayed. Any local screen selection and/or editing data may be lost when the screen is changed. Since it may be desirable to preserve this information, the UI View 6208 may request that the UI Model/UI Controller 6303 stores information related to the screen displayed just prior to the alarm condition (i.e., the screen related to the normal state). At the conclusion of the alarm, if the normal state has not changed, the UI View 6208 may retrieve the stored information and restore the screen display. As an additional benefit, this feature may be used to restore the prior view in the event that the user interface computer 6119 is inadvertently reset.

Figure 66:
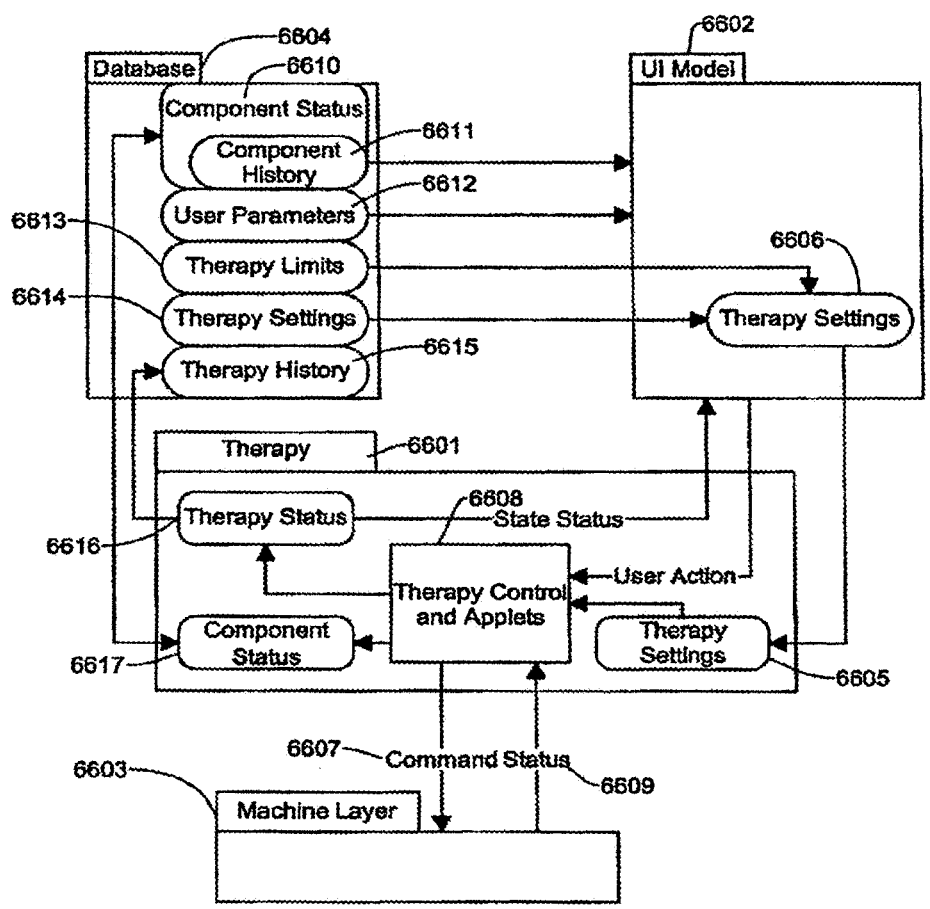
FIG. 66 is a schematic view showing how the Therapy Layer interfaces with other layers, such as the Machine Layer and User Interface Model Layer.

Therapy behavior is modeled and implemented as hierarchical state machines that define each activity and user interaction as discrete states. As shown in FIG. 66, the Therapy Layer 6601 is between the User Interface Model Layer 6602 and the Machine Layer 6603. The Therapy Layer both generates data and uses data stored in the Database 6604, which also shares data with the User Interface Model Layer.

The Therapy Layer 6601 controls the state of the system as a whole, and dictates available user interface interactions. The Therapy Layer 6601 is polled for state/status information by the User Interface Model Layer 6602. The Therapy Layer 6601 accepts user state change requests and changes to the Therapy Settings 6605 from the therapy settings 6606 on the User Interface Model Layer 6602. The Therapy Layer 6601 directs the Machine Layer 6603 in controlling the fluid path flows by issuing commands 6607 from Therapy Control and Applets 6608. The Therapy Layer 6601 polls status information 6609 from the Machine Layer 6603 to determine the state of processes.

Information read from and written to the Database 6604 may include Component Status 6610, Component History 6611, User Parameters 6612, Therapy Limits 6613, Therapy Settings 6614, and Therapy History 6615. For example, replaceable component information may be read from and updated to the Database 6604, and required fluid use and disinfect information may be read from the Database 6604. The Therapy Layer 6601 periodically writes Therapy Status 6616 information to the Database 6604 for logging purposes and to facilitate recovery in the event of a temporary power loss. The Therapy Layer 6601 also updates the Database 6604 with Component Status information 6617.

All inter-processor communications may be performed via server-defined client application programming interfaces (APIs) as remote process calls. The Therapy Layer 6601 may block when making Machine Layer and Database interface calls via their respective Client APIs. However, during critical functions, such as while performing patient therapy, the Therapy Layer generally will not perform any blocking database accesses. Generally, only non-critical updates to the database are performed using asynchronous (one-way) writes.

The User Interface Model Layer 6602 may block when making Therapy Layer calls via the Therapy Client API. The processes of the Therapy Layer may be considered higher-priority than those of its clients, such as the User Interface Model Layer 6602.

The system may handle exception conditions or errors generally in one of at least three ways. A system error detected in the software or associated with the CPU (such as, for example, a memory failure) call the reliability of the system into question, and trigger a failsafe state. A therapy error or condition may occur if a therapy variable approaches or exceeds permissible bounds. At least an alert or alarm (an event requiring user action) are triggered, and the condition is logged. Finally, system operation conditions can be triggered and logged to the database for later retrieval and analysis if problems are reported by an operator or service technician.

Generally, the Machine Layer 6603 will not change state unless explicitly requested by the Therapy Layer 6601. Thus, the Machine Layer 6603 generally should not generate an error in response to a change requested by the Therapy Layer 6601, assuming that the Therapy Layer 6601 makes change requests that are valid for the current operating state. As a result, Machine Layer 6603 command errors may not be tolerated. An exception is when a "Pause-Freeze-Stop" button is acted upon directly by the Machine Layer 6603 prior to Therapy Layer 6601 interaction. In this case, the Machine Layer 6603 will ignore any subsequent Therapy Layer 6601 commands until the Therapy Layer confirms the "Pause-Stop-Freeze" action.

Exception cases (e.g. in the event of a blood leak, or air in a line) and orthogonal states may be prioritized such that the state presented to the external User Interface Model Layer 6602 can be resolved to a unique current state. If multiple orthogonals attempt to set the user interface state, generally only the last orthogonal processed will be presented. Unexpected exceptions may be handled by commanding a Fail Safe state.

As explained above, the Therapy Layer 6601 software is a state-based control layer between the Machine Layer 6603, and the User Interface Model Layer 6602. The interface and access methodology that the Therapy Layer 6601 presents to the User Interface Model Layer 6602 are discussed below.

The Therapy Layer 6601 is a state-based layer that receives command requests from the User Interface Model Layer 6602. Some commands are valid from any state. Others are state specific, and the Therapy Layer 6601 will decide if the current command request will be acted upon or not. If the current state is not valid for the command request, the request from the User Interface Model Layer 6602 will be rejected and an appropriate reason for the rejection will be returned to the client. In this way, safety-critical operations will be protected from commands that are inappropriate in the current state. Only safe and validated operator command activities may be processed. The Therapy Layer 6601 interface to the User Interface Model Layer 6602 may be a server, and the User Interface Model Layer 6602 may access it as a client process using standard IPC client/server connection methods.

Synchronization between the Therapy Layer 6601 and the User Interface Model Layer 6602 may be based on two state-based enumerated types: the "Master State" and the "Sub-State." The Master State indicates the currently active Therapy Layer 6601 state machine. The Sub-State provides a unique state indication that can identify all of the alarms, user interaction, or the therapy sub-states that have duration. These state variables are updated in Therapy Status messages. This allows the Therapy Layer 6601 to verify what the active user operation is in a response to and provides the context to commands like "continue."

Figure 67:
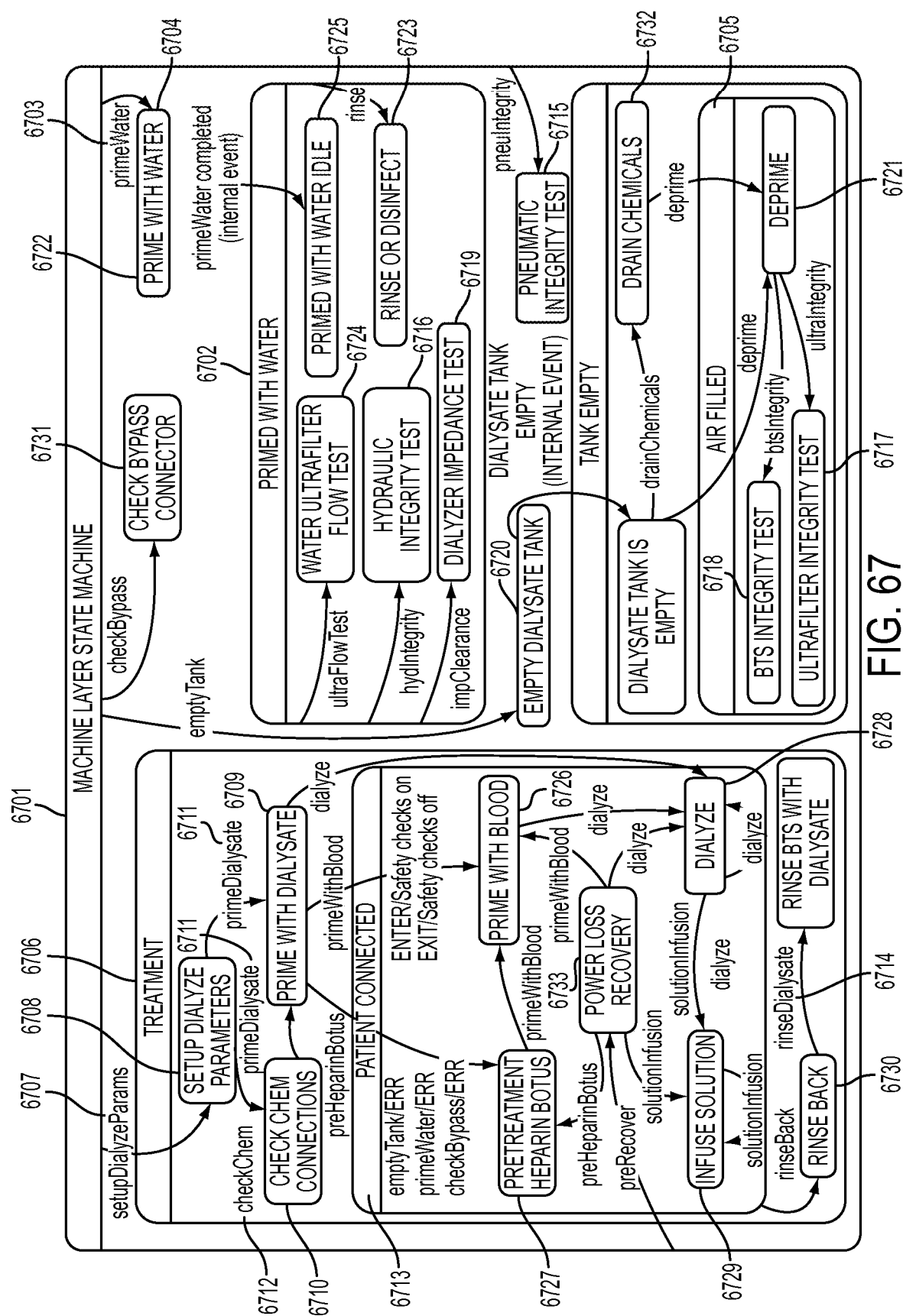
FIG. 67 is a schematic view showing an exemplary implementation of the Machine Layer shown in FIG. 66.

Turning now to the Machine Layer 6603 shown in FIG. 66, an exemplary implementation of the Machine Layer is shown in FIG. 67. The machine software is a layer of abstraction that provides the ability to implement a specific set of operations. These operations include priming the system, performing dialysis, disinfecting, draining and self testing. The machine software operates specific valves, runs pumps, controls flow paths and takes measurements. During the operations of the Machine Layer, status information can be requested at any time without interfering with operations.

With reference to FIG. 67, one state of the Machine Layer State Machine 6701 is the Primed With Water state 6702. This state is reached by sending the primeWater command 6703 and allowing the operation Prime with Water 6704 to complete. In the Primed With Water state 6702, the fluid paths are filled with reverse osmosis (RO) water and purged of air. In addition, this state is used to rinse, disinfect and perform various tests including flow tests and hydraulic integrity tests.

The Air Filled state 6705 is used to run the dialyzer and ultra filter integrity tests and for replacing components. In this state, the system may have had as much of the fluids removed as practically possible.

Dialysis treatment is performed in the Treatment state 6706. This state is entered by sending a command 6707 to set up the parameters of the dialyzer and the ultrafilter. For example, the setupDialyzeParams command 6707 may communicate the parameters of the installed disposable filters and the size of the needle/catheter. The initial state of the Treatment state 6706 is the Setup Dialyze Parameters state 6708.

The command issued by the Setup Dialyze Parameters state 6708 depends on the dialysate source. If the source is bagged dialysate, the primeDialysate command 6711 is issued and the process proceeds directly to Prime with Dialysate 6709. If the system is making dialysate from a bicarbonate cartridge and acid, the connections have to be verified. In this case, the CheckChem command 6712 is issued and the process proceeds to the Check Chem Connections state 6710. A dry test can be used to verify that an empty chemical container is connected. A wet test can be used to verify that a primed chemical container is connected by detecting the presence of no or minimal air in the container. Positive or negative pressure can be applied to the chemical container to detect the presence of loose connections or leaks. Conversely, a "CheckBypass" test can be performed to verify that the bypass connector is in place. Positive or negative pressure in the flow path can be measured to determine whether the chemical concentrate containers and tubing or the bypass connector are present. Positive or negative pressure can also be applied to determine the presence of any leaks associated with the connector. When this state is complete, the primeDialysate command 6711 is issued and the process proceeds to Prime with Dialysate 6709.

When using bagged dialysate, the priming process begins immediately. When making dialysate from reverse osmosis water, the system should prime the bicarbonate cartridge and cause the conductivity of the dialysate to stabilize at the requested level. Then, the dialysate tank should be filled to a minimum level. The system primes itself by running the pumps in the dialysate circuit forward and backward to drive air out of the cassette. The conductivity sensors can be checked during priming to ensure that their readings remain consistent. The system finishes priming by driving dialysate through the dialyzer and into the blood loop. Priming here can also involve forward and backward flow to help purge any air from the blood loop. The arterial and venous lines can also be isolated at times to purge the air more efficiently. Priming of the blood loop also serves to meet the minimum rinse volume required for the dialyzer before treatment. When this process is complete, the patient can be connected.

Before the start of a treatment, a Set Fluid Production Parameters command may be sent to the machine layer 6701. This command communicates the necessary information to either make dialysate or use pre-made dialysate. For example, the following dialysate information may be provided: bicarbonate cartridge priming volume (ml), bicarbonate volumetric ratio (mg/ml), target dialysate conductivity (mS/cm @ 25° C.) after addition of acid and salt (final dialysate composition), and acid volumetric mixture (ml acid/ml water). The following dialysate source information may be provided: reverse osmosis (RO) water or premade dialysate (RO/Bagged), and pre-made dialysate volume (ml).

The Pneumatic Integrity Test operation 6715 verifies the pneumatic devices in the system. This operation may check for leaks and verify sensors. This operation may comprise the following individual tests, which may be run individually or all in sequence: a cassette leak test, a pressure pump test, a dialysate tank test, and a valve speed test. The system may be prevented from initiating a therapy if any of these tests fails.

The cassette leak test is configured to identify gross pneumatic leaks in the system and determine whether they exist in the cassette or the manifold. An exemplary implementation of the cassette leak test is described below. At the beginning of the test, the pneumatic tank controller is disabled so that the test can control the positive and negative compressors manually. First, all valves and pumps are opened to positive pressure, while all pathways to negative pressure are closed off. The tanks are charged and then turned off in order to perform a leak down test. A leak may be detected by monitoring system pressures with respect to a predetermined threshold for a predetermined period of time. A leak in the positive reservoir pressure reflects a leak in the cassette, since everything is opened to the positive source. A leak in the negative reservoir pressure reflects a leak in the manifold, since little is drawing off the negative source. Next, all valves and pumps are opened to negative pressure, while all pathways to positive pressure are closed off. The tanks are again charged and turned off in order to perform a leak down test. In this case, a leak in the negative reservoir pressure reflects a leak in the cassette, since everything is opened to the negative source. A leak in the positive reservoir pressure reflects a leak in the manifold, since little is drawing off the positive source. The pneumatic tank controller is then re-enabled, the fluid valves are closed, and the pumps are closed off from both pressure sources.

The cassette leak test also tests the air flow capacity of the positive and negative compressors. To test the negative air flow, a positive valve and a negative valve associated with the bicarbonate pump 183 (FIG. 3A) are opened at the same or substantially the same time. The negative reservoir pressure is then monitored while the negative compressor is turned on. The test may fail if the negative pressure exceeds a predetermined threshold. To test the positive air flow, a positive variable valve and a vent variable valve associated with pod pump 161 (FIG. 5) are opened to a full open position at the same or substantially the same time. The positive reservoir pressure is then monitored while the positive compressor is being controlled by the pneumatic tank controller. The test may fail if the positive pressure is less than a predetermined threshold.

The metering pump test is configured to detect pneumatic leaks in the reference and pump chambers of the metering pumps described herein. According to an exemplary implementation of the metering pump test, all reference and pump chambers are first charged with positive pressure by opening the positive source and FMS valves. The test verifies that each chamber reaches a predetermined pressure and that the reference and pump chamber pressure readings are in agreement. Next, the positive source valve is closed and a leak down test is performed on the pump and reference chambers at the same or substantially the same time. The same test may be repeated using the negative source valve. Afterwards, each pump chamber is charged with negative pressure. The FMS valve is then closed and the reference chamber is charged positive. The chamber pressures are checked against their target pressures before the positive source valve is closed to perform a leak down test on both chambers. In some cases, the pressure decay rate is used to determine whether a leak test passes.

The pressure pump test is configured to detect pneumatic leaks in the eight pressure pump chambers. According to an exemplary implementation of the pressure pump test, the chambers are first charged close to the low positive pressure and a leak down test is performed. Next, the chambers are charged close to the negative pressure and another leak down test is performed. An additional leak down test on the inner pump chambers is then performed at a lower pressure with tighter constraints. Finally, all chambers are actively controlled to four different pressures to check that the pods can be accurately charged and controlled.

The dialysate tank test is configured to detect pneumatic leaks in the dialysate tank and the FMS reference chamber used to take fluid level readings. According to an exemplary implementation of the dialysate tank test, the reference chamber is first charged with the two-way binary FMS valve associated with the dialysate tank in a closed position. A leak test is then performed. Next, the dialysate tank is charged by closing the surrounding valves, and then stepping up the pressure by repeatedly charging up the reference chamber and opening the two-way binary FMS valve associated with the dialysate tank. Once the tank is sufficiently charged, a leak down test is performed. Afterwards, the three-way low pressure vent valve associated with the dialysate tank is opened and it is verified that the tank can successfully vent pressure.

The valve speed test is configured to measure the open speed of the variable valves, metering pump valves and select fluid valves. The close speed of the select fluid valves may also be measured.

The Hydraulic Integrity Test operation 6716 verifies the fluid valves in the system. In particular, the operation tests whether each of the fluid valves opens and closes properly. If the operation reveals that any of the fluid valves is not operating properly, as evidenced by a failure, the dialysis system may be prevented from initiating a therapy. The operation is divided up into test sets based on which pump chambers drive fluid through which valves. Each test set comprises a pump chamber, a set of test valves, and a set of valves to open. The pump chamber is used to fill and charge the test pathway with fluid. The set of test valves are the valves that are under test for that test set. The set of valves to open are the valves that are left open in order to create a path to drain or back to the tank.

In this test, the fluid pathways associated with a pump chamber are first primed with a fluid (e.g., water), and the pump chamber is filled with the fluid. Then the pump chamber is pressurized. The steps involved in pressurizing the pumping chamber may comprise, for example: (1) closing the valves associated with the pump chamber, (2) opening any valves necessary to provide a clear path away from the valve under test to atmospheric pressure (e.g., to drain or back to the tank), (3) pressurizing the pump chamber to a predetermined pressure (e.g., 600 mmHg above atmosphere) from the positive pressure gas reservoir, and (4) closing the connection to the reservoir. After pressurizing the pump chamber, a test may be performed to verify proper operation of the test valves in the closed state. In particular, the pressure of the pump chamber may be monitored, and a failure may be logged if the pressure decays more than a predetermined maximum decay limit over a predetermined minimum decay time. Such a failure may indicate that one or more valves is leaking sufficiently to allow the current pump chamber to deliver fluid.

Next, for each test valve, the following test may be performed to verify proper operation of a test valve in the open position. First, the pump chamber may be pressurized according to steps (1) through (4), described above, and the test valve may be opened. Next, the pressure of the pump chamber may be monitored, and a failure may be logged if the pressure decays less than a predetermined minimum decay limit over a predetermined maximum decay time. Once this test is completed for a current test valve, the test valve is closed, and the test is performed for another test valve. If all the valves in the current test set have been tested, all the test valves and opened valves are closed, and the test set may be deemed complete.

One, some or all of the test sets, or portions thereof, may be tested during the Hydraulic Integrity Test operation 6716. It should be appreciated that any of the predetermined maximum decay limit, predetermined minimum decay limit, predetermined minimum decay time and predetermined maximum decay time may correspond to a particular test set, such that the predetermined values may vary from one test set to the next. Further, it should be appreciated that the operation described above is merely exemplary, and that variations are possible. For example, the test valves may be tested in just one of the open position and the closed position, and different factors may be used to determine a failure.

The Ultrafilter Integrity Test operation 6717 is a pressure test of the ultrafilter membrane to check for leakage. Air pressure is applied to the inlet side of the ultrafilter. Air pressure is maintained, since air generally will not pass through a wet intact filter. This test is performed in the "Air Filled" state, and verifies the ultrafilter by pressurizing the outer dialysate side and measuring the pressure drop over time.

The BTS/Dialyzer Integrity Test operation 6718 is a pressure test of the blood loop including the dialyzer. In this test, the blood loop is pressurized with air drawn from the anticoagulant pump air filter 81 (e.g., FIG. 4A) and the pressure is monitored over time. If the measured pressure drop is less than the input decay threshold, the test passes. As the blood tubing, pump and dialyzer are replaced as a unit, this test need not determine where the leak is.

The Dialyzer Impedance Clearance operation 6719 verifies that the blood path through the dialyzer has low enough resistance to provide efficient dialysis therapy. Before starting the impedance test, the system is primed with water. During the test, flow is forced across the dialyzer. As water flows across the dialyzer, the pumping pressures will be monitored, which provides a measure of the dialyzer impedance. Alternatively, a constant pressure can be applied, and the time taken for a fixed volume to cross the filter membrane can be measured. The dialysate circuit is set to provide a constant low impedance destination of the fluid being pushed through the membrane. If the dialyzer impedance is too high, a failure will be reported and the dialyzer will need to be replaced. An Ultrafilter Flow Test operation 6724 may be also performed to ensure that the ultrafilter impedance is low enough to support the flow rate required for therapy. This test has the benefit of ensuring that the result of the integrity test will be valid.

The Empty Dialysate Tank state 6720 may stop fluid production and run the dialysate pump at the fastest reasonable rate to pump the contents of the dialysate tank to drain until some amount (e.g., 3000 ml) has been transferred, or air is detected in the drain. The Deprime operation 6721 is used to purge the system of fluid, filling the blood tube set and the dialysate circuit outside of the ultrafilter with air. This condition is used to perform pressure-decay tests to verify the integrity of the dialyzer and ultrafilter, as well as to change the fluid components and to prepare the unit for transport. The inner dialysate circuit generally cannot be deprimed because it may not be possible to pump air through an intact dialyzer or ultrafilter, and there may be no air vent in the inner circuit. However, if depriming the inner dialysate circuit is necessary, then one may first deprime all other components, and then remove the top of the ultrafilter to allow air to enter the system. The dialysate mixing water pump (e.g., pump 280 in FIG. 89) can then be used to pull air from the ultrafilter connection and to deliver it to the inner dialysate circuit, alternating the inner dialysate pump flow paths to pull as much water out of the system as possible.

The Prime with Water operation 6722 fills the system with water and purges the air. It may fill the system in stages, starting with the fluid production section, and moving to the outer dialysate, inner dialysate, and then the blood loop. The bicarbonate cartridge and acid bag should be removed, and a bypass connector should be in place before this operation is performed. According to one exemplary implementation, the bypass connector comprises three connection points respectively corresponding to a bicarbonate charge line, an acid flow line and a bicarbonate return line of the mixing circuit 25. The bypass connector has three parallel prongs respectively corresponding to the three connection points. Channels in the prongs of the bypass connector terminate within a common chamber within the bypass connector. Thus, during a disinfect procedure, the bicarbonate charge line, acid flow line and bicarbonate return line are all interconnected, permitting disinfection of each of these flow lines during the disinfect procedure. An exemplary embodiment of such a bypass connector is the "disinfect connector" described in U.S. patent application Ser. No. 12/199,055 filed on Aug. 27, 2008 and incorporated by reference herein.

The Disinfect/Rinse state 6723 is used to run reverse osmosis water through all fluid paths at a specified temperature. Before this operation, the system should be in the "Primed With Water" state 6725. Disinfection occurs when this operation is performed at an elevated temperature. The tank is filled with reverse osmosis ("RO") water at the start of the operation. The water in the dialysate tank is recirculated from the Dialysate Circuit disinfect path through all Fluid Production fluid paths and blood tubing set paths, and back into the dialysate tank. As recirculated water is lost (sent to drain), reverse osmosis water may be added to maintain a minimum level in the dialysate tank. Alternatively, in a preferred embodiment, no further water is introduced in order to avoid the possibility of contamination. The chemical cartridge is not attached during this operation.

The Prime with Dialysate operation 6709, described above, is used to flush dialysate through all fluid paths and remove any air or water in the system. This operation must be completed before the system can move on to the Patient Connected state 6713. This operation activates the fluid production sub-system, which is responsible for mixing the RO water with the chemicals, and for maintaining the dialysate tank level. If the tank is less than 75% full, priming may be delayed until that level is reached. The tank level is preferably maintained at more than 1.1 liters; otherwise, a signal may be generated to stop therapy. This amount allows for a sufficient rinseback volume and a sufficiently large averaging volume needed for mixing control accuracy. During prime, the air-in-line sensors, the blood-leak sensor and the safety system are tested.

In the Patient Connected state 6713, a dialysis treatment can be performed. Prior to issuing the RinseDialysate command 6714, the blood tubes are returned to drain connections. For safety purposes, while in the Patient Connected state 6713, the dialysate temperature may be constrained, and the dialysate conductivity and flow rates may be monitored.

The Prime With Blood operation 6726 removes dialysate from the blood circuit and replaces it with patient blood. Dialysate is pulled across the dialyzer membrane into the dialyze circuit and is discarded to drain. Blood is pulled into the blood circuit from the patient to replace the dialysate pulled across the membrane. Thus most of the priming fluid occupying the BTS need not be administered to the patient at the start of dialysis. Optionally, the patient can choose to be administered the priming fluid by canceling this operation. This may be desirable, for example, if the patient is in need of additional fluid at the start of dialysis. This operation transitions the machine software into the Patient Connected state 6713, activating safety constraints such as temperature limiting.

The Heparin Bolus operation 6727 delivers a bolus of heparin before treatment without requiring patient interaction. Before normal dialysis operation, and to minimize the amount of fluid administered to the patient, the bolus can be delivered down the arterial line, which is a shorter route to the patient's vascular access. In the event of the detection or presence of an air-in-line condition, the heparin bolus can optionally be delivered down the venous line, which incorporates air-trapping mechanisms or devices. Prior to the Heparin Bolus operation 6727, a Heparin Vial Connection test may be performed to verify that a heparin vial is attached to the heparin/medication infusion spike on the blood pump cassette.

The Dialyze operation 6728 is used to administer dialysis treatment to the patient. The rate of the blood circuit and the dialysate circuit may be specified independently. This operation can have a time limit or be terminated with a stop command. By way of example, the following parameters may be specified: the temperature at which the dialysate flowing through the system is heated and maintained, the rate at which dialysate is circulated through the blood circuit, the rate at which basal or maintenance heparin is added to the blood circuit, the rate at which dialysate is circulated through the dialysate circuit, and the rate at which dialysate is pumped through the ultrafiltration pump, among other parameters. During dialysis, the ultrafilter is periodically 'burped' to remove any gas that has accumulated within it during treatment. This can be accomplished by opening the pathway from the top of the ultrafilter to drain while closing the pathway from the top of the ultrafilter to the dialysate circuit. Any air trapped in the top of the dialyzer can then be flushed to drain. After two or more pump strokes to divert the air and fluid to drain, the valves are reset and dialysis operations can continue.

During dialysis, the flow of dialysate may be adjusted automatically based on one or more factors. One such factor is the amount of remaining dialysate, which may include both the dialysate in the tank 169 (FIG. 3*a*) and the dialysate that can be produced from the remaining dialysate ingredients 49 (FIG. 3*a*). For example, if it is determined that the remaining dialysate would be exhausted before the treatment was completed at the current dialysis flow rate, the rate can be slowed so that the remaining dialysate will last for the full length of treatment. According to an exemplary implementation, the dialysis system automatically adjusts dialysate production based on the actual or predicted dialysate tank level and/or the actual or predicted remaining ingredients used in dialysate production. Another factor that may serve as the basis for adjusting the flow of dialysate is the potential for clogging the dialyzer. In particular, the flow of dialysate may also be adjusted automatically to minimize clogging of the dialyzer during therapy. For example, to avoid clogging the dialyzer fibers, the flow back and forth across the dialyzer may be timed and balanced. In addition to automatically adjusting the flow of dialysate, the dialysis system may automatically adjust dialysate production based on one or more factors.

For example, using a current or average rate of use of dialysate and an expected length of treatment remaining, an estimate of the volume of dialysate required to complete a treatment may be calculated. To calculate the amount of additional dialysate that needs to be produced to complete the treatment, the liquid volume of dialysate in the tank may be subtracted from the estimate of the volume of dialysate required to complete a treatment, as calculated above. The determination of how much additional dialysate should be produced may be implemented, for example, by a processor applying the algorithm described above. It should be appreciated that the determination is not limited to the amount of additional dialysate that needs to be produced to complete a treatment, as the amount of additional dialysate that needs to be produced to complete some other operation may be performed in a corresponding manner.

The amount of remaining dialysate may be calculated from the amount of dialysis ingredients 49 (FIG. 3A) that have been used. Full containers with known masses of bicarbonate powder and acid liquid may be installed in the dialysis unit at the start of a therapy. With reference to FIG. 3A, the mix cassette 25 adds these chemicals to the RO water to make dialysate. Some RO water flows through the bicarbonate container to produce a saturated bicarbonate water mixture. The bicarbonate pump 183 and acid pump 184 each have RMS systems to accurately measure the flow rate of these chemicals into the water to form the dialysate that flows into the dialysate tank 169. The amount of remaining chemicals can be calculated from the assumed full container amount minus any material pumped out by the two pumps 183, 184. The amount of bicarbonate removed by the pump 183 may be calculated by assuming the fluid is a fully saturated mixture. The amount of water used may be measured based on the number strokes by the water pump 180. The automation computer 6106 (FIG. 61) calculates the remaining amount of dialysate that can be produced using the remaining amount of bicarbonate and acid and the amount of these chemicals it takes to produce a unit of dialysate. According to one exemplary implementation, the amount of dialysate produced per unit of chemical is a known number. Alternatively, the amount of dialysate produced per unit of chemical can be determined from the measured flow of chemicals through the pumps 183, 184 and the measured flow of water in the water pump 180.

The Power Loss Recovery 6733 command may be sent to tell the machine software that there was loss of power while it was in the Patient Connected state 6713. This forces the machine software into a Patient Disconnected state so that the dialysis machine can recover properly and prepare itself for the next treatment (e.g., Recycle Preparation).

The Solution Infusion operation 6729 delivers dialysate into the patient. Dialysate is pushed across the dialyzer by the outer dialysate pump and delivered to the patient by the blood pump. This command causes the system to prepare for the infusion by stopping dialyzing, freezing the inner pump, and filling the outer pump with dialysate to deliver to the patient. After receiving this command, the machine software expects one of the following commands: Solution Infusion Confirm (proceed with solution infusion), Solution Infusion Stop (do not perform solution infusion, resume dialyzing instead), or StopCmd (return the system to an idle state). Preferably, the blood pump continues to run during solution infusion.

A Backflush operation can be programmed during dialysis to periodically flush dialysate backwards across the dialyzer membranes in order to help prevent clogging of the membranes. The Rinse Back operation 6730 pushes dialysate into the patient to return their blood in preparation for disconnection. Dialysate is pushed across the dialyzer by the outer dialysate pump and delivered to the patient. This is automated for both venous and arterial paths. The arterial path can use the blood pump for delivery.

The Check Bypass operation 6731 checks for the presence of the bypass connector for the acid container and the bicarbonate cartridge or container. In a preferred embodiment, the operation causes a vacuum to pull on the bypass connector to detect leaks. Referring to FIG. 89, an exemplary method of performing the Check Bypass operation 6731 to detect the presence of bypass connector 276 may include filling the bicarbonate water pump 282 with air obtained by opening the dialysate tank 169 air vent valve 260, dialysate tank recirculation valve 264 and the disinfection pathway valve 266. The pump chamber may then be filled with air and positively pressurized. The contents of the dialysate mixing water pump 280 may then be delivered to drain via dialysate mix drain 262. Acid metering pump 184 is also depressurized in this step. A flow path is then established between the bicarbonate water pump 282, bicarbonate cartridge 28, and bypass connector 276, through acid metering pump 184 to the dialysate mixing water pump 280 (closing dialysate mix drain valve 262). Having set the dialysate mixing water pump 280 to atmospheric pressure, a pre-determined increase in pressure measured by pressure sensor 286 indicates that bypass connector 276 is properly installed.

The Drain Chemicals operation 6732 empties the contents of the chemical containers to the drain. In a preferred embodiment, the contents of the chemical containers are discarded after each treatment, making cleanup easier for the patient and discouraging potential problems in trying to reuse chemicals. Referring to FIG. 89, for example, the controller can initiate an Acid Drain state in which the dialysate mixing pump 280 can pump fluid from the acid container 29 to drain via valve 262. This can be accomplished by opening the valves 277, 278 of the acid pump 184, and using the outlet of acid pump 184 as the inlet of dialysate mixing pump 280 by opening valve 274, closing valve 271 and actuating a fill stroke in pump 280. After filling pump 280, its contents can be discharged by closing valves 277 and 261 and opening valve 262. Pressure sensor 286, for example, can be used to determine whether acid container 29 is empty by detecting that air is being pumped by pump 280. The pressure signal generated by the pumping of air (e.g., rapid movement of the flexible membrane to an end-of-stroke position) is sufficiently different from the signal generated by pumping of liquid that the controller can be programmed to distinguish them. Upon this determination, the controller can infer that the acid container 29 is empty, and that further pumping from the acid container 29 can be halted.

The controller can initiate a Bicarb Drain state in which the dialysate mixing pump 280 can also pump fluid from the bicarbonate container 28 to drain via valve 262. This can be accomplished by first venting the top of the bicarbonate container 28. For example, a fluid path can be opened from the top of the bicarbonate container 28, through the bicarbonate mixing pump 282, valves 270, 266, 264 and 260 at the dialysate tank 169. Bicarbonate pump valves 272 and 273 can be opened, and pump 280 can then draw fluid from the bottom of bicarbonate container 28, and pump it to drain via valve 262. In an embodiment, the pump 280 can be set to pump about twice the volume contained in bicarbonate container 28 in order to ensure that it has been completely emptied of liquid.

A CheckDoors operation verifies that the doors of the hemodialysis machine are closed, helping to ensure that the patient is disconnected. A CheckDCA operation can then verify that the patient has plugged the vascular access connectors of the blood tubing set back into the DCA/DCV ports of the machine for rinsing and disinfecting after a treatment session.

Referring to FIGS. 5 and 89, the system can automatically check that the venous and arterial line connectors have been plugged back into the DCA/DCV ports of the machine by selectively pressurizing the lines and monitoring for a pressure decay. For example, valves 231, 232, 221, 222, and 223 may be opened, and valves 263, 264, 266 and 267 may be closed, to allow outer dialysate pumps 159 to pump dialysate from dialysate tank 169 through dialyzer 14 and into blood flow circuit 141. Both blood pumps 13 may be filled with fluid. Then valves on the dialysate side may be closed to prevent fluid from crossing over from the blood side to the dialysate side of the dialyzer 14. For example, valves 211, 212, 213, 221, 222, 223, 231, 232, 241, 242 and 210 may be closed on the dialysate side.

To determine that the venous line 204 is properly plugged into its port, tubing clamp 202 and valve 207 may be opened, and valve 206 may be closed. Then blood pump valve 195 may be opened, while blood pump valves 192, 193, 194 are closed. Blood pump chamber 23*a* may then be pressurized with a pre-determined amount of pressure (e.g., 400 mm Hg). The test may be considered to have failed if the pressure monitored by pressure sensor 197 drops at a pre-determined rate or greater (e.g., 130 mm Hg drop over 1 sec.). The proper operation of valve 206 may then be tested by opening the valve and having pressure sensor 197 monitor the pressure drop (e.g., test considered to fail if the monitored pressure does not drop by at least about 130 mm Hg over 1 sec.).

To determine that the arterial line 203 is properly plugged into its port, both valves 206 and 207 may be closed. Then blood pump valve 192 may be opened, while blood pump valves 193, 194, 195 are closed. Blood pump chamber 23*b* may then be pressurized with a pre-determined amount of pressure (e.g., 400 mm Hg). This test may be considered to have failed if the pressure monitored by pressure sensor 196 drops at a pre-determined rate or greater (e.g., 130 mm Hg drop over 1 sec.). The proper operation of valve 207 may then be tested by opening the valve and having pressure sensor 196 monitor the pressure drop (e.g., test considered to fail if the monitored pressure does not drop by at least about 130 mm Hg over 1 sec.).

In addition, a Clean Blood Path operation may be performed to push the contents of the dialysate tank through the blood circuit and out the drain. Rinsing is used to flush residual blood from the blood circuit and dialyzer after the dialysis treatment. In an embodiment, air is introduced into the fluid to enhance the mechanical action of loosening debris from the dialyzer and tubing components. During this operation, fluid production may deliver water, which will dilute the dialysate in the tank.

A Circulate Dialysate operation may be used to maintain the temperature and dialysate freshness in the system after it has been primed when the patient is not yet connected. This is accomplished by running dialysate through the heater, ultrafilter into the inner pump, and passing it through the dialyzer, while also running the blood pump. A small amount of the dialysate can be constantly sent to drain.

The Machine Layer 6701 may also respond to stop, freeze, resume, and shut down commands. The stop command terminates the operation being performed by machine. When the stop command is issued, the current pump cycle is completed, then the appropriate valves are closed. Because the stroke is completed, all fluid accounting will be accurate. After the valves are closed and pumping completes, the state machine returns to the "idle" condition where it waits for the next command. This command does not affect the getStatusCmd, setupDialyzeParams or setupFluidParams commands because they do not start operations.

The freeze command causes the system to close all valves on its current cycle. This includes the fluid production valves. The heater is turned off to prevent overheating of the fluid within it. Fluid volume accounting will be correct if the resume command is issued after the freeze command. If the freeze command is followed by a stop command and then another command to enter an operation other than the one that was frozen, fluid volumes are assigned to the new operation regardless of the fact that there may be partial fluid delivery in the original state. State history of the current operation is retained so the "resume" command can be used to continue the operation. The resume command causes the machine to continue processing the command that was frozen. The shut down command is used to terminate the machine software process.

The operations described above in connection with FIG. 67 may be implemented by corresponding state machines at the machine layer level. Described below in connection with FIGS. 67A-67E are exemplary implementations of state machines performing the following operations: (1) Dialyzer Impedance Clearance, (2) Circulate Dialysate, (3) Heparin Vial Connection Test, (4) Heparin Bolusing, and (5) Empty Tank.

(1) Dialyzer Impedance Clearance

The Dialyzer Impedance Clearance operation may be used to measure the water permeability of the dialyzer, which may indicate the fitness of the dialyzer for performing additional treatments. A failure of a Dialyzer Clearance operation may indicate that the dialyzer is clogged and needs to be replaced. According to one exemplary implementation, the Dialyzer Impedance Clearance operation is performed prior to each treatment before a patient is connected. There may be two modes of operation; one checking the flow of fluid across the dialyzer fiber membranes, and one checking flow along the hollow fibers.

Figure 67A:
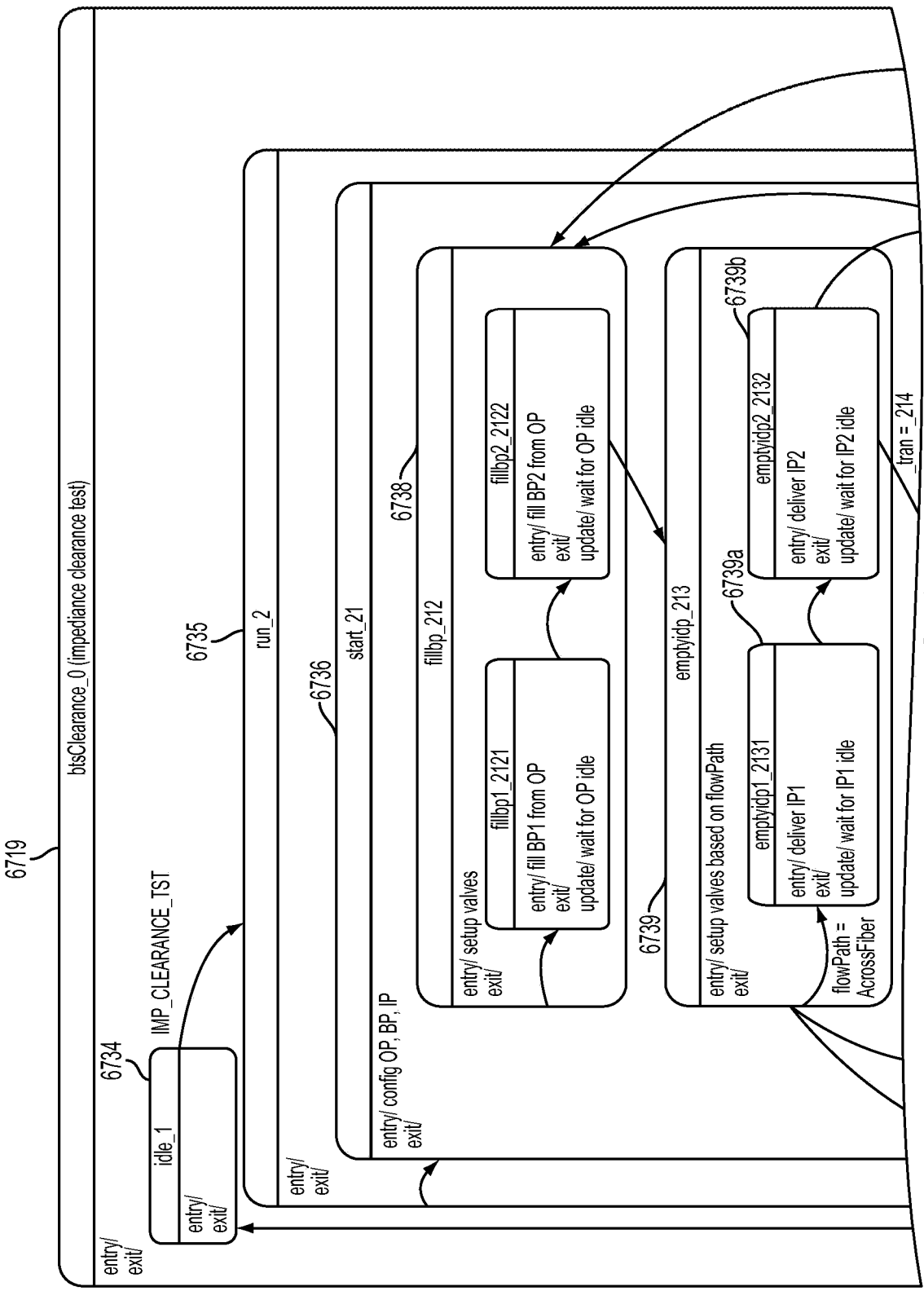
FIG. 67A is a schematic view showing an exemplary implementation of the Dialyzer Impedance Clearance operation.
Figure 67A:
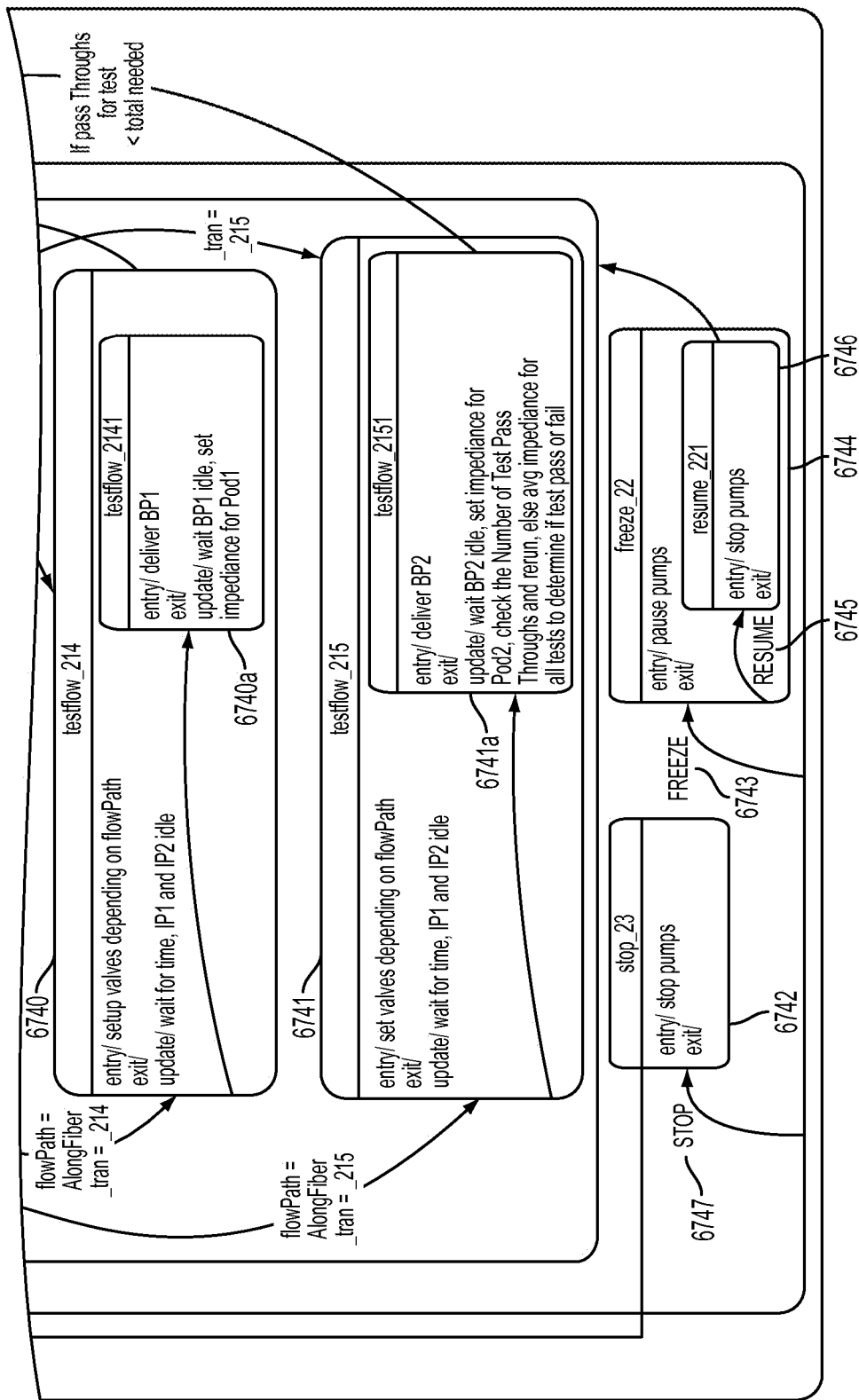

During the operation, water is forced across the dialyzer. As water flows across the dialyzer, the pumping pressures are monitored, which gives a measure of the dialyzer impedance. An impedance above a predetermined threshold may indicate that the dialyzer needs to be replaced. The dialyzer impedance is measured from the blood side flowing to the dialysate side. To prepare for the test, both chambers of the blood pump are filled with water and both chambers of the inner dialysate pump are emptied to drain. FIG. 67A shows an exemplary implementation of the Dialyzer Impedance Clearance operation 6719 described in connection with FIG. 67.

Referring to FIG. 67A, the operation transitions to the Run state 6735 from the Idle state 6734. Once idle, the test transitions to the Start state 6736. The Start state 6736 configures the outer, inner, and blood pump.

Next, the Fill Blood Pumps 6738 state sets up the valves so that the blood pumps may be filled. A first blood pump chamber is filled with water from the outer dialysate pump, which is used to pump dialysate through the outer dialysate fluid path. Then, a second blood pump chamber is filled with water from the outer dialysate pump. Each chamber is filled individually, with a path being opened through the inner pump from the outer pump to the blood pump.

In the Empty Inner Dialysate Pumps state 6739, the valves are set up based on the flow path (e.g., across the dialyzer fibers). In the Empty Inner Dialysate Pump 1 state 6739*a*, a first inner dialysate pump is emptied to the drain. Similarly, in the Empty Inner Dialysate Pump 2 state 6739*b*, a second inner dialysate pump is emptied to the drain.

To conduct the dialyzer impedance clearance test, the blood pump pushes each chamber of water across the dialyzer to the inner dialysate pump chambers. The inner dialysate pump chambers start out empty, and are vented to atmosphere during this test so the chambers present atmospheric pressure on the dialysate side of the dialyzer. Each blood pump chamber delivers water using a specific pressure and monitors for end-of-stroke to determine the flow rate. Each chamber provides one pressure/flow data point, and the process is repeated to obtain additional data points.

In the First Blood Pump Chamber Test Flow state 6740, the valves are set up based on the flow path. If the flow path is across the dialyzer fibers, the inner dialysate pump is opened to the drain. If the flow path is along the dialyzer, a flow path is opened to the blood tubing set drain. In state 6740*a*, the first blood pump chamber is delivered. Once the chamber is idle, test data is calculated. The state 6740*a* then transitions back to the Fill Blood Pumps 6738 state, so that the second blood pump chamber can be tested.

In the Second Blood Pump Chamber Test Flow state 6741, the valves are set up based on the flow path. Again, if the flow path is across the dialyzer fibers, the inner dialysate pump is opened to the drain. If the flow path is along the dialyzer, a flow path is opened to the blood tubing set drain. In state 6741*a*, the second blood pump chamber is delivered. Once the chamber is idle, test data is calculated. The state checks how many total passes are needed through the test (e.g., 9 passes) before it can average out the test data and determine a pass/fail condition. If the test needs to run through again, the operation transitions to the Fill Blood Pumps 6738 state. If the test is complete, the average impedance is calculated and the operation transitions to the Stop state 6742.

The Freeze command 6743 is commanded from the therapy layer to freeze the operation. This command is handled in the Run state 6735. The Freeze state 6744 pauses the running pumps, and closes the valves used in this operation. The state of the pumps and valves do not need to be saved in response to the Freeze command 6743, since the test and check operations may be restarted when the operation is resumed.

The Resume command 6745 is commanded from the therapy layer to resume the operation from a frozen state. This command transitions the Operation to the Resume state 6746. As noted above, when the operations resumes, the Dialyzer Impedance Clearance operation may be restarted so that the test begins anew.

The Stop command 6747 is commanded from the therapy layer to terminate the test. This state is also called at the end of the operation to insure that all pumps are stopped and all valves are closed. In particular, this state stops fluid production, the outer pump, the inner pump, and the blood pump. The state then waits for the pumps to be idle and closes the operation valves before transitioning to the Idle state 6734.

(2) Circulate Dialysate

Once the dialysis system is primed with dialysate, a user may connect to the system. While waiting for the user to connect, the dialysis system may circulate dialysate to keep the dialysate warm and remove any air that arises in the blood tubing set. The system may refresh the dialysate by pumping the blood circuit backwards with respect to normal therapy flow at a predetermined rate (e.g., 200 mL/min) and pumping fresh dialysate from the tank to the blood tubing set at another predetermined rate (e.g., 100 mL/min). Backwards flow in the blood circuit encourages any air that arises from the dialysate to migrate to the air trap between the arterial and venous lines. Pumping fresh dialysate all the way to the blood tubing set drain refreshes the entire prime.

Figure 67B:
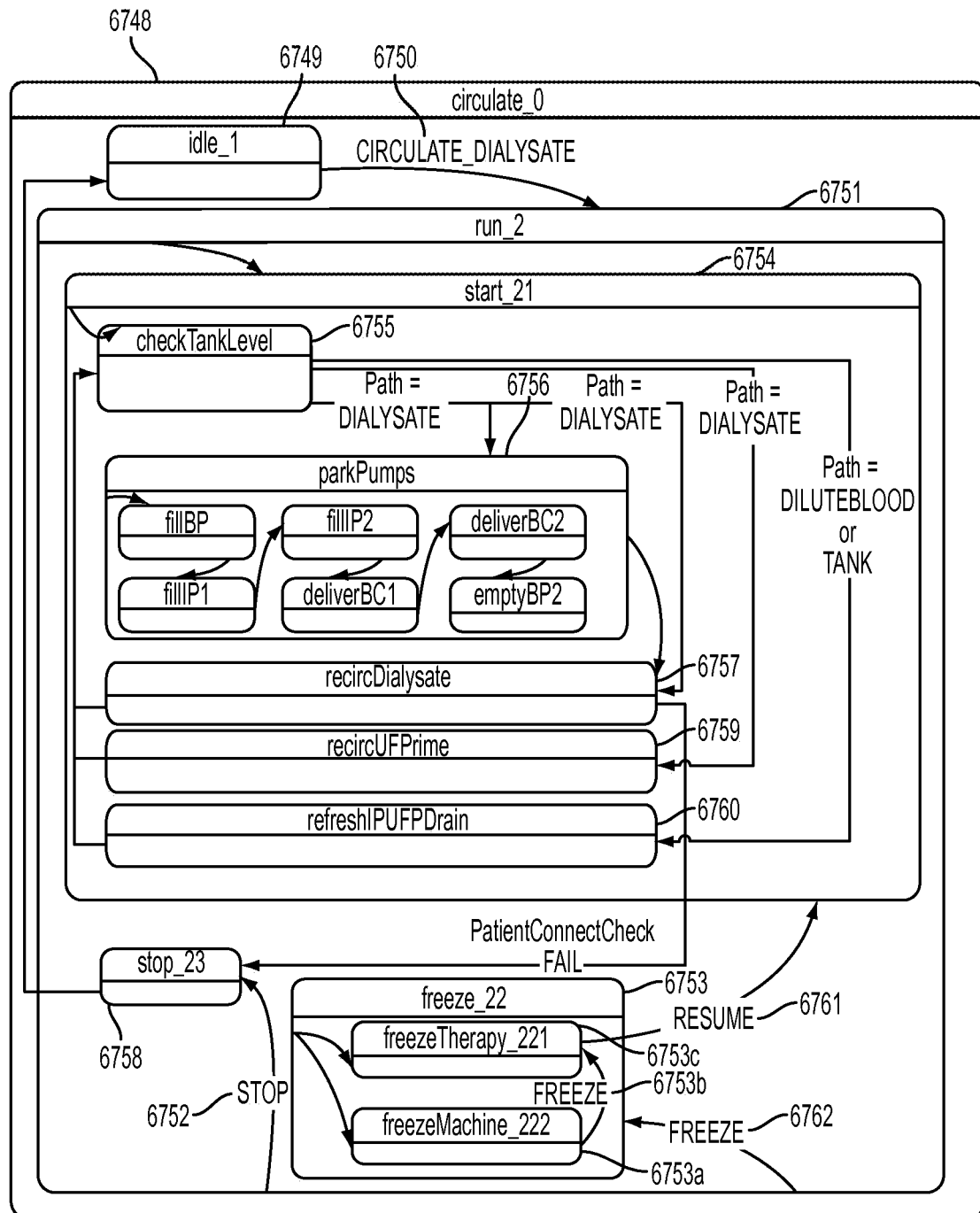
FIG. 67B is a schematic view showing an exemplary implementation of the Circulate Dialysate operation.

FIG. 67B shows an exemplary implementation of a Circulate Dialysate operation 6748, which may correspond to the Circulate Dialysate operation described in connection with FIG. 67. Referring to FIG. 67B, the initial state of the operation is the Idle state 6749. In response to the Circulate Dialysate machine command 6750, the operation transitions to the Run state 6751. The Run state 6751 catches the Stop command 6752 and the Freeze command 6762. The Run state 6751 is the super state for all operation code of this operation (e.g., start, freeze, stop). The Start state 6754, which is under the Run state 6751, is the super state for all running operation code.

According to one exemplary implementation, there are four different paths through which dialysate may be circulated. These paths are as follows: (1) the "Dilute Blood Path," which is used to keep dilute blood that is in the blood tubing system circulating and warm; (2) the "Dialysate Path," which is used to keep fresh dialysate in the blood tubing set and in the inner pump which would push to the user; (3) the "Blood Sample Path," which is used to circulate the blood tubing set for a blood sample and to keep the fluid in the tank fresh; and (4) the "Tank Path," which is used to keep fluid in the tank fresh.

From the Start state 6754, the operation transitions to the Check Tank Level state 6755. This state ensures that the outer pump is stopped and, if dialysate is being circulated through the Dialysate Path, also ensures that the blood pump is stopped. The Check Tank Level state 6755 initiates a tank FMS reading and waits for the tank to be full.

The Park Pumps state 6756, which is used only in connection with the Dialysate Path, parks the blood pump so that blood pump chamber 1 is full and blood pump chamber 2 is empty.

Likewise, the Recirculate Dialysate state 6757 is used only in connection with the Dialysate Path. This state uses a flow path through the bottom of the inner pump to the blood tubing set. The blood pump is chamber level driven according to outer pump fill strokes so that the pumps can remain synchronized. If a fluid production operation requests a tank level reading, the Recirculate Dialysate state 6757 may transition to the Check Tank Level state 6755.

The Recirculate Dialysate state 6757 may also monitor aspects related to a user connection to the dialysis system. For example, this state may notify the therapy layer when the system is at a predetermined temperature. Thus, the therapy layer may notify a user who wishes to connect to the system that the system is not as warm as desired if it has not yet reached the predetermined temperature. In addition, this state may perform checks to ensure, for example, that a user is not connected if the conductivity is out of range or the temperature is too hot. If one of the checks fails, the operation will transition to the Stop state 6758.

A patient may be connected after the Circulate Dialysate operation 6748 if dialysate is being circulated through the Blood Sample Path or the Dilute Blood Path. Safety checks may be performed, the machine layer may send a freeze command to the application and notify the therapy layer if a check fails. For example, if monitored sensors such as temperature or dialysate conductivity go out of range, a freeze command may be issued and the therapy layer may be notified. The therapy layer may then inform the user and/or instruct them to disconnect from the machine.

The Recirculate Ultrafilter Prime state 6759 is used to keep fresh dialysate in the tank. In particular, this state is used in connection with the Blood Sample Path so that fresh dialysate is kept in the tank while the blood pump is circulating for a blood sample. In this case, dialysate should not make it to the inner pump.

The Refresh Inner Pump Ultrafilter Prime Drain state 6760 is used to keep fresh dialysate in the inner pump and in the tank. This state is used in connection with the Dilute Blood Path to run the blood pump backwards so that dialysate does not stagnate. This state is also used in connection with Tank Path to keep fresh dialysate in the tank and the inner pump.

The Freeze command 6762, which is handled in the Run state 6751, is commanded from the therapy layer to freeze the operation. The Freeze state 6761 freezes the blood pump and outer pump. The Freeze state 6753 may be exited by the Resume command 6761 or the Stop command 6752. If a patient connect flag is set during this operation, indicating that a user may be connected to the dialysis system, the machine layer may freeze itself by transitioning to the Freeze Machine state 6753*a*. This state will ignore all commands until the therapy layer sends another Freeze command 6753*b* causing the operation to transition to the Freeze Therapy state 6753*c*. Likewise, if the therapy layer, rather than the machine layer, sends a freeze command, the operation will transition to the Freeze Therapy state 6753*c*.

The Resume command 6761, which may be handled from the Freeze Therapy state 6753*c*, is commanded from the therapy layer to resume the operation from a frozen state. This command resumes the pumps and transitions the operation to its prior saved state. The Stop state 6758 is commanded from the therapy layer to cause dialysate to stop circulating, and is handled in the Run state 6751. The Stop state 6758 stops the blood pump and outer pump. It then waits for the pumps to be idle and closes the operation valves. Once completed, the operation transitions to the Idle state 6749.

(3) Heparin Vial Connection Test

Figure 67C:
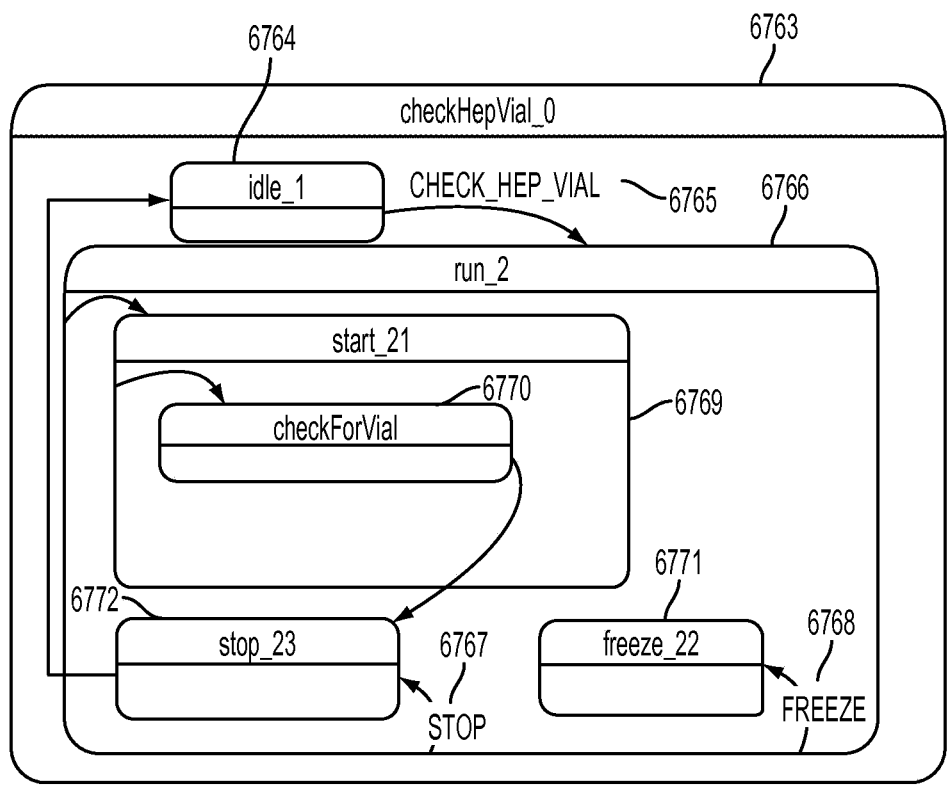
FIG. 67C is a schematic view showing an exemplary implementation of the Heparin Vial Connection Test operation.

As discussed herein, a Heparin Vial Connection test may also be performed to verify that a vial is attached to the heparin/medication infusion spike on the blood pump cassette. A patient is typically not connected during this operation. FIG. 67C shows an exemplary implementation of the Check Heparin Vial operation. Throughout this application, the words "heparin" and "anticoagulant" are used interchangeably. It should be appreciated that reference to "heparin" is not limited to that particular anticoagulant. It refers to an exemplary anticoagulant that may be suitably substituted for another anticoagulant.

The initial state of the Check Heparin Vial operation 6763 is the Idle state 6764. In response to the Check Heparin Vial machine command 6765, the operation transitions to the Run state 6766. The Run state 6766 catches the Stop command 6767 and the Freeze command 6768. The Run state 6766 is the super state for all operation code of this operation (e.g., start, freeze, stop). The Start state 6769, which is under the Run state 6766, is the super state for all running operation code. The Start state 6769 stops the anticoagulant pump (e.g., anticoagulant pump 80).

The Check for Vial state 6770 opens a flow path to the blood tubing set drain and commands the anticoagulant pump to check the anticoagulant (e.g., heparin) vial. Once the heparin pump is complete, the state checks if the vial is detected and will register a fail if it is not.

The Freeze command 6768 is commanded from the therapy layer to freeze the operation. This command is handled in the Run state 6766. The Freeze state 6771 freezes the anticoagulant pump. The Freeze state 6771 may be exited by the Resume Command or the Stop Command 6767.

The Resume command is commanded from the therapy layer to resume the operation from a frozen state. This command transitions the operation to the Start state 6769, which will restart the check for the anticoagulant vial.

The Stop state 6772 is commanded from the therapy layer to terminate the test. This state is also called at the end of the operation to insure that all pumps, such as the anticoagulant pump, are stopped. The state then waits for the pumps to be idle and closes the operation valves before transitioning to the Idle state 6764. If the Stop state 6767 is called before the operation finishes, the operation will fail.

Other checks of the anticoagulant vial, not shown in FIG. 67C, may also be performed. For example, the system may check for: (1) an empty anticoagulant vial, (2) an occluded anticoagulant vial, (3) excessive anticoagulant delivery, (4) a leak in the anticoagulant pump valves and/or (5) excessive pressure inside the anticoagulant vial.

If an empty anticoagulant vial is detected during therapy, the system may halt operation of the anticoagulant pump and alert the patient. This prevents the anticoagulant pump from adding air to the blood flow. Similarly, if the anticoagulant vial becomes occluded during a therapy, the system may halt operation of the anticoagulant pump and alert the patient.

If the anticoagulant delivered to the patient exceeds the prescribed value by a particular amount (e.g., more than 1 mL), the system may perform a forced disconnect and rinse back. This mitigates the risk that the machine subsystem executes the anticoagulant delivery erroneously, e.g., due to isolated data corruption. In some cases, for example where the anticoagulant bolus is potentially unsafe, a forced disconnect without rinse back may occur prior to delivering any anticoagulant to the patient.

If any of the anticoagulant pump valves leak fluid while in the closed state and while the patient is connected, the system may perform a forced disconnect without rinse back. This mitigates the risk that anticoagulant is pulled from the vial into the blood flow in an uncontrolled fashion. This check may be run frequently during therapy while the patient is connected.

If the pressure inside the anticoagulant vial is observed to be more than a predetermined threshold (e.g., 50 mmHg above atmosphere) during a therapy, the system may perform a forced disconnect without rinse back. The vial pressure may be observed when filling for a basal delivery stroke. This check may protect the patient from an unsafe off-label usage.

(4) Heparin Bolusing

Figure 67D:
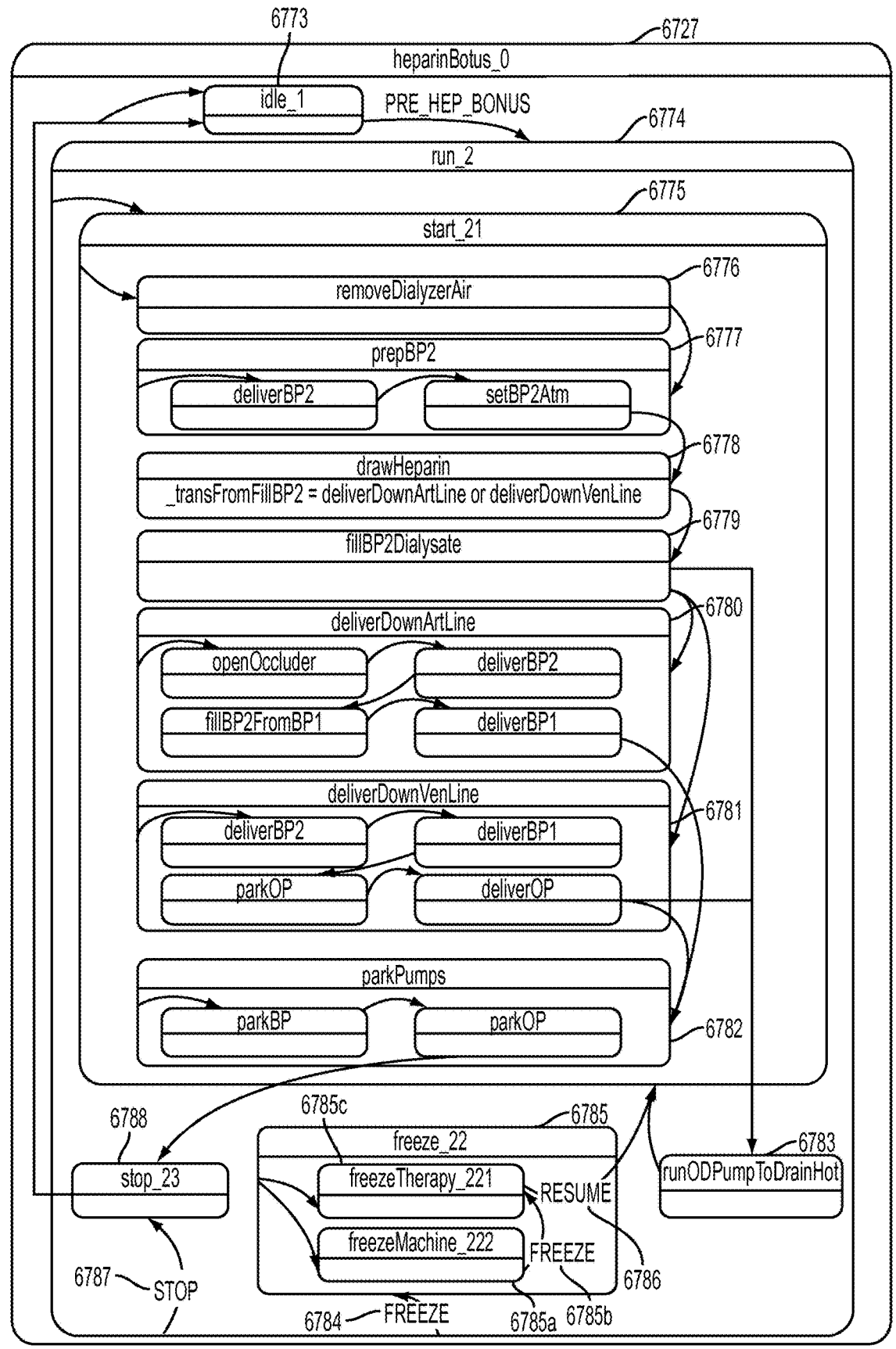
FIG. 67D is a schematic view showing an exemplary implementation of the Heparin Bolusing operation.

The Heparin Bolus operation is responsible for administering a heparin bolus to the patient before treatment begins. Conventionally, a heparin bolus is administered by a nurse via syringe into an access line. Advantageously, the Heparin Bolus operation allows a heparin bolus to be delivered by the dialysis system itself, without intervention by a nurse or other individual. FIG. 67D shows an exemplary implementation of the Heparin Bolus operation 6727 described in connection with FIG. 67.

Referring to FIG. 67D, the operation transitions to the Run state 6774 from the Idle state 6773, then to the Start state 6775, and finally to the Remove Dialyzer Air state 6776. The Remove Dialyzer Air state 6776 mitigates the air at the top of the dialyzer. To do so, both chambers of the blood pump are delivered down the dialysate drain. An air settle time helps the air come together before it is mitigated. The left blood chamber (i.e., chamber 2) is filled with dialysate. This dialysate is then transferred into the right blood chamber (i.e., chamber 1) over the top of the blood pump. The outer pump chamber is left full of fluid so that it can be used to quickly fill blood pump chamber 2 after the air mitigation.

Next, the Prep Blood Pump Chamber 2 for Heparin state 6777 sets blood pump chamber 2 to atmosphere. To do this, the chamber is delivered to a pressure of 0.0. This is done so that the heparin pump can pump the bolus volume into blood pump chamber 2 in the Draw Heparin state 6778. The Fill Blood Pump Chamber 2 with Dialysate state 6779 fills what is remaining in blood pump chamber 2 with dialysate so that a known volume can be pumped to the patient.

According to one implementation, the bolus is delivered down the arterial line, which is a shorter route to the patient's vascular access than the venous line. As a result of the shorter route, less fluid needs to be delivered to and subsequently removed from the patient when the arterial line is used. The Deliver Bolus down Arterial Line state 6780 delivers both blood pump chambers down the arterial line to the patient. Blood pump chamber 2, which contains the bolus, is delivered first. Next, blood pump chamber 2 is filled with dialysate from the outer dialysate pump, and blood pump chamber 2 is delivered. The net result is that two full blood pump chambers containing the prescribed heparin, or about 56 mL of fluid total, is given to the patient.

If air is detected during the arterial bolus delivery, or if venous delivery is selected by the patient, the bolus may alternatively be delivered down the venous line, which incorporates air-trapping mechanisms or devices. The Deliver Bolus down Venous Line state 6781 first delivers blood pump chamber 2, which contains the bolus, then delivers blood pump chamber 1 down the venous line toward the dialyzer. The remainder of the bolus is chased down the venous line across the dialyzer by a set volume of dialysate (e.g., 200 mL) of the outer pump. Before the outer pump is started, it may need to be "parked," since filling the chambers with dialysate could leave it in a state where both chambers are delivered. The Park Pumps state 6782 parks the blood pump and outer pump so that one chamber is full and the other is empty.

The Run Outer Dialysate Pump To Drain Hot state 6783 is used when the dialysate gets too hot to deliver to the patient. In such a case, a path is opened down the dialysate drain (through the ultrafilter prime path). Once the temperature of the dialysate is back within range and the heater has cooled off, the operation transitions back to its prior state.

The Freeze command 6784 is commanded from the therapy layer to freeze the operation. This command is handled in the Run state 6774. The Freeze state 6785 freezes the blood pump and outer pump. The only exit from the Freeze state 6785 is by a Resume command 6786 or Stop command 6787.

Since the patient is connected during the Heparin Bolus operation, the safety system is enabled. The machine layer monitors patient-connected checks and informs the therapy layer of pass or fail results. If a patient disconnection is detected during the Heparin Bolus operation, the machine layer may freeze itself. If this happens, the operation will transition to the Freeze Machine state 6785*a*. The operation will remain in this state until the therapy layer sends another Freeze command 6785*b*, which will transition the algorithm to the Freeze Therapy state 6785*c*.

The Resume command 6786 is commanded from the therapy layer to resume the operation from a frozen state. This command, which is handled in the Freeze Therapy state 6785*c*, causes the pumps to resume and the operation to transition to the saved state to continue the operation.

If the machine layer sees air in the air sensors, it will send a freeze command preventing the operation from delivering air to the patient. If air is detected during an arterial line deliver, the chambers are forced idle and the remainder of the heparin bolus is delivered down the venous line.

The Stop state 6788 is commanded either from the therapy layer or automatically when the when the operation is complete. After all the pumps are stopped and valves closed, a transition to the Idle state 6773 occurs.

(5) Empty Tank

Figure 67E:
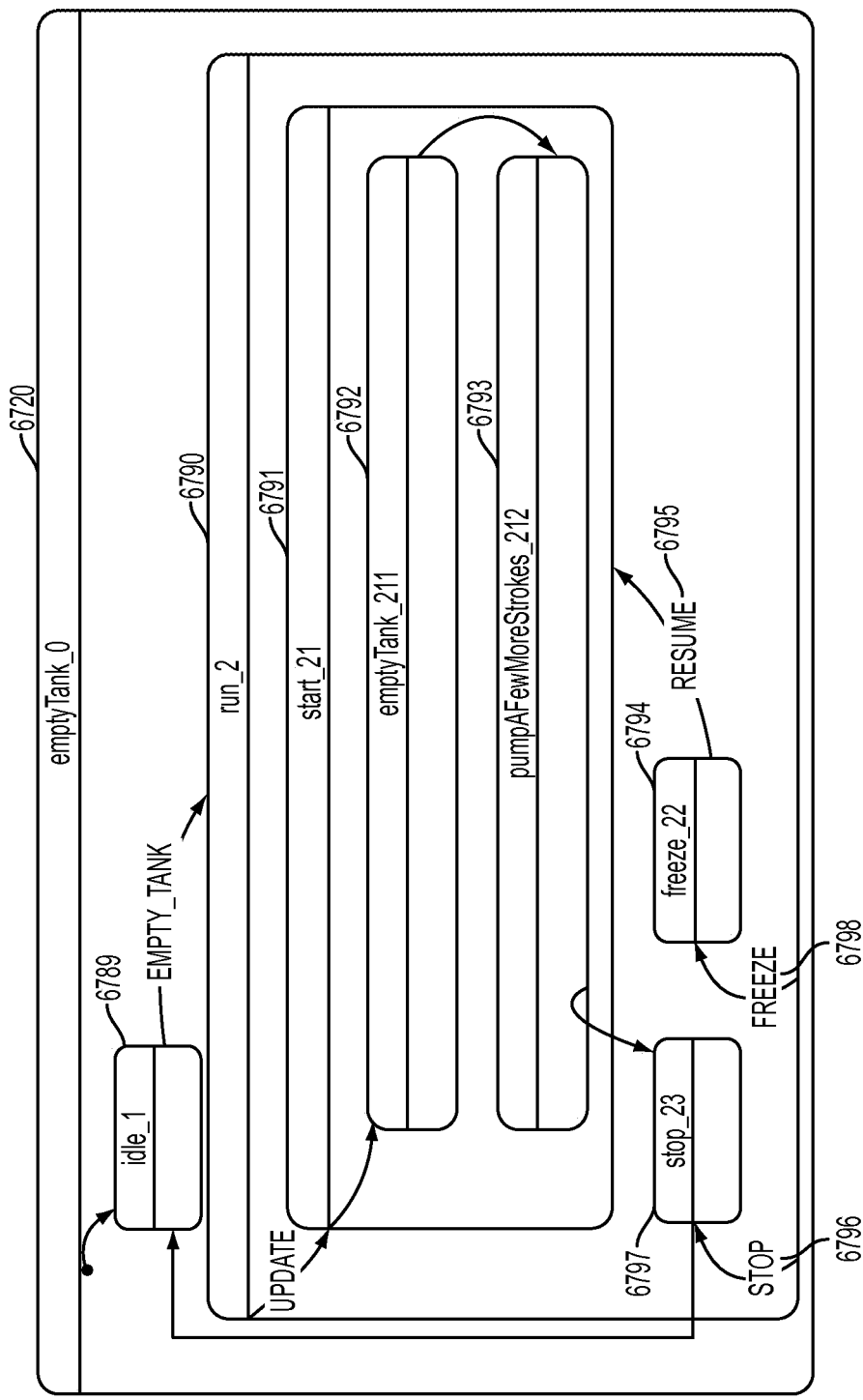
FIG. 67E is a schematic view showing an exemplary implementation of the Empty Tank operation.

The Empty Tank operation is used to drain a fluid tank of its contents (e.g., dialysate, water and/or citric acid). For example, the Empty Tank operation may be used to drain the dialysate tank 169. Fluid is pumped out of the tank down the dialysate drain. This operation may be performed after a treatment is complete, when the patient is not connected to the dialysis system. FIG. 67E shows an exemplary implementation of the Empty Tank operation 6720 described in connection with FIG. 67.

Referring to FIG. 67E, the operation transitions to the Run state 6790 from the Idle state 6789. The Start state 6791 is under the Run state 6790. The Start state 6791 transitions to the Empty Tank state 6792 once fluid production and the outer pump are idle.

The Empty Tank state 6792 configures the outer pump in a manner so that occlusions can be detected and it can be known when the tank is empty. A flow path is opened via the ultrafilter prime line down the dialysate drain. According to one exemplary implementation, the pump is started with a flow rate of 1000.0 mL/min, and is pumped for a total of 40 strokes (e.g., 2 Liters) to empty the tank. If an occlusion is detected, the pump may be stopped. Following the Empty Tank state 6792, the operation transitions to Pump a Few More Strokes state 6793.

The Pump a Few More Strokes state 6793 is used to ensure that the tank is empty. The same flow path that is used in the Empty Tank state 6792, that is the ultrafilter prime line down the dialysate drain, is used in this state. According to one exemplary implementation, the outer pump is started with a flow rate of 600.0 mL/min for a total of 10 strokes. Since the fluid tank is presumed empty, air is expected in the drain line. A drain air-in-line sensor is used to detect the presence of air. If air is detected, the Empty Tank operation 6792 passes. If air is not detected, the Empty Tank operation 6792 fails. A failure could indicate that the drain line is occluded, such that the tank did not empty, or that the drain air-in-line sensor is not working.

In response to the Freeze command 6798, the Freeze state 6794 freezes the outer pump. This state may be exited by either the Resume command 6795 or the Stop command 6796. The Resume command 6795 resumes the operation from the frozen state. In particular, the outer pump is restarted and transitions to the state that was saved when the Start state 6791 was exited. The Stop state 6797 stops the outer pump, waits for the outer pump to be idle, and closes the operation valves. The operation then transitions to the Idle state 6789. If the Empty Tank operation is stopped prematurely, the operation fails.

Attention is now turned to the Therapy Applications shown in FIGS. 62 and 63. The Therapy Applications 6203 shown and described in connection with FIGS. 62 and 63 run state machines that implement therapies implemented by the Machine Controller and I/O Server Process. The state machines may perform such functions as treatment preparation, patient connection, dialysis, solution infusion, patient disconnect, recycle preparation, disinfect, rinse, and disposable replacement. The Therapy Applications 6203 also comprise a master control module responsible for sequencing the activity of all other therapy applications that prepare for and deliver daily treatment.

Referring to FIGS. 62 and 63, the Therapy Applications 6203 provide an interface that allows the UI Model 6206 to start, stop and configure therapies, as well as report therapy status. The Therapy Applications 6203 also interface with the Machine Controller. In particular, the Therapy Applications 6203 issue commands to and request status from the Machine Controller in order to implement the therapy operations. In order to access patient, therapy and machine information, the Therapy Applications 6203 interface with the database 6302. It also uses this interface to store treatment status information.

Described below are individual applications of the Therapy Applications 6203. These applications are (1) Recycle Preparation, (2) Clean Blood Path, (3) Disinfect, (4) Rinse Endotoxins, (5) Treatment Preparation, (6) Patient Connect, (7) Dialyze, (8) Solution Infusion, (9) Rinseback, (10) Take Samples, (11) Replace Components, and (12) Install Chemicals.

(1) Recycle Preparation

Figure 68:
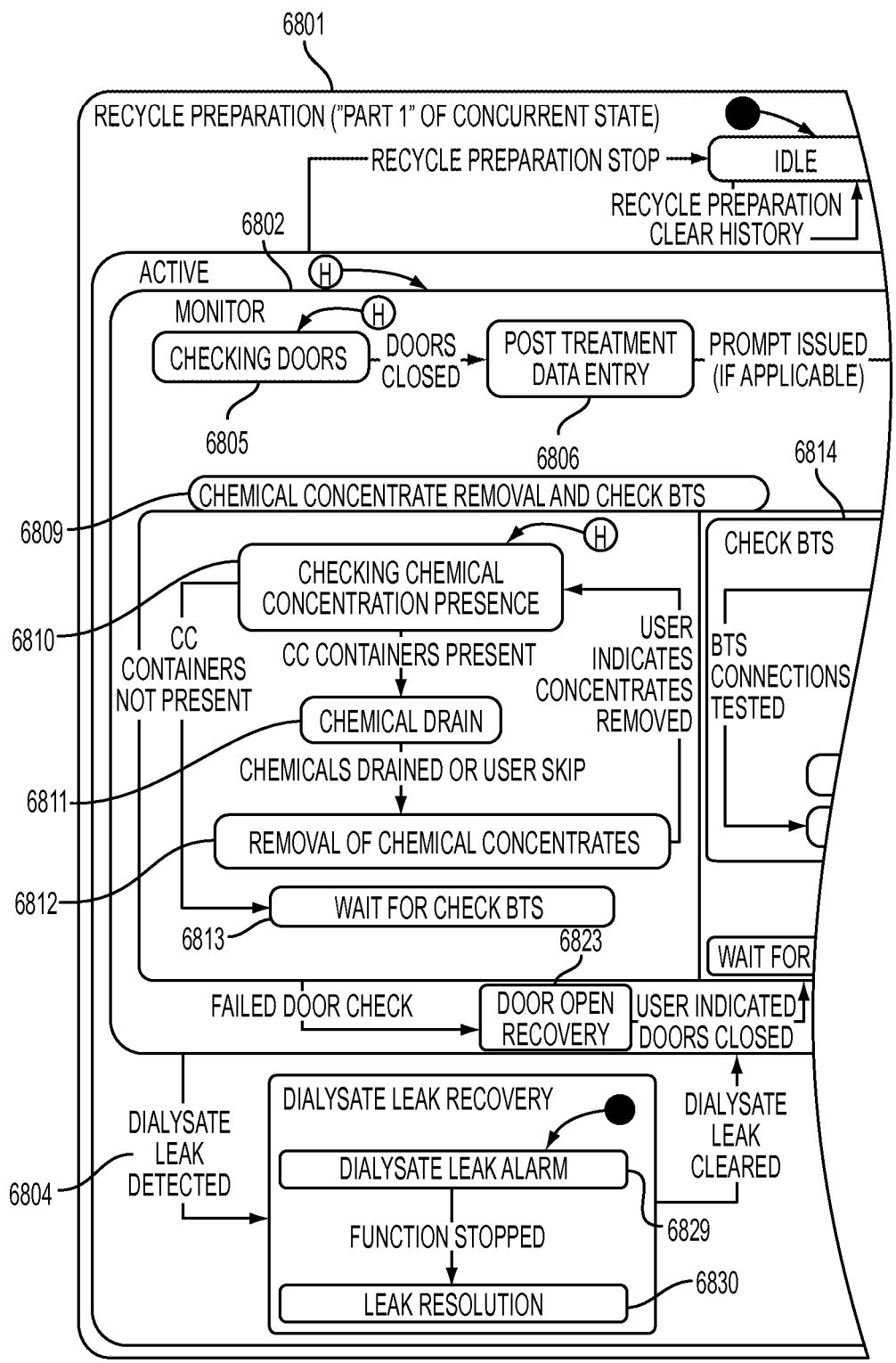
Figure 68:
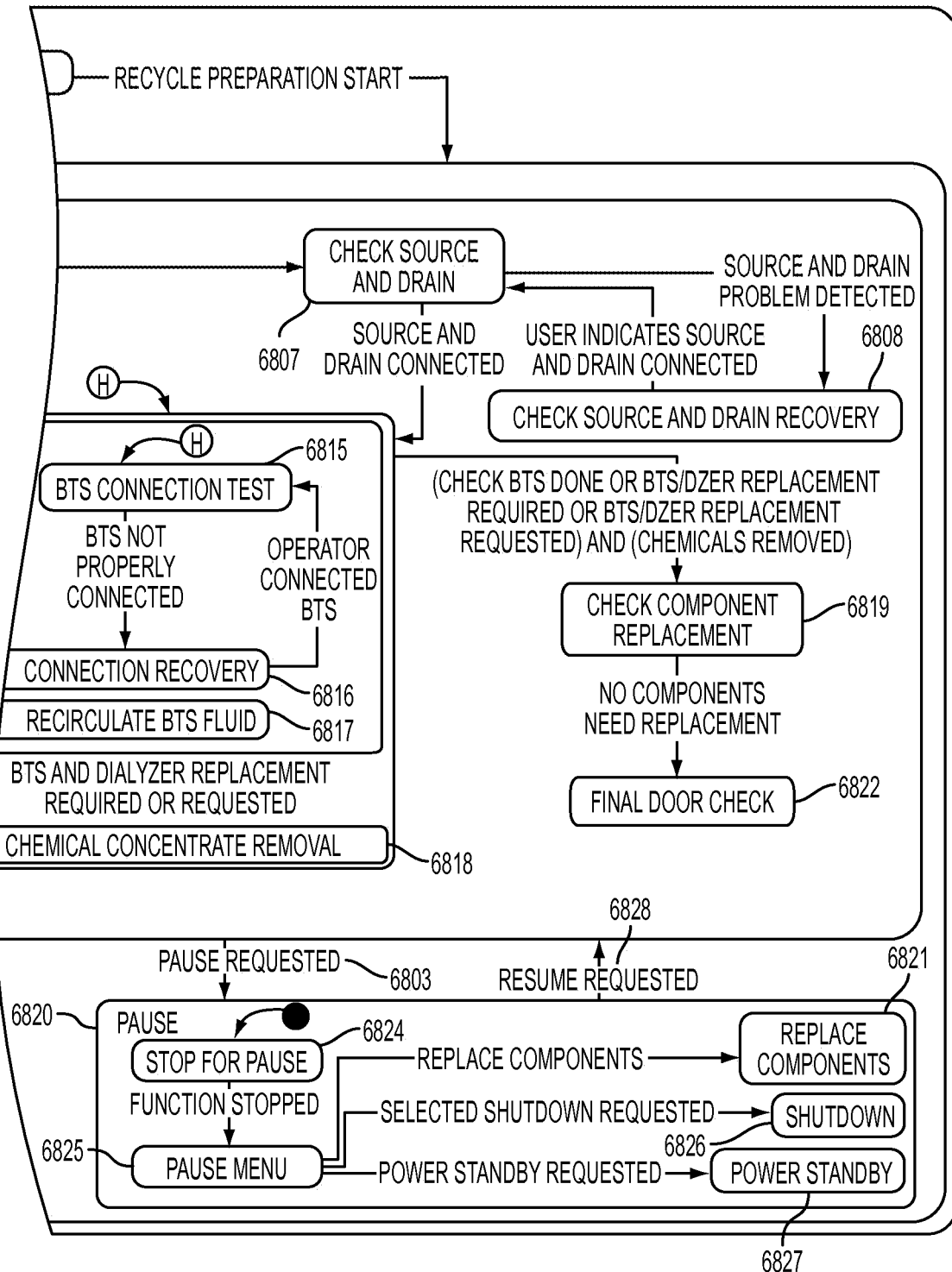

FIG. 68 shows an exemplary implementation of the Recycle Preparation application. The Recycle Preparation application prepares the system for recycling. Prior to initiating recycling, the system confirms that the doors are closed. This will allow the system to clean and disinfect successfully, but also ensures that the patient has not inadvertently failed to disconnect.

Next, the system prompts the user to remove and discard the chemical concentrate cartridge. The system first drains any remaining chemicals to minimize any spillage upon removal. The user may elect to bypass this draining step if they wish to remove their cartridge immediately. Once the cartridge is removed and discarded, the user prepares the system for recycling by installing the chemical bypass connector.

During chemical cartridge drain and removal, the system simultaneously performs pressure tests to ensure that the operator has connected the blood tubing set (BTS) properly, including installing a vial on the heparin connector. In this way, the operator can be notified of and correct any problems while they are present. Then, the system can successfully navigate through the remainder of recycling unattended. Testing is achieved by sequentially pressurizing the various sections of the BTS to ensure there are no kinks, clamps closed, or clots. BTS integrity can also be checked by pressurizing the entire BTS and dialyzer with air after the dialyzer has been wet, and monitoring for a threshold pressure decay value that would indicate a leak in the blood tubing, blood tubing connections, dialyzer or dialyzer connections. The disinfection ports are also checked to confirm that the venous and arterial lines are securely locked into their ports. If any of these tests fail, the user may be notified of the specific failure and instructed on how to correct it. The tests are repeated until all have passed.

If the dialyzer and blood tubing set have reached the treatment or disinfection usage limits or the operator chooses to replace them, then they may be replaced prior to recycling. If the ultrafilter has exceeded the ultrafilter transmembrane pressure (TMP) or impedance test limit, reached its disinfection usage limit, or the operator chooses to replace it, then the ultrafilter may be replaced prior to recycling. To replace these components, the user may invoke the Replace Components application described in connection with FIGS. 78A-78C.

With reference to FIG. 68, Recycle Preparation application 6801 is shown. The Monitor state 6802 monitors for a Pause request 6803 or a dialysate leak 6804. Further during this state 6802, the system will confirm that the doors are closed. The fact that the doors are closed implies that the patient is not currently connected to the machine. This check will be performed in the Checking Doors state 6805. If the doors are closed, the process proceeds to the Post Treatment Data Entry state 6806.

The Post Treatment Data Entry state 6806 may prompt the patient/operator to enter miscellaneous post treatment data. If system indicates that pre treatment data was entered, the system will prompt the operator/patient to enter the post treatment data. The following post treatment data may be requested: Post Treatment Weight, Blood Pressure, and Pulse Rate. The information from these entries may be included in a systems log of treatment report information. In addition, the system will not require this information to be entered in order to continue on with the recycling process. If the system indicates that pre treatment data was not entered, the system will not prompt the operator/patient to enter the post treatment data.

The Check Source And Drain state 6807 confirms that the inlet water source and drain are properly connected. This ensures that the system can successfully perform recycling. The Check Source And Drain Recovery state 6808 provides the operator with information pertaining to a source/drain failure detected as well and required corrective actions. For example, the user may be notified that the inlet water source or drain is not installed properly and may be instructed on how to correct the problem.

The Chemical Concentrate Removal & Check BTS state 6809 will run two operations concurrently. Completion of both operations will allow the system to continue on with the recycling operations. The operations that take place during this state are: disposal and removal of the chemical concentrates and checking the BTS connections. The BTS and Dialyzer replacement is also evaluated at this time. In the first operation, the Checking Chemical Concentration Presence state 6810 detects whether chemicals are present or not to determine the next step. In particular, through the use of an air integrity test, the system will be able to detect the presence of the chemical concentrate container. This may be achieved for the bicarbonate cartridge, for example, by applying a negative pressure or vacuum to the air inside the bicarbonate chemical cartridge 28, isolating cartridge 28 while in fluid communication with water pump 280, and monitoring the pressure in pump 280 to determine whether the cartridge 28 is able to hold a negative pressure. (Applying a negative pressure may be preferable to a positive pressure when testing the integrity of the cartridge connections, in order to avoid unintended external leaking of chemicals if the cartridge connections are loose).

For example, referring to FIG. 89, and assuming that bypass connector 276 is not present, a path for air to be introduced into the bicarbonate water pump 282 (which provides water to bicarbonate cartridge 28 to create a saturated solution of bicarbonate) can be created by opening the dialysate tank vent valve 260, dialysate tank recirculation valve 264, disinfection path valve 266, and the inlet valve 270 of the bicarbonate water pump 282. The path may be isolated by closing dialysate tank inlet valve 261, dialysate drain valve 262, water inlet valve 265 and ultrafilter priming valve 267. Bicarbonate water pump 282 may then be actuated to fill the pumping chamber with air. The inlet valve 270 of bicarbonate water pump 282 may then be closed. The pressure in the bicarbonate water pump 282 can then be set to atmosphere. Next, the inlet valve 271 of the dialysate mixing pump 280 may be closed, whereas the inlet valve 273 of the bicarbonate metering pump 183 and the dialysate mixture drain valve 262 are opened. Then using the bicarbonate metering pump 183 outlet valve 272 as an inlet valve to dialysate mixing pump 280, air may be pumped out of bicarbonate cartridge 28 to drain. The decreasing pressure in bicarbonate cartridge 28 can be monitored by the pressure transducer 284 connected to bicarbonate water pump 282. When a pre-determined negative pressure has been generated, the dialysate mixing pump 280 outlet valve 274 can be closed and the pump turned off. The pressure transducer 284 can then be used to monitor the pressure in bicarbonate water pump 282 pump chamber and bicarbonate cartridge 28, to ensure that the vacuum generated is held. If not, an alarm condition may be triggered by the controller, and an appropriate message may be provided to the graphical user interface to advise the user.

In the Chemical Drain state 6811, the system will perform the necessary operations to drain any residual chemical concentrates from the containers. The purpose is to make removal and disposal of the containers cleaner and easier, producing as little waste as possible. The user may be prompted that they can choose to bypass draining. The Removal of Chemical Concentrates state 6812 provides instructions to the user to remove the chemical concentrates and close the chemical bypass doors, and may provide instructions. Included in the instructions may be how to configure the machine so that it will be able to effectively disinfect the chemical concentrate ports. The Wait for Check BTS state 6813 is an end point for the Chemical Disposal and Removal operations. The system will remain in this state until other concurrently performed operations are complete.

Turning to the second operation that is run by the Chemical Concentrate Removal & Check BTS state 6809, during the Check BTS state 6814 the system evaluates whether BTS and Dialyzer replacement is required. An option may also be displayed allowing the operator to choose dialyzer and BTS replacement. This option may include data entry as to the clotting status of the dialyzer, and may remain available to the user until the Chemical Concentrate Removal & Check BTS state 6809 is complete. If no replacement of the BTS and Dialyzer is required or requested, the system ensures that the BTS is properly connected for recycling and then recirculates the BTS fluid to prevent clotting. The BTS Connection Test 6815 confirms that the BTS has been connected properly for recycling. This may include ensuring that the patient connectors have been properly installed into their disinfection ports, that the clamps have been opened and the BTS is not kinked, and that the BTS is properly installed in the air detectors and occluders. The Connection Recovery state 6816 provides the user with information that pertains to the failure detected, as well as corrective actions that are required. For example, the user may be notified that the BTS is not installed properly, and indicate the specific problem. The notification may include corrective actions that should be performed based upon a failure code from the BTS Connection test 6815. A DC Connection test may be performed to verify that the patient has plugged the vascular access connectors of the blood tubing set back into the DCA/DCV ports of the machine for rinsing and disinfecting after a treatment session. A Heparin Vial Connection test may also be performed to verify that a vial is attached to the heparin/medication infusion spike on the blood pump cassette. This ensures that disinfection fluid can enter and exit the vial and clean the vial spike and heparin fluid path in the process.

The Recirculate BTS Fluid state 6817 will start recirculating the fluid in the BTS to prevent the residual patient blood from becoming stagnant and developing clots. The system may be configured such that this process can only be performed once the system has detected that the BTS connections are properly inserted into the disinfection ports. The Wait for Chemical Concentrate Removal state 6818 acts as a wait state that will allow the other operations that are concurrently taking place to complete. Once the system indicates that chemical concentrate removal is complete, the system will continue.

Regardless of which components are being replaced, the Check Component Replacement state 6819 may act as a transition point for the component replacements. It also evaluates whether ultrafilter replacement is required. If the ultrafilter has exceeded its TMP test limit or reached its disinfection usage limit, then ultrafilter replacement may be required. If BTS and dialyzer replacement was previously determined to be required or was requested by the user, then the BTS and dialyzer should be replaced. If any replacement is required, this data is transferred to the Pause state 6820 where Replace Components 6821 executes the activity. Once the replacement process has been completed by the system and the operator, the Recycle Preparation application will resume.

The Final Door Check state 6822 will perform a final check of the doors to confirm that the doors are still closed. This is intended to prevent any unnecessary alarms that might prevent the machine from recycling. The Doors Open Recovery state 6823 notifies the patient the doors are open, and prompts the user to close the door.

The Pause state 6820 will halt operation and may allow the patient to choose to perform additional activities. The Stop for Pause state 6824 halts all machine operations. For example, the state may stop all flows. The Pause Menu state 6825 allows the patient to choose to perform additional activities, and may display the following options: Replace Components 6821, Shutdown 6826, Power Standby 6827, and Resume Recycling Prep 6828.

The Dialysate Leak Alarm state 6829 will stop operation and notify the user that a dialysate leak has been detected. The Leak Resolution state 6830 waits for the user to clear the leak, and for an indication from the user of the same.

(2) Clean Blood Path

Next, a method may be performed to clean blood and dialysate from pathways prior to disinfection. Residual blood and dialysate, left over from treatment, is rinsed from the dialysis unit prior to performing disinfection. It is desirable to remove these substances because the disinfect process makes subsequent removal more difficult. Further, is desirable to remove residual blood and dialysate, as they are sources of bacteria. Special care may be taken to clean the dialyzer effectively so that its performance degrades as little as possible over multiple reuses.

Cleaning the blood and dialysate pathways may be accomplished by flushing a certain amount of fluid through those pathways and directing that fluid to a drain. Cleaning the blood pathways may take more effort and require more thoroughness than cleaning the dialysate pathways due to the blood and blood clots that reside in the blood pathways. Clots typically attach themselves to the venous and arterial headers of the dialyzer, which may reduce dialyzer efficiency by obstructing its fibers. Cleaning the arterial and venous headers may be difficult because their large volumes provide spaces of low flow where clots can migrate. In order to remove these residual clots from the dialyzer headers, it is desirable to first loosen or dislodge them. This may be accomplished by pushing fluid both through the dialyzer and across it, while increasing or maximizing flow rates, thereby creating or maximizing turbulence. Turbulence or other disruption in flow may also be caused by the addition of air to the BTS, and circulating the air-containing liquid so as to increase mechanical action in loosening clots or other debris. Blood clots may also be loosened by moving fluid inside the BTS back and forth by controlling each blood pump chamber individually. In this case, the inner dialysate pumps and the BTS drain are closed, and blood chamber 1 (one of the blood pump pods) is made to deliver fluid as blood chamber 2 (the other blood pump pod) fills. Once both are idle, blood chamber 1 fills as blood chamber 2 delivers. This cycle may be repeated a number of times (e.g., approximately 20 cycles). To introduce air into the BTS, air may be drawn through the anticoagulant air filter (see filter 81 in FIG. 4A) by the anticoagulant pump 80 and subsequently provided to one or both of the blood pumps 23. For example, the valve between the pump 80 and the air filter 81 may be opened and the pump 80 operated to draw air into the pump 80 with the valves between the pump 80 and the anticoagulant source 11 and the main blood circuit closed. Thereafter, the valve between the pump 80 and the air filter 81 may be closed, and the valve between the pump 80 and the main blood circuit opened to allow the pump to deliver the air to one of the pumps 23 or other portions of the BTS. Any fluid in the BTS that is displaced by the air introduced into the BTS may be discharged to the drain 31. With air introduced into one or both of the pumps 23, the blood pump(s) 23 can then be run for a number of cycles (e.g. 40 cycles) at a specified rate and direction (e.g., 500 ml/min in a backwards direction).

Figure 69A:
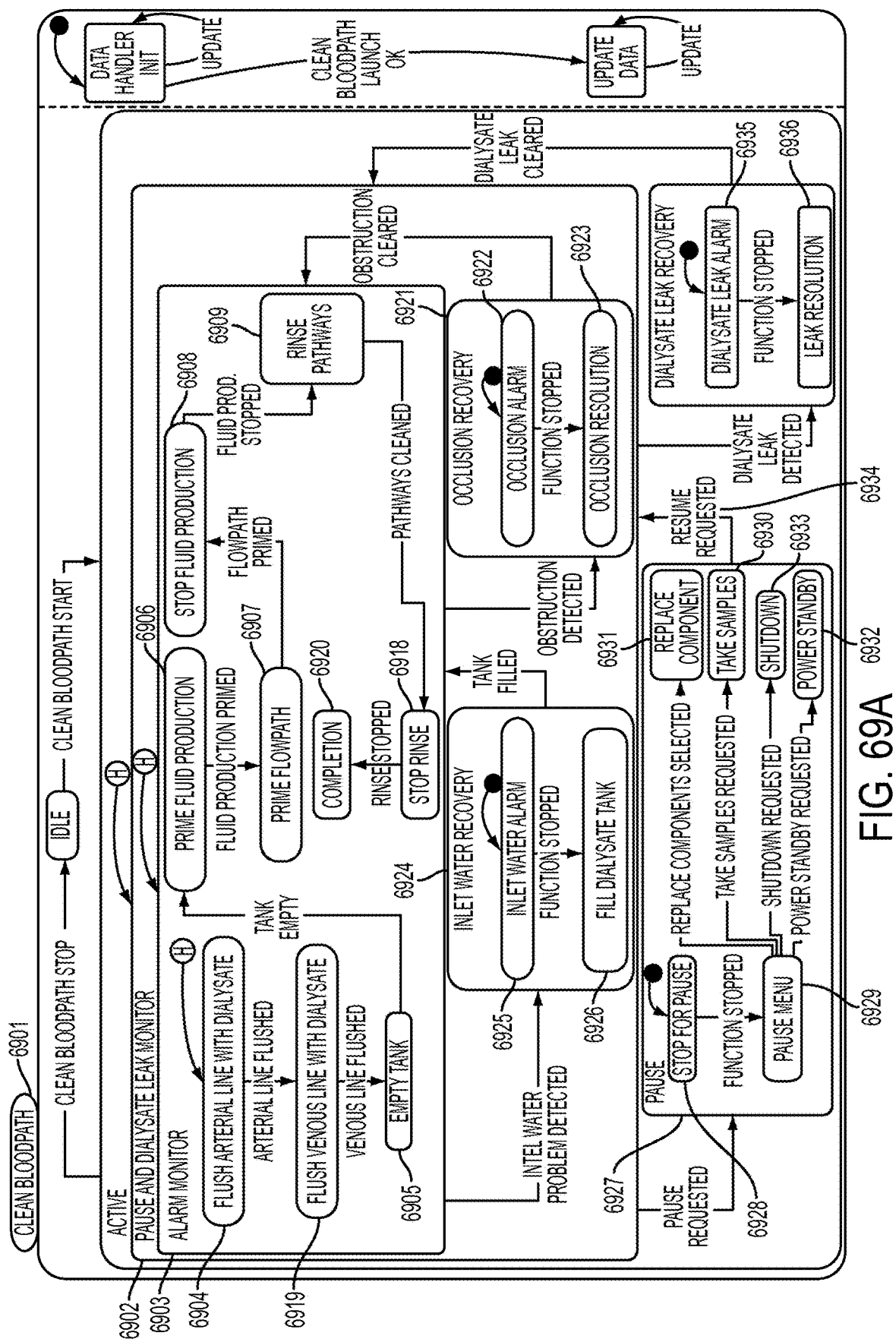
Figure 69B:
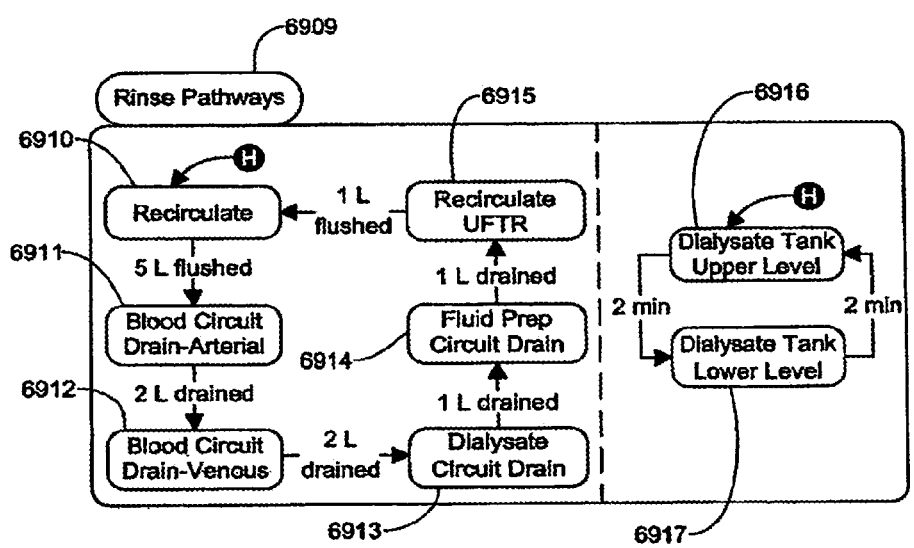

FIGS. 69A and 69B show an exemplary implementation of the Clean Blood Path application. With reference to FIG. 69A, Clean Blood Path 6901 is the top level state which coordinates the actions of the overall process. This state runs concurrently with the data handling elements of the state machine. During this state, residual blood and dialysate, left over from treatment, are rinsed from the machine. Updates to data of interest to the application will be processed by the data handling elements of the state machine. The Pause and Dialysate Leak Monitor state 6902 watches for certain failures and pause requests. Dialysate leak monitoring may be requested. The Alarm Monitor state 6903 watches for certain failures. Complete blood-side occlusion monitoring is requested, and inlet water monitoring is enabled. The Flush Arterial Line with Dialysate state 6904 takes a portion of the residual dialysate left over from treatment and flushes it through the arterial line and out to a drain. Flushing blood out with physiological fluid, such as dialysate, prior to sending water to the blood tubing set (BTS) may be done in order to minimize the hemolysis and foaming that occurs when blood is exposed to water. When blood foams, it typically makes cleaning more difficult. Similarly, the venous line may be flushed with dialysate in state 6919. The Empty Tank state 6905 removes any residual dialysate from the dialysate tank by sending it to a drain. The Prime Fluid Production state 6906 primes the fluid production module with water in preparation for rinsing. The Prime Flowpath state 6907 primes the entire flowpath with water in preparation for rinsing. The Stop Fluid Production state 6908 primes the entire flow path with water in preparation for rinsing, and stops fluid production.

The Rinse Pathways state 6909, shown in FIG. 69B, rinses all fluid pathways in order to flush residual blood and dialysate out of the system. This state will also start fluid production. With reference to FIG. 69B, the Recirculate state 6910 recirculates fluid in both the blood circuit and the dialysate circuit. The Blood Circuit Drain—Arterial state 6911 flushes fluid out through the arterial blood circuit line to a drain. The Blood Circuit Drain—Venous state 6912 flushes fluid out through the venous blood circuit line to drain. Flushing blood out with physiological fluid such as dialysate prior to sending water to the BTS is done in order to minimize the hemolysis and foaming that occurs when blood is exposed to water.

Turbowash Feature

A 'swishing' procedure, in which the cleaning fluid (e.g., water) is pushed back and forth within a fluid flowpath may improve the dislodgment of debris (e.g., blood components or proteinaceous material) from the flowpath. The swishing procedure may be further enhanced by using an increased pressure gradient in the flowpath by having a system controller direct the application of a negative pressure to a receiving or downstream pump and a positive pressure to a delivering or upstream pump. In an embodiment, the flow velocity of the water used to clean the fluid flow paths in a cassette housing a pair of reciprocating positive displacement pumps, in a connected tubing set, and in any other connected components may be enhanced by applying a negative pneumatic pressure to the diaphragm of of the receiving or downstream pump (whose pumping chamber has been emptied of fluid) and then applying a positive pneumatic pressure to the diaphragm of the delivering or upstream pump (whose pumping chamber has been filled with fluid). The valving within the flowpath is arranged to cause the upstream pump to deliver its fluid charge ultimately to the downstream pump that is under negative pressure. During this time, the valves in the flowpath defining a desired cleaning path are open, while valves in other flow paths remain closed. The application of positive and negative pressure on the pumps may be reversed to cause a reverse high pressure fluid flow from one pump to the other in order to 'swish' the fluid back and forth and increase the effectiveness of the cleaning. This cycle may be repeated a pre-determined number of times to ensure adequacy of the cleaning process. In an alternate embodiment, the increased pressure gradient may be created by applying a negative pressure on the downstream pump while applying a positive pressure on the upstream pump, while the pump inlet and outlet valves are closed, and then opening the valves corresponding to the flowpath that is intended to be cleaned.

Referring to FIG. 89, in order to dislodge debris or proteinaceous material from the blood pump cassette 13, a system controller may establish an isolated flow path that includes the outlet valves 193, 195 or the inlet valves 192, 194 of the blood pump cassette 13. Fluid present in one of the pump chambers may be swished back and forth between the two pumps using an increased pressure gradient by applying a negative pressure to the downstream pump diaphragm and applying a positive pressure to the upstream pump diaphragm. The pressure gradient may then be reversed to allow enhanced flow velocity in alternating directions along the flowpath being cleaned.

For example, to clean outlet path 400 (see FIG. 21A), a flowpath is created by closing the inlet valves 192, 194 of the blood pump cassette 13 and the flow path leading to the dialyzer. The flow path leading to the dialyzer may be closed in a number of ways, one of which is accomplished by activating the arterial and venous line occluder 202 and closing off flow through the dialyzer by closing valves associated with the inner dialysate pumps (e.g., valves 232, 242) and the ultrafiltration pump (e.g. valve 210), and by closing valves associated with the balance chambers (e.g., valves 231, 241) (see FIG. 84). The system controller may control the opening and closing of the various valves above, and may then direct the application of a negative pneumatic pressure on pump 23a, for example, and finally direct the application of positive pneumatic pressure on pump 23b. In an embodiment, negative pressure (or vacuum) is first applied, placing the fully extended diaphragm of pump 23a under tension. After a short time (e.g., about one second to allow for full development of negative pressure from the diaphragm of pump 23a through the flowpath to be cleaned), the pneumatic manifold valve supplying pump 23b may be actuated to supply positive pressure on the fully retracted diaphragm of fluid-filled pump 23b. The pre-existing negative pressure on pump 23a magnifies the pressure differential in the selected flow path, and pump 23b rapidly delivers its chamber of fluid to the pumping chamber of pump 23a, while producing highly turbulent flow through the selected path 400 (see FIG. 21A) and enhancing the dislodgment of any debris therein. The time delay between the application of negative pressure on the downstream pump and positive pressure on the upstream pump may depend, among other things, on the length of the fluid path between the upstream and downstream pumps. The controller may then reverse the application of positive and negative pressure on pumps 23a and 23b once the fluid in pump 23b has been transferred to pump 23a. In this example, the controller causes the application of a negative pressure on the diaphragm of pump 23b, adds a short delay (e.g., one second), and then causes the application of positive pressure on the diaphragm of pump 23a, causing a reversal of flow along path 400 under a heightened pressure differential. This cycle may be repeated several times to ensure a thorough washing of path 400.

Debris dislodged in path 400 may then be sent to drain via arterial line 203 (see FIG. 21B) or venous line 204 (see also FIG. 21C). Preferably, line 203 is used first in order to prevent any large fragments of debris from passing through dialyzer 14 on its way to drain. Whichever pump 23a or 23b contains the residual fluid from the washing procedure may deliver the fluid to line 408, thence 203 (see FIG. 21B) via that pump's inlet valve 192 or 194. Pumps 23a and 23b may then be re-filled with water from dialysate tank 169 via dialyzer 14, this water then being used for repeated rinses to drain for a pre-selected number of times. This can be accomplished by the controller directing the opening of valves 231 and/or 241 (see FIG. 84), and the activation of outer dialysate pump set 159 to draw water from dialysate tank 169 and deliver it through dialyzer 14 to flowpath 402 (see FIG. 21B). In the illustrated embodiment shown in FIG. 89, for each rinse to drain via arterial line 203, the controller is programmed to open occluder 202, close venous line valve 206 and open drain valve 207 (see FIG. 89). Of course, the specific opening and closing of valves may vary depending on how the hemodialysis flowpath has been structured and where valves have been positioned.

An additional rinse to drain may optionally be performed via line 404 to dialyzer 14, through line 406, then to venous line 204 (see FIGS. 21A, 21C). In this case, pumps 23a and 23b can be primed with water through dialyzer 14 from dialysate tank 169 through the opening and closing of the appropriate valves. Both pumps 23a and 23b may then deliver fluid to venous line 204 by closing inlet valves 192, 194, opening valves 193, 195, blocking flow across the dialyzer 14 membrane by closing the appropriate valves on the dialysate side, opening occluder 202, venous line valve 206 and drain valve 207. This sequence may be repeated a pre-selected number of times.

Figure 21B:
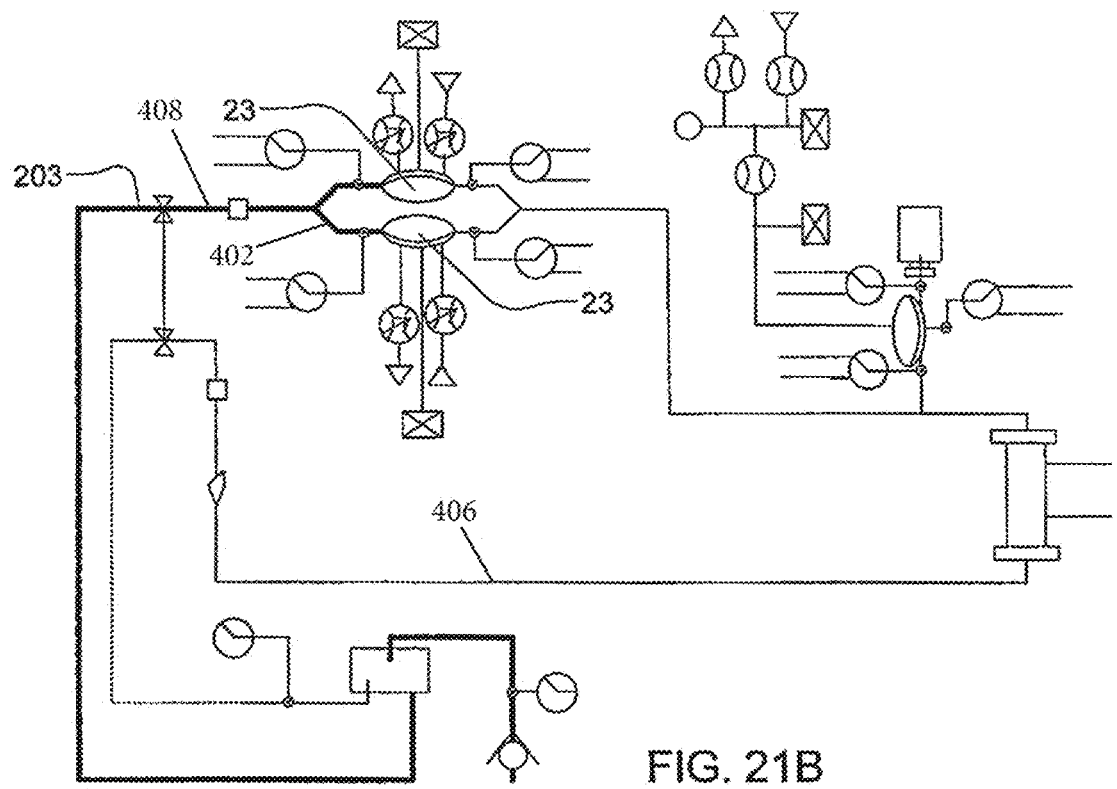
Figure 21C:
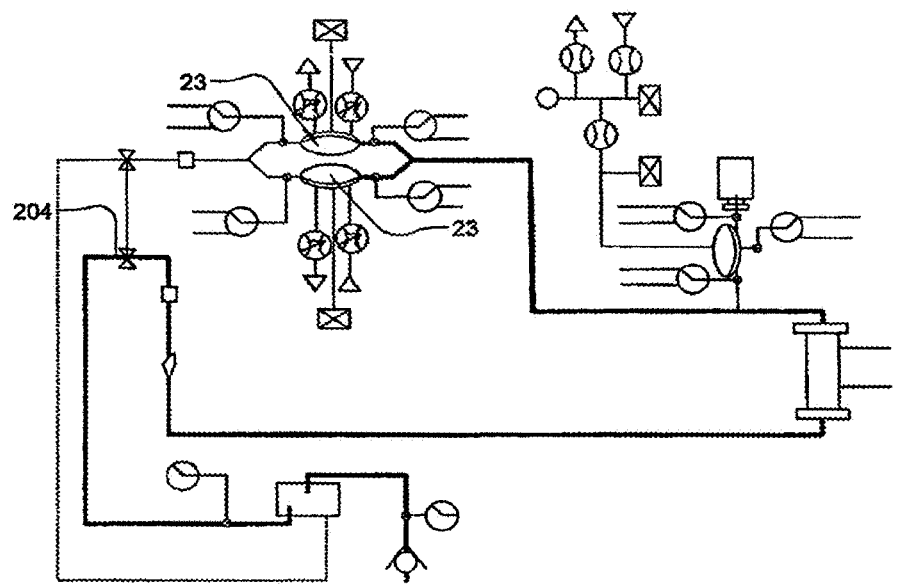

As shown in FIG. 21B, the procedure to clean flowpath 402 may follow an equivalent procedure to that used for flowpath 400, this time having the controller direct the closure of outlet valves 193, 195 and the opening of inlet valves 192, 194. The back-and-forth swishing procedure between the pumps 23a and 23b may be enabled by alternating the application of negative and positive pressure to the respective pumps in order to enhance the pressure gradient in alternating directions. Following the high pressure swishing of fluid in flowpath 402, a rinse to drain via arterial line 203 may be performed a pre-determined number of times as discussed above. Optionally, a rinse to drain may also be performed via venous line 204 following a procedure similar to that discussed above.

The high pressure cleaning procedure may also be applied to the arterial and venous tubing, and any attached components, such as the dialyzer 14 and an air trap 19. As shown in FIGS. 89, 21A and 21B, a flowpath comprising the inlet path of one pump and the outlet path of the opposing pump allows for a back-and-forth swishing procedure under high pressure involving the entire arterial 203, 408 and venous 204, 404, 406 blood tubing. In this case, the circuit is completed by having the controller close drain valve 207 and open venous line valve 206. The inlet path of the pump 23a or 23b may be selected, as long as the outlet path of the opposing pump 23b or 23a is also selected. In the example illustrated in FIG. 89, the inlet path of the pump 23a and the outlet path of the pump 23b have been selected. Alternatively, the inlet path of the pump 23b and the outlet path of the pump 23a may be selected. As in the procedure described to rinse to drain via the venous line 204, flow through the dialyzer 14 to the dialysate circuit is prevented by the closure of the appropriate valves in the flowpaths on the dialysate circuit side of the dialyzer 14. As described above for the cleaning of flowpaths 400 and 402, the upstream pump 23a or 23b is charged with a chamber full of cleaning fluid (e.g., water) with its diaphragm in a retracted position, and the opposing downstream pump 23b or 23a is empty with its diaphragm in an extended position. The controller first directs the application of negative pressure to the downstream diaphragm and then directs the application of positive pressure to the upstream diaphragm, with the appropriate valves closed (such as, for example, valves 193, 194 and 207 in FIG. 89). The controller may then switch the application of the positive and negative pneumatic pressures to cause a reversal of fluid flow through the selected flow-path under high pressure. The cycle may be repeated a pre-determined number of times to achieve an adequate amount of cleaning of the venous and arterial lines. Finally, the venous and arterial lines may be rinsed to drain using the rinsing procedures described above.

The Dialysate Circuit Drain state 6913 flushes fluid out to drain from the dialysate circuit, while recirculating fluid in the blood tubing set. The Fluid Prep Circuit Drain state 6914 flushes fluid out to drain from the fluid preparation circuit, while reverse recirculating fluid in the blood tubing set. The Recirculate UFTR state 6915 recirculates fluid through the ultrafilter flush port, while recirculating fluid in the blood tubing set. The fluid optionally may be recirculated to the dialysate tank or to drain. In choosing whether to recirculate fluid to the dialysate tank, one consideration is the amount of time spent in this state, because as dialysate ages, some of its characteristics (such as pH) may change, which may prompt the system to direct the fluid to drain in favor of continued production of fresh dialysate. The Dialysate Tank Upper Level state 6916 maintains the dialysate tank at a full level. Cycling the fluid level in the tank up and down acts to rinse the tank. The Dialysate Tank Lower Level state 6917 maintains the dialysate tank at a near empty level.

Either at this stage or near the beginning Disinfect, the metering pump (e.g. heparin pump) on the blood pump cassette may be directed to empty the medication (e.g. heparin) container. The medication may be replaced with either dialysate or water, but preferably the container is filled with air in preparation for the instillation and withdrawal of disinfection fluid during Disinfect. If the medication is heparin, any residual heparin remaining in the container or vial after a treatment session can be emptied into the BTS at this stage. Circulating the residual heparin through the BTS during Clean Blood Path or Disinfect may help to reduce clot formation and thus increase the efficiency of the cleaning process. Alternatively, the heparin may be discarded to drain.

Referring again to FIG. 69A, the Stop Rinse state 6918 stops the rinsing process. The Completion state 6920 finishes the application by emptying the dialysate tank. The Occlusion Recovery state 6921 handles the correction of any occlusions that have been detected by the system. The Occlusion Alarm state 6922 will stop Clean Blood Path 6901 and notify the patient there is an occlusion. The Occlusion Resolution state 6923 waits for the patient to clear the occlusion.

The Inlet Water Recovery state 6924 may handle the correction of any inlet water occlusion that has been detected by the system. The Inlet Water Alarm state 6925 will stop Clean Blood Path 6901 and notify the patient there is a problem with the incoming water. The Fill Dialysate Tank state 6926 attempts to fill the dialysate tank. The Pause state 6927 will halt operation. Additionally, the patient can choose to perform additional activities. The Stop for Pause state 6928 will halt all machine operation. The Pause Menu state 6929 allows the patient to choose to perform additional activities. The following options may be displayed: Take Samples (RO Sample) 6930, Replace Component 6931, Power Standby 6932, Shutdown 6933 and Continue Operation 6934.

The Dialysate Leak Alarm state 6935 will stop operation and notify the patient a dialysate leak has been detected. The Leak Resolution state 6936 waits for the patient to clear the leak, and may allow the continue button to be displayed on the GUI.

(3) Disinfect

Following the recycle preparation and the cleaning of the blood path, the Disinfection Application may implement the disinfection of fluid pathways. Disinfection is performed to provide fluid that is of infusible quality. To achieve this goal, the disinfection process may kill all vegetative bacterial cells, fungi, and all small or non-lipid viruses. Because the machine is generally dedicated to one patient, it is not imperative that the disinfection process eliminate viral contamination. Switching the machine between patients may require steps beyond this process. Disinfection may be achieved by bringing all fluid pathways to a certain temperature and holding that temperature for a minimum amount of time. For example, water circulated through the dialyzer, blood treatment set, ultrafilter, and dialysate set may be heated to a temperature of 85° C., ±5° C. for approximately one hour. Hot water pasteurization may be suitable for high-level disinfection. Exemplary conditions for hot water pasteurization may comprise a temperature of approximately 68° C. for a minimum of about 30 minutes. The Disinfect state is able to monitor the temperature at various points in the system and delays disinfection until the sensors are at least about 1° C. above the target temperature, for example, at pre-determined temperature thresholds, such as 85 degrees C. and 75 degrees C. The state monitors the temperature at various points and takes action to increase fluid heating if any sensor falls below the target temperature, for example, for more than 10 consecutive seconds.

The various circuits through which fluid is routed during disinfection may be arranged in any suitable way, e.g., to help ensure that all desired portions of the system reach a suitable temperature for a suitable period of time, to help flush endotoxins and other debris from the system, to help ready the system for a next treatment, and so on. In one illustrative embodiment and with reference to FIG. 3A, a primary flow path of fluid during disinfection may include:

the water supply conduit leading from the water supply 30 and drain 31 to the pumps 180 of the mixing circuit 25, lines leading from the pumps 180 to the bicarbonate pump 183, the ingredients 49 (for disinfection, a connector is provided in place of the ingredients 49 that fluidly connects the three lines into and out of the ingredients 49), the acid pump 184 and the bicarbonate water supply pump (the lower pump 180 in FIG. 3A—that is pump 282 in FIG. 24B), the dialysate supply line from the pumps 180 to the dialysate tank 169, lines from the dialysate tank 169 through the outer dialysate pumps 159 and the heater 72 to the ultrafilter 73, lines leading from the ultrafilter 73 to the balancing chambers of the dialysate circuit 143 and the dialyzer 14, lines from the dialyzer 14 through the inner dialysate pumps 15 and bypass pump 35 to the drain 31 and water supply 30, and the entire blood flow circuit 141 with the venous and arterial patient conduits 67 connected to the directing circuit 142.

During disinfection, fluid may be circulated around the main flow path continuously, with some amount of the disinfecting liquid being optionally directed to the drain 31, e.g., to help purge endotoxins and other materials and help disinfect additional flow circuits of the system. However, in some embodiments no liquid exits or enters the system during disinfection. Instead, liquid may be directed to drain 31 during a cleaning or rinsing operation prior to, or after, disinfection. For example, liquid may be directed from the venous and arterial patient conduits 67 to the drain 31, e.g., as shown in FIG. 17C, prior to, during or after disinfection. In addition, liquid flowing from the mixing circuit 25 to the dialysate tank 169 may be at least partially directed along a path 48 (as shown in FIG. 23), and/or liquid may be directed from the ultrafilter 73 to along a path 731 (as also shown in FIG. 23) during disinfection as desired. While flow through these secondary pathways may be intermittent, the circuits through which fluid is moved during disinfection may include those circuits shown in bold in FIG. 23.

To cause flow in the main disinfection flow path, all of the pumps in the mixing circuit 25 except for the mix water pump (see pump 280 in FIG. 24A), the pumps in the directing circuit 142, the bypass pump 35 in the dialysate circuit 143 and the blood pumps 13 in the blood circuit 141 may run continuously. The mix water pump 280 and the inner dialysate pumps 15 may remain completely open to accommodate continuous flow through the main disinfection flow path. In addition, various valves are opened and closed to cause desired flow in the system, e.g., to cause flow into and out of the balancing chambers of the dialysate circuit 143. Flow may also be permitted in the paths 48 and 731 by suitable valve control to allow these flow paths to received disinfecting fluid. Although the mix water pump 280 may normally remain open, the pump 280 may be exercised along with suitable valve control to ensure that disinfecting fluid flows into and out of an accumulator 33, if provided. (See FIG. 89.)

Flow through the heater 72 in the directing circuit 142 allows the heater 72 to heat the liquid to a suitable temperature for disinfection, e.g., to 85 degrees C. +/−5 degrees. The control system may monitor the fluid or other system component temperature at a plurality of locations, e.g., to help ensure that portions of the system are exposed to suitably high temperatures for a sufficient time period to achieve disinfection. For example, the temperature immediately downstream of the mix water pump 280, the temperature at the mixing chamber for acid with water/bicarbonate, the temperature at the ultrafilter, and/or the temperature at a front panel connection where the venous and arterial conduits 67 are connected may be monitored. In one embodiment, if any of these temperatures vary relative to each other (or relative to some other reference) by more than about 5 degrees C., the system may take suitable action, such as alerting a user to a problem, stopping the disinfection process, attempting to identify a problem causing the temperature variation, etc. Temperature variations may indicate that flow in one or more system components is not suitably high or low, which may be caused by a pump, valve or other malfunction, a clog or kink in a flow line, or other problem. When temperatures at a desired number of system locations have exceeded a threshold, such as 85 degrees C. for fluid temperatures in the main flow path and 75 degrees C. for a system front panel temperature, the system may start a time accumulation, and continue disinfection until a desired time, such as 1 hour, has elapsed. If at any point in the disinfection process a temperature at one or more locations drops below a particular value, such as below 76.5 degrees C. for fluid temperatures in the main flow path or 67.5 degrees C. for a temperature at the system front panel, the system may take suitable action, such as discontinuing disinfection, preventing future use of the system until a repair or other correction is made and the system successfully completes a disinfection process, notification of a user, or other. Similarly, if any system temperature exceeds a particular value, such as 100 degrees C., the system may take suitable action, such as discontinuing disinfection, preventing future use of the system prior to system repair, etc.

As mentioned above, the anticoagulant vial 11 (shown, for example in FIG. 4A) may be emptied prior to disinfection, during disinfection and/or after disinfection. In addition, disinfecting liquid may be introduced into the anticoagulant vial 11 during the disinfection process, e.g., to help raise the temperature in the vial 11 to a desired level. Emptying of the vial 11 may be done by forcing air into the vial 11 so as to pressurize the vial 11, and then releasing the pressure to cause the pressure to force any liquid in the vial 11 to exit the spike 201. Disinfecting liquid may be introduced into the vial by lowering a pressure in the vial, e.g., below atmospheric pressure, and pumping liquid into the vial. Subsequently, the vial 11 may be emptied of the disinfecting liquid.

Figure 70A:
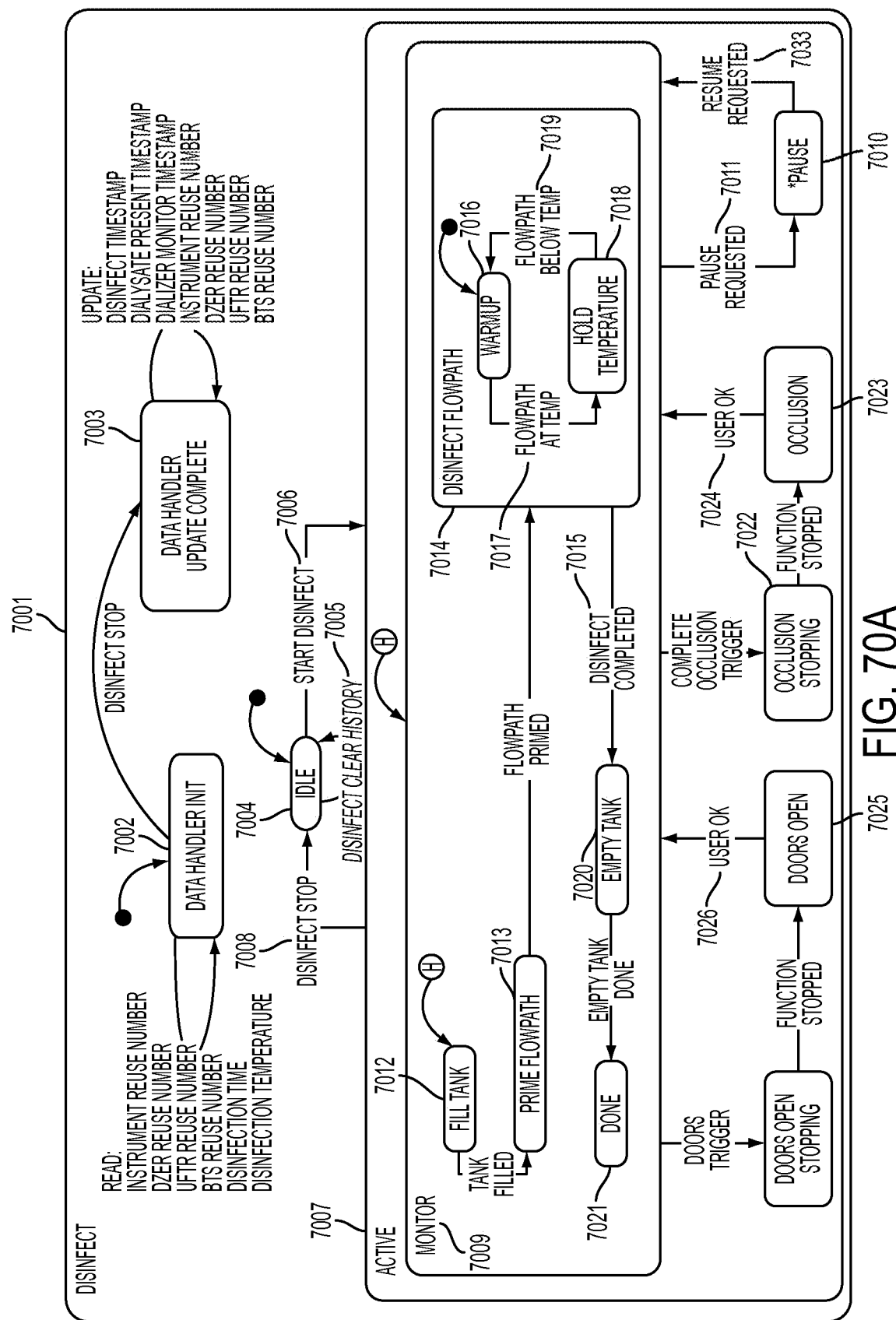
Figure 70B:
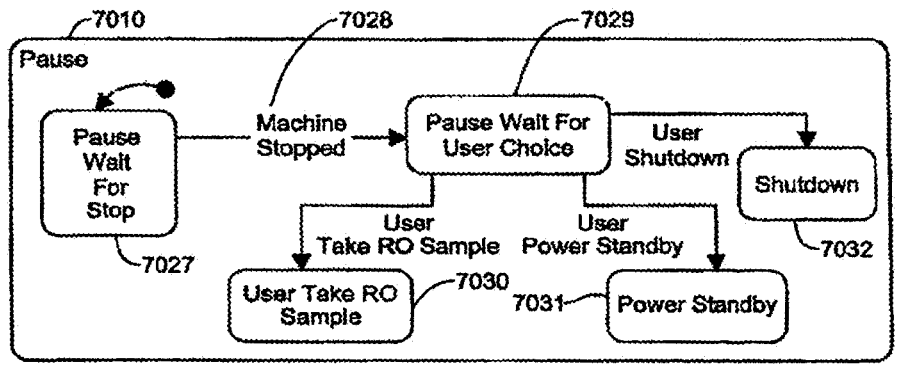

FIGS. 70A and 70B show an exemplary implementation of the Disinfect application. FIG. 70A shows the Disinfect state 7001, which enables the dialysis unit to disinfect itself. The Data Handler Init state 7002 handles reading data values from the database. The values may be in the following tables: Instrument, Dialyzer Use and Reuse, Ultrafilter Use and Reuse, Blood Tubing Set Use and Reuse, Disinfection, Expirations, and Treatment Flow sheet. The Data Handler Update Complete state 7003 handles updating data values in the Database once Disinfect has been completed. During the Idle state 7004, the history of the Disinfect state 7001 is cleared upon performance of Clear Disinfect History 7005. Start Disinfect 7006 transitions the process to the Active state 7007. The Active state 7007 watches for Disinfect Stop 7008. Disinfect Stop 7008 transitions the process back to the Idle state 7004. The Monitor state 7009 watches for the doors of the dialysis unit being opened, occlusions, and requests to Pause 7011 dialysis unit operations. If the user requests Pause 7011, the application proceeds to the Pause state 7010.

In the Monitor state 7009, the Fill Tank state 7012 starts reverse osmosis (RO) water production and fills the tank prior to priming the flow path. The Prime Flow path state 7013 primes the entire flow path with water in preparation for disinfection. The Disinfect Flow path state 7014 oversees disinfection of the machine and determines when it is complete. It starts flows and recirculates fluid in both the blood circuit as well as the dialysate circuit. Disinfection may be deemed complete when all temperature sensors remain at least 1° C. above the target temperature, or in another aspect, at or above a threshold temperature at the heater (e.g., 95 degrees C.) for a selected number of consecutive minutes. Of course, alternative parameters may be used to deem the disinfection complete. When such a determination is made, the event Disinfect Complete 7015 is generated. The Warm Up state 7016 monitors the temperature at various points and waits for portions of the dialysis unit to heat up. When all temperature sensors are at least 1° C. above the target temperature, the event Flowpath At Temp 7017 may be is generated. The Hold Temperature state 7018 monitors the temperature at various points and takes action if the monitored temperatures drop too low. For example, the event Flowpath Below Temp 7019 may be generated when the temperature at any sensor falls below the target temperature for more than 10 consecutive seconds. Other parameters may alternatively be used. The Empty Tank state 7020 empties the dialysate tank. In this way, the drain line receives a final round of disinfection. Further, an empty tank end condition allows for future applications to start with a known tank level. The Done state 7021 is the completion state for Disinfect.

The Occlusion Stopping state 7022 stops all flows and notifies the user that an occlusion has been detected. The Occlusion state 7023 waits for the user to indicate that the obstruction has been cleared. Once the User indicates that the problems have been corrected, the event User OK 7024 is accepted. The Doors Open Stopping state 7034 stops all flows. The Doors Open state 7025 prompts the user to close the doors of the dialysis unit. Once the user indicates the doors have been closed, the event User OK 7026 is accepted.

Referring now to FIG. 70B, the pause behavior will be discussed. The Pause Wait for Stop state 7027 waits for all operations to stop. When the machine is stopped, the event 7028 is generated. The Pause Wait For User Choice state 7029 prompts the user to choose the next step and waits for the user to choose what they want to do. The patient will have the following options: Take RO Sample 7030, Power Standby 7031, and Shutdown 7032. The User Take RO Sample state 7030 waits while the user takes an RO Sample, the Power Standby state 7031 waits for Power Standby, and the Shutdown state 7032 waits for Shutdown. The user may also select a Resume operations option to generate a Resume Requested event 7033 (FIG. 70A).

(4) Rinse Endotoxins

Following disinfection of the fluid pathways, endotoxins and dead biofilm may be rinsed from the pathways via the Rise Endotoxins Application. Endotoxins are part of the outer cell wall of bacteria and are released when bacteria are killed. Biofilm is a complex collection of microorganisms that attach to available surfaces. While the disinfection process kills viable biofilm bacteria, it may not remove all the biomass components, including endotoxins.

To remove dead biofilm and endotoxins, a certain amount of fluid is flushed throughout the flow path at a certain flow rate. This application is designed to rinse each tubing segment with at least three times the holding volume of that segment, although other implementations are possible. According to one exemplary implementation, the dead biofilm may be removed to achieve a Reynolds number of at least 100. According to another exemplary implementation, the Rinse Endotoxins application may be designed to achieve a Reynolds number of 200 or more.

Figure 71:
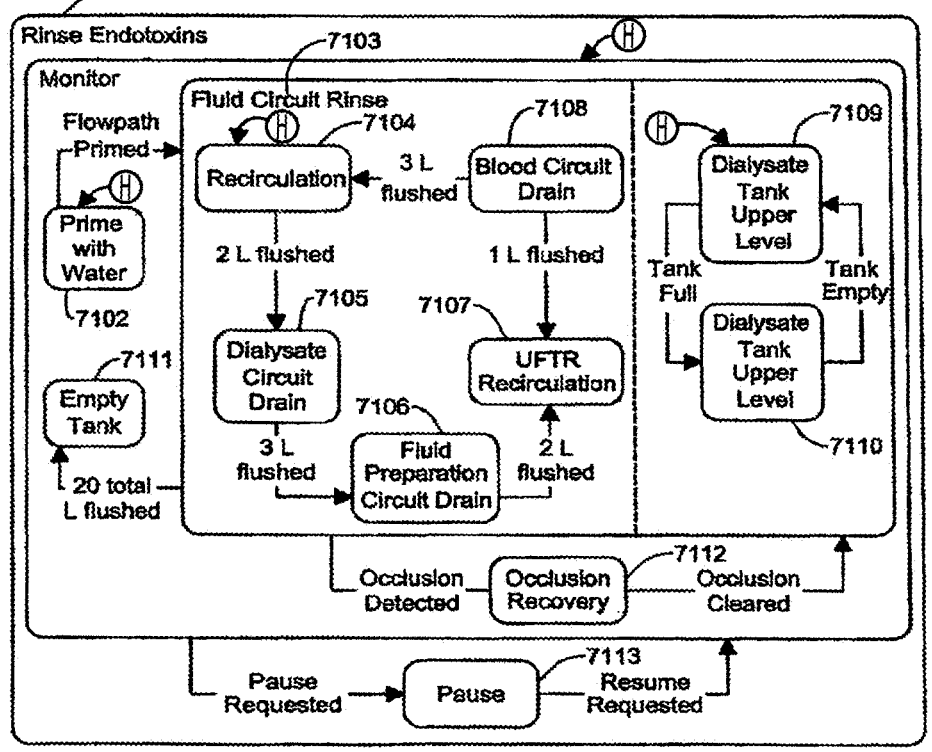

FIG. 71 shows an exemplary implementation of the Rinse Endotoxins application. In the Rinse Endotoxins application 7101, the Prime With Water state 7102 introduces fresh cool reverse osmosis water into the system that has just completed disinfect. Fluid Circuit Rinse 7103 is designed to rinse every fluid line of the system. The Recirculation state 7104 flushes the Fluid Production, Fluid Preparation, Recirculator, Dialyzer, Blood Circuit and access lines with reverse osmosis water. The flushing of these circuits rinses the system of endotoxins and biofilm that remain in the system after disinfect is complete.

Each of the remaining states are alternative pathways of the flow path that allow certain segments to be drained. The subsequent states will be performed for a percentage of the time or a percentage of fluid delivered. The Dialysate Circuit Drain 7105 state flushes fluid out to drain from the dialysate circuit, while recirculating fluid in the blood tubing set. The Fluid Prep Circuit Drain state 7106 flushes fluid out to drain from the fluid preparation circuit, while reverse recirculating fluid in the blood tubing set. The Ultrafilter Recirculation state 7107 recirculates fluid through the ultrafilter flush port, while recirculating fluid in the blood tubing set. The Blood Circuit Drain state 7108 flushes fluid out through the blood circuit to drain. The Dialysate Tank Upper Level state 7109 maintains the dialysate tank at a full level. Cycling the fluid level in the tank up and down acts to rinse the tank. The Dialysate Tank Lower Level state 7110 maintains the dialysate tank at a near empty level.

The Empty Tank state 7111 removes any residual dialysate from the dialysate tank by sending it to drain. The Occlusion Recovery state 7112 notifies the user that an occlusion has been detected, but does not stop any flows. The Pause state 7113 will halt operation. Additionally, the patient can choose to perform additional activities. The patient will have the following options: Replace Components (ultrafilter or Dialyzer/blood tubing set), Take Samples (RO Sample), Restart Recycling, Power Standby, and Shutdown.

(5) Treatment Preparation

The Treatment Preparation application performs a series of actions that prepare the system to perform a dialysis session. During this application, the chemical concentrates are installed, dissolved, and mixed to produce the prescribed dialysate composition. The system also tests the integrity of the ultrafilter, the dialyzer and blood tubing set, as well as key valves, pumps, and pneumatics. Fresh dialysate is used to fully prime the system, and then flush the blood tubing set and dialyzer. Further during this application, the clearance of the dialyzer and the transmembrane pressure of the ultrafilter are tested, and the protective systems are self-tested by simulating trigger conditions through electrical offsets.

When the user requests that a dialysis session be initiated, the system will allow the user to collect any scheduled samples. The user is also prompted to install their prescribed chemical concentrate cartridge. To mitigate possible user errors, the system prompts the user to verify that their chemical concentrate cartridge matches their prescription. Furthermore, the system checks to ensure that the cartridge is present and installed properly once the user indicates it to be so.

Reverse osmosis water is added to the powder chemicals and they are agitated to uniformly dissolve them. Once the powder chemicals are dissolved, they are mixed with the acid concentrate and the conductivity of the finished dialysate solution is checked against the expected conductivity. Acceptable dialysate is routed to the dialysate tank while unacceptable dialysate is routed to drain.

While the dialysate is being mixed, a series of integrity tests are performed. In each case, the component under test is pressurized and then isolated, while the pressure decay is measured over time. If pressure escapes too quickly, the component fails the test and should be replaced. The dialyzer, blood tubing set, and ultrafilter are generally replaced by the user, while other items are generally replaced by service personnel. The functionality of the blood line clamps is verified to ensure that the system can successfully isolate the patient from the machine in the event of a hazard detection. Daily integrity testing of the ultrafilter is desirable because repeated heat disinfection and high pressure flow may damage the filter fibers. If the ultrafilter fails integrity testing, endotoxins may be present downstream, including the dialyzer and blood tubing set. Therefore, all three components should be replaced in this case. Next, daily integrity testing of the dialyzer and blood tubing set is desirable because repeated treatments and heat disinfections may damage these disposables. A broken dialyzer fiber could cause a blood leak out of the blood side of the dialyzer and into the system and/or compromise its ability to prevent endotoxins from crossing from the dialysate side of the dialyzer and into the blood.

Key valves, pumps, pneumatics, and various replaceable cartridges are tested using pressure and vacuum tests. Either a pressure or a vacuum may be delivered to the component in test and then isolated while the pressure decay is measured over time. If pressure escapes too quickly, the component fails the test, indicating that it should be replaced.

The system is primed with the fresh dialysate. The dialyzer clearance is measured to determine whether its solute removal performance is acceptable. As the dialyzer is reused, the fibers can become clogged with blood clots and biofilm, reducing the effective surface area available for solute transfer (diffusion and convection). As this happens, the dialyzer's ability to "clear" the blood of toxins is reduced, hence the term clearance. If the clearance value has declined more than the allowable prescribed percentage, the operator may be notified and replacement may be performed following the completion of treatment.

The ultrafilter transmembrane pressure (TMP) may be tested daily to ensure that it does not exceed the maximum operating limit. The TMP limit is typically a manufacturer's specification used to prevent damage to the ultrafilter fibers or housing, which could lead to an external leak or endotoxins crossing the ultrafilter. Over time, the ultrafilter gradually becomes clogged with biofilm and other debris which causes the pressure drop across its fibers to increase. The TMP test sends the maximum system flow rate used through the ultrafilter and measures the pressure drop. If the pressure drop exceeds the maximum operating limit, the ultrafilter should be replaced following the completion of treatment.

The reverse osmosis water in the dialyzer and blood tubing set should be replaced with physiological fluid prior to treatment in order to prevent hemolysis. Further, any residual ethylene oxide (ETO) that may be present in the dialyzer prior to treatment should be flushed out in order to prevent First Use Syndrome-1 (FUS-1). Since dialysate is a microbial growth medium, the blood tubing prime is late in the application process to reduce stagnant time in the set.

Protective system self tests may be performed. This is accomplished by creating offsets in safety sensors to simulate unsafe conditions and then confirming that each protective system reacts as intended.

Figure 72:
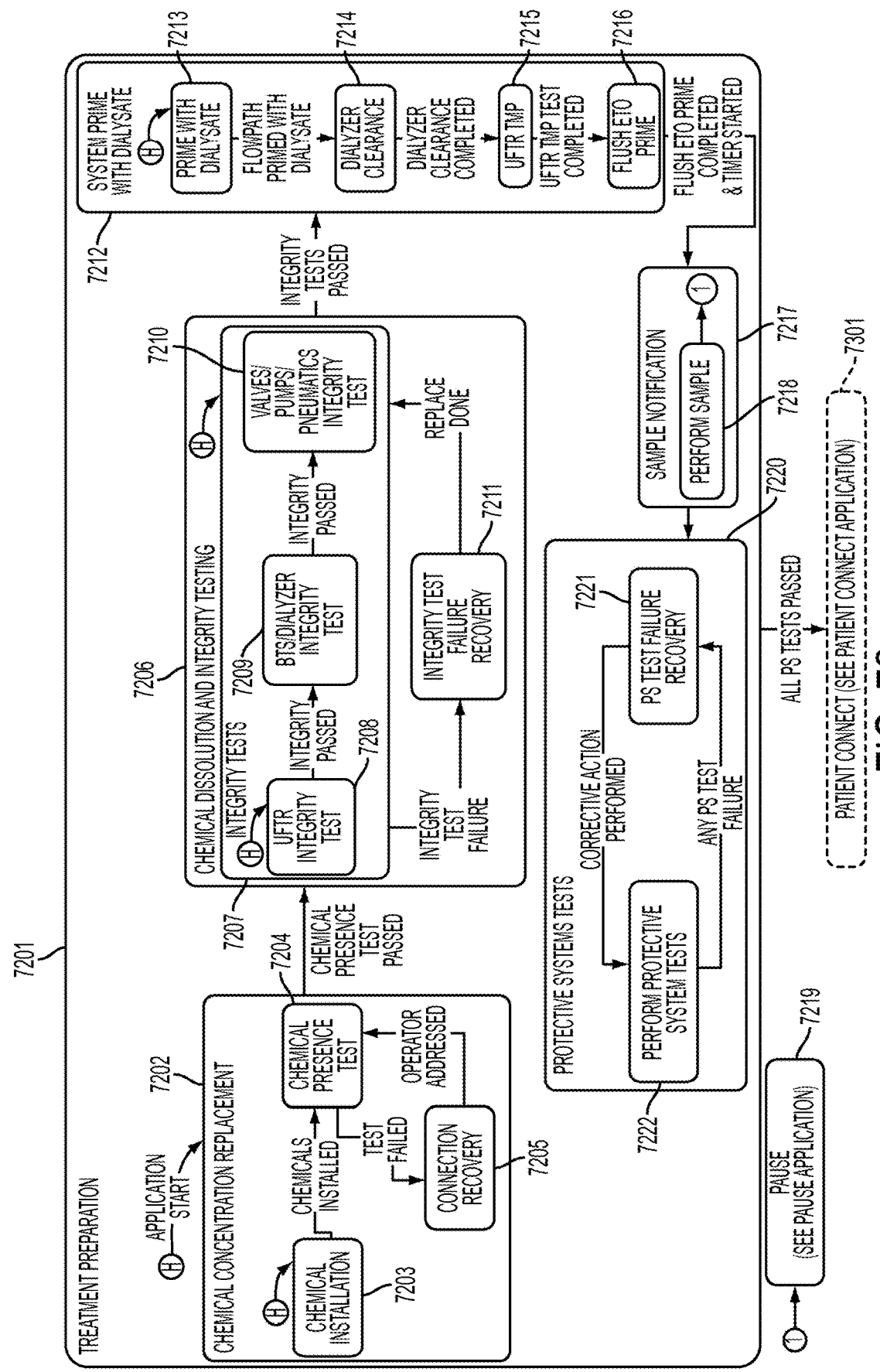

FIG. 72 shows an exemplary implementation of the Treatment Preparation application. Referring to FIG. 72, states of the Treatment Preparation application 7201 are described. The Chemical Concentration Replacement state 7202 will perform the necessary operations to allow the user to connect the chemical concentrates to begin the process for preparing the dialysate. This state will indicate when the machine is ready to receive the chemical concentrates. Also during this time, the system will verify that the chemical concentrate containers are present and connected properly. During the Chemical Installation state 7203, the system will prompt the user to install the chemical concentrates when it indicates it is ready. Included in the prompt may be instructions on how to perform the installation. The system may display an instructional prompt to install the chemical concentrates whether they are in a cartridge or bottle form. The operator may confirm installation by indicating their prescription using the user interface. The Chemical Presence Test 7204 detects whether the chemicals have been installed properly in the system. The system may verify that the chemicals have been installed by using a presence sensor to detect whether the chemicals have been installed or not. If the system indicates that the cartridges are not present, the system will transition to Connection Recovery 7205. In addition, the system monitors whether the chemical bypass door is opened, which implies that the chemical tubing is connected. The connections may also be verified by drawing a vacuum on the chemical container to confirm that the chemical addition ports are not open to atmosphere. Connection Recovery 7205 will handle the user interaction in the event that the system detects that the chemical concentrates are not installed properly. This recovery need only be performed in the event that the system is unable to detect the presence of the chemical concentrates or the vacuum integrity test fails. When the system indicates that the chemical concentrates are not installed properly, the system will instruct the user to verify that the chemicals are properly installed and that all connections are securely fastened. The system will then wait for the user to indicate that the connections have been checked and allow the system to perform the Chemical Presence Test 7204 again.

Upon successful completion of the Chemical Presence Test 7204, the system will transition to Chemical Dissolution and Integrity Tests 7206. During the Chemical Dissolution and Integrity Tests state 7206, the system will start the process of dissolving and combining the chemical concentrates to achieve the prescribed dialysate prescription. In addition, this state will perform routine daily integrity tests of the particular components. The actions of Dialysate Preparation and performing the Integrity Tests will be performed by the system concurrently to use time more efficiently.

The Integrity Tests state 7207 will handle the integrity testing of the Ultrafilter, Blood Tubing Set and Dialyzer, and the dialysate circuit. The Ultrafilter (UFTR) Integrity Test 7208 verifies the integrity of the Ultrafilter. The water in the housing is forced out, and then the air is pressurized and held against the fibers from the outside. If the allowable decay limit is exceeded, the filter should be replaced. During this state, in the event that the UFTR integrity test returns an indication that the test has failed, the system will relay this information to the user. The user will be instructed to Replace the UFTR via the transition to Replace Components. Upon completion of the installation of the new ultrafilter, the system will re-perform the integrity test and resume normal operation. The Blood Tubing Set (BTS)/Dialyzer Integrity Test sub-state 7209 is intended to test the integrity of the Blood Tubing Set and Dialyzer. This is accomplished by generating a pressure, and then measuring the decay. If the dialyzer/blood tubing set fails the integrity test, the user is notified to replace the dialyzer and blood tubing set. During this state, if the system returns a Failed status for the BTS and/or Dialyzer Integrity, the system will notify the operator that the BTS and/or Dialyzer Integrity test failed. The user will be provided with information and the ability to replace these components through the Replace Components option. Once the component(s) have been replaced, the system will re-perform the integrity test. If desired, a general system integrity test may be performed during a Valves/Pumps/Pneumatics Integrity state 7210.

The Integrity Test Failure Recovery state 7211 provides instructions to handle any integrity test failures identified during the integrity tests. If the system indicates that there was an integrity test failure, the user will be notified by the system of the failure, as well which component failed. The user may then perform the necessary actions to perform the replacement. Upon the user's indication that the new component has been installed, the system will resume normal operation.

The System Prime with Dialysate state 7212 will perform the necessary actions to prime the system with dialysate. This state includes a Prime with Dialysate state 7213, a Dialyzer Clearance state 7214, an Ultrafilter Transmembrane Pressure (UFTR TMP) state 7215, and a Flush ETO Prime state 7216. The Prime with Dialysate state 7213 begins chemical production and primes the system with dialysate. The Dialyzer Clearance state 7214 quantifies the amount of sodium clearance, used as a surrogate for urea clearance, that can pass across the dialyzer membrane under given flow rate and temperature conditions. The UFTR TMP state 7215 measures the transmembrane pressure (TMP) across the ultrafilter at the maximum system flow rate, to ensure that is does not exceed the specified maximum ultrafilter TMP. In the event that the UFTR TMP exceeds the acceptable limit, the system may continue with its normal operation. The user will be notified that the ultrafilter (UFTR) requires replacement due to a failed TMP test and that the replacement will be performed during Recycle Preparation. The Flush ETO Prime state 7216 flushes the dialyzer of ethylene oxide (ETO) that may have leached out.

During the Sample Notification state 7217, the system will identify if any samples have been previously scheduled by the patient or clinical representative. This state also notifies the operator of the samples scheduled. The following are samples that the operator may be notified to collect: Blood Samples, Chlorine Sample/Test, Chloramines Sample/Test, and RO Water Sample. During the Perform Sample state 7218, the system will notify the user that there are samples scheduled to be taken. During this state, the user will have the opportunity to accept or decline taking these samples. The system will evaluate whether there are samples scheduled or not. If the system indicates that there are sample(s) scheduled and the user elects to perform the sample, the system will transfer responsibility to Pause 7219, where each of the samples will be handled.

The system will create conditions that allow self-testing of the protective systems before a patient is connected to the machine. Upon the detection of a protective systems test failure, the Protective Systems Tests state 7220 will initiate corrective action if applicable. The following protective systems may be tested prior to patient connection: Air Detection (Venous and Arterial), Dialysate Conductivity, Dialysate Temperature, Blood Leak Test, Fluid Leak Test, and Doors Open. This may be accomplished by offsetting each of the sensors to simulate a condition where the protective system will trigger. The system will confirm that the proper protective system was initiated.

The Protective Systems Test Failure Recovery 7221 is triggered in the event that one of self tests returns a failed status. This state is entered upon the completion of all of the Protective System Tests 7222. In the event that any of the Dialysate Conductivity Protective System Test, Dialysate Temperature Protective System Test, Blood Leak Protective System Test, and Fluid Leak Protective System Test return the failed status, the operator may be instructed that operation cannot continue. In the event that either of the Air Detection Protective System Test or the Door Protective System Test return the failed status, the operator may be instructed to perform the corrective actions related to the failure.

(6) Patient Connect

Following the treatment preparation, the patient connection to the system is made and the extracorporeal blood tubing circuit is primed with blood. There are at least two priming prescription options: the first method is "Prime Discarded" (or Prime Not Returned) where the dialysate priming solution is drawn into the machine as blood is introduced into the extracorporeal circuit. The second method is "Prime Returned" where the dialysate priming solution is given to the patient as blood is introduced into the extracorporeal circuit. Choice of these two methods depends on how much volume the patient wants to remove during the priming process and whether their venous access can tolerate fluid being drawn from it.

For Prime Discarded, blood is drawn from the patient's arterial and venous access sites simultaneously into the machine as the priming solution is discarded to drain. This priming method is often preferred, because patients typically begin dialysis treatment volume overloaded and therefore wish to accomplish priming without taking on additional fluid. The user may chose to switch priming methods to Prime Returned if their access cannot tolerate the reverse flow up the venous line. The arterial and venous flow rates may be matched as closely as possible such that the blood fronts just meet inside the dialyzer fibers. The extracorporeal circuit may be purposefully slightly "underprimed" in order to avoid localized hemoconcentration that could occur if the blood is ultrafiltrated during the priming process.

For Prime Returned, blood is drawn up the arterial line and the priming solution is displaced down the venous line to the patient. This priming method may be prescribed for those patients whose accesses cannot tolerate the reverse flow up the venous line used during Prime Discarded, or who are sensitive to hypovolemia. If the patient cannot tolerate losing volume quickly, this method allows them to keep their volume during prime.

Additionally, if the patient still needs extra volume, they can initiate a solution infusion any time they are connected. Especially for patients who are sensitive to hypovolemia, they may choose to start treatment with a slight excess of fluid.

For either priming method, the operator may choose to change the priming blood flow rate at any time. However, any changes do not affect the prescribed setting for the subsequent treatment. Access site compromise and pressure/flow problems are common at the initiation of treatment, and therefore the operator may wish to slow down the blood flow rate during priming.

While the dialyzer and blood tubing set have already been flushed to match the dialyzer manufacturer's instructions sheet, there is an industry concern about further leaching of sterilant out of dialyzers when they sit with fluid stagnate in them. Therefore, if the dialyzer sits stagnant for too long, it may be re-flushed.

Figure 73A:
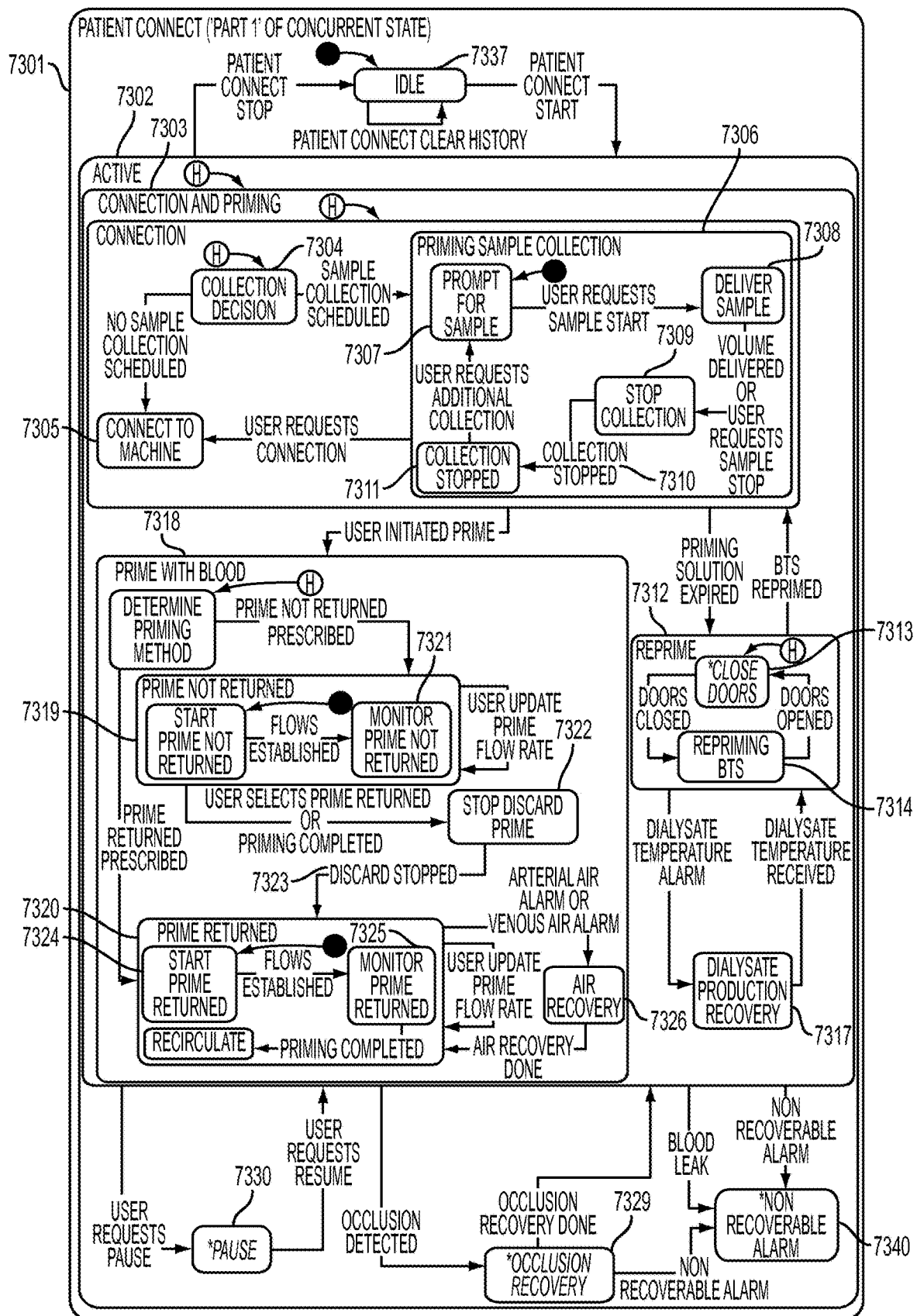

FIGS. 73A-73D show an exemplary implementation of the Patient Connect application. With reference to FIG. 73A, the Connection and Priming state 7302 of the Patient Connection application 7301 allows the patient to take a priming sample if scheduled, connect to the machine, and prime the blood tubing set with blood. Within the Connection and Priming state 7302, the Connection state 7303 encompasses taking a priming sample and connecting to the machine. During this state, the system may determine whether the priming solution has expired. For brand new dialyzer, priming solution expires approximately 15 minutes after the last flush of dialyzer and blood tubing set. For a dialyzer that has at least one heat disinfect, priming solution may expire approximately 30 minutes after the last flush of dialyzer and blood tubing set.

There is an industry concern about leaching of sterilant out of dialyzers when they sit with fluid stagnant in them. Therefore, if the previous flush of the dialyzer occurred 15 minutes ago for a new dialyzer, or 30 minutes ago for a dialyzer that has one or more disinfects, the dialyzer may be re-flushed. This flush will remove any residual ethylene oxide (ETO) that may be present in the BTS in order to prevent First Use Syndrome-1 (FUS-1). The rationale for differing times between a brand new dialyzer and a dialyzer with one or more heat disinfects is that a brand new dialyzer will likely have more ETO that can leach out. A used dialyzer will have little or no residual ETO.

The Collection Decision state 7304 determines whether a priming sample is scheduled or not, based on certain database items. The Connect to Machine state 7305 prompts the patient to enter their weight and connect to the machine. It waits until they indicate they are connected. The state will post a message indicating the connection procedure and the means for entering patient weight. If heparin is prescribed, it will also prompt the patient to load a heparin vial into the pump.

The Priming Sample Collection state 7306 allows the patient to collect a priming sample. The priming solution sample is used to perform a microbiological evaluation of the dialysate fluid used to prime the dialyzer and blood tubing set. Within the Priming Sample Collection state 7306, the Prompt for Sample state 7307 prompts the patient to collect a priming sample. The Deliver Sample state 7308 pushes fluid across the dialyzer and out the venous line, providing the patient with a sample of the priming solution. A notice may be provided to the patient allowing them to terminate sample collection at any time.

The allowable volume for a priming solution sample may be 500 ml, for example. Typically, a sample of 150 ml is needed for microbiological evaluation. Sterile sample collection generally requires that some fluid flow into a waste container prior to taking the sample. A maximum volume of 500 ml also allows the user to take an additional sample if the first sample gets contaminated. The request for sample collection duration may be approximately 30 seconds or less. To obtain a 150-ml sample, the desired flow rate from the venous line may be 300 ml/min. The dialysate may be heated to the prescribed temperature in preparation for priming with blood. Should the patient elect to receive the dialysate prime in the blood tubing set, it will be a comfortable temperature.

The Stop Collection state 7309 stops fluid flow and waits for the machine stop to be completed. This state is entered either due to a sample volume limit being reached, or due to patient request. When the machine has stopped, a Collection Stopped event 7310 is triggered, causing a transition to the Collection Stopped state 7311. The Collection Stopped state 7311 waits for the patient to indicate they are ready to move on to connection. Alternatively, the patient may request additional sample collection.

Figure 73B:
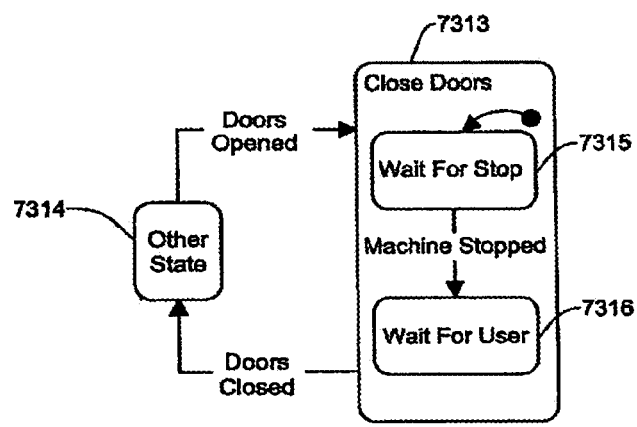

The Reprime state 7312 ensures the patient reconnects the blood tubing set and closes the doors. The dialysate and blood tubing set are then re-flushed. The Close Doors state 7313 prompts the user to close the doors. Referring to FIG. 73B, The Doors Wait For Stop state 7315 issues a stop command and waits for the machine to stop. The Doors Wait For User state 7316 waits for the common monitoring application to indicate that the doors are closed, either because the user or a detector indicated that the doors are closed. The Repriming blood tubing set state 7314 re-flushes any residual ETO that may have leached out during a period of inactivity.

Referring again to FIG. 73A, the Dialysate Production Recovery state 7317 allows the machine to recover from a scenario where the dialysate temperature is out of specification. Once the temperature of the dialysate is within 1° C. of the prescription temperature, for example, the process may transition to the Reprime state 7312.

The Prime With Blood state 7318 primes the blood tubing set and dialyzer using either the Prime Returned 7319 or Prime Not Returned 7320 method. If a blood leak is detected, an alarm event is generated. The Prime Not Returned state 7319 primes the blood tubing set by pulling blood up both the arterial and venous lines, and displacing the dialysate through the dialyzer and down to drain. The system may notify the patient that at any time during the state they can select Prime Returned 7320 or modify the priming blood flow rate. The arterial priming rate is a prescription item and may be modified by the patient. The blood tubing set and dialyzer volume may be slightly less than nominal in order to reflect dialyzer bundle volume decreases over time and also to avoid hemoconcentration. The Monitor Prime Not Returned state 7321 monitors priming of the blood tubing set by checking the status of the priming process.

The Stop Discard Prime 7322 state stops fluid and waits for the machine stop to be completed. When the machine has stopped, the Discard Stopped event 7323 is triggered, causing a transition to Prime Returned 7320. The Prime Returned state 7320 primes the blood tubing set by pulling blood up the arterial line and displacing dialysate down the venous line to the patient. Arterial air may be monitored. The patient may be notified of the ability to modify the priming blood flow rate at any time during the state. The Start Prime Returned state 7324 starts priming the blood tubing. While blood is being drawn up the arterial line, the priming solution will be given to the patient through the venous line. Rate is a prescription item and may be modified by the patient. The Monitor Prime Returned state 7325 monitors priming of the blood tubing set by accumulating the total volume pumped and comparing it to the total volume in the dialyzer and blood tubing set. When the volume pumped is greater than total dialyzer and blood circuit volume, priming is complete. If the patient started Prime Not Returned 7319, the amount primed during that state will be carried forward to this state. The patient is notified when they can begin treatment. If the patient indicates they are ready to begin treatment, the Patient Connection application is stopped and the Dialyze Application will be started.

Figure 73C:
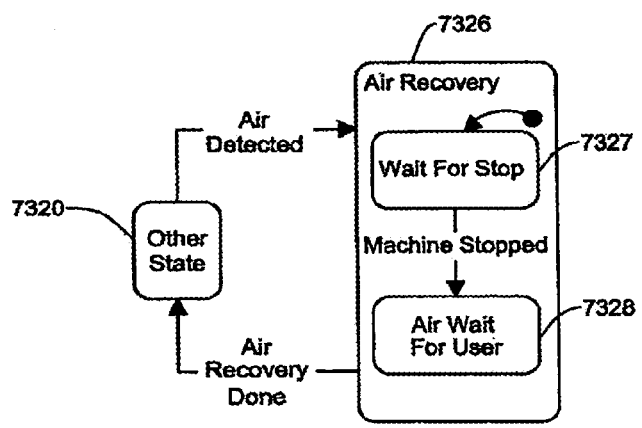

The Air Recovery state 7326, shown in FIG. 73c, allows the user to recover from air intrusion into the blood tubing set. The Air Wait for Stop state 7327 waits for the flow to stop. The Air Wait For User state 7328 waits for the common monitoring application to indicate that the alarm is cleared.

The Occlusion Recovery state 7329 notifies the user that an occlusion has been detected, but does not stop any flows. Within the Occlusion Recovery state 7329, an Occlusion Wait For Stop state issues a stop command and waits for the machine to stop. An Occlusion Wait For User state waits for the common monitoring application to indicate that the occlusion is cleared.

Figure 73D:
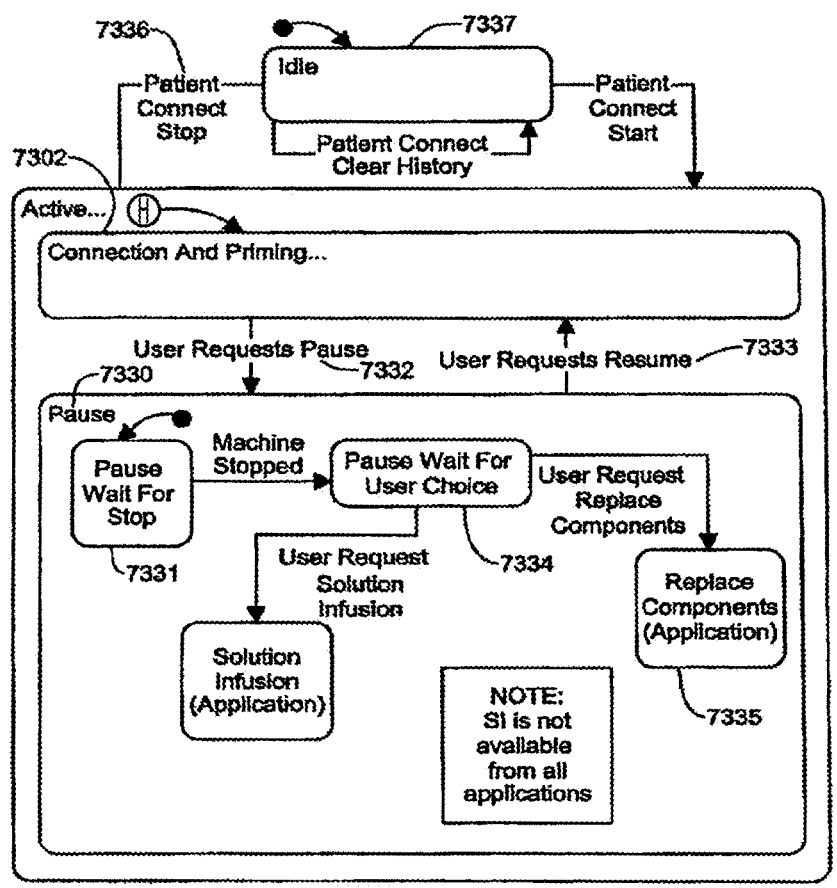

Referring to FIG. 73d, the Pause state 7330 is shown in detail. The Pause state 7330 will halt operation. Additionally, the patient can choose to perform additional activities. In particular, the patient may have the following options: Take RO Sample, Resume Active, Rinseback, Disconnect, Power Standby, and Shutdown. Since the Pause state 7330, does not have history, the state machine transitions to Pause Wait For Stop 7331, which issues the stop functions. Again, if the patient selects to resume operation, the process returns to the Connection And Priming state 7302, which dispatches to the prior sub-state(s) via a history mechanism. When the user selects a Pause button, the User Requests Pause event 7332 may be sent, causing the Patient Connect state machine to transition into Pause and then into the initial state Pause Wait For Stop. The entry action on Pause Wait For Stop calls the machine stop functions. Once the machine has stopped, the state machine transitions to Pause Wait For User Choice 7334. If the user selects Resume, the event User Requests Resume 7333 is accepted.

If the patient chooses to run another application, such as the Replace Components Application 7335, the Master Control triggers the Patient Connect Stop event 7336, causing the Patient Connect state machine to transition to the Idle state 7337. Once the machine has stopped, the state machine transitions to Pause Wait For User Choice 7334. When the User Requests Resume event 7333 is triggered, e.g., by the user pressing the resume button, the state machine transitions back to Connection And Priming 7302, and will resume according to the history within that state and its sub-states.

Referring again to FIG. 73A, the Nonrecoverable Alarm 7340 state notifies the patient that there is an unrecoverable alarm. The current application stops, and the patient may be instructed to disconnect from the system after acknowledging the alarm.

(7) Dialyze

Following connection to the dialysis unit, dialysis therapy may be delivered to a patient. Dialysis therapy removes toxins and excess fluid from a patient's blood, using diffusion, forward ultrafiltration and backward filtration (convection). In addition, heparin may be administered to the blood to prevent coagulation during treatment.

Diffusion is accomplished by exposing the patient's blood to a dialysate solution through a semi-permeable membrane. Blood may be drawn from the patient's arterial access and returned to their venous access. Simultaneously, fresh dialysate may be produced from reverse osmosis water and chemical concentrates, heated to the prescribed temperature, and delivered to the dialysate side of the dialyzer while spent dialysate is routed to drain. The concentration gradient at the dialyzer membrane causes toxins of various molecular sizes to equilibrate, by moving from the blood into the dialysate. The prescribed blood and dialysate flow rate settings and their accuracy is important in achieving the desired amount and rate of toxin removal. The flow of the blood and dialysate is countercurrent in order to maximize the concentration gradient at all points, increasing the amount of diffusion that will occur. Diffusion is also enhanced by the fact that dialysate delivered to the dialyzer is fresh rather than recirculated. Further factors that may affect dialysis therapy dose delivered include patient size, prescribed treatment duration, dialyzer effective surface area and dialyzer clearance.

Forward ultrafiltration removes excess fluid from the patient's blood. The prescribed fluid volume is removed by generating a lower pressure on the dialysate side of the dialyzer, thereby pulling fluid from the blood. The ultrafiltration rate is calculated using the prescribed fluid volume to be removed and also takes into account any dialysate volumes delivered to the patient during the priming, backflushing, and rinseback processes.

Backward filtration, or backflushing, is the inverse of forward ultrafiltration. Instead of pulling fluid from the blood side of the dialyzer to the dialysate side, fluid is pushed from the dialysate side to the blood side. This process helps to prevent clot formation within the blood tubing and dialyzer, which in turn may allow for a smaller heparin dosage, prolong the useful life of the dialyzer, and facilitate dialyzer cleaning and re-use. Backflushing has the additional benefit of promoting better solute removal through convection. Like diffusion, convection removes toxins from the blood. But unlike diffusion, which relies on a concentration gradient, convection relies on the active movement of fluid across the dialyzer to carry solutes. Backflushing is controlled by the synchronization of the blood and dialysate portions of the flow path. By changing the phase between blood and dialysate sides, there is constant and repeated shifting of fluid across the dialyzer in small increments. This shifting of fluid pushes dialysate into the blood circuit and then pulls it back, but results in no net ultrafiltration.

While dialysis is occurring, heparin may be administered. This administration can be handled either as a series of one or more boluses of fluid, or on a continuous basis. The patient may also choose to receive an additional bolus or boluses of heparin in the event that unexpected coagulation occurs.

Figure 74A:
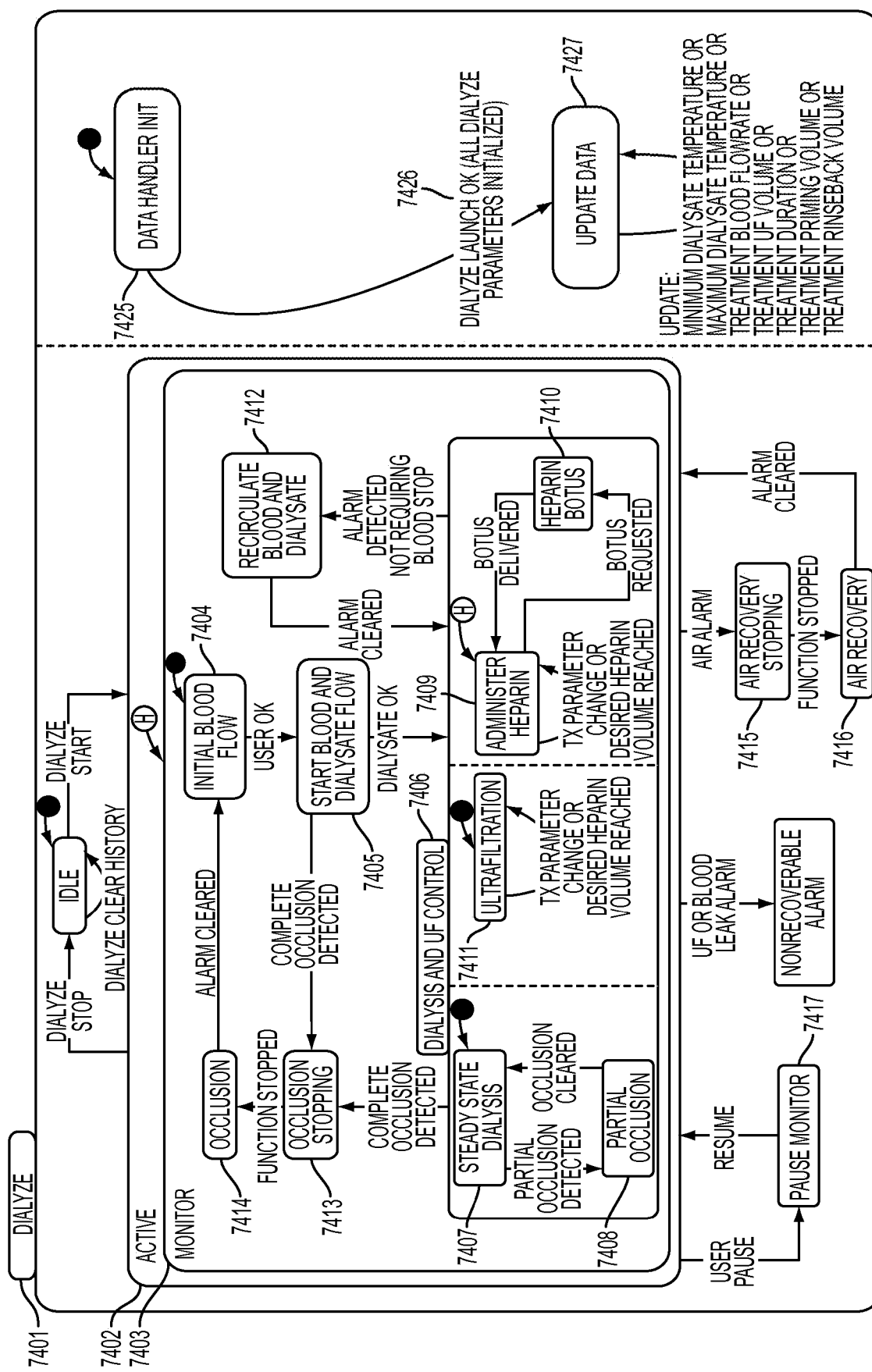
Figure 74B:
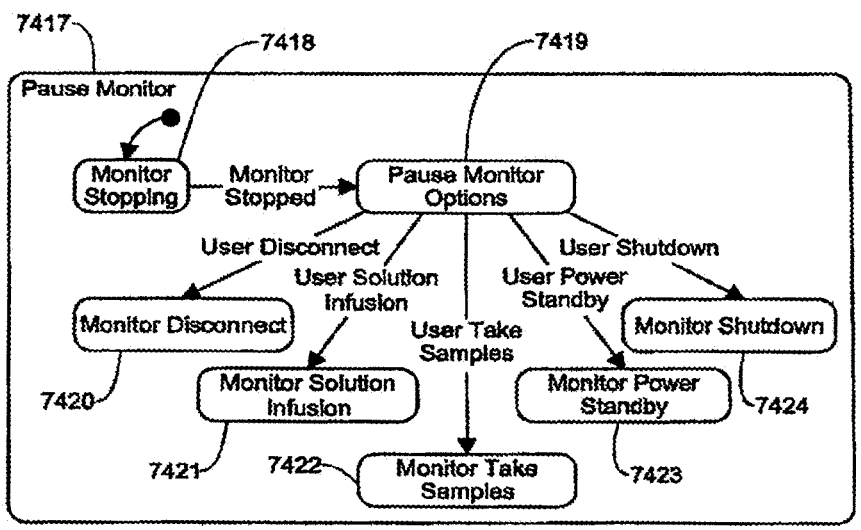

FIGS. 74A and 74B show an exemplary implementation of the Dialyze application. Referring to FIG. 74A, the Dialyze state 7401 is the top level state that coordinates the actions that lead to the overall dialysis therapy. This state runs concurrently with the data handling elements of the state machine. During this state, dialysate will be produced and an adequate buffer will be maintained in the dialysate tank. Updates to data of interest to the dialyze application will be processed by the data handling elements of the state machine.

The Active state 7402 of the dialyze application is where all dialysis related processing occurs. Dialysis is complete when the dialysis time remaining expires. The Monitor state 7403 is responsible for initiating the blood and dialysate flow rates so that treatment can be performed. Blood leak monitoring and air monitoring may be requested, and ultrafiltration monitoring may be enabled. The Initial Blood Flow state 7404 starts the blood pump at a low rate in order for the patient to check their access before starting treatment. The Start Blood and Dialysate Flow state 7405 increases the blood flow rate to the prescribed flow rate. It also starts dialysate flow by heating the fluid from the dialysate tank and diverting it around the dialyzer.

The Dialysis and UF Control state 7406 is responsible performing hemodialysis. Dialysis will occur with ultrafiltration and heparin administration. A dialysate temperature alarm may be generated if the temperature is not within acceptable limits. Complete blood side occlusion monitoring may be is requested, and partial blood side occlusion monitoring may be requested to stop. The Steady State Dialysis state 7407 performs dialysis by circulating blood and dialysate through the dialyzer. It also collects certain treatment related information. The Partial Occlusion state 7408 notifies the user that an occlusion has been detected, but does not stop any flows. The Administer Heparin state 7409 will administer heparin at a prescribed rate. Heparin will be stopped if the amount of heparin delivered is equal to the prescribed amount or the patient requests that heparin delivery be stopped. The Heparin Bolus state 7410 will deliver a bolus of heparin.

The Ultrafiltration state 7411 performs ultrafiltration. The ultrafiltration rate is determined by taking the amount of fluid needed to be removed divided by the time remaining in the treatment. If the target ultrafiltration volume differs by more than 500 ml from the current ultrafiltration volume, an ultrafiltration alarm may result. If either of the following is true, ultrafiltration may be stopped: (1) the amount of ultrafiltration is greater then or equal to Prescribed volume needed to be removed+Rinseback Volume+Priming Volume, or (2) the patient requests ultrafiltration to stop and the amount of ultrafiltration is greater then or equal to the Rinseback Volume+Priming Volume.

A counting algorithm may be used to compare the actual strokes of the ultrafiltration ("UF") pump with the predicted number of strokes to achieve the target volume of ultrafiltrate. The expected number of strokes can be synthesized based on the requested volume and rate of ultrafiltration. The actual strokes of the pump can be counted by having the controller monitor the valve states of the ultrafiltration pump. In one implementation, if the actual strokes exceed the expected strokes by greater than a safety threshold, the machine can be placed in a safe state. If the actual strokes fall behind the expected strokes by a threshold amount, the pumping rate or duration can be extended to avoid having the treatment session undershoot the desired ultrafiltration amount.

The Recirculate Blood and Dialysate state 7412 recirculates blood and dialysate, with dialysate bypassing the dialyzer, in order to bring the temperature of the dialysate into treatment limits.

The Occlusion Stopping state 7413 stops blood flow if the blood flow rate drops too far notifies the user that a problem exists. When no occlusion is detected in the Occlusion state 7414, the machine will continue to the Initial Blood Flow state 7404.

The Air Recovery Stopping state 7415 notifies the user that air intrusion into the blood tubing set has occurred and waits for the function to stop. The Air Recovery state 7416 allows the user to recover from air intrusion into the blood tubing set.

The Pause Monitor state 7417 is responsible for pausing the device and displaying pause menu options. Referring to FIG. 74B, the Monitor Stopping state 7418 will stop the device and give visual feedback to the user that the pause button was processed. The Pause Monitor Options state 7419 will display all the Pause menu options. The Monitor Disconnect application 7420 will wait in the state to be stopped by master control. The Monitor Solution Infusion application 7421 will wait in the state to be stopped by master control. The Monitor Take Samples application 7422 will wait in the state to be stopped by master control. The Monitor Power Standby application 7423 will wait in the state to be stopped by master control. The Monitor Shutdown application 7424 will wait in the state to be stopped my master control.

Referring again to FIG. 74A, the Data Handler Init state 7425 is responsible for initializing all the data of interest for the Dialyze application. Upon completion of this initialization it will generate a Dialyze Launch Ok event 7426 to indicate to Master Control the application is ready to be started. The Update Data state 7427 is responsible for maintaining up to date values or all the data of interest for the Dialyze application.

(8) Solution Infusion

To counteract a hypotensive event, the system may deliver a bolus of fluid volume to a patient. As the system removes fluid volume from the patient during treatment, it is possible that an unexpected drop in patient systemic blood pressure may occur. This hypotensive event can lead to patient lightheadedness, fainting, or even more serious complications. To prevent these outcomes, the user need only request a solution infusion. The system may then deliver a prescribed bolus of ultrapure dialysate.

Once the user has requested a solution infusion, the blood pump may be left running to prevent clotting. The Solution Infusion application will assess whether there is enough dialysate volume available to deliver the infusion and still have enough reserve volume to rinse back the patient's blood. If not, the user may be notified that infusion is not possible, and may be instructed to either select rinseback or resume treatment. If there is enough dialysate, a short countdown be displayed to the user prior to starting the infusion. Since solution infusion is available via a single button press, it is possible that the user may have pressed the button in error. This delay gives them the opportunity to cancel the infusion before it begins.

Following the delay, fresh, heated dialysate fluid is sent across the dialyzer and down the venous line to the patient. At the same time, the blood pump is slowly run forward to continue circulating blood and prevent clotting. In order to deliver relief as quickly as possible, the flow rate used for the infusion is as fast as reasonably tolerable by most patients' accesses and vasculature. A flow rate that is too high may create high pressures in the blood tubing set and lead to nuisance interruptions of the infusion delivery. Further, the infusion flow rate approximates the flow from a saline bag that a nurse might hang to counteract a hypotensive episode on other devices.

After the prescribed solution infusion volume has been delivered, if the patient continues to experience hypotensiveness, they may choose to infuse smaller additional boluses as long as enough dialysate volume is available. Once the patient leaves this application and returns back to the previous activity (e.g., Patient Connect or Dialyze), subsequent requests for a solution infusion may be for the full prescribed solution infusion volumes.

Figure 75A:
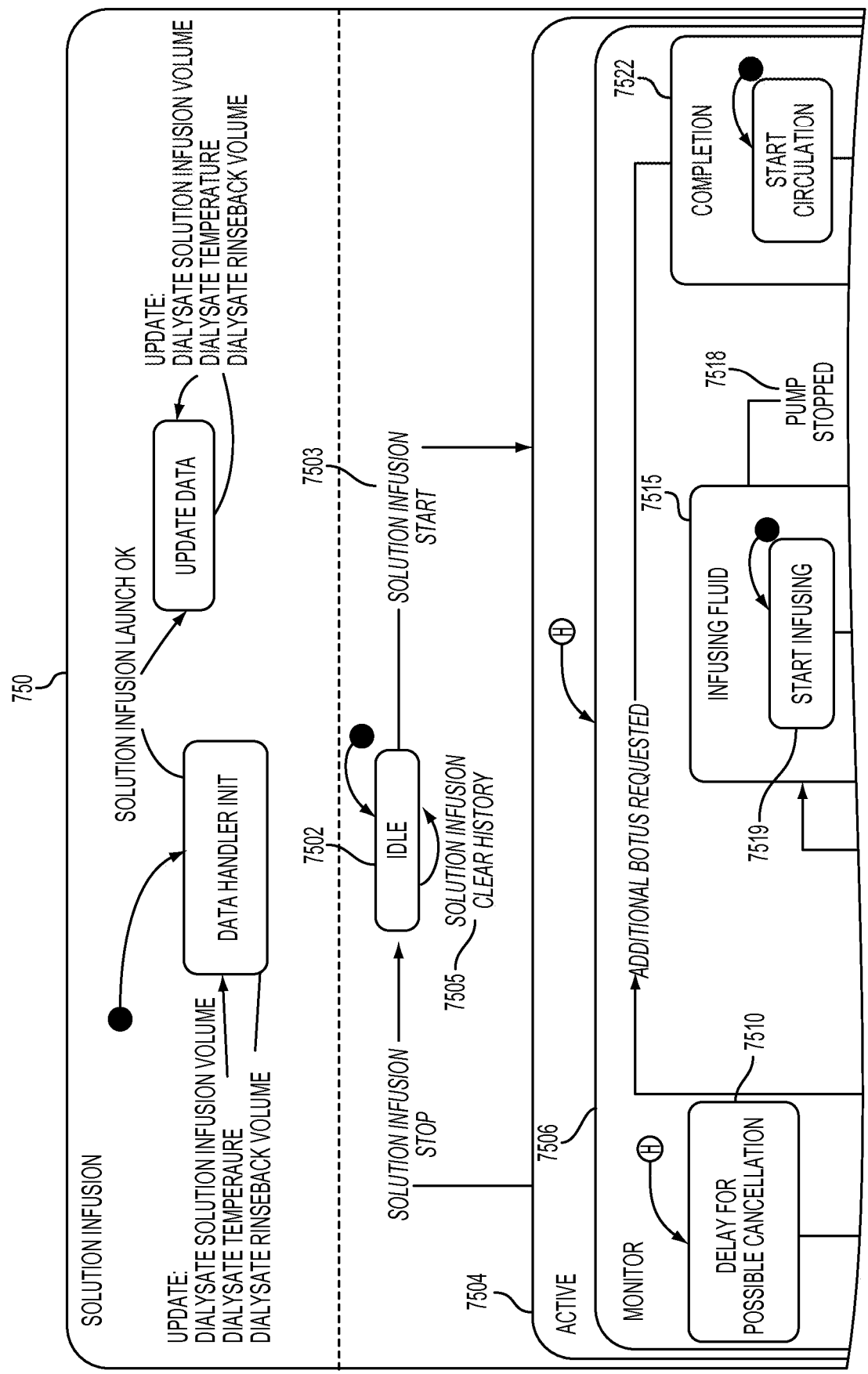
Figure 75A:
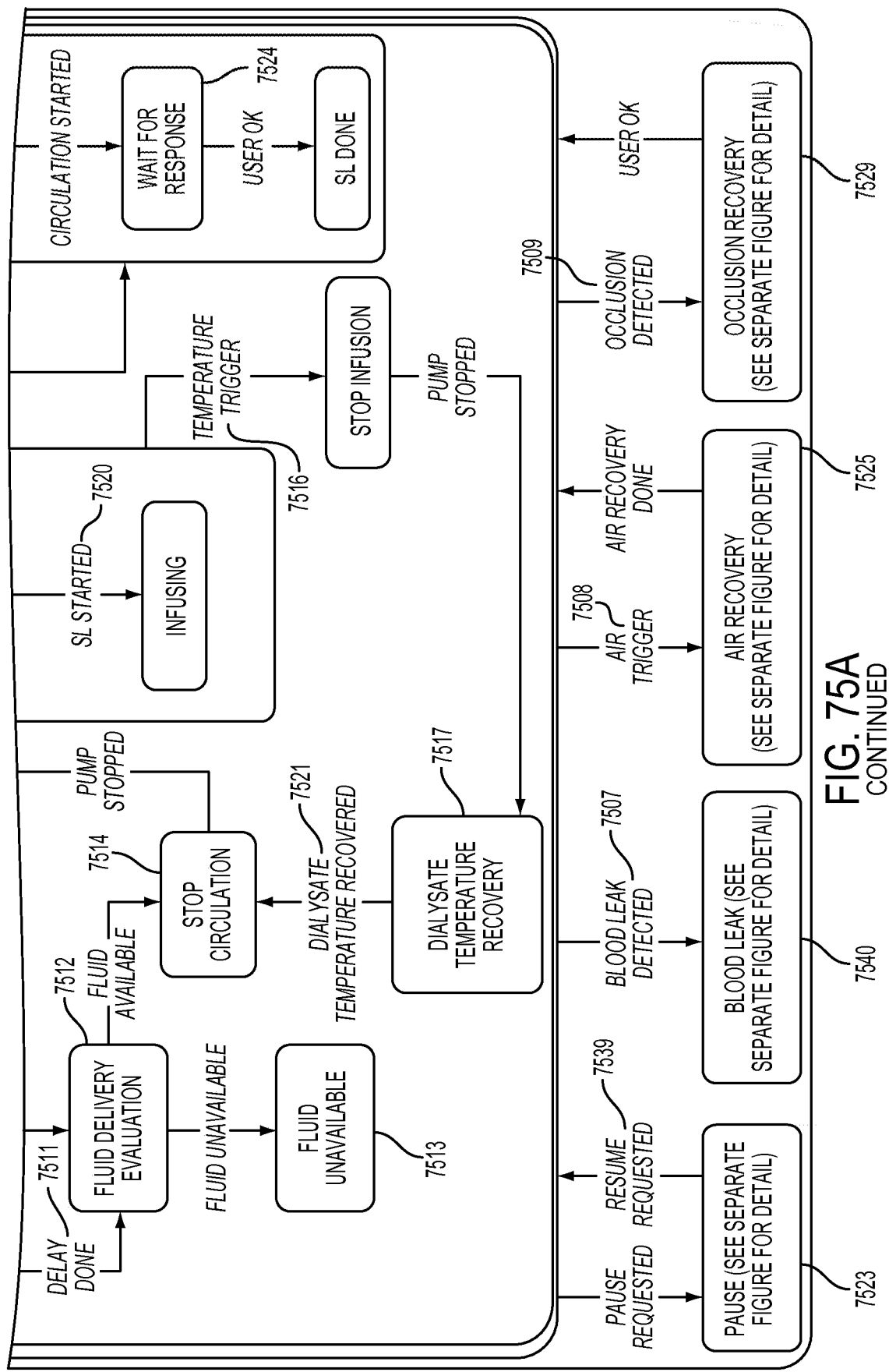

FIGS. 75A-75E show an exemplary implementation of the Solution Infusion application. With reference to FIG. 75A, Solution Infusion 7501 is the top level state which coordinates the actions that lead to the delivery of a solution infusion. This state runs concurrently with the data handling elements of the state machine. Updates to data of interest to the Solution Infusion application will be processed by the data handling elements of the state machine. The Idle state 7502 is the state of the Solution Infusion application during all other system processing. Upon receiving a Solution Infusion Start event 7503 the Solution Infusion application will transition to the Active state 7504. The Solution Infusion application will indicate it has started when transitioning to the Active state. Upon receiving a Solution Infusion Clear History event 7505, the Solution Infusion application will clear the history and remain in the Idle State 7502. During the Active state 7504 of the Solution Infusion application, the solution infusion volume to be delivered is set.

The Monitor state 7506 watches for common hazards, such as Blood Leak 7507, Arterial and Venous Air 7508, and Occlusion 7509. The Monitor state 7506 starts the monitors by sending events to the monitoring process, and Starts dialysate production in case it has been stopped by a Pause or other interruption.

The Delay for Possible Cancellation state 7510 allows the patient to cancel the Solution Infusion if they choose. During the delay (e.g., 3 seconds), the user interface may give the user an updating visual indication of the time until the infusion will start and the ability to cancel the infusion. If the delay elapses without cancellation, the Delay Done 7511 event will occur.

The Fluid Delivery Evaluation state 7512 evaluates whether there is sufficient dialysate available to deliver the requested infusion. It also calculates the solution infusion volume to be given in the Infusing Fluid state. The Fluid Unavailable state 7513 will notify the patient that there is not enough fluid to perform the requested infusion. The blood pump will continue to circulate while the patient responds. If there is sufficient fluid, the Stop Circulation state 7514 will stop the circulation of blood so that the solution infusion may begin.

The Infusing Fluid super-state 7515 encapsulates the behavior of the application while the solution infusion machine layer command is running. The solution infusion operation pushes ultrapure dialysate across the dialyzer and down the venous line to the patient. Dialysate is heated before it is pushed across the dialyzer. At the same time, the blood pump is slowly run forward to minimize blood clotting. The volume of fluid left to be infused may be updated during this state. A static variable representing this volume may be initially set in the Fluid Delivery Evaluation state 7512 and then updated in this state as volume is accumulated in the machine layer status variable, Dialysate Circuit Volume. The volume to be infused should be decremented by the delivered volume. If the Dialysate Temperature Out of Spec 7516 event occurs, the transition will be to the Dialysate Temperature Recovery state 7517. If the volume to be infused is less than 25 ml due to interruption and re-entrance, the Pump Stopped event 7518 may be immediately issued and no infusion should be given.

In the Start Infusing state 7519, the solution infusion machine layer command is started. The volume to be infused is being continually updated as volume is delivered so that the correct volume is entered whenever the infusion is started or restarted. When the machine layer status indicates that the command has been started, the SI Started event 7520 is issued to cause the transition to the next state.

The Dialysate Temperature Recovery state 7517 allows the machine to recover from a situation in which the dialysate temperature is out of specification. Dialysate is routed directly to the drain, while the temperature is monitored for a return to its acceptable range. If the temperature of the dialysate is within the target range for five consecutive readings, for example, the recovery is complete and the Dialysate Temperature Recovered event 7521 is issued.

The Completion super-state 7522 starts blood circulation to prevent clotting, and waits for the patient to either indicate they would like an additional infusion, or that they are done with infusions. If a Pause occurs during any state within this super-state, the Pause state 7523 will stop the circulation. Upon returning from Pause, circulation will be restarted and the user will again be asked whether an additional bolus is required. The Wait for Response state 7524 waits for the patient to either indicate they would like an additional infusion, or that they are done with infusions. If no further infusions are desired, this application is ended. The patient will be notified by the user interface that Solution Infusion is complete and they have the option of performing additional bolus infusions. If the user indicates that an additional infusion is needed, the local variable solution infusion volume may be set to deliver equal to 100 ml and transition to the Fluid Delivery Evaluation state 7512.

Figure 75B:
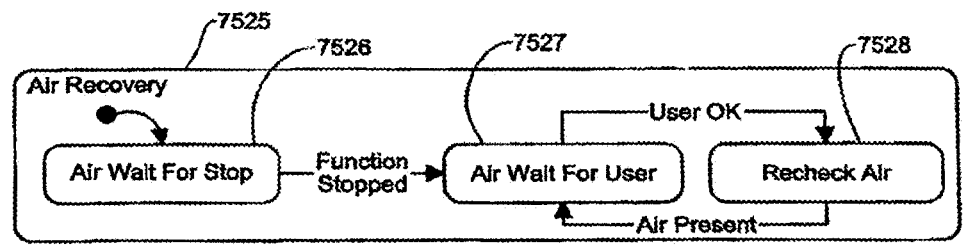

Referring to FIG. 75B, the Air Recovery state 7525 allows the user to recover from air intrusion into the blood tubing set. The machine layer fluid delivery function will be stopped, the user will be notified that air is present, and the application will remain in this state until the user indicates that the air has been cleared and the sensors do not detect air. The state machine history will return the application to the state that was interrupted. Following the Air Wait for Stop state 7526, the Air Wait for User state 7527 notifies the user that air is present in the blood tubing and provides instruction for removing the air, then waits for the user to indicate that the air is no longer present. When the user indicates that the air has been removed, the application will transition to the Recheck Air state 7528.

Figure 75C:
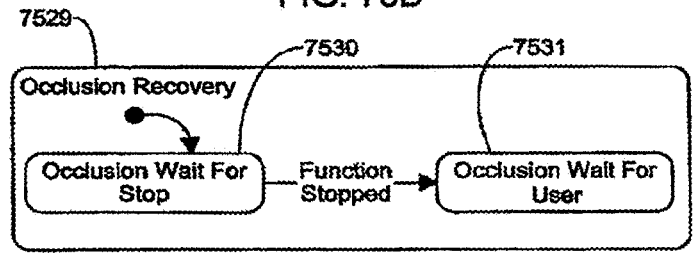

Referring to FIG. 75C, the Occlusion Recovery state 7529 notifies the user that an occlusion has been detected and waits for the user to respond. Following the Occlusion Wait for Stop 7530, the Occlusion Wait for User state 7531 notifies the user that an occlusion is present in the blood tubing and provides instruction for removing the occlusion, then waits for the user to indicate that the occlusion is no longer present.

Figure 75D:
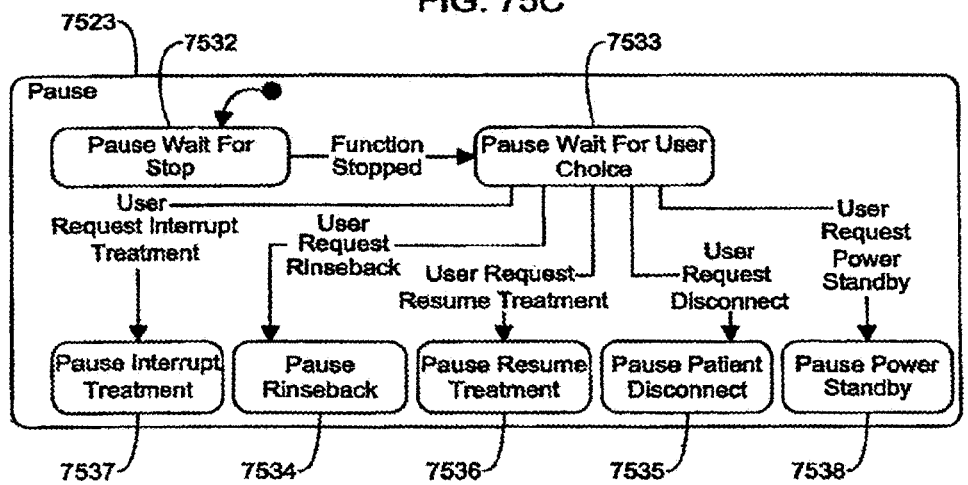

Referring to FIG. 75D, the Pause state 7523 will halt operation. Additionally, the patient can choose to perform additional activities. When the Pause operation has finished and the user chooses to resume this application, the history mechanism will return this application to the interrupted state. Following the Pause Wait for Stop state 7532, the Pause Wait for User Choice state 7533 presents options for the user and waits for the user to choose an option. In particular, the following options may be presented: Rinseback 7534, Patient Disconnect 7535, Resume Treatment 7536, Interrupt Treatment 7537, Power Standby 7538, and Resume Solution Infusion 7539.

Figure 75E:
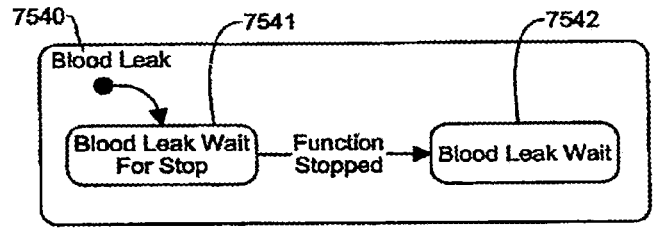

Referring to FIG. 75E, the Blood Leak state 7540 stops the current operation in state 7541 and notifies the patient that there is a nonrecoverable alarm in state 7542.

(9) Rinseback

The Rinseback application implements the process of returning the patient's blood and guiding the patient through disconnection from the extracorporeal circuit. This process occurs at the end of treatment. Treatment may end once the prescribed dialysis duration has elapsed, at any time as requested by the user, or due to a hazard detection by the system.

When the patient has requested that their blood be rinsed back, the system forces a FMS reading of the dialysate tank as discussed below to confirm that actual dialysate level. Next, the system begins sending fresh, heated, ultrapure dialysate across the dialyzer to send the blood back to the patient. At the same time, the blood pump is run slowly in reverse such that both the arterial and venous lines clear simultaneously. The prescribed rinseback volume includes the total volume of the blood tubing set and dialyzer plus additional dialysate volume to flush the patient access and rinse the tubing lines clear of nearly all blood traces.

After this volume has been delivered, the user may choose to infuse an additional smaller rinseback bolus. This may be done to counteract patient hypotensive sensations and/or return visible blood traces remaining in the tubing. The user can request additional rinseback boluses in 50 mL increments until, for example, the total additional bolus volume delivered reaches 500 mL. The limit may be selected to prevent operator misuse, leading to fluid overload. Furthermore, rinseback fluid delivery may be limited by fresh dialysate availability.

In order to complete rinseback as quickly as possible, the flow rate used may be as fast as reasonably tolerable by most patients' accesses and vasculature. A flow rate that is too high may create high pressures in the blood tubing set and lead to nuisance interruptions of the rinseback process. Further, the flow rate may approximate the flow from a saline bag that a nurse might hang to rinseback blood on other devices.

The air trapped in the blood pumps 13 (FIG. 4A) and the top of the dialyzer 14 must be segregated before any fluid can be pushed back along the arterial line 82 toward the patient. The system isolates any air trapped in the blood pump 13 and dialyzer header 14 by collecting this air in one of the blood pod pumps (e.g., the upper pump 23) and isolating that pod, while using the other blood pod pump (e.g., the lower pump 23) to flow dialysate back through the arterial line 82. Alternatively, the air is collected in lower blood pod pump 23 and the upper pump 23 is used to flow dialysate back through the arterial line 82. The steps to collect and isolate the air are: 1) Deliver both upper and lower blood pump chambers 23 toward the dialyzer 14 (this will force all the air in blood pumps 23 into the dialyzer 14, where it will collect at the top); 2) Fill a first blood pod pump 23 by pulling liquid and any air back from the dialyzer; 3) Fill a second blood pod pump 23 by delivering the liquid and any air in the first blood pod pump 23 through the two inlet valves 192 and 194 (FIG. 89) (this step sweeps any air in the first pod pump 23 along with the air from the dialyzer into the second pod pump 23); 4) Isolate any collected air in the second pod pump 23 by leaving it full and closing the inlet and outlet valves of the second pod pump 194, 195. 5) Use only the first blood pod pump to push fluid to the patient via the arterial blood line.

If air-in-line detector 33a detects air in the arterial line, the operator will be notified, and rinseback will continue down the venous line only, where air can be trapped by the air trap 19.

FIGS. 76A and 76B show an exemplary implementation of the Rinseback application. With reference to FIG. 76A, the Active state 7602 of the Rinseback application 7601 is the state in which Rinseback processing occurs. The state 7602 generates the event Rinseback Stopped 7603 on transitioning to Idle 7604.

With reference to FIG. 76B, the Monitor state 7605 monitors for Pause requests 7606, venous air in the blood tubing set 7607, dialysate leaks 7608, and dialysate production problems 7609.

The Administer Fluid state 7610 administers the infusion and monitors for occlusions, dialysate temperature out of limits, conditions of unavailable fluid and inlet water out of limits. The Arterial and Venous Infusion state 7611 pushes ultrapure dialysate across the dialyzer. Dialysate may be heated as it is pushed across the dialyzer. Arterial air and venous air may be monitored by air-in-line detectors 33a, 33b (FIG. 89). The Arterial Air Recovery state 7612 handles a recovery from an arterial air alarm. The Stop A&V Infusion state 7613 stops the infusion and posts an alarm to the GUI. The Arterial Air Resolution state 7614 waits for the user to indicate they are ready to continue with Venous-only Rinseback. The Venous Infusion state 7615 pushes ultrapure dialysate across the dialyzer. Again, dialysate may be heated as it is pushed across the dialyzer.

Therapy and Ultrafiltration Profiles

Ultrafiltration (UF) may be considered to be a process that removes water from the blood across a semi-permeable membrane of a dialyzer in the presence of either an osmotic or hydrostatic trans-membrane pressure gradient. It is a measure of the net amount of fluid that is removed from the patient's body while on dialysis. Typically, patients with renal failure receiving dialysis begin treatment sessions with some degree of fluid overload, manifested by their 'wet weight,' and have a goal of achieving their 'dry weight' (a weight representing a euvolemic state) by the end of treatment. UF can be measured as the amount of net fluid flow out of the dialyzer via the dialysate outflow path that exceeds the net fluid flow into the dialyzer via the dialysate inflow path. A system controller can adjust the UF flow rate to meet a prescribed net patient fluid removal goal over the planned duration of dialysis therapy. Generally, a goal of dialysis is to return a patient to his or her target weight—an established 'dry' weight based on the patient's particular physical and medical characteristics. The UF flow rate is primarily determined by the rate at which the UF pump draws fluid from the dialyzer when the blood pumps are circulating blood through the dialyzer. The activity of the UF pump is generally independent of the overall dialysate flow through the dialyzer, which is controlled by the inner and outer dialysate pumps. The UF flow rate may be subject to an upper safety limit for each treatment session, and may additionally be subject to an upper operational limit to avoid excessive hemo-concentration on the blood side of the dialyzer membrane during treatment. Furthermore, a clinician may modify a prescription for clinical reasons to limit the maximum UF rate. For example, the average UF flow rate may be set at less than or equal to about 10% of the blood flow rate through the dialyzer. The maximum instantaneous UF flow rate, on the other hand, may be somewhat higher (for example, about 15% of the instantaneous blood flow rate) because of various interruptions in ultrafiltration that may occur during a dialysis treatment. As a first approximation, the UF pumping goal can be considered to be the amount of fluid removal desired, plus volume of dialysate or other electrolyte solution used to rinse back blood to the patient at the end of therapy, minus the volume of priming solution discarded from the blood circuit (blood tubing, dialyzer, blood pumps, air trap, etc.) at the start of treatment when the patient's blood is being pulled into these components of the hemodialysis machine. The UF pumping goal may also be adjusted up to account for fluid infusions during treatment (IV medications such as heparin, oral fluid intake, IV solution infusions, etc. . . . ), or adjusted down to account for fluid losses during treatment (such as, e.g., gastrointestinal or urinary fluid losses). The rinseback volume should be sufficient to deliver nearly all of the patient's blood back into his or her circulation, by filling the blood circuit with dialysate, and optionally adding an additional nominal rinseback volume.

A system controller can set the UF pumping rate by dividing the UF pumping goal by the estimated treatment time. In some embodiments, the UF pumping rate may be limited by the maximum prescribed UF pumping rate, the blood pumping rate, as well as by the available flow rate of the dialysate flowing through the dialyzer via the inner and outer dialysate pumps.

In addition, in some embodiments, the system controller may adjust the UF pumping rate to account for planned periodic pauses in dialysis and ultrafiltration. For example, dialysis may be suspended periodically to allow one or more controllers to perform maintenance functions on components of the hemodialysis machine. In one aspect, the hemodialysis system may be programmed to pause dialysis every 50-100 pump strokes of the outer or inner dialysate pumps to purge air from an inline ultrafilter, to run integrity checks on valves in the system, and to perform FMS-based volume measurements of the dialysate tank to ensure an accurate accounting of dialysate in the tank. During this process, the outer, inner and UF pumps may be halted, while the blood pumps continue to pump blood on the blood side of the dialyzer. These maintenance functions typically may take several seconds to a minute or more. The duration of maintenance procedures may occasionally be greater, for example, if the system determines that additional dialysate should be produced and placed in the dialysate tank prior to resumption of dialysis. The system controller can account retrospectively for variable maintenance periods, as well as for projected future maintenance periods during treatment to adjust the UF pumping rate to meet the UF pumping goal.

In an embodiment, the hemodialysis system is also capable of performing periodic backflushing of dialysate solution through the membrane of the dialyzer. Periodic backflushing may be useful, for example, in keeping proteinaceous or other debris from accumulating on the dialyzer membrane, and maintaining or extending its operational life. In addition, a backflushing feature may allow the use of high-flux dialyzers in convective filtration (such as, e.g., hemodiafiltration), in which high UF flow rates are used to enhance the flow of larger solutes across a dialyzer membrane (through convective flow or other mechanisms). Backflushing can be accomplished, for example, by bypassing the inner dialysate pumps and balancing circuit and having the outer dialysate pump push a pre-determined amount of fresh dialysate (e.g., about 100-200 ml of fluid) into the dialyzer via the dialysate inlet of the dialyzer, while closing the appropriate valves on the dialysate outflow path of the dialyzer. The controller may be programmed to perform a backflushing operation, for example, every 10 to 40 minutes during a dialysis treatment session. The UF pump flow rate may be adjusted between backflushes to recover over a defined period of time the amount backflushed plus an amount of fluid to maintain a pre-determined base rate of ultrafiltration. The controller may be programmed to perform backflushing at pre-determined intervals of time during treatment; and preferably, the controller is programmed to have the UF pump pull off the fluid necessary for a backflushing operation prior to the backflush. Optionally, the controller may delay a backflush procedure if the UF pump has not met its expected pumping volume by the time a backflush procedure is scheduled to occur. Optionally, the timing of each backflush procedure may be reset at a pre-determined time interval from the last-performed backflush, so that the interval between backflushing operations remains relatively constant.

In an embodiment, backflushing may be terminated if the amount of fluid removed from the patient exceeds a pre-determined threshold volume at any time, or if the controller predicts that it will be exceeded within the next backflush period. For example, the controller can estimate whether the volume ultrafiltered at the current rate will likely exceed the threshold amount before the next backflushing operation. In another embodiment, the controller may terminate a backflush procedure if it occurs within a pre-determined amount of time before the expected end of treatment. For example, the controller may be programmed to terminate backflushing if it occurs within 50% of a backflush duration of the expected end of treatment.

In one embodiment, the user may request a solution infusion via a user interface on the hemodialysis machine. A solution infusion may be characterized as a pre-determined volume of dialysate solution that the system controller can deliver to the patient across the dialyzer membrane. The user may be permitted to request and obtain two or more solution infusions during the course of a dialysis treatment. In an embodiment, an entry by the user on a user interface device (e.g., touch-sensitive graphical user interface) requesting a solution infusion automatically triggers the controller to reset the UF pumping goal to the amount already pumped, and set the remaining UF pumping rate to zero. If the user has obtained fluid through a request for a solution infusion, the volume infused may be subtracted from the UF pumping goal, or the amount of fluid that the user planned to have removed. In one aspect, the user has the option to reset the UF pumping goal to the original UF pumping goal, which may be interpreted by the controller as a command to remove from the patient the originally planned volume of fluid plus the amount of the solution infusion. In this case, the UF pumping rate is adjusted to ultimately remove the additional fluid infused through the solution infusion. Optionally, the user may set the UF pumping goal to the original UF pumping goal minus the amount infused. This optional mode allows a user to preserve the volume of fluid gained from a solution infusion during treatment.

Both backflushing and solution infusions may be performed by turning off the inner dialysate pumps and the UF pump, and pushing dialysate fluid across the dialyzer membrane using the outer dialysate pump. In a preferred embodiment, the outlet valves of the blood pumps may be closed during a solution infusion in order to maximize the amount of dialysate solution being pushed through the venous blood line into the patient. In contrast, it may be preferable to keep the outlet valves of the blood pumps open during a backflushing procedure to help take up the volume of dialysate being backflushed.

In another embodiment, a user may enter a new UF pumping goal at any time during treatment, adjusting, for example, for liquids he or she may consume during treatment, or for intravenous infusions of medications, or for unanticipated gastrointestinal or urinary fluid losses. The system controller may then re-calculate and reset the UF pumping rate to achieve the new UF pumping goal before the remaining treatment time has expired. If the new UF pumping goal is less than or equal to the ultrafiltration volume already pumped, then the UF pump may be halted for the remainder of the treatment session.

Additionally, the system controller may be programmed to automatically adjust the UF pumping rate upon the occurrence of an unplanned addition of fluid to or loss of fluid from the user. For example, the system controller may be programmed to account for the infusion of a pre-determined amount of fluid to the patient when a heparin bolus is administered at the start of treatment. The amount of this fluid is generally a function of the volume of blood tubing and blood pump conduit between the location where heparin enters the blood pump and the intravenous catheter connected to the blood tubing. In general, the most direct route to the patient is via the arterial blood tubing, and in one embodiment, this volume can be approximately 65 cc's. However, if air is detected at the air-in-line detector of the arterial tubing, a system controller may be programmed to stop the blood pump from infusing heparin via this route, cause the blood pump to pull the fluid (and air) back toward the blood pump, and then configure the blood pump valves to cause the heparin to be administered to the patient via the venous tubing. In one embodiment, the venous tubing route to the patient from the blood pump includes the blood-side volume of the dialyzer, as well as the volume of the air trap in the blood circuit. In this case, the volume of fluid necessary to deliver a bolus of heparin to the patient may be significantly greater than via the arterial tubing route. (In one embodiment, this venous route may require as much as 260 cc's of fluid to deliver the heparin bolus to the user). Thus, the system controller can be programmed to adjust the UF pumping goal to be greater than the original goal if the alternate venous tubing route is used for the heparin bolus.

In some embodiments, the maintenance periods are timed according to the number of dialysate pump strokes, and their number may therefore increase or decrease depending on the dialysate flow rate through the dialyzer, as well as the total planned treatment time. The dialysate flow rate can vary for each patient, and can be a function of the blood flow rate achievable, the rate of dialysate production and storage, and the duration of a dialysis therapy desired by the patient. The system controller may calculate the predicted cumulative effect of the number and length these delays in determining the time of actual treatment, and adjust the UF pumping rate accordingly. In an embodiment, the controller may be programmed to set the UF pumping rate at a calculated base rate plus an additional factor (e.g., about 5-10% above the basal rate) in order to ensure that the UF pumping goal is reached before the predicted end of therapy. If a maximum UF pumping rate is reached, then the controller may increase the total planned treatment time and so inform the user via a message or other alert on the graphical user interface.

In addition, the system controller may adjust the UF pumping rate to account for unanticipated pauses in dialysis and ultrafiltration. For example, if the monitored temperature of the dialysate exiting the ultrafilter is outside of a pre-determined range (e.g., above 41 deg.C.), the output of the outer dialysate pumps may be diverted to drain or to the dialysate tank until the monitored temperature of the dialysate returns to the specified range. During this time, the system may enter a state (e.g., a 'DivertHot' state) in which the inner dialysate pumps and UF pump are paused, and the inner pump valves are closed. Furthermore, the system may account for any pause in dialysis caused by a user request for dialysate solution infusion, by a user request to pause dialysis treatment, or by alarm states that may occur (e.g., air-in-line detection or fluid leaks). Calls for a solution infusion may prompt the system to undergo a maintenance check of the dialysate tank level after the infusion. Thus, a solution infusion state may trigger an additional delay in dialysis treatment. Following any of these or other pauses in dialysis treatment, the system controller may then adjust the UF pumping rate upon resumption of dialysis to meet the originally calculated UF pumping goal.

In an embodiment, the system controller may periodically perform a UF re-assessment, recalculating the remaining treatment time as well as the remaining UF pumping volume periodically during therapy (e.g., about every 20 minutes), to adjust the UF pumping rate and to ensure that the UF pumping goal can be achieved. The remaining treatment time may be extended, for example, because the cumulative duration of one or more suspensions of dialysis has exceeded a minimum value. In an embodiment, the UF re-assessment can be programmed to occur in approximate 20-minute intervals. At the time of re-assessment, the controller will have tracked (1) the amount of fluid already pumped by the UF pump, (2) the UF pumping goal (whether as originally entered or updated by the user during treatment), and (3) the remaining treatment time. From this data, the controller may then adjust the UF pumping rate (with or without the 5-10% additional margin described above) to ensure that the UF pumping goal will be achieved by the end of treatment. Once the UF pumping goal has been reached, the system may cease further ultrafiltration and backflushing.

The total available treatment time may be limited, however, because of other system constraints or because of medical constraints. For example, to reduce the risk of complications, total treatment time may be limited to about 10 hours from the start of a dialysis treatment session, and to about 16 hours from the time that anything (such as reverse osmosis water) is brought into the hemodialysis system. Should the calculated treatment time approach a maximum, the system controller may default to a lowered UF pumping goal, and so inform the user via the graphical user interface.

Thus, during dialysis treatment, the system may be programmed to:
1) stop ultrafiltration if the user modifies the UF pumping goal down to the UF volume already removed;
2) lengthen the planned total treatment time if the user modifies the UF pumping goal above that which can be achieved at the maximum allowable UF pumping rate;
3) adjust the UF pumping rate up to reach the UF pumping goal if the user decreases the planned treatment time, or change the UF pumping goal downward if the maximum UF pumping rate has been reached;
4) reset the UF pumping goal to the UF volume actually removed in response to a user command to suspend further ultrafiltration (unless the UF pumping goal is later reset by the user); and
5) in response to a user command for a solution infusion, reset the UF pumping goal to the UF volume actually removed minus the solution infusion volume (unless the UF pumping goal is later reset by the user).

FIG. 76C illustrates an example of fluid movements across a dialyzer during a typical course of dialysis. In this example, the patient has entered a target volume of net fluid to be removed of 400 cc's (400). At the start of treatment, some of the priming solution in the blood circuit is discarded to drain as blood is drawn into the blood circuit from the patient. The system at time zero automatically withdraws approximately 130 cc's of priming fluid (402) from the blood side of the dialyzer to load the blood circuit with the patient's blood. The prime discard volume is a function of (among other things) the hold-up volume of the blood circuit components (tubing, dialyzer, blood pump, air trap, etc.), minus a safety factor to prevent excessive hemo-concentration in the dialyzer. Some dilution of the patient's blood in the blood circuit may be acceptable in order to avoid possible complications through the prime discard operation. For example, the holdup volume of the blood circuit may be about 257 cc's, but the prime discard volume may only be about 130 cc's. At the end of treatment, the controller may direct the outer dialysate pump to push a volume of dialysate approximately equal to the entire hold-up volume of the blood circuit components (e.g., in this case about 257 cc's.) to move the blood in the blood circuit back to the patient. Optionally, a larger amount of fluid may be rinsed back through the dialyzer membrane, in order to ensure that most of the red cells in the blood circuit are returned to the patient. For example, an additional nominal rinseback volume of about 100 cc's may be pushed through. Thus, in an embodiment, a total rinseback volume of dialysate amounting to about 357 cc's may be pushed to the blood side by the outer dialysate pump through the dialyzer membrane at the end of treatment (404). In this case the UF pumping goal (408) includes only 227 cc's (406) of the 357 cc rinseback volume, because the remaining 130 cc's (404) is accounted for by the initial prime volume discarded (402) at the start of treatment. From these pre-determined conditions (which are a function of the volume of the blood circuit components, the amount of prime volume to be discarded, and the nominal rinseback volume chosen to assure nearly complete return of the patient's blood cells at the end of treatment), a system controller can calculate a UF pumping goal of about 630 cc's (408), which in this case is the sum of the fluid the patient desires to have removed (400 cc's) plus that portion of the of fluid returned in the rinseback operation that is not accounted for by the prime volume initially discarded (about 227 cc's). In this way, by the end of dialysis treatment, a sufficient amount of ultrafiltration has taken place to account for the rinseback volume planned at the end of treatment, minus the amount already removed through prime discard (402). The system controller can therefore calculate and set the UF pumping rate needed to reach the UF pumping goal over the anticipated total treatment time (which is approximately 120 minutes in this example). In this embodiment, the priming volume discarded at the start of treatment, and the rinseback volume re-infused at the end of treatment are performed by the outer dialysate pump rather than the UF pump. In other embodiments, the UF pump can be used to perform some or all of these tasks.

FIG. 76D illustrates the fluid movements across a dialyzer during a course of treatment that includes periodic backflushing through the dialyzer membrane. In this example, the expected net fluid to be removed is 1000 cc's (410), the priming volume to be discarded is about 130 cc's (412), and the rinseback volume is about 357 cc's (414). In the example shown, the outer dialysate pump pushes a volume of dialysate (416) (e.g., approximately 200 cc's) back across the dialyzer membrane about every 30 minutes during treatment. In this case each backflush operation (e.g., 416) is preceded by UF pumping (e.g. 417) that is sufficient to account for the following backflush. In one aspect, a system controller may calculate the initial UF pumping rate (420) as: [the base UF pumping rate] plus [the anticipated backflush volume divided by the backflush period]. The base UF pumping rate may be calculated as: [the volume of fluid to be removed from the patient (410), plus the rinseback volume (414) at the end of treatment, minus the prime volume discarded (412) at the start of treatment] divided by [the total treatment time]. (Optionally, a margin, such as 2-10% of the base rate, may be added to this base UF pumping rate to ensure completion of ultrafiltration before the end of treatment). In one embodiment, before the end of treatment, the system controller may be programmed to terminate backflushes at a time (418) early enough to ensure that fluid removed from the patient does not exceed at any time the fluid removal goal (410) plus the rinseback volume (414). Alternatively, the controller may be programmed to prevent fluid from being removed from the patient at any time in an amount that exceeds the fluid removal goal (410) plus the rinseback volume (414), minus the prime discard volume (412). After the last backflush operation, the controller may then adjust the UF pumping rate (422) to the base UF pumping rate calculated above, with or without the added margin. Alternatively, the controller may calculate the difference between the UF pumping goal (424) and the UF volume actually pumped by the time of the last backflush operation (418), and divide this amount by the remaining treatment time. The controller may calculate the UF pumping goal (424) as the patient fluid removal goal (410), plus the total volume of backflushes (approximately 1600 ccs' in this example), plus the rinseback volume (414), minus the prime discard volume (412). The terminal UF pumping rate (422) may then be calculated by dividing this quantity by the remaining treatment time (treatment end time at 424 minus backflush end time at 418).

FIG. 76E illustrates the fluid movements across a dialyzer during a course of therapy in which the user requests a solution infusion of 200 cc's forty minutes into therapy, and requests resumption of ultrafiltration after a twenty minute delay. In this scenario, the user requests re-establishment of the original UF pumping goal, in which the controller is programmed to have the UF pump reclaim from the blood compartment an amount equal to the solution infusion by the time treatment has ended. In this example, the patient's fluid removal goal is set at 400 cc's (426). At the start of treatment, the expected UF pumping goal is about 630 cc's (428) (i.e., the fluid removal goal of 400 cc's plus the rinseback volume of about 357 cc's, minus the prime discard volume of about 130 cc's). However, at the 40-minute point, the user initiates a solution infusion of 200 cc's (430). In one embodiment of the invention, the controller is programmed to halt further UF pumping. The user has the option to re-establish the originally intended UF pumping goal, and in this example, does so at the 60-minute point in treatment. Optionally, the user may choose an alternate UF pumping goal for resumption of ultrafiltration, as long as it has not already been achieved, and as long as the maximum permissible UF pumping rate will not be exceeded. In response to a user entry of the original UF pumping goal, the controller may be programmed in one embodiment to perform a total volume of ultrafiltration that includes the original UF pumping goal plus the amount of solution infused at the 40-minute point. To set the UF pumping rate under this scenario, for example, the controller may add the volume infused (i.e., 200 cc's) to the UF pumping goal (630 cc's) to yield a new UF pumping goal of 830 cc's at the end of treatment (432). The new UF pumping rate (434) may then be calculated to be the new UF pumping goal (432) minus the accumulated UF pumping volume at resumption of therapy (436), divided by the estimated remaining treatment time.

In other embodiments, the system controller may adjust the UF pumping rate periodically to catch up with temporary or unexpected suspensions of dialysis, and the catch-up period may be programmed to occur before the next scheduled maintenance pause (subject to the maximum UF pumping rate, set by prescription or otherwise). Also, in cases in which backflushing is enabled, the controller may adaptively reduce the number of backflushes depending on the available remaining ultrafiltration volume. For example, the high limit for ultrafiltration volume may be set to be no more than a small percentage above the patient's fluid loss goal, plus the total of the backflush volumes, plus the rinseback volume, in order to keep the net fluid loss by the patient at or only slightly above the final rinseback volume plus the patient's fluid loss goal.

In other embodiments, the system controller may be programmed to vary the UF pumping rate during treatment. For example, the controller may be programmed to set the UF pumping rate higher at the start of therapy (at a time in which it is presumed that the patient may be relatively fluid overloaded and able to comfortably sustain a higher rate of fluid removal), and to reduce the UF pumping rate later in the course of therapy, keeping the average UF pumping rate sufficient to meet the UF pumping goal by the end of therapy. In other cases, more complex patterns of ultrafiltration may be desirable, and the controller may be programmed to accommodate such patterns when setting the UF pumping goal. In some embodiments, a UF pumping rate profile may be individualized for a particular patient as part of the patient's prescription parameters, initially set and modifiable by the patient's physician at any time.

FIG. 76F is an exemplary screen view for display on a graphical user interface that summarizes the results of a dialysis treatment session. At the end of treatment, the system controller will have tallied—and may display—the total dialysis time 440, the total amount of fluid lost by the patient (reflected in the ending weight) 444, the final UF pumping goal after any adjustments 446, the amount of actual ultrafiltration 448, the volume of fluid delivered to the patient at the end of treatment to account for the priming volume of the blood circuit and a nominal rinseback amount 450, any net adjustments of the ultrafiltration 452 and the corresponding amount of fluid infused or withdrawn 454. The patient's starting weight 442 may also be displayed to provide a convenient reference point for the patient. This summary information may assist the patient and/or patient's physician in planning his or her next dialysis treatment.

The Dialysate Tank Empty Alarm state 7616 will stop Rinseback and notify the patient there is not enough dialysate to continue with Rinseback. A dialysate tank low alarm may be posted to the GUI. Fluid production may be restarted, if stopped. The Wait for Fluid state 7617 waits for fluid to become available. Once the dialysate tank volume reaches a certain level, e.g., 300 ml, a Dialysate Tank Filled event 7618 may be generated. If the tank has not reached the given level in a selected period of time, e.g., 2 minutes, an error event may be generated.

It may be possible to improve the accuracy of liquid volume determinations in the dialysate tank by using at least two independent methods of measurement. One method, for example, counts the number of pump chamber strokes that deliver liquid to the tank, and subtracts the number of pump chamber strokes that withdraw fluid from the tank. Assuming that each pump stroke moves a known, fixed quantity of liquid, a cumulative net liquid volume in the tank can be tracked. A second exemplary method involves taking an FMS measurement by charging a reference chamber from a reservoir, measuring the resulting pressure, and then venting the reference chamber to the dialysate tank. The volume of air in the dialysate tank can then be calculated from the equalized pressure between the tank and the reference chamber. A third exemplary method involves taking an FMS measurement by charging a reference chamber to a predetermined pressure, and then venting the reference chamber to the dialysate tank. The volume of air in the dialysate tank can then be calculated from the equalized pressure between the tank and the reference chamber. Although an FMS-based method may yield more accurate results, it may also be more time-consuming. Thus it may be desirable to have the system controller keep track of the tank volume continuously by pump stroke accounting, and have it perform an FMS measurement periodically to verify the ongoing accuracy of the pump stroke accounting. A controller applying one or both of these methods can use this data to determine whether fluid should be added to or removed from the tank, and whether the fluid level is below the minimum deemed necessary to safely continue therapy.

The following section describes a method of measuring the volume of dialysate in a container by a first method of counting known volumes pumped into or out-of the container, and a second method using an improved FMS measurement. The improved FMS measurement is used periodically to correct the first method, if necessary. The improved FMS method assumes a form of an equation that relates FMS pressure drop and the gas volume in the container. In one embodiment, constants in the equation are correlated to measured FMS pressure drop and measured volumes during a calibrated filling of the container.

Pump stroke accounting operates by polling the pumps that can deliver fluid into and out of the tank, continuously accounting for completed strokes and discounting incomplete strokes due to occlusions. New fluid can be supplied to the dialysate tank by the mixing pump 180 (FIG. 3A) and the bicarbonate and acid pumps 183, 184, and pump strokes may be tallied when the outflow valve 155 to the tank 169 is registered as being open and the mix drain valve 154 is registered as being closed. The state of the valves can be monitored by reading the valve state via the I/O subsystem; or in a simpler arrangement, the valve state can be assumed according to the particular operation being performed at the machine level. Fluid can be removed from the dialysate tank by the outer dialysate pump 159 when the dialysate drain valve 151 is open and the tank recirculation valve 152 and disinfection valve 153 are closed. Fluid is also removed by the outer dialysate pump 159 when the disinfect path is open (tank recirculation valve 152 and dialysate drain valve 151 are closed, while the disinfection valve 153 and mix drain valve 154 are open). The pumps 180, 159 can be polled for completed strokes, and strokes can be discounted if a chamber fill occlusion is detected. In a second exemplary method, incomplete strokes by the mixing pump 180 are discounted, but all incomplete strokes by the dialysate pump 159 are counted as full strokes. The incomplete strokes are discounted only on the fill side in order to bias the measured tank level low, so the dialysate tank is more likely to be overfilled than empty. Should an occlusion be detected with any of the pumps, the pump stroke accounting value can be flagged as suspect or invalid, and a tank volume measurement can be taken using an independent method, for example the FMS method.

The FMS method of measuring the air (and therefore the liquid) volume in the dialysate tank is based on Boyle's law. A reference volume is pressurized and then vented into the closed dialysate tank, the volume then being calculated from the final pressure reached by the combined reference and tank air volumes. This method may be prone to some error because of delays in or incomplete closures of the valves that communicate with the tank, or because of physical distortion of the tank under pressure. The measurement may also take a substantial amount of time, which could reduce the efficiency of dialysate delivery for dialysis. Thus some of the physical characteristics of the dialysate tank and valves may introduce measurement error if the classical FMS equation $P1V1=P2V2$ is used, e.g., distortion of the dialysate tank may introduce error in a measurement using this equation as a model of the system.

The FMS measurement method may be improved by using a third order equation, which may increase the accuracy of the volume determination at the target tank fluid level of 50-75%. Such an equation can take several forms, and is based on fitting experimentally derived pressure-volume data to a curve defined by the third-order equation. The measurement of the volume in the dialysate tank can be calibrated, for example, by incrementally filling the tank and performing FMS measurements on the tank at each increment. Data points are collected and a mathematical model correlating the FMS data to the actual fluid volume within the tank can then be generated. For example, the controller can perform an "AutoCal" or other calibration function that empties the tank, and then fills it incrementally with seven 300 ml volumes of liquid, making an FMS volume measurement with each incremental fill. These measurements can then be inputted in the form of a vector into a function that calculates the coefficients for the third order equation using a least squares algorithm, for example, to minimize the error between the observed and predicted volumes. The function may then update the coefficients used in the third order FMS equation that are stored in a calibration data file on a hard drive or in the system memory. Thereafter, the third order equation, including the coefficient values determined during calibration, may be used with an FMS measured pressure difference value to determine a volume of liquid in the dialysate tank.

In one illustrative embodiment, the FMS measurement is not used for primary dialysate tank level determination, e.g., because the measurement takes approximately 20 seconds to perform and performing this measurement on every outer pump stroke could degrade pumping capacity. Instead, a primary determination of the volume of dialysate in the dialysate tank is computed based on an accounting of the number of pump strokes used to place dialysate into the tank and the number of pump strokes used to remove dialysate from the tank. In addition, FMS is used to measure the volume of dialysate in the dialysate tank, for example, about every 20 minutes during treatment, or approximately once for every 100 pump strokes of dialysate placed into the dialysate tank. The FMS determination of the dialysate volume is compared to the volume predicted by the accounting of the number of pump strokes of dialysate into and out of the dialysate tank. If the difference between the measured volume and the volume from pump stroke accounting is greater than a threshold amount (e.g., 100 ml), an error is returned and therapy may be discontinued. If the difference is smaller (e.g., less than 100 ml), then the accounting volume is adjusted and updated to the newly measured value and therapy may be continued.

As mentioned above, in this embodiment, a third order equation is used to determine volume in the dialysate tank. Coefficients for the third order equation are determined during a calibration function by providing known quantities of liquid to the tank and effectively plotting the liquid volumes for a plurality of measured pressure differences and minimizing the error between the curve representing the known liquid volumes and the measured pressure differences and a curve representing calculated volumes and measured pressure differences using the third order equation. In one example, a pressure measurement may be taken every time an additional fixed amount of liquid (e.g., 150 or 300 ml) is placed into the dialysate tank, where the calibration process is limited to a typical operating range of the dialysate tank volume (e.g., between 1-2 liters of a 2-liter tank). The FMS pressure differences measured at each volume step are plotted and the sum of the squares of the errors between the known volume/pressure difference at each step and the calculated volume/pressure difference using the third order equation at each step is minimized to determine the coefficients of the third order equation which are stored in a calibration data file and used in future FMS determinations of liquid volume in the dialysate tank. The accuracy of the coefficients may be checked, e.g., by again filling the dialysate tank with known volumes of liquid, measuring the liquid volume using the FMS pressure measurements and the third order equation, and comparing the known and determined volumes. If a difference between the known and determined volumes is below a threshold, e.g., a difference of 5% or less, a determination may be made that the calibration process was accurately done and the coefficients for the third order equation can be used for accurate measurement.

In one illustrative embodiment, to perform the calibration function and determine the coefficients for the third order function, the system initially empties the dialysate tank, and adds 300 ml amounts of liquid to the tank in seven intervals. After each 300 ml interval, the system makes an FMS pressure difference measurement of the dialysate tank, e.g., determines a pressure difference before and after the tank is fluidly coupled to the pressurized reference chamber. These measurements are inputted in the form of a vector into a function that calculates the coefficients for a least square fit curve for the third order equation that closely approximates a curve defining the known volumes for each of the seven fill intervals.

In this illustrative embodiment, the third order function f(x) is shown in Equation 1, $$f(x) = ax_i^3 + bx_i^2 + cx_i + d \quad (1)$$

where f(x) gives the calculated fluid volume in the dialysate tank based on the measured FMS pressure difference, x is the measured FMS pressure difference, and a, b, c and d are coefficients to be determined in the calibration process. (Note that the liquid volume in the dialysate tank is equal to the total tank volume less the gas volume. Thus, by determining a gas volume in the tank, a liquid volume in the tank is determined.)

To obtain the least square fit of the third order equation to the actual fluid volumes for each measured FMS pressure difference, the error [ε] of third order equation f(x) in relation to the known volume/measured pressure difference curve is determined and minimized. The solutions that minimize error are the coefficients a, b, c and d for the third order equation. Equation (2) gives the error ε in this embodiment $$\varepsilon = \sum_{i=1}^{n} (y_i - f(x_i))^2 \quad (2)$$

where y is the known liquid volume, $x_i$ is the measured pressure difference between the initial pressure of the dialysate tank before being coupled to the reference chamber and the final pressure after being coupled to the reference chamber (i.e., the FMS pressure difference), i is the current iteration, and n is the total number of instances. By inserting the third order function for f(x) of Equation 1 into Equation 2 we get Equation 3

$$\varepsilon = \sum_{i=1}^{n} (y_i - ax_i^3 - bx_i^2 - cx_i - d)^2 \quad (3)$$

To find the minimum error, the partial derivative of the error function is taken with respect to each coefficient and set equal to zero as shown in Equation 4.

$$\text{For } \varepsilon \to \min \frac{\partial \varepsilon}{\partial a} = \frac{\partial \varepsilon}{\partial b} = \frac{\partial \varepsilon}{\partial c} = \frac{\partial \varepsilon}{\partial d} = 0 \quad (4)$$

After substituting Equation 3 into Equation 4, Equation 5 results.

$$\frac{\partial \varepsilon}{\partial a} = 2 \cdot \sum_{i=1}^{n} (y_i - a_i^3 - bx_i^2 - cx_i - d) \cdot (x_i^3) = 0 \quad (5)$$

$$\frac{\partial \varepsilon}{\partial b} = 2 \cdot \sum_{i=1}^{n} (y_i - a_i^3 - bx_i^2 - cx_i - d) \cdot (x_i^2) = 0$$

$$\frac{\partial \varepsilon}{\partial c} = 2 \cdot \sum_{i=1}^{n} (y_i - a_i^3 - bx_i^2 - cx_i - d) \cdot (x_i) = 0$$

$$\frac{\partial \varepsilon}{\partial d} = 2 \cdot \sum_{i=1}^{n} (y_i - a_i^3 - bx_i^2 - cx_i - d) \cdot (1) = 0$$

From the partial derivatives, the following set of linear equations results, as shown in Equation 6.

$$\sum_{i=1}^{n} y_i \cdot x_i^3 = a \cdot \sum_{i=1}^{n} x_i^6 + b \cdot \sum_{i=1}^{n} x_i^5 + c \cdot \sum_{i=1}^{n} x_i^4 + d \cdot \sum_{i=1}^{n} x_i^3 \quad (6)$$

$$\sum_{i=1}^{n} y_i \cdot x_i^2 = a \cdot \sum_{i=1}^{n} x_i^5 + b \cdot \sum_{i=1}^{n} x_i^4 + c \cdot \sum_{i=1}^{n} x_i^3 + d \cdot \sum_{i=1}^{n} x_i^2$$

$$\sum_{i=1}^{n} y_i \cdot x_i = a \cdot \sum_{i=1}^{n} x_i^4 + b \cdot \sum_{i=1}^{n} x_i^3 + c \cdot \sum_{i=1}^{n} x_i^2 + d \cdot \sum_{i=1}^{n} x_i$$

$$\sum_{i=1}^{n} y_i = a \cdot \sum_{i=1}^{n} x_i^3 + b \cdot \sum_{i=1}^{n} x_i^2 + c \cdot \sum_{i=1}^{n} x_i + d \cdot \sum_{i=1}^{n} 1$$

The linear equations of Equation 6 are put into a matrix, as shown in Equation 7.

$$\begin{bmatrix} \sum_{i=1}^{n} x_i^6 & \sum_{i=1}^{n} x_i^5 & \sum_{i=1}^{n} x_i^4 & \sum_{i=1}^{n} x_i^3 \\ \sum_{i=1}^{n} x_i^5 & \sum_{i=1}^{n} x_i^4 & \sum_{i=1}^{n} x_i^3 & \sum_{i=1}^{n} x_i^2 \\ \sum_{i=1}^{n} x_i^4 & \sum_{i=1}^{n} x_i^3 & \sum_{i=1}^{n} x_i^2 & \sum_{i=1}^{n} x_i \\ \sum_{i=1}^{n} x_i^3 & \sum_{i=1}^{n} x_i^2 & \sum_{i=1}^{n} x_i & n \end{bmatrix} \cdot \begin{bmatrix} a \\ b \\ c \\ d \end{bmatrix} = \begin{bmatrix} \sum_{i=1}^{n} y_i \cdot x_i^3 \\ \sum_{i=1}^{n} y_i \cdot x_i^2 \\ \sum_{i=1}^{n} y_i \cdot x_i \\ \sum_{i=1}^{n} y_i \end{bmatrix} \quad (7)$$

And an augmented matrix is formed from Equation 7, as shown in Equation 8.

$$\begin{bmatrix} \sum_{i=1}^{n} x_i^6 & \sum_{i=1}^{n} x_i^5 & \sum_{i=1}^{n} x_i^4 & \sum_{i=1}^{n} x_i^3 & \bigg| & \sum_{i=1}^{n} y_i \cdot x_i^3 \\ \sum_{i=1}^{n} x_i^5 & \sum_{i=1}^{n} x_i^4 & \sum_{i=1}^{n} x_i^3 & \sum_{i=1}^{n} x_i^2 & \bigg| & \sum_{i=1}^{n} y_i \cdot x_i^2 \\ \sum_{i=1}^{n} x_i^4 & \sum_{i=1}^{n} x_i^3 & \sum_{i=1}^{n} x_i^2 & \sum_{i=1}^{n} x_i & \bigg| & \sum_{i=1}^{n} y_i \cdot x_i \\ \sum_{i=1}^{n} x_i^3 & \sum_{i=1}^{n} x_i^2 & \sum_{i=1}^{n} x_i & n & \bigg| & \sum_{i=1}^{n} y_i \end{bmatrix} = \begin{bmatrix} a \\ b \\ c \\ d \end{bmatrix} \quad (8)$$

A least square fit function uses the augmented matrix in Equation 8 to solve for the coefficients of the third order equation. Specifically, the AutoCal function first declares two vectors and inputs in them the measured pressure differences and the known volume values for each fill and measurement interval. AutoCal then calls a leastSquareFit function, which calls an inputMatrix function to make a matrix, a makeResutVector function to make the result vector for that matrix, an augmentedMatrix function to combine the two into an augmented matrix, a triangularMatrix function to reduce the augmented matrix into a triangular matrix (matrix with only one pivot per column), a reduceEchelonForm function to reduce the triangular matrix into its echelon form (matrix with only one pivot per row and column) and a coefficients function to update and display the calculated coefficients. inputMatrix and makeResultVector perform the summations before inputting the pressure difference and volume values so that the end augmented matrix only has numbers.

Some of these operations called by the leastSquareFit function call smaller functions as well; inputMatrix calls sumVectorPower, triangularMatrix calls swapRows, normalizeRow, subtractRows, and absolute Value, and reduceEchelonForm calls backwardsMultiply. inputMatrix inputs summation terms into a matrix. makeResultVector inputs summation terms into the result vector for the augmented matrix. augmentedMatrix converts the 4×4 matrix and the result vector into an augmented matrix. triangularMatrix reduces an augmented matrix into a triangular matrix. reduceEchelonForm reduces a triangular matrix to Echelon form by backwards multiplication. coefficients updates the default coefficients to the new ones and displays them. sumVectorPower performs a summation of the elements of a vector raised to the desired power. swapRows swaps the elements from two rows in a matrix. normalizeRow divides all the elements of a row in a matrix by the first element, making that element equal one. substractRows subtracts the elements in one row from the corresponding ones from another. absolute Value returns the absolute value of a number. backwardsMultiply subtracts one row from another after multiplying one of the rows by the integer needed so that the subtraction makes one of the elements in the row equal zero.

Having determined the values for the coefficients a, b, c, and d, the control system may use the third order equation f(x) along with the measured FMS pressure difference to determine the liquid volume in the dialysate tank. That is, for a given FMS measurement, f(x) of Equation 1 calculates the liquid volume using the values for a, b, c and d determined in the calibration process.

The Occlusion Alarm state 7619 will stop Rinseback and notify the patient there is an occlusion, e.g., by posting an occlusion alarm to the GUI. The Occlusion Resolution state 7620 waits for the patient to clear the occlusion.

The Dialysate Temperature Alarm state 7621 will stop Rinseback and notify the patient the dialysate temperature is out of range, e.g., by posting a temperature alarm to the GUI. The Recirculate Dialysate state 7622 allows the machine to recover from a scenario where the dialysate temperature is out of specification. At the same time, blood may continue to circulate to prevent clotting. In this state, dialysate may be routed directly to drain as the machine attempts to bring the limits within range.

The High Inlet Water Temp Alarm state 7623 will stop Rinseback and notify the patient the water entering the machine is too hot, e.g., by posting an inlet water temperature high alarm to the GUI. This state diverts hot water to drain and waits for the water to reach nominal temperature.

The Wait state 7624 is intended to handle the transitions between Rinseback and Disconnection. This state will essentially put the system into an idle state. Besides handling the transitions between Rinseback and Disconnection, this state will also control the ability to perform additional bolus infusions. The Wait for User state 7625 waits for the user to either request an additional Rinseback or to indicate they are done with this process. If the patient indicates they are done with Rinseback, an event may be generated to terminate Rinseback.

The Venous Air Alarm state 7626 will stop Rinseback and notify the patient venous air has been detected. The Venous Air Resolution state 7627 waits for the patient to clear the air bubble and for an indication of the same from the patient.

The Dialysate Leak Alarm state 7628 will stop operation and notify the patient a dialysate leak has been detected. A dialysate leak alarm may be posted to the GUI. The Leak Resolution state 7629 waits for the patient to clear the leak and for an indication of the same from the patient.

The Dialysate Production Alarm state 7630 will stop operation and notify the patient a dialysate leak has been detected. A dialysate production alarm may be posted to the GUI. The End Rinseback state 7631 waits for the patient to acknowledge the alarm. Upon acknowledgement of the alarm, an event may be generated to end Rinseback.

The Pause Menu state 7632 allows the patient to choose to perform additional activities. The following options may be displayed and selected by a user: Patient Disconnect, Power Standby, and Shutdown.

(10) Take Samples

The Take Samples application gives the operator the ability to take certain fluid samples. In order to safely and effectively administer dialysis treatment, it may be necessary to periodically collect samples of dialysate and reverse osmosis water for laboratory analysis. This application allows the user to more easily collect these samples by presenting the fluid for sampling at a convenient location for collection.

For dialysate sample collection, dialysate is circulated through the dialyzer. For reverse osmosis (RO) sample collection, the reverse osmosis system is turned on and flushed for a predetermined amount of time to initiate production of reverse osmosis water. Then the user is prompted to collect the sample by tapping into this flow.

FIG. 77 shows an exemplary implementation of the Take Samples application. The Evaluate Dialysate Sample state 7702 of the Take Samples application 7701 determines whether a dialysate sample is scheduled. The Start Dialysate Sample state 7703 starts dialysate flow, allowing the patient to take a sample. The Evaluate RO Sample state 7704 determines whether a reverse osmosis sample is scheduled. The Start RO Production state 7705 starts RO production in preparation for an RO sample. A timer may allow the reverse osmosis membrane to be adequately flushed such that water quality is acceptable. The Collect RO Sample state 7706 allows the patient to collect an RO Sample.

Collection of a blood sample by the user can occur during or at the end of a therapy. In one arrangement, the system may set a blood flow rate of about 100 ml/min. in the blood set, while setting the ultrafiltration pump flow rate and dialysate pump flow rate to zero. Optionally, during this time, dialysate production may continue at a pre-determined rate to maintain fresh dialysate, and additions of fresh dialysate to the dialysate tank may be used to replace an equivalent amount of dialysate sent from the dialysate tank and from the outer dialysate circuit to drain.

(11) Replace Components

The Replace Components application gives the user the ability to replace certain components when they have reached the end of their life. FIGS. 78A-78C show an exemplary implementation of the Replace Components application.

The Requesting Component Replacement state 7802 of the application 7801 shows which components should be replaced and allows the user to request additional replacements. The Deprime Flow path state 7803 decides which, if any, part of the machine needs to be deprimed. The Evaluating Blood Side Drain state 7804 determines if the blood side needs to be drained. It evaluates the different ways in which the dialyzer and blood tubing set could require replacement. If the dialyzer and blood tubing set need to be changed, but are not clotted off, then the state may request that they be drained of fluid. The Evaluating Dialysate Side Drain state 7805 determines if the dialysate side needs to be drained. It evaluates the different ways in which the dialysate-side components could require replacement; if so, then the state will request they be drained of fluid. The Empty Dialysate Tank state 7806 removes any residual dialysate or reverse osmosis water from the dialysate tank by sending it to drain. When the Empty Tanks command has completed, the event Tank Empty 7807 is emitted. The Draining Dialysate Side state 7808 removes fluid from the ultrafilter.

The Evaluating Dialyzer Replacement state 7809 determines whether the dialyzer and blood tubing set require replacement. The Replacing Dialyzer state 7810 steps the patient through dialyzer (and blood tubing set) replacement. For example, directions for replacing the dialyzer may be displayed. When the user indicates the dialyzer has been replaced, the Dialyzer Replaced event may be emitted. The Evaluating Ultrafilter Replacement state 7811 determines if the ultrafilter requires replacement. The Replacing Ultrafilter state 7812 steps the patient through ultrafilter replacement. The Replacing Drain Cassette state 7813 steps the patient through ultrafilter replacement. For example, directions for replacing the drain cassette may be displayed. When the user indicates the drain cassette has been replaced, a Drain Cassette Replaced event 7814 may be emitted. The Evaluating Dialysate Cartridge Replacement state 7815 determines if the Dialysate Cartridge requires replacement. For example, directions for replacing the dialysate cartridge may be displayed. When the user has indicated they have completed replacement, the Components Replaced event 7816 may be emitted.

The Evaluating Dialyzer Connections state 7817 determines whether the dialyzer and blood tubing set connections require testing. The Checking Dialyzer state 7818 may ensure that the dialyzer has been replaced correctly and that there are no leaking connections. If the dialyzer check is okay, the Dialyzer Check Okay event 7819 may be emitted. The Fixing Dialyzer Connections state 7820 allows the patient to correct a misplaced connection. For example, instructions for fixing the dialyzer connection may be displayed. The Evaluating Ultrafilter Connections state 7821 determines whether the dialyzer and blood tubing set connections require testing. The Fixing Ultrafilter Connections state 7822 allows the patient to correct a misplaced connection. For example, instructions for fixing the ultrafilter connection may be displayed. If the ultrafilter check 7823 is okay, the Ultrafilter Check Okay event 7824 is emitted. The Evaluating Drain Cassette Connections state 7825 determines whether the drain cassette connections require testing. The Fixing Drain Connections 7826 state allows the patient to correct a misplaced connection. Instructions for fixing the drain cassette connections may be displayed. The Checking Dialysate Cartridge state 7827 ensures the dialysate cartridge has been replaced correctly and that there are no leaking connections. If the dialysate cartridge check is okay, the Connections Checked event 7828 may be emitted. The Fixing Dialysate Cartridge Connections state 7829 allows the patient to correct a misplaced connection.

(12) Install Chemicals

The Install Chemicals application allows the user to install chemical concentrates in preparation for dialysate production. Dialysate is made from chemical concentrates that are diluted with reverse osmosis water. The chemical concentrates are connected to the machine prior to dialysate production, but not during recycling. The machine checks the connection of the chemical concentrates following their installation. In the case that the chemical concentrates are not properly connected to the machine, the user will have the opportunity to correct the situation.

FIGS. 79A and 79B show an exemplary implementation of the Install Chemicals application. The Active state 7902 of the application 7901 is the state in which Install Chemicals processing occurs. The state generates the event Install Chemicals Stopped 7903 on transitioning to the Idle state 7904.

Referring to FIG. 79B, the Install new Concentrates state 7905 prompts the user to replace the chemical concentrate container. The Ensure Connection test 7906 detects whether the chemicals have been installed properly in the system. The Connection Recovery state 7907 handles the user interaction in the event that the system detects that the chemical concentrates are not installed properly. The system may notify the user to verify that the chemicals are properly installed and all connection are securely fastened. The Dilute Chemicals state 7908 fills the chemical bags with water to dilute the chemicals. The Start Dialysate Production state 7909 is responsible for starting Dialysate production.

The Dialysate Leak Alarm state 7910 will stop Operation and notify the user a dialysate leak has been detected. The Leak Resolution state 7911 waits for the user to clear the leak, and for an indication from the user of the same.

Referring again to FIG. 79A, the Data Handler Init state 7912 is responsible for initializing the data items for Install Chemicals. On completing this initialization, it will generate a Install Chemicals Launch OK event 7913 to indicate that Install Chemicals is ready for activation. The Update Data state 7914 is responsible for maintaining up to date values for the data items for Install Chemicals, such as the treatment prescription and mix.

A number of features or attributes may be desirable in the hemodialysis system embodiments described herein. These features or attributes may relate, for example, to automation, safety, usability, the user interface, therapy programming, prescription data, patient entry data, summary data, and/or therapy display data. Exemplary features or attributes of the hemodialysis system embodiments are described below. Various features or attributes or combinations of such features or attributes may be incorporated in embodiments of the hemodialysis systems described herein. However, such features and attributes may not be required by the system. Thus, while the features or attributes described may be advantageously incorporated into one or more hemodialysis system embodiments in some circumstances, the hemodialysis system need not include any of the described features or attributes, and the system is not limited to the inclusion of any such features or attributes.

Exemplary features or attributes of the automation of the system will be described first. Embodiments of the hemodialysis system described herein may be designed to permit the patient to operate the system and/or be treated from a standing, sitting and/or reclining position. As described herein, the hemodialysis system may automatically perform a number of functions, including: priming the blood set and dialysate pathways prior to treatment; rinsing and disinfecting; testing the integrity of ultrafilters and dialyzers; priming blood into the blood set, either through a prime returned or prime discarded operation; and rinsing back blood at the conclusion of a treatment. The hemodialysis system may minimize the residual red blood cells in the blood set at the completion of rinseback, and may ensure that the per-treatment red cell loss is less than or equal to the per-treatment red cell loss for traditional thrice weekly hemodialysis treatments. The hemodialysis system may automatically perform a solution infusion, upon request, at any time from the moment priming has started until rinseback is completed. The treatment device may automatically deliver heparin during treatment. The hemodialysis system may automatically record patient blood pressure and weight. This may be accomplished through the use of wireless communications with external, stand-alone sensor modules. The hemodialysis system may confirm that components have been loaded correctly and that the correct and sufficient supplies (i.e. solutions, concentrates, etc.) have been connected. The hemodialysis system may verify that the blood treatment set has been loaded correctly.

The hemodialysis system may comply with the FDA and AAMI guidelines on dialyzer reuse in testing and monitoring of the dialyzer's performance. The hemodialysis system may allow the patient to schedule their next treatment to reduce preparation time at the time of treatment. The hemodialysis system may provide a feature to allow the user to safely disconnect temporarily with a rinse back during treatment for 30 minutes or less. Alternatively, the hemodialysis system may permit a user to temporarily disconnect without rinseback of blood to the user. Upon disconnecting from the arterial and venous lines, the user can connect the arterial line to the venous line via a pass-through connector. The system may then circulate the blood in the blood set, pause the dialysate pumps, and pause heparin infusion for the duration of the disconnect period. The hemodialysis system may provide the ability for the Healthcare Professional to disable the temporary disconnect feature. The hemodialysis system may minimize therapy interruptions by preventing or attempting to self-resolve conditions that may lead to an interruption (i.e. an alarm).

Next, exemplary safety features and attributes will be described. The hemodialysis may be designed to meet certain safety standards. For example, the hemodialysis system may meet all relevant AAMI and IEC safety requirements for hemodialysis machines, and may be designed such that exterior exposed surfaces stay below the levels indicated in the IEC-60601-1 standard during operation. Further, the user interface for the dialysis system may certain safety control features. For example, the hemodialysis system may provide a mechanism for the patient to terminate a therapy and rinseback at any point during treatment. Further, a method for the patient to rinse back their blood even if a nonrecoverable alarm occurs or power is lost may be provided. The user may also be able to bring the instrument to a safe state (i.e. pause all instrument activities) at any time during operation with a single button press.

As described herein, air bubbles may be dangerous to a patient. Thus, the hemodialysis system may be constructed to prevent air bubbles sized 20 microliters or larger from reaching the patient. The hemodialysis system may trigger an alarm when streams of bubbles greater than or equal to 1 microliter accumulate to exceed 20 microliters total within 30 sec. Further, the hemodialysis system may trigger an alarm when streams of bubbles greater than or equal to 3 microliters accumulate to exceed 20 microliters total within 30 sec.

The hemodialysis system may include a number of safety detection features. For example, the hemodialysis system may include, or interface to, a feature to detect venous needle dislodgement. The hemodialysis system may detect the passage of blood across the dialyzer membrane. The hemodialysis system may also detect and alert the user to dripping leaks from the portions of the blood circuit contained within the confines of the device. In addition, fluid in the blood circuit that the patient is exposed to may be of "dialysate for injection" quality.

The hemodialysis system may be designed to be usable to patients of varying physical and mental abilities. For example, the hemodialysis system user interface may be compatible with dialysis operators suffering from retinopathy and neuropathy and readable by someone who is color blind. In particular, critical information displayed by the user interface may be viewable from a distance of 3 feet by a user with 20/70 vision, and non-critical information displayed by the user interface may be viewable from a distance of 2 feet by a user with 20/70 vision. The hemodialysis system user interface may be designed to be intuitive, so that it may be understood by an operator with a 5th grade reading level. In addition, the hemodialysis system may be designed to be operated one-handed, including during therapy. This assists patients who have one arm immobilized due to needles being present in the access site.

The user interface may also be designed to be flexible and functional. For example, the hemodialysis system user interface may be splash/spill resistant and cleanable with the following cleaning solutions without degradation of operation: wiped 5.25% sodium hypochlorite bleach diluted 1:10, wiped accelerated hydrogen peroxide (made by Virox Tech Inc), and wiped PDI Sani-Cloth Plus.

Illumination may be controllable by the user or based on certain factors. For example, the hemodialysis system may be provided with a mechanism to dim the user interface and minimize all other light emissions either by request or automatically. In addition, it may be possible to turn off all light emitting sources except those necessary to locate safety-critical controls such as the stop button. In the event of a power outage, illumination of the blood set and dialyzer may be provided to support the patient managing their blood lines and access. The hemodialysis system may provide illumination to the appropriate controls when user interaction with the controls is necessary. This assists the user in finding necessary controls when performing therapy in a dark environment.

As discussed herein, alarms may be triggered during use of the dialysis system. The hemodialysis system may provide audible and visual indication of alarm conditions. Further, the hemodialysis system may distinguish the importance of an alarm condition. The audio abilities of the hemodialysis system may allow for a range of frequencies and sound levels, e.g., for alarm and alert situations, which may be adjustable by a user. The hemodialysis system may provide the ability for the user to mute an alarm. The hemodialysis system may have a visual indicator, in addition to the GUI, to call attention to alarms and alerts. For example, the hemodialysis system may generate a "light pole" or other such visual alarm indicator that can be viewed from a significant distance in all directions (e.g., 20 feet).

The hemodialysis system GUI may explain possible causes of an alarm and whether the alarm is correctable or not correctable. If an alarm is correctable, the hemodialysis system user interface may guide the user through resolving the alarm. The hemodialysis system may also provide instructions on when to call service or a Healthcare Professional.

The user interface and labeling may support a number of different languages and alternative character sets. Further, the hemodialysis system may provide voice guidance in the supported languages. Where possible, connections may be keyed and color-coded to facilitate correct connections.

The hemodialysis system user interface may provide the user with an option to receive a notification at the end of treatment, and may allow the user to review relevant treatment data at the end of the treatment.

It may be desirable that the hemodialysis system be easy to operate and user friendly for non-professionals. The user interface and industrial design of the hemodialysis system may allow the device to look and feel like a home product, and have a simple interface. Operations to be performed by a patient may be graphically simulated on-screen. A properly trained patient may be able to initiate treatment within 10 minutes of requesting a therapy. The hemodialysis system user interface may be configurable into "novice" and "advanced" modes that help encourage and guide novice users, while providing quick navigation for advanced users.

The hemodialysis system may allow the user to recover from missteps and mistakes, for example through use of back navigation in the user interface or an undo function. Further, the hemodialysis system user interface may minimize the user time and effort required to obtain help. The hemodialysis system may provide Healthcare Professional-specific training manuals, patient-specific training manuals, and an operator's manual.

The hemodialysis system may support Healthcare Professional localization of the device consisting of setting the language for display of text elements, setting the time, and setting units for parameters (i.e. lbs or kgs). The hemodialysis system may support Healthcare Professional configuration of the patient prescription, including setting the patient's target weight, the allowable therapy configurations (i.e. short daily, extended treatment) and the associated blood flow rate, the flexibility to set either dialysate flow rate and time or the dialysate volume and time for each therapy configuration (i.e. short daily, extended treatment), the prescribed heparin protocol, the maximum ultrafiltration rate, the dialysate composition, the dialyzer identification, solution infusion bolus size and limits, arterial and venous pressure limits, rinseback volume, and prime method (prime return or prime dump). The hemodialysis system may provide the option to prevent the patient adjustment of each prescription parameter and provide maximum/minimum limits on patient adjustment of the prescription parameters.

The hemodialysis system may support manual and electronic input of the patient prescription. The hemodialysis system may be designed to minimize the amount of information that is required to be manually entered for each therapy.

The device may require the patient to provide the following inputs at the start of therapy: therapy type (e.g. short daily, extended duration) and pre-dialysis weight. Prior to and during therapy, the hemodialysis system may allow the user to adjust the therapy end time. The hemodialysis system may provide the ability for input of the sitting and/or standing patient blood pressure both prior to therapy and after therapy completion.

The device may display, for confirmation, the following calculated parameters, at a minimum, on the summary screen prior to the start of treatment: therapy duration/end time and the patient's end weight. The hemodialysis system may allow the user to adjust the end weight for the therapy prior to and during therapy. in addition, prior to and during therapy, the hemodialysis system may allow the user to adjust the therapy end time/duration for the therapy.

Unless superseded by an alarm or user request, the hemodialysis system may always display the following information: current system state (i.e. priming, therapy, etc.), current blood flow rate, current patient weight and target patient weight, cumulative therapy time and therapy end time, and volume of heparin delivered. When using an associated blood pressure monitor (cuff), the hemodialysis system may display a new blood pressure measurement for 5 minutes after that measurement was taken. The hemodialysis system may display, on demand, real-time feedback on actual blood flow. This facilitates needle adjustment for optimal blood flow. On demand, the hemodialysis system may provide a means for the user to view the following information: dialysate conductivity and flow rate, the most recent blood pressure measurement, current ultrafiltration removal rate, cumulative bolus volume infused, dialysate temperature, current arterial and venous pump pressures, and the blood volume processed.

The following are each incorporated herein by reference in their entireties: U.S. Provisional Patent Application Ser. No. 60/903,582, filed Feb. 27, 2007, entitled "Hemodialysis System and Methods"; U.S. Provisional Patent Application Ser. No. 60/904,024, filed Feb. 27, 2007, entitled "Hemodialysis System and Methods"; U.S. patent application Ser.

No. 11/787,213, filed Apr. 13, 2007, entitled "Heat Exchange Systems, Devices and Methods"; U.S. patent application Ser. No. 11/787,212, filed Apr. 13, 2007, entitled "Fluid Pumping Systems, Devices and Methods"; U.S. patent application Ser. No. 11/787,112, filed Apr. 13, 2007, entitled "Thermal and Conductivity Sensing Systems, Devices and Methods"; U.S. patent application Ser. No. 11/871,680, filed Oct. 12, 2007, entitled "Pumping Cassette"; U.S. patent application Ser. No. 11/871,712, filed Oct. 12, 2007, entitled "Pumping Cassette"; U.S. patent application Ser. No. 11/871,787, filed Oct. 12, 2007, entitled "Pumping Cassette"; U.S. patent application Ser. No. 11/871,793, filed Oct. 12, 2007, entitled "Pumping Cassette"; and U.S. patent application Ser. No. 11/871,803, filed Oct. 12, 2007, entitled "Cassette System Integrated Apparatus." In addition, the following are incorporated by reference in their entireties: U.S. Pat. No. 4,808,161, issued Feb. 28, 1989, entitled "Pressure-Measurement Flow Control System"; U.S. Pat. No. 4,826,482, issued May 2, 1989, entitled "Enhanced Pressure Measurement Flow Control System"; U.S. Pat. No. 4,976,162, issued Dec. 11, 1990, entitled "Enhanced Pressure Measurement Flow Control System"; U.S. Pat. No. 5,088,515, issued Feb. 18, 1992, entitled "Valve System with Removable Fluid Interface"; and U.S. Pat. No. 5,350,357, issued Sep. 27, 1994, entitled "Peritoneal Dialysis Systems Employing a Liquid Distribution and Pumping Cassette that Emulates Gravity Flow." Also incorporated herein by reference are U.S. patent application Ser. No. 12/038,474, entitled "Sensor Apparatus Systems, Devices and Methods," filed on Feb. 27, 2008; U.S. patent application Ser. No. 12/038,648, entitled "Cassette System Integrated Apparatus," filed on Feb. 27, 2008; and U.S. patent application Ser. No. 12/072,908, filed Feb. 27, 2008, entitled "Hemodialysis Systems and Methods."

In addition, incorporated herein by reference in their entireties, and filed on an even date herewith, are the following: U.S. patent application Ser. No. 12/198,947, entitled "Occluder for a Medical Infusion System"; U.S. patent application Ser. No. 12/199,055, entitled "Enclosure for a Portable Hemodialysis System"; U.S. patent application Ser. No. 12/199,062, entitled "Dialyzer Cartridge Mounting Arrangement for a Hemodialysis System"; U.S. patent application Ser. No. 12/199,068, entitled "Modular Assembly for a Portable Hemodialysis System"; U.S. patent application Ser. No. 12/199,077, entitled "Blood Circuit Assembly for a Hemodialysis System"; U.S. patent application Ser. No. 12/199,166, entitled "Air Trap for a Medical Infusion Device"; U.S. patent application Ser. No. 12/199,176, entitled "Blood Line Connector for a Medical Infusion Device"; U.S. patent application Ser. No. 12/199,196, entitled "Reagent Supply for a Hemodialysis System"; and U.S. patent application Ser. No. 12/199,452, filed Aug. 27, 2008, and entitled "Hemodialysis System and Methods."

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for controlling fluid flow in a hemodialysis apparatus comprising:
    receiving, at a controller, fluid pressure information from a pressure sensor in fluid communication with a control chamber of a blood pump comprising a reciprocating diaphragm between a blood chamber and the control chamber;
    causing, in response to control signals from the controller, a pneumatic valve to open and close to apply a time-varying pressure waveform on the diaphragm of the blood pump during a fill stroke of the blood pump, the pneumatic valve fluidly connecting the control chamber with a pressure source;
    monitoring, by the controller, a pressure variation in the control chamber measured by the pressure sensor;
    determining, by the controller, a blood flow metric based on a variation of a peak-to-peak pressure in the control chamber during the fill stroke; and
    alerting, by the controller, a user based on the blood flow metric.

2. The method of claim 1, wherein alerting the user includes alerting the user after the blood flow metric remains below a predetermined standard for a plurality of fill strokes.

3. The method of claim 1, further comprising:
    evaluating, by the controller, a measured pressure in the control chamber during time periods when an absolute value of fluid pressure in the control chamber is decreasing, and
    pausing or stopping, by the controller, the dialysate pump based on the blood flow metric.

4. The method of claim 1, further comprising pausing or stopping a dialysate pump when the blood flow metric drops below a predefined value.

5. The method of claim 4, wherein determining the blood flow metric includes determining the blood flow metric after an initial delay period.

6. The method of claim 1, wherein the time-varying pressure waveform is controlled by the pneumatic valve opening in a periodic fashion characterized by a frequency and duration of an open period.

7. The method of claim 1, wherein a dialysate pump comprises a reciprocating diaphragm-based pump, and wherein alerting the user includes comparing the blood flow metric to a pre-determined value based on a pressure over a period of time generated by the blood pump that provides sufficient pressure in a blood compartment of a dialyzer to allow the dialysate pump to receive a full stroke-volume of fluid from the dialyzer.

8. The method of claim 2, wherein alerting the user includes alerting the user, by the controller, after the blood flow metric remains below the predetermined standard for two fill strokes.

9. The method of claim 1, wherein the controller alerts the user before the blood flow metric is low enough to require stopping a dialysate pump.

10. The method of claim 9, wherein alerting the user includes alerting the user to provide an opportunity to correct a poor blood flow condition caused by a constricted blood tubing or a restriction in the fistula.

11. The method of claim 1, wherein alerting the user includes alerting the user based on a comparison of the blood flow metric to an expected value or a value obtained previously.

12. The method of claim 1, further comprising sending, by the controller, a blood flow metric value to a graphical user interface.

13. The method of claim 12, wherein determining the blood flow metric includes regularly updating, by the controller, the displayed blood flow metric value.

14. The method of claim 12, further comprising displaying by the graphical user interface the blood flow metric value as a numeral or a graphical indicator.

15. The method of claim 4, further comprising restarting, by the controller, the dialysate pump after the blood flow metric is above a predetermined blood flow metric for a predetermined number of fill strokes.

16. A method for controlling fluid flow in a hemodialysis apparatus where a reciprocating diaphragm blood pump moves blood through a dialyzer and a dialysate pump moves dialysate through the dialyzer, the method comprising:
    receiving, by a controller, fluid pressure information from a pressure sensor in fluid communication with a control chamber of a blood pump comprising a reciprocating diaphragm between a blood chamber and the control chamber;
    causing, by the controller, a pneumatic valve to open and close to thereby apply time-varying pressure on the diaphragm of the blood pump during a fill stroke of the blood pump, the pneumatic valve fluidly connecting the control chamber with a pressure source;
    monitoring, by the controller, a pressure variation in the control chamber measured by the pressure sensor;
    determining, by the controller, a blood flow metric based on the pressure variation measured during the fill stroke;
    alerting, by the controller, a user that blood flow is inadequate via a graphical user interface when the blood flow metric drops below a predetermined value; and
    completing one or more blood pump fill strokes after alerting the user that blood flow is inadequate and before stopping the dialysate pump in response to the blood flow metric.

17. The method of claim 16, further comprising:
    stopping, by the controller, the dialysate pump and continuing to operate the blood pump after alerting the user that blood flow is inadequate.

18. The method of claim 17, further comprising restarting, by the controller, the dialysate pump when the blood flow metric exceeds a second predetermined value.

19. The method of claim 18, wherein restarting the dialysate pump includes restarting the dialysate pump when the blood flow metric exceeds the second predetermined value for more than one stroke of the blood pump diaphragm.

20. The method of claim 18, wherein restarting the dialysate pump includes restarting the dialysate pump when the blood flow metric exceeds the second predetermined value for more than five strokes of the blood pump diaphragm.

21. The method of claim 16, wherein determining the blood flow metric includes determining the blood flow metric after an initial delay period.

22. The method of claim 16, wherein alerting the user includes alerting the user that blood flow is inadequate when the blood flow metric drops below the predetermined value for one stroke of the blood pump diaphragm.

23. The method of claim 16, wherein alerting the user includes alerting the user that blood flow is inadequate when the blood flow metric drops below the predetermined value for two strokes of the blood pump diaphragm.

24. The method of claim 16, wherein alerting the user includes alerting the user that blood flow is inadequate when the blood flow metric drops below the predetermined value for three strokes of the blood pump diaphragm.

\* \* \* \* \*

UNITED STATES PATENT AND TRADEMARK OFFICE
CERTIFICATE OF CORRECTION

PATENT NO. : 11,725,645 B2
APPLICATION NO. : 16/723408
DATED : August 15, 2023
INVENTOR(S) : Michael J. Wilt et al.

It is certified that error appears in the above-identified patent and that said Letters Patent is hereby corrected as shown below:

On the Title Page

Item (60), should read:
(60) Division of application No. 15/445,683, filed on Feb. 28, 2017, now Pat. No. 10,537,671, which is a continuation-in-part of application No. 14/666,059, filed on Mar. 23, 2015, now Pat. No. 9,951,768, said application No. 15/445,633, filed on Feb. 28, 2017, now Pat. No. 10,537,671 is a continuation-in-part of application No. 14/525,071, filed on Oct. 27, 2014, now Pat. No. 10,302,075, and a continuation-in-part of application No. 14/213,702, filed on Mar. 14, 2014, now abandoned.

Signed and Sealed this
Thirteenth Day of February, 2024

Katherine Kelly Vidal
*Director of the United States Patent and Trademark Office*